(12) United States Patent
Fujishita et al.

(10) Patent No.: US 7,098,201 B2
(45) Date of Patent: Aug. 29, 2006

(54) HETEROAROMATIC DERIVATIVES HAVING AN INHIBITORY ACTIVITY AGAINST HIV INTEGRASE

(75) Inventors: Toshio Fujishita, Osaka (JP);
Tomokazu Yoshinaga, Settsu (JP);
Akihiko Sato, Settsu (JP)

(73) Assignee: Shionogi & Co., Ltd., Osaka (JP)

( * ) Notice: Subject to any disclaimer, the term of this patent is extended or adjusted under 35 U.S.C. 154(b) by 371 days.

(21) Appl. No.: 10/463,816

(22) Filed: Jun. 18, 2003

(65) Prior Publication Data

US 2004/0002485 A1 Jan. 1, 2004

Related U.S. Application Data

(62) Division of application No. 10/288,380, filed on Nov. 6, 2002, which is a division of application No. 09/857,632, filed as application No. PCT/JP99/07101 on Dec. 17, 1999, now Pat. No. 6,620,841.

(30) Foreign Application Priority Data

Dec. 25, 1998 (JP) .......................... 10-371270
Sep. 1, 1999 (JP) .......................... 11-247479

(51) Int. Cl.
*A61K 31/33* (2006.01)

(52) U.S. Cl. .................... 514/183; 514/383; 514/363; 514/449; 514/461; 548/262.2; 549/229; 549/483; 549/491; 549/495; 549/497; 549/505

(58) Field of Classification Search ................ 514/183, 514/383, 363, 449, 461; 548/262.2; 549/229, 549/483, 491, 495, 497, 505
See application file for complete search history.

(56) References Cited

U.S. PATENT DOCUMENTS

| | | | |
|---|---|---|---|
| 3,899,508 A | 8/1975 | Wikel .......................... 260/310 |
| 3,931,247 A | 1/1976 | Pelosi, Jr. ................. 260/347.2 |
| 4,273,776 A | 6/1981 | Hoehn ........................ 424/263 |
| 4,332,735 A | 6/1982 | Alaimo et al. |
| 4,336,397 A | 6/1982 | Cragoe et al. ................. 560/51 |
| 4,386,092 A | 5/1983 | Oe et al. .................... 424/256 |
| 4,423,063 A | 12/1983 | Rooney et al. ............. 424/218 |
| 4,637,829 A | 1/1987 | Schurter et al. ................ 71/90 |
| 5,112,848 A | 5/1992 | Brooks et al. .............. 514/424 |
| 5,292,732 A | 3/1994 | Rover ........................ 514/249 |
| 5,475,109 A | 12/1995 | Selnick et al. ............. 546/225 |
| 5,516,797 A | 5/1996 | Armistead et al. .......... 514/548 |
| 5,618,830 A | 4/1997 | Selnick et al. ............. 514/358 |

FOREIGN PATENT DOCUMENTS

| EP | 0 418 845 | 3/1991 |
|---|---|---|
| EP | 658559 | * 6/1995 |
| EP | 1 069 111 | 1/2001 |
| JP | 51-75096 | 6/1976 |
| JP | 51-075096 | 6/1976 |
| JP | 61-134346 | 6/1986 |
| JP | 2-38403 | 2/1990 |
| WO | 9616052 | * 5/1996 |
| WO | 98/45268 | 10/1998 |
| WO | 99/30699 | 6/1999 |
| WO | 99/48371 | 9/1999 |
| WO | 99/62513 | 12/1999 |
| WO | 99/62520 | 12/1999 |
| WO | 99/62897 | 12/1999 |
| WO | 01/00578 | 1/2001 |
| WO | 100578 | 4/2001 |

OTHER PUBLICATIONS

Chemical Abstract DN 67:53943.*
Chemical Abstract DN 123:313992, also cited as EP 658559.*
Chemical Abstract DN 125:142771, also cited as WO 9616052.*
Debnath et al, Structure of Small Molecule Antiviral Compounds, J.Med.Chem.42,3203–9(1999).*
PubMed 12462390, also cited as Current Mol. Med. 2/8, 691–702(2002).*
Floris–Moore et al,PubMed Abstract 14632594, also cited as Ann. Pharmacother. 37/12,1810–3(2003).*
Markovitz DM,PubMed Abstract 8380244, also cited as Ann Intern Med., 118/3,211–8(1993).*
Sainsbury, Malcolm et al., "Improved synthesis of 6H–pyrido[4,3–b] carbazole derivatives", J. Chem. Soc., Perkin Trans. 1 (1975), (3), pp. 289–298.

(Continued)

*Primary Examiner*—Richard L. Raymond
*Assistant Examiner*—Sudhaker B. Patel
(74) *Attorney, Agent, or Firm*—Wenderoth, Lind & Ponack, L.L.P.

(57) ABSTRACT

A compound of the formula (I):

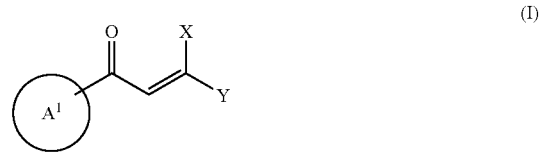

wherein X is hydroxy, protected hydroxy or optionally substituted amino; Y is —COOR$^A$ wherein R$^A$ is hydrogen or ester residue, —CONR$^B$R$^C$ wherein R$^B$ and R$^C$ each is independently hydrogen or amide residue, optionally substituted aryl or optionally substituted heteroaryl; and A$^1$ is optionally substituted heteroaryl; provided that a compound wherein Y and/or A$^1$ is optionally substituted indol-3-yl is excluded, a tautomer, a prodrug, a pharmaceutically acceptable salt or a hydrate thereof has an inhibitory activity against an integrase.

24 Claims, No Drawings

OTHER PUBLICATIONS

Lesiak, Tadeusz et al., "New β–diketones of furan series", Rocz. Chem. (1971), 45(5), pp. 903–909.

Kurkovskaya, L. N. et al., "Intramolecular hydrogen bonding in selenophene β–diketones studied by a PMR method", Teor. Eksp. Khim. (1972), 8(5), pp. 688–691.

Spirkova, K. et al., "Furan derivatives. 202. Nucleophilic substitution reactions of 2–cyano–3–methyl–3–(5–X–2–furyl) acrylonitriles", Chem. Pap. (1987), 41(6), pp. 787–792, see Compound I, II.

Kazuaki Oda, et al., "Photochemistry of the nitrogen–thiocarbonyl systems. part 24. Photoreactions of thiobenzamide with various substituted furans: regioselective β–benzoylation and transformation of furans to other aromatic compounds", J. Chem. Soc., Perkin Trans. 1 (1995), (22), pp. 2931–2935.

Zani, C. L. et al., "Efficient directed ortho metalation–based route to cytotoxic furanonaphthoquinone natural products", Tetrahedron Letter, (1987), 28(52), pp. 6561–6564.

Itahara, Toshio et al., "Arylation of aromatic heterocycles with arenes and palladium (II) acetate", J. Org. Chem. (1985), 50(25), pp. 5272–5275.

Oleinik, A. F. et al., "Synthesis and antileishmaniasis activity of arylfurylquinoxalines", Khim.–Farm, Zh. (1978), 12(7), pp. 71–77.

Cernak, Jozef et al., "Electrochemical reduction of para–substituted 2–acyl–5–phenylfurans in dimenthylformamide", Collect. Czech. Chem. Commun. (1981), 46(2), 498–502.

Sarma, C. R. et al., "Antiinflammatory agents. Part X. Synthesis and antiinflammatory activity of some new [4–[5 [formyl(acyl)–2–furyl]oxy]phenyl]alkanoic acid esters", Indian J. Chem., Sect. B (1989), 28B(11), pp. 993–995.

Koyanagi, Jyunichi et al., "A facile synthesis of 2–acetyl–naphthol[2,3–b]furan–4, 9–dione", J. Heterocycl. Chem. (1995), 32(4), pp. 1289–1291.

Bisagni, Emile et al., "2,3–Disubstituted furans and pyrroles. I. Extension of the Feist–Benary reaction to β–diketones. New synthesis of 3–acylated furans and pyrroles", Bull. Soc. Chim. Fr. (1967), (8), pp. 2796–2780.

Aly, El–Said Ahmed et al., "A new synthetic route to various 2, 5–distributed furan derivatives", Proc. Pak. Acad. Sci. (1993), 30(3), pp. 163–167.

Kondrat'eva, G. Ya. et al., "Reaction of oxazoles with acetylenic aldehydes and ketones", Izv. Akad. Nauk SSSR, Ser. Khim. (1972), (6), pp. 1363–1364.

Ma, Yinmin et al., "Synthesis and ultraviolet–visible spectrum of arylfurylphenylpropenones", Xibei Daxue Xuebao, Ziran Kexueban (1991), 21(3), pp. 55–59.

Sjoholm, Rainer et al., "Reactions between furylketones and grignard reagents, I. Conjugate additions to 2–acetylfuran", Acta Acad. Abo., Ser. B (1978), 38(1), p. 9.

Mndzhoyan, A. L. et al., "Furan–derivatives, XXXI. Some acid 2–alkylidene hydrazides and N,N'–diacyl hydrazines as potential antitubercular agents", Arm. Khim. Zh. (1966), 19 (10), pp. 793–805.

N.S. Prostakov et al., Lhim, Geterotsikl. Soedin. 1973(2), pp. 230–240.

R.A. Bol'shedvorskaya et al., Zh Organ Khim, 1968, 4(9), pp. 1541–1545.

J. Larkin et al., "Enol Benzoates of β–Diketones", J. Chem. Soc. Perkin Trans I, 1976, (4), pp. 380–383.

L.N. Kurkovskaya et al., Zh Strukt Khim, 1972, 13(6), pp. 1026–1032.

Khim. Geterotsikl. Soedin. 1973, (11), pp. 519–1522.

T. Gardner et al., "Synthesis of 5–Substituted 3–Isoxazolecarboxylic Acid Hydrazides and Derivatives", J. Org. Chem., 1961, vol. 26, pp. 1515–1519.

M. Ferles et al., "Synthesis and Reactions of Novel 1,3–dipyridinyl–1,3–Propanediones", Collect. Czech. Chem., Commun., vol. 55, 1990, pp. 1228–1233.

J. Barluenga et al., "Reactions of N–Unsubstituted 4–Amino–1–azadienes Towards Electrophiles", Synthesis, Jan. 1996, vol. 1, pp. 133–140.

R.M. Saleh, "Use of ethyl 2–thenoylpyruvate in the synthesis of heterocycles and their derivatives", Indian Journal of Chemistry, vol. 30B, Mar. 1991, pp. 313–319.

Y. Goldgur et al., "Structure of the HIV–1 integrase catalytic domain complexed with an inhibitor: A platform for antiviral drug design", Pro. Natl. Acad. Sci. USA, 1999, vol. 96, No. 23, pp. 13040–13043.

K. Oda et al., "Photochemistry of the nitrogen–thiocarbonyl systems. Part. 24. Photoreactions of thiobenzamide with various substituted furans: regioselective β–benzoylation and transormation of furans to other aromatic compounds", J. Chem. Soc. Perkin Trans. 1, 1995, vol. 22, pp. 2931–2935.

C. L. Zani et al., "Efficient Directed Ortho Metalation–Based Route to Cytotoxic Furanonaphthoquinone Natural Products", Tetrahedron Letters, vol. 28, No. 52, pp. 6561–6564, 1987.

T. Itahara, "Arylation of Aromatic Heterocycles with Arenes and Palladium (II) Acetate", J. Org. Chem. 1985, No. 50, pp 5272–5275.

Oleinik, A.F. et al., "nthesis and antileishmaniasis activity of arylfurylquinoxalines", Khim.–Farm. Zh. 1978, vol. 12, No. 7, pp. 71–77.

J. Cernak et al., "Electrochemical Reduction of para–Substituted 2–Acyl–5–phenylfuranes in Dimethyl–Formamide", Collection Czechoslovak Chem., Commun., vol. 46, No. 2, 1981, pp. 498–502.

C. R. Sarma et al., "Antiinflammatory agents: Part X +–Synthesis and antiinflammatory activity of some new 4–[5–formyl(acyl)–2–furanoxyl]–phenylalkanoic acid esters", Indian Journal of Chemistry, vol. 28B, No. 11, Nov. 1989, pp. 993–995.

J. Koyanagi et al., "A Facile Synthesis of 2–Acetylnaphtho [2,3–b]furan–4,9–dione", J. Heterocycl., Chem. 1995, vol. 32, No. 4, p. 1289–1291.

E. Bisagni et al., "2,3–Disubstituted furans and pyrroles. I. Extension of the Feist–Benary reaction β–diketones. New synthesis of 3–acylated furans and pyrroles", Bull. Soc. Chim. Fr., 1967, vol. 8, pp. 2796–2780.

E. Aly et al., "A New Synthetic Route to Various 2,5–Distributed Furan Derivatives", Proc. Pakistan Acad. Sci., vol. 30, No. 3, 1993, pp. 163–167.

Kondrat'eva, G. Ya. et al., "Reaction of oxazoles with Acetylenic Aldehydes and Ketones", Izv. Akad. Nauk SSSR, Ser. Khim., 1971, vol. 6, pp. 1363–1364.

Mndzhoyan, A. L. et al., "Furan derivatives. XXXI. Some acid 2–alkylidene hydrazides and N,N'–diacyl hydrazines as potential antitubercular agents", Arm. Khim. Zh. 1966, vol. 19, No. 10, pp. 793–805.

Chem. Abstract, vol. 131, No. 16, Oct. 18, 1999 (Columbus, OH, USA), p. 701, col. 2, Abstract No. 21423d, Dengle, R.V. et al., "Synthesis and Microbial Activity of New Thiazolyl–1,4–benzothiazines", Indian J. Chem., Sect. B: Org. Chem. Incl. Med. Chem. 1999, 38B(2), pp. 390–393 (English).

Chem. Abstract, vol. 125, No. 18, Oct. 28, 1996, (Columbus, OH, USA), p. 981, col. 1, Abstract No. 234411m, Okamura, H. et al., "Photothermographic Imaging Method", Japan Kokai Tokkyo Koho JP 08, 171, 212 [96,171,212], Jul. 2, 1996, Appln.94/345,112, Dec. 19, 1994, pp. 1–25.

Chem. Abstract, vol. 124, No. 22, May 27, 1996, (Columbus, OH, USA), p. 1227, col. 1, Abstract No. 305594r, Phillips, I.G., "Syntheses of a new Segmental Penta–Heterocyclic Ligand and its Dinuclear Ruthenium(II) Complex", Inorg. Chim. Acta, 1996, 244(1), pp. 1–5 (English).

O.M. Usov et al., Heterocyclic Derivatives of Long–Chain Diacetylenic Acids, 1995, vol. 10, pp. 2013–2016 (Abstract in English).

M. Marei et al., "The Synthesis and Cyclodehydration of 4–(3–Aryl–1,3–dioxopropyl)–5–phenyl–1H–1,2,3–triazoles. Novel substituted Pyrrolo[1,2–c][1,2,3]triazoles", The Chemical Society of Japan, Bull. Chem. Soc. Japan., vo. 67, No. 1, 1994, pp. 144–148.

Ri Dowell et al., "Novel Inhibitors of Prolyl 4–hydroxylase. Part 4. Pyridine–2–carboxylic Acid Analogues with Alternative 2–substituents", Eur. J. Med. Chem, vol. 28, 1993, pp. 513–516.

C. Passarotti et al., "Synthesis of some 5–azaflavones", Boll. Chim. Far. 1991, vol. 130, vol. 8, pp. 312–314.

J. Pons et al., "Dinuclear μ–Pyrazole Nickel(II), Cobalt(II), Cadmium(II) and Zinc(II) Complexes with Dinucleating Pyrazole–Derived Ligands", Polyhedron, vol. 9, No. 23, pp. 2839–2845, 1990.

S. Batori et al., "Synthesis and Regiospecificity in Methylation of Pyrido[1,2–α]pyrazinium–1– and 3–olates and Pyrido[1,2–b]pyridazinium–2– and 4–olates [1]", J. heterocycl. Chem. 1990, vol. 27, No. 6, pp. 1673–1680.

E. Belgodere et al., "Studies on Isomeric Pyridylisoxazoles", Heterocycles, 1983, vol. 20, No. 3, pp. 501–504.

Chem. Abst., vol. 78, No. 21, May 28, 1973, p. 358, col. 2, Abstract No. 13601w, Prostakov, N.S. et al. "β–Diketones with Heterocyclic Radicals", 1873, 2, pp. 230–234.

J. Tanaka et al., "Studies on Aromatic Sesquiterpenes. XI. Synthesis of 7–Isopropyl–3,5–dimethyl–1–napthol." Bull. Chem. Soc. Japan 1989, vol. 62, No. 6, pp. 2102–2104.

Murray et al., "A Simple Regioselective Synthesis of Ethyl 1,5–Diarylpyrazole–3–carboxylates", J. Heterocyclic Chem. Sep.–Oct. 1989, vol. 26, pp. 1389–1392.

T. Witiak et al., "Synthesis of Ethyl 6–Substituted–Chroman– and –Chromone–2–carboxylates. A Comparative Structure–Activity Study Employing the 6–Phenyl and Phenoxy Analogs in the Triton Hyperlipidemic Rat Model", Journal of Medicinal Chemistry, 1975, vol. 18, No. 9.

J. Tomassini et al., "Inhibition of Cap ($m^7$ GpppXm)–Dependent Endonuclease of Influenza Virus by 4–Substituted 2,4–Dioxobutanoic Acid Compounds. Antimicrobial Agents and Chemotherapy", Dec. 1994, vol. 38, No. 12, pp. 2827–2837.

Database HCAPLUS on STN, AN 1996:13275. LIN, "Substituted pyrazolyl compounds and methods employing these compounds", Chemical Abstracts, vol. 24, No. 202242, 1996.

Database HCAPLUS on STN, AN 1991:228873., R. M. Saleh "Use of ethyl 2–thenoylpyruvate in the synthesis of heterocycles and their derivatives", Chemical Abstracts, vol. 114, No. 228839, 1991.

Database HCAPLUS on STN, AN 1998:153601. T. N. Yanborisov, "Synthesis and pharmacological activity of hereroylpyruvic acids and their derivatives", Chemical Abstracts, vol. 130, No. 153601, 1998.

Howarth et al., "Pyrroles and Related Compounds. Part XXVI. Pyrrole β–keto–esters", J.C.S. Perkin Trans. I, 1974, vol. 4, pp. 490–501.

CAOLD: CAA55:7267b; Mndzhoyan et al., also cited as Tsdatel Akad. Nauk. Armyan SSR 4, pp. 12–14 (1959).

CAOLD: CA52:12868b; Reid et al., also cited as Ann. 611 108, (1958).

Li et al., Pub Med. Abstract 11170440; also cited as Biochemistry, 40/5, pp. 1150–1158, (2001).

P. Volberding, Pub Med. Abstract 12229892; also cited as AIDS Read, 12/8, pp. 349–350, 356–357, 368, (2002).

Ahlsen et al., Pub Med. Abstract 12180647; also cited as Antivir, Chem. Chemother. 13/1, pp. 27–37, (2002).

Debyser et al, Pub Med Abstract 1180645; also cited as Antiv. Chem. Chemother 13/ pp. 1–15, (2002).

News Paper Article, Pub Med 12171017; also cited as Prij Inf Perspect, 20, 9 (2000).

Chemical Abstract DN 125:142771.*

* cited by examiner

HETEROAROMATIC DERIVATIVES HAVING AN INHIBITORY ACTIVITY AGAINST HIV INTEGRASE

This application is a divisional of Ser. No. 10/288,380 filed Nov. 6, 2002, now U.S. Pat. No. 6,645,956, which is a divisional of Ser. No. 09/857,632 filed Jun. 7, 2001, now U.S. Pat. No. 6,620,841, which is a U.S. national stage of PCT/JP99/07101 filed Dec. 17, 1999.

TECHNICAL FIELD

The present invention relates to a novel compound having an antiviral activity, in detail heteroaromatic derivatives having an inhibitory activity against HIV integrase, a pharmaceutical composition containing the same, especially an anti-HIV agent and a process for preparing the same.

BACKGROUND ART

Among viruses, human immunodeficiency virus (HIV), a kind of retrovirus, is known to cause acquired immunodeficiency syndrome (AIDS). The therapeutic agent for AIDS is mainly selected from the group of reverse transcriptase inhibitors (e.g., AZT, 3TC, and the like) and protease inhibitors (e.g., Indinavir and the like), but they are proved to be accompanied by side effects such as nephropathy and the emergence of resistant viruses. Thus, the development of anti-HIV agents having the other mechanism of action has been desired.

On the other hand, a combination therapy is reported to be efficient in treatment for acquired immunodeficiency syndrome because of the frequent emergence of the resistant mutant in Balzarini, J. et al, Proc. Natl. Acad. Sci. USA 1996, 93, p13152–13157. Reverse transcriptase inhibitors and protease inhibitors are clinically used as an anti-HIV agent but agents having the same mechanism of action often exhibit cross resistance or only an additional activity. Therefore, anti-HIV agents having the other mechanism of action are desired.

Under the above circumstance, the research has been focused on integrase, which is an enzyme relating to the site-specific recombination or insertion of viral DNA into chromosomes in animal cells, and the research for anti-HIV agents based on the enzyme inhibitory activity has been performed; (1) KOURILSKY P et al., Proc. Natl. Acad. Sci. USA 61 (3), 1013–1020 (1968); (2) F Barin et al., J. VIROL. METHODS (NETHERLANDS), 17/1–2(55–61) (1987); (3) Fesen. M R, Proc. Natl. Acad. Sci. USA 90: 2399, (1993); (4) DeNoon, D J, CDC AIDS Weekly Pagination:P2 (1990).

On the other hand, a gene therapy has been applied to thirteen hereditary diseases such as adenosine deaminase deficiency, familial hypercholesterolemia, haemophilia and the like, and recently extended to rheumatics, cancer, infectious diseases such as HIV and the like. Namely, the number of diseases as an object of a gene therapy is increasing year by year. The gene therapies have been applied on more than three thousands patients in the world, especially in the U.S.A. Several methods for transfections of genes have been developed such as a lipofectin method and a transfection with an adenovirus vector, an adeno-associated virus vector, and the like. Over fifty percents of the gene therapies are performed by using a retrovirus vector prepared from MLV (Moloney murine leukemia virus, Mo-MLV, MMLV). Though each method has merits and demerits, a retrovirus vector is expected to stably express the gene for a long term without disappearance of the gene by cell divisions because it is inserted into host cells. However, the clinically used retrovirus vector derived from MLV can infect only proliferating cells because it is not able to actively transfer to the nucleus. Therefore, the retrovirus vector derived from HIV can overcome the above problem, which is being researched.

The problems accompanied by these retrovirus vectors include 1) the emergence of self-replicating viruses by mutation or transformation with endogenous virus, 2) cytotoxicity, 3) oncogenicity and the like. Therefore, it is important to solve the problems accompanied by these retrovirus vectors and various types of the improved vectors are studied. (Takashi Yoshida, The Japanese Association of Gene, Handbook of the development of the gene therapy, N.T.S., 1999).

Some integrase inhibitors have recently been reported, for example, peptide derivatives described in U.S. Pat. No. 5,578,573, tetrahydronaphthyl derivatives described in GB 2306476A, and acrydone derivatives described in WO 97/38999.

Additionally, in Khim. Geterotsikl. Soedin. 1973, (11), 1519, the following 2-hydroxy-4-oxo-2-butenoic acid derivatives substituted with indolyl at the 4-position are described without showing any therapeutic activity.

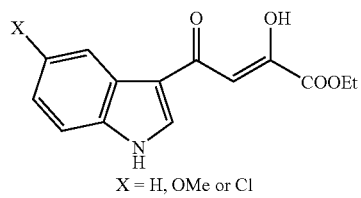

X = H, OMe or Cl

Gardner, T. S. reported, in J. Org. Chem. 1961, (26), 1514, the following 2-hydroxy-4-oxo-2-butenoic acid esters substituted with heteroaryl at the 4-position, but their therapeutic activity is not described therein.

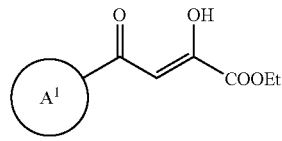

A¹ = 2-pyridyl, 3-pyridyl, 4-pyridyl, 2-furyl or 5-methylthiophen-2-yl

It is described in JP-A 61-134346 that the following 2-hydroxy-4-oxo-2-butenoic acid derivatives substituted with heteroaryl at the 4-position are useful as an antiulcer agent.

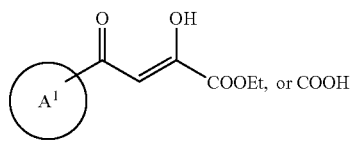

A¹ = Pyrrol-2-yl, 1-methylpyrrol-2-yl, furan-2-yl, pyridin-3-yl, thiophen-2-yl, 5-methylthiophen-2-yl or 2,5-dimethylthiophen-3-yl Ferles, M. Collect. Czech. Chem. Commun., 1990, 55, p1228–1233 and Barluenga, J. Synthesis 1996, 1, p133–140 disclose the following heteroaromatic derivatives having 1-hydroxy-3-oxo-propenylene group are described without any therapeutic activity.

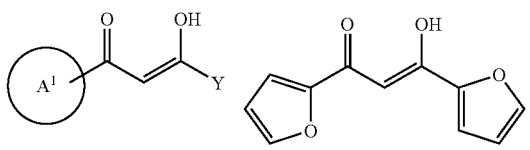

Ferles, M.
A¹, Y = pyridyl

Barluenga, J.

Moreover, in U.S. Pat. No. 5,475,109, dioxobutanoic acid derivatives substituted with non-aromatic heterocycles are described to be useful as an anti influenza viral agent, whose mechanism of the action is the inhibition of cap-dependent endonuclease.

1-(5-Phenylaminotriazol-3-yl)-3-hydroxy-(thiophen-2-yl)-propenone, 1-[5-(4-tolylamino)triazol-3-yl]-3-hydroxy-(thiophen-2-yl)-propenone and the like are described in Indian. Journal of Chemistry Vol. 30B, March 1991, pp. 313–319, but their therapeutic activity is not described.

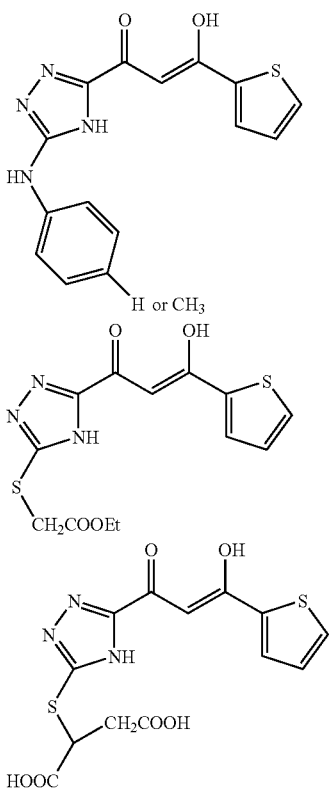

DISCLOSURE OF INVENTION

Under the above circumstance, the development of a novel integrase inhibitor has been desired. The present inventors have intensively studied to find that a novel heteroaromatic derivative, namely, a compound of the general formula (I) or (II):

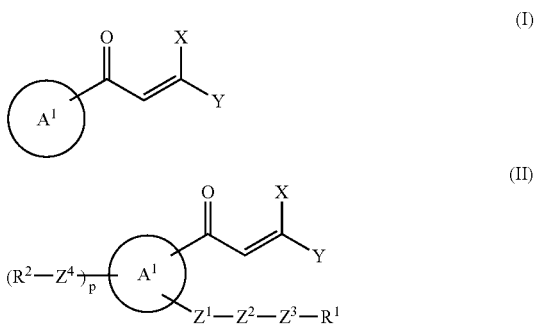

wherein X is hydroxy, protected hydroxy or optionally substituted amino; Y is —COOR$^A$ wherein R$^A$ is hydrogen or ester residue, —CONR$^B$R$^C$ wherein R$^B$ and R$^C$ each is independently hydrogen or amide residue, optionally substituted aryl or optionally substituted heteroaryl; A$^1$ is optionally substituted heteroaryl; Z$^1$ and Z$^3$ each is independently a bond, lower alkylene or lower alkenylene; Z$^2$ and Z$^4$ each is independently a bond, lower alkylene, lower alkenylene, —CH(OH)—, —S—, —SO—, —SO$_2$—, —SO$_2$NR$^{21}$—, —NR$^{21}$SO$_2$—, —O—, —NR$^{21}$—, —NR$^{21}$CO—, —CONR$^{21}$—, —C(=O)—O—, —O—C(=O)— or —CO—; R$^{21}$ is hydrogen, lower alkyl or lower alkenyl; R$^1$ is optionally substituted aryl, optionally substituted heteroaryl, optionally substituted cycloalkyl, optionally substituted cycloalkenyl or optionally substituted heterocycle; R$^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercapto, optionally substituted amino, nitro or halogen; and p is 0 or 1, (hereinafter referred to as "a compound of the present invention"), a tautomer, a prodrug, a pharmaceutically acceptable salt or a hydrate thereof has an inhibitory activity against integrase and is useful as an antiviral agent, an antiretroviral agent, an anti-HIV agent, an anti-HTLV-1 (Human T cell leukemia virus type 1) agent, an anti-FIV (Feline immunodeficiency virus) agent or an anti-SIV (Simian immunodeficiency virus) agent, especially an anti-HIV agent or an integrase inhibitor, to accomplish the present invention.

Moreover, the present inventors have discovered that the compound of the present invention inhibits not only integrase of HIV, SIV and FIV, but also that of MLV, which is often used in the gene therapy.

In addition, the present inventors have discovered a process for producing the compound of the formula (I) or (II) and a useful intermediate thereof.

BEST MODE FOR CARRYING OUT THE INVENTION

The present invention relates to the following compounds and pharmaceutical compositions;

(1) a pharmaceutical composition for inhibition of an integrase which contains as an active ingredient a compound of the formula (I):

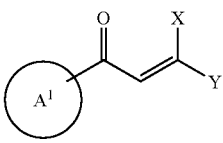

wherein X is hydroxy, protected hydroxy or optionally substituted amino; Y is —COOR$^A$ wherein R$^A$ is hydrogen or ester residue, —CONR$^B$R$^C$ wherein R$^B$ and R$^C$ each is independently hydrogen or amide residue, optionally substituted aryl or optionally substituted heteroaryl; and A$^1$ is optionally substituted heteroaryl; provided that a compound wherein Y and/or A$^1$ is optionally substituted indol-3-yl is excluded, a tautomer, a prodrug, a pharmaceutically acceptable salt or a hydrate thereof, (2) a compound of the formula (I):

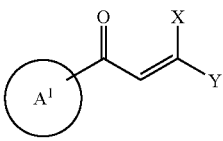

wherein X is hydroxy, protected hydroxy or optionally substituted amino; Y is —CONR$^B$R$^C$ wherein R$^B$ and R$^C$ each is independently hydrogen or amide residue, or optionally substituted heteroaryl; and A$^1$ is optionally substituted heteroaryl; provided that a compound wherein Y and/or A$^1$ is optionally substituted indol-3-yl is excluded, a tautomer, a prodrug, a pharmaceutically acceptable salt or a hydrate thereof; provided that compounds wherein (1) X is hydroxy, Y and A$^1$ are pyridyl; (2) X is hydroxy, Y and A$^1$ are 2-furyl; (3) X is hydroxy, one of Y and A$^1$ is 2-thienyl, the other is 5-ethoxycarbonylmethylsulfanyl-1H-1,2,4-triazol-3-yl, 5-p-tolylamino-1H-1,2,4-triazol-3-yl, 5-phenylamino-1H-1,2,4-triazol-3-yl, 5-hydrazino-1H-1,2,4-triazol-3-yl, 5-(3,6-dioxo-hexahydro-pyridazin-4-ylsulfanyl)-1H-1,2,4-triazol-3-yl, 5-[3-(3,4-dimethylphenyl)-6-oxo-1-phenyl-1,4,5,6-tetrahydro-pyridazin-4-ylsulfanyl]-1H-1,2,4-triazol-3-yl, 5-(1,2-dicarboxyethylsulfanyl)-1H-1,2,4-triazol-3-yl, 5-[1-carboxy-3-(3,4-dimethylphenyl)-3-oxo-propylsulfanyl]-1H-1,2,4-triazol-3-yl or 5-(2-cyano-2-ethoxycarbonyl-1-phenyl-ethylsulfanyl)-1H-1,2,4-triazol-3-yl; (4) X is hydroxy, Y and A$^1$ are [3-(2-methoxycarbonylethyl)-4-methoxycarbonylmethyl-5-methyl]-1H-pyrrol-2-yl and (5) X is hydroxy, Y and A$^1$ are 3-methylpyrazol-1-yl; are excluded, (3) a compound of the formula (II):

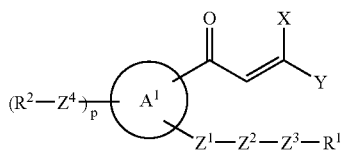

wherein X is hydroxy, protected hydroxy or optionally substituted amino; Y is —COOR$^A$ wherein R$^A$ is hydrogen or ester residue, —CONR$^B$R$^C$ wherein R$^B$ and R$^C$ each is independently hydrogen or amide residue, optionally substituted aryl or optionally substituted heteroaryl; A$^1$ is optionally substituted heteroaryl; Z$^1$ and Z$^3$ each is independently a bond, lower alkylene or lower alkenylene; Z$^2$ and Z$^4$ each is independently a bond, lower alkylene, lower alkenylene, —CH(OH)—, —S—, —SO—, —SO$_2$—, —SO$_2$NR$^{21}$, —NR$^{21}$SO$_2$—, —O—, —NR$^{21}$—, —NR$^{21}$CO—, —CONR$^{21}$—, —C(=O)—O—, —O—C (=O)— or —CO—; R$^{21}$ is hydrogen, lower alkyl or lower alkenyl; R$^1$ is optionally substituted aryl, optionally substituted heteroaryl, optionally substituted cycloalkyl, optionally substituted cycloalkenyl or optionally substituted heterocycle; R$^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercapto, optionally substituted amino, nitro or halogen; and p is 0 or 1; provide that compounds wherein (1) Y and/or A$^1$ is optionally substituted indol-3-yl and (2) X is hydroxy, Y is 2-thienyl, A$^1$ is 1H-1,2,4-triazol-3-yl, Z$^1$ and Z$^3$ each is a bond, Z$^2$ is —NH—, R$^1$ is phenyl or p-tolyl, and p is 0, are excluded, a tautomer, a prodrug, a pharmaceutically acceptable salt or a hydrate thereof, (4) the compound according to the above (2) or (3) wherein A$^1$ is optionally substituted furyl, optionally substituted thienyl, optionally substituted pyrrolyl, optionally substituted imidazolyl, optionally substituted pyrazolyl, optionally substituted benzofuryl, optionally substituted benzothienyl, optionally substituted benzimidazolyl, optionally substituted indolidinyl, optionally substituted quinolinyl, optionally substituted isoxazolyl, optionally substituted pyridyl, optionally substituted thiazolyl or optionally substituted oxazolyl, a tautomer, a prodrug, a pharmaceutically acceptable salt or a hydrate thereof, (5) the compound according to the above (4) wherein A$^1$ is optionally substituted furyl, optionally substituted thienyl, optionally substituted pyrrolyl, optionally substituted imidazolyl, optionally substituted pyrazolyl, optionally substituted isoxazolyl, optionally substituted pyridyl, optionally substituted thiazolyl or optionally substituted oxazolyl, a tautomer, a prodrug, a pharmaceutically acceptable salt or a hydrate thereof, (6) the compound according to the above (5) wherein A$^1$ is optionally substituted furyl, optionally substituted pyrrolyl or optionally substituted oxazolyl, a tautomer, a prodrug, a pharmaceutically acceptable salt or a hydrate thereof, (7) the compound according to any one of the above (3) to (6) wherein Y is —COOR$^A$ wherein R$^A$ is hydrogen or ester residue, —CONR$^B$R$^C$ wherein R$^B$ and R$^C$ each is independently hydrogen or amide residue, or heteroaryl optionally substituted with a substituent selected from the group consisting of halogen, lower alkyl, lower haloalkyl, lower alkyloxy(lower)alkyl, carboxy, lower alkyloxycarbonyl, optionally substituted aryl(lower)alkyl and optionally substituted arylsulfonyl, a tautomer, a prodrug, a pharmaceutically acceptable salt or a hydrate thereof, (8) the compound according to the above (7) wherein Y is —COOH; tetrazolyl optionally substituted with lower alkyl or lower alkyloxy(lower)alkyl; triazolyl optionally substituted with halogen, lower alkyl, lower haloalkyl or lower alkyloxy(lower)alkyl; pyridyl optionally substituted with lower alkyl, carboxy or lower alkyloxycarbonyl; pyrrolyl optionally substituted with lower alkyl or optionally substituted arylsulfonyl; isoquinolinyl optionally substituted with lower alkyl; pyradinyl optionally substituted with lower alkyl; pyrimidinyl optionally substituted with lower alkyl; oxadiazolyl optionally substituted with optionally substituted aryl or lower alkyl;

isoxazolyl optionally substituted with lower alkyl; thiazolyl optionally substituted with lower alkyl; thienyl optionally substituted with lower alkyl; furyl optionally substituted with lower alkyl; thiadiazolyl optionally substituted with lower alkyl; oxazolyl optionally substituted with lower alkyl; or imidazolyl optionally substituted with lower alkyl; a tautomer, a prodrug, a pharmaceutically acceptable salt or a hydrate thereof, (9) the compound according to the above (8) wherein Y is tetrazolyl optionally substituted with lower alkyl or lower alkyloxy(lower)alkyl; triazolyl optionally substituted with halogen, lower alkyl, lower haloalkyl or lower alkyloxy(lower)alkyl; pyridyl optionally substituted with lower alkyl, carboxy or lower alkyloxycarbonyl; or pyrimidinyl optionally substituted with lower alkyl; a tautomer, a prodrug, a pharmaceutically acceptable salt or a hydrate thereof,

(10) the compound according to any one of the above (2) to (9) wherein X is hydroxy, a tautomer, a prodrug, a pharmaceutically acceptable salt or a hydrate thereof,

(11) the compound according to the above (3) to (10) wherein $Z^1$ and $Z^3$ each is a bond, a tautomer, a prodrug, a pharmaceutically acceptable salt or a hydrate thereof,

(12) the compound according to any one of the above (3) to (11) wherein $Z^2$ is a bond, —CO—, —O—, —S—, —SO$_2$—, —CH$_2$— or —(CH$_2$)$_2$—, a tautomer, a prodrug, a pharmaceutically acceptable salt or a hydrate thereof,

(13) the compound according to any one of the above (3) to (12) wherein $R^1$ is optionally substituted phenyl, a tautomer, a prodrug, a pharmaceutically acceptable salt or a hydrate thereof,

(14) the compound according to the above (13) wherein $R^1$ is p-fluorophenyl, a tautomer, a prodrug, a pharmaceutically acceptable salt or a hydrate thereof,

(15) a pharmaceutical composition which contains as an active ingredient the compound according to any one of the above (2) to (14),

(16) a pharmaceutical composition having an antiviral activity which contains as an active ingredient the compound according to any one of the above (2) to (14),

(17) a pharmaceutical composition having an antiretroviral activity which contains as an active ingredient the compound according to any one of the above (2) to (14),

(18) a pharmaceutical composition having an anti-HIV activity which contains as an active ingredient the compound according to any one of the above (2) to (14),

(19) a pharmaceutical composition having an anti-HTLV-1 activity which contains as an active ingredient the compound according to any one of the above (2) to (14),

(20) a pharmaceutical composition having an anti-FIV activity which contains as an active ingredient the compound according to any one of the above (2) to (14),

(21) a pharmaceutical composition having an anti-SIV activity which contains as an active ingredient the compound according to any one of the above (2) to (14),

(22) a pharmaceutical composition inhibiting integrase which contains as an active ingredient the compound according to any one of the above (2) to (14),

(23) an anti-HIV medical mixture which comprises one or two inhibitor(s) selected from a group consisting of an absorption inhibitor, a TAT inhibitor, a REV inhibitor, a reverse transcriptase inhibitor and a protease inhibitor in addition to the integrase inhibitor according to the above (1) or (22),

(24) the pharmaceutical composition according to the above (1) or (22) which enhances an anti-HIV activity of one or two inhibitor(s) selected from a group consisting of an absorption inhibitor, a TAT inhibitor, a REV inhibitor, a reverse transcriptase inhibitor and a protease inhibitor,

(25) a method for treating AIDS which comprises administering the compound according to any one of the above (1) to (14),

(26) use of the compound according to any one of the above (1) to (14) for the manufacture of medicament for treating AIDS.

The present invention relates to the following processes and intermediates;

(27) a process for producing a compound of the formula (V):

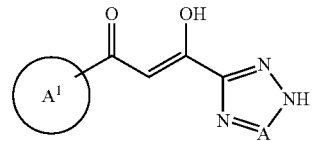

(V)

wherein $A^1$ is optionally substituted heteroaryl and A is C—W wherein W is hydrogen, lower alkyl, lower haloalkyl or halogen, or N, provided that a compound wherein $A^1$ is optionally substituted indol-3-yl is excluded, which comprises reacting a compound of the formula (III):

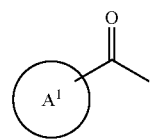

(III)

wherein $A^1$ is as defined above, with a compound of the formula (IV):

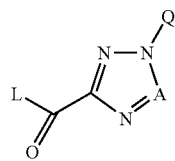

(IV)

wherein A is as defined above, Q is a protective group and L is a leaving group, in the presence of a base, and deprotecting Q.

(28) the process according to the above (27) wherein a group of the formula:

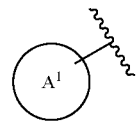

is a group of the formula:

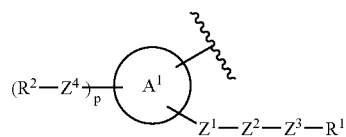

wherein $A^1$ is optionally substituted heteroaryl; $Z^1$ and $Z^3$ each is independently a bond, lower alkylene or lower alkenylene; $Z^2$ and $Z^4$ each is independently a bond, lower alkylene, lower alkenylene, —CH(OH)—, —S—, —SO—, —SO$_2$—, —SO$_2$NR$^{21}$—, —NR$^{21}$SO$_2$—, —O—, —NR$^{21}$—, —NR$^{21}$CO—, —CONR$^{21}$—, —C(=O)—O—, —O—C(=O)— or —CO—; R$^{21}$ is hydrogen, lower alkyl or lower alkenyl; R$^1$ is optionally substituted aryl, optionally substituted heteroaryl, optionally substituted cycloalkyl, optionally substituted cycloalkenyl or optionally substituted heterocycle; R$^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, cycloalkyl, hydroxy, mercapto, optionally substituted amino, nitro or halogen; and p is 0 or 1; provided that a group wherein A$^1$ is optionally substituted indol-3-yl is excluded,

(29) the process according to the above (28) wherein A$^1$ is optionally substituted furyl, Z$^1$ and Z$^3$ each is a bond, Z$^2$ is a bond, —CO—, —O—, —S—, —SO$_2$—, —CH$_2$— or —(CH$_2$)$_2$— and R$^1$ is optionally substituted phenyl,

(30) a compound of the formula (VI):

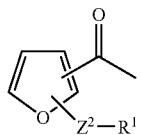

(VI)

wherein Z$^2$ is a bond, —CO—, —O—, —S—, —SO$_2$—, —CH$_2$— or —(CH$_2$)$_2$— and R$^1$ is optionally substituted phenyl,

(31) the compound according to the above (30) wherein Z$^2$ is —SO$_2$—, —CH$_2$— or —(CH$_2$)$_2$— and R$^1$ is phenyl optionally substituted with halogen,

(32) a compound of the formula (IV):

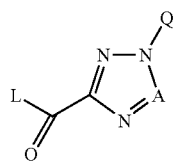

(IV)

wherein A is C—W wherein W is hydrogen, lower alkyl, lower haloalkyl or halogen or N, Q is trityl and L is ethoxy.

One of the structural characters of the compound of the present invention is that optionally substituted heteroaryl of A$^1$ is substituted with the group of the formula: —C(=O)—CH=C(X)Y wherein X is hydroxy, protected hydroxy or optionally substituted amino; Y is —COOR$^A$ wherein R$^A$ is hydrogen or ester residue, —CONR$^B$R$^C$ wherein R$^B$ and R$^C$ each is independently hydrogen or amide residue, optionally substituted aryl or optionally substituted heteroaryl, provided that A$^1$ is not optionally substituted indol-3-yl.

One of the structural characters of the compound of the formula (II) is that optionally substituted heteroaryl of A$^1$ is substituted with not only the above group of the formula: —C(=O)—CH=C(X)Y wherein X and Y are as defined above but also the group of the formula: -Z$^1$-Z$^2$-Z$^3$-R$^1$ wherein Z$^1$ and Z$^3$ each is independently a bond, lower alkylene or lower alkenylene; Z$^2$ is a bond, lower alkylene, lower alkenylene, —CH(OH)—, —S—, —SO—, —SO$_2$—, —SO$_2$NR$^{21}$—, —NR$^{21}$SO$_2$—, —O—, —NR$^{21}$—, —NR$^{21}$CO—, —CONR$^{21}$—, —C(=O)—O—, —O—C(=O)— or —CO—; R$^{21}$ is hydrogen, lower alkyl or lower alkenyl; R$^1$ is optionally substituted aryl, optionally substituted heteroaryl, optionally substituted cycloalkyl, optionally substituted cycloalkenyl or optionally substituted heterocycle, and further optionally substituted with the group of the formula: -Z$^4$-R$^2$ wherein Z$^4$ is a bond, lower alkylene, lower alkenylene, —CH(OH)—, —S—, —SO—, —SO$_2$—, —SO$_2$NR$^{21}$—, —NR$^{21}$SO$_2$—, —O—, —NR$^{21}$—, —NR$^{21}$CO—, —CONR$^{21}$—, —C(=O)—O—, —O—C(=O)— or —CO—; R$^{21}$ is hydrogen, lower alkyl or lower alkenyl; R$^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercapto, optionally substituted amino, nitro or halogen, provided that A$^1$ is not optionally substituted indol-3-yl.

Since A$^1$ of the formula (II) is substituted with both the group of the formula: —C(=O)—CH=C(X)Y wherein X and Y are as defined above and the group of the formula: -Z$^1$-Z$^2$-Z$^3$-R$^1$ wherein R$^1$, Z$^1$, Z$^2$ and Z$^3$ are as defined above, heteroaryl (A$^1$) of the formula (II) is termed as heteroaryl being attached to the group of the formula: —C(=O)—CH=C(X)Y wherein X and Y are as defined above. For instance, heteroaryl of A$^1$ is termed as shown below when A$^1$ is furyl or pyridyl. The other heteroaryl groups of A$^1$ are termed as well.

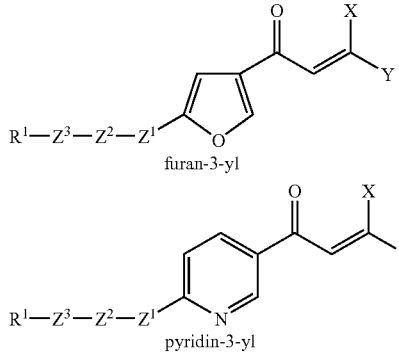

furan-3-yl pyridin-3-yl

A$^1$ of the formula (I) and (II) is optionally substituted heteroaryl, which includes monocyclic heteroaryl and fused heteroaryl, provided that A$^1$ is not optionally substituted indol-3-yl. In the case that A$^1$ is monocyclic heteroaryl, specially preferred is the embodiment represented by the formula (II). In the case that A$^1$ is fused heteroaryl, preferred are both of the embodiments represented by the formula (I) and the formula (II).

A more preferable embodiment of the compound of the present invention is, for example, a compound shown as the following (A-1) to (A-54). In the case that a compound wherein Y is optionally substituted aryl or optionally substituted heteroaryl is termed as a propenone derivative, the carbon atom substituted with A$^1$ is the 1-position and the carbon atom substituted with the group of the formula: —Y is the 3-position of the propenone as shown below. In the case that Y is the group of the formula: —COOR$^A$ wherein R$^A$ is hydrogen or ester residue; or —CONR$^B$R$^C$ wherein R$^B$ and R$^C$ each is independently hydrogen or amide residue, such compound may be termed as a butenoic acid as follows.

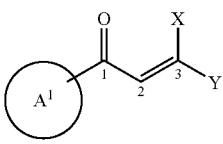

in the case that Y is optionally substituted aryl or optionally substituted heteroaryl

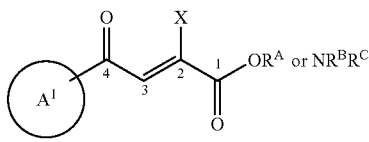

in the case that Y is ——COOR$^A$ wherein R$^A$ is hydrogen or ester residue or ——CONR$^B$R$^C$ wherein R$^B$ and R$^C$ each is independently hydrogen or amide residue (A-1) 1-[1H-1-(4-Fluorobenzyl)pyrazol-4-yl]-3-hydroxy-3-(1H-1,2,4-triazol-3-yl)-propenone,
(A-2) 1-[4-(4-Fluorobenzyl)furan-2-yl]-3-hydroxy-3-(1H-1,2,4-triazol-3-yl)-propenone,
(A-3) 1-[5-(4-Fluorobenzyl)furan-2-yl]-3-hydroxy-3-(2H-tetrazol-5-yl)-propenone,
(A-4) 3-Hydroxy-1-(5-phenylthiofuran-2-yl)-3-(1H-1,2,4-triazol-3-yl)-propenone,
(A-5) 1-(5-Benzenesulfonylfuran-2-yl)-3-hydroxy-3-(1H-1,2,4-triazol-3-yl)-propenone,
(A-6) 4-[5-(4-Fluorobenzyl)furan-2-yl]-2-hydroxy-4-oxo-2-butenoic acid,
(A-7) 4-[5-(4-Fluorobenzyl)furan-2-yl]-2-hydroxy-4-oxo-2-butenoic acid methyl ester,
(A-8) 1-(5-n-Butylfuran-2-yl)-3-hydroxy-3-(1H-1,2,4-triazol-3-yl)-propenone,
(A-9) 1-[5-(4-Fluorobenzyl)thiophen-2-yl]-3-hydroxy-3-(1H-1,2,4-triazol-3-yl)-propenone,
(A-10) 1-(5-n-Butylfuran-2-yl)-3-hydroxy-3-(2H-tetrazol-5-yl)-propenone,
(A-11) 1-[5-(4-Fluorobenzyl)furan-3-yl]-3-hydroxy-3-(1H-1,2,4-triazol-3-yl)-propenone,
(A-12) 1-[5-(4-Fluorobenzyl)pyrrol-2-yl]-3-hydroxy-3-(1H-1,2,4-triazol-3-yl)-propenone,
(A-13) 1-[3-(4-Fluorobenzyl)furan-2-yl]-3-hydroxy-3-(2H-tetrazol-5-yl)-propenone,
(A-14) 1-[3-(4-Fluorobenzyl)furan-2-yl]-3-hydroxy-3-(1H-1,2,4-triazol-3-yl)-propenone,
(A-15) 1-[4-(4-Fluorobenzyl)furan-3-yl]-3-hydroxy-3-(1H-1,2,4-triazol-3-yl)-propenone,
(A-16) 1-[2H-2-(4-Fluorobenzyl)pyrazol-3-yl]-3-hydroxy-3-(2H-tetrazol-5-yl)-propenone,
(A-17) 1-[[4-(4-Fluorobenzyl)-1-methoxymethyl]pyrrol-3-yl]-3-hydroxy-3-(1H-1,2,4-triazol-3-yl)-propenone,
(A-18) 1-[5-(4-Fluorobenzyl)furan-3-yl]-3-hydroxy-3-(1H-1,2,4-triazol-3-yl)-propenone,
(A-19) 1-[[4-(4-Fluorobenzyl)-1-propyl]pyrrol-3-yl]-3-hydroxy-3-(1H-1,2,4-triazol-3-yl)-propenone,
(A-20) 1-[1,4-Di-(4-fluorobenzyl)pyrrol-3-yl]-3-hydroxy-3-(1H-1,2,4-triazol-3-yl)-propenone,
(A-21) 1-[4-(4-fluorobenzyl)pyrrol-3-yl]-3-hydroxy-3-(1H-1,2,4-triazol-3-yl)-propenone,
(A-22) 1-[2-(4-Fluorobenzyl)furan-3-yl]-3-hydroxy-3-(2H-tetrazol-5-yl)-propenone,
(A-23) 1-[[1-Benzenesulfonyl-4-(2-phenylethyl)]pyrrol-3-yl]-3-hydroxy-3-(2H-tetrazol-5-yl)-propenone,
(A-24) 3-Hydroxy-1-[(4-(2-phenylethyl))pyrrol-3-yl]-3-(2H-tetrazol-5-yl)-propenone,
(A-25) 1-[[1-Benzyl-4-(2-carboxyvinyl)]pyrrol-2-yl]-3-hydroxy-3-(1H-1,2,4-triazol-3-yl)-propenone,
(A-26) 1-[[1-Benzyl-4-(2-carboxyvinyl)]pyrrol-3-yl]-3-hydroxy-3-(1H-1,2,4-triazol-3-yl)-propenone,
(A-27) 1-[2-(4-Fluorobenzyl)furan-3-yl]-3-hydroxy-3-(1H-1,2,4-triazol-3-yl)-propenone,
(A-28) 1-[1-(4-Fluorobenzyl)pyrrol-3-yl]-3-hydroxy-3-(2H-tetrazol-5-yl)-propenone,
(A-29) 1-[2-(4-Fluorobenzyl)benzothiophen-3-yl]-3-hydroxy-3-(1H-1,2,4-triazol-3-yl)-propenone,
(A-30) 1-[2-(4-Fluorobenzyl)benzofuran-3-yl]-3-hydroxy-3-(1H-1,2,4-triazol-3-yl)-propenone,
(A-31) 1-[(1-Benzyl-5-carboxyl)pyrrol-3-yl]-3-hydroxy-3-(1H-1,2,4-triazol-3-yl)-propenone,
(A-32) 1-[(1-Benzyl-5-ethoxycarbonyl)pyrrol-3-yl]-3-hydroxy-3-(1H-1,2,4-triazol-3-yl)-propenone,
(A-33) 1-[[1-Benzyl-5-(2-carboxyvinyl)]pyrrol-3-yl]-3-hydroxy-3-(1H-1,2,4-triazole-3-yl)-propenone,
(A-34) 1-[1-(4-Fluorobenzyl)pyrrol-2-yl]-3-hydroxy-3-(1H-1,2,4-triazol-3-yl)-propenone,
(A-35) 1-[1-(4-Fluorobenzyl)pyrrol-2-yl]-3-hydroxy-3-(2H-tetrazol-5-yl)-propenone,
(A-36) 1-(1-Benzenesulfonylpyrrol-3-yl)-3-hydroxy-3-(1H-1,2,4-triazol-3-yl)-propenone,
(A-37) 1-[2-(4-Fluorobenzyl)benzofuran-3-yl]-3-hydroxy-3-(2H-tetrazol-5-yl)-propenone,
(A-38) 1-(2-Benzylbenzofuran-3-yl)-3-hydroxy-3-(2H-tetrazol-5-yl)-propenone,
(A-39) 1-[(1-Benzenesulfonyl-4-ethyl)pyrrol-3-yl]-3-hydroxy-3-(2H-tetrazol-5-yl)-propenone,
(A-40) 1-(1-Benzylpyrrol-3-yl)-3-hydroxy-3-(1H-1,2,4-triazol-3-yl)-propenone,
(A-41) 1-[[1-Benzyl-5-(2-methoxycarbonylethyl)]pyrrol-3-yl]-3-hydroxy-3-(2H-tetrazol-5-yl)-propenone,
(A-42) 1-[[1-Benzyl-5-(2-methoxycarbonylvinyl)]pyrrol-3-yl]-3-hydroxy-3-(2H-tetrazol-5-yl)-propenone,
(A-43) 1-[(1-Benzyl-5-ethoxycarbonyl)pyrrol-3-yl]-3-hydroxy-3-(2H-tetrazol-5-yl)-propenone,
(A-44) 1-[(1-Benzyl-5-n-butyl)pyrrol-3-yl]-3-hydroxy-3-(2H-tetrazol-5-yl)-propenone,
(A-45) 1-[(1-Benzyl-5-n-propyl)pyrrol-3-yl]-3-hydroxy-3-(2H-tetrazol-5-yl)-propenone,
(A-46) 1-(1-Benzylpyrrol-3-yl)-3-hydroxy-3-(2H-tetrazol-5-yl)-propenone,
(A-47) 1-(1-Benzenesulfonylpyrrol-3-yl)-3-hydroxy-3-(2H-tetrazol-5-yl)-propenone,
(A-48) 2-Hydroxy-4-oxo-4-(pyrrol-3-yl)-2-butenoic acid,
(A-49) 1-[5-(4-Fluorobenzyl)furan-2-yl]-3-hydroxy-3-(pyridin-2-yl)-propenone,
(A-50) 1-[5-(4-fluorobenzyl)furan-2-yl]-3-hydroxy-3-(pyrimidin-2-yl)-propenone,
(A-51) 3-(5-Carboxypyridin-2-yl)-1-[5-(4-fluorobenzyl)furan-2-yl]-3-hydroxy-propenone,
(A-52) 3-(4-Carboxypyridin-2-yl)-1-[5-(4-fluorobenzyl)furan-2-yl]-3-hydroxy-propenone,
(A-53) 1-[2-(4-Fluorobenzyl)oxazol-5-yl]-3-hydroxy-3-(pyridin-2-yl)-propenone,
(A-54) 1-[2-(4-Fluorobenzyl)oxazol-5-yl]-3-hydroxy-3-(pyrimidin-2-yl)-propenone.

The terms to be used in the present specification are explained as follows.

The term "heteroaryl" includes monocyclic heteroaryl and fused heteroaryl as defined below. The term "heteroaryl" of A$^1$ and Y does not include indol-3-yl.

The term "monocyclic heteroaryl" means a 5- to 8-membered heteroaromatic group containing 1 to 4 oxygen atom, sulfur atom and/or nitrogen atom in the ring, which may have a radical group at any substitutable position such as carbon atom or nitrogen atom. Examples of pyrrolyl are shown below. Other heteroaryl groups are shown as well.

in case that a radical group is at nitrogen atom

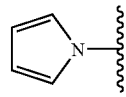

pyrrol-1-yl in case that a radical group is at carbon atom

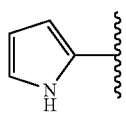 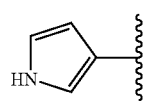

pyrrol-2-yl    pyrrol-3-yl

The term "monocyclic heteroaryl" includes furyl (e.g., furan-2-yl, furan-3-yl), thienyl (e.g., thiophen-2-yl, thiophen-3-yl), pyrrolyl (e.g., pyrrol-1-yl, pyrrol-2-yl, pyrrol-3-yl), imidazolyl (e.g., imidazol-1-yl, imidazol-2-yl, imidazol-4-yl), pyrazolyl (e.g., pyrazol-1-yl, pyrazol-3-yl, pyrazol-4-yl), triazolyl (e.g., 1H-1,2,4-triazol-1-yl, 4H-1,2,4-triazol-1-yl, 1H-1,2,4-triazol-3-yl), tetrazolyl (e.g., 1H-tetrazol-1-yl, 2H-tetrazol-2-yl, 1H-tetrazol-5-yl, 2H-tetrazol-5-yl), oxazolyl (e.g., oxazol-2-yl, oxazol-4-yl, oxazol-5-yl), isoxazolyl (e.g., isoxazol-3-yl, isoxazol-4-yl, isoxazol-5-yl), thiazolyl (e.g., thiazol-2-yl, thiazol-4-yl, thiazol-5-yl), isothiazolyl (e.g., isothiazol-3-yl, isothiazol-4-yl, isothiazol-5-yl), pyridyl (e.g., pyridin-2-yl, pyridin-3-yl, pyridin-4-yl), pyridazinyl (e.g., pyridazin-3-yl, pyridazin-4-yl), pyrimidinyl (e.g., pyrimidin-2-yl, pyrimidin-4-yl, pyrimidin-5-yl), furazanyl (e.g., furazan-3-yl), pyrazinyl (e.g., pyrazin-2-yl), thiadiazolyl (e.g., [1,3,4]thiadiazol-2-yl), oxadiazolyl (e.g., [1,3,4]-oxadiazol-2-yl) and the like.

The term "fused heteroaryl" means a heteroaromatic group wherein a 5- to 8-membered aromatic ring containing 1 to 4 oxygen atom, sulfur atom and/or nitrogen atom in the ring is fused with one to four 5- to 8-membered aromatic carbon ring or other 5- to 8-membered heteroaromatic ring, which has a radical group at any substitutable position such as carbon atom or nitrogen atom as well as monocyclic heteroaryl. The radical group may be at heteroaromatic ring or aromatic carbon ring. Examples of benzothienyl are shown below. Other heteroaryl groups are shown as well.
In the case that a radical group is on carbon aromatic ring

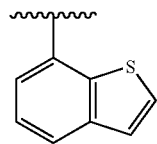

Benzo[b]thiophen-7-yl

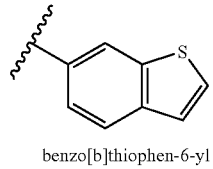

benzo[b]thiophen-6-yl

-continued

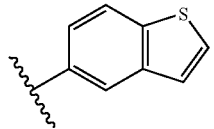

benzo[b]thiophen-5-yl

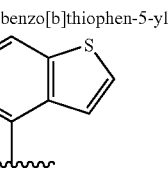

benzo[b]thiophen-4-yl

In the case that a radical group is on hetero aromatic ring

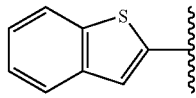

benz[b]thiophen-2-yl

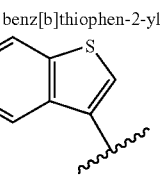

benz[b]thiophen-3-yl

The term "fused heteroaryl" includes, for example, benzofuryl (e.g., benzo[b]furan-2-yl, benzo[b]furan-3-yl, benzo[b]furan-4-yl, benzo[b]furan-5-yl, benzo[b]furan-6-yl, benzo[b]furan-7-yl), benzothienyl (e.g., benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), benzimidazolyl (e.g., benzimidazol-1-yl, benzimidazol-2-yl, benzimidazol-4-yl, benzimidazol-5-yl), benzothiazolyl(e.g., benzothiazol-2-yl, benzothiazol-3-yl, benzothiazol-4-yl, benzothiazol-5-yl, benzothiazol-6-yl, benzothiazol-7-yl), indolyl (e.g., indol-1-yl, indol-2-yl, indol-4-yl, indol-5-yl, indol-6-yl, indol-7-yl), dibenzofuryl, quinolinyl (e.g., quinolin-2-yl, quinolin-3-yl, quinolin-4-yl, quinolin-5-yl, quinolin-6-yl, quinolin-7-yl, quinolin-8-yl), isoquinolinyl (e.g., isoquinolin-1-yl, isoquinolin-3-yl, isoquinolin-4-yl, isoquinolin-5-yl, isoquinolin-6-yl, isoquinolin-7-yl, isoquinolin-8-yl), cinnolinyl (e.g., cinnolin-3-yl, cinnolin-4-yl, cinnolin-5-yl, cinnolin-6-yl, cinnolin-7-yl, cinnolin-8-yl), quinazolinyl (e.g., quinazolin-2-yl, quinazolin-4-yl, quinazolin-5-yl, quinazolin-6-yl, quinazolin-7-yl, quinazolin-8-yl), quinoxalinyl (e.g., quinoxalin-2-yl, quinoxalin-5-yl, quinoxalin-6-yl), phthalazinyl (e.g., phthalazin-1-yl, phthalazin-5-yl, phthalazin-6-yl), purinyl (e.g., purin-2-yl, purin-6-yl, purin-7-yl, purin-8-yl, purin-9-yl), pteridinyl, carbazolyl, phenanthridinyl, acridinyl, phenazinyl, 1,10-phenanthrolinyl, isoindolyl, 1H-indazolyl, indolidinyl (e.g., indolidin-1-yl) or the like.

Moreover, the above "heteroaryl" further includes heteroaryl group containing a quaternary atom such as pyridin-1-yl, quinolin-1-yl, isoquinolin-2-yl or the like as show below. In this case, a counter ion includes halogen ion and the like. Other heteroaryl groups are shown as well.

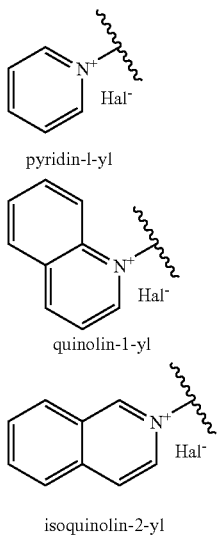

pyridin-1-yl quinolin-1-yl isoquinolin-2-yl

Hal = halogen ion

The term "aryl" means a monocyclic aromatic hydrocarbon group like phenyl or a polycyclic aromatic hydrocarbon group such as naphthyl, phenanthryl and the like. Preferred is phenyl or naphthyl.

The term "lower alkylene" means a C1–C6 straight or branched alkylene group, for example, methylene, ethylene, trimethylene, propylene, tetramethylene, ethylethylene, pentamethylene, hexamethylene or the like. Preferred is a C1–C4 straight alkylene group such as methylene, ethylene, trimethylene or tetramethylene.

The term "lower alkenylene" means a C2–C6 straight or branched alkenylene group which is the above "lower alkylene" having one or more double bond, for example, vinylene, propenylene, butenylene or the like. Preferred is a C2–3 straight alkenylene group such as vinylene or propenylene.

The term "lower alkyl" means a C1–C6 straight or branched alkyl group, for example, methyl, ethyl, n-propyl, isopropyl, n-butyl, isobutyl, sec-buthyl, tert-butyl, n-pentyl, isopentyl, neopentyl, tert-pentyl, n-hexyl, isohexyl or the like. Preferred is a C1–C4 straight or branched alkyl group such as methyl, ethyl, n-propyl, isopropyl, n-butyl, isobutyl, sec-buthyl, tert-butyl or the like.

The term "lower haloalkyl" means the above "lower alkyl" group substituted with 1 to 6 halogen atom, for example, trifluoromethyl, difluoromethyl, 2,2,2-trifluoroethyl, 1,1-difluoroethyl, 3,3,3-trifluoro-n-propyl, trichloromethyl, dichloromethyl, 2,2,2-trichloroethyl, 1,1-dichloroethyl, 3,3,3-trichloro-n-propyl or the like. Preferred is trichloromethyl or 2,2,2-trichloroethyl.

The term "lower alkenyl" means a C2–C6 straight or branched alkenyl group which is the above "lower alkyl" having one or more double bond, for example, vinyl, 1propenyl, 2-propenyl, 1-butenyl, 2-butenyl, 3-butenyl, 1,3-butadienyl or the like. Preferred is a C2–3 straight alkenyl group such as vinyl, 1-propenyl or 2-propenyl.

The term "cycloalkyl" means a C3–C8 cyclic alkyl group, for example, cyclopropyl, cyclobutyl, cyclopentyl, cyclohexyl, cycloheptyl, cyclooctyl or the like. Preferred is a C3–6 cyclic alkyl group such as cyclopropyl, cyclobutyl, cyclopentyl or cyclohexyl.

The term "cycloalkenyl" means a C3–C8 cyclic alkenyl group which is the above "cycloalkyl" having one or more double bond, for example, 1-cyclopropen-1-yl, 2-cyclopropen-1-yl, 1-cyclobuten-1-yl, 2-cyclobuten-1-yl, 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 1-cyclohepten-1-yl, 2-cyclohepten-1-yl, 3-cyclohepten-1-yl, 4-cyclohepten-1-yl or the like. Preferred is a C3–C6 cyclic alkenyl group, for example, 1-cyclopropen-1-yl, 2-cyclopropen-1-yl, 1-cyclobuten-1-yl, 2-cyclobuten-1-yl, 1-cyclopenten-1-yl, 2-cyclopenten-1-yl, 3-cyclopenten-1-yl, 1-cyclohexen-1-yl, 2-cyclohexen-1-yl or 3-cyclohexen-1-yl.

The term "heterocycle" means a non-aromatic group which is the above "cycloalkyl" or "cycloalkenyl" having 1 to 3 oxygen atom, sulfur atom and/or nitrogen atom in the ring, for example, aziridinyl (e.g., aziridin-1-yl, aziridin-2-yl), piperidino, piperidyl (e.g., 2-piperidyl, 3-piperidyl, 4-piperidyl), morpholino, morpholinyl (e.g., 2-morpholinyl, 3-morpholinyl), pyrrolinyl (e.g., 1-pyrrolinyl, 2-pyrrolinyl, 3-pyrrolinyl, 4-pyrrolinyl, 5-pyrrolinyl), pyrrolidinyl (e.g., 1-pyrrolidinyl, 2-pyrrolidinyl, 3-pyrrolidinyl), imidazolinyl (e.g., 1-imidazolinyl, 2-imidazolinyl, 4-imidazolinyl), piperazino, piperazinyl (e.g., 2-piperazinyl), thiolanyl (e.g., thiolan-2-yl, thiolan-3-yl), tetrahydrofuranyl (e.g., tetrahydrofuran-2-yl, tetrahydrofuran-3-yl), dioxanyl (e.g., 1,4-dioxan-2-yl), oxathianyl (e.g., 1,4-oxathian-2-yl, 1,4-oxathian-3-yl), tetrahydropyranyl (e.g., tetrahydropyran-2-yl, tetrahydropyran-3-yl, tetrahydropyran-4-yl) or the like. Preferred is a 5- or 6-membered N-containing heterocycle such as piperidino, piperidyl (e.g., 2-piperidyl, 3-piperidyl, 4-piperidyl), morpholino, morpholinyl (e.g., 2-morpholinyl, 3-morpholinyl), pyrrolinyl (e.g., 1-pyrrolinyl, 2-pyrrolinyl, 3-pyrrolinyl, 4-pyrrolinyl, 5-pyrrolinyl), pyrrolidinyl (e.g., 1-pyrrolidinyl, 2-pyrrolidinyl, 3-pyrrolidinyl), imidazolinyl (e.g., 1-imidazolinyl, 2-imidazolinyl, 4-imidazolinyl), piperazino, piperazinyl (e.g., 2-piperazinyl). Said heterocycle as well as the above "heteroaryl" may have a radical group at carbon atom or nitrogen atom. A nitrogen atom which is a constituent element of the ring may be a quaternary nitrogen.

The term "halogen" means fluoro, chloro, bromo or iodo.

Each term by itself or as part of (an)other substituent(s) has the same meaning unless the term is otherwise defined. Examplified that the term "lower alkyl" has the same meaning as lower alkyl in "lower alkyloxy", "lower alkyloxycarbonyl", "lower alkyloxy(lower)alkyl" and "aryl (lower)alkyl". The term "aryl" has the same meaning as aryl in "aryloxy", "aryloxycarbonyl", "arylsulfonyl" and "aryl (lower)alkyl".

Preferable embodiments of each substituent are described below.

Preferred as "lower alkyloxy" is a C1–C4 straight or branched alkyloxy group, for example, methoxy, ethoxy, n-propoxy, isopropoxy, n-butoxy, isobutoxy, sec-butoxy or tert-butoxy.

Preferred as "lower alkyloxycarbonyl" is a carbonyl group substituted with a C1–C4 straight or branched alkyloxy group, for example, methoxycarbonyl, ethoxycarbonyl, n-propoxycarbonyl, isopropoxycarbonyl, n-butoxycarbonyl, isobutoxycarbonyl, sec-butoxycarbonyl or tert-butoxycarbonyl. More preferred is methoxycarbonyl or ethoxycarbonyl.

Preferred as "lower alkyloxy(lower)alkyl" is a C1–C4 straight or branched alkyl group mono- or di-substituted with a C1–C4 straight or branched alkyloxy group, for example, methoxymethyl, dimethoxymethyl, ethoxymethyl, n-propoxymethyl, isopropoxymethyl, n-butoxymethyl, isobutoxymethyl, sec-butoxymethyl, tert-butoxymethyl, 2-methoxyethyl, 2-ethoxyethyl, 2-(n-propoxy)ethyl or the like. More preferred is methoxymethyl, ethoxymethyl, 2-methoxyethyl, 2-ethoxyethyl.

Preferred as "aryloxy" is phenoxy or naphthoxy (e.g., 1-naphthoxy, 2-naphthoxy).

Preferred as "aryloxycarbonyl" is phenoxycarbonyl or naphthoxycarbonyl (e.g., 1-naphthoxycarbonyl, 2-naphthoxycarbonyl).

Preferred as "arylsulfonyl" is phenylsulfonyl (benzenesulfonyl) or naphthylsulfonyl (e.g., 1-naphthylsulfonyl, 2-naphthylsulfonyl).

Preferred as "aryl(lower)alkyl" is a C1–C4 straight or branched alkyl group mono- or di-substituted with the above "aryl", for example, benzyl, diphenylmethyl, phenethyl(2-phenylethyl), 1-phenylethyl, 3-phenylpropyl, 2-phenylpropyl, 1-phenylpropyl, 1-naphthylmethyl, 2-naphthylmethyl or the like. More preferred is benzyl or phenethyl.

"Protected hydroxy" includes lower alkyloxy (e.g., methoxy, ethoxy, n-propoxy), lower alkenyloxy (e.g., vinyloxy, aryloxy), cycloalkyloxy (e.g., cyclopropyloxy, cyclobutyloxy, cyclopentyloxy), aryl(lower)alkyloxy (e.g., benzyloxy, phenethyloxy), lower alkylcarbonyloxy (e.g., acetyloxy), arylcarbonyloxy (e.g., benzoyloxy), lower alkyloxycarbonyloxy (e.g., tert-botoxycarbonyloxy).

"Ester residue" or "amide residue" includes lower alkyl (e.g., methyl, ethyl, n-propyl, isopropyl, n-butyl, isobutyl, sec-butyl, tert-butyl, n-pentyl, isopentyl, neopentyl, tert-pentyl, n-hexyl, isohexyl), lower alkenyl (e.g., vinyl, 1-propenyl, 2-propenyl, 1-butenyl, 2-butenyl, 3-butenyl, 1,3-butadienyl), cycloalkenyl (e.g., cyclopropyl, cyclobutyl, cyclopentyl, cyclohexyl), cycloalkenyl (1-cyclopropen-1-yl, 2-cyclopropen-1-yl, 1-cyclobuten-1-yl, 2-cyclobuten-1-yl, 1-cyclopenten-1-yl, 2-cyclopenten-1-yl, 3-cyclopenten-1-yl, 1-cyclohexen-1-yl, 2-cyclohexen-1-yl, 3-cyclohexen-1-yl), cycloalkyl(lower)alkyl (e.g., cyclopropylmethyl, 2-cyclopropylethyl, 1-2-cyclopropylethyl, cyclobutylmethyl, 2-cyclobutylethyl, 1-2-cyclobutylethyl, cyclopentylmethyl, cyclohexylmethyl), aryl (e.g., phenyl, naphthyl), aryl(lower)alkyl (e.g., benzyl, diphenylmethyl), heteroaryl (e.g., pyridin-2-yl, pyridin-3-yl, pyridin-4-yl, thiazol-2-yl, 1H-1,2,4-triazol-3-yl, 1,2,4-triazol-4-yl, 1,3,4-thiazol-2-yl) or the like.

When the above "aryl", "aryloxy", "aryloxycarbonyl", "aryl(lower)alkyl", "arylsulfonyl", "heteroaryl", "cycloalkyl", "cycloalkenyl", "heterocycle", "lower alkyl", "lower alkyloxy" or "lower alkyloxycarbonyl" has a substituent(s), one to four, same or different substituent(s) may be at any substitutable position(s).

Examples of the substituent include hydroxy, carboxy, halogen (F, Cl, Br, I), lower haloalkyl (e.g., $CF_3$, $CH_2CF_3$), lower alkyl (e.g., methyl, ethyl, isopropyl, tert-butyl), lower alkenyl (e.g., vinyl, allyl), lower alkynyl (e.g., ethynyl), cycloalkyl (e.g., cyclopropyl, cyclobutyl, cyclohexyl), cycloalkenyl (e.g., 1-cyclohexenyl), lower alkyloxy (e.g., methoxy, ethoxy, propoxy, butoxy), lower alkyloxycarbonyl (e.g., methoxycarbonyl, ethoxycarbonyl, tert-butoxylcarbonyl), nitro, nitroso, amino, amino substituted with lower alkyl (e.g., methylamino, ethylamino, dimethylamino), azido, amidino, guanidino, optionally substituted aryl (e.g., phenyl, p-tolyl), heteroaryl (e.g., pyridyl, furyl), heteroaryl(lower)alkyl (e.g., picolyl), optionally substituted aryl(lower)alkyl (e.g., benzyl, 4-methylbenzyl, 4-fluorobenzyl), aryl(lower)alkyloxy (e.g., benzyloxy), aryl(lower)alkylthio (e.g., benzylthio), cyano, isocyano, hydroxyamino, mercapto, lower alkylthio (e.g., methylthio), carbamoyl, carbamoyl substituted with lower alkyl (e.g., N-methylcarbamoyl), lower alkylsulfonyl (e.g., mesyl, ethanesulfonyl), optionally substituted arylsulfonyl (e.g., benzenesulfonyl, 2-toluenesulfonyl, 4-toluenesulfonyl), sulfamoyl, sulfoamino, formyl, lower alkylcarbonyl (e.g., acetyl, propionyl, benzoyl, p-toluoyl, cyclohexylcarbonyl), lower alkylcarbonyloxy (e.g., acetyloxy, benzoyloxy), hydrazino, arylamino (e.g., anilino, toluidino, xylidino), lower alkylcarbonylamino (e.g., acetamido), arylcarbonylamino (e.g., benzamido), morpholino and the like.

When the constitutive atoms of ring of "optionally substituted heteroaryl" include (a) nitrogen atom(s), the nitrogen atom may be a quaternary nitrogen atom. In such a case, the substituent on the nitrogen atom includes formyl, lower alkylcarbonyl, arylcarbonyl, lower alkyl, lower haloalkyl, aryl(lower)alkyl or the like. A counter ion includes halogen ion and the like. Examples are shown below. Other heteroaryl groups are shown as well.

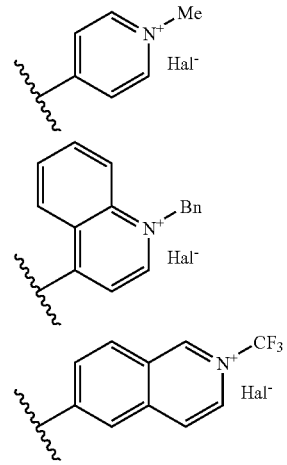

Hal = halogen ion or the like

The substituent of "optionally substituted heteroaryl" in $A^1$ of the formula (I) includes not only the above-shown substituent, but also the group of the formula: $-Z^1-Z^2-Z^3-R^1$ wherein $Z^1$, $Z^2$, $Z^3$ and $R^1$ are as defined above and/or the group of the formula: $-Z^4-R^2$ wherein $Z^4$ and $R^2$ are as defined above.

The substituent of "optionally substituted heteroaryl" in $A^1$ of the formula (II) includes not only the group of the formula: $-Z^1-Z^2-Z^3-R^1$ wherein $Z^1$, $Z^2$, $Z^3$ and $R^1$ are as defined above and/or the group of the formula: $-Z^4-R^2$ wherein $Z^4$ and $R^2$ are as defined above, but also the above-shown substituents.

The substituent of "optionally substituted amino" includes lower alkyl (e.g., methyl, ethyl or the like), lower alkyloxy(lower)alkyl (e.g., ethoxymethyl, ethoxyethyl or the like), formyl, lower alkylcarbonyl (e.g., acetyl or the like), arylcarbonyl (e.g., benzoyl or the like), aryl(lower)alkyl (e.g., benzyl or the like) or the like.

The group of the formula: $-Z^1-Z^2-Z^3-R^1$ includes, for example, —$R^1$, —$CH_2$—$R^1$, —CH=CH—$R^1$, —CH(OH)—$R^1$, —S—$R^1$, —SO—$R^1$, —$SO_2$—$R^1$, —$SO_2NH$—$R^1$, —$NHSO_2$—$R^1$, —O—$R^1$, —NH—$R^1$, —NHCO—$R^1$, —CONH—$R^1$, —C(=O)—O—$R^1$, —O—C(=O)—$R^1$, —CO—$R^1$, —$C_2H_4$—$R^1$, —CH=CH—$CH_2$—$R^1$, —CH(OH)—$CH_2$—$R^1$, —S—$CH_2$—$R^1$, —SO—$CH_2$—$R^1$, —$SO_2$—$CH_2$—$R^1$, —$SO_2NH$—$CH_2$—$R^1$, —$NHSO_2$—$CH_2$—$R^1$, —O—$CH_2$—$R^1$, —NH—$CH_2$—$R^1$, —NHCO—$CH_2$—$R^1$, —CONH—$CH_2$—$R^1$, —C(=O)—O—$CH_2$—$R^1$, —O—C(=O)—$CH_2$—$R^1$, —CO—$CH_2$—$R^1$, —CH=CH—CH=CH—R$^1$, —CH=CH—CH(OH)—R$^1$, —CH=CH—S—R$^1$, —CH=CH—SO—R$^1$, —CH=CH—SO$_2$—R$^1$, —CH=CH—SO$_2$NH—R$^1$, —CH=CH—NHSO$_2$—R$^1$, —CH=CH—O—R$^1$, —CH=CH—NH—R$^1$, —CH=CH—NHCO—R$^1$, —CH=CH—CONH—R$^1$, —CH=CH—C(=O)—O—R$^1$, —CH=CH—O—C(=O)—R$^1$, —CH=CH—CO—R$^1$, —CH$_2$—CH=CH—R$^1$, —CH$_2$—CH(OH)—R$^1$, —CH$_2$—S—R$^1$, —CH$_2$—SO—R$^1$, —CH$_2$—SO$_2$—R$^1$, —CH$_2$—SO$_2$NH—R$^1$, —CH$_2$—NHSO$_2$—R$^1$, —CH$_2$—O—R$^1$, —CH$_2$—NH—R$^1$, —CH$_2$—NHCO—R$^1$, —CH$_2$—CONH—R$^1$, —CH$_2$—C(=O)—O—R$^1$, —CH$_2$—O—C(=O)—R$^1$, —CH$_2$—CO—R$^1$, —CH(OH)—CH=CH—R$^1$, —S—CH=CH—R$^1$, —SO—CH=CH—R$^1$, —SO$_2$—CH=CH—R$^1$, —SO$_2$NH—CH=CH—R$^1$, —NHSO$_2$—CH=CH—R$^1$, —O—CH=CH—R$^1$, —NH—CH=CH—R$^1$, —NHCO—CH=CH—R$^1$, —CONH—CH=CH—R$^1$, —C(=O)—O—CH=CH—R$^1$, —O—C(=O)—CH=CH—R$^1$, —CO—CH=CH—R$^1$, —C$_3$H$_6$—R$^1$, —CH$_2$—CH=CH—CH$_2$—R$^1$, —CH$_2$—CH(OH)—CH$_2$—R$^1$, —CH$_2$—S—CH$_2$—R$^1$, —CH$_2$—SO—CH$_2$—R$^1$, —CH$_2$—SO$_2$—CH$_2$—R$^1$, —CH$_2$—SO$_2$NH—CH$_2$—R$^1$, —CH$_2$—NHSO$_2$—CH$_2$—R$^1$, —CH$_2$—O—CH$_2$—R$^1$, —CH$_2$—NH—CH$_2$—R$^1$, —CH$_2$—NHCO—CH$_2$—R$^1$, —CH$_2$—CONH—CH$_2$—R$^1$, —CH$_2$—C(=O)—O—CH$_2$—R$^1$, —CH$_2$—O—C(=O)—CH$_2$—R$^1$, —CH$_2$—CO—CH$_2$—R$^1$, —C$_2$H$_4$—CH=CH—R$^1$, —CH$_2$—CH=CH—CH=CH—R$^1$, —CH$_2$—CH(OH)—CH=CH—R$^1$, —CH$_2$—S—CH=CH—R$^1$, —CH$_2$—SO—CH=CH—R$^1$, —CH$_2$—SO$_2$—CH=CH—R$^1$, —CH$_2$—SO$_2$NH—CH=CH—R$^1$, —CH$_2$—NHSO$_2$—CH=CH—R$^1$, —CH$_2$—O—CH=CH—R$^1$, —CH$_2$—NH—CH=CH—R$^1$, —CH$_2$—NHCO—CH=CH—R$^1$, —CH$_2$—CONH—CH=CH—R$^1$, —CH$_2$—C(=O)—O—CH=CH—R$^1$, —CH$_2$—O—C(=O)—CH=CH—R$^1$, —CH$_2$—CO—CH=CH—R$^1$, —CH=CH—C$_2$H$_4$—R$^1$, —CH=CH—CH=CH—CH$_2$—R$^1$, —CH=CH—CH(OH)—CH$_2$—R$^1$, —CH=CH—S—CH$_2$—R$^1$, —CH=CH—SO—CH$_2$—R$^1$, —CH=CH—SO$_2$—CH$_2$—R$^1$, —CH=CH—SO$_2$NH—CH$_2$—R$^1$, —CH=CH—NHSO$_2$—CH$_2$—R$^1$, —CH=CH—O—CH$_2$—R$^1$, —CH=CH—NH—CH$_2$—R$^1$, —CH=CH—NHCO—CH$_2$—R$^1$, —CH=CH—CONH—CH$_2$—R$^1$, —CH=CH—C(=O)—O—CH$_2$—R$^1$, —CH=CH—O—C(=O)—CH$_2$—R$^1$ or —CH=CH—CO—CH$_2$—R$^1$ wherein R$^1$ is optionally substituted aryl, optionally substituted heteroaryl, optionally substituted cycloalkyl, optionally substituted cycloalkenyl or optionally substituted heterocycle, or the like.

The substituent of the formula: -Z$^4$-R$^2$ includes, for example, —R$^2$, —CH$_2$—R$^2$, —CH=CH—R$^2$, —CH(OH)—R$^2$, —S—R$^2$, —SO—R$^2$, —SO$_2$—R$^2$, —SO$_2$NR$^{21}$—R$^2$, —NR$^{21}$SO$_2$—R$^2$, —O—R$^2$, —NR$^{21}$—R$^2$, —NR$^{21}$CO—R$^2$, —CONR$^{21}$—R$^2$, —C(=O)—O—R$^2$, —O—C(=O)—R$^2$, or —CO—R$^2$ wherein R$^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, cycloalkyl, hydroxy, mercapto, optionally substituted amino, nitro or halogen, or the like.

Preferable examples of the ring (A$^1$) and the substituent (X, Y, the group of the formula: -Z$^1$-Z$^2$-Z$^3$-R$^1$ or the group of the formula: -Z$^4$-R$^2$) of the compound of the present invention are shown below.

A preferable example of heteroaryl in A$^1$ is furyl (especially, furan-2-yl, furan-3-yl), thienyl (especially, thiophen-2-yl, thiophen-3-yl), pyrrolyl (especially, pyrrol-2-yl, pyrrol-3-yl), imidazolyl (especially, imidazol-4-yl), pyrazolyl (especially, pyrazol-3-yl), benzofuryl (especially, benzo[b]furan-3-yl), benzothienyl(especially, benzo[b]thiophen-3-yl), benzimidazolyl(especially, benzimidazol-2-yl), indolidinyl (especially, indolidin-1-yl), quinolinyl (especially, quinolin-3-yl), isoxazolyl (especially, isoxazol-3-yl), pyridyl (especially, pyridin-2-yl), thiazolyl (especially, thiazol-2-yl) or oxazolyl (especially, oxazol-5-yl). A more preferable example is monocyclic heteroaryl such as furyl, thienyl, pyrrolyl, imidazolyl, pyrazolyl, isoxazolyl, pyridyl, thiazolyl, oxazolyl or the like. Most preferred is furyl, pyrrolyl or oxazolyl.

A preferable example of X is hydroxy.

A preferable example of Y is —COOH or optionally substituted heteroaryl. A preferable example of heteroaryl in Y is 5- or 6-membered heteroaryl containing at least one nitrogen atom in the ring, for example, pyridyl (especially, pyridin-2-yl, pyridin-3-yl, pyridin-4-yl), pyrrolyl (especially, pyrrol-2-yl), imidazolyl (especially, imidazol-2-yl), thiazolyl (especially, thiazol-4-yl, thiazol-2-yl), oxazolyl (especially, oxazol-2-yl), isoxazolyl (especially, isoxazol-3-yl, isoxazol-5-yl), pyrazinyl (especially, pyrazin-2-yl), oxadiazolyl (especially, 1,3,4-oxadiazol-2-yl), thiadiazolyl (especially, 1,3,4-thiadiazol-2-yl), triazolyl (especially, 1H-1,2,4-triazol-3-yl), tetrazolyl (especially, 2H-tetrazol-5-yl), pyrimidinyl (especially, pyrimidin-2-yl). More preferred is pyridyl, tetrazolyl, triazolyl, imidazolyl, pyrimidinyl or thiazolyl. Most preferred is tetrazolyl (especially, 2H-tetrazol-5-yl), triazolyl (especially, 1H-1,2,4-triazol-3-yl), pyrimidinyl (especially, pyrimidin-2-yl), pyridyl (especially, pyridin-2-yl).

A preferable example of optionally substituted heteroaryl in Y is unsubstituted heteroaryl or mono-substituted heteroaryl. The substituent of that includes the above shown substituents, especially, lower alkyl (e.g., methyl, ethyl, n-propyl, isopropyl or the like), lower haloalkyl (e.g., trifluoromethyl, 2,2,2-trifluoroethyl or the like), lower alkyloxy (e.g., methoxy or the like), halogen (e.g., F, Cl or the like), lower alkyloxy(lower)alkyl (e.g., methoxymethyl or the like), carboxy, lower alkyloxycarbonyl (e.g., methoxycarbonyl, ethoxycarbonyl or the like), optionally substituted arylsulfonyl (e.g., benzenesulfonyl or the like), optionally substituted aryl(lower)alkyl (e.g., benzyl, p-fluorobenzyl) or the like. A more preferable example of Y is tetrazolyl optionally substituted with lower alkyl or lower alkyloxy(lower)alkyl; triazolyl optionally substituted with halogen, lower alkyl, lower haloalkyl or lower alkyloxy (lower)alkyl; pyridyl optionally substituted with lower alkyl, carboxy or lower alkyloxycarbonyl; pyrrolyl optionally substituted with lower alkyl or optionally substituted arylsulfonyl; isoquinolinyl optionally substituted with lower alkyl; pyrazinyl optionally substituted with lower alkyl; pyrimidinyl optionally substituted with lower alkyl; oxadiazolyl optionally substituted with optionally substituted aryl or lower alkyl; isoxazolyl optionally substituted with lower alkyl; thiazolyl optionally substituted with lower alkyl; thienyl optionally substituted with lower alkyl; furyl optionally substituted with lower alkyl; thiadiazolyl optionally substituted with lower alkyl; oxazolyl optionally substituted with lower alkyl; or imidazolyl optionally substituted with lower alkyl. Especially, preferred is 5-methyl-1H-1,2,4-triazolyl-3-yl, 5-ethyl-1H-1,2,4-triazolyl-3-yl, 5-isopropyl-1H-1,2,4-triazolyl-3-yl, 5-methoxy-1H-1,2,4-triazolyl-3-yl, 5-chloro-1H-1,2,4-triazolyl-3-yl, 2-methylthiazol-4-yl, 5-methoxymethyl-1H-1,2,4-triazolyl-3-yl, 1-methylimidazol-2-yl, 5-methylisoxazol-3-yl, 3-methylisoxazol-5-yl, 5-methyloxadiazol-2-yl, 5-(p-fluorobenzyl)oxadiazol-2-yl, 6-carboxypyridin-2-yl, 6-ethoxycarbonylpyridin-3-yl, 6-methylpyridin-2-yl, 5-carboxypyridin-2-yl, 5-methoxycarbonylpyridin-2-yl, 4-carboxypyridin-2-yl, 4-methoxycarbonylpyridin-2-yl, 1-benzenesulfonylpyrrol-2-yl, 1-methylpyrrol-2-yl or the like. Most preferred as Y is tetrazolyl optionally substituted with lower alkyl or lower alkyloxy(lower)alkyl; triazolyl optionally substituted with halogen, lower alkyl, lower haloalkyl or lower alkyloxy(lower)alkyl; pyridyl optionally substituted with lower alkyl, carboxy or lower alkyloxycarbonyl; or pyrimidinyl optionally substituted with lower alkyl.

Preferred as the group of the formula: $-Z^1-Z^2-Z^3-R^1$ wherein $Z^1$, $Z^2$, $Z^3$ and $R^1$ are as defined above is the group 1) wherein $Z^1$ and $Z^3$ each is a bond, 2) wherein $Z^2$ is a bond, —CO—, —O—, —S—, —SO$_2$— or lower alkylene (especially, —CH$_2$—, —(CH$_2$)$_2$—) in addition to 1), 3) wherein $R^1$ is optionally substituted aryl or optionally substituted heteroaryl in addition to 1) and 2). Especially preferred is the group wherein $Z^1$ and $Z^3$ each is a bond; $Z^2$ is —SO$_2$—, —CH$_2$— or —C$_2$H$_4$—; $R^1$ is optionally substituted aryl (especially, phenyl). The substituent of optionally substituted aryl in $R^1$ includes the above shown substituents, especially, lower alkyl, lower haloalkyl (especially, trifluoromethyl), halogen (especially F, Cl, Br), lower alkyloxy (especially, methoxy) or the like. Preferred is mono- or di-substituted group.

Preferred examples of the group of the formula: $-Z^1-Z^2-Z^3-R^1$ include phenyl, 2-fluorophenyl, 3-fluorophenyl, 4-fluorophenyl, 2-chlorophenyl, 3-chlorophenyl, 4-chlorophenyl, 2,4-difluorophenyl, 2,6-difluorophenyl, 2,5-difluorophenyl, 3,4-difluorophenyl, 4-methylphenyl, 3-trifluoromethylphenyl, 4-trifluoromethylphenyl, 4-hydroxyphenyl, 4-methoxyphenyl, 4-bromophenyl, 4-biphenyl, benzyl, 2-fluorobenzyl, 3-fluorobenzyl, 4-fluorobenzyl, 2-chlorobenzyl, 3-chlorobenzyl, 4-chlorobenzyl, 2,4-difluorobenzyl, 2,6-difluorobenzyl, 2,5-difluorobenzyl, 3,4-difluorobenzyl, 3,6-difluorobenzyl, 4-methylbenzyl, 3-trifluoromethylbenzyl, 4-trifluoromethylbenzyl, 4-hydroxybenzyl, 4-methoxybenzyl, 4-bromobenzyl, 4-phenylbenzyl, 2-phenylethyl, 2-(2-fluorophenyl)ethyl, 2-(3-fluorophenyl)ethyl, 2-(4-fluorophenyl)ethyl, 2-(2-chlorophenyl)ethyl, 2-(3-chlorophenyl)ethyl, 2-(4-chlorophenyl)ethyl, 2-(2,4-difluorophenyl)ethyl, 2-(2,6-difluorophenyl)ethyl, 2-(2,5-difluorophenyl)ethyl, 2-(3,4-difluorophenyl)ethyl, 2-(4-methylphenyl)ethyl, 2-(3-trifluoromethylphenyl)ethyl, 2-(4-trifluoromethylphenyl)ethyl, 2-(4-hydroxyphenyl)ethyl, 2-(4-methoxyphenyl)ethyl, 2-(4-bromophenyl)ethyl, 2-(4-biphenyl)ethyl, benzenesulfonyl, 2-fluorobenzenesulfonyl, 3-fluorobenzenesulfonyl, 4-fluorobenzenesulfonyl, 2-chlorobenzenesulfonyl, 3-chlorobenzenesulfonyl, 4-chlorobenzenesulfonyl, 2,4-difluorobenzenesulfonyl, 2,6-difluorobenzenesulfonyl, 2,5-difluorobenzenesulfonyl, 3,4-difluorobenzenesulfonyl, 4-methylbenzenesulfonyl, 3-trifluoromethylbenzenesulfonyl, 4-trifluoromethylbenzenesulfonyl, 4-hydroxybenzenesulfonyl, 4-methoxybenzenesulfonyl, 4-bromobenzenesulfonyl, 4-phenylbenzenesulfonyl, phenylthio, 2-fluorophenylthio, 3-fluorophenylthio, 4-fluorophenylthio, 2-chlorophenylthio, 3-chlorophenylthio, 4-chlorophenylthio, 2,4-difluorophenylthio, 2,6-difluorophenylthio, 2,5-difluorophenylthio, 3,4-difluorophenylthio, 4-methylphenylthio, 3-trifluoromethylphenylthio, 4-trifluoromethylphenylthio, 4-hydroxyphenylthio, 4-methoxyphenylthio, 4-bromophenylthio, 4-biphenylthio, phenoxy, 2-fluorophenoxy, 3-fluorophenoxy, 4-fluorophenoxy, 2-chlorophenoxy, 3-chlorophenoxy, 4-chlorophenoxy, 2,4-difluorophenoxy, 2,6-difluorophenoxy, 2,5-difluorophenoxy, 3,4-difluorophenoxy, 4-methylphenoxy, 3-trifluoromethylphenoxy, 4-trifluoromethylphenoxy, 4-hydroxyphenoxy, 4-methoxyphenoxy, 4-bromophenoxy, 4-phenylphenoxy, benzoyl, 2-fluorobenzoyl, 3-fluorobenzoyl, 4-fluorobenzoyl, 2-chlorobenzoyl, 3-chlorobenzoyl, 4-chlorobenzoyl, 2,4-difluorobenzoyl, 2,6-difluorobenzoyl, 2,5-difluorobenzoyl, 3,4-difluorobenzoyl, 4-methylbenzoyl, 3-trifluoromethylbenzoyl, 4-trifluoromethylbenzoyl, 4-hydroxybenzoyl, 4-methoxybenzoyl, 4-bromobenzoyl, 4-phenylbenzoyl, 2-thienyl, 3-thienyl, furfuryl, 3-furylmethyl, (2-chlorothiophen-3-yl)methyl, 2-picolyl, 3-picolyl, 4-picolyl, (2-fluoropyridin-3-yl)methyl, (2-fluoropyridin-5-yl)methyl or (5-fluoropyridin-2-yl)methyl. More preferred example is benzyl, 2-fluorobenzyl, 3-fluorobenzyl, 4-fluorobenzyl, 2-chlorobenzyl, 3-chlorobenzyl, 4-chlorobenzyl, 2,4-difluorobenzyl, 2,6-difluorobenzyl, 2,5-difluorobenzyl, 3,4-difluorobenzyl, 4-methylbenzyl, 3-trifluoromethylbenzyl, 4-trifluoromethylbenzyl, 4-hydroxybenzyl, 4-methoxybenzyl, 4-bromobenzyl, 4-phenylbenzyl, 2-phenylethyl, 2-(2-fluorophenyl)ethyl, 2-(3-fluorophenyl)ethyl, 2-(4-fluorophenyl)ethyl, 2-(2-chlorophenyl)ethyl, 2-(3-chlorophenyl)ethyl, 2-(4-chlorophenyl)ethyl, 2-(2,4-difluorophenyl)ethyl, 2-(2,6-difluorophenyl)ethyl, 2-(2,5-difluorophenyl)ethyl, 2-(3,4-difluorophenyl)ethyl, 2-(4-methylphenyl)ethyl, 2-(3-trifluoromethylphenyl)ethyl, 2-(4-trifluoromethylphenyl)ethyl, 2-(4-hydroxyphenyl)ethyl, 2-(4-methoxyphenyl)ethyl, 2-(4-bromophenyl)ethyl, 2-(4-biphenylyl)ethyl, benzenesulfonyl, 2-fluorobenzenesulfonyl, 3-fluorobenzenesulfonyl, 4-fluorobenzenesulfonyl, 2-chlorobenzenesulfonyl, 3-chlorobenzenesulfonyl, 4-chlorobenzenesulfonyl, 2,4-difluorobenzenesulfonyl, 2,6-difluorobenzenesulfonyl, 2,5-difluorobenzenesulfonyl, 3,4-difluorobenzenesulfonyl, 4-methylbenzenesulfonyl, 3-trifluoromethylbenzenesulfonyl, 4-trifluoromethylbenzenesulfonyl, 4-hydroxybenzenesulfonyl, 4-methoxybenzenesulfonyl, 4-bromobenzenesulfonyl, 4-phenylbenzenesulfonyl or the like, especially, benzyl, 4-fluorobenzyl, benzenesulfonyl, 4-fluorobenzenesulfonyl or the like.

Preferred as the group of the formula: $-Z^4-R^2$ wherein $Z^4$ and $R^2$ each is as defined above is lower alkyl (e.g., methyl, ethyl, n-propyl, n-butyl, n-octyl or the like), lower alkyloxycarbonyl (e.g., methoxycarbonyl, ethoxycarbonyl or the like), carboxy, lower alkyloxycarbonyl lower alkyl (e.g., 2-methoxycarbonylethyl, 2-ethoxycarbonylethyl or the like), carboxy lower alkyl (e.g., 2-carboxyethyl or the like), lower alkyloxycarbonyl lower alkenyl (e.g., 2-methoxycarbonylvinyl, 2-ethoxycarbonylvinyl), carboxy lower alkenyl (e.g., 2-carboxyvinyl), formyl, lower alkylcarbonyl (e.g., acetyl), arylcarbonyl (e.g., benzoyl), aryl (lower)alkyl (e.g., benzyl, 4-fluorobenzyl, phenethyl or the like), lower alkyloxy(lower)alkyl (e.g., methoxymethyl or the like), aryloxy lower alkyl (e.g., phenoxymethyl) or the like.

A more preferable embodiment of the compound of the formula (II) is a compound wherein $A^1$ is furyl, thienyl, pyrrolyl, imidazolyl, pyrazolyl, isoxazolyl, pyridyl, thiazolyl or oxazolyl; X is hydroxy; Y is —COOH, optionally substituted tetrazolyl, optionally substituted triazolyl or optionally substituted pyridyl; $Z^1$ and $Z^3$ each is a bond; $Z^2$ is a bond, lower alkylene, lower alkenylene, —CH(OH)—, —S—, —SO—, —SO$_2$—, —SO$_2$NH—, —NHSO$_2$—, —O—, —NH—, —NHCO—, —CONH—, —C(=O)—O—, —O—C(=O)— or —CO—; R$^1$ is optionally substituted aryl or optionally substituted heteroaryl; Z$^4$ is a bond; R$^2$ is lower alkyl or halogen; and p is 0 or 1.

Consequently, the following embodiments, B-1 to B-2592, are preferred. When A$^1$ is 5-menbered heteroaryl, q, z and w each is a different integer of 1 to 5. When A$^1$ is 6-menbered heteroaryl, q, z and w each is a different integer of 1 to 6. "n" is an integer of 1 to 3. The term "[substituted]" means "optionally substituted" and represents "unsubstituted or substituted". The substituents include the above-mentioned substituents.

(B-1) 1-[(q-(([substituted]heteroaryl)alkenyl)-z-halogeno)furan-w-yl]-3-hydroxy-3-([substituted]-1H-1,2,4-triazol-3-yl)-propenone (B-2) 1-[(z-alkyl-q-(([substituted]heteroaryl)thio))thiophen-w-yl]-3-hydroxy-3-([substituted]-1H-1,2,4-triazol-3-yl)-propenone (B-3) 4-[q-(([substituted]aryl)alkenyl)-z-halogeno)thiazol-w-yl]-2-hydroxy-4-oxo-2-butenoic acid (B-4) 1-[(z-halogeno-q-(([substituted]heteroaryl)sulfonyl))pyridin-w-yl]-3-hydroxy-3-([substituted]-1H-1,2,4-triazol-3-yl)-propenone (B-5) 2-hydroxy-4-(nH-q-(1-hydroxy-([substituted]aryl)methyl)imidazol-w-yl)-4-oxo-2-butenoic acid (B-6) 1-[(z-alkyl-q-(([substituted]aryl)aminocarbonyl))furan-w-yl]-3-hydroxy-3-([substituted]-2H-tetrazol-5-yl)-propenone (B-7) 1-[nH-(z-halogeno-q-(([substituted]heteroaryl)sulfinyl))imidazol-w-yl]-3-hydroxy-3-([substituted]-1H-1,2,4-triazol-3-yl)-propenone (B-8) 3-hydroxy-1-(q-(([substituted]heteroaryl)oxycarbonyl)thiophen-w-yl)-3-([substituted]-1H-1,2,4-triazol-3-yl)-propenone (B-9) 3-hydroxy-1-(q-(1-hydroxy-([substituted]aryl)methyl)pyrrol-w-yl)-3-([substituted]-2H-tetrazol-5-yl)-propenone (B-10) 4-[z-alkyl-q-(1-hydroxy-([substituted]aryl)methyl))oxazol-w-yl]-2-hydroxy-4-oxo-2-butenoic acid (B-11) 1-(q-(([substituted]heteroaryl)amino)furan-w-yl)-3-hydroxy-3-([substituted]-2H-tetrazol-5-yl)-propenone (B-12) 4-[z-alkyl-q-(([substituted]aryl)oxy))thiazol-w-yl]-2-hydroxy-4-oxo-2-butenoic acid (B-13) 1-[(z-halogeno-q-(([substituted]aryl)sulfonyl))thiophen-w-yl]-3-hydroxy-3-([substituted]-2H-tetrazol-5-yl)-propenone (B-14) 3-hydroxy-1-(q-(1-hydroxy-([substituted]heteroaryl)methyl)furan-w-yl)-3-([substituted]-2H-tetrazol-5-yl)-propenone (B-15) 1-[(z-halogeno-q-(([substituted]heteroaryl)sulfonylamino))oxazol-w-yl]-3-hydroxy-3-([substituted]-1H-1,2,4-triazol-3-yl)-propenone (B-16) 1-(q-(([substituted]aryl)carboxy)pyrrol-w-yl)-3-hydroxy-3-([substituted]-2H-tetrazol-5-yl)-propenone (B-17) 1-(nH-q-(([substituted]aryl)carbonylamino)imidazol-w-yl)-3-hydroxy-3-([substituted]-1H-1,2,4-triazol-3-yl)-propenone (B-18) 1-(nH-q-(([substituted]heteroaryl)carbonylamino)imidazol-w-yl)-3-hydroxy-3-([substituted]-2H-tetrazol-5-yl)-propenone (B-19) 1-[(q-(([substituted]aryl)alkenyl)-z-halogeno)isoxazol-w-yl]-3-hydroxy-3-([substituted]-1H-1,2,4-triazol-3-yl)-propenone (B-20) 1-(q-(([substituted]aryl)alkyl)pyrrol-w-yl)-3-hydroxy-3-([substituted]-1H-1,2,4-triazol-3-yl)-propenone (B-21) 1-[(z-halogeno-q-(([substituted]aryl)sulfonylamino))oxazol-w-yl]-3-hydroxy-3-([substituted]-2H-tetrazol-5-yl)-propenone (B-22) 1-[(z-halogeno-q-(([substituted]heteroaryl)thio))thiazol-w-yl]-3-hydroxy-3-([substituted]-2H-tetrazol-5-yl)-propenone (B-23) 1-[(z-halogeno-q-(1-hydroxy-([substituted]heteroaryl)methyl))furan-w-yl]-3-hydroxy-3-([substituted]-1H-1,2,4-triazol-3-yl)-propenone (B-24) 4-(nH-q-(([substituted]heteroaryl)carboxy)imidazol-w-yl)-2-hydroxy-4-oxo-2-butenoic acid (B-25) 1-[nH-(q-(([substituted]aryl)alkyl)-z-halogeno)imidazol-w-yl]-3-hydroxy-3-([substituted]-1H-1,2,4-triazol-3-yl)-propenone (B-26) 4-[(q-(([substituted]aryl)aminocarbonyl)-z-halogeno)oxazol-w-yl]-2-hydroxy-4-oxo-2-butenoic acid (B-27) 1-[(q-([substituted]aryl)-z-halogeno)thiazol-w-yl]-3-hydroxy-3-([substituted]-2H-tetrazol-5-yl)-propenone (B-28) 1-(q-(([substituted]heteroaryl)amino)thiophen-w-yl)-3-hydroxy-3-([substituted]-2H-tetrazol-5-yl)-propenone (B-29) 2-hydroxy-4-oxo-4-(q-(([substituted]heteroaryl)sulfonyl)pyridin-w-yl)-2-butenoic acid (B-30) 1-[(q-(([substituted]heteroaryl)carbonylamino)-z-halogeno)oxazol-w-yl]-3-hydroxy-3-([substituted]-2H-tetrazol-5-yl)-propenone (B-31) 4-[(q-(([substituted]heteroaryl)carbonylamino)-z-halogeno)thiophen-w-yl]-2-hydroxy-4-oxo-2-butenoic acid (B-32) 1-(q-(([substituted]aryl)carbonyl)pyrrol-w-yl)-3-hydroxy-3-([substituted]-1H-1,2,4-triazol-3-yl)-propenone (B-33) 1-[(q-(([substituted]heteroaryl)aminocarbonyl)-z-halogeno)pyridin-w-yl]-3-hydroxy-3-([substituted]-1H-1,2,4-triazol-3-yl)-propenone (B-34) 3-hydroxy-1-(q-(1-hydroxy-([substituted]aryl)methyl)thiophen-w-yl)-3-([substituted]-2H-tetrazol-5-yl)-propenone (B-35) 1-(q-([substituted]aryl)furan-w-yl)-3-hydroxy-3-([substituted]-2H-tetrazol-5-yl)-propenone (B-36) 3-hydroxy-1-(q-(([substituted]heteroaryl)sulfonyl)thiophen-w-yl)-3-([substituted]-1H-1,2,4-triazol-3-yl)-propenone (B-37) 1-[nH-(z-halogeno-q-(([substituted]aryl)thio))imidazol-w-yl]-3-hydroxy-3-([substituted]-2H-tetrazol-5-yl)-propenone (B-38) 1-[(q-(([substituted]aryl)aminocarbonyl)-z-halogeno)furan-w-yl]-3-hydroxy-3-([substituted]-1H-1,2,4-triazol-3-yl)-propenone (B-39) 1-[nH-(z-alkyl-q-(([substituted]heteroaryl)thio))pyrazol-w-yl]-3-hydroxy-3-([substituted]-2H-tetrazol-5-yl)-propenone (B-40) 4-[nH-(q-(([substituted]aryl)alkenyl)-z-alkyl)pyrazol-w-yl]-2-hydroxy-4-oxo-2-butenoic acid (B-41) 1-[nH-(q-(([substituted]aryl)alkenyl)-z-alkyl)pyrazol-w-yl]-3-hydroxy-3-([substituted]-1H-1,2,4-triazol-3-yl)-propenone (B-42) 4-[(z-alkyl-q-(([substituted]aryl)alkyl))pyridin-w-yl]-2-hydroxy-4-oxo-2-butenoic acid (B-43) 1-[(z-halogeno-q-(([substituted]aryl)thio))isoxazol-w-yl]-3-hydroxy-3-([substituted]-2H-tetrazol-5-yl)-propenone (B-44) 4-[nH-(z-alkyl-q-([substituted]aryl))pyrazol-w-yl]-2-hydroxy-4-oxo-2-butenoic acid (B-45) 1-[(z-alkyl-q-(([substituted]heteroaryl)aminosulfonyl))furan-w-yl]-3-hydroxy-3-([substituted]-1H-1,2,4-triazol-3-yl)-propenone (B-46) 1-[(z-halogeno-q-(1-hydroxy-([substituted]aryl)methyl))pyrrol-w-yl]-3-hydroxy-3-([substituted]-2H-tetrazol-5-yl)-propenone (B-47) 1-[nH-(z-halogeno-q-(([substituted]aryl)sulfonylamino))pyrazol-w-yl]-3-hydroxy-3-([substituted]-1H-1,2,4-triazol-3-yl)-propenone (B-48) 4-[(z-alkyl-q-(([substituted]aryl)alkyl))pyrrol-w-yl]-2-hydroxy-4-oxo-2-butenoic acid (B-49) 1-[nH-(q-(([substituted]aryl)alkenyl)-z-alkyl)pyrazol-w-yl]-3-hydroxy-3-([substituted]-2H-tetrazol-5-yl)-propenone (B-50) 1-[nH-(z-alkyl-q-(1-hydroxy-([substituted]aryl)methyl))imidazol-w-yl]-3-hydroxy-3-([substituted]-2H-tetrazol-5-yl)-propenone (B-51) 1-[(z-alkyl-q-(([substituted]heteroaryl)sulfinyl))thiazol-w-yl]-3-hydroxy-3-([substituted]-1H-1,2,4-triazol-3-yl)-propenone (B-52) 1-[nH-(q-([substituted]aryl)-z-halogeno)pyrazol-w-yl]-3-hydroxy-3-([substituted]-2H-tetrazol-5-yl)-propenone (B-53) 1-[(z-halogeno-q-([substituted]heteroaryl))furan-w-yl]-3-hydroxy-3-([substituted]-2H-tetrazol-5-yl)-propenone (B-54) 4-[(z-alkyl-q-(([substituted]heteroaryl)oxycarbonyl))thiazol-w-yl]-2-hydroxy-4-oxo-2-butenoic acid (B-55) 2-hydroxy-4-oxo-4-(q-(([substituted]aryl)sulfinyl)thiazol-w-yl)-2-butenoic acid (B-56) 4-(q-(([substituted]heteroaryl)alkyl)pyridin-w-yl)-2-hydroxy-4-oxo-2-butenoic acid (B-57) 1-[(z-alkyl-q-(([substituted]heteroaryl)sulfonyl))thiophen-w-yl]-3-hydroxy-3-([substituted]-1H-1,2,4-triazol-3-yl)-propenone (B-58) 1-[(z-alkyl-q-(([substituted]heteroaryl)sulfonyl))pyridin-w-yl]-3-hydroxy-3-([substituted]-2H-tetrazol-5-yl)-propenone (B-59) 1-[(z-halogeno-q-(([substituted]heteroaryl)oxycarbonyl))furan-w-yl]-3-hydroxy-3-([substituted]-1H-1,2,4-triazol-3-yl)-propenone (B-60) 1-[(z-halogeno-q-(1-hydroxy-([substituted]heteroaryl)methyl))thiophen-w-yl]-3-hydroxy-3-([substituted]-2H-tetrazol-5-yl)-propenone (B-61) 4-[nH-(z-alkyl-q-(([substituted]aryl)carboxy))imidazol-w-yl]-2-hydroxy-4-oxo-2-butenoic acid (B-62) 1-[(q-(([substituted]aryl)amino)-z-halogeno)pyrrol-w-yl]-3-hydroxy-3-([substituted]-2H-tetrazol-5-yl)-propenone (B-63) 1-[nH-(z-halogeno-q-(([substituted]aryl)oxycarbonyl))pyrazol-w-yl]-3-hydroxy-3-([substituted]-2H-tetrazol-5-yl)-propenone (B-64) 4-(nH-q-([substituted]aryl)pyrazol-w-yl)-2-hydroxy-4-oxo-2-butenoic acid (B-65) 1-[nH-(z-alkyl-q-(([substituted]heteroaryl)oxycarbonyl))imidazol-w-yl]-3-hydroxy-3-([substituted]-1H-1,2,4-triazol-3-yl)-propenone (B-66) 1-[nH-(z-halogeno-q-(([substituted]aryl)oxycarbonyl))pyrazol-w-yl]-3-hydroxy-3-([substituted]-1H-1,2,4-triazol-3-yl)-propenone (B-67) 4-[(z-alkyl-q-(([substituted]aryl)amino))thiazol-w-yl]-2-hydroxy-4-oxo-2-butenoic acid (B-68) 1-[(z-alkyl-q-([substituted]heteroaryl))furan-w-yl]-3-hydroxy-3-([substituted]-1H-1,2,4-triazol-3-yl)-propenone (B-69) 1-[(z-alkyl-q-(([substituted]aryl)oxycarbonyl))pyridin-w-yl]-3-hydroxy-3-([substituted]-2H-tetrazol-5-yl)-propenone (B-70) 1-[(z-halogeno-q-(([substituted]heteroaryl)oxy))thiophen-w-yl]-3-hydroxy-3-([substituted]-2H-tetrazol-5-yl)-propenone (B-71) 1-(nH-q-(([substituted]heteroaryl)aminosulfonyl)imidazol-w-yl)-3-hydroxy-3-([substituted]-2H-tetrazol-5-yl)-propenone (B-72) 1-[nH-(z-halogeno-q-(([substituted]heteroaryl)oxycarbonyl))pyrazol-w-yl]-3-hydroxy-3-([substituted]-1H-1,2,4-triazol-3-yl)-propenone (B-73) 1-(nH-q-([substituted]heteroaryl)pyrazol-w-yl)-3-hydroxy-3-([substituted]-2H-tetrazol-5-yl)-propenone (B-74) 4-[(z-alkyl-q-(([substituted]aryl)sulfonyl))thiophen-w-yl]-2-hydroxy-4-oxo-2-butenoic acid (B-75) 1-[nH-(z-alkyl-q-(([substituted]aryl)carbonyl))imidazol-w-yl]-3-hydroxy-3-([substituted]-2H-tetrazol-5-yl)-propenone (B-76) 4-[(z-halogeno-q-(([substituted]heteroaryl)oxycarbonyl))thiazol-w-yl]-2-hydroxy-4-oxo-2-butenoic acid (B-77) 1-[(z-alkyl-q-(([substituted]heteroaryl)carbonyl))pyridin-w-yl]-3-hydroxy-3-([substituted]-1H-1,2,4-triazol-3-yl)-propenone (B-78) 1-(nH-q-(([substituted]aryl)aminosulfonyl)pyrazol-w-yl)-3-hydroxy-3-([substituted]-2H-tetrazol-5-yl)-propenone (B-79) 1-[nH-(q-(([substituted]heteroaryl)alkenyl)-z-alkyl)pyrazol-w-yl]-3-hydroxy-3-([substituted]-2H-tetrazol-5-yl)-propenone (B-80) 1-[nH-(z-halogeno-q-(([substituted]aryl)sulfonyl))pyrazol-w-yl]-3-hydroxy-3-([substituted]-2H-tetrazol-5-yl)-propenone (B-81) 4-[(z-alkyl-q-(([substituted]heteroaryl)oxycarbonyl))oxazol-w-yl]-2-hydroxy-4-oxo-2-butenoic acid (B-82) 1-[(z-alkyl-q-(([substituted]aryl)alkyl))furan-w-yl]-3-hydroxy-3-([substituted]-1H-1,2,4-triazol-3-yl)-propenone (B-83) 4-[(z-halogeno-q-(([substituted]heteroaryl)sulfinyl))pyridin-w-yl]-2-hydroxy-4-oxo-2-butenoic acid (B-84) 1-[(z-halogeno-q-(1-hydroxy-([substituted]heteroaryl)methyl))thiazol-w-yl]-3-hydroxy-3-([substituted]-2H-tetrazol-5-yl)-propenone (B-85) 1-[nH-(z-alkyl-q-(([substituted]aryl)aminocarbonyl))imidazol-w-yl]-3-hydroxy-3-([substituted]-1H-1,2,4-triazol-3-yl)-propenone (B-86) 4-(q-(([substituted]heteroaryl)alkyl)oxazol-w-yl)-2-hydroxy-4-oxo-2-butenoic acid (B-87) 4-[nH-(z-alkyl-q-(([substituted]heteroaryl)oxy))imidazol-w-yl]-2-hydroxy-4-oxo-2-butenoic acid (B-88) 1-[(q-(([substituted]heteroaryl)carbonylamino)-z-halogeno)isoxazol-w-yl]-3-hydroxy-3-([substituted]-2H-tetrazol-5-yl)-propenone (B-89) 1-[(q-(([substituted]heteroaryl)alkenyl)-z-alkyl)isoxazol-w-yl]-3-hydroxy-3-([substituted]-1H-1,2,4-triazol-3-yl)-propenone (B-90) 1-(q-(([substituted]aryl)alkenyl)thiazol-w-yl)-3-hydroxy-3-([substituted]-1H-1,2,4-triazol-3-yl)-propenone (B-91) 1-(q-([substituted]aryl)thiazol-w-yl)-3-hydroxy-3-([substituted]-2H-tetrazol-5-yl)-propenone (B-92) 4-[(q-(([substituted]heteroaryl)carboxy)-z-halogeno)thiazol-w-yl]-2-hydroxy-4-oxo-2-butenoic acid (B-93) 1-[(z-alkyl-q-(([substituted]aryl)oxy))furan-w-yl]-3-hydroxy-3-([substituted]-2H-tetrazol-5-yl)-propenone (B-94) 3-hydroxy-1-(q-(([substituted]aryl)sulfonyl)oxazol-w-yl)-3-([substituted]-2H-tetrazol-5-yl)-propenone (B-95) 2-hydroxy-4-oxo-4-(q-(([substituted]aryl)thio)thiazol-w-yl)-2-butenoic acid (B-96) 1-[nH-(z-alkyl-q-([substituted]heteroaryl))pyrazol-w-yl]-3-hydroxy-3-([substituted]-1H-1,2,4-triazol-3-yl)-propenone (B-97) 4-(q-(([substituted]aryl)aminosulfonyl)thiophen-w-yl)-2-hydroxy-4-oxo-2-butenoic acid
(B-98) 1-[(z-halogeno-q-(([substituted]heteroaryl)sulfinyl))thiophen-w-yl]-3-hydroxy-3-([substituted]-1H-1,2,4-triazol-3-yl)-propenone
(B-99) 1-(q-([substituted]aryl)pyridin-w-yl)-3-hydroxy-3-([substituted]-1H-1,2,4-triazol-3-yl)-propenone
(B-100) 1-[nH-(q-(([substituted]heteroaryl)alkyl)-z-halogeno)imidazol-w-yl]-3-hydroxy-3-([substituted]-1H-1,2,4-triazol-3-yl)-propenone
(B-101) 1-[(z-alkyl-q-(([substituted]aryl)oxy))isoxazol-w-yl]-3-hydroxy-3-([substituted]-2H-tetrazol-5-yl)-propenone
(B-102) 1-[(z-halogeno-q-(1-hydroxy-([substituted]heteroaryl)methyl))pyrrol-w-yl]-3-hydroxy-3-([substituted]-1H-1,2,4-triazol-3-yl)-propenone
(B-103) 1-[(z-alkyl-q-(([substituted]heteroaryl)thio))oxazol-w-yl]-3-hydroxy-3-([substituted]-2H-tetrazol-5-yl)-propenone
(B-104) 4-[(q-([substituted]aryl)-z-halogeno)isoxazol-w-yl]-2-hydroxy-4-oxo-2-butenoic acid
(B-105) 3-hydroxy-1-(nH-q-(([substituted]aryl)sulfonylamino)pyrazol-w-yl)-3-([substituted]-1H-1,2,4-triazol-3-yl)-propenone
(B-106) 4-(q-(([substituted]heteroaryl)alkyl)thiazol-w-yl)-2-hydroxy-4-oxo-2-butenoic acid
(B-107) 1-[(q-(([substituted]aryl)carbonyl)-z-halogeno)pyrrol-w-yl]-3-hydroxy-3-([substituted]-2H-tetrazol-5-yl)-propenone
(B-108) 1-[(z-halogeno-q-(([substituted]heteroaryl)sulfonyl))pyrrol-w-yl]-3-hydroxy-3-([substituted]-1H-1,2,4-triazol-3-yl)-propenone
(B-109) 4-[(q-(([substituted]heteroaryl)alkyl)-z-halogeno)furan-w-yl]-2-hydroxy-4-oxo-2-butenoic acid
(B-110) 1-[(z-alkyl-q-(([substituted]aryl)carbonylamino))oxazol-w-yl]-3-hydroxy-3-([substituted]-1H-1,2,4-triazol-3-yl)-propenone
(B-111) 4-[(z-alkyl-q-(([substituted]heteroaryl)amino))oxazol-w-yl]-2-hydroxy-4-oxo-2-butenoic acid
(B-112) 1-[(q-(([substituted]heteroaryl)carbonyl)-z-halogeno)pyridin-w-yl]-3-hydroxy-3-([substituted]-1H-1,2,4-triazol-3-yl)-propenone
(B-113) 4-[(z-alkyl-q-(([substituted]aryl)carbonyl))thiophen-w-yl]-2-hydroxy-4-oxo-2-butenoic acid
(B-114) 4-[(z-halogeno-q-(1-hydroxy-([substituted]heteroaryl)methyl))furan-w-yl]-2-hydroxy-4-oxo-2-butenoic acid
(B-115) 4-[(q-(([substituted]aryl)carbonylamino)-z-halogeno)oxazol-w-yl]-2-hydroxy-4-oxo-2-butenoic acid
(B-116) 4-[(z-alkyl-q-(([substituted]heteroaryl)thio))isoxazol-w-yl]-2-hydroxy-4-oxo-2-butenoic acid
(B-117) 1-[(z-halogeno-q-(([substituted]aryl)oxy))thiophen-w-yl]-3-hydroxy-3-([substituted]-1H-1,2,4-triazol-3-yl)-propenone
(B-118) 1-[(z-alkyl-q-(([substituted]heteroaryl)carbonyl))isoxazol-w-yl]-3-hydroxy-3-([substituted]-1H-1,2,4-triazol-3-yl)-propenone
(B-119) 1-[(z-alkyl-q-([substituted]aryl))thiazol-w-yl]-3-hydroxy-3-([substituted]-1H-1,2,4-triazol-3-yl)-propenone
(B-120) 4-[(z-alkyl-q-(([substituted]heteroaryl)sulfinyl))oxazol-w-yl]-2-hydroxy-4-oxo-2-butenoic acid
(B-121) 1-[(z-halogeno-q-(([substituted]aryl)thio))pyrrol-w-yl]-3-hydroxy-3-([substituted]-2H-tetrazol-5-yl)-propenone
(B-122) 1-[(q-(([substituted]heteroaryl)carboxy)-z-halogeno)pyridin-w-yl]-3-hydroxy-3-([substituted]-1H-1,2,4-triazol-3-yl)-propenone
(B-123) 3-hydroxy-3-([substituted]-2H-tetrazol-5-yl)-1-(q-((([substituted]aryl)thio)thiazol-w-yl)-propenone
(B-124) 4-(q-(([substituted]heteroaryl)carbonyl)pyrrol-w-yl)-2-hydroxy-4-oxo-2-butenoic acid
(B-125) 4-(q-(([substituted]aryl)alkyl)thiazol-w-yl)-2-hydroxy-4-oxo-2-butenoic acid
(B-126) 1-[(z-halogeno-q-(([substituted]heteroaryl)sulfonyl))thiazol-w-yl]-3-hydroxy-3-([substituted]-1H-1,2,4-triazol-3-yl)-propenone
(B-127) 1-[(z-halogeno-q-(([substituted]heteroaryl)sulfonyl))thiophen-w-yl]-3-hydroxy-3-([substituted]-2H-tetrazol-5-yl)-propenone
(B-128) 4-(q-(([substituted]aryl)carbonylamino)furan-w-yl)-2-hydroxy-4-oxo-2-butenoic acid
(B-129) 1-[(z-halogeno-q-(([substituted]aryl)thio))pyridin-w-yl]-3-hydroxy-3-([substituted]-1H-1,2,4-triazol-3-yl)-propenone
(B-130) 4-(q-(([substituted]heteroaryl)amino)thiazol-w-yl)-2-hydroxy-4-oxo-2-butenoic acid
(B-131) 4-[nH-(q-(([substituted]heteroaryl)alkenyl)-z-alkyl)imidazol-w-yl]-2-hydroxy-4-oxo-2-butenoic acid
(B-132) 1-[nH-(z-halogeno-q-(1-hydroxy-([substituted]heteroaryl)methyl))imidazol-w-yl]-3-hydroxy-3-([substituted]-2H-tetrazol-5-yl)-propenone
(B-133) 1-[(q-(([substituted]heteroaryl)carboxy)-z-halogeno)thiophen-w-yl]-3-hydroxy-3-([substituted]-2H-tetrazol-5-yl)-propenone
(B-134) 1-[(q-(([substituted]aryl)alkenyl)-z-alkyl)pyrrol-w-yl]-3-hydroxy-3-([substituted]-2H-tetrazol-5-yl)-propenone
(B-135) 1-[nH-(z-halogeno-q-(1-hydroxy-([substituted]heteroaryl)methyl))imidazol-w-yl]-3-hydroxy-3-([substituted]-1H-1,2,4-triazol-3-yl)-propenone
(B-136) 1-[(z-halogeno-q-(([substituted]heteroaryl)sulfonylamino))furan-w-yl]-3-hydroxy-3-([substituted]-2H-tetrazol-5-yl)-propenone
(B-137) 1-[(z-alkyl-q-(([substituted]heteroaryl)alkyl))pyridin-w-yl]-3-hydroxy-3-([substituted]-1H-1,2,4-triazol-3-yl)-propenone
(B-138) 1-(q-(([substituted]aryl)alkyl)oxazol-w-yl)-3-hydroxy-3-([substituted]-2H-tetrazol-5-yl)-propenone
(B-139) 1-[(z-alkyl-q-(([substituted]aryl)alkyl))isoxazol-w-yl]-3-hydroxy-3-([substituted]-2H-tetrazol-5-yl)-propenone
(B-140) 4-[(z-halogeno-q-(([substituted]heteroaryl)sulfonyl))pyrrol-w-yl]-2-hydroxy-4-oxo-2-butenoic acid
(B-141) 1-(q-(([substituted]aryl)alkyl)isoxazol-w-yl)-3-hydroxy-3-([substituted]-2H-tetrazol-5-yl)-propenone
(B-142) 1-[nH-(z-alkyl-q-(([substituted]aryl)aminosulfonyl))pyrazol-w-yl]-3-hydroxy-3-([substituted]-2H-tetrazol-5-yl)-propenone
(B-143) 1-[(z-halogeno-q-(([substituted]aryl)sulfonyl))furan-w-yl]-3-hydroxy-3-([substituted]-1H-1,2,4-triazol-3-yl)-propenone
(B-144) 4-[nH-(z-alkyl-q-(([substituted]aryl)oxycarbonyl))imidazol-w-yl]-2-hydroxy-4-oxo-2-butenoic acid
(B-145) 3-hydroxy-1-(q-(1-hydroxy-([substituted]aryl)methyl)pyridin-w-yl)-3-([substituted]-2H-tetrazol-5-yl)-propenone
(B-146) 1-(q-(([substituted]aryl)carbonyl)pyridin-w-yl)-3-hydroxy-3-([substituted]-2H-tetrazol-5-yl)-propenone
(B-147) 1-[(z-alkyl-q-(([substituted]heteroaryl)oxy))isoxazol-w-yl]-3-hydroxy-3-([substituted]-2H-tetrazol-5-yl)-propenone
(B-148) 1-[(z-alkyl-q-(([substituted]aryl)aminosulfonyl))furan-w-yl]-3-hydroxy-3-([substituted]-1H-1,2,4-triazol-3-yl)-propenone (B-149) 1-[(z-alkyl-q-(([substituted]aryl)aminosulfonyl)) pyridin-w-yl]-3-hydroxy-3-([substituted]-1H-1,2,4-triazol-3-yl)-propenone (B-150) 4-(q-(([substituted]heteroaryl)carbonyl)thiazol-w-yl)-2-hydroxy-4-oxo-2-butenoic acid (B-151) 1-[(z-alkyl-q-(([substituted]aryl)oxy))pyridin-w-yl]-3-hydroxy-3-([substituted]-2H-tetrazol-5-yl)-propenone (B-152) 4-[(z-halogeno-q-(1-hydroxy-([substituted] heteroaryl)methyl))pyridin-w-yl]-2-hydroxy-4-oxo-2-butenoic acid (B-153) 1-[(z-halogeno-q-(([substituted]aryl)oxy))furan-w-yl]-3-hydroxy-3-([substituted]-1H-1,2,4-triazol-3-yl)-propenone (B-154) 1-[(z-alkyl-q-(([substituted]aryl)aminocarbonyl)) thiophen-w-yl]-3-hydroxy-3-([substituted]-2H-tetrazol-5-yl)-propenone (B-155) 1-[(q-(([substituted]aryl)alkenyl)-z-alkyl)oxazol-w-yl]-3-hydroxy-3-([substituted]-2H-tetrazol-5-yl)-propenone (B-156) 3-hydroxy-1-(q-(([substituted]aryl)oxy)furan-w-yl)-3-([substituted]-1H-1,2,4-triazol-3-yl)-propenone (B-157) 4-[(z-alkyl-q-(([substituted]heteroaryl) aminocarbonyl))oxazol-w-yl]-2-hydroxy-4-oxo-2-butenoic acid (B-158) 1-[(z-alkyl-q-(([substituted]heteroaryl)sulfonyl)) pyrrol-w-yl]-3-hydroxy-3-([substituted]-1H-1,2,4-triazol-3-yl)-propenone (B-159) 1-[(q-(([substituted]heteroaryl)carboxy)-z-alkyl) thiazol-w-yl]-3-hydroxy-3-([substituted]-1H-1,2,4-triazol-3-yl)-propenone (B-160) 4-[nH-(z-halogeno-q-(([substituted]heteroaryl) sulfinyl))imidazol-w-yl]-2-hydroxy-4-oxo-2-butenoic acid (B-161) 4-[(z-halogeno-q-(([substituted]heteroaryl)thio)) pyrrol-w-yl]-2-hydroxy-4-oxo-2-butenoic acid (B-162) 1-[(z-halogeno-q-(([substituted]heteroaryl) sulfinyl))pyrrol-w-yl]-3-hydroxy-3-([substituted]-1H-1,2,4-triazol-3-yl)-propenone (B-163) 3-hydroxy-1-(q-(([substituted]aryl)sulfonylamino) thiazol-w-yl)-3-([substituted]-1H-1,2,4-triazol-3-yl)-propenone (B-164) 3-hydroxy-1-(q-(([substituted]heteroaryl) oxycarbonyl)pyridin-w-yl)-3-([substituted]-2H-tetrazol-5-yl)-propenone (B-165) 1-[(z-alkyl-q-(([substituted]heteroaryl))thiophen-w-yl]-3-hydroxy-3-([substituted]-2H-tetrazol-5-yl)-propenone (B-166) 1-[(z-halogeno-q-(([substituted]heteroaryl) sulfonylamino))thiophen-w-yl]-3-hydroxy-3-([substituted]-2H-tetrazol-5-yl)-propenone (B-167) 1-[(z-alkyl-q-(1-hydroxy-([substituted]aryl) methyl))pyrrol-w-yl]-3-hydroxy-3-([substituted]-2H-tetrazol-5-yl)-propenone (B-168) 2-hydroxy-4-oxo-4-(nH-q-(([substituted] heteroaryl)sulfonyl)pyrazol-w-yl)-2-butenoic acid (B-169) 2-hydroxy-4-oxo-4-(q-(([substituted]aryl)sulfonyl) isoxazol-w-yl)-2-butenoic acid (B-170) 4-[(z-alkyl-q-(([substituted]aryl)aminocarbonyl)) isoxazol-w-yl]-2-hydroxy-4-oxo-2-butenoic acid (B-171) 1-[(z-halogeno-q-(([substituted]aryl)sulfinyl)) thiophen-w-yl]-3-hydroxy-3-([substituted]-1H-1,2,4-triazol-3-yl)-propenone (B-172) 4-[(q-(([substituted]aryl)alkenyl)-z-alkyl)thiazol-w-yl]-2-hydroxy-4-oxo-2-butenoic acid (B-173) 1-[(z-alkyl-q-(([substituted]aryl)carbonyl))pyridin-w-yl]-3-hydroxy-3-([substituted]-1H-1,2,4-triazol-3-yl)-propenone (B-174) 1-((q-(([substituted]heteroaryl)aminocarbonyl) thiophen-w-yl)-3-hydroxy-3-([substituted]-1H-1,2,4-triazol-3-yl)-propenone (B-175) 1-[(z-alkyl-q-(([substituted]aryl)thio))furan-w-yl]-3-hydroxy-3-([substituted]-1H-1,2,4-triazol-3-yl)-propenone (B-176) 3-hydroxy-1-(q-(([substituted]aryl)oxycarbonyl) pyridin-w-yl)-3-([substituted]-1H-1,2,4-triazol-3-yl)-propenone (B-177) 1-[(z-alkyl-q-(1-hydroxy-([substituted]aryl) methyl))thiazol-w-yl]-3-hydroxy-3-([substituted]-1H-1,2,4-triazol-3-yl)-propenone (B-178) 2-hydroxy-4-oxo-4-(q-(([substituted]aryl)thio) pyridin-w-yl)-2-butenoic acid (B-179) 4-[(z-alkyl-q-(([substituted]heteroaryl)sulfinyl)) pyrrol-w-yl]-2-hydroxy-4-oxo-2-butenoic acid (B-180) 1-[(z-alkyl-q-(([substituted]aryl)oxycarbonyl)) thiazol-w-yl]-3-hydroxy-3-([substituted]-2H-tetrazol-5-yl)-propenone (B-181) 4-[nH-(z-halogeno-q-(([substituted]aryl) oxycarbonyl))pyrazol-w-yl]-2-hydroxy-4-oxo-2-butenoic acid (B-182) 1-[nH-(q-(([substituted]aryl)aminocarbonyl)-z-halogeno)imidazol-w-yl]-3-hydroxy-3-([substituted]-2H-tetrazol-5-yl)-propenone (B-183) 4-(q-([substituted]heteroaryl)pyridin-w-yl)-2-hydroxy-4-oxo-2-butenoic acid (B-184) 1-[(q-(([substituted]heteroaryl)alkenyl)-z-alkyl) furan-w-yl]-3-hydroxy-3-([substituted]-1H-1,2,4-triazol-3-yl)-propenone (B-185) 1-[(z-alkyl-q-(([substituted]heteroaryl)sulfinyl)) thiophen-w-yl]-3-hydroxy-3-([substituted]-2H-tetrazol-5-yl)-propenone (B-186) 4-[nH-(z-halogeno-q-(([substituted]heteroaryl) sulfinyl))pyrazol-w-yl]-2-hydroxy-4-oxo-2-butenoic acid (B-187) 1-[(z-alkyl-q-(([substituted]heteroaryl) aminosulfonyl))pyrrol-w-yl]-3-hydroxy-3-([substituted]-2H-tetrazol-5-yl)-propenone (B-188) 1-[nH-(z-halogeno-q-(1-hydroxy-([substituted] aryl)methyl))imidazol-w-yl]-3-hydroxy-3-([substituted]-2H-tetrazol-5-yl)-propenone (B-189) 1-[(z-halogeno-q-(([substituted]heteroaryl) sulfonylamino))pyridin-w-yl]-3-hydroxy-3-([substituted]-2H-tetrazol-5-yl)-propenone (B-190) 1-[(z-alkyl-q-(([substituted]heteroaryl)sulfonyl)) pyrrol-w-yl]-3-hydroxy-3-([substituted]-2H-tetrazol-5-yl)-propenone (B-191) 4-[(z-alkyl-q-(([substituted]heteroaryl)oxy))pyrrol-w-yl]-2-hydroxy-4-oxo-2-butenoic acid (B-192) 3-hydroxy-1-(nH-q-(([substituted]aryl) oxycarbonyl)pyrazol-w-yl)-3-([substituted]-1H-1,2,4-triazol-3-yl)-propenone (B-193) 1-[(q-(([substituted]heteroaryl)amino)-z-halogeno) thiazol-w-yl]-3-hydroxy-3-([substituted]-1H-1,2,4-triazol-3-yl)-propenone (B-194) 3-hydroxy-1-(nH-q-(([substituted]heteroaryl) oxycarbonyl)pyrazol-w-yl)-3-([substituted]-1H-1,2,4-triazol-3-yl)-propenone (B-195) 1-[(z-alkyl-q-(([substituted]heteroaryl)oxy)) thiazol-w-yl]-3-hydroxy-3-([substituted]-2H-tetrazol-5-yl)-propenone (B-196) 1-[(z-halogeno-q-(([substituted]aryl) sulfonylamino))pyrrol-w-yl]-3-hydroxy-3-([substituted]-1H-1,2,4-triazol-3-yl)-propenone (B-197) 1-[(z-alkyl-q-(([substituted]aryl)aminocarbonyl)) thiazol-w-yl]-3-hydroxy-3-([substituted]-2H-tetrazol-5-yl)-propenone (B-198) 4-[(q-(([substituted]aryl)alkenyl)-z-halogeno)isoxazol-w-yl]-2-hydroxy-4-oxo-2-butenoic acid
(B-199) 1-[nH-(z-halogeno-q-(([substituted]heteroaryl)sulfonylamino))pyrazol-w-yl]-3-hydroxy-3-([substituted]-1H-1,2,4-triazol-3-yl)-propenone
(B-200) 1-[(z-alkyl-q-(([substituted]aryl)thio))thiophen-w-yl]-3-hydroxy-3-([substituted]-2H-tetrazol-5-yl)-propenone
(B-201) 1-[(z-alkyl-q-(([substituted]aryl)carboxy))thiazol-w-yl]-3-hydroxy-3-([substituted]-2H-tetrazol-5-yl)-propenone
(B-202) 1-(q-(([substituted]aryl)alkyl)furan-w-yl)-3-hydroxy-3-([substituted]-2H-tetrazol-5-yl)-propenone
(B-203) 4-[(z-halogeno-q-(([substituted]aryl)oxy))pyridin-w-yl]-2-hydroxy-4-oxo-2-butenoic acid
(B-204) 4-[(z-halogeno-q-(([substituted]aryl)oxy))thiophen-w-yl]-2-hydroxy-4-oxo-2-butenoic acid
(B-205) 1-(nH-q-(([substituted]heteroaryl)aminosulfonyl)pyrazol-w-yl)-3-hydroxy-3-([substituted]-1H-1,2,4-triazol-3-yl)-propenone
(B-206) 1-[nH-(q-(([substituted]heteroaryl)carboxy)-z-alkyl)imidazol-w-yl]-3-hydroxy-3-([substituted]-1H-1,2,4-triazol-3-yl)-propenone
(B-207) 1-[(z-alkyl-q-(([substituted]aryl)amino))pyridin-w-yl]-3-hydroxy-3-([substituted]-1H-1,2,4-triazol-3-yl)-propenone
(B-208) 3-hydroxy-1-(q-(([substituted]heteroaryl)sulfinyl)thiazol-w-yl)-3-([substituted]-2H-tetrazol-5-yl)-propenone
(B-209) 1-[nH-(z-alkyl-q-(([substituted]heteroaryl)alkyl))imidazol-w-yl]-3-hydroxy-3-([substituted]-1H-1,2,4-triazol-3-yl)-propenone
(B-210) 1-[(z-alkyl-q-(([substituted]aryl)carbonyl))furan-w-yl]-3-hydroxy-3-([substituted]-2H-tetrazol-5-yl)-propenone
(B-211) 4-[(z-halogeno-q-(1-hydroxy-([substituted]aryl)methyl))pyridin-w-yl]-2-hydroxy-4-oxo-2-butenoic acid
(B-212) 1-[(z-alkyl-q-(([substituted]aryl)sulfinyl))furan-w-yl]-3-hydroxy-3-([substituted]-2H-tetrazol-5-yl)-propenone
(B-213) 4-[(q-(([substituted]aryl)alkyl)-z-halogeno)thiophen-w-yl]-2-hydroxy-4-oxo-2-butenoic acid
(B-214) 4-[nH-(z-halogeno-q-(([substituted]aryl)sulfonylamino))pyrazol-w-yl]-2-hydroxy-4-oxo-2-butenoic acid
(B-215) 1-[(z-alkyl-q-(([substituted]heteroaryl)thio))thiophen-w-yl]-3-hydroxy-3-([substituted]-1H-1,2,4-triazol-3-yl)-propenone
(B-216) 4-[(z-alkyl-q-(1-hydroxy-([substituted]heteroaryl)methyl))furan-w-yl]-2-hydroxy-4-oxo-2-butenoic acid
(B-217) 4-(q-(([substituted]aryl)carboxy)thiophen-w-yl)-2-hydroxy-4-oxo-2-butenoic acid
(B-218) 1-[(q-(([substituted]heteroaryl)aminosulfonyl)-z-halogeno)oxazol-w-yl]-3-hydroxy-3-([substituted]-2H-tetrazol-5-yl)-propenone
(B-219) 1-[nH-(z-halogeno-q-(([substituted]aryl)thio))pyrazol-w-yl]-3-hydroxy-3-([substituted]-1H-1,2,4-triazol-3-yl)-propenone
(B-220) 1-(q-(([substituted]heteroaryl)alkyl)furan-w-yl)-3-hydroxy-3-([substituted]-2H-tetrazol-5-yl)-propenone
(B-221) 4-[(q-(([substituted]heteroaryl)carbonylamino)-z-halogeno)furan-w-yl]-2-hydroxy-4-oxo-2-butenoic acid
(B-222) 4-[(z-alkyl-q-(1-hydroxy-([substituted]heteroaryl)methyl))pyridin-w-yl]-2-hydroxy-4-oxo-2-butenoic acid
(B-223) 1-(nH-q-(([substituted]aryl)alkyl)pyrazol-w-yl)-3-hydroxy-3-([substituted]-2H-tetrazol-5-yl)-propenone
(B-224) 1-[(z-halogeno-q-(([substituted]aryl)sulfonylamino))thiazol-w-yl]-3-hydroxy-3-([substituted]-1H-1,2,4-triazol-3-yl)-propenone
(B-225) 4-[nH-(z-alkyl-q-(([substituted]aryl)oxy))imidazol-w-yl]-2-hydroxy-4-oxo-2-butenoic acid
(B-226) 1-[nH-(z-alkyl-q-(([substituted]aryl)sulfonylamino))pyrazol-w-yl]-3-hydroxy-3-([substituted]-2H-tetrazol-5-yl)-propenone
(B-227) 1-[nH-(z-halogeno-q-(1-hydroxy-([substituted]aryl)methyl))pyrazol-w-yl]-3-hydroxy-3-([substituted]-1H-1,2,4-triazol-3-yl)-propenone
(B-228) 4-[(z-alkyl-q-(1-hydroxy-([substituted]heteroaryl)methyl))pyrrol-w-yl]-2-hydroxy-4-oxo-2-butenoic acid
(B-229) 4-[(z-alkyl-q-(1-hydroxy-([substituted]heteroaryl)methyl))thiazol-w-yl]-2-hydroxy-4-oxo-2-butenoic acid
(B-230) 4-[(z-alkyl-q-(([substituted]heteroaryl)carbonylamino))isoxazol-w-yl]-2-hydroxy-4-oxo-2-butenoic acid
(B-231) 3-hydroxy-1-(nH-q-(1-hydroxy-([substituted]heteroaryl)methyl)imidazol-w-yl)-3-([substituted]-1H-1,2,4-triazol-3-yl)-propenone
(B-232) 3-hydroxy-1-(q-(([substituted]heteroaryl)oxycarbonyl)pyrrol-w-yl)-3-([substituted]-1H-1,2,4-triazol-3-yl)-propenone
(B-233) 1-[(z-alkyl-q-(([substituted]heteroaryl)alkyl))pyrrol-w-yl]-3-hydroxy-3-([substituted]-1H-1,2,4-triazol-3-yl)-propenone
(B-234) 1-[(z-alkyl-q-(([substituted]aryl)carbonylamino))thiophen-w-yl]-3-hydroxy-3-([substituted]-2H-tetrazol-5-yl)-propenone
(B-235) 1-[(z-halogeno-q-(([substituted]aryl)oxy))thiazol-w-yl]-3-hydroxy-3-([substituted]-2H-tetrazol-5-yl)-propenone
(B-236) 4-[(z-halogeno-q-(([substituted]aryl)sulfonyl))isoxazol-w-yl]-2-hydroxy-4-oxo-2-butenoic acid
(B-237) 4-[(q-(([substituted]heteroaryl)amino)-z-halogeno)thiazol-w-yl]-2-hydroxy-4-oxo-2-butenoic acid
(B-238) 4-[nH-(z-alkyl-q-(([substituted]heteroaryl)aminosulfonyl))imidazol-w-yl]-2-hydroxy-4-oxo-2-butenoic acid
(B-239) 3-hydroxy-1-(q-(([substituted]aryl)oxycarbonyl)thiophen-w-yl)-3-([substituted]-1H-1,2,4-triazol-3-yl)-propenone
(B-240) 2-hydroxy-4-oxo-4-(q-(([substituted]heteroaryl)oxycarbonyl)thiazol-w-yl)-2-butenoic acid
(B-241) 4-[(z-halogeno-q-(1-hydroxy-([substituted]aryl)methyl))furan-w-yl]-2-hydroxy-4-oxo-2-butenoic acid
(B-242) 1-[(z-alkyl-q-(([substituted]aryl)sulfonylamino))pyrrol-w-yl]-3-hydroxy-3-([substituted]-2H-tetrazol-5-yl)-propenone
(B-243) 1-[(z-alkyl-q-(([substituted]aryl)amino))thiazol-w-yl]-3-hydroxy-3-([substituted]-1H-1,2,4-triazol-3-yl)-propenone
(B-244) 4-(q-(([substituted]heteroaryl)carbonylamino)thiophen-w-yl)-2-hydroxy-4-oxo-2-butenoic acid
(B-245) 1-[(z-alkyl-q-(([substituted]aryl)carbonylamino))thiazol-w-yl]-3-hydroxy-3-([substituted]-2H-tetrazol-5-yl)-propenone
(B-246) 1-[(z-halogeno-q-(([substituted]aryl)oxycarbonyl))isoxazol-w-yl]-3-hydroxy-3-([substituted]-2H-tetrazol-5-yl)-propenone
(B-247) 4-(nH-q-(([substituted]aryl)aminosulfonyl)imidazol-w-yl)-2-hydroxy-4-oxo-2-butenoic acid
(B-248) 1-[(q-(([substituted]heteroaryl)carboxy)-z-alkyl)pyrrol-w-yl]-3-hydroxy-3-([substituted]-2H-tetrazol-5-yl)-propenone
(B-249) 4-(q-(([substituted]aryl)carboxy)thiazol-w-yl)-2-hydroxy-4-oxo-2-butenoic acid
(B-250) 1-[(z-alkyl-q-(([substituted]aryl)oxycarbonyl))isoxazol-w-yl]-3-hydroxy-3-([substituted]-2H-tetrazol-5-yl)-propenone (B-251) 1-[(z-alkyl-q-(([substituted]aryl)thio))thiazol-w-yl]-3-hydroxy-3-([substituted]-1H-1,2,4-triazol-3-yl)-propenone (B-252) 1-(q-(([substituted]heteroaryl)alkyl)thiazol-w-yl)-3-hydroxy-3-([substituted]-1H-1,2,4-triazol-3-yl)-propenone (B-253) 1-[(z-alkyl-q-(([substituted]heteroaryl)sulfonylamino))thiophen-w-yl]-3-hydroxy-3-([substituted]-2H-tetrazol-5-yl)-propenone (B-254) 1-[(z-alkyl-q-([substituted]heteroaryl))oxazol-w-yl]-3-hydroxy-3-([substituted]-1H-1,2,4-triazol-3-yl)-propenone (B-255) 4-[(q-(([substituted]heteroaryl)carbonyl)-z-halogeno)isoxazol-w-yl]-2-hydroxy-4-oxo-2-butenoic acid (B-256) 1-[(z-alkyl-q-(([substituted]heteroaryl)aminocarbonyl))oxazol-w-yl]-3-hydroxy-3-([substituted]-1H-1,2,4-triazol-3-yl)-propenone (B-257) 1-[(q-(([substituted]heteroaryl)aminocarbonyl)-z-halogeno)thiazol-w-yl]-3-hydroxy-3-([substituted]-1H-1,2,4-triazol-3-yl)-propenone (B-258) 4-[(z-halogeno-q-(([substituted]aryl)thio))isoxazol-w-yl]-2-hydroxy-4-oxo-2-butenoic acid (B-259) 1-(q-([substituted]heteroaryl)furan-w-yl)-3-hydroxy-3-([substituted]-1H-1,2,4-triazol-3-yl)-propenone (B-260) 3-hydroxy-1-(q-(1-hydroxy-([substituted]aryl)methyl)pyridin-w-yl)-3-([substituted]-1H-1,2,4-triazol-3-yl)-propenone (B-261) 4-[(z-alkyl-q-(([substituted]heteroaryl)sulfonylamino))isoxazol-w-yl]-2-hydroxy-4-oxo-2-butenoic acid (B-262) 3-hydroxy-1-(q-(([substituted]heteroaryl)sulfinyl)oxazol-w-yl)-3-([substituted]-2H-tetrazol-5-yl)-propenone (B-263) 4-[(z-alkyl-q-(([substituted]heteroaryl)aminosulfonyl))thiazol-w-yl]-2-hydroxy-4-oxo-2-butenoic acid (B-264) 4-[(z-alkyl-q-(([substituted]heteroaryl))thiazol-w-yl]-2-hydroxy-4-oxo-2-butenoic acid (B-265) 1-[(z-halogeno-q-([substituted]heteroaryl))oxazol-w-yl]-3-hydroxy-3-([substituted]-2H-tetrazol-5-yl)-propenone (B-266) 1-[(z-alkyl-q-(([substituted]aryl)aminosulfonyl))isoxazol-w-yl]-3-hydroxy-3-([substituted]-1H-1,2,4-triazol-3-yl)-propenone (B-267) 4-[(q-(([substituted]aryl)carbonylamino)-z-halogeno)pyridin-w-yl]-2-hydroxy-4-oxo-2-butenoic acid (B-268) 1-[(q-(([substituted]heteroaryl)carboxy)-z-alkyl)thiophen-w-yl]-3-hydroxy-3-([substituted]-2H-tetrazol-5-yl)-propenone (B-269) 4-[nH-(q-(([substituted]aryl)alkyl)-z-halogeno)imidazol-w-yl]-2-hydroxy-4-oxo-2-butenoic acid (B-270) 4-[(z-alkyl-q-(([substituted]aryl)sulfinyl))pyrrol-w-yl]-2-hydroxy-4-oxo-2-butenoic acid (B-271) 1-[(q-(([substituted]aryl)alkyl)-z-halogeno)pyrrol-w-yl]-3-hydroxy-3-([substituted]-1H-1,2,4-triazol-3-yl)-propenone (B-272) 1-(q-([substituted]aryl)pyrrol-w-yl)-3-hydroxy-3-([substituted]-2H-tetrazol-5-yl)-propenone (B-273) 4-[(q-(([substituted]aryl)aminosulfonyl)-z-halogeno)pyrrol-w-yl]-2-hydroxy-4-oxo-2-butenoic acid (B-274) 1-(q-([substituted]heteroaryl)pyrrol-w-yl)-3-hydroxy-3-([substituted]-1H-1,2,4-triazol-3-yl)-propenone (B-275) 4-[(z-halogeno-q-(([substituted]aryl)thio))thiophen-w-yl]-2-hydroxy-4-oxo-2-butenoic acid (B-276) 1-[(z-halogeno-q-(([substituted]heteroaryl)thio))isoxazol-w-yl]-3-hydroxy-3-([substituted]-1H-1,2,4-triazol-3-yl)-propenone (B-277) 4-[(z-alkyl-q-(([substituted]heteroaryl)oxycarbonyl))pyrrol-w-yl]-2-hydroxy-4-oxo-2-butenoic acid (B-278) 1-(q-(([substituted]heteroaryl)carbonylamino)pyridin-w-yl)-3-hydroxy-3-([substituted]-1H-1,2,4-triazol-3-yl)-propenone (B-279) 3-hydroxy-1-(q-(([substituted]heteroaryl)sulfonyl)pyridin-w-yl)-3-([substituted]-1H-1,2,4-triazol-3-yl)-propenone (B-280) 4-[(z-halogeno-q-(([substituted]heteroaryl)oxycarbonyl))furan-w-yl]-2-hydroxy-4-oxo-2-butenoic acid (B-281) 1-[(z-alkyl-q-(([substituted]aryl)carbonyl))oxazol-w-yl]-3-hydroxy-3-([substituted]-1H-1,2,4-triazol-3-yl)-propenone (B-282) 1-[(z-alkyl-q-([substituted]aryl))furan-w-yl]-3-hydroxy-3-([substituted]-1H-1,2,4-triazol-3-yl)-propenone (B-283) 1-[(q-(([substituted]heteroaryl)alkenyl)-z-alkyl)oxazol-w-yl]-3-hydroxy-3-([substituted]-2H-tetrazol-5-yl)-propenone (B-284) 1-(q-([substituted]heteroaryl)thiophen-w-yl)-3-hydroxy-3-([substituted]-1H-1,2,4-triazol-3-yl)-propenone (B-285) 4-[(z-alkyl-q-(([substituted]aryl)alkyl))furan-w-yl]-2-hydroxy-4-oxo-2-butenoic acid (B-286) 4-[(z-alkyl-q-(([substituted]heteroaryl)amino))furan-w-yl]-2-hydroxy-4-oxo-2-butenoic acid (B-287) 1-(q-(([substituted]aryl)amino)pyrrol-w-yl)-3-hydroxy-3-([substituted]-1H-1,2,4-triazol-3-yl)-propenone (B-288) 1-[(z-alkyl-q-(([substituted]aryl)carbonylamino))thiazol-w-yl]-3-hydroxy-3-([substituted]-1H-1,2,4-triazol-3-yl)-propenone (B-289) 1-[(z-alkyl-q-(([substituted]heteroaryl)aminosulfonyl))thiazol-w-yl]-3-hydroxy-3-([substituted]-1H-1,2,4-triazol-3-yl)-propenone (B-290) 3-hydroxy-1-(nH-q-(([substituted]aryl)sulfonyl)pyrazol-w-yl)-3-([substituted]-2H-tetrazol-5yl)-propenone (B-291) 1-[(z-alkyl-q-(([substituted]aryl)thio))thiazol-w-yl]-3-hydroxy-3-([substituted]-2H-tetrazol-5-yl)-propenone (B-292) 1-(q-([substituted]heteroaryl)pyridin-w-yl)-3-hydroxy-3-([substituted]-2H-tetrazol-5-yl)-propenone (B-293) 1-(q-(([substituted]aryl)carbonyl)oxazol-w-yl)-3-hydroxy-3-([substituted]-2H-tetrazol-5-yl)-propenone (B-294) 1-(nH-q-(([substituted]aryl)alkyl)imidazol-w-yl)-3-hydroxy-3-([substituted]-2H-tetrazol-5-yl)-propenone (B-295) 4-[nH-(z-alkyl-q-(([substituted]heteroaryl)sulfonyl))imidazol-w-yl]-2-hydroxy-4-oxo-2-butenoic acid (B-296) 4-[nH-(z-alkyl-q-(([substituted]heteroaryl)amino))imidazol-w-yl]-2-hydroxy-4-oxo-2-butenoic acid (B-297) 3-hydroxy-1-(q-((([substituted]heteroaryl)oxycarbonyl)pyrrol-w-yl)-3-([substituted]-2H-tetrazol-5-yl)-propenone (B-298) 4-[(z-alkyl-q-(1-hydroxy-([substituted]aryl)methyl))pyridin-w-yl]-2-hydroxy-4-oxo-2-butenoic acid (B-299) 1-[(z-alkyl-q-(([substituted]aryl)sulfonylamino))furan-w-yl]-3-hydroxy-3-([substituted]-1H-1,2,4-triazol-3-yl)-propenone (B-300) 4-[(z-alkyl-q-(([substituted]aryl)oxy))furan-w-yl]-2-hydroxy-4-oxo-2-butenoic acid (B-301) 4-(q-(([substituted]aryl)carboxy)furan-w-yl)-2-hydroxy-4-oxo-2-butenoic acid
(B-302) 1-(q-(([substituted]heteroaryl)carbonyl)isoxazol-w-yl)-3-hydroxy-3-([substituted]-1H-1,2,4-triazol-3-yl)-propenone
(B-303) 1-[(z-halogeno-q-(([substituted]heteroaryl)oxy)thiazol-w-yl]-3-hydroxy-3-([substituted]-2H-tetrazol-5-yl)-propenone
(B-304) 3-hydroxy-1-(q-(([substituted]heteroaryl)oxycarbonyl)oxazol-w-yl)-3-([substituted]-2H-tetrazol-5-yl)-propenone
(B-305) 2-hydroxy-4-oxo-4-(q-(([substituted]aryl)thio)pyrrol-w-yl)-2-butenoic acid
(B-306) 4-[(z-halogeno-q-(([substituted]heteroaryl)oxy))pyrrol-w-yl]-2-hydroxy-4-oxo-2-butenoic acid
(B-307) 4-(q-(([substituted]aryl)alkenyl)thiazol-w-yl)-2-hydroxy-4-oxo-2-butenoic acid
(B-308) 4-[(q-(([substituted]heteroaryl)carbonyl)-z-halogeno)furan-w-yl]-2-hydroxy-4-oxo-2-butenoic acid
(B-309) 1-[(z-alkyl-q-(([substituted]aryl)sulfonylamino))thiophen-w-yl)-3-hydroxy-3-([substituted]-2H-tetrazol-5-yl)-propenone
(B-310) 3-hydroxy-1-(q-(([substituted]aryl)sulfonyl)pyrrol-w-yl)-3-([substituted]-2H-tetrazol-5-yl)-propenone
(B-311) 1-(q-(([substituted]aryl)aminocarbonyl)isoxazol-w-yl)-3-hydroxy-3-([substituted]-2H-tetrazol-5-yl)-propenone
(B-312) 1-[(q-(([substituted]aryl)alkenyl)-z-halogeno)thiophen-w-yl]-3-hydroxy-3-([substituted]-1H-1,2,4-triazol-3-yl)-propenone
(B-313) 1-[(z-alkyl-q-(([substituted]heteroaryl)amino))furan-w-yl]-3-hydroxy-3-([substituted]-1H-1,2,4-triazol-3-yl)-propenone
(B-314) 4-(q-(([substituted]heteroaryl)alkyl)isoxazol-w-yl)-2-hydroxy-4-oxo-2-butenoic acid
(B-315) 4-(q-(([substituted]aryl)amino)furan-w-yl)-2-hydroxy-4-oxo-2-butenoic acid
(B-316) 4-(q-(([substituted]heteroaryl)carbonyl)furan-w-yl)-2-hydroxy-4-oxo-2-butenoic acid
(B-317) 1-[(z-alkyl-q-([substituted]aryl))thiophen-w-yl]-3-hydroxy-3-([substituted]-2H-tetrazol-5-yl)-propenone
(B-318) 1-(q-(([substituted]aryl)alkenyl)furan-w-yl)-3-hydroxy-3-([substituted]-2H-tetrazol-5-yl)-propenone
(B-319) 3-hydroxy-1-(q-((substituted]aryl)sulfonylamino)oxazol-w-yl)-3-([substituted]-1H-1,2,4-triazol-3-yl)-propenone
(B-320) 4-(q-(([substituted]aryl)alkyl)isoxazol-w-yl)-2-hydroxy-4-oxo-2-butenoic acid
(B-321) 1-[(z-alkyl-q-(([substituted]aryl)carbonylamino))isoxazol-w-yl]-3-hydroxy-3-([substituted]-2H-tetrazol-5-yl)-propenone
(B-322) 3-hydroxy-1-(q-(([substituted]heteroaryl)sulfonylamino)isoxazol-w-yl)-3-([substituted]-1H-1,2,4-triazol-3-yl)-propenone
(B-323) 1-[(z-halogeno-q-(([substituted]aryl)sulfinyl))isoxazol-w-yl]-3-hydroxy-3-([substituted]-1H-1,2,4-triazol-3-yl)-propenone
(B-324) 4-[(z-halogeno-q-(1-hydroxy-([substituted]aryl)methyl))pyrrol-w-yl]-2-hydroxy-4-oxo-2-butenoic acid
(B-325) 3-hydroxy-1-(q-(([substituted]aryl)oxy)pyridin-w-yl)-3-([substituted]-2H-tetrazol-5-yl)-propenone
(B-326) 1-[nH-(z-halogeno-q-(1-hydroxy-([substituted]aryl)methyl))pyrazol-w-yl]-3-hydroxy-3-([substituted]-2H-tetrazol-5-yl)-propenone
(B-327) 3-hydroxy-1-(nH-q-(([substituted]heteroaryl)sulfonylamino)imidazol-w-yl)-3-([substituted]-1H-1,2,4-triazol-3-yl)-propenone
(B-328) 1-[(z-alkyl-q-(([substituted]aryl)sulfinyl))pyridin-w-yl]-3-hydroxy-3-([substituted]-2H-tetrazol-5-yl)-propenone
(B-329) 1-[(z-halogeno-q-(1-hydroxy-([substituted]heteroaryl)methyl))oxazol-w-yl]-3-hydroxy-3-([substituted]-2H-tetrazol-5-yl)-propenone
(B-330) 3-hydroxy-1-(nH-q-(([substituted]heteroaryl)oxy)imidazol-w-yl)-3-([substituted]-2H-tetrazol-5-yl)-propenone
(B-331) 4-[(q-(([substituted]heteroaryl)alkyl)-z-halogeno)thiophen-w-yl]-2-hydroxy-4-oxo-2-butenoic acid
(B-332) 1-[(q-(([substituted]heteroaryl)alkenyl)-z-alkyl)thiophen-w-yl]-3-hydroxy-3-([substituted]-1H-1,2,4-triazol-3-yl)-propenone
(B-333) 4-(nH-q-(([substituted]heteroaryl)alkyl)pyrazol-w-yl)-2-hydroxy-4-oxo-2-butenoic acid
(B-334) 1-(q-(([substituted]heteroaryl)carbonyl)furan-w-yl)-3-hydroxy-3-([substituted]-2H-tetrazol-5-yl)-propenone
(B-335) 4-[nH-(z-alkyl-q-(([substituted]heteroaryl)alkyl))imidazol-w-yl]-2-hydroxy-4-oxo-2-butenoic acid
(B-336) 1-(q-(([substituted]aryl)aminocarbonyl)pyridin-w-yl)-3-hydroxy-3-([substituted]-2H-tetrazol-5-yl)-propenone
(B-337) 1-[(q-(([substituted]heteroaryl)alkyl)-z-halogeno)thiophen-w-yl]-3-hydroxy-3-([substituted]-2H-tetrazol-5-yl)-propenone
(B-338) 4-(q-(([substituted]aryl)carbonyl)furan-w-yl)-2-hydroxy-4-oxo-2-butenoic acid
(B-339) 1-[(z-alkyl-q-(([substituted]aryl)carboxy))furan-w-yl]-3-hydroxy-3-([substituted]-1H-1,2,4-triazol-3-yl)-propenone
(B-340) 3-hydroxy-3-([substituted]-2H-tetrazol-5-yl)-1-(q-(([substituted]aryl)thio)oxazol-w-yl)-propenone
(B-341) 1-[(z-halogeno-q-([substituted]heteroaryl))isoxazol-w-yl]-3-hydroxy-3-([substituted]-2H-tetrazol-5-yl)-propenone
(B-342) 4-(q-(([substituted]aryl)aminosulfonyl)isoxazol-w-yl)-2-hydroxy-4-oxo-2-butenoic acid
(B-343) 1-[(z-alkyl-q-(([substituted]heteroaryl)alkyl))thiazol-w-yl]-3-hydroxy-3-([substituted]-2H-tetrazol-5-yl)-propenone
(B-344) 2-hydroxy-4-oxo-4-(nH-q-(([substituted]heteroaryl)sulfonylamino)imidazol-w-yl)-2-butenoic acid
(B-345) 3-hydroxy-1-(q-(([substituted]aryl)sulfonylamino)pyrrol-w-yl)-3-([substituted]-2H-tetrazol-5-yl)-propenone
(B-346) 1-(nH-q-(([substituted]aryl)carbonylamino)imidazol-w-yl)-3-hydroxy-3-([substituted]-2H-tetrazol-5-yl)-propenone
(B-347) 3-hydroxy-1-(q-(([substituted]aryl)thio)thiophen-w-yl)-3-([substituted]-1H-1,2,4-triazol-3-yl)-propenone
(B-348) 1-[(q-(([substituted]aryl)carbonyl)-z-halogeno)furan-w-yl]-3-hydroxy-3-([substituted]-1H-1,2,4-triazol-3-yl)-propenone
(B-349) 1-[(z-alkyl-q-(([substituted]aryl)sulfonyl))oxazol-w-yl]-3-hydroxy-3-([substituted]-2H-tetrazol-5-yl)-propenone
(B-350) 1-[(q-(([substituted]heteroaryl)aminosulfonyl)-z-halogeno)pyridin-w-yl]-3-hydroxy-3-([substituted]-2H-tetrazol-5-yl)-propenone
(B-351) 1-[(z-alkyl-q-(([substituted]aryl)oxy))pyridin-w-yl]-3-hydroxy-3-([substituted]-1H-1,2,4-triazol-3-yl)-propenone
(B-352) 4-(q-(([substituted]heteroaryl)aminocarbonyl)pyrrol-w-yl)-2-hydroxy-4-oxo-2-butenoic acid
(B-353) 1-(q-(([substituted]aryl)alkenyl)oxazol-w-yl)-3-hydroxy-3-([substituted]-1H-1,2,4-triazol-3-yl)-propenone (B-354) 3-hydroxy-1-(q-(([substituted]heteroaryl)carboxy)pyrrol-w-yl)-3-([substituted]-2H-tetrazol-5-yl)-propenone
(B-355) 1-[(z-alkyl-q-(([substituted]aryl)amino))thiazol-w-yl]-3-hydroxy-3-([substituted]-2H-tetrazol-5-yl)-propenone
(B-356) 3-hydroxy-1-(nH-q-(([substituted]aryl)oxy)pyrazol-w-yl)-3-([substituted]-2H-tetrazol-5-yl)-propenone
(B-357) 1-[(z-halogeno-q-(1-hydroxy-([substituted]aryl)methyl))furan-w-yl]-3-hydroxy-3-([substituted]-2H-tetrazol-5-yl)-propenone
(B-358) 1-[(z-alkyl-q-(([substituted]aryl)thio))pyrrol-w-yl]-3-hydroxy-3-([substituted]-1H-1,2,4-triazol-3-yl)-propenone
(B-359) 1-[(z-alkyl-q-(([substituted]aryl)carbonyl))thiophen-w-yl]-3-hydroxy-3-([substituted]-2H-tetrazol-5-yl)-propenone
(B-360) 1-[(z-alkyl-q-([substituted]aryl))pyridin-w-yl]-3-hydroxy-3-([substituted]-2H-tetrazol-5-yl)-propenone
(B-361) 1-[(z-alkyl-q-(([substituted]aryl)sulfonyl))pyrrol-w-yl]-3-hydroxy-3-([substituted]-1H-1,2,4-triazol-3-yl)-propenone
(B-362) 2-hydroxy-4-oxo-4-(q-(([substituted]aryl)thio)thiophen-w-yl)-2-butenoic acid
(B-363) 2-hydroxy-4-oxo-4-(nH-q-(([substituted]heteroaryl)oxy)pyrazol-w-yl)-2-butenoic acid
(B-364) 1-[(q-(([substituted]heteroaryl)carboxy)-z-alkyl)furan-w-yl]-3-hydroxy-3-([substituted]-1H-1,2,4-triazol-3-yl)-propenone
(B-365) 1-[(q-(([substituted]heteroaryl)alkenyl)-z-halogeno)pyridin-w-yl]-3-hydroxy-3-([substituted]-1H-1,2,4-triazol-3-yl)-propenone
(B-366) 1-[(z-alkyl-q-(([substituted]heteroaryl)aminocarbonyl))thiazol-w-yl]-3-hydroxy-3-([substituted]-2H-tetrazol-5-yl)-propenone
(B-367) 4-[(z-alkyl-q-(([substituted]aryl)sulfinyl))isoxazol-w-yl]-2-hydroxy-4-oxo-2-butenoic acid
(B-368) 1-[nH-(q-(([substituted]aryl)aminocarbonyl)-z-halogeno)pyrazol-w-yl]-3-hydroxy-3-([substituted]-1H-1,2,4-triazol-3-yl)-propenone
(B-369) 1-[(q-(([substituted]aryl)carbonyl)-z-halogeno)isoxazol-w-yl]-3-hydroxy-3-([substituted]-1H-1,2,4-triazol-3-yl)-propenone
(B-370) 1-[(z-halogeno-q-(([substituted]aryl)oxy))oxazol-w-yl]-3-hydroxy-3-([substituted]-1H-1,2,4-triazol-3-yl)-propenone
(B-371) 1-(q-(([substituted]aryl)alkyl)pyrrol-w-yl)-3-hydroxy-3-([substituted]-2H-tetrazol-5-yl)-propenone
(B-372) 1-(q-(([substituted]aryl)aminosulfonyl)thiophen-w-yl)-3-hydroxy-3-([substituted]-1H-1,2,4-triazol-3-yl)-propenone
(B-373) 1-[(q-(([substituted]aryl)amino)-z-halogeno)oxazol-w-yl]-3-hydroxy-3-([substituted]-2H-tetrazol-5-yl)-propenone
(B-374) 1-[(z-alkyl-q-(([substituted]heteroaryl)sulfonyl))thiophen-w-yl]-3-hydroxy-3-([substituted]-2H-tetrazol-5-yl)-propenone
(B-375) 1-[(z-alkyl-q-(1-hydroxy-([substituted]aryl)methyl))thiophen-w-yl]-3-hydroxy-3-([substituted]-2H-tetrazol-5-yl)-propenone
(B-376) 1-[(q-([substituted]aryl)-z-halogeno)oxazol-w-yl]-3-hydroxy-3-([substituted]-2H-tetrazol-5-yl)-propenone
(B-377) 1-[(q-(([substituted]aryl)carbonyl)-z-halogeno)thiophen-w-yl]-3-hydroxy-3-([substituted]-1H-1,2,4-triazol-3-yl)-propenone
(B-378) 3-hydroxy-1-(nH-q-(([substituted]heteroaryl)sulfonyl)imidazol-w-yl)-3-([substituted]-2H-tetrazol-5-yl)-propenone
(B-379) 1-[(q-([substituted]aryl)-z-halogeno)pyrrol-w-yl]-3-hydroxy-3-([substituted]-2H-tetrazol-5-yl)-propenone
(B-380) 1-[nH-(z-alkyl-q-(([substituted]aryl)oxycarbonyl))imidazol-w-yl]-3-hydroxy-3-([substituted]-2H-tetrazol-5-yl)-propenone
(B-381) 4-[nH-(z-halogeno-q-(([substituted]heteroaryl)thio))imidazol-w-yl]-2-hydroxy-4-oxo-2-butenoic acid
(B-382) 3-hydroxy-1-(q-(([substituted]aryl)sulfonyl)thiazol-w-yl)-3-([substituted]-2H-tetrazol-5-yl)-propenone
(B-383) 4-[(z-alkyl-q-(([substituted]heteroaryl)aminosulfonyl))pyridin-w-yl]-2-hydroxy-4-oxo-2-butenoic acid
(B-384) 1-[(z-halogeno-q-(([substituted]aryl)sulfinyl))pyrrol-w-yl]-3-hydroxy-3-([substituted]-1H-1,2,4-triazol-3-yl)-propenone
(B-385) 1-[(q-(([substituted]aryl)aminosulfonyl)-z-halogeno)pyridin-w-yl]-3-hydroxy-3-([substituted]-2H-tetrazol-5-yl)-propenone
(B-386) 4-[(z-alkyl-q-(([substituted]aryl)sulfinyl))oxazol-w-yl]-2-hydroxy-4-oxo-2-butenoic acid
(B-387) 2-hydroxy-4-oxo-4-(q-(([substituted]aryl)sulfonylamino)oxazol-w-yl)-2-butenoic acid
(B-388) 3-hydroxy-1-(q-(([substituted]aryl)sulfinyl)pyridin-w-yl)-3-([substituted]-1H-1,2,4-triazol-3-yl)-propenone
(B-389) 1-[(q-(([substituted]aryl)aminosulfonyl)-z-halogeno)thiazol-w-yl]-3-hydroxy-3-([substituted]-1H-1,2,4-triazol-3-yl)-propenone
(B-390) 4-[(q-(([substituted]aryl)carbonylamino)-z-halogeno)isoxazol-w-yl]-2-hydroxy-4-oxo-2-butenoic acid
(B-391) 4-[(z-alkyl-q-(1-hydroxy-([substituted]aryl)methyl))furan-w-yl]-2-hydroxy-4-oxo-2-butenoic acid
(B-392) 1-[nH-(z-alkyl-q-(([substituted]heteroaryl)aminosulfonyl))imidazol-w-yl]-3-hydroxy-3-([substituted]-2H-tetrazol-5-yl)-propenone
(B-393) 3-hydroxy-1-(q-(([substituted]heteroaryl)thio)thiazol-w-yl)-3-([substituted]-1H-1,2,4-triazol-3-yl)-propenone
(B-394) 1-[(q-(([substituted]heteroaryl)alkenyl)-z-alkyl)thiazol-w-yl]-3-hydroxy-3-([substituted]-2H-tetrazol-5-yl)-propenone
(B-395) 4-[(z-alkyl-q-(([substituted]aryl)sulfonylamino))oxazol-w-yl]-2-hydroxy-4-oxo-2-butenoic acid
(B-396) 3-hydroxy-1-(q-(([substituted]heteroaryl)sulfonylamino)pyrrol-w-yl)-3-([substituted]-1H-1,2,4-triazol-3-yl)-propenone
(B-397) 4-[(q-(([substituted]aryl)carboxy)-z-halogeno)thiophen-w-yl]-2-hydroxy-4-oxo-2-butenoic acid
(B-398) 1-[(q-(([substituted]heteroaryl)alkenyl)-z-alkyl)pyrrol-w-yl]-3-hydroxy-3-([substituted]-2H-tetrazol-5-yl)-propenone
(B-399) 4-[nH-(z-alkyl-q-(([substituted]aryl)thio))pyrazol-w-yl]-2-hydroxy-4-oxo-2-butenoic acid
(B-400) 4-[(z-halogeno-q-(([substituted]aryl)sulfinyl))furan-w-yl]-2-hydroxy-4-oxo-2-butenoic acid
(B-401) 4-(nH-q-(([substituted]aryl)aminocarbonyl)pyrazol-w-yl)-2-hydroxy-4-oxo-2-butenoic acid
(B-402) 3-hydroxy-1-(q-(([substituted]aryl)sulfinyl)isoxazol-w-yl)-3-([substituted]-1H-1,2,4-triazol-3-yl)-propenone
(B-403) 2-hydroxy-4-oxo-4-(q-(([substituted]heteroaryl)oxy)furan-w-yl)-2-butenoic acid
(B-404) 1-[(z-halogeno-q-(1-hydroxy-([substituted]heteroaryl)methyl))furan-w-yl]-3-hydroxy-3-([substituted]-2H-tetrazol-5-yl)-propenone (B-405) 1-[(z-alkyl-q-(([substituted]aryl)oxy))pyrrol-w-yl]-3-hydroxy-3-([substituted]-2H-tetrazol-5-yl)-propenone
(B-406) 4-[(z-halogeno-q-(([substituted]heteroaryl)oxycarbonyl))isoxazol-w-yl]-2-hydroxy-4-oxo-2-butenoic acid
(B-407) 1-[(z-alkyl-q-(([substituted]aryl)alkyl))pyridin-w-yl]-3-hydroxy-3-([substituted]-1H-1,2,4-triazol-3-yl)-propenone
(B-408) 1-(q-(([substituted]aryl)amino)furan-w-yl)-3-hydroxy-3-([substituted]-2H-tetrazol-5-yl)-propenone
(B-409) 1-(q-(([substituted]aryl)aminocarbonyl)isoxazol-w-yl)-3-hydroxy-3-([substituted]-1H-1,2,4-triazol-3-yl)-propenone
(B-410) 1-[(q-(([substituted]aryl)alkyl)-z-halogeno)pyridin-w-yl]-3-hydroxy-3-([substituted]-1H-1,2,4-triazol-3-yl)-propenone
(B-411) 4-[(z-alkyl-q-([substituted]heteroaryl))pyridin-w-yl]-2-hydroxy-4-oxo-2-butenoic acid
(B-412) 1-[(z-alkyl-q-([substituted]heteroaryl))thiazol-w-yl]-3-hydroxy-3-([substituted]-2H-tetrazol-5-yl)-propenone
(B-413) 1-[(z-alkyl-q-(([substituted]heteroaryl)carbonylamino))isoxazol-w-yl]-3-hydroxy-3-([substituted]-1H-1,2,4-triazol-3-yl)-propenone
(B-414) 1-[(z-alkyl-q-(([substituted]aryl)sulfonylamino))furan-w-yl]-3-hydroxy-3-([substituted]-2H-tetrazol-5-yl)-propenone
(B-415) 1-[(z-alkyl-q-(([substituted]aryl)sulfonyl))furan-w-yl]-3-hydroxy-3-([substituted]-2H-tetrazol-5-yl)-propenone
(B-416) 4-[(q-(([substituted]aryl)carbonyl)-z-halogeno)furan-w-yl]-2-hydroxy-4-oxo-2-butenoic acid
(B-417) 3-hydroxy-1-(q-(1-hydroxy-([substituted]heteroaryl)methyl)isoxazol-w-yl)-3-([substituted]-2H-tetrazol-5-yl)-propenone
(B-418) 4-[(q-(([substituted]heteroaryl)aminocarbonyl)-z-halogeno)pyrrol-w-yl]-2-hydroxy-4-oxo-2-butenoic acid
(B-419) 3-hydroxy-1-(q-(([substituted]heteroaryl)sulfonyl)thiophen-w-yl)-3-([substituted]-2H-tetrazol-5-yl)-propenone
(B-420) 3-hydroxy-1-(q-(([substituted]heteroaryl)sulfinyl)furan-w-yl)-3-([substituted]-1H-1,2,4-triazol-3-yl)-propenone
(B-421) 4-(q-(([substituted]aryl)carbonylamino)thiophen-w-yl)-2-hydroxy-4-oxo-2-butenoic acid
(B-422) 1-[(z-alkyl-q-(([substituted]heteroaryl)aminosulfonyl))thiophen-w-yl]-3-hydroxy-3-([substituted]-2H-tetrazol-5-yl)-propenone
(B-423) 1-[(z-alkyl-q-([substituted]aryl))pyrrol-w-yl]-3-hydroxy-3-([substituted]-2H-tetrazol-5-yl)-propenone
(B-424) 1-[(z-alkyl-q-(([substituted]heteroaryl)oxy))thiophen-w-yl]-3-hydroxy-3-([substituted]-2H-tetrazol-5-yl)-propenone
(B-425) 1-[nH-(z-halogeno-q-(([substituted]heteroaryl)sulfonyl))imidazol-w-yl]-3-hydroxy-3-([substituted]-2H-tetrazol-5-yl)-propenone
(B-426) 3-hydroxy-1-(q-(([substituted]heteroaryl)oxy)thiophen-w-yl)-3-([substituted]-2H-tetrazol-5-yl)-propenone
(B-427) 3-hydroxy-1-(q-(([substituted]aryl)sulfinyl)thiophen-w-yl)-3-([substituted]-1H-1,2,4-triazol-3-yl)-propenone
(B-428) 1-[(z-alkyl-q-(([substituted]aryl)sulfinyl))thiophen-w-yl]-3-hydroxy-3-([substituted]-2H-tetrazol-5-yl)-propenone
(B-429) 1-[(q-(([substituted]aryl)amino)-z-halogeno)pyrrol-w-yl]-3-hydroxy-3-([substituted]-1H-1,2,4-triazol-3-yl)-propenone
(B-430) 2-hydroxy-4-oxo-4-(q-(([substituted]aryl)oxycarbonyl)thiophen-w-yl)-2-butenoic acid
(B-431) 1-[(z-halogeno-q-(([substituted]aryl)oxy)furan-w-yl]-3-hydroxy-3-([substituted]-2H-tetrazol-5-yl)-propenone
(B-432) 1-[nH-(z-alkyl-q-(([substituted]heteroaryl)aminocarbonyl))imidazol-w-yl]-3-hydroxy-3-([substituted]-2H-tetrazol-5-yl)-propenone
(B-433) 1-[(z-halogeno-q-(1-hydroxy-([substituted]aryl)methyl))isoxazol-w-yl]-3-hydroxy-3-([substituted]-1H-1,2,4-triazol-3-yl)-propenone
(B-434) 1-(nH-q-(([substituted]aryl)aminocarbonyl)pyrazol-w-yl)-3-hydroxy-3-([substituted]-1H-1,2,4-triazol-3-yl)-propenone
(B-435) 1-[nH-(z-halogeno-q-(([substituted]aryl)sulfinyl))pyrazol-w-yl]-3-hydroxy-3-([substituted]-1H-1,2,4-triazol-3-yl)-propenone
(B-436) 1-[nH-(z-alkyl-q-(([substituted]heteroaryl)sulfonylamino))pyrazol-w-yl]-3-hydroxy-3-([substituted]-2H-tetrazol-5-yl)-propenone
(B-437) 1-[(z-halogeno-q-([substituted]heteroaryl))pyridin-w-yl]-3-hydroxy-3-([substituted]-1H-1,2,4-triazol-3-yl)-propenone
(B-438) 4-[nH-(z-alkyl-q-(([substituted]aryl)alkyl))pyrazol-w-yl]-2-hydroxy-4-oxo-2-butenoic acid
(B-439) 4-[(q-(([substituted]aryl)alkenyl)-z-alkyl)furan-w-yl]-2-hydroxy-4-oxo-2-butenoic acid
(B-440) 4-[(q-(([substituted]aryl)amino)-z-halogeno)pyridin-w-yl]-2-hydroxy-4-oxo-2-butenoic acid
(B-441) 4-[(q-(([substituted]heteroaryl)alkenyl)-z-halogeno)isoxazol-w-yl]-2-hydroxy-4-oxo-2-butenoic acid
(B-442) 3-hydroxy-1-(q-(([substituted]heteroaryl)sulfinyl)pyrrol-w-yl)-3-([substituted]-1H-1,2,4-triazol-3-yl)-propenone
(B-443) 1-(nH-q-(([substituted]heteroaryl)carbonyl)pyrazol-w-yl)-3-hydroxy-3-([substituted]-2H-tetrazol-5-yl)-propenone
(B-444) 1-(nH-q-(([substituted]aryl)amino)imidazol-w-yl)-3-hydroxy-3-([substituted]-2H-tetrazol-5-yl)-propenone
(B-445) 1-[(z-alkyl-q-(([substituted]heteroaryl)amino))pyrrol-w-yl]-3-hydroxy-3-([substituted]-1H-1,2,4-triazol-3-yl)-propenone
(B-446) 1-[(z-halogeno-q-(([substituted]aryl)oxy))thiazol-w-yl]-3-hydroxy-3-([substituted]-1H-1,2,4-triazol-3-yl)-propenone
(B-447) 1-(q-(([substituted]aryl)carbonyl)furan-w-yl)-3-hydroxy-3-([substituted]-2H-tetrazol-5-yl)-propenone
(B-448) 4-[(z-halogeno-q-(([substituted]aryl)thio))pyridin-w-yl]-2-hydroxy-4-oxo-2-butenoic acid
(B-449) 1-[(z-alkyl-q-(([substituted]heteroaryl)sulfinyl))thiophen-w-yl]-3-hydroxy-3-([substituted]-1H-1,2,4-triazol-3-yl)-propenone
(B-450) 4-[(q-(([substituted]aryl)aminocarbonyl)-z-halogeno)pyridin-w-yl]-2-hydroxy-4-oxo-2-butenoic acid
(B-451) 1-[nH-(z-alkyl-q-(([substituted]heteroaryl)sulfonyl))imidazol-w-yl]-3-hydroxy-3-([substituted]-2H-tetrazol-5-yl)-propenone
(B-452) 3-hydroxy-1-(nH-q-(([substituted]heteroaryl)carboxy)pyrazol-w-yl)-3-([substituted]-2H-tetrazol-5-yl)-propenone
(B-453) 1-(q-(([substituted]aryl)alkenyl)thiophen-w-yl)-3-hydroxy-3-([substituted]-2H-tetrazol-5-yl)-propenone
(B-454) 1-[(z-halogeno-q-(([substituted]heteroaryl)oxy))oxazol-w-yl]-3-hydroxy-3-([substituted]-1H-1,2,4-triazol-3-yl)-propenone (B-455) 4-[(q-(([substituted]aryl)alkyl)-z-halogeno)oxazol-w-yl]-2-hydroxy-4-oxo-2-butenoic acid
(B-456) 1-(nH-q-(([substituted]heteroaryl)alkyl)pyrazol-w-yl)-3-hydroxy-3-([substituted]-1H-1,2,4-triazol-3-yl)-propenone
(B-457) 4-[(q-(([substituted]heteroaryl)alkyl)-z-halogeno)pyrrol-w-yl]-2-hydroxy-4-oxo-2-butenoic acid
(B-458) 4-[(q-(([substituted]heteroaryl)amino)-z-halogeno)isoxazol-w-yl]-2-hydroxy-4-oxo-2-butenoic acid
(B-459) 4-[(z-halogeno-q-(1-hydroxy-([substituted]aryl)methyl))isoxazol-w-yl]-2-hydroxy-4-oxo-2-butenoic acid
(B-460) 1-[(q-(([substituted]heteroaryl)alkenyl)-z-halogeno)pyrrol-w-yl]-3-hydroxy-3-([substituted]-1H-1,2,4-triazol-3-yl)-propenone
(B-461) 2-hydroxy-4-oxo-4-(q-(([substituted]aryl)sulfonylamino)pyrrol-w-yl)-2-butenoic acid
(B-462) 1-[(z-halogeno-q-(([substituted]heteroaryl)sulfinyl))isoxazol-w-yl]-3-hydroxy-3-([substituted]-1H-1,2,4-triazol-3-yl)-propenone
(B-463) 1-[(z-alkyl-q-(([substituted]heteroaryl)amino))isoxazol-w-yl]-3-hydroxy-3-([substituted]-2H-tetrazol-5-yl)-propenone
(B-464) 1-[(q-(([substituted]heteroaryl)carbonyl)-z-halogeno)isoxazol-w-yl]-3-hydroxy-3-([substituted]-2H-tetrazol-5-yl)-propenone
(B-465) 4-[(q-(([substituted]aryl)carbonyl)-z-halogeno)pyrrol-w-yl]-2-hydroxy-4-oxo-2-butenoic acid
(B-466) 2-hydroxy-4-oxo-4-(nH-q-(([substituted]aryl)thio)pyrazol-w-yl)-2-butenoic acid
(B-467) 3-hydroxy-1-(q-(([substituted]heteroaryl)sulfonyl)isoxazol-w-yl)-3-([substituted]-2H-tetrazol-5-yl)-propenone
(B-468) 1-(nH-q-(([substituted]heteroaryl)aminocarbonyl)pyrazol-w-yl)-3-hydroxy-3-([substituted]-2H-tetrazol-5-yl)-propenone
(B-469) 3-hydroxy-3-([substituted]-2H-tetrazol-5-yl)-1-(q-((([substituted]heteroaryl)carboxy)thiophen-w-yl)-propenone
(B-470) 1-[(z-halogeno-q-(([substituted]heteroaryl)sulfonylamino))thiophen-w-yl]-3-hydroxy-3-([substituted]-1H-1,2,4-triazol-3-yl)-propenone
(B-471) 3-hydroxy-1-(q-(([substituted]aryl)sulfinyl)oxazol-w-yl)-3-([substituted]-1H-1,2,4-triazol-3-yl)-propenone
(B-472) 4-(q-(([substituted]heteroaryl)amino)pyrrol-w-yl)-2-hydroxy-4-oxo-2-butenoic acid
(B-473) 1-(nH-q-(([substituted]aryl)aminocarbonyl)imidazol-w-yl)-3-hydroxy-3-([substituted]-2H-tetrazol-5-yl)-propenone
(B-474) 1-(q-(([substituted]aryl)amino)pyrrol-w-yl)-3-hydroxy-3-([substituted]-2H-tetrazol-5-yl)-propenone
(B-475) 1-[nH-(z-alkyl-q-(([substituted]aryl)oxycarbonyl))pyrazol-w-yl]-3-hydroxy-3-([substituted]-2H-tetrazol-5-yl)-propenone
(B-476) 1-(q-(([substituted]aryl)carbonylamino)thiazol-w-yl)-3-hydroxy-3-([substituted]-1H-1,2,4-triazol-3-yl)-propenone
(B-477) 1-[(z-alkyl-q-(([substituted]aryl)thio))isoxazol-w-yl]-3-hydroxy-3-([substituted]-2H-tetrazol-5-yl)-propenone
(B-478) 4-[(z-alkyl-q-(([substituted]heteroaryl)carbonyl))thiophen-w-yl]-2-hydroxy-4-oxo-2-butenoic acid
(B-479) 4-(nH-q-(([substituted]aryl)alkenyl)pyrazol-w-yl)-2-hydroxy-4-oxo-2-butenoic acid
(B-480) 4-[(z-halogeno-q-(([substituted]heteroaryl)sulfonylamino))pyridin-w-yl]-2-hydroxy-4-oxo-2-butenoic acid
(B-481) 4-(q-(([substituted]aryl)carbonyl)pyrrol-w-yl)-2-hydroxy-4-oxo-2-butenoic acid
(B-482) 1-[nH-(q-(([substituted]heteroaryl)amino)-z-halogeno)pyrazol-w-yl]-3-hydroxy-3-([substituted]-1H-1,2,4-triazol-3-yl)-propenone
(B-483) 4-[(z-alkyl-q-(([substituted]heteroaryl)thio))furan-w-yl]-2-hydroxy-4-oxo-2-butenoic acid
(B-484) 1-[nH-(z-alkyl-q-(([substituted]heteroaryl)oxy))imidazol-w-yl]-3-hydroxy-3-([substituted]-1H-1,2,4-triazol-3-yl)-propenone
(B-485) 1-(nH-q-([substituted]heteroaryl)imidazol-w-yl)-3-hydroxy-3-([substituted]-1H-1,2,4-triazol-3-yl)-propenone
(B-486) 1-[(z-alkyl-q-(([substituted]aryl)sulfinyl))pyrrol-w-yl]-3-hydroxy-3-([substituted]-2H-tetrazol-5-yl)-propenone
(B-487) 1-[(z-halogeno-q-(([substituted]heteroaryl)oxycarbonyl))isoxazol-w-yl]-3-hydroxy-3-([substituted]-2H-tetrazol-5-yl)-propenone
(B-488) 1-(q-(([substituted]aryl)carboxy)thiophen-w-yl)-3-hydroxy-3-([substituted]-2H-tetrazol-5-yl)-propenone
(B-489) 1-[(z-alkyl-q-([substituted]heteroaryl))isoxazol-w-yl]-3-hydroxy-3-([substituted]-2H-tetrazol-5-yl)-propenone
(B-490) 1-[nH-(z-halogeno-q-(([substituted]aryl)sulfonyl))imidazol-w-yl]-3-hydroxy-3-([substituted]-2H-tetrazol-5-yl)-propenone
(B-491) 4-[(z-alkyl-q-([substituted]aryl))pyridin-w-yl]-2-hydroxy-4-oxo-2-butenoic acid
(B-492) 3-hydroxy-1-(q-(([substituted]aryl)sulfonylamino)isoxazol-w-yl)-3-([substituted]-2H-tetrazol-5-yl)-propenone
(B-493) 1-[(z-halogeno-q-([substituted]heteroaryl))pyrrol-w-yl]-3-hydroxy-3-([substituted]-2H-tetrazol-5-yl)-propenone
(B-494) 1-[(z-halogeno-q-(([substituted]heteroaryl)sulfonyl))furan-w-yl]-3-hydroxy-3-([substituted]-2H-tetrazol-5-yl)-propenone
(B-495) 1-[(z-alkyl-q-(([substituted]aryl)alkyl))furan-w-yl]-3-hydroxy-3-([substituted]-2H-tetrazol-5-yl)-propenone
(B-496) 4-(q-(([substituted]heteroaryl)aminosulfonyl)pyridin-w-yl)-2-hydroxy-4-oxo-2-butenoic acid
(B-497) 4-[(z-alkyl-q-([substituted]heteroaryl))isoxazol-w-yl]-2-hydroxy-4-oxo-2-butenoic acid
(B-498) 1-[(q-(([substituted]aryl)carbonyl)-z-halogeno)furan-w-yl]-3-hydroxy-3-([substituted]-2H-tetrazol-5-yl)-propenone
(B-499) 4-[(q-(([substituted]heteroaryl)carboxy)-z-alkyl)pyrrol-w-yl]-2-hydroxy-4-oxo-2-butenoic acid
(B-500) 1-[(z-alkyl-q-(([substituted]aryl)carbonylamino))pyridin-w-yl]-3-hydroxy-3-([substituted]-2H-tetrazol-5-yl)-propenone
(B-501) 4-[(z-halogeno-q-(([substituted]aryl)sulfonylamino))thiophen-w-yl]-2-hydroxy-4-oxo-2-butenoic acid
(B-502) 1-[(q-(([substituted]aryl)amino)-z-halogeno)thiazol-w-yl]-3-hydroxy-3-([substituted]-2H-tetrazol-5-yl)-propenone
(B-503) 1-[nH-(q-(([substituted]aryl)carbonyl)-z-halogeno)imidazol-w-yl]-3-hydroxy-3-([substituted]-1H-1,2,4-triazol-3-yl)-propenone
(B-504) 1-[(z-halogeno-q-(([substituted]aryl)sulfonyl))pyridin-w-yl]-3-hydroxy-3-([substituted]-2H-tetrazol-5-yl)-propenone
(B-505) 1-[(q-(([substituted]aryl)alkenyl)-z-halogeno)pyridin-w-yl]-3-hydroxy-3-([substituted]-1H-1,2,4-triazol-3-yl)-propenone
(B-506) 4-(q-([substituted]aryl)pyridin-w-yl)-2-hydroxy-4-oxo-2-butenoic acid (B-507) 1-[(z-alkyl-q-(1-hydroxy-([substituted]heteroaryl)methyl))isoxazol-w-yl]-3-hydroxy-3-([substituted]-2H-tetrazol-5-yl)-propenone (B-508) 1-[(z-halogeno-q-(1-hydroxy-([substituted]aryl)methyl))thiazol-w-yl]-3-hydroxy-3-([substituted]-1H-1,2,4-triazol-3-yl)-propenone (B-509) 1-(q-(([substituted]heteroaryl)alkenyl)pyrrol-w-yl)-3-hydroxy-3-([substituted]-2H-tetrazol-5-yl)-propenone (B-510) 1-[(z-alkyl-q-(([substituted]aryl)carbonyl))thiazol-w-yl]-3-hydroxy-3-([substituted]-2H-tetrazol-5-yl)-propenone (B-511) 1-[(q-([substituted]aryl)-z-halogeno)isoxazol-w-yl]-3-hydroxy-3-([substituted]-1H-1,2,4-triazol-3-yl)-propenone (B-512) 3-hydroxy-3-([substituted]-2H-tetrazol-5-yl)-1-(q-(([substituted]aryl)thio)pyridin-w-yl)-propenone (B-513) 1-[(q-(([substituted]aryl)amino)-z-halogeno)thiophen-w-yl]-3-hydroxy-3-([substituted]-1H-1,2,4-triazol-3-yl)-propenone (B-514) 1-[(z-alkyl-q-(([substituted]heteroaryl)oxycarbonyl))furan-w-yl]-3-hydroxy-3-([substituted]-1H-1,2,4-triazol-3-yl)-propenone (B-515) 1-[(q-(([substituted]heteroaryl)aminosulfonyl)-z-halogeno)isoxazol-w-yl]-3-hydroxy-3-([substituted]-2H-tetrazol-5-yl)-propenone (B-516) 4-(q-(([substituted]aryl)aminosulfonyl)oxazol-w-yl)-2-hydroxy-4-oxo-2-butenoic acid (B-517) 1-(nH-q-(([substituted]heteroaryl)alkyl)pyrazol-w-yl)-3-hydroxy-3-([substituted]-2H-tetrazol-5-yl)-propenone (B-518) 1-[(q-(([substituted]aryl)carbonylamino)-z-halogeno)isoxazol-w-yl]-3-hydroxy-3-([substituted]-1H-1,2,4-triazol-3-yl)-propenone (B-519) 1-[(z-halogeno-q-(([substituted]aryl)oxycarbonyl))pyrrol-w-yl]-3-hydroxy-3-([substituted]-1H-1,2,4-triazol-3-yl)-propenone (B-520) 1-[(z-alkyl-q-(([substituted]heteroaryl)alkyl))furan-w-yl]-3-hydroxy-3-([substituted]-2H-tetrazol-5-yl)-propenone (B-521) 1-(q-(([substituted]aryl)carboxy)furan-w-yl)-3-hydroxy-3-([substituted]-2H-tetrazol-5-yl)-propenone (B-522) 1-[(z-alkyl-q-(([substituted]aryl)oxy))thiazol-w-yl]-3-hydroxy-3-([substituted]-1H-1,2,4-triazol-3-yl)-propenone (B-523) 1-[(z-alkyl-q-(([substituted]heteroaryl)sulfinyl))pyridin-w-yl]-3-hydroxy-3-([substituted]-2H-tetrazol-5-yl)-propenone (B-524) 2-hydroxy-4-oxo-4-(q-(([substituted]aryl)oxycarbonyl)oxazol-w-yl)-2-butenoic acid (B-525) 1-[(z-alkyl-q-(([substituted]aryl)thio))oxazol-w-yl]-3-hydroxy-3-([substituted]-2H-tetrazol-5-yl)-propenone (B-526) 1-[(z-halogeno-q-(([substituted]heteroaryl)thio))pyridin-w-yl]-3-hydroxy-3-([substituted]-2H-tetrazol-5-yl)-propenone (B-527) 1-[nH-(q-(([substituted]heteroaryl)amino)-z-halogeno)pyrazol-w-yl]-3-hydroxy-3-([substituted]-2H-tetrazol-5-yl)-propenone (B-528) 1-[(q-(([substituted]heteroaryl)aminocarbonyl)-z-halogeno)oxazol-w-yl]-3-hydroxy-3-([substituted]-2H-tetrazol-5-yl)-propenone (B-529) 1-[(z-alkyl-q-(([substituted]aryl)sulfinyl))thiazol-w-yl]-3-hydroxy-3-([substituted]-2H-tetrazol-5-yl)-propenone (B-530) 3-hydroxy-1-(q-(([substituted]aryl)sulfinyl)thiophen-w-yl)-3-([substituted]-2H-tetrazol-5-yl)-propenone (B-531) 1-[(z-alkyl-q-(([substituted]heteroaryl)sulfonyl))thiazol-w-yl]-3-hydroxy-3-([substituted]-2H-tetrazol-5-yl)-propenone (B-532) 4-[(q-(([substituted]heteroaryl)amino)-z-halogeno)furan-w-yl]-2-hydroxy-4-oxo-2-butenoic acid (B-533) 3-hydroxy-1-(q-(([substituted]aryl)oxy)thiophen-w-yl)-3-([substituted]-2H-tetrazol-5-yl)-propenone (B-534) 4-[(z-alkyl-q-(([substituted]aryl)sulfonyl))pyridin-w-yl]-2-hydroxy-4-oxo-2-butenoic acid (B-535) 1-[(z-alkyl-q-(([substituted]aryl)amino))oxazol-w-yl]-3-hydroxy-3-([substituted]-1H-1,2,4-triazol-3-yl)-propenone (B-536) 1-[(q-(([substituted]heteroaryl)carbonylamino)-z-halogeno)isoxazol-w-yl]-3-hydroxy-3-([substituted]-1H-1,2,4-triazol-3-yl)-propenone (B-537) 1-[nH-(z-alkyl-q-([substituted]heteroaryl))imidazol-w-yl]-3-hydroxy-3-([substituted]-1H-1,2,4-triazol-3-yl)-propenone (B-538) 4-[(z-halogeno-q-(([substituted]aryl)oxy))pyrrol-w-yl]-2-hydroxy-4-oxo-2-butenoic acid (B-539) 1-(q-(([substituted]heteroaryl)carbonylamino)furan-w-yl)-3-hydroxy-3-([substituted]-2H-tetrazol-5-yl)-propenone (B-540) 4-[(z-alkyl-q-(([substituted]aryl)sulfonyl))pyrrol-w-yl]-2-hydroxy-4-oxo-2-butenoic acid (B-541) 1-[(z-halogeno-q-(([substituted]aryl)sulfonylamino))oxazol-w-yl]-3-hydroxy-3-([substituted]-1H-1,2,4-triazol-3-yl)-propenone (B-542) 1-[nH-(q-(([substituted]heteroaryl)alkenyl)-z-halogeno)pyrazol-w-yl]-3-hydroxy-3-([substituted]-1H-1,2,4-triazol-3-yl)-propenone (B-543) 1-[nH-(z-alkyl-q-(([substituted]heteroaryl)oxy))pyrazol-w-yl]-3-hydroxy-3-([substituted]-2H-tetrazol-5-yl)-propenone (B-544) 1-[(q-(([substituted]heteroaryl)alkenyl)-z-halogeno)pyrrol-w-yl]-3-hydroxy-3-([substituted]-2H-tetrazol-5-yl)-propenone (B-545) 1-[(z-halogeno-q-(([substituted]aryl)oxy))isoxazol-w-yl]-3-hydroxy-3-([substituted]-2H-tetrazol-5-yl)-propenone (B-546) 1-[(z-halogeno-q-(1-hydroxy-([substituted]heteroaryl)methyl))isoxazol-w-yl]-3-hydroxy-3-([substituted]-1H-1,2,4-triazol-3-yl)-propenone (B-547) 1-[(z-alkyl-q-([substituted]heteroaryl))oxazol-w-yl]-3-hydroxy-3-([substituted]-2H-tetrazol-5-yl)-propenone (B-548) 1-[(z-halogeno-q-(([substituted]heteroaryl)oxy))pyrrol-w-yl]-3-hydroxy-3-([substituted]-2H-tetrazol-5-yl)-propenone (B-549) 2-hydroxy-4-oxo-4-(q-(([substituted]aryl)sulfonylamino)thiophen-w-yl)-2-butenoic acid (B-550) 4-(nH-q-(([substituted]aryl)carbonylamino)imidazol-w-yl)-2-hydroxy-4-oxo-2-butenoic acid (B-551) 2-hydroxy-4-(q-(([substituted]heteroaryl)carboxy)oxazol-w-yl)-4-oxo-2-butenoic acid (B-552) 1-[(q-(([substituted]heteroaryl)carbonyl)-z-halogeno)pyrrol-w-yl]-3-hydroxy-3-([substituted]-1H-1,2,4-triazol-3-yl)-propenone (B-553) 1-[(z-alkyl-q-(([substituted]aryl)sulfinyl))thiazol-w-yl]-3-hydroxy-3-([substituted]-1H-1,2,4-triazol-3-yl)-propenone (B-554) 4-(q-(([substituted]heteroaryl)alkenyl)thiazol-w-yl)-2-hydroxy-4-oxo-2-butenoic acid (B-555) 4-(q-(([substituted]heteroaryl)carbonyl)pyridin-w-yl)-2-hydroxy-4-oxo-2-butenoic acid (B-556) 4-[(z-alkyl-q-(([substituted]heteroaryl)aminosulfonyl))pyrrol-w-yl]-2-hydroxy-4-oxo-2-butenoic acid (B-557) 4-(q-(([substituted]aryl)carbonylamino)oxazol-w-yl)-2-hydroxy-4-oxo-2-butenoic acid
(B-558) 1-[(z-alkyl-q-(([substituted]heteroaryl)sulfonylamino))pyridin-w-yl]-3-hydroxy-3-([substituted]-1H-1,2,4-triazol-3-yl)-propenone
(B-559) 1-(q-(([substituted]heteroaryl)aminosulfonyl)furan-w-yl)-3-hydroxy-3-([substituted]-1H-1,2,4-triazol-3-yl)-propenone
(B-560) 2hydroxy-4-oxo-4-(q-(([substituted]heteroaryl)thio)oxazol-w-yl)-2-butenoic acid
(B-561) 1-[(z-halogeno-q-([substituted]hetoroaryl))furan-w-yl]-3-hydroxy-3-([substituted]-1H-1,2,4-triazol-3-yl)-propenone
(B-562) 1-[(q-(([substituted]aryl)amino)-z-halogeno)pyridin-w-yl]-3-hydroxy-3-([substituted]-2H-tetrazol-5-yl)-propenone
(B-563) 4-[(q-(([substituted]heteroaryl)carbonyl)-z-halogeno)pyrrol-w-yl]-2-hydroxy-4-oxo-2-butenoic acid
(B-564) 4-[(z-halogeno-q-(([substituted]aryl)oxy))oxazol-w-yl]-2-hydroxy-4-oxo-2-butenoic acid
(B-565) 1-[(q-(([substituted]heteroaryl)carbonyl)-z-halogeno)isoxazol-w-yl]-3-hydroxy-3-([substituted]-1H-1,2,4-triazol-3-yl)-propenone
(B-566) 1-[(z-halogeno-q-(1-hydroxy-([substituted]aryl)methyl))oxazol-w-yl]-3-hydroxy-3-([substituted]-2H-tetrazol-5-yl)-propenone
(B-567) 4-(nH-q-(([substituted]heteroaryl)aminosulfonyl)pyrazol-w-yl)-2-hydroxy-4-oxo-2-butenoic acid
(B-568) 4-(q-(([substituted]aryl)alkenyl)pyrrol-w-yl)-2-hydroxy-4-oxo-2-butenoic acid
(B-569) 1-[(z-halogeno-q-(([substituted]aryl)sulfonylamino))thiophen-w-yl]-3-hydroxy-3-([substituted]-2H-tetrazol-5-yl)-propenone
(B-570) 4-(q-(([substituted]aryl)alkyl)thiophen-w-yl)-2-hydroxy-4-oxo-2-butenoic acid
(B-571) 1-[(q-(([substituted]heteroaryl)alkyl)-z-halogeno)furan-w-yl]-3-hydroxy-3-([substituted]-1H-1,2,4-triazol-3-yl)-propenone
(B-572) 2-hydroxy-4-oxo-4-(nH-q-(([substituted]aryl)oxy)imidazol-w-yl)-2-butenoic acid
(B-573) 1-(q-([substituted]aryl)oxazol-w-yl)-3-hydroxy-3-([substituted]-1H-1,2,4-triazol-3-yl)-propenone
(B-574) 1-(q-(([substituted]heteroaryl)aminocarbonyl)thiophen-w-yl)-3-hydroxy-3-([substituted]-2H-tetrazol-5-yl)-propenone
(B-575) 4-[(z-halogeno-q-(([substituted]aryl)sulfonyl))pyrrol-w-yl]-2-hydroxy-4-oxo-2-butenoic acid
(B-576) 3-hydroxy-1-(q-(1-hydroxy-([substituted]heteroaryl)methyl)pyrrol-w-yl)-3-([substituted]-1H-1,2,4-triazol-3-yl)-propenone
(B-577) 1-(q-(([substituted]heteroaryl)carbonyl)pyridin-w-yl)-3-hydroxy-3-([substituted]-1H-1,2,4-triazol-3-yl)-propenone
(B-578) 4-[(z-alkyl-q-(([substituted]aryl)amino))pyridin-w-yl]-2-hydroxy-4-oxo-2-butenoic acid
(B-579) 1-[(q-(([substituted]aryl)carboxy)-z-halogeno)pyridin-w-yl]-3-hydroxy-3-([substituted]-1H-1,2,4-triazol-3-yl)-propenone
(B-580) 1-(q-(([substituted]aryl)aminosulfonyl)pyrrol-w-yl)-3-hydroxy-3-([substituted]-2H-tetrazol-5-yl)-propenone
(B-581) 3-hydroxy-1-(q-(([substituted]aryl)oxy)isoxazol-w-yl)-3-([substituted]-1H-1,2,4-triazol-3-yl)-propenone
(B-582) 3-hydroxy-1-(q-(([substituted]aryl)sulfonyl)pyridin-w-yl)-3-([substituted]-1H-1,2,4-triazol-3-yl)-propenone
(B-583) 4-[(z-alkyl-q-(([substituted]heteroaryl)sulfinyl))isoxazol-w-yl]-2-hydroxy-4-oxo-2-butenoic acid
(B-584) 4-[(z-alkyl-q-(([substituted]heteroaryl)carbonylamino))thiazol-w-yl]-2-hydroxy-4-oxo-2-butenoic acid
(B-585) 3-hydroxy-1-(q-(([substituted]heteroaryl)oxy)oxazol-w-yl)-3-([substituted]-1H-1,2,4-triazol-3-yl)-propenone
(B-586) 4-[nH-(q-(([substituted]aryl)aminosulfonyl)-z-halogeno)imidazol-w-yl]-2-hydroxy-4-oxo-2-butenoic acid
(B-587) 4-[(z-halogeno-q-(1-hydroxy-([substituted]aryl)methyl))thiophen-w-yl]-2-hydroxy-4-oxo-2-butenoic acid
(B-588) 1-[(q-(([substituted]aryl)carbonylamino)-z-halogeno)thiazol-w-yl]-3-hydroxy-3-([substituted]-2H-tetrazol-5-yl)-propenone
(B-589) 1-(q-([substituted]heteroaryl)thiazol-w-yl)-3-hydroxy-3-([substituted]-1H-1,2,4-triazol-3-yl)-propenone
(B-590) 1-[(z-alkyl-q-(([substituted]heteroaryl)oxycarbonyl))thiazol-w-yl]-3-hydroxy-3-([substituted]-1H-1,2,4-triazol-3-yl)-propenone
(B-591) 1-[nH-(q-(([substituted]aryl)aminocarbonyl)-z-halogeno)pyrazol-w-yl]-3-hydroxy-3-([substituted]-2H-tetrazol-5-yl)-propenone
(B-592) 3-hydroxy-1-(q-(1-hydroxy-([substituted]aryl)methyl)oxazol-w-yl)-3-([substituted]-1H-1,2,4-triazol-3-yl)-propenone
(B-593) 1-[(z-alkyl-q-(1-hydroxy-([substituted]heteroaryl)methyl))pyridin-w-yl]-3-hydroxy-3-([substituted]-2H-tetrazol-5-yl)-propenone
(B-594) 2-hydroxy-4-(q-(1-hydroxy-([substituted]heteroaryl)methyl)pyrrol-w-yl)-4-oxo-2-butenoic acid
(B-595) 4-[nH-(z-alkyl-q-(([substituted]aryl)aminosulfonyl))imidazol-w-yl]-2-hydroxy-4-oxo-2-butenoic acid
(B-596) 1-[(z-alkyl-q-(([substituted]aryl)carboxy))pyrrol-w-yl]-3-hydroxy-3-([substituted]-1H-1,2,4-triazol-3-yl)-propenone
(B-597) 1-[(q-([substituted]aryl)-z-halogeno)furan-w-yl]-3-hydroxy-3-([substituted]-2H-tetrazol-5-yl)-propenone
(B-598) 1-[(z-alkyl-q-(([substituted]aryl)sulfinyl))thiophen-w-yl]-3-hydroxy-3-([substituted]-1H-1,2,4-triazol-3-yl)-propenone
(B-599) 4-[(z-alkyl-q-(([substituted]aryl)sulfonyl))isoxazol-w-yl]-2-hydroxy-4-oxo-2-butenoic acid
(B-600) 1-[nH-(q-(([substituted]heteroaryl)carbonyl)-z-halogeno)pyrazol-w-yl]-3-hydroxy-3-([substituted]-2H-tetrazol-5-yl)-propenone
(B-601) 4-[nH-(q-(([substituted]aryl)alkenyl)-z-halogeno)pyrazol-w-yl]-2-hydroxy-4-oxo-2-butenoic acid
(B-602) 3-hydroxy-1-(q-(([substituted]aryl)sulfonyl)thiazol-w-yl)-3-([substituted]-1H-1,2,4-triazol-3-yl)-propenone
(B-603) 1-(q-(([substituted]heteroaryl)alkenyl)furan-w-yl)-3-hydroxy-3-([substituted]-1H-1,2,4-triazol-3-yl)-propenone
(B-604) 3-hydroxy-1-(q-(([substituted]aryl)sulfonyl)isoxazol-w-yl)-3-([substituted]-1H-1,2,4-triazol-3-yl)-propenone
(B-605) 4-[(q-(([substituted]aryl)alkenyl)-z-alkyl)thiophen-w-yl]-2-hydroxy-4-oxo-2-butenoic acid
(B-606) 4-[(z-halogeno-q-(1-hydroxy-([substituted]heteroaryl)methyl))isoxazol-w-yl]-2-hydroxy-4-oxo-2-butenoic acid
(B-607) 1-[(z-halogeno-q-(([substituted]aryl)oxy))pyrrol-w-yl]-3-hydroxy-3-([substituted]-1H-1,2,4-triazol-3-yl)-propenone (B-608) 1-(q-(([substituted]heteroaryl)alkenyl)thiophen-w-yl]-3-hydroxy-3-([substituted]-1H-1,2,4-triazol-3-yl)-propenone (B-609) 4-[(z-alkyl-q-(([substituted]heteroaryl)thio))thiophen-w-yl]-2-hydroxy-4-oxo-2-butenoic acid (B-610) 4-[nH-(q-(([substituted]heteroaryl)aminosulfonyl)-z-halogeno)imidazol-w-yl]-2-hydroxy-4-oxo-2-butenoic acid (B-611) 1-[(z-halogeno-q-(([substituted]aryl)oxy))isoxazol-w-yl]-3-hydroxy-3-([substituted]-1H-1,2,4-triazol-3-yl)-propenone (B-612) 1-[(q-(([substituted]aryl)carbonylamino)-z-halogeno)isoxazol-w-yl]-3-hydroxy-3-([substituted]-2H-tetrazol-5-yl)-propenone (B-613) 1-[(q-(([substituted]aryl)alkyl)-z-halogeno)isoxazol-w-yl]-3-hydroxy-3-([substituted]-1H-1,2,4-triazol-3-yl)-propenone (B-614) 4-[(z-alkyl-q-(1-hydroxy-([substituted]heteroaryl)methyl))oxazol-w-yl]-2-hydroxy-4-oxo-2-butenoic acid (B-615) 2-hydroxy-4-oxo-4-(nH-q-(([substituted]heteroaryl)oxycarbonyl)imidazol-w-yl)-2-butenoic acid (B-616) 4-[(z-alkyl-q-(([substituted]aryl)oxycarbonyl))isoxazol-w-yl]-2-hydroxy-4-oxo-2-butenoic acid (B-617) 1-(q-(([substituted]heteroaryl)aminosulfonyl)thiophen-w-yl)-3-hydroxy-3-([substituted]-1H-1,2,4-triazol-3-yl)-propenone (B-618) 4-[(z-alkyl-q-(([substituted]heteroaryl)alkyl))furan-w-yl]-2-hydroxy-4-oxo-2-butenoic acid (B-619) 4-(q-(([substituted]aryl)carbonyl)oxazol-w-yl)-2-hydroxy-4-oxo-2-butenoic acid (B-620) 4-[(q-(([substituted]aryl)aminocarbonyl)-z-halogeno)isoxazol-w-yl]-2-hydroxy-4-oxo-2-butenoic acid (B-621) 4-[(q-(([substituted]aryl)amino)-z-halogeno)furan-w-yl]-2-hydroxy-4-oxo-2-butenoic acid (B-622) 1-[(z-alkyl-q-(([substituted]heteroaryl)sulfonylamino))thiophen-w-yl]-3-hydroxy-3-([substituted]-1H-1,2,4-triazol-3-yl)-propenone (B-623) 1-[nH-(q-(([substituted]aryl)aminosulfonyl)-z-halogeno)pyrazol-w-yl]-3-hydroxy-3-([substituted]-2H-tetrazol-5-yl)-propenone (B-624) 1-[(q-(([substituted]aryl)carboxy)-z-halogeno)furan-w-yl]-3-hydroxy-3-([substituted]-1H-1,2,4-triazol-3-yl)-propenone (B-625) 1-[(z-alkyl-q-(([substituted]heteroaryl)carbonylamino))isoxazol-w-yl]-3-hydroxy-3-([substituted]-2H-tetrazol-5-yl)-propenone (B-626) 4-[nH-(q-(([substituted]heteroaryl)amino)-z-halogeno)pyrazol-w-yl]-2-hydroxy-4-oxo-2-butenoic acid (B-627) 1-[(z-alkyl-q-(([substituted]aryl)carbonyl))oxazol-w-yl]-3-hydroxy-3-([substituted]-2H-tetrazol-5-yl)-propenone (B-628) 1-[(z-halogeno-q-(([substituted]heteroaryl)sulfinyl))oxazol-w-yl]-3-hydroxy-3-([substituted]-2H-tetrazol-5-yl)-propenone (B-629) 1-[(q-(([substituted]heteroaryl)amino)-z-halogeno)pyridin-w-yl]-3-hydroxy-3-([substituted]-2H-tetrazol-5-yl)-propenone (B-630) 1-(nH-q-([substituted]heteroaryl)pyrazol-w-yl)-3-hydroxy-3-([substituted]-1H-1,2,4-triazol-3-yl)-propenone (B-631) 2-hydroxy-4-oxo-4-(q-(([substituted]heteroaryl)oxy)isoxazol-w-yl)-2-butenoic acid (B-632) 1-[(z-halogeno-q-(([substituted]aryl)thio))oxazol-w-yl]-3-hydroxy-3-([substituted]-1H-1,2,4-triazol-3-yl)-propenone (B-633) 1-[nH-(z-alkyl-q-(([substituted]heteroaryl)alkyl))pyrazol-w-yl]-3-hydroxy-3-([substituted]-1H-1,2,4-triazol-3-yl)-propenone (B-634) 3-hydroxy-1-(q-(([substituted]heteroaryl)sulfonylamino)furan-w-yl)-3-([substituted]-2H-tetrazol-5-yl)-propenone (B-635) 4-[(q-(([substituted]heteroaryl)alkenyl)-z-alkyl)pyrrol-w-yl]-2-hydroxy-4-oxo-2-butenoic acid (B-636) 1-[nH-(q-(([substituted]aryl)amino)-z-halogeno)imidazol-w-yl]-3-hydroxy-3-([substituted]-1H-1,2,4-triazol-3-yl)-propenone (B-637) 1-[(q-(([substituted]heteroaryl)aminosulfonyl)-z-halogeno)pyrrol-w-yl]-3-hydroxy-3-([substituted]-2H-tetrazol-5-yl)-propenone (B-638) 1-(nH-q-(([substituted]heteroaryl)alkyl)imidazol-w-yl)-3-hydroxy-3-([substituted]-2H-tetrazol-5-yl)-propenone (B-639) 3-hydroxy-1-(q-(([substituted]heteroaryl)sulfinyl)thiophen-w-yl)-3-([substituted]-1H-1,2,4-triazol-3-yl)-propenone (B-640) 1-[nH-(q-([substituted]aryl)-z-halogeno)pyrazol-w-yl]-3-hydroxy-3-([substituted]-1H-1,2,4-triazol-3-yl)-propenone (B-641) 1-[(q-(([substituted]aryl)aminocarbonyl)-z-halogeno)furan-w-yl]-3-hydroxy-3-([substituted]-2H-tetrazol-5-yl)-propenone (B-642) 4-[(q-(([substituted]aryl)aminocarbonyl)-z-halogeno)thiophen-w-yl]-2-hydroxy-4-oxo-2-butenoic acid (B-643) 1-(q-(([substituted]aryl)aminosulfonyl)furan-w-yl)-3-hydroxy-3-([substituted]-2H-tetrazol-5-yl)-propenone (B-644) 4-[(z-alkyl-q-(([substituted]heteroaryl)aminocarbonyl))thiophen-w-yl]-2-hydroxy-4-oxo-2-butenoic acid (B-645) 3-hydroxy-1-(q-(1-hydroxy-([substituted]heteroaryl)methyl)oxazol-w-yl)-3-([substituted]-1H-1,2,4-triazol-3-yl)-propenone (B-646) 3-hydroxy-1-(q-(([substituted]aryl)sulfonylamino)pyridin-w-yl)-3-([substituted]-1H-1,2,4-triazol-3-yl)-propenone (B-647) 4-[nH-(q-(([substituted]heteroaryl)aminocarbonyl)-z-halogeno)pyrazol-w-yl]-2-hydroxy-4-oxo-2-butenoic acid (B-648) 1-[nH-(z-alkyl-q-(([substituted]heteroaryl)thio))imidazol-w-yl]-3-hydroxy-3-([substituted]-2H-tetrazol-5-yl)-propenone (B-649) 1-[nH-(z-halogeno-q-(([substituted]heteroaryl)sulfinyl))pyrazol-w-yl]-3-hydroxy-3-([substituted]-2H-tetrazol-5-yl)-propenone (B-650) 1-[nH-(z-alkyl-q-(([substituted]aryl)carboxy))imidazol-w-yl]-3-hydroxy-3-([substituted]-2H-tetrazol-5-yl)-propenone (B-651) 3-hydroxy-3-([substituted]-2H-tetrazol-5-yl)-1-(q-(([substituted]heteroaryl)thio)thiophen-w-yl)-propenone (B-652) 4-[(q-(([substituted]aryl)alkenyl)-z-alkyl)oxazol-w-yl]-2-hydroxy-4-oxo-2-butenoic acid (B-653) 4-[(z-alkyl-q-(([substituted]heteroaryl)carbonyl))furan-w-yl]-2-hydroxy-4-oxo-2-butenoic acid (B-654) 1-[(z-halogeno-q-(([substituted]aryl)sulfonyl))thiazol-w-yl]-3-hydroxy-3-([substituted]-1H-1,2,4-triazol-3-yl)-propenone (B-655) 3-hydroxy-1-(q-(([substituted]aryl)thio)pyridin-w-yl)-3-([substituted]-1H-1,2,4-triazol-3-yl)-propenone (B-656) 4-(q-([substituted]aryl)isoxazol-w-yl)-2-hydroxy-4-oxo-2-butenoic acid (B-657) 1-[(z-alkyl-q-(1-hydroxy-([substituted]aryl)methyl))furan-w-yl]-3-hydroxy-3-([substituted]-1H-1,2,4-triazol-3-yl)-propenone (B-658) 4-[(z-alkyl-q-([substituted]heteroaryl))pyrrol-w-yl]-2-hydroxy-4-oxo-2-butenoic acid
(B-659) 4-[(q-(([substituted]heteroaryl)amino)-z-halogeno)pyridin-w-yl]-2-hydroxy-4-oxo-2-butenoic acid
(B-660) 1-[(z-alkyl-q-((([substituted]heteroaryl)oxycarbonyl))pyridin-w-yl]-3-hydroxy-3-([substituted]-2H-tetrazol-5-yl)-propenone
(B-661) 1-[(q-(([substituted]aryl)amino)-z-halogeno)isoxazol-w-yl]-3-hydroxy-3-([substituted]-1H-1,2,4-triazol-3-yl)-propenone
(B-662) 1-[nH-(z-alkyl-q-((([substituted]heteroaryl)carbonyl))pyrazol-w-yl]-3-hydroxy-3-([substituted]-2H-tetrazol-5-yl)-propenone
(B-663) 3-hydroxy-1-(q-(([substituted]heteroaryl)sulfinyl)thiazol-w-yl)-3-([substituted]-1H-1,2,4-triazol-3-yl)-propenone
(B-664) 1-[nH-(q-(([substituted]aryl)amino)-z-halogeno)imidazol-w-yl]-3-hydroxy-3-([substituted]-2H-tetrazol-5-yl)-propenone
(B-665) 1-(q-(([substituted]aryl)aminosulfonyl)isoxazol-w-yl)-3-hydroxy-3-([substituted]-1H-1,2,4-triazol-3-yl)-propenone
(B-666) 1-[nH-(z-halogeno-q-((([substituted]heteroaryl)oxycarbonyl))pyrazol-w-yl]-3-hydroxy-3-([substituted]-2H-tetrazol-5-yl)-propenone
(B-667) 3-hydroxy-1-(nH-q-(([substituted]heteroaryl)sulfinyl)pyrazol-w-yl)-3-([substituted]-2H-tetrazol-5-yl)-propenone
(B-668) 1-(q-(([substituted]aryl)amino)pyridin-w-yl)-3-hydroxy-3-([substituted]-1H-1,2,4-triazol-3-yl)-propenone
(B-669) 1-[(q-(([substituted]heteroaryl)carbonyl)-z-halogeno)oxazol-w-yl]-3-hydroxy-3-([substituted]-2H-tetrazol-5-yl)-propenone
(B-670) 4-[nH-(q-(([substituted]aryl)carbonyl)-z-halogeno)imidazol-w-yl]-2-hydroxy-4-oxo-2-butenoic acid
(B-671) 1-(q-(([substituted]aryl)carboxy)thiophen-w-yl)-3-hydroxy-3-([substituted]-1H-1,2,4-triazol-3-yl)-propenone
(B-672) 4-[nH-(z-halogeno-q-(1-hydroxy-([substituted]heteroaryl)methyl))pyrazol-w-yl]-2-hydroxy-4-oxo-2-butenoic acid
(B-673) 1-[(q-([substituted]aryl)carbonylamino)-z-halogeno)thiazol-w-yl]-3-hydroxy-3-([substituted]-1H-1,2,4-triazol-3-yl)-propenone
(B-674) 1-[nH-(z-alkyl-q-(([substituted]aryl)thio))pyrazol-w-yl]-3-hydroxy-3-([substituted]-1H-1,2,4-triazol-3-yl)-propenone
(B-675) 3-hydroxy-1-(q-(([substituted]heteroaryl)carboxy)thiazol-w-yl)-3-([substituted]-1H-1,2,4-triazol-3-yl)-propenone
(B-676) 1-[(z-alkyl-q-(([substituted]aryl)aminosulfonyl))thiazol-w-yl]-3-hydroxy-3-([substituted]-1H-1,2,4-triazol-3-yl)-propenone
(B-677) 1-[(z-alkyl-q-(([substituted]heteroaryl)alkyl))isoxazol-w-yl]-3-hydroxy-3-([substituted]-2H-tetrazol-5-yl)-propenone
(B-678) 1-[(z-alkyl-q-(([substituted]heteroaryl)aminocarbonyl))thiophen-w-yl]-3-hydroxy-3-([substituted]-2H-tetrazol-5-yl)-propenone
(B-679) 3-hydroxy-1-(q-((([substituted]heteroaryl)thio)furan-w-yl)-3-([substituted]-1H-1,2,4-triazol-3-yl)-propenone
(B-680) 1-(q-(([substituted]aryl)alkenyl)furan-w-yl)-3-hydroxy-3-([substituted]-1H-1,2,4-triazol-3-yl)-propenone
(B-681) 4-(nH-q-((([substituted]heteroaryl)aminosulfonyl)imidazol-w-yl)-2-hydroxy-4-oxo-2-butenoic acid
(B-682) 1-(nH-q-((([substituted]heteroaryl)carbonylamino)pyrazol-w-yl)-3-hydroxy-3-([substituted]-1H-1,2,4-triazol-3-yl)-propenone
(B-683) 4-(q-(([substituted]aryl)amino)pyrrol-w-yl)-2-hydroxy-4-oxo-2-butenoic acid
(B-684) 1-[nH-(z-alkyl-q-((([substituted]heteroaryl)sulfonylamino))imidazol-w-yl]-3-hydroxy-3-([substituted]-2H-tetrazol-5-yl)-propenone
(B-685) 4-[nH-(z-alkyl-q-((([substituted]heteroaryl)sulfonylamino))pyrazol-w-yl]-2-hydroxy-4-oxo-2-butenoic acid
(B-686) 1-(nH-q-(([substituted]aryl)carbonyl)pyrazol-w-yl)-3-hydroxy-3-([substituted]-2H-tetrazol-5-yl)-propenone
(B-687) 1-[(z-alkyl-q-(([substituted]aryl)carboxy))oxazol-w-yl]-3-hydroxy-3-([substituted]-1H-1,2,4-triazol-3-yl)-propenone
(B-688) 4-[nH-(z-halogeno-q-(([substituted]aryl)sulfinyl))pyrazol-w-yl]-2-hydroxy-4-oxo-2-butenoic acid
(B-689) 1-[nH-(z-halogeno-q-(([substituted]heteroaryl)sulfonyl))pyrazol-w-yl]-3-hydroxy-3-([substituted]-1H-1,2,4-triazol-3-yl)-propenone
(B-690) 4-[(z-alkyl-q-(([substituted]aryl)aminosulfonyl))oxazol-w-yl]-2-hydroxy-4-oxo-2-butenoic acid
(B-691) 1-[(z-alkyl-q-(([substituted]aryl)aminocarbonyl))pyrrol-w-yl]-3-hydroxy-3-([substituted]-2H-tetrazol-5-yl)-propenone
(B-692) 1-[(q-(([substituted]heteroaryl)alkenyl)-z-alkyl)pyrrol-w-yl]-3-hydroxy-3-([substituted]-1H-1,2,4-triazol-3-yl)-propenone
(B-693) 1-(q-(([substituted]aryl)aminosulfonyl)thiazol-w-yl)-3-hydroxy-3-([substituted]-1H-1,2,4-triazol-3-yl)-propenone
(B-694) 1-[(q-(([substituted]heteroaryl)alkyl)pyrrol-w-yl)-3-hydroxy-3-([substituted]-2H-tetrazol-5-yl)-propenone
(B-695) 1-[(q-(([substituted]heteroaryl)alkyl)-z-halogeno)oxazol-w-yl]-3-hydroxy-3-([substituted]-2H-tetrazol-5-yl)-propenone
(B-696) 4-[(z-halogeno-q-(([substituted]heteroaryl)oxycarbonyl))thiophen-w-yl]-2-hydroxy-4-oxo-2-butenoic acid
(B-697) 4-[nH-(q-(([substituted]heteroaryl)carboxy)-z-alkyl)pyrazol-w-yl]-2-hydroxy-4-oxo-2-butenoic acid
(B-698) 1-[(z-alkyl-q-(([substituted]heteroaryl)amino))isoxazol-w-yl]-3-hydroxy-3-([substituted]-1H-1,2,4-triazol-3-yl)-propenone
(B-699) 2-hydroxy-4-oxo-4-(q-(([substituted]heteroaryl)sulfonylamino)thiazol-w-yl)-2-butenoic acid
(B-700) 3-hydroxy-1-(q-(1-hydroxy-([substituted]aryl)methyl)isoxazol-w-yl)-3-([substituted]-1H-1,2,4-triazol-3-yl)-propenone
(B-701) 1-[(z-alkyl-q-(([substituted]heteroaryl)oxy))furan-w-yl]-3-hydroxy-3-([substituted]-1H-1,2,4-triazol-3-yl)-propenone
(B-702) 1-[(q-(([substituted]aryl)aminosulfonyl)-z-halogeno)thiophen-w-yl]-3-hydroxy-3-([substituted]-2H-tetrazol-5-yl)-propenone
(B-703) 1-[(z-alkyl-q-((([substituted]heteroaryl)oxycarbonyl))isoxazol-w-yl]-3-hydroxy-3-([substituted]-2H-tetrazol-5-yl)-propenone
(B-704) 4-[(z-alkyl-q-(([substituted]aryl)oxy))pyridin-w-yl]-2-hydroxy-4-oxo-2-butenoic acid
(B-705) 4-(q-(([substituted]heteroaryl)aminosulfonyl)thiophen-w-yl)-2-hydroxy-4-oxo-2-butenoic acid
(B-706) 1-(q-([substituted]heteroaryl)thiophen-w-yl)-3-hydroxy-3-([substituted]-2H-tetrazol-5-yl)-propenone
(B-707) 4-[nH-(z-alkyl-q-((([substituted]aryl)carbonylamino))pyrazol-w-yl]-2-hydroxy-4-oxo-2-butenoic acid (B-708) 2-hydroxy-4-oxo-4-(q-(([substituted]aryl)sulfonyl)furan-w-yl)-2-butenoic acid
(B-709) 3-hydroxy-1-(q-(([substituted]heteroaryl)sulfinyl)pyridin-w-yl)-3-([substituted]-1H-1,2,4-triazol-3-yl)-propenone
(B-710) 1-(q-(([substituted]heteroaryl)alkyl)oxazol-w-yl)-3-hydroxy-3-([substituted]-1H-1,2,4-triazol-3-yl)-propenone
(B-711) 1-[(q-(([substituted]heteroaryl)carbonyl)-z-halogeno)thiophen-w-yl]-3-hydroxy-3-([substituted]-1H-1,2,4-triazol-3-yl)-propenone
(B-712) 1-[(z-halogeno-q-(([substituted]aryl)sulfinyl))pyrrol-w-yl]-3-hydroxy-3-([substituted]-2H-tetrazol-5-yl)-propenone
(B-713) 1-[(z-alkyl-q-(([substituted]heteroaryl)alkyl))isoxazol-w-yl]-3-hydroxy-3-([substituted]-1H-1,2,4-triazol-3-yl)-propenone
(B-714) 4-(q-([substituted]heteroaryl)isoxazol-w-yl)-2-hydroxy-4-oxo-2-butenoic acid
(B-715) 1-[(z-alkyl-q-(([substituted]heteroaryl)aminocarbonyl))pyridin-w-yl]-3-hydroxy-3-([substituted]-2H-tetrazol-5-yl)-propenone
(B-716) 4-(nH-q-(([substituted]aryl)carboxy)pyrazol-w-yl)-2-hydroxy-4-oxo-2-butenoic acid
(B-717) 1-[(z-halogeno-q-(([substituted]aryl)sulfinyl))pyridin-w-yl]-3-hydroxy-3-([substituted]-2H-tetrazol-5-yl)-propenone
(B-718) 1-[(z-alkyl-q-(([substituted]aryl)carbonylamino))isoxazol-w-yl]-3-hydroxy-3-([substituted]-1H-1,2,4-triazol-3-yl)-propenone
(B-719) 1-[(z-halogeno-q-(([substituted]aryl)sulfonylamino))isoxazol-w-yl]-3-hydroxy-3-([substituted]-2H-tetrazol-5-yl)-propenone
(B-720) 1-(q-(([substituted]heteroaryl)carbonylamino)pyrrol-w-yl)-3-hydroxy-3-([substituted]-1H-1,2,4-triazol-3-yl)-propenone
(B-721) 2-hydroxy-4-oxo-4-(nH-q-(([substituted]aryl)sulfinyl)pyrazol-w-yl)-2-butenoic acid
(B-722) 2-hydroxy-4-oxo-4-(q-([substituted]aryl)sulfinyl)thiazol-w-yl)-2-butenoic acid
(B-723) 4-[(z-alkyl-q-(([substituted]aryl)thio))thiazol-w-yl]-2-hydroxy-4-oxo-2-butenoic acid
(B-724) 1-[nH-(q-(([substituted]aryl)alkyl)-z-halogeno)imidazol-w-yl]-3-hydroxy-3-([substituted]-2H-tetrazol-5-yl)-propenone
(B-725) 4-[(z-halogeno-q-(([substituted]heteroaryl)oxy))thiazol-w-yl]-2-hydroxy-4-oxo-2-butenoic acid
(B-726) 1-[(z-alkyl-q-(([substituted]heteroaryl)oxy))isoxazol-w-yl]-3-hydroxy-3-([substituted]-1H-1,2,4-triazol-3-yl)-propenone
(B-727) 4-[(q-(([substituted]aryl)alkenyl)-z-halogeno)oxazol-w-yl]-2-hydroxy-4-oxo-2-butenoic acid
(B-728) 4-[nH-(z-halogeno-q-(([substituted]aryl)oxycarbonyl))imidazol-w-yl]-2-hydroxy-4-oxo-2-butenoic acid
(B-729) 3-hydroxy-1-(q-(([substituted]aryl)sulfonylamino)pyridin-w-yl)-3-([substituted]-2H-tetrazol-5-yl)-propenone
(B-730) 1-[nH-(z-alkyl-q-(([substituted]heteroaryl)aminocarbonyl))pyrazol-w-yl]-3-hydroxy-3-([substituted]-1H-1,2,4-triazol-3-yl)-propenone
(B-731) 4(q-(([substituted]heteroaryl)aminocarbonyl)furan-w-yl)-2-hydroxy-4-oxo-2-butenoic acid
(B-732) 1-[(z-alkyl-q-(([substituted]aryl)amino))oxazol-w-yl]-3-hydroxy-3-([substituted]-2H-tetrazol-5-yl)-propenone
(B-733) 1-[nH-(z-halogeno-q-(1-hydroxy-([substituted]heteroaryl)methyl))pyrazol-w-yl]-3-hydroxy-3-([substituted]-1H-1,2,4-triazol-3-yl)-propenone
(B-734) 1-[(z-alkyl-q-([substituted]heteroaryl))furan-w-yl]-3-hydroxy-3-([substituted]-2H-tetrazol-5-yl)-propenone
(B-735) 1-(q-(([substituted]aryl)carbonylamino)pyrrol-w-yl)-3-hydroxy-3-([substituted]-2H-tetrazol-5-yl)-propenone
(B-736) 1-[nH-(z-alkyl-q-(([substituted]aryl)alkyl))imidazol-w-yl]-3-hydroxy-3-([substituted]-1H-1,2,4-triazol-3-yl)-propenone
(B-737) 1-[(z-halogeno-q-(([substituted]aryl)sulfonyl))pyrrol-w-yl]-3-hydroxy-3-([substituted]-2H-tetrazol-5-yl)-propenone
(B-738) 1-[(z-alkyl-q-(([substituted]heteroaryl)sulfinyl))oxazol-w-yl]-3-hydroxy-3-([substituted]-1H-1,2,4-triazol-3-yl)-propenone
(B-739) 1-[(q-(([substituted]aryl)carbonyl)-z-halogeno)oxazol-w-yl]-3-hydroxy-3-([substituted]-1H-1,2,4-triazol-3-yl)-propenone
(B-740) 2-hydroxy-4-oxo-4-(q-(([substituted]heteroaryl)oxy)oxazol-w-yl)-2-butenoic acid
(B-741) 3-hydroxy-1-(q-(([substituted]aryl)oxycarbonyl)thiophen-w-yl)-3-([substituted]-2H-tetrazol-5-yl)-propenone
(B-742) 2-hydroxy-4-oxo-4-(q-(([substituted]heteroaryl)sulfonylamino)pyridin-w-yl)-2-butenoic acid
(B-743) 1-[(z-alkyl-q-(1-hydroxy-([substituted]heteroaryl)methyl))furan-w-yl]-3-hydroxy-3-([substituted]-1H-1,2,4-triazol-3-yl)-propenone
(B-744) 4-[(z-alkyl-q-(([substituted]aryl)thio))pyrrol-w-yl]-2-hydroxy-4-oxo-2-butenoic acid
(B-745) 4-(nH-q-([substituted]heteroaryl)imidazol-w-yl)-2-hydroxy-4-oxo-2-butenoic acid
(B-746) 1-[(z-alkyl-q-(([substituted]heteroaryl)aminosulfonyl))pyridin-w-yl]-3-hydroxy-3-([substituted]-2H-tetrazol-5-yl)-propenone
(B-747) 1-[(q-(([substituted]heteroaryl)aminocarbonyl)-z-halogeno)furan-w-yl]-3-hydroxy-3-([substituted]-2H-tetrazol-5-yl)-propenone
(B-748) 2-hydroxy-4-oxo-4-(q-(([substituted]aryl)sulfonylamino)pyridin-w-yl)-2-butenoic acid
(B-749) 4-[nH-(z-alkyl-q-([substituted]aryl))imidazol-w-yl]-2-hydroxy-4-oxo-2-butenoic acid
(B-750) 4-[(z-alkyl-q-(([substituted]aryl)sulfonylamino))furan-w-yl]-2-hydroxy-4-oxo-2-butenoic acid
(B-751) 4-[(z-alkyl-q-(([substituted]aryl)aminocarbonyl))pyrrol-w-yl]-2-hydroxy-4-oxo-2-butenoic acid
(B-752) 2-hydroxy-4-(nH-q-(1-hydroxy-([substituted]heteroaryl)methyl)imidazol-w-yl)-4-oxo-2-butenoic acid
(B-753) 1-[(z-alkyl-q-(([substituted]heteroaryl)sulfinyl))pyrrol-w-yl]-3-hydroxy-3-([substituted]-1H-1,2,4-triazol-3-yl)-propenone
(B-754) 1-[(z-halogeno-q-(1-hydroxy-([substituted]heteroaryl)methyl))pyridin-w-yl]-3-hydroxy-3-([substituted]-1H-1,2,4-triazol-3-yl)-propenone
(B-755) 3-hydroxy-1-(q-(([substituted]heteroaryl)sulfinyl)thiophen-w-yl)-3-([substituted]-2H-tetrazol-5-yl)-propenone
(B-756) 4-(q-(([substituted]aryl)alkyl)oxazol-w-yl)-2-hydroxy-4-oxo-2-butenoic acid
(B-757) 1-[(z-alkyl-q-(([substituted]aryl)alkyl))thiazol-w-yl]-3-hydroxy-3-([substituted]-2H-tetrazol-5-yl)-propenone
(B-758) 4-[nH-(z-alkyl-q-(([substituted]aryl)sulfonylamino))imidazol-w-yl]-2-hydroxy-4-oxo-2-butenoic acid
(B-759) 4-[(q-(([substituted]aryl)carboxy)-z-halogeno)pyridin-w-yl]-2-hydroxy-4-oxo-2-butenoic acid
(B-760) 3-hydroxy-3-([substituted]-2H-tetrazol-5-yl)-1-(nH-q-(([substituted]aryl)thio)pyrazol-w-yl)-propenone (B-761) 1-[(q-(([substituted]heteroaryl)carboxy)-z-alkyl)pyrrol-w-yl]-3-hydroxy-3-([substituted]-1H-1,2,4-triazol-3-yl)-propenone (B-762) 4-[(q-(([substituted]heteroaryl)alkyl)-z-halogeno)isoxazol-w-yl]-2-hydroxy-4-oxo-2-butenoic acid (B-763) 1-[(z-alkyl-q-(([substituted]heteroaryl)carbonyl))thiazol-w-yl]-3-hydroxy-3-([substituted]-1H-1,2,4-triazol-3-yl)-propenone (B-764) 4-[nH-(z-alkyl-q-(([substituted]aryl)sulfonyl))imidazol-w-yl]-2-hydroxy-4-oxo-2-butenoic acid (B-765) 1-(q-(([substituted]heteroaryl)aminocarbonyl)pyridin-w-yl)-3-hydroxy-3-([substituted]-1H-1,2,4-triazol-3-yl)-propenone (B-766) 3-hydroxy-1-(nH-q-(([substituted]heteroaryl)oxycarbonyl)pyrazol-w-yl)-3-([substituted]-2H-tetrazol-5-yl)-propenone (B-767) 1-(q-(([substituted]aryl)aminocarbonyl)thiazol-w-yl)-3-hydroxy-3-([substituted]-1H-1,2,4-triazol-3-yl)-propenone (B-768) 4-(q-([substituted]heteroaryl)pyrrol-w-yl)-2-hydroxy-4-oxo-2-butenoic acid (B-769) 2-hydroxy-4-oxo-4-(q-(([substituted]aryl)oxy)thiophen-w-yl)-2-butenoic acid (B-770) 4-[nH-(z-alkyl-q-(1-hydroxy-([substituted]heteroaryl)methyl))pyrazol-w-yl]-2-hydroxy-4-oxo-2-butenoic acid (B-771) 1-[(z-alkyl-q-(([substituted]aryl)amino))thiophen-w-yl]-3-hydroxy-3-([substituted]-1H-1,2,4-triazol-3-yl)-propenone (B-772) 3-hydroxy-1-(nH-q-(([substituted]heteroaryl)oxy)pyrazol-w-yl)-3-([substituted]-1H-1,2,4-triazol-3-yl)-propenone (B-773) 1-[(q-(([substituted]aryl)amino)-z-halogeno)pyridin-w-yl]-3-hydroxy-3-([substituted]-1H-1,2,4-triazol-3-yl)-propenone (B-774) 1-[(z-alkyl-q-(([substituted]aryl)sulfonylamino))pyridin-w-yl]-3-hydroxy-3-([substituted]-2H-tetrazol-5-yl)-propenone (B-775) 1-[(q-(([substituted]aryl)carbonyl)-z-halogeno)pyridin-w-yl]-3-hydroxy-3-([substituted]-1H-1,2,4-triazol-3-yl)-propenone (B-776) 1-[(z-alkyl-q-([substituted]aryl))oxazol-w-yl]-3-hydroxy-3-([substituted]-1H-1,2,4-triazol-3-yl)-propenone (B-777) 1-[(q-(([substituted]aryl)alkenyl)-z-halogeno)oxazol-w-yl]-3-hydroxy-3-([substituted]-2H-tetrazol-5-yl)-propenone (B-778) 1-[(q-(([substituted]heteroaryl)alkenyl)-z-halogeno)isoxazol-w-yl]-3-hydroxy-3-([substituted]-1H-1,2,4-triazol-3-yl)-propenone (B-779) 1-[nH-(z-alkyl-q-(([substituted]aryl)carbonylamino))imidazol-w-yl]-3-hydroxy-3-([substituted]-2H-tetrazol-5-yl)-propenone (B-780) 3-hydroxy-1-(nH-q-(([substituted]aryl)oxycarbonyl)pyrazol-w-yl)-3-([substituted]-2H-tetrazol-5-yl)-propenone (B-781) 4-(q-(([substituted]heteroaryl)carboxy)furan-w-yl)-2-hydroxy-4-oxo-2-butenoic acid (B-782) 1-[(z-halogeno-q-([substituted]heteroaryl))thiazol-w-yl]-3-hydroxy-3-([substituted]-1H-1,2,4-triazol-3-yl)-propenone (B-783) 1-[(q-(([substituted]aryl)amino)-z-halogeno)furan-w-yl]-3-hydroxy-3-([substituted]-2H-tetrazol-5-yl)-propenone (B-784) 3-hydroxy-1-(q-(([substituted]heteroaryl)sulfonylamino)pyrrol-w-yl)-3-([substituted]-2H-tetrazol-5-yl)-propenone (B-785) 1-[(z-alkyl-q-(([substituted]heteroaryl)sulfinyl))furan-w-yl]-3-hydroxy-3-([substituted]-2H-tetrazol-5-yl)-propenone (B-786) 4-(q-(([substituted]aryl)aminosulfonyl)thiazol-w-yl)-2-hydroxy-4-oxo-2-butenoic acid (B-787) 2-hydroxy-4-oxo-4-(q-(([substituted]aryl)sulfinyl)pyrrol-w-yl)-2-butenoic acid (B-788) 1-[(z-halogeno-q-(([substituted]aryl)sulfonylamino))pyrrol-w-yl]-3-hydroxy-3-([substituted]-2H-tetrazol-5-yl)-propenone (B-789) 2-hydroxy-4-oxo-4-(q-(([substituted]aryl)thio)furan-w-yl)-2-butenoic acid (B-790) 1-[nH-(z-alkyl-q-(([substituted]heteroaryl)aminocarbonyl))imidazol-w-yl]-3-hydroxy-3-([substituted]-1H-1,2,4-triazol-3-yl)-propenone (B-791) 1-[(z-alkyl-q-(([substituted]heteroaryl)amino))oxazol-w-yl]-3-hydroxy-3-([substituted]-2H-tetrazol-5-yl)-propenone (B-792) 4-[(z-halogeno-q-(1-hydroxy-([substituted]heteroaryl)methyl))thiophen-w-yl]-2-hydroxy-4-oxo-2-butenoic acid (B-793) 3-hydroxy-1-(q-(([substituted]aryl)oxycarbonyl)pyridin-w-yl)-3-([substituted]-2H-tetrazol-5-yl)-propenone (B-794) 3-hydroxy-1-(nH-q-(([substituted]aryl)oxy)imidazol-w-yl)-3-([substituted]-1H-1,2,4-triazol-3-yl)-propenone (B-795) 1-[(z-halogeno-q-(1-hydroxy-([substituted]aryl)methyl))thiophen-w-yl]-3-hydroxy-3-([substituted]-2H-tetrazol-5-yl)-propenone (B-796) 4-[nH-(z-halogeno-q-(([substituted]heteroaryl)sulfonyl))imidazol-w-yl]-2-hydroxy-4-oxo-2-butenoic acid (B-797) 3-hydroxy-1-(q-(([substituted]heteroaryl)sulfonyl)pyrrol-w-yl)-3-([substituted]-2H-tetrazol-5-yl)-propenone (B-798) 4-[(z-alkyl-q-(([substituted]aryl)carbonylamino))thiazol-w-yl]-2-hydroxy-4-oxo-2-butenoic acid (B-799) 4-[(q-(([substituted]aryl)alkyl)-z-halogeno)thiazol-w-yl]-2-hydroxy-4-oxo-2-butenoic acid (B-800) 4-[nH-(z-alkyl-q-(1-hydroxy-([substituted]aryl)methyl))imidazol-w-yl]-2-hydroxy-4-oxo-2-butenoic acid (B-801) 4-[(q-(([substituted]heteroaryl)alkenyl)-z-alkyl)thiazol-w-yl]-2-hydroxy-4-oxo-2-butenoic acid (B-802) 1-(q-(([substituted]aryl)amino)thiophen-w-yl)-3-hydroxy-3-([substituted]-1H-1,2,4-triazol-3-yl)-propenone (B-803) 4-[(z-alkyl-q-(([substituted]heteroaryl)oxy))thiazol-w-yl]-2-hydroxy-4-oxo-2-butenoic acid (B-804) 1-[nH-(q-(([substituted]heteroaryl)carboxy)-z-halogeno)imidazol-w-yl]-3-hydroxy-3-([substituted]-1H-1,2,4-triazol-3-yl)-propenone (B-805) 1-(q-([substituted]aryl)thiazol-w-yl)-3-hydroxy-3-([substituted]-1H-1,2,4-triazol-3-yl)-propenone (B-806) 3-hydroxy-1-(nH-q-(([substituted]aryl)sulfinyl)pyrazol-w-yl)-3-([substituted]-2H-tetrazol-5-yl)-propenone (B-807) 3-hydroxy-1-(nH-q-(([substituted]heteroaryl)sulfinyl)pyrazol-w-yl)-3-([substituted]-1H-1,2,4-triazol-3-yl)-propenone (B-808) 1-(q-(([substituted]aryl)aminosulfonyl)oxazol-w-yl)-3-hydroxy-3-([substituted]-1H-1,2,4-triazol-3-yl)-propenone (B-809) 1-(q-([substituted]aryl)thiophen-w-yl)-3-hydroxy-3-([substituted]-1H-1,2,4-triazol-3-yl)-propenone (B-810) 1-[(z-alkyl-q-(([substituted]heteroaryl)sulfonyl))isoxazol-w-yl]-3-hydroxy-3-([substituted]-2H-tetrazol-5-yl)-propenone (B-811) 2-hydroxy-4-oxo-4-(nH-q-(([substituted]aryl)oxycarbonyl)pyrazol-w-yl)-2-butenoic acid
(B-812) 1-[(q-(([substituted]heteroaryl)alkenyl)-z-halogeno)thiophen-w-yl]-3-hydroxy-3-([substituted]-1H-1,2,4-triazol-3-yl)-propenone
(B-813) 1-[(z-alkyl-q-(([substituted]aryl)aminosulfonyl))pyrrol-w-yl]-3-hydroxy-3-([substituted]-2H-tetrazol-5-yl)-propenone
(B-814) 1-[(q-(([substituted]aryl)aminosulfonyl)-z-halogeno)isoxazol-w-yl]-3-hydroxy-3-([substituted]-1H-1,2,4-triazol-3-yl)-propenone
(B-815) 1-[(z-alkyl-q-(([substituted]aryl)sulfonylamino))isoxazol-w-yl]-3-hydroxy-3-([substituted]-2H-tetrazol-5-yl)-propenone
(B-816) 1-[nH-(z-halogeno-q-([substituted]heteroaryl))imidazol-w-yl]-3-hydroxy-3-([substituted]-2H-tetrazol-5-yl)-propenone
(B-817) 1-[(z-halogeno-q-(([substituted]aryl)oxy))pyridin-w-yl]-3-hydroxy-3-([substituted]-2H-tetrazol-5-yl)-propenone
(B-818) 1-[(z-alkyl-q-([substituted]aryl))thiophen-w-yl]-3-hydroxy-3-([substituted]-1H-1,2,4-triazol-3-yl)-propenone
(B-819) 1-[(z-alkyl-q-(([substituted]aryl)carbonylamino))oxazol-w-yl]-3-hydroxy-3-([substituted]-2H-tetrazol-5-yl)-propenone
(B-820) 1-[(q-(([substituted]aryl)alkenyl)-z-halogeno)pyrrol-w-yl]-3-hydroxy-3-([substituted]-1H-1,2,4-triazol-3-yl)-propenone
(B-821) 1-[(z-alkyl-q-(([substituted]heteroaryl)alkyl))thiophen-w-yl]-3-hydroxy-3-([substituted]-2H-tetrazol-5-yl)-propenone
(B-822) 1-[(z-alkyl-q-(([substituted]heteroaryl)amino))pyridin-w-yl]-3-hydroxy-3-([substituted]-1H-1,2,4-triazol-3-yl)-propenone
(B-823) 1-[(z-alkyl-q-(([substituted]aryl)aminosulfonyl))isoxazol-w-yl]-3-hydroxy-3-([substituted]-2H-tetrazol-5-yl)-propenone
(B-824) 4-[(q-(([substituted]heteroaryl)alkenyl)-z-alkyl)isoxazol-w-yl]-2-hydroxy-4-oxo-2-butenoic acid
(B-825) 1-[(z-halogeno-q-(([substituted]aryl)sulfinyl))isoxazol-w-yl]-3-hydroxy-3-([substituted]-2H-tetrazol-5-yl)-propenone
(B-826) 1-[(q-(([substituted]heteroaryl)aminosulfonyl)-z-halogeno)furan-w-yl]-3-hydroxy-3-([substituted]-1H-1,2,4-triazol-3-yl)-propenone
(B-827) 1-[nH-(z-halogeno-q-(([substituted]heteroaryl)sulfinyl))pyrazol-w-yl]-3-hydroxy-3-([substituted]-1H-1,2,4-triazol-3-yl)-propenone
(B-828) 4-[(z-alkyl-q-(([substituted]heteroaryl)amino))thiazol-w-yl]-2-hydroxy-4-oxo-2-butenoic acid
(B-829) 4-[nH-(q-(([substituted]heteroaryl)alkenyl)-z-alkyl)pyrazol-w-yl]-2-hydroxy-4-oxo-2-butenoic acid
(B-830) 3-hydroxy-3-([substituted]-2H-tetrazol-5-yl)-1-(q-(([substituted]heteroaryl)thio)thiazol-w-yl)-propenone
(B-831) 4-[nH-(q-(([substituted]aryl)amino)-z-halogeno)imidazol-w-yl]-2-hydroxy-4-oxo-2-butenoic acid
(B-832) 1-[(z-alkyl-q-([substituted]heteroaryl))thiophen-w-yl]-3-hydroxy-3-([substituted]-1H-1,2,4-triazol-3-yl)-propenone
(B-833) 4-[(z-halogeno-q-(([substituted]aryl)oxycarbonyl))thiazol-w-yl]-2-hydroxy-4-oxo-2-butenoic acid
(B-834) 4-[(q-(([substituted]heteroaryl)carboxy)-z-halogeno)pyrrol-w-yl]-2-hydroxy-4-oxo-2-butenoic acid
(B-835) 3-hydroxy-1-(q-(([substituted]aryl)sulfinyl)thiazol-w-yl)-3-([substituted]-2H-tetrazol-5-yl)-propenone
(B-836) 1-[nH-(z-alkyl-q-(([substituted]heteroaryl)oxycarbonyl))imidazol-w-yl]-3-hydroxy-3-([substituted]-2H-tetrazol-5-yl)-propenone
(B-837) 3-hydroxy-1-(q-(([substituted]heteroaryl)oxy)pyridin-w-yl)-3-([substituted]-1H-1,2,4-triazol-3-yl)-propenone
(B-838) 4-[(z-alkyl-q-(1-hydroxy-([substituted]aryl)methyl))pyrrol-w-yl]-2-hydroxy-4-oxo-2-butenoic acid
(B-839) 1-[nH-(q-(([substituted]heteroaryl)carbonyl)-z-halogeno)imidazol-w-yl]-3-hydroxy-3-([substituted]-2H-tetrazol-5-yl)-propenone
(B-840) 1-(nH-q-(([substituted]heteroaryl)carbonyl)imidazol-w-yl)-3-hydroxy-3-([substituted]-1H-1,2,4-triazol-3-yl)-propenone
(B-841) 4-(q-(([substituted]aryl)carbonylamino)pyridin-w-yl)-2-hydroxy-4-oxo-2-butenoic acid
(B-842) 1-[(z-alkyl-q-(([substituted]aryl)carbonyl))pyrrol-w-yl]-3-hydroxy-3-([substituted]-1H-1,2,4-triazol-3-yl)-propenone
(B-843) 3-hydroxy-1-(q-(([substituted]aryl)sulfonyl)thiophen-w-yl)-3-([substituted]-1H-1,2,4-triazol-3-yl)-propenone,
(B-844) 1-[nH-(z-alkyl-q-(([substituted]heteroaryl)aminosulfonyl))imidazol-w-yl]-3-hydroxy-3-([substituted]-1H-1,2,4-triazol-3-yl)-propenone
(B-845) 3-hydroxy-1-(q-(1-hydroxy-([substituted]aryl)methyl)furan-w-yl)-3-([substituted]-1H-1,2,4-triazol-3-yl)-propenone
(B-846) 4-[(q-(([substituted]aryl)aminosulfonyl)-z-halogeno)thiazol-w-yl]-2-hydroxy-4-oxo-2-butenoic acid
(B-847) 4-[(q-(([substituted]aryl)amino)-z-halogeno)isoxazol-w-yl]-2-hydroxy-4-oxo-2-butenoic acid
(B-848) 1-(nH-q-(([substituted]heteroaryl)alkenyl)pyrazol-w-yl)-3-hydroxy-3-([substituted]-2H-tetrazol-5-yl)-propenone
(B-849) 4-[(z-halogeno-q-(([substituted]heteroaryl)sulfonyl))oxazol-w-yl]-2-hydroxy-4-oxo-2-butenoic acid
(B-850) 3-hydroxy-1-(nH-q-(1-hydroxy-([substituted]aryl)methyl)pyrazol-w-yl)-3-([substituted]-1H-1,2,4-triazol-3-yl)-propenone
(B-851) 2-hydroxy-4-oxo-4-(q-(([substituted]heteroaryl)thio)isoxazol-w-yl)-2-butenoic acid
(B-852) 4-[(z-alkyl-q-(([substituted]aryl)sulfonylamino))pyridin-w-yl]-2-hydroxy-4-oxo-2-butenoic acid
(B-853) 1-(nH-q-(([substituted]aryl)aminosulfonyl)pyrazol-w-yl)-3-hydroxy-3-([substituted]-1H-1,2,4-triazol-3-yl)-propenone
(B-854) 1-(q-(([substituted]heteroaryl)carbonylamino)thiophen-w-yl)-3-hydroxy-3-([substituted]-2H-tetrazol-5-yl)-propenone
(B-855) 1-[nH-(z-halogeno-q-(([substituted]heteroaryl)oxy))pyrazol-w-yl]-3-hydroxy-3-([substituted]-2H-tetrazol-5-yl)-propenone
(B-856) 4-[nH-(q-(([substituted]aryl)aminocarbonyl)-z-halogeno)pyrazol-w-yl]-2-hydroxy-4-oxo-2-butenoic acid
(B-857) 1-[(z-alkyl-q-(([substituted]aryl)oxy))thiazol-w-yl]-3-hydroxy-3-([substituted]-2H-tetrazol-5-yl)-propenone
(B-858) 1-[(q-(([substituted]heteroaryl)carboxy)-z-alkyl)pyridin-w-yl]-3-hydroxy-3-([substituted]-1H-1,2,4-triazol-3-yl)-propenone
(B-859) 1-[nH-(z-alkyl-q-(([substituted]heteroaryl)sulfonyl))imidazol-w-yl]-3-hydroxy-3-([substituted]-1H-1,2,4-triazol-3-yl)-propenone
(B-860) 1-(q-(([substituted]heteroaryl)amino)oxazol-w-yl)-3-hydroxy-3-([substituted]-1H-1,2,4-triazol-3-yl)-propenone
(B-861) 1-[(q-(([substituted]heteroaryl)aminosulfonyl)-z-halogeno)oxazol-w-yl]-3-hydroxy-3-([substituted]-1H-1,2,4-triazol-3-yl)-propenone (B-862) 1-[(z-alkyl-q-(([substituted]aryl)aminosulfonyl))thiazol-w-yl]-3-hydroxy-3-([substituted]-2H-tetrazol-5-yl)-propenone (B-863) 1-[nH-(z-alkyl-q-(([substituted]aryl)aminocarbonyl))imidazol-w-yl]-3-hydroxy-3-([substituted]-2H-tetrazol-5-yl)-propenone (B-864) 2-hydroxy-4-oxo-4-(nH-q-(([substituted]aryl)thio)imidazol-w-yl)-2-butenoic acid (B-865) 1-(q-(([substituted]aryl)alkenyl)isoxazol-w-yl)-3-hydroxy-3-([substituted]-2H-tetrazol-5-yl)-propenone (B-866) 3-hydroxy-1-(q-(([substituted]aryl)oxycarbonyl)isoxazol-w-yl)-3-([substituted]-1H-1,2,4-triazol-3-yl)-propenone (B-867) 1-[(z-alkyl-q-([substituted]heteroaryl))pyrrol-w-yl]-3-hydroxy-3-([substituted]-2H-tetrazol-5-yl)-propenone (B-868) 1-[(z-alkyl-q-(([substituted]aryl)amino))furan-w-yl]-3-hydroxy-3-([substituted]-2H-tetrazol-5-yl)-propenone (B-869) 1-[(z-alkyl-q-(([substituted]aryl)oxycarbonyl))furan-w-yl]-3-hydroxy-3-([substituted]-1H-1,2,4-triazol-3-yl)-propenone (B-870) 2-hydroxy-4-oxo-4-(q-(([substituted]heteroaryl)oxy)pyrrol-w-yl)-2-butenoic acid (B-871) 3-hydroxy-1-(nH-q-((([substituted]aryl)oxycarbonyl)imidazol-w-yl)-3-([substituted]-1H-1,2,4-triazol-3-yl)-propenone (B-872) 2-hydroxy-4-oxo-4-(nH-q-((([substituted]aryl)sulfonylamino)imidazol-w-yl)-2-butenoic acid (B-873) 1-[(z-alkyl-q-(([substituted]heteroaryl)oxy))thiophen-w-yl]-3-hydroxy-3-([substituted]-1H-1,2,4-triazol-3-yl)-propenone (B-874) 3-hydroxy-1-(q-(([substituted]aryl)sulfonylamino)oxazol-w-yl)-3-([substituted]-2H-tetrazol-5-yl)-propenone (B-875) 1-[nH-(z-halogeno-q-([substituted]heteroaryl))pyrazol-w-yl]-3-hydroxy-3-([substituted]-1H-1,2,4-triazol-3-yl)-propenone (B-876) 2-hydroxy-4-(q-(1-hydroxy-([substituted]aryl)methyl)pyrrol-w-yl)-4-oxo-2-butenoic acid (B-877) 1-[(z-alkyl-q-(([substituted]aryl)alkyl))thiazol-w-yl]-3-hydroxy-3-([substituted]-1H-1,2,4-triazol-3-yl)-propenone (B-878) 3-hydroxy-1-(q-(([substituted]aryl)oxycarbonyl)isoxazol-w-yl)-3-([substituted]-2H-tetrazol-5-yl)-propenone (B-879) 1-[nH-(z-alkyl-q-(([substituted]heteroaryl)sulfonylamino))imidazol-w-yl]-3-hydroxy-3-([substituted]-1H-1,2,4-triazol-3-yl)-propenone (B-880) 1-[(z-alkyl-q-(([substituted]heteroaryl)sulfinyl))pyridin-w-yl]-3-hydroxy-3-([substituted]-1H-1,2,4-triazol-3-yl)-propenone (B-881) 4-[(z-halogeno-q-(([substituted]heteroaryl)sulfonylamino))pyrrol-w-yl]-2-hydroxy-4-oxo-2-butenoic acid (B-882) 1-[(z-halogeno-q-(([substituted]aryl)oxy))pyridin-w-yl]-3-hydroxy-3-([substituted]-1H-1,2,4-triazol-3-yl)-propenone (B-883) 2-hydroxy-4-oxo-4-(nH-q-(([substituted]aryl)sulfinyl)imidazol-w-yl)-2-butenoic acid (B-884) 2-hydroxy-4-oxo-4-(q-(([substituted]heteroaryl)sulfinyl)oxazol-w-yl)-2-butenoic acid (B-885) 1-[(q-(([substituted]heteroaryl)aminosulfonyl)-z-halogeno)thiazol-w-yl]-3-hydroxy-3-([substituted]-1H-1,2,4-triazol-3-yl)-propenone (B-886) 4-(q-([substituted]aryl)pyrrol-w-yl)-2-hydroxy-4-oxo-2-butenoic acid (B-887) 3-hydroxy-1-(q-(([substituted]aryl)sulfinyl)furan-w-yl)-3-([substituted]-2H-tetrazol-5-yl)-propenone (B-888) 1-[(z-halogeno-q-(([substituted]heteroaryl)sulfinyl))furan-w-yl]-3-hydroxy-3-([substituted]-1H-1,2,4-triazol-3-yl)-propenone (B-889) 2-hydroxy-4-oxo-4-(q-(([substituted]aryl)oxycarbonyl)isoxazol-w-yl)-2-butenoic acid (B-890) 1-[(q-(([substituted]heteroaryl)aminocarbonyl)-z-halogeno)isoxazol-w-yl]-3-hydroxy-3-([substituted]-2H-tetrazol-5-yl)-propenone (B-891) 3-hydroxy-1-(q-(([substituted]aryl)sulfinyl)furan-w-yl)-3-([substituted]-1H-1,2,4-triazol-3-yl)-propenone (B-892) 1-[(z-alkyl-q-(([substituted]heteroaryl)oxy))pyrrol-w-yl]-3-hydroxy-3-([substituted]-2H-tetrazol-5-yl)-propenone (B-893) 1-[(z-alkyl-q-(([substituted]aryl)aminocarbonyl))thiophen-w-yl]-3-hydroxy-3-([substituted]-1H-1,2,4-triazol-3-yl)-propenone (B-894) 4-[(q-(([substituted]aryl)alkenyl)-z-halogeno)pyridin-w-yl]-2-hydroxy-4-oxo-2-butenoic acid (B-895) 4-[(z-halogeno-q-(([substituted]aryl)thio))pyrrol-w-yl]-2-hydroxy-4-oxo-2-butenoic acid (B-896) 1-[nH-(z-alkyl-q-(1-hydroxy-([substituted]aryl)methyl))pyrazol-w-yl]-3-hydroxy-3-([substituted]-2H-tetrazol-5-yl)-propenone (B-897) 1-[nH-(z-alkyl-q-(([substituted]heteroaryl)sulfinyl))pyrazol-w-yl]-3-hydroxy-3-([substituted]-1H,2,4-triazol-3-yl)-propenone (B-898) 4-[(q-(([substituted]heteroaryl)carbonyl)-z-halogeno)oxazol-w-yl]-2-hydroxy-4-oxo-2-butenoic acid (B-899) 4-[(z-halogeno-q-(([substituted]aryl)sulfonyl))furan-w-yl]-2-hydroxy-4-oxo-2-butenoic acid (B-900) 1-[(z-halogeno-q-(([substituted]heteroaryl)oxycarbonyl))pyrrol-w-yl]-3-hydroxy-3-([substituted]-2H-tetrazol-5-yl)-propenone (B-901) 4-[(z-alkyl-q-(([substituted]aryl)carboxy))pyridin-w-yl]-2-hydroxy-4-oxo-2-butenoic acid (B-902) 3-hydroxy-1-(q-(([substituted]aryl)thio)pyrrol-w-yl)-3-([substituted]-1H-1,2,4-triazol-3-yl)-propenone (B-903) 1-[(z-alkyl-q-(1-hydroxy-([substituted]heteroaryl)methyl))furan-w-yl]-3-hydroxy-3-([substituted]-2H-tetrazol-5-yl)-propenone (B-904) 1-(q-(([substituted]heteroaryl)aminocarbonyl)isoxazol-w-yl)-3-hydroxy-3-([substituted]-1H-1,2,4-triazol-3-yl)-propenone (B-905) 1-(q-(([substituted]heteroaryl)alkyl)pyridin-w-yl)-3-hydroxy-3-([substituted]-2H-tetrazol-5-yl)-propenone (B-906) 1-(nH-q-(([substituted]heteroaryl)aminocarbonyl)imidazol-w-yl)-3-hydroxy-3-([substituted]-2H-tetrazol-5-yl)-propenone (B-907) 4-(nH-q-(([substituted]heteroaryl)alkenyl)pyrazol-w-yl)-2-hydroxy-4-oxo-2-butenoic acid (B-908) 4-[(z-alkyl-q-(([substituted]aryl)oxy))pyrrol-w-yl]-2-hydroxy-4-oxo-2-butenoic acid (B-909) 1-[(z-alkyl-q-(([substituted]aryl)carbonylamino))furan-w-yl]-3-hydroxy-3-([substituted]-1H-1,2,4-triazol-3-yl)-propenone (B-910) 1-[(q-(([substituted]heteroaryl)carboxy)-z-alkyl)oxazol-w-yl]-3-hydroxy-3-([substituted]-1H-1,2,4-triazol-3-yl)-propenone (B-911) 1-[(z-alkyl-q-(([substituted]aryl)sulfonyl))thiophen-w-yl]-3-hydroxy-3-([substituted]-2H-tetrazol-5-yl)-propenone (B-912) 1-[(z-alkyl-q-(([substituted]heteroaryl)aminocarbonyl))furan-w-yl]-3-hydroxy-3-([substituted]-1H-1,2,4-triazol-3-yl)-propenone (B-913) 1-(q-(([substituted]aryl)alkyl)isoxazol-w-yl)-3-hydroxy-3-([substituted]-1H-1,2,4-triazol-3-yl)-propenone (B-914) 1-[nH-(q-(([substituted]heteroaryl)carbonyl)-z-halogeno)pyrazol-w-yl]-3-hydroxy-3-([substituted]-1H-1,2,4-triazol-3-yl)-propenone
(B-915) 4-[(q-(([substituted]aryl)alkenyl)-z-alkyl)isoxazol-w-yl]-2-hydroxy-4-oxo-2-butenoic acid
(B-916) 1-(q-(([substituted]heteroaryl)amino)thiazol-w-yl)-3-hydroxy-3-([substituted]-1H-1,2,4-triazol-3-yl)-propenone
(B-917) 1-[(q-(([substituted]aryl)aminosulfonyl)-z-halogeno)furan-w-yl]-3-hydroxy-3-([substituted]-1H-1,2,4-triazol-3-yl)-propenone
(B-918) 3-hydroxy-1-(nH-q-(([substituted]aryl)sulfinyl)imidazol-w-yl)-3-([substituted]-2H-tetrazol-5-yl)-propenone
(B-919) 1-[(z-halogeno-q-(([substituted]heteroaryl)sulfonyl))thiazol-w-yl]-3-hydroxy-3-([substituted]-2H-tetrazol-5-yl)-propenone
(B-920) 4-[(z-halogeno-q-(([substituted]heteroaryl)thio))pyridin-w-yl]-2-hydroxy-4-oxo-2-butenoic acid
(B-921) 4-[nH-(z-alkyl-q-(([substituted]heteroaryl)aminocarbonyl))imidazol-w-yl]-2-hydroxy-4-oxo-2-butenoic acid
(B-922) 1-[nH-(z-alkyl-q-(([substituted]aryl)oxycarbonyl))imidazol-w-yl]-3-hydroxy-3-([substituted]-1H-1,2,4-triazol-3-yl)-propenone
(B-923) 3-hydroxy-1-(q-(([substituted]heteroaryl)oxycarbonyl)pyridin-w-yl)-3-([substituted]-1H-1,2,4-triazol-3-yl)-propenone
(B-924) 1-(nH-q-(([substituted]aryl)carboxy)pyrazol-w-yl)-3-hydroxy-3-([substituted]-2H-tetrazol-5-yl)-propenone
(B-925) 1-[(q-(([substituted]aryl)aminosulfonyl)-z-halogeno)pyrrol-w-yl]-3-hydroxy-3-([substituted]-2H-tetrazol-5-yl)-propenone
(B-926) 4-[(z-halogeno-q-(([substituted]heteroaryl)sulfonylamino))isoxazol-w-yl]-2-hydroxy-4-oxo-2-butenoic acid
(B-927) 1-[(z-halogeno-q-(([substituted]heteroaryl)oxy))isoxazol-w-yl]-3-hydroxy-3-([substituted]-2H-tetrazol-5-yl)-propenone
(B-928) 3-hydroxy-1-(nH-q-(1-hydroxy-([substituted]aryl)methyl)pyrazol-w-yl)-3-([substituted]-2H-tetrazol-5-yl)-propenone
(B-929) 1-[(z-alkyl-q-(([substituted]heteroaryl)aminosulfonyl))oxazol-w-yl]-3-hydroxy-3-([substituted]-1H-1,2,4-triazol-3-yl)-propenone
(B-930) 1-[(z-halogeno-q-(([substituted]aryl)sulfonylamino))furan-w-yl]-3-hydroxy-3-([substituted]-1H-1,2,4-triazol-3-yl)-propenone
(B-931) 4-[nH-(q-(([substituted]heteroaryl)carbonyl)-z-halogeno)pyrazol-w-yl]-2-hydroxy-4-oxo-2-butenoic acid
(B-932) 4-[(z-alkyl-q-(([substituted]aryl)alkyl))isoxazol-w-yl]-2-hydroxy-4-oxo-2-butenoic acid
(B-933) 1-[(q-(([substituted]heteroaryl)carbonyl)-z-halogeno)thiophen-w-yl]-3-hydroxy-3-([substituted]-2H-tetrazol-5-yl)-propenone
(B-934) 1-[(q-(([substituted]heteroaryl)carboxy)-z-halogeno)oxazol-w-yl]-3-hydroxy-3-([substituted]-1H-1,2,4-triazol-3-yl)-propenone
(B-935) 1-(q-(([substituted]aryl)carbonylamino)isoxazol-w-yl)-3-hydroxy-3-([substituted]-1H-1,2,4-triazol-3-yl)-propenone
(B-936) 4-(q-(([substituted]aryl)alkenyl)pyridin-w-yl)-2-hydroxy-4-oxo-2-butenoic acid
(B-937) 1-[(z-alkyl-q-(([substituted]aryl)thio))furan-w-yl]-3-hydroxy-3-([substituted]-2H-tetrazol-5-yl)-propenone
(B-938) 4-(q-(([substituted]aryl)aminosulfonyl)pyrrol-w-yl)-2-hydroxy-4-oxo-2-butenoic acid
(B-939) 4-[nH-(q-(([substituted]heteroaryl)alkenyl)-z-halogeno)pyrazol-w-yl]-2-hydroxy-4-oxo-2-butenoic acid
(B-940) 1-[nH-(q-(([substituted]heteroaryl)carbonylamino)-z-halogeno)pyrazol-w-yl]-3-hydroxy-3-([substituted]-2H-tetrazol-5-yl)-propenone
(B-941) 4-[(z-halogeno-q-(([substituted]heteroaryl)sulfonyl))thiophen-w-yl]-2-hydroxy-4-oxo-2-butenoic acid
(B-942) 1-(q-(([substituted]aryl)aminocarbonyl)furan-w-yl)-3-hydroxy-3-([substituted]-2H-tetrazol-5-yl)-propenone
(B-943) 1-[(z-alkyl-q-(([substituted]heteroaryl)aminocarbonyl))pyridin-w-yl]-3-hydroxy-3-([substituted]-1H-1,2,4-triazol-3-yl)-propenone
(B-944) 4-[(q-(([substituted]aryl)aminosulfonyl)-z-halogeno)pyridin-w-yl]-2-hydroxy-4-oxo-2-butenoic acid
(B-945) 4-[nH-(z-halogeno-q-(([substituted]heteroaryl)sulfonylamino))imidazol-w-yl]-2-hydroxy-4-oxo-2-butenoic acid
(B-946) 1-(q-(([substituted]heteroaryl)alkyl)thiazol-w-yl)-3-hydroxy-3-([substituted]-2H-tetrazol-5-yl)-propenone
(B-947) 1-[(z-alkyl-q-(([substituted]heteroaryl)carbonyl))thiazol-w-yl]-3-hydroxy-3-([substituted]-2H-tetrazol-5-yl)-propenone
(B-948) 1-[(z-halogeno-q-(([substituted]heteroaryl)thio))oxazol-w-yl]-3-hydroxy-3-([substituted]-1H-1,2,4-triazol-3-yl)-propenone
(B-949) 1-(q-(([substituted]heteroaryl)carbonylamino)oxazol-w-yl)-3-hydroxy-3-([substituted]-2H-tetrazol-5-yl)-propenone
(B-950) 1-[(q-(([substituted]aryl)alkenyl)-z-alkyl)pyridin-w-yl]-3-hydroxy-3-([substituted]-2H-tetrazol-5-yl)-propenone
(B-951) 3-hydroxy-1-(nH-q-(1-hydroxy-([substituted]heteroaryl)methyl)imidazol-w-yl)-3-([substituted]-2H-tetrazol-5-yl)-propenone
(B-952) 1-[nH-(z-alkyl-q-(1-hydroxy-([substituted]heteroaryl)methyl))pyrazol-w-yl]-3-hydroxy-3-([substituted]-1H-1,2,4-triazol-3-yl)-propenone
(B-953) 1-(q-(([substituted]heteroaryl)alkenyl)pyridin-w-yl)-3-hydroxy-3-([substituted]-1H-1,2,4-triazol-3-yl)-propenone
(B-954) 4-[nH-(q-([substituted]aryl)-z-halogeno)imidazol-w-yl]-2-hydroxy-4-oxo-2-butenoic acid
(B-955) 1-(q-(([substituted]aryl)aminocarbonyl)thiophen-w-yl)-3-hydroxy-3-([substituted]-2H-tetrazol-5-yl)-propenone
(B-956) 1-(q-(([substituted]aryl)aminosulfonyl)thiophen-w-yl)-3-hydroxy-3-([substituted]-2H-tetrazol-5-yl)-propenone
(B-957) 1-[nH-(z-alkyl-q-(([substituted]aryl)sulfonylamino))imidazol-w-yl]-3-hydroxy-3-([substituted]-2H-tetrazol-5-yl)-propenone
(B-958) 4-(q-(([substituted]heteroaryl)amino)thiophen-w-yl)-2-hydroxy-4-oxo-2-butenoic acid
(B-959) 4-[(z-alkyl-q-(([substituted]heteroaryl)carbonylamino))pyridin-w-yl]-2-hydroxy-4-oxo-2-butenoic acid
(B-960) 4-[(q-(([substituted]heteroaryl)carbonylamino)-z-halogeno)pyridin-w-yl]-2-hydroxy-4-oxo-2-butenoic acid
(B-961) 1-[(z-halogeno-q-(([substituted]heteroaryl)sulfonylamino))thiazol-w-yl]-3-hydroxy-3-([substituted]-1H-1,2,4-triazol-3-yl)-propenone
(B-962) 1-[(q-([substituted]aryl)-z-halogeno)thiophen-w-yl]-3-hydroxy-3-([substituted]-1H-1,2,4-triazol-3-yl)-propenone (B-963) 1-[nH-(z-alkyl-q-(([substituted]aryl)amino))imidazol-w-yl]-3-hydroxy-3-([substituted]-1H-1,2,4-triazol-3-yl)-propenone (B-964) 4-[(z-alkyl-q-(([substituted]heteroaryl)sulfinyl))furan-w-yl]-2-hydroxy-4-oxo-2-butenoic acid (B-965) 3-hydroxy-1-(q-(([substituted]heteroaryl)thio)oxazol-w-yl)-3-([substituted]-1H-1,2,4-triazol-3-yl)-propenone (B-966) 1-(nH-q-(([substituted]heteroaryl)alkenyl)pyrazol-w-yl)-3-hydroxy-3-([substituted]-1H-1,2,4-triazol-3-yl)-propenone (B-967) 3-hydroxy-1-(q-(([substituted]heteroaryl)carboxy)thiophen-w-yl)-3-([substituted]-1H-1,2,4-triazol-3-yl)-propenone (B-968) 1-(nH-q-(([substituted]heteroaryl)amino)pyrazol-w-yl)-3-hydroxy-3-([substituted]-2H-tetrazol-5-yl)-propenone (B-969) 1-(q-(([substituted]aryl)carbonylamino)thiophen-w-yl)-3-hydroxy-3-([substituted]-2H-tetrazol-5-yl)-propenone (B-970) 4-(q-(([substituted]aryl)carboxy)isoxazol-w-yl)-2-hydroxy-4-oxo-2-butenoic acid (B-971) 4-[(q-(([substituted]heteroaryl)carboxy)-z-halogeno)thiophen-w-yl]-2-hydroxy-4-oxo-2-butenoic acid (B-972) 4-[nH-(z-alkyl-q-(([substituted]heteroaryl)oxycarbonyl))imidazol-w-yl]-2-hydroxy-4-oxo-2-butenoic acid (B-973) 1-[(z-alkyl-q-(1-hydroxy-([substituted]heteroaryl)methyl))oxazol-w-yl]-3-hydroxy-3-([substituted]-1H-1,2,4-triazol-3-yl)-propenone (B-974) 4-(q-(([substituted]aryl)carbonyl)pyridin-w-yl)-2-hydroxy-4-oxo-2-butenoic acid (B-975) 4-[(z-alkyl-q-(([substituted]heteroaryl)sulfonyl))furan-w-yl]-2-hydroxy-4-oxo-2-butenoic acid (B-976) 4-(q-(([substituted]heteroaryl)alkenyl)isoxazol-w-yl)-2-hydroxy-4-oxo-2-butenoic acid (B-977) 4-[(q-(([substituted]heteroaryl)carbonyl)-z-halogeno)thiophen-w-yl]-2-hydroxy-4-oxo-2-butenoic acid (B-978) 1-[(q-(([substituted]heteroaryl)carbonyl)-z-halogeno)furan-w-yl]-3-hydroxy-3-([substituted]-1H-1,2,4-triazol-3-yl)-propenone (B-979) 1-[(z-alkyl-q-(([substituted]heteroaryl)oxy))oxazol-w-yl]-3-hydroxy-3-([substituted]-2H-tetrazol-5-yl)-propenone (B-980) 1-[(q-(([substituted]aryl)alkyl)-z-halogeno)thiophen-w-yl]-3-hydroxy-3-([substituted]-1H-1,2,4-triazol-3-yl)-propenone (B-981) 4-[(q-([substituted]aryl)-z-halogeno)thiophen-w-yl]-2-hydroxy-4-oxo-2-butenoic acid (B-982) 1-[(z-alkyl-q-(([substituted]aryl)amino))isoxazol-w-yl]-3-hydroxy-3-([substituted]-1H-1,2,4-triazol-3-yl)-propenone (B-983) 1-(nH-q-(([substituted]aryl)carbonyl)imidazol-w-yl)-3-hydroxy-3-([substituted]-1H-1,2,4-triazol-3-yl)-propenone (B-984) 1-[(z-halogeno-q-(([substituted]heteroaryl)thio))furan-w-yl]-3-hydroxy-3-([substituted]-2H-tetrazol-5-yl)-propenone (B-985) 4-[(z-alkyl-q-(([substituted]heteroaryl)aminocarbonyl))isoxazol-w-yl]-2-hydroxy-4-oxo-2-butenoic acid (B-986) 1-[(q-(([substituted]heteroaryl)aminocarbonyl)-z-halogeno)thiophen-w-yl]-3-hydroxy-3-([substituted]-2H-tetrazol-5-yl)-propenone (B-987) 2-hydroxy-4-oxo-4-(q-(([substituted]heteroaryl)thio)thiophen-w-yl)-2-butenoic acid (B-988) 1-[nH-(z-alkyl-q-(([substituted]heteroaryl)sulfinyl))imidazol-w-yl]-3-hydroxy-3-([substituted]-2H-tetrazol-5-yl)-propenone (B-989) 1-[(z-alkyl-q-(([substituted]heteroaryl)aminosulfonyl))oxazol-w-yl]-3-hydroxy-3-([substituted]-2H-tetrazol-5-yl)-propenone (B-990) 2-hydroxy-4-(q-(([substituted]heteroaryl)carboxy)isoxazol-w-yl)-4-oxo-2-butenoic acid (B-991) 3-hydroxy-1-(q-(([substituted]heteroaryl)oxy)thiazol-w-yl)-3-([substituted]-1H-1,2,4-triazol-3-yl)-propenone (B-992) 3-hydroxy-3-([substituted]-2H-tetrazol-5-yl)-1-(nH-q-(([substituted]heteroaryl)thio)imidazol-w-yl)-propenone (B-993) 1-[(z-alkyl-q-(([substituted]aryl)aminocarbonyl))oxazol-w-yl]-3-hydroxy-3-([substituted]-1H-1,2,4-triazol-3-yl)-propenone (B-994) 4-(nH-q-(([substituted]heteroaryl)carbonyl)pyrazol-w-yl)-2-hydroxy-4-oxo-2-butenoic acid (B-995) 1-[nH-(z-alkyl-q-(([substituted]heteroaryl)oxy))pyrazol-w-yl]-3-hydroxy-3-([substituted]-1H-1,2,4-triazol-3-yl)-propenone (B-996) 1-[(z-halogeno-q-(([substituted]aryl)oxycarbonyl))pyrrol-w-yl]-3-hydroxy-3-([substituted]-2H-tetrazol-5-yl)-propenone (B-997) 1-[nH-(z-halogeno-q-(([substituted]aryl)sulfinyl))imidazol-w-yl]-3-hydroxy-3-([substituted]-2H-tetrazol-5-yl)-propenone (B-998) 1-[(z-alkyl-q-(([substituted]heteroaryl)thio))thiophen-w-yl]-3-hydroxy-3-([substituted]-2H-tetrazol-5-yl)-propenone (B-999) 1-[(z-alkyl-q-(([substituted]heteroaryl)sulfonylamino))pyrrol-w-yl]-3-hydroxy-3-([substituted]-2H-tetrazol-5-yl)-propenone (B-1000) 2-hydroxy-4-oxo-4-(q-(([substituted]heteroaryl)sulfonylamino)pyrrol-w-yl)-2-butenoic acid (B-1001) 1-[nH-(z-halogeno-q-(([substituted]aryl)thio))pyrazol-w-yl]-3-hydroxy-3-([substituted]-2H-tetrazol-5-yl)-propenone (B-1002) 4-(nH-q-(([substituted]aryl)alkenyl)imidazol-w-yl)-2-hydroxy-4-oxo-2-butenoic acid (B-1003) 1-[(q-(([substituted]heteroaryl)aminocarbonyl)-z-halogeno)furan-w-yl]-3-hydroxy-3-([substituted]-1H-1,2,4-triazol-3-yl)-propenone (B-1004) 4-[(z-alkyl-q-(([substituted]heteroaryl)oxy))pyridin-w-yl]-2-hydroxy-4-oxo-2-butenoic acid (B-1005) 4-(q-(([substituted]heteroaryl)alkenyl)oxazol-w-yl)-2-hydroxy-4-oxo-2-butenoic acid (B-1006) 1-[(z-alkyl-q-(([substituted]heteroaryl)sulfinyl))furan-w-yl]-3-hydroxy-3-([substituted]-1H-1,2,4-triazol-3-yl)-propenone (B-1007) 4-[(q-(([substituted]heteroaryl)alkenyl)-z-halogeno)oxazol-w-yl]-2-hydroxy-4-oxo-2-butenoic acid (B-1008) 1-(nH-q-([substituted]aryl)pyrazol-w-yl)-3-hydroxy-3-([substituted]-1H-1,2,4-triazol-3-yl)-propenone (B-1009) 1-[(z-halogeno-q-(([substituted]heteroaryl)thio))thiophen-w-yl]-3-hydroxy-3-([substituted]-2H-tetrazol-5-yl)-propenone (B-1010) 1-[(q-(([substituted]aryl)carboxy)-z-halogeno)thiazol-w-yl]-3-hydroxy-3-([substituted]-2H-tetrazol-5-yl)-propenone (B-1011) 1-(nH-q-(([substituted]heteroaryl)carbonyl)pyrazol-w-yl)-3-hydroxy-3-([substituted]-1H-1,2,4-triazol-3-yl)-propenone (B-1012) 2-hydroxy-4-oxo-4-(q-(([substituted]heteroaryl)sulfonyl)pyrrol-w-yl)-2-butenoic acid (B-1013) 3-hydroxy-1-(nH-q-(([substituted]heteroaryl)thio) imidazol-w-yl)-3-([substituted]-1H-1,2,4-triazol-3-yl)-propenone (B-1014) 1-[(z-alkyl-q-(([substituted]aryl)amino))isoxazol-w-yl]-3-hydroxy-3-([substituted]-2H-tetrazol-5-yl)-propenone (B-1015) 1-[nH-(z-alkyl-q-(([substituted]aryl)sulfonyl))pyrazol-w-yl]-3-hydroxy-3-([substituted]-1H-1,2,4-triazol-3-yl)-propenone (B-1016) 4-[nH-(q-(([substituted]heteroaryl)amino)-z-halogeno)imidazol-w-yl]-2-hydroxy-4-oxo-2-butenoic acid (B-1017) 3-hydroxy-1-(q-(([substituted]heteroaryl)sulfonyl)oxazol-w-yl)-3-([substituted]-2H-tetrazol-5-yl)-propenone (B-1018) 4-[(z-alkyl-q-(([substituted]aryl)aminosulfonyl))isoxazol-w-yl]-2-hydroxy-4-oxo-2-butenoic acid (B-1019) 1-[(z-halogeno-q-(([substituted]aryl)oxycarbonyl))oxazol-w-yl]-3-hydroxy-3-([substituted]-1H-1,2,4-triazol-3-yl)-propenone (B-1020) 1-[(q-(([substituted]aryl)aminocarbonyl)-z-halogeno)isoxazol-w-yl]-3-hydroxy-3-([substituted]-1H-1,2,4-triazol-3-yl)-propenone (B-1021) 1-(q-(([substituted]aryl)aminosulfonyl)thiazol-w-yl)-3-hydroxy-3-([substituted]-2H-tetrazol-5-yl)-propenone (B-1022) 1-(q-(([substituted]aryl)amino)oxazol-w-yl)-3-hydroxy-3-([substituted]-2H-tetrazol-5-yl)-propenone (B-1023) 4-[(z-alkyl-q-(([substituted]aryl)aminosulfonyl))thiophen-w-yl]-2-hydroxy-4-oxo-2-butenoic acid (B-1024) 1-(q-(([substituted]aryl)carbonyl)isoxazol-w-yl)-3-hydroxy-3-([substituted]-2H-tetrazol-5-yl)-propenone (B-1025) 1-(q-(([substituted]heteroaryl)aminocarbonyl)thiazol-w-yl)-3-hydroxy-3-([substituted]-1H-1,2,4-triazol-3-yl)-propenone (B-1026) 4-[(z-alkyl-q-(([substituted]heteroaryl)carbonylamino))oxazol-w-yl]-2-hydroxy-4-oxo-2-butenoic acid (B-1027) 1-[(z-alkyl-q-(([substituted]heteroaryl)aminocarbonyl))furan-w-yl]-3-hydroxy-3-([substituted]-2H-tetrazol-5-yl)-propenone (B-1028) 1-[(z-halogeno-q-(([substituted]aryl)sulfinyl))oxazol-w-yl]-3-hydroxy-3-([substituted]-1H-1,2,4-triazol-3-yl)-propenone (B-1029) 1-[(z-alkyl-q-(([substituted]heteroaryl)carbonyl))isoxazol-w-yl]-3-hydroxy-3-([substituted]-2H-tetrazol-5-yl)-propenone (B-1030) 4-[nH-(z-alkyl-q-(([substituted]aryl)oxycarbonyl))pyrazol-w-yl]-2-hydroxy-4-oxo-2-butenoic acid (B-1031) 2-hydroxy-4-oxo-4-(q-(([substituted]heteroaryl)carboxy)pyridin-w-yl)-2-butenoic acid (B-1032) 4-(q-([substituted]heteroaryl)thiazol-w-yl)-2-hydroxy-4-oxo-2-butenoic acid (B-1033) 1-[nH-(z-alkyl-q-(([substituted]aryl)aminocarbonyl))pyrazol-w-yl]-3-hydroxy-3-([substituted]-2H-tetrazol-5-yl)-propenone (B-1034) 1-(nH-q-([substituted]aryl)imidazol-w-yl)-3-hydroxy-3-([substituted]-2H-tetrazol-5-yl)-propenone (B-1035) 1-[(z-alkyl-q-(([substituted]heteroaryl)aminocarbonyl))pyrrol-w-yl]-3-hydroxy-3-([substituted]-2H-tetrazol-5-yl)-propenone (B-1036) 1-[(z-halogeno-q-(([substituted]aryl)thio))pyrrol-w-yl]-3-hydroxy-3-([substituted]-1H-1,2,4-triazol-3-yl)-propenone (B-1037) 4-[(q-(([substituted]heteroaryl)carboxy)-z-halogeno)oxazol-w-yl]-2-hydroxy-4-oxo-2-butenoic acid (B-1038) 4-[(z-alkyl-q-(([substituted]aryl)oxycarbonyl))oxazol-w-yl]-2-hydroxy-4-oxo-2-butenoic acid (B-1039) 3-hydroxy-1-(q-(([substituted]aryl)oxycarbonyl)furan-w-yl)-3-([substituted]-2H-tetrazol-5-yl)-propenone (B-1040) 1-[nH-(z-halogeno-q-(([substituted]aryl)sulfonyl))imidazol-w-yl]-3-hydroxy-3-([substituted]-1H-1,2,4-triazol-3-yl)-propenone (B-1041) 1-[(z-halogeno-q-(([substituted]heteroaryl)sulfinyl))thiazol-w-yl]-3-hydroxy-3-([substituted]-1H-1,2,4-triazol-3-yl)-propenone (B-1042) 1-(q-(([substituted]aryl)aminosulfonyl)isoxazol-w-yl)-3-hydroxy-3-([substituted]-2H-tetrazol-5-yl)-propenone (B-1043) 1-[(z-alkyl-q-(([substituted]heteroaryl)sulfonylamino))isoxazol-w-yl]-3-hydroxy-3-([substituted]-1H-1,2,4-triazol-3-yl)-propenone (B-1044) 1-[nH-(z-halogeno-q-(([substituted]heteroaryl)oxy))imidazol-w-yl]-3-hydroxy-3-([substituted]-2H-tetrazol-5-yl)-propenone (B-1045) 4-[(q-(([substituted]heteroaryl)amino)-z-halogeno)pyrrol-w-yl]-2-hydroxy-4oxo-2-butenoic acid (B-1046) 1-[(z-alkyl-q-(1-hydroxy-([substituted]aryl)methyl))furan-w-yl]-3-hydroxy-3-([substituted]-2H-tetrazol-5-yl)-propenone (B-1047) 1-(q-(([substituted]heteroaryl)aminosulfonyl)oxazol-w-yl)-3-hydroxy-3-([substituted]-2H-tetrazol-5-yl)-propenone (B-1048) 1-[(z-alkyl-q-(([substituted]heteroaryl)thio))furan-w-yl]-3-hydroxy-3-([substituted]-2H-tetrazol-5-yl)-propenone (B-1049) 3-hydroxy-1-(q-(([substituted]aryl)oxycarbonyl)oxazol-w-yl)-3-([substituted]-2H-tetrazol-5-yl)-propenone (B-1050) 4-[nH-(z-halogeno-q-(([substituted]aryl)thio))pyrazol-w-yl]-2-hydroxy-4-oxo-2-butenoic acid (B-1051) 1-[(q-(([substituted]heteroaryl)aminosulfonyl)-z-halogeno)furan-w-yl]-3-hydroxy-3-([substituted]-2H-tetrazol-5-yl)-propenone (B-1052) 1-(q-(([substituted]heteroaryl)aminocarbonyl)pyridin-w-yl)-3-hydroxy-3-([substituted]-2H-tetrazol-5-yl)-propenone (B-1053) 4-[(q-(([substituted]heteroaryl)carbonylamino)-z-halogeno)oxazol-w-yl]-2-hydroxy-4-oxo-2-butenoic acid (B-1054) 1-[(q-(([substituted]aryl)carbonyl)-z-halogeno)pyridin-w-yl]-3-hydroxy-3-([substituted]-2H-tetrazol-5-yl)-propenone (B-1055) 1-(q-(([substituted]aryl)alkenyl)isoxazol-w-yl)-3-hydroxy-3-([substituted]-1H-1,2,4-triazol-3-yl)-propenone (B-1056) 1-[(q-(([substituted]heteroaryl)carbonyl)-z-halogeno)thiazol-w-yl]-3-hydroxy-3-([substituted]-1H-1,2,4-triazol-3-yl)-propenone (B-1057) 1-[(q-(([substituted]aryl)aminocarbonyl)-z-halogeno)isoxazol-w-yl]-3-hydroxy-3-([substituted]-2H-tetrazol-5-yl)-propenone (B-1058) 1-[nH-(q-(([substituted]heteroaryl)alkyl)-z-halogeno)pyrazol-w-yl]-3-hydroxy-3-([substituted]-1H-1,2,4-triazol-3-yl)-propenone (B-1059) 4-[(q-(([substituted]heteroaryl)carbonylamino)-z-halogeno)thiazol-w-yl]-2-hydroxy-4-oxo-2-butenoic acid (B-1060) 4-[nH-(z-alkyl-q-(([substituted]heteroaryl)alkyl))pyrazol-w-yl]-2-hydroxy-4-oxo-2-butenoic acid (B-1061) 4-[(q-(([substituted]aryl)amino)-z-halogeno)thiophen-w-yl]-2-hydroxy-4-oxo-2-butenoic acid (B-1062) 1-[(z-alkyl-q-(([substituted]heteroaryl)oxycarbonyl))thiazol-w-yl]-3-hydroxy-3-([substituted]-2H-tetrazol-5-yl)-propenone (B-1063) 1-[(q-(([substituted]aryl)carbonyl)-z-halogeno)isoxazol-w-yl]-3-hydroxy-3-([substituted]-2H-tetrazol-5-yl)-propenone
(B-1064) 1-[(q-(([substituted]aryl)alkyl)-z-halogeno)isoxazol-w-yl]-3-hydroxy-3-([substituted]-2H-tetrazol-5-yl)-propenone
(B-1065) 1-(q-(([substituted]aryl)aminocarbonyl)thiazol-w-yl)-3-hydroxy-3-([substituted]-2H-tetrazol-5-yl)-propenone
(B-1066) 1-[(q-(([substituted]aryl)alkyl)-z-halogeno)pyridin-w-yl]-3-hydroxy-3-([substituted]-2H-tetrazol-5-yl)-propenone
(B-1067) 4-[(z-alkyl-q-(([substituted]heteroaryl)sulfonylamino))oxazol-w-yl]-2-hydroxy-4-oxo-2-butenoic acid
(B-1068) 3-hydroxy-1-(nH-q-(([substituted]aryl)sulfonyl)imidazol-w-yl)-3-([substituted]-1H-1,2,4-triazol-3-yl)-)propenone
(B-1069) 1-[(z-alkyl-q-(([substituted]heteroaryl)amino))furan-w-yl]-3-hydroxy-3-([substituted]-2H-tetrazol-5-yl)-propenone
(B-1070) 1-[nH-(q-(([substituted]heteroaryl)aminosulfonyl)-z-halogeno)imidazol-w-yl]-3-hydroxy-3-([substituted]-2H-tetrazol-5-yl)-propenone
(B-1071) 1-(q-(([substituted]aryl)carbonyl)oxazol-w-yl)-3-hydroxy-3-([substituted]-1H-1,2,4-triazol-3-yl)-propenone
(B-1072) 1-[(z-halogeno-q-(1-hydroxy-([substituted]heteroaryl)methyl))oxazol-w-yl]-3-hydroxy-3-([substituted]-1H-1,2,4-triazol-3-yl)-propenone
(B-1073) 4-[(q-(([substituted]aryl)alkenyl)-z-halogeno)pyrrol-w-yl]-2-hydroxy-4-oxo-2-butenoic acid
(B-1074) 1-(nH-q-([substituted]aryl)pyrazol-w-yl)-3-hydroxy-3-([substituted]-2H-tetrazol-5-yl)-propenone
(B-1075) 4-[nH-(z-alkyl-q-(([substituted]heteroaryl)carbonylamino))pyrazol-w-yl]-2-hydroxy-4-oxo-2-butenoic acid
(B-1076) 4-[(z-alkyl-q-(([substituted]aryl)aminocarbonyl))oxazol-w-yl]-2-hydroxy-4-oxo-2-butenoic acid
(B-1077) 4-(nH-q-(([substituted]heteroaryl)amino)l)pyrazol-w-yl)-2-hydroxy-4-oxo-2-butenoic acid
(B-1078) 2-hydroxy-4-oxo-4-(q-(([substituted]aryl)oxy)furan-w-yl)-2-butenoic acid
(B-1079) 1-[(q-(([substituted]aryl)carbonylamino)-z-halogeno)pyridin-w-yl]-3-hydroxy-3-([substituted]-2H-tetrazol-5-yl)-propenone
(B-1080) 4-[nH-(z-alkyl-q-(([substituted]aryl)sulfinyl))imidazol-w-yl]-2-hydroxy-4-oxo-2-butenoic acid
(B-1081) 1-[(z-halogeno-q-([substituted]heteroaryl))thiophen-w-yl]-3-hydroxy-3-([substituted]-1H-1,2,4-triazol-3-yl)-propenone
(B-1082) 1-[(q-(([substituted]heteroaryl)carboxy)-z-halogeno)thiazol-w-yl]-3-hydroxy-3-([substituted]-2H-tetrazol-5-yl)-propenone
(B-1083) 1-[(z-alkyl-q-([substituted]heteroaryl))thiazol-w-yl]-3-hydroxy-3-([substituted]-1H-1,2,4-triazol-3-yl)-propenone
(B-1084) 1-[(z-halogeno-q-(([substituted]heteroaryl)oxycarbonyl))isoxazol-w-yl]-3-hydroxy-3-(([substituted]-1H-1,2,4-triazol-3-yl)-propenone
(B-1085) 1-(q-(([substituted]aryl)carbonyl)isoxazol-w-yl)-3-hydroxy-3-([substituted]-1H-1,2,4-triazol-3-yl)-propenone
(B-1086) 1-(q-(([substituted]heteroaryl)alkyl)isoxazol-w-yl)-3-hydroxy-3-([substituted]-1H-1,2,4-triazol-3-yl)-propenone
(B-1087) 1-[nH-(z-alkyl-q-(([substituted]heteroaryl)aminocarbonyl))pyrazol-w-yl]-3-hydroxy-3-([substituted]-2H-tetrazol-5-yl)-propenone
(B-1088) 4-(q-(([substituted]heteroaryl)carbonylamino)furan-w-yl)-2-hydroxy-4-oxo-2-butenoic acid
(B-1089) 4-[(z-alkyl-q-(([substituted]heteroaryl)alkyl))oxazol-w-yl]-2-hydroxy-4-oxo-2-butenoic acid
(B-1090) 1-[nH-(z-alkyl-q-(([substituted]heteroaryl)alkyl))imidazol-w-yl]-3-hydroxy-3-([substituted]-2H-tetrazol-5-yl)-propenone
(B-1091) 1-[(q-(([substituted]heteroaryl)alkyl)-z-halogeno)pyrrol-w-yl]-3-hydroxy-3-([substituted]-2H-tetrazol-5-yl)-propenone
(B-1092) 1-[(q-(([substituted]aryl)alkenyl)-z-halogeno)thiophen-w-yl]-3-hydroxy-3-([substituted]-2H-tetrazol-5-yl)-propenone
(B-1093) 3-hydroxy-1-(q-(([substituted]aryl)sulfonylamino)furan-w-yl)-3-([substituted]-2H-tetrazol-5-yl)-propenone
(B-1094) 1-[(z-alkyl-q-(([substituted]heteroaryl)aminocarbonyl))isoxazol-w-yl]-3-hydroxy-3-([substituted]-1H-1,2,4-triazol-3-yl)-propenone
(B-1095) 3-hydroxy-1-(q-(([substituted]heteroaryl)oxycarbonyl)furan-w-yl)-3-([substituted]-2H-tetrazol-5-yl)-propenone
(B-1096) 4-[(q-(([substituted]aryl)alkyl)-z-halogeno)pyridin-w-yl]-2-hydroxy-4-oxo-2-butenoic acid
(B-1097) 1-[(q-(([substituted]heteroaryl)amino)-z-halogeno)pyridin-w-yl]-3-hydroxy-3-([substituted]-1H-1,2,4-triazol-3-yl)-propenone
(B-1098) 1-[nH-(q-(([substituted]aryl)carbonylamino)-z-halogeno)imidazol-w-yl]-3-hydroxy-3-([substituted]-2H-tetrazol-5-yl)-propenone
(B-1099) 1-[(q-(([substituted]aryl)alkenyl)-z-alkyl)pyridin-w-yl]-3-hydroxy-3-([substituted]-1H-1,2,4-triazol-3-yl)-propenone
(B-1100) 1-[(z-halogeno-q-(([substituted]heteroaryl)sulfonyl))pyridin-w-yl]-3-hydroxy-3-([substituted]-2H-tetrazol-5-yl)-propenone
(B-1101) 1-[(q-(([substituted]heteroaryl)carbonylamino)-z-halogeno)pyridin-w-yl]-3-hydroxy-3-([substituted]-2H-tetrazol-5-yl)-propenone
(B-1102) 4-[(z-alkyl-q-(([substituted]heteroaryl)sulfonyl))thiophen-w-yl]-2-hydroxy-4-oxo-2-butenoic acid
(B-1103) 4-[(z-alkyl-q-(([substituted]aryl)carbonylamino))isoxazol-w-yl]-2-hydroxy-4-oxo-2-butenoic acid
(B-1104) 3-hydroxy-1-(q-(([substituted]aryl)oxy)oxazol-w-yl)-3-([substituted]-2H-tetrazol-5-yl)-propenone
(B-1105) 4-(q-(([substituted]aryl)alkenyl)oxazol-w-yl)-2-hydroxy-4-oxo-2-butenoic acid
(B-1106) 1-(q-(([substituted]aryl)aminosulfonyl)furan-w-yl)-3-hydroxy-3-([substituted]-1H-1,2,4-triazol-3-yl)-propenone
(B-1107) 1-[(q-(([substituted]aryl)alkenyl)-z-halogeno)pyrrol-w-yl]-3-hydroxy-3-([substituted]-2H-tetrazol-5-yl)-propenone
(B-1108) 1-[(z-halogeno-q-(([substituted]heteroaryl)oxy))thiazol-w-yl]-3-hydroxy-3-([substituted]-1H-1,2,4-triazol-3-yl)-propenone
(B-1109) 1-(q-(([substituted]heteroaryl)carbonyl)pyridin-w-yl)-3-hydroxy-3-([substituted]-2H-tetrazol-5-yl)-propenone
(B-1110) 4-[(z-alkyl-q-(([substituted]heteroaryl)carbonyl))thiazol-w-yl]-2-hydroxy-4-oxo-2-butenoic acid
(B-1111) 1-(q-(([substituted]heteroaryl)amino)pyrrol-w-yl)-3-hydroxy-3-([substituted]-2H-tetrazol-5-yl)-propenone
(B-1112) 4-(q-(([substituted]aryl)alkyl)pyrrol-w-yl)-2-hydroxy-4-oxo-2-butenoic acid
(B-1113) 1-[(z-alkyl-q-(([substituted]aryl)aminosulfonyl))furan-w-yl]-3-hydroxy-3-([substituted]-2H-tetrazol-5-yl)-propenone (B-1114) 4-[(z-alkyl-q-(([substituted]aryl)thio))thiophen-w-yl]-2-hydroxy-4-oxo-2-butenoic acid
(B-1115) 1-[(q-([substituted]aryl)-z-halogeno)pyrrol-w-yl]-3-hydroxy-3-([substituted]-1H-1,2,4-triazol-3-yl)-propenone
(B-1116) 1-(q-(([substituted]aryl)alkyl)thiophen-w-yl)-3-hydroxy-3-([substituted]-2H-tetrazol-5-yl)-propenone
(B-1117) 1-(q-([substituted]heteroaryl)thiazol-w-yl)-3-hydroxy-3-([substituted]-2H-tetrazol-5-yl)-propenone
(B-1118) 1-[(z-alkyl-q-(([substituted]heteroaryl)aminosulfonyl))isoxazol-w-yl]-3-hydroxy-3-([substituted]-2H-tetrazol-5-yl)-propenone
(B-1119) 4-[nH-(q-(([substituted]aryl)carboxy)-z-halogeno)imidazol-w-yl]-2-hydroxy-4-oxo-2-butenoic acid
(B-1120) 3-hydroxy-1-(nH-q-(([substituted]heteroaryl)carboxy)pyrazol-w-yl)-3-([substituted]-1H-1,2,4-triazol-3-yl)-propenone
(B-1121) 1-(q-(([substituted]aryl)carbonylamino)oxazol-w-yl)-3-hydroxy-3-([substituted]-2H-tetrazol-5-yl)-propenone
(B-1122) 1-[nH-(z-alkyl-q-(([substituted]heteroaryl)carbonylamino))pyrazol-w-yl]-3-hydroxy-3-([substituted]-2H-tetrazol-5-yl)-propenone
(B-1123) 1-(q-(([substituted]aryl)amino)isoxazol-w-yl)-3-hydroxy-3-([substituted]-1H-1,2,4-triazol-3-yl)-propenone
(B-1124) 3-hydroxy-1-(nH-q-(([substituted]aryl)sulfonylamino)imidazol-w-yl)-3-([substituted]-2H-tetrazol-5-yl)-propenone
(B-1125) 3-hydroxy-1-(q-(1-hydroxy-([substituted]heteroaryl)methyl)isoxazol-w-yl)-3-([substituted]-1H-1,2,4-triazol-3-yl)-propenone
(B-1126) 1-[(z-alkyl-q-(([substituted]heteroaryl)carbonylamino))oxazol-w-yl]-3-hydroxy-3-([substituted]-1H-1,2,4-triazol-3-yl)-propenone
(B-1127) 1-[(z-halogeno-q-(([substituted]heteroaryl)oxy))oxazol-w-yl]-3-hydroxy-3-([substituted]-2H-tetrazol-5-yl)-propenone
(B-1128) 4-[(z-alkyl-q-(([substituted]heteroaryl)aminocarbonyl))thiazol-w-yl]-2-hydroxy-4-oxo-2-butenoic acid
(B-1129) 1-[(z-alkyl-q-(([substituted]aryl)aminocarbonyl))oxazol-w-yl]-3-hydroxy-3-([substituted]-2H-tetrazol-5-yl)-propenone
(B-1130) 1-[(z-alkyl-q-(([substituted]heteroaryl)sulfonyl))thiazol-w-yl]-3-hydroxy-3-([substituted]-1H-1,2,4-triazol-3-yl)-propenone
(B-1131) 1-[(z-alkyl-q-(([substituted]aryl)sulfinyl))isoxazol-w-yl]-3-hydroxy-3-([substituted]-2H-tetrazol-5-yl)-propenone
(B-1132) 4-[(z-alkyl-q-(([substituted]heteroaryl)sulfonyl))oxazol-w-yl]-2-hydroxy-4-oxo-2-butenoic acid
(B-1133) 4-[(q-(([substituted]heteroaryl)amino)-z-halogeno)thiophen-w-yl]-2-hydroxy-4-oxo-2-butenoic acid
(B-1134) 1-[nH-(q-(([substituted]aryl)carbonyl)-z-halogeno)pyrazol-w-yl]-3-hydroxy-3-([substituted]-1H-1,2,4-triazol-3-yl)-propenone
(B-1135) 2-hydroxy-4-(q-(1-hydroxy-([substituted]heteroaryl)methyl)thiazol-w-yl)-4-oxo-2-butenoic acid
(B-1136) 1-[(z-alkyl-q-(([substituted]heteroaryl)oxycarbonyl))oxazol-w-yl]-3-hydroxy-3-([substituted]-1H-1,2,4-triazol-3-yl)-propenone
(B-1137) 2-hydroxy-4-oxo-4-(q-(([substituted]heteroaryl)thio)pyrrol-w-yl)-2-butenoic acid
(B-1138) 1-[(z-halogeno-q-(([substituted]heteroaryl)oxy))pyrrol-w-yl]-3-hydroxy-3-([substituted]-1H-1,2,4-triazol-3-yl)-propenone
(B-1139) 4-[(z-alkyl-q-(([substituted]aryl)carboxy))isoxazol-w-yl]-2-hydroxy-4-oxo-2-butenoic acid
(B-1140) 1-[(q-(([substituted]aryl)alkyl)-z-halogeno)thiophen-w-yl]-3-hydroxy-3-([substituted]-2H-tetrazol-5-yl)-propenone
(B-1141) 1-[(z-alkyl-q-(([substituted]heteroaryl)oxycarbonyl))pyrrol-w-yl]-3-hydroxy-3-([substituted]-1H-1,2,4-triazol-3-yl)-propenone
(B-1142) 4-[(z-halogeno-q-(([substituted]heteroaryl)thio))thiophen-w-yl]-2-hydroxy-4-oxo-2-butenoic acid
(B-1143) 3-hydroxy-1-(q-(([substituted]aryl)oxycarbonyl)thiazol-w-yl)-3-([substituted]-2H-tetrazol-5-yl)-propenone
(B-1144) 4-[(z-alkyl-q-(([substituted]heteroaryl)amino))isoxazol-w-yl]-2-hydroxy-4-oxo-2-butenoic acid
(B-1145) 1-(q-(([substituted]aryl)carboxy)furan-w-yl)-3-hydroxy-3-([substituted]-1H-1,2,4-triazol-3-yl)-propenone
(B-1146) 1-(q-(([substituted]aryl)carbonyl)pyridin-w-yl)-3-hydroxy-3-([substituted]-1H-1,2,4-triazol-3-yl)-propenone
(B-1147) 1-[(q-(([substituted]aryl)carbonylamino)-z-halogeno)pyridin-w-yl]-3-hydroxy-3-([substituted]-1H-1,2,4-triazol-3-yl)-propenone
(B-1148) 1-[nH-(q-(([substituted]heteroaryl)alkyl)-z-halogeno)imidazol-w-yl]-3-hydroxy-3-([substituted]-2H-tetrazol-5-yl)-propenone
(B-1149) 1-[nH-(z-halogeno-q-(([substituted]heteroaryl)thio))pyrazol-w-yl]-3-hydroxy-3-([substituted]-2H-tetrazol-5-yl)-propenone
(B-1150) 1-[(z-alkyl-q-(([substituted]heteroaryl)amino))thiophen-w-yl]-3-hydroxy-3-([substituted]-2H-tetrazol-5-yl)-propenone
(B-1151) 1-[(z-alkyl-q-(([substituted]aryl)alkyl))oxazol-w-yl]-3-hydroxy-3-([substituted]-2H-tetrazol-5-yl)-propenone
(B-1152) 4-[(z-alkyl-q-(([substituted]aryl)alkyl))oxazol-w-yl]-2-hydroxy-4-oxo-2-butenoic acid
(B-1153) 1-[nH-(z-alkyl-q-(([substituted]aryl)sulfonyl))imidazol-w-yl]-3-hydroxy-3-([substituted]-1H-1,2,4-triazol-3-yl)-propenone
(B-1154) 4-(q-(([substituted]aryl)carbonylamino)isoxazol-w-yl)-2-hydroxy-4-oxo-2-butenoic acid
(B-1155) 1-[(z-halogeno-q-(([substituted]heteroaryl)thio))oxazol-w-yl]-3-hydroxy-3-([substituted]-2H-tetrazol-5-yl)-propenone
(B-1156) 2-hydroxy-4-oxo-4-(nH-q-(([substituted]heteroaryl)thio)imidazol-w-yl)-2-butenoic acid
(B-1157) 3-hydroxy-1-(nH-q-(([substituted]heteroaryl)oxycarbonyl)imidazol-w-yl)-3-([substituted]-2H-tetrazol-5-yl)-propenone
(B-1158) 1-[(q-(([substituted]aryl)carbonylamino)-z-halogeno)pyrrol-w-yl]-3-hydroxy-3-([substituted]-2H-tetrazol-5-yl)-propenone
(B-1159) 4-[(z-alkyl-q-(([substituted]aryl)thio))oxazol-w-yl]-2-hydroxy-4-oxo-2-butenoic acid
(B-1160) 1-[(q-(([substituted]heteroaryl)carboxy)-z-alkyl)pyridin-w-yl]-3-hydroxy-3-([substituted]-2H-tetrazol-5-yl)-propenone
(B-1161) 4-(q-(([substituted]aryl)alkenyl)furan-w-yl)-2-hydroxy-4-oxo-2-butenoic acid
(B-1162) 1-[(z-halogeno-q-(([substituted]heteroaryl)oxy))isoxazol-w-yl]-3-hydroxy-3-([substituted]-1H-1,2,4-triazol-3-yl)-propenone
(B-1163) 4-[nH-(q-(([substituted]aryl)carbonylamino)-z-halogeno)imidazol-w-yl]-2-hydroxy-4-oxo-2-butenoic acid (B-1164) 1-[nH-(z-alkyl-q-([substituted]heteroaryl))imidazol-w-yl]-3-hydroxy-3-([substituted]-2H-tetrazol-5-yl)-propenone (B-1165) 1-(q-(([substituted]heteroaryl)alkyl)pyrrol-w-yl)-3-hydroxy-3-([substituted]-1H-1,2,4-triazol-3-yl)-propenone (B-1166) 1-[nH-(z-halogeno-q-(([substituted]aryl)oxycarbonyl))imidazol-w-yl]-3-hydroxy-3-([substituted]-2H-tetrazol-5-yl)-propenone (B-1167) 1-[(z-alkyl-q-(([substituted]aryl)thio))pyridin-w-yl]-3-hydroxy-3-([substituted]-2H-tetrazol-5-yl)-propenone (B-1168) 1-[nH-(q-(([substituted]aryl)carboxy)-z-halogeno)imidazol-w-yl]-3-hydroxy-3-([substituted]-2H-tetrazol-5-yl)-propenone (B-1169) 1-[(q-(([substituted]heteroaryl)carboxy)-z-alkyl)isoxazol-w-yl]-3-hydroxy-3-([substituted]-2H-tetrazol-5-yl)-propenone (B-1170) 1-(q-([substituted]aryl)oxazol-w-yl)-3-hydroxy-3-([substituted]-2H-tetrazol-5-yl)-propenone (B-1171) 4-[(z-halogeno-q-(([substituted]aryl)oxycarbonyl))thiophen-w-yl]-2-hydroxy-4-oxo-2-butenoic acid (B-1172) 1-[(q-(([substituted]aryl)carbonylamino)-z-halogeno)thiophen-w-yl]-3-hydroxy-3-([substituted]-2H-tetrazol-5-yl)-propenone (B-1173) 1-(q-(([substituted]aryl)amino)isoxazol-w-yl)-3-hydroxy-3-([substituted]-2H-tetrazol-5-yl)-propenone (B-1174) 1-[(q-(([substituted]heteroaryl)amino)-z-halogeno)thiazol-w-yl]-3-hydroxy-3-([substituted]-2H-tetrazol-5-yl)-propenone (B-1175) 1-[(z-alkyl-q-(([substituted]heteroaryl)aminocarbonyl))pyrrol-w-yl]-3-hydroxy-3-([substituted]-1H-1,2,4-triazol-3-yl)-propenone (B-1176) 1-[(z-halogeno-q-(([substituted]heteroaryl)sulfinyl))isoxazol-w-yl]-3-hydroxy-3-([substituted]-2H-tetrazol-5-yl)-propenone (B-1177) 1-[(q-(([substituted]heteroaryl)carboxy)-z-halogeno)pyrrol-w-yl]-3-hydroxy-3-([substituted]-2H-tetrazol-5-yl)-propenone (B-1178) 1-[nH-(q-(([substituted]aryl)carbonyl)-z-halogeno)imidazol-w-yl]-3-hydroxy-3-([substituted]-2H-tetrazol-5-yl)-propenone (B-1179) 1-[nH-(z-alkyl-q-(([substituted]aryl)carboxy))pyrazol-w-yl]-3-hydroxy-3-([substituted]-1H-1,2,4-triazol-3-yl)-propenone (B-1180) 1-[(z-alkyl-q-(([substituted]aryl)aminosulfonyl))oxazol-w-yl]-3-hydroxy-3-([substituted]-1H-1,2,4-triazol-3-yl)-propenone (B-1181) 4-[(z-alkyl-q-(([substituted]aryl)carbonylamino))thiophen-w-yl]-2-hydroxy-4-oxo-2-butenoic acid (B-1182) 4-[nH-(z-alkyl-q-(([substituted]aryl)carbonyl))pyrazol-w-yl]-2-hydroxy-4-oxo-2-butenoic acid (B-1183) 1-[(z-halogeno-q-(([substituted]aryl)sulfonylamino))furan-w-yl]-3-hydroxy-3-([substituted]-2H-tetrazol-5-yl)-propenone (B-1184) 3-hydroxy-1-(nH-q-(([substituted]aryl)oxy)imidazol-w-yl)-3-([substituted]-2H-tetrazol-5-yl)-propenone (B-1185) 1-[(q-(([substituted]aryl)carboxy)-z-halogeno)thiophen-w-yl]-3-hydroxy-3-([substituted]-1H-1,2,4-triazol-3-yl)-propenone (B-1186) 4-[(z-halogeno-q-(([substituted]heteroaryl)sulfinyl))thiophen-w-yl]-2-hydroxy-4-oxo-2-butenoic acid (B-1187) 1-(q-(([substituted]heteroaryl)aminosulfonyl)thiophen-w-yl)-3-hydroxy-3-([substituted]-2H-tetrazol-5-yl)-propenone (B-1188) 4-[(z-halogeno-q-(([substituted]heteroaryl)oxycarbonyl))pyrrol-w-yl]-2-hydroxy-4-oxo-2-butenoic acid (B-1189) 1-[(z-alkyl-q-(([substituted]aryl)thio))oxazol-w-yl]-3-hydroxy-3-([substituted]-1H-1,2,4-triazol-3-yl)-propenone (B-1190) 2-hydroxy-4-(q-(1-hydroxy-([substituted]aryl)methyl)thiophen-w-yl)-4-oxo-2-butenoic acid (B-1191) 1-[(z-halogeno-q-([substituted]heteroaryl))oxazol-w-yl]-3-hydroxy-3-([substituted]-1H-1,2,4-triazol-3-yl)-propenone (B-1192) 4-[(q-(([substituted]aryl)carbonylamino)-z-halogeno)thiazol-w-yl]-2-hydroxy-4-oxo-2-butenoic acid (B-1193) 4-(nH-q-([substituted]heteroaryl)pyrazol-w-yl)-2-hydroxy-4-oxo-2-butenoic acid (B-1194) 1-[(z-alkyl-q-([substituted]aryl))isoxazol-w-yl]-3-hydroxy-3-([substituted]-1H-1,2,4-triazol-3-yl)-propenone (B-1195) 4-[(z-halogeno-q-(([substituted]heteroaryl)sulfinyl))furan-w-yl]-2-hydroxy-4-oxo-2-butenoic acid (B-1196) 2-hydroxy-4-oxo-4-(q-(([substituted]aryl)sulfinyl)furan-w-yl)-2-butenoic acid (B-1197) 1-[(z-alkyl-q-(substituted]aryl))furan-w-yl]-3-hydroxy-3-([substituted]-2H-tetrazol-5-yl)-propenone (B-1198) 1-[(q-(([substituted]aryl)alkenyl)-z-halogeno)furan-w-yl]-3-hydroxy-3-([substituted]-1H-1,2,4-triazol-3-yl)-propenone (B-1199) 4-[(z-alkyl-q-(([substituted]heteroaryl)carbonylamino))pyrrol-w-yl]-2-hydroxy-4-oxo-2-butenoic acid (B-1200) 3-hydroxy-1-(q-(([substituted]heteroaryl)oxycarbonyl)furan-w-yl)-3-([substituted]-1H-1,2,4-triazol-3-yl)-propenone (B-1201) 1-[(z-halogeno-q-(([substituted]aryl)sulfonylamino))thiophen-w-yl]-3-hydroxy-3-([substituted]-1H-1,2,4-triazol-3-yl)-propenone (B-1202) 1-[(z-alkyl-q-([substituted]heteroaryl))isoxazol-w-yl]-3-hydroxy-3-([substituted]-1H-1,2,4-triazol-3-yl)-propenone (B-1203) 1-(q-(([substituted]heteroaryl)alkenyl)oxazol-w-yl)-3-hydroxy-3-([substituted]-1H-1,2,4-triazol-3-yl)-propenone (B-1204) 4-[(q-(([substituted]heteroaryl)carboxy)-z-alkyl)isoxazol-w-yl]-2-hydroxy-4-oxo-2-butenoic acid (B-1205) 1-[(z-halogeno-q-([substituted]heteroaryl))thiazol-w-yl]-3-hydroxy-3-([substituted]-2H-tetrazol-5-yl)-propenone (B-1206) 1-[(q-(([substituted]heteroaryl)alkenyl)-z-alkyl)furan-w-yl]-3-hydroxy-3-([substituted]-2H-tetrazol-5-yl)-propenone (B-1207) 1-[(z-alkyl-q-(1-hydroxy-([substituted]heteroaryl)methyl))thiophen-w-yl]-3-hydroxy-3-([substituted]-1H-1,2,4-triazol-3-yl)-propenone (B-1208) 1-[(z-halogeno-q-(([substituted]aryl)oxycarbonyl))thiazol-w-yl]-3-hydroxy-3-([substituted]-1H-1,2,4-triazol-3-yl)-propenone (B-1209) 1-[nH-(z-alkyl-q-(([substituted]aryl)carbonylamino))pyrazol-w-yl]-3-hydroxy-3-([substituted]-2H-tetrazol-5-yl)-propenone (B-1210) 1-[nH-(z-alkyl-q-(([substituted]heteroaryl)alkyl))pyrazol-w-yl]-3-hydroxy-3-([substituted]-2H-tetrazol-5-yl)-propenone (B-1211) 1-[nH-(z-halogeno-q-(([substituted]heteroaryl)thio))imidazol-w-yl]-3-hydroxy-3-([substituted]-1H-1,2,4-triazol-3-yl)-propenone (B-1212) 3-hydroxy-1-(q-(([substituted]aryl)oxycarbonyl)thiazol-w-yl)-3-([substituted]-1H-1,2,4-triazol-3-yl)-propenone (B-1213) 3-hydroxy-1-(q-(([substituted]aryl)oxycarbonyl)pyrrol-w-yl)-3-([substituted]-2H-tetrazol-5-yl)-propenone (B-1214) 1-[nH-(q-(([substituted]heteroaryl)carboxy)-z-alkyl)pyrazol-w-yl]-3-hydroxy-3-([substituted]-1H-1,2,4-triazol-3-yl)-propenone (B-1215) 4-[(q-(([substituted]heteroaryl)alkenyl)-z-halogeno)thiophen-w-yl]-2-hydroxy-4-oxo-2-butenoic acid (B-1216) 4-[(q-([substituted]aryl)-z-halogeno)furan-w-yl]-2-hydroxy-4-oxo-2-butenoic acid (B-1217) 4-[(z-alkyl-q-(([substituted]heteroaryl)sulfonyl))pyrrol-w-yl]-2-hydroxy-4-oxo-2-butenoic acid (B-1218) 3-hydroxy-1-(q-((([substituted]heteroaryl)thio)pyridin-w-yl)-3-([substituted]-1H-1,2,4-triazol-3-yl)-propenone (B-1219) 1-[(z-halogeno-q-(([substituted]aryl)thio))thiazol-w-yl]-3-hydroxy-3-([substituted]-1H-1,2,4-triazol-3-yl)-propenone (B-1220) 1-[(z-alkyl-q-(([substituted]aryl)carbonyl))pyrrol-w-yl]-3-hydroxy-3-([substituted]-2H-tetrazol-5-yl)-propenone (B-1221) 1-[nH-(z-alkyl-q-(([substituted]heteroaryl)aminosulfonyl))pyrazol-w-yl]-3-hydroxy-3-([substituted]-2H-tetrazol-5-yl)-propenone (B-1222) 4-(q-(([substituted]heteroaryl)alkyl)pyrrol-w-yl)-2-hydroxy-4-oxo-2-butenoic acid (B-1223) 1-[(q-3(([substituted]heteroaryl)carbonyl)-z-halogeno)oxazol-w-yl]-3-hydroxy-3-([substituted]-1H-1,2,4-triazol-3-yl)-propenone (B-1224) 4-(q-(([substituted]aryl)alkenyl)isoxazol-w-yl)-2-hydroxy-4-oxo-2-butenoic acid (B-1225) 1-[nH-(q-(([substituted]heteroaryl)alkenyl)-z-alkyl)imidazol-w-yl]-3-hydroxy-3-([substituted]-2H-tetrazol-5-yl)-propenone (B-1226) 3-hydroxy-1-(q-((([substituted]heteroaryl)sulfonylamino)pyridin-w-yl)-3-([substituted]-2H-tetrazol-5-yl)-propenone (B-1227) 4-[(z-halogeno-q-([substituted]heteroaryl))thiazol-w-yl]-2-hydroxy-4-oxo-2-butenoic acid (B-1228) 1-[(z-halogeno-q-(1-hydroxy-([substituted]aryl)methyl))furan-w-yl]-3-hydroxy-3-([substituted]-1H-1,2,4-triazol-3-yl)-propenone (B-1229) 2-hydroxy-4-oxo-4-(q-(([substituted]heteroaryl)sulfonyl)thiazol-w-yl)-2-butenoic acid (B-1230) 1-(q-(([substituted]aryl)alkyl)thiazol-w-yl)-3-hydroxy-3-([substituted]-1H-1,2,4-triazol-3-yl)-propenone (B-1231) 4-[(q-(([substituted]heteroaryl)aminocarbonyl)-z-halogeno)oxazol-w-yl]-2-hydroxy-4-oxo-2-butenoic acid (B-1232) 4-(q-(([substituted]aryl)carbonylamino)thiazol-w-yl)-2-hydroxy-4-oxo-2-butenoic acid (B-1233) 1-[(q-(([substituted]heteroaryl)aminosulfonyl)-z-halogeno)thiophen-w-yl]-3-hydroxy-3-([substituted]-2H-tetrazol-5-yl)-propenone (B-1234) 1-(q-((([substituted]aryl)aminosulfonyl)pyridin-w-yl)-3-hydroxy-3-([substituted]-1H-1,2,4-triazol-3-yl)-propenone (B-1235) 4-[(q-((([substituted]aryl)carbonyl)-z-halogeno)thiophen-w-yl]-2-hydroxy-4-oxo-2-butenoic acid (B-1236) 2-hydroxy-4-oxo-4-(q-(([substituted]aryl)sulfinyl)thiophen-w-yl)-2-butenoic acid (B-1237) 4-[(q-(([substituted]heteroaryl)carboxy)-z-alkyl)pyridin-w-yl]-2-hydroxy-4-oxo-2-butenoic acid (B-1238) 4-[(z-alkyl-q-(([substituted]heteroaryl)oxy))furan-w-yl]-2-hydroxy-4-oxo-2-butenoic acid (B-1239) 1-[(q-((([substituted]aryl)aminosulfonyl)-z-halogeno)thiazol-w-yl]-3-hydroxy-3-([substituted]-2H-tetrazol-5-yl)-propenone (B-1240) 1-[(q-((([substituted]aryl)alkyl)-z-halogeno)thiazol-w-yl]-3-hydroxy-3-([substituted]-2H-tetrazol-5-yl)-propenone (B-1241) 1-[nH-(z-alkyl-q-(([substituted]aryl)sulfinyl))imidazol-w-yl]-3-hydroxy-3-([substituted]-1H-1,2,4-triazol-3-yl)-propenone (B-1242) 1-(q-(([substituted]aryl)alkenyl)thiazol-w-yl)-3-hydroxy-3-([substituted]-2H-tetrazol-5-yl)-propenone (B-1243) 1-[(q-((([substituted]aryl)alkyl)-z-halogeno)furan-w-yl]-3-hydroxy-3-([substituted]-2H-tetrazol-5-yl)-propenone (B-1244) 1-(q-([substituted]heteroaryl)pyrrol-w-yl)-3-hydroxy-3-([substituted]-2H-tetrazol-5-yl)-propenone (B-1245) 1-[nH-(z-alkyl-q-(([substituted]aryl)oxy))pyrazol-w-yl]-3-hydroxy-3-([substituted]-1H-1,2,4-triazol-3-yl)-propenone (B-1246) 1-(q-(([substituted]heteroaryl)amino)furan-w-yl)-3-hydroxy-3-([substituted]-1H-1,2,4-triazol-3-yl)-propenone (B-1247) 1-[nH-(q-([substituted]aryl)-z-halogeno)imidazol-w-yl]-3-hydroxy-3-([substituted]-1H-1,2,4-triazol-3-yl)-propenone (B-1248) 4-[(z-alkyl-q-(([substituted]heteroaryl)aminocarbonyl))furan-w-yl]-2-hydroxy-4-oxo-2-butenoic acid (B-1249) 4-[nH-(q-(([substituted]aryl)alkenyl)-z-halogeno)imidazol-w-yl]-2-hydroxy-4-oxo-2-butenoic acid (B-1250) 2-hydroxy-4-oxo-4-(q-(([substituted]heteroaryl)oxy)thiazol-w-yl)-2-butenoic acid (B-1251) 3-hydroxy-1-(q-((([substituted]aryl)sulfonylamino)pyrrol-w-yl)-3-([substituted]-1H-1,2,4-triazol-3-yl)-propenone (B-1252) 1-[(q-(([substituted]aryl)carbonyl)-z-halogeno)thiophen-w-yl]-3-hydroxy-3-([substituted]-2H-tetrazol-5-yl)-propenone (B-1253) 4-[(q-((([substituted]heteroaryl)alkyl)-z-halogeno)oxazol-w-yl]-2-hydroxy-4-oxo-2-butenoic acid (B-1254) 3-hydroxy-1-(q-((([substituted]heteroaryl)oxy)thiazol-w-yl)-3-([substituted]-2H-tetrazol-5-yl)-propenone (B-1255) 4-(q-(([substituted]aryl)carbonyl)thiazol-w-yl)-2-hydroxy-4-oxo-2-butenoic acid (B-1256) 3-hydroxy-1-(q-((([substituted]aryl)sulfonyl)pyrrol-w-yl)-3-([substituted]-1H-1,2,4-triazol-3-yl)-propenone (B-1257) 1-(nH-q-(([substituted]aryl)alkenyl)pyrazol-w-yl)-3-hydroxy-3-([substituted]-1H-1,2,4-triazol-3-yl)-propenone (B-1258) 4-[(z-alkyl-q-(([substituted]heteroaryl)alkyl))thiazol-w-yl]-2-hydroxy-4-oxo-2-butenoic acid (B-1259) 1-[(q-(([substituted]aryl)alkenyl)-z-halogeno)isoxazol-w-yl]-3-hydroxy-3-([substituted]-2H-tetrazol-5-yl)-propenone (B-1260) 3-hydroxy-1-(q-((([substituted]heteroaryl)sulfonyl)thiazol-w-yl)-3-([substituted]-1H-1,2,4-triazol-3-yl)-propenone (B-1261) 1-(q-((([substituted]heteroaryl)alkenyl)pyrrol-w-yl)-3-hydroxy-3-([substituted]-1H-1,2,4-triazol-3-yl)-propenone (B-1262) 4-[(q-((([substituted]heteroaryl)carboxy)-z-alkyl)oxazol-w-yl]-2-hydroxy-4-oxo-2-butenoic acid (B-1263) 4-(nH-q-(([substituted]aryl)carbonyl)pyrazol-w-yl)-2-hydroxy-4-oxo-2-butenoic acid (B-1264) 1-[(z-alkyl-q-(([substituted]heteroaryl)thio))pyrrol-w-yl]-3-hydroxy-3-([substituted]-2H-tetrazol-5-yl)-propenone (B-1265) 4-[(z-alkyl-q-(([substituted]heteroaryl)amino))pyrrol-w-yl]-2-hydroxy-4-oxo-2-butenoic acid (B-1266) 1-[nH-(z-alkyl-q-(1-hydroxy-([substituted]heteroaryl)methyl))imidazol-w-yl]-3-hydroxy-3-([substituted]-2H-tetrazol-5-yl)-propenone
(B-1267) 1-[(z-halogeno-q-(([substituted]aryl)sulfonyl))thiazol-w-yl]-3-hydroxy-3-([substituted]-2H-tetrazol-5-yl)-propenone
(B-1268) 1-(q-(([substituted]heteroaryl)alkenyl)thiophen-w-yl)-3-hydroxy-3-([substituted]-2H-tetrazol-5-yl)-propenone
(B-1269) 1-[(z-alkyl-q-(([substituted]aryl)carbonylamino))pyrrol-w-yl]-3-hydroxy-3-([substituted]-2H-tetrazol-5-yl)-propenone
(B-1270) 1-[(q-(([substituted]aryl)aminocarbonyl)-z-halogeno)thiophen-w-yl]-3-hydroxy-3-([substituted]-2H-tetrazol-5-yl)-propenone
(B-1271) 2-hydroxy-4-oxo-4-(q-(([substituted]heteroaryl)thio)pyridin-w-yl)-2-butenoic acid
(B-1272) 4-[(z-halogeno-q-(([substituted]aryl)sulfinyl))pyridin-w-yl]-2-hydroxy-4-oxo-2-butenoic acid
(B-1273) 1-[(z-alkyl-q-(([substituted]aryl)carbonylamino))pyrrol-w-yl]-3-hydroxy-3-([substituted]-1H-1,2,4-triazol-3-yl)-propenone
(B-1274) 2-hydroxy-4-oxo-4-(q-(([substituted]aryl)oxycarbonyl)pyrrol-w-yl)-2-butenoic acid
(B-1275) 1-[(z-halogeno-q-(([substituted]heteroaryl)oxycarbonyl))furan-w-yl]-3-hydroxy-3-([substituted]-2H-tetrazol-5-yl)-propenone
(B-1276) 1-(q-([substituted]heteroaryl)pyridin-w-yl)-3-hydroxy-3-([substituted]-1H-1,2,4-triazol-3-yl)-propenone
(B-1277) 1-[nH-(z-alkyl-q-(([substituted]aryl)oxy))pyrazol-w-yl]-3-hydroxy-3-([substituted]-2H-tetrazol-5-yl)-propenone
(B-1278) 1-[nH-(z-halogeno-q-(([substituted]heteroaryl)sulfinyl))imidazol-w-yl]-3-hydroxy-3-([substituted]-2H-tetrazol-5-yl)-propenone
(B-1279) 3-hydroxy-3-([substituted]-2H-tetrazol-5-yl)-1-(q-(([substituted]heteroaryl)thio)oxazol-w-yl)-propenone
(B-1280) 4-[(z-halogeno-q-(1-hydroxy-([substituted]heteroaryl)methyl))thiazol-w-yl]-2-hydroxy-4-oxo-2-butenoic acid
(B-1281) 1-[nH-(z-alkyl-q-(([substituted]aryl)carbonylamino))pyrazol-w-yl]-3-hydroxy-3-([substituted]-1H-1,2,4-triazol-3-yl)-propenone
(B-1282) 1-[(q-(([substituted]heteroaryl)alkyl)-z-halogeno)furan-w-yl]-3-hydroxy-3-([substituted]-2H-tetrazol-5-yl)-propenone
(B-1283) 3-hydroxy-1-(q-(([substituted]heteroaryl)oxy)furan-w-yl)-3-([substituted]-1H-1,2,4-triazol-3-yl)-propenone
(B-1284) 1-(q-([substituted]heteroaryl)furan-w-yl)-3-hydroxy-3-([substituted]-2H-tetrazol-5-yl)-propenone
(B-1285) 1-[(q-([substituted]aryl)-z-halogeno)furan-w-yl]-3-hydroxy-3-([substituted]-1H-1,2,4-triazol-3-yl)-propenone
(B-1286) 1-[(z-halogeno-q-(([substituted]heteroaryl)sulfonyl))isoxazol-w-yl]-3-hydroxy-3-([substituted]-1H-1,2,4-triazol-3-yl)-propenone
(B-1287) 1-[(z-alkyl-q-(([substituted]heteroaryl)sulfonylamino))furan-w-yl]-3-hydroxy-3-([substituted]-2H-tetrazol-5-yl)-propenone
(B-1288) 1-[(z-alkyl-q-(([substituted]aryl)oxy))pyrrol-w-yl]-3-hydroxy-3-([substituted]-1H-1,2,4-triazol-3-yl)-propenone
(B-1289) 4-(q-(([substituted]aryl)aminocarbonyl)thiophen-w-yl)-2-hydroxy-4-oxo-2-butenoic acid
(B-1290) 1-[nH-(z-alkyl-q-(([substituted]aryl)alkyl))pyrazol-w-yl]-3-hydroxy-3-([substituted]-2H-tetrazol-5-yl)-propenone
(B-1291) 4-[(z-alkyl-q-(([substituted]aryl)oxycarbonyl))thiophen-w-yl]-2-hydroxy-4-oxo-2-butenoic acid
(B-1292) 1-(q-(([substituted]aryl)carbonylamino)oxazol-w-yl)-3-hydroxy-3-([substituted]-1H-1,2,4-triazol-3-yl)-propenone
(B-1293) 4-[(z-alkyl-q-(([substituted]heteroaryl)alkyl))pyrrol-w-yl]-2-hydroxy-4-oxo-2-butenoic acid
(B-1294) 2-hydroxy-4-oxo-4-(q-(([substituted]heteroaryl)sulfinyl)thiophen-w-yl)-2-butenoic acid
(B-1295) 2-hydroxy-4-oxo-4-(q-(([substituted]heteroaryl)sulfinyl)pyrrol-w-yl)-2-butenoic acid
(B-1296) 3-hydroxy-1-(q-(([substituted]heteroaryl)sulfonylamino)isoxazol-w-yl)-3-([substituted]-2H-tetrazol-5-yl)-propenone
(B-1297) 1-[(z-alkyl-q-(([substituted]aryl)sulfonyl))thiazol-w-yl]-3-hydroxy-3-([substituted]-2H-tetrazol-5-yl)-propenone
(B-1298) 1-[(q-(([substituted]aryl)aminosulfonyl)-z-halogeno)oxazol-w-yl]-3-hydroxy-3-([substituted]-1H-1,2,4-triazol-3-yl)-propenone
(B-1299) 1-(q-([substituted]aryl)furan-w-yl)-3-hydroxy-3-([substituted]-1H-1,2,4-triazol-3-yl)-propenone
(B-1300) 1-[nH-(q-(([substituted]heteroaryl)carboxy)-z-alkyl)pyrazol-w-yl]-3-hydroxy-3-([substituted]-2H-tetrazol-5-yl)-propenone
(B-1301) 1-[(z-halogeno-q-(([substituted]heteroaryl)sulfinyl))thiazol-w-yl]-3-hydroxy-3-([substituted]-2H-tetrazol-5-yl)-propenone
(B-1302) 1-[(z-alkyl-q-(([substituted]aryl)carbonylamino))pyridin-w-yl]-3-hydroxy-3-([substituted]-1H-1,2,4-triazol-3-yl)-propenone
(B-1303) 4-(nH-q-(([substituted]aryl)aminosulfonyl)pyrazol-w-yl)-2-hydroxy-4-oxo-2-butenoic acid
(B-1304) 3-hydroxy-1-(q-(([substituted]aryl)sulfonyl)isoxazol-w-yl)-3-([substituted]-2H-tetrazol-5-yl)-propenone
(B-1305) 4-[nH-(z-halogeno-q-(([substituted]heteroaryl)thio))pyrazol-w-yl]-2-hydroxy-4-oxo-2-butenoic acid
(B-1306) 4-(nH-q-(([substituted]aryl)carbonylamino)pyrazol-w-yl)-2-hydroxy-4-oxo-2-butenoic acid
(B-1307) 1-[(q-(([substituted]heteroaryl)alkenyl)-z-halogeno)thiazol-w-yl]-3-hydroxy-3-([substituted]-1H-1,2,4-triazol-3-yl)-propenone
(B-1308) 1-[(z-halogeno-q-(([substituted]heteroaryl)oxy))pyridin-w-yl]-3-hydroxy-3-([substituted]-2H-tetrazol-5-yl)-propenone
(B-1309) 4-(nH-q-(([substituted]aryl)amino)imidazol-w-yl)-2-hydroxy-4-oxo-2-butenoic acid
(B-1310) 1-[nH-(z-halogeno-q-(([substituted]aryl)sulfinyl))imidazol-w-yl]-3-hydroxy-3-([substituted]-1H-1,2,4-triazol-3-yl)-propenone
(B-1311) 4-[(q-(([substituted]aryl)carboxy)-z-halogeno)isoxazol-w-yl]-2-hydroxy-4-oxo-2-butenoic acid
(B-1312) 3-hydroxy-1-(q-(([substituted]aryl)sulfonylamino)thiophen-w-yl)-3-([substituted]-2H-tetrazol-5-yl)-propenone
(B-1313) 1-(q-(([substituted]aryl)carbonyl)thiazol-w-yl)-3-hydroxy-3-([substituted]-1H-1,2,4-triazol-3-yl)-propenone
(B-1314) 1-[(z-alkyl-q-(([substituted]aryl)oxycarbonyl))pyrrol-w-yl]-3-hydroxy-3-([substituted]-1H-1,2,4-triazol-3-yl)-propenone
(B-1315) 4-[nH-(q-(([substituted]heteroaryl)aminocarbonyl)-z-halogeno)imidazol-w-yl]-2-hydroxy-4-oxo-2-butenoic acid
(B-1316) 1-[nH-(q-(([substituted]aryl)alkenyl)-z-halogeno)imidazol-w-yl]-3-hydroxy-3-([substituted]-1H-1,2,4-triazol-3-yl)-propenone (B-1317) 4-[(z-alkyl-q-(([substituted]aryl)carbonylamino))pyrrol-w-yl]-2-hydroxy-4-oxo-2-butenoic acid (B-1318) 1-[(q-(([substituted]heteroaryl)aminocarbonyl)-z-halogeno)thiophen-w-yl]-3-hydroxy-3-([substituted]-1H-1,2,4-triazol-3-yl)-propenone (B-1319) 4-[(z-halogeno-q-(([substituted]aryl)sulfonylamino))pyridin-w-yl]-2-hydroxy-4-oxo-2-butenoic acid (B-1320) 1-[(z-alkyl-q-(([substituted]heteroaryl)sulfonylamino))furan-w-yl]-3-hydroxy-3-([substituted]-1H-1,2,4-triazol-3-yl)-propenone (B-1321) 1-[nH-(q-(([substituted]heteroaryl)amino)-z-halogeno)imidazol-w-yl]-3-hydroxy-3-([substituted]-1H-1,2,4-triazol-3-yl)-propenone (B-1322) 1-[(q-(([substituted]heteroaryl)alkyl)-z-halogeno)thiazol-w-yl]-3-hydroxy-3-([substituted]-1H-1,2,4-triazol-3-yl)-propenone (B-1323) 1-[(z-halogeno-q-(([substituted]aryl)oxycarbonyl))thiophen-w-yl]-3-hydroxy-3-([substituted]-1H-1,2,4-triazol-3-yl)-propenone (B-1324) 1-[(z-halogeno-q-(([substituted]heteroaryl)oxycarbonyl))oxazol-w-yl]-3-hydroxy-3-([substituted]-1H-1,2,4-triazol-3-yl)-propenone (B-1325) 1-[(z-alkyl-q-(([substituted]aryl)carbonylamino))thiophen-w-yl]-3-hydroxy-3-([substituted]-1H-1,2,4-triazol-3-yl)-propenone (B-1326) 1-(nH-q-([substituted]aryl)imidazol-w-yl)-3-hydroxy-3-([substituted]-1H-1,2,4-triazol-3-yl)-propenone (B-1327) 1-[(q-(([substituted]aryl)alkenyl)-z-halogeno)furan-w-yl]-3-hydroxy-3-([substituted]-2H-tetrazol-5-yl)-propenone (B-1328) 1-[nH-(z-alkyl-q-(([substituted]heteroaryl)thio))imidazol-w-yl]-3-hydroxy-3-([substituted]-1H-1,2,4-triazol-3-yl)-propenone (B-1329) 1-[(q-(([substituted]heteroaryl)aminosulfonyl)-z-halogeno)pyrrol-w-yl]-3-hydroxy-3-([substituted]-1H-1,2,4-triazol-3-yl)-propenone (B-1330) 4-[(z-halogeno-q-(([substituted]aryl)sulfonyl))pyridin-w-yl]-2-hydroxy-4-oxo-2-butenoic acid (B-1331) 1-(q-(([substituted]heteroaryl)carbonyl)isoxazol-w-yl)-3-hydroxy-3-([substituted]-2H-tetrazol-5-yl)-propenone (B-1332) 4-[(z-halogeno-q-(([substituted]heteroaryl)thio))furan-w-yl]-2-hydroxy-4-oxo-2-butenoic acid (B-1333) 1-[(z-alkyl-q-(([substituted]aryl)sulfinyl))oxazol-w-yl]-3-hydroxy-3-([substituted]-1H-1,2,4-triazol-3-yl)-propenone (B-1334) 1-[(z-alkyl-q-(([substituted]heteroaryl)sulfonyl))oxazol-w-yl]-3-hydroxy-3-([substituted]-2H-tetrazol-5-yl)-propenone (B-1335) 1-[(z-alkyl-q-(([substituted]aryl)aminosulfonyl))pyridin-w-yl]-3-hydroxy-3-([substituted]-2H-tetrazol-5-yl)-propenone (B-1336) 4-[(z-alkyl-q-(([substituted]aryl)aminosulfonyl))pyridin-w-yl]-2-hydroxy-4-oxo-2-butenoic acid (B-1337) 1-[(z-alkyl-q-(([substituted]heteroaryl)oxycarbonyl))oxazol-w-yl]-3-hydroxy-3-([substituted]-2H-tetrazol-5-yl)-propenone (B-1338) 1-[(z-alkyl-q-(([substituted]heteroaryl)oxy))pyridin-w-yl]-3-hydroxy-3-([substituted]-2H-tetrazol-5-yl)-propenone (B-1339) 1-[(q-(([substituted]aryl)alkyl)-z-halogeno)pyrrol-w-yl]-3-hydroxy-3-([substituted]-2H-tetrazol-5-yl)-propenone (B-1340) 4-[(z-alkyl-q-(([substituted]heteroaryl)sulfonylamino))thiophen-w-yl]-2-hydroxy-4-oxo-2-butenoic acid (B-1341) 1-[(z-alkyl-q-(([substituted]aryl)amino))pyrrol-w-yl]-3-hydroxy-3-([substituted]-1H-1,2,4-triazol-3-yl)-propenone (B-1342) 1-[(z-alkyl-q-(([substituted]heteroaryl)thio))pyrrol-w-yl]-3-hydroxy-3-([substituted]-1H-1,2,4-triazol-3-yl)-propenone (B-1343) 1-[(z-alkyl-q-(([substituted]aryl)thio))thiophen-w-yl]-3-hydroxy-3-([substituted]-1H-1,2,4-triazol-3-yl)-propenone (B-1344) 1-[nH-(z-alkyl-q-(([substituted]heteroaryl)carbonylamino))imidazol-w-yl]-3-hydroxy-3-([substituted]-2H-tetrazol-5-yl)-propenone (B-1345) 1-[(z-alkyl-q-(1-hydroxy-([substituted]heteroaryl)methyl))oxazol-w-yl]-3-hydroxy-3-([substituted]-2H-tetrazol-5-yl)-propenone (B-1346) 1-(q-(([substituted]aryl)aminosulfonyl)oxazol-w-yl)-3-hydroxy-3-([substituted]-2H-tetrazol-5-yl)-propenone (B-1347) 1-[(z-alkyl-q-(([substituted]aryl)aminocarbonyl))pyrrol-w-yl]-3-hydroxy-3-([substituted]-1H-1,2,4-triazol-3-yl)-propenone (B-1348) 1-(q-(([substituted]aryl)alkenyl)pyrrol-w-yl)-3-hydroxy-3-([substituted]-1H-1,2,4-triazol-3-yl)-propenone (B-1349) 1-[(z-alkyl-q-(([substituted]aryl)carbonyl))thiazol-w-yl]-3-hydroxy-3-([substituted]-1H-1,2,4-triazol-3-yl)-propenone (B-1350) 1-[(z-alkyl-q-([substituted]heteroaryl))pyridin-w-yl]-3-hydroxy-3-([substituted]-2H-tetrazol-5-yl)-propenone (B-1351) 1-(q-([substituted]aryl)isoxazol-w-yl)-3-hydroxy-3-([substituted]-1H-1,2,4-triazol-3-yl)-propenone (B-1352) 4-(q-(([substituted]heteroaryl)aminocarbonyl)thiazol-w-yl)-2-hydroxy-4-oxo-2-butenoic acid (B-1353) 3-hydroxy-1-(q-(([substituted]heteroaryl)sulfonyl)isoxazol-w-yl)-3-([substituted]-1H-1,2,4-triazol-3-yl)-propenone (B-1354) 1-(q-(([substituted]heteroaryl)aminocarbonyl)pyrrol-w-yl)-3-hydroxy-3-([substituted]-2H-tetrazol-5-yl)-propenone (B-1355) 1-(nH-q-(([substituted]aryl)alkyl)pyrazol-w-yl)-3-hydroxy-3-([substituted]-1H-1,2,4-triazol-3-yl)-propenone (B-1356) 1-[(z-alkyl-q-(1-hydroxy-([substituted]aryl)methyl))pyridin-w-yl]-3-hydroxy-3-([substituted]-1H-1,2,4-triazol-3-yl)-propenone (B-1357) 1-[nH-(z-alkyl-q-(([substituted]aryl)carbonyl))pyrazol-w-yl]-3-hydroxy-3-([substituted]-1H-1,2,4-triazol-3-yl)-propenone (B-1358) 1-(q-(([substituted]heteroaryl)carbonyl)thiophen-w-yl)-3-hydroxy-3-([substituted]-2H-tetrazol-5-yl)-propenone (B-1359) 1-[nH-(q-([substituted]aryl)-z-halogeno)imidazol-w-yl]-3-hydroxy-3-([substituted]-2H-tetrazol-5-yl)-propenone (B-1360) 1-[nH-(q-(([substituted]heteroaryl)aminocarbonyl)-z-halogeno)imidazol-w-yl]-3-hydroxy-3-([substituted]-1H-1,2,4-triazol-3-yl)-propenone (B-1361) 4-(nH-q-(([substituted]heteroaryl)alkenyl)imidazol-w-yl)-2-hydroxy-4-oxo-2-butenoic acid (B-1362) 4-[nH-(q-(([substituted]heteroaryl)carboxy)-z-alkyl)imidazol-w-yl]-2-hydroxy-4-oxo-2-butenoic acid (B-1363) 3-hydroxy-1-(q-(([substituted]heteroaryl)carboxy)isoxazol-w-yl)-3-([substituted]-1H-1,2,4-triazol-3-yl)-propenone (B-1364) 4-[(z-halogeno-q-(([substituted]aryl)oxy))isoxazol-w-yl]-2-hydroxy-4-oxo-2-butenoic acid (B-1365) 1-[(z-alkyl-q-(([substituted]aryl)sulfonyl))pyridin-w-yl]-3-hydroxy-3-([substituted]-1H-1,2,4-triazol-3-yl)-propenone (B-1366) 1-(q-(([substituted]heteroaryl)amino)isoxazol-w-yl)-3-hydroxy-3-([substituted]-2H-tetrazol-5-yl)-propenone (B-1367) 4-(q-(([substituted]aryl)alkyl)furan-w-yl)-2-hydroxy-4-oxo-2-butenoic acid (B-1368) 1-[(z-alkyl-q-(([substituted]aryl)oxycarbonyl))thiazol-w-yl]-3-hydroxy-3-([substituted]-1H-1,2,4-triazol-3-yl)-propenone (B-1369) 4-(q-(([substituted]heteroaryl)alkenyl)pyridin-w-yl)-2-hydroxy-4-oxo-2-butenoic acid (B-1370) 4-(q-(([substituted]aryl)aminosulfonyl)pyridin-w-yl)-2-hydroxy-4-oxo-2-butenoic acid (B-1371) 4-[(q-(([substituted]aryl)carbonyl)-z-halogeno)thiazol-w-yl]-2-hydroxy-4-oxo-2-butenoic acid (B-1372) 1-[(z-alkyl-q-(1-hydroxy-([substituted]aryl)methyl))isoxazol-w-yl]-3-hydroxy-3-([substituted]-2H-tetrazol-5-yl)-propenone (B-1373) 4-[(z-halogeno-q-(([substituted]aryl)oxy))thiazol-w-yl]-2-hydroxy-4-oxo-2-butenoic acid (B-1374) 4-(q-(([substituted]heteroaryl)alkenyl)pyrrol-w-yl)-2-hydroxy-4-oxo-2-butenoic acid (B-1375) 4-[(z-alkyl-q-(([substituted]aryl)carboxy))thiazol-w-yl]-2-hydroxy-4-oxo-2-butenoic acid (B-1376) 1-(q-(([substituted]heteroaryl)aminocarbonyl)oxazol-w-yl)-3-hydroxy-3-([substituted]-2H-tetrazol-5-yl)-propenone (B-1377) 1-[(z-alkyl-q-(([substituted]heteroaryl)sulfinyl))oxazol-w-yl]-3-hydroxy-3-([substituted]-2H-tetrazol-5-yl)-propenone (B-1378) 4-[nH-(z-alkyl-q-(([substituted]heteroaryl)carbonyl))imidazol-w-yl]-2-hydroxy-4-oxo-2-butenoic acid (B-1379) 1-[(z-alkyl-q-(([substituted]heteroaryl)sulfonylamino))oxazol-w-yl]-3-hydroxy-3-([substituted]-1H-1,2,4-triazol-3-yl)-propenone (B-1380) 4-[(z-alkyl-q-(([substituted]aryl)aminosulfonyl))furan-w-yl]-2-hydroxy-4-oxo-2-butenoic acid (B-1381) 1-[(z-alkyl-q-(([substituted]aryl)oxy))oxazol-w-yl]-3-hydroxy-3-([substituted]-1H-1,2,4-triazol-3-yl)-propenone (B-1382) 1-[(z-halogeno-q-(1-hydroxy-([substituted]aryl)methyl))thiophen-w-yl]-3-hydroxy-3-([substituted]-1H-1,2,4-triazol-3-yl)-propenone (B-1383) 3-hydroxy-3-([substituted]-2H-tetrazol-5-yl)-1-(q-(([substituted]heteroaryl)carboxy)thiazol-w-yl)-propenone (B-1384) 4-(q-(([substituted]heteroaryl)alkenyl)thiophen-w-yl)-2-hydroxy-4-oxo-2-butenoic acid (B-1385) 2-hydroxy-4-oxo-4-(q-(([substituted]aryl)sulfonyl)thiophen-w-yl)-2-butenoic acid (B-1386) 4-[(z-alkyl-q-(([substituted]heteroaryl)carbonylamino))furan-w-yl]-2-hydroxy-4-oxo-2-butenoic acid (B-1387) 4-[(z-halogeno-q-(([substituted]aryl)sulfonyl))oxazol-w-yl]-2-hydroxy-4-oxo-2-butenoic acid (B-1388) 3-hydroxy-1-(q-(([substituted]heteroaryl)oxycarbonyl)isoxazol-w-yl)-3-([substituted]-1H-1,2,4-triazol-3-yl)-propenone (B-1389) 1-[(z-alkyl-q-(([substituted]aryl)carboxy))thiophen-w-yl]-3-hydroxy-3-([substituted]-1H-1,2,4-triazol-3-yl)-propenone (B-1390) 4-[(z-alkyl-q-(1-hydroxy-([substituted]heteroaryl)methyl))thiophen-w-yl]-2-hydroxy-4-oxo-2-butenoic acid (B-1391) 2-hydroxy-4-oxo-4-(q-(([substituted]heteroaryl)oxycarbonyl)pyrrol-w-yl)-2-butenoic acid (B-1392) 1-[(z-alkyl-q-(1-hydroxy-([substituted]heteroaryl)methyl))pyrrol-w-yl]-3-hydroxy-3-([substituted]-1H-1,2,4-triazol-3-yl)-propenone (B-1393) 4-[(q-(([substituted]aryl)carboxy)-z-halogeno)thiazol-w-yl]-2-hydroxy-4-oxo-2-butenoic acid (B-1394) 3-hydroxy-3-([substituted]-2H-tetrazol-5-yl)-1-(q-(([substituted]aryl)thio)thiophen-w-yl)-propenone (B-1395) 1-[(z-alkyl-q-([substituted]aryl))pyrrol-w-yl]-3-hydroxy-3-([substituted]-1H-1,2,4-triazol-3-yl)-propenone (B-1396) 3-hydroxy-1-(q-(([substituted]heteroaryl)thio)thiophen-w-yl)-3-([substituted]-1H-1,2,4-triazol-3-yl)-propenone (B-1397) 4-(q-([substituted]heteroaryl)furan-w-yl)-2-hydroxy-4-oxo-2-butenoic acid (B-1398) 1-(q-(([substituted]heteroaryl)aminocarbonyl)oxazol-w-yl)-3-hydroxy-3-([substituted]-1H-1,2,4-triazol-3-yl)-propenone (B-1399) 4-[(z-alkyl-q-(([substituted]aryl)alkyl))thiophen-w-yl]-2-hydroxy-4-oxo-2-butenoic acid (B-1400) 1-[(z-alkyl-q-(([substituted]aryl)carbonyl))isoxazol-w-yl]-3-hydroxy-3-([substituted]-1H-1,2,4-triazol-3-yl)-propenone (B-1401) 1-[(z-alkyl-q-(([substituted]heteroaryl)carbonylamino))oxazol-w-yl]-3-hydroxy-3-([substituted]-2H-tetrazol-5-yl)-propenone (B-1402) 1-[(q-(([substituted]heteroaryl)carbonylamino)-z-halogeno)thiophen-w-yl]-3-hydroxy-3-([substituted]-1H-1,2,4-triazol-3-yl)-propenone (B-1403) 1-(nH-q-(([substituted]heteroaryl)carbonylamino)pyrazol-w-yl)-3-hydroxy-3-([substituted]-2H-tetrazol-5-yl)-propenone (B-1404) 4-(q-(([substituted]aryl)carboxy)oxazol-w-yl)-2-hydroxy-4-oxo-2-butenoic acid (B-1405) 1-(nH-q-(([substituted]heteroaryl)carbonyl)imidazol-w-yl)-3-hydroxy-3-([substituted]-2H-tetrazol-5-yl)-propenone (B-1406) 1-(q-(([substituted]aryl)aminosulfonyl)pyrrol-w-yl)-3-hydroxy-3-([substituted]-1H-1,2,4-triazol-3-yl)-propenone (B-1407) 1-(nH-q-(([substituted]heteroaryl)aminosulfonyl)imidazol-w-yl)-3-hydroxy-3-([substituted]-1H-1,2,4-triazol-3-yl)-propenone (B-1408) 4-(q-(([substituted]heteroaryl)aminocarbonyl)isoxazol-w-yl)-2-hydroxy-4-oxo-2-butenoic acid (B-1409) 1-[(q-(([substituted]aryl)alkyl)-z-halogeno)thiazol-w-yl]-3-hydroxy-3-([substituted]-1H-1,2,4-triazol-3-yl)-propenone (B-1410) 4-[(z-alkyl-q-(([substituted]aryl)carbonylamino))furan-w-yl]-2-hydroxy-4-oxo-2-butenoic acid (B-1411) 4-[(z-halogeno-q-(([substituted]heteroaryl)thio))thiazol-w-yl]-2-hydroxy-4-oxo-2-butenoic acid (B-1412) 3-hydroxy-1-(q-(([substituted]aryl)sulfonyl)oxazol-w-yl)-3-([substituted]-1H-1,2,4-triazol-3-yl)-propenone (B-1413) 4-[(q-(([substituted]aryl)amino)-z-halogeno)oxazol-w-yl]-2-hydroxy-4-oxo-2-butenoic acid (B-1414) 4-(q-([substituted]heteroaryl)thiophen-w-yl)-2-hydroxy-4-oxo-2-butenoic acid (B-1415) 1-[(z-halogeno-q-(([substituted]heteroaryl)sulfonyl))pyrrol-w-yl]-3-hydroxy-3-([substituted]-2H-tetrazol-5-yl)-propenone (B-1416) 4-[(z-alkyl-q-(([substituted]aryl)thio))furan-w-yl]-2-hydroxy-4-oxo-2-butenoic acid (B-1417) 1-(q-(([substituted]aryl)carbonylamino)pyridin-w-yl)-3-hydroxy-3-([substituted]-1H-1,2,4-triazol-3-yl)-propenone (B-1418) 1-[nH-(z-alkyl-q-(([substituted]aryl)sulfonylamino))pyrazol-w-yl]-3-hydroxy-3-([substituted]-1H-1,2,4-triazol-3-yl)-propenone
(B-1419) 4-(q-(([substituted]aryl)carbonyl)thiophen-w-yl)-2-hydroxy-4-oxo-2-butenoic acid
(B-1420) 1-[nH-(q-(([substituted]heteroaryl)alkenyl)-z-halogeno)pyrazol-w-yl]-3-hydroxy-3-([substituted]-2H-tetrazol-5-yl)-propenone
(B-1421) 4-[nH-(q-([substituted]aryl)-z-halogeno)pyrazol-w-yl]-2-hydroxy-4-oxo-2-butenoic acid
(B-1422) 1-[(z-alkyl-q-(([substituted]heteroaryl)sulfonylamino))thiazol-w-yl]-3-hydroxy-3-([substituted]-1H-1,2,4-triazol-3-yl)-propenone
(B-1423) 4-(q-(([substituted]heteroaryl)carbonylamino)thiazol-w-yl)-2-hydroxy-4-oxo-2-butenoic acid
(B-1424) 2-hydroxy-4-oxo-4-(q-(([substituted]heteroaryl)sulfonyl)thiophen-w-yl)-2-butenoic acid
(B-1425) 1-(q-(([substituted]aryl)aminocarbonyl)oxazol-w-yl)-3-hydroxy-3-([substituted]-1H-1,2,4-triazol-3-yl)-propenone
(B-1426) 1-[(q-(([substituted]heteroaryl)alkyl)-z-halogeno)pyridin-w-yl]-3-hydroxy-3-([substituted]-1H-1,2,4-triazol-3-yl)-propenone
(B-1427) 4-[nH-(q-(([substituted]aryl)aminosulfonyl)-z-halogeno)pyrazol-w-yl]-2-hydroxy-4-oxo-2-butenoic acid
(B-1428) 1-[(z-alkyl-q-(([substituted]aryl)sulfonyl))isoxazol-w-yl]-3-hydroxy-3-([substituted]-2H-tetrazol-5-yl)-propenone
(B-1429) 1-[(q-(([substituted]aryl)aminocarbonyl)-z-halogeno)oxazol-w-yl]-3-hydroxy-3-([substituted]-2H-tetrazol-5-yl)-propenone
(B-1430) 2-hydroxy-4-oxo-4-(nH-q-(([substituted]aryl)sulfonylamino)pyrazol-w-yl)-2-butenoic acid
(B-1431) 3-hydroxy-1-(q-(([substituted]heteroaryl)carboxy)pyridin-w-yl)-3-([substituted]-2H-tetrazol-5-yl)-propenone
(B-1432) 1-[nH-(z-alkyl-q-(([substituted]aryl)sulfonyl))pyrazol-w-yl]-3-hydroxy-3-([substituted]-2H-tetrazol-5-yl)-propenone
(B-1433) 4-[(z-alkyl-q-(1-hydroxy-([substituted]aryl)methyl))thiophen-w-yl]-2-hydroxy-4-oxo-2-butenoic acid
(B-1434) 4-[(q-(([substituted]aryl)carbonyl)-z-halogeno)pyridin-w-yl]-2-hydroxy-4-oxo-2-butenoic acid
(B-1435) 1-[(q-(([substituted]aryl)carbonyl)-z-halogeno)thiazol-w-yl]-3-hydroxy-3-([substituted]-2H-tetrazol-5-yl)-propenone
(B-1436) 3-hydroxy-1-(q-(1-hydroxy-([substituted]heteroaryl)methyl)thiazol-w-yl)-3-([substituted]-2H-tetrazol-5-yl)-propenone
(B-1437) 1-[(q-(([substituted]aryl)aminocarbonyl)-z-halogeno)pyrrol-w-yl]-3-hydroxy-3-([substituted]-1H-1,2,4-triazol-3-yl)-propenone
(B-1438) 1-(nH-q-(([substituted]aryl)amino)pyrazol-w-yl)-3-hydroxy-3-([substituted]-2H-tetrazol-5-yl)-propenone
(B-1439) 1-(q-(([substituted]heteroaryl)alkenyl)pyridin-w-yl)-3-hydroxy-3-([substituted]-2H-tetrazol-5-yl)-propenone
(B-1440) 4-[q-(([substituted]aryl)alkyl)-z-halogeno)isoxazol-w-yl]-2-hydroxy-4-oxo-2-butenoic acid
(B-1441) 1-[(z-halogeno-q-(([substituted]aryl)sulfonyl))isoxazol-w-yl]-3-hydroxy-3-([substituted]-2H-tetrazol-5-yl)-propenone
(B-1442) 3-hydroxy-1-(nH-q-(([substituted]heteroaryl)sulfonyl)pyrazol-w-yl)-3-([substituted]-1H-1,2,4-triazol-3-yl)-propenone
(B-1443) 1-[(z-halogeno-q-(1-hydroxy-([substituted]aryl)methyl))pyridin-w-yl]-3-hydroxy-3-([substituted]-2H-tetrazol-5-yl)-propenone
(B-1444) 1-[nH-(z-alkyl-q-(([substituted]heteroaryl)aminosulfonyl))pyrazol-w-yl]-3-hydroxy-3-([substituted]-1H-1,2,4-triazol-3-yl)-propenone
(B-1445) 1-(q-(([substituted]aryl)amino)thiazol-w-yl)-3-hydroxy-3-([substituted]-2H-tetrazol-5-yl)-propenone
(B-1446) 1-[(q-(([substituted]heteroaryl)amino)-z-halogeno)thiophen-w-yl]-3-hydroxy-3-([substituted]-1H-1,2,4-triazol-3-yl)-propenone
(B-1447) 4-(q-(([substituted]heteroaryl)aminocarbonyl)pyridin-w-yl)-2-hydroxy-4-oxo-2-butenoic acid
(B-1448) 1-[(z-alkyl-q-(([substituted]heteroaryl)sulfinyl))isoxazol-w-yl]-3-hydroxy-3-([substituted]-2H-tetrazol-5-yl)-propenone
(B-1449) 1-[(z-halogeno-q-(([substituted]aryl)sulfinyl))furan-w-yl]-3-hydroxy-3-([substituted]-1H-1,2,4-triazol-3-yl)-propenone
(B-1450) 1-[(q-(([substituted]heteroaryl)carbonylamino)-z-halogeno)pyrrol-w-yl]-3-hydroxy-3-([substituted]-1H-1,2,4-triazol-3-yl)-propenone
(B-1451) 4-(q-([substituted]heteroaryl)oxazol-w-yl)-2-hydroxy-4-oxo-2butenoic acid
(B-1452) 1-(q-(([substituted]aryl)alkyl)pyridin-w-yl)-3-hydroxy-3-([substituted]-2H-tetrazol-5-yl)-propenone
(B-1453) 1-(q-(([substituted]heteroaryl)carbonyl)furan-w-yl)-3-hydroxy-3-([substituted]-1H-1,2,4-triazol-3-yl)-propenone
(B-1454) 1-[(z-alkyl-q-(1-hydroxy-([substituted]heteroaryl)methyl))thiazol-w-yl]-3-hydroxy-3-([substituted]-1H-1,2,4-triazol-3-yl)-propenone
(B-1455) 1-[(z-halogeno-q-(([substituted]aryl)thio))thiophen-w-yl]-3-hydroxy-3-([substituted]-1H-1,2,4-triazol-3-yl)-propenone
(B-1456) 1-[(z-alkyl-q-(([substituted]heteroaryl)thio))thiazol-w-yl]-3-hydroxy-3-([substituted]-2H-tetrazol-5-yl)-propenone
(B-1457) 1-(q-(([substituted]aryl)amino)pyridin-w-yl)-3-hydroxy-3-([substituted]-2H-tetrazol-5-yl)-propenone
(B-1458) 2-hydroxy-4-oxo-4-(q-(([substituted]heteroaryl)sulfinyl)thiazol-w-yl)-2-butenoic acid
(B-1459) 1-[nH-(z-alkyl-q-(([substituted]heteroaryl)sulfinyl))imidazol-w-yl]-3-hydroxy-3-([substituted]-1H-1,2,4-triazol-3-yl)-propenone
(B-1460) 4-[(z-halogeno-q-(([substituted]heteroaryl)oxy))oxazol-w-yl]-2-hydroxy-4-oxo-2-butenoic acid
(B-1461) 1-[(q-(([substituted]heteroaryl)carbonyl)-z-halogeno)pyridin-w-yl]-3-hydroxy-3-([substituted]-2H-tetrazol-5-yl)-propenone
(B-1462) 4-[(q-(([substituted]aryl)carbonylamino)-z-halogeno)thiophen-w-yl]-2-hydroxy-4-oxo-2-butenoic acid
(B-1463) 4-[(z-halogeno-q-(([substituted]heteroaryl)sulfonylamino))thiophen-w-yl]-2-hydroxy-4-oxo-2-butenoic acid
(B-1464) 1-[nH-(q-(([substituted]heteroaryl)aminocarbonyl)-z-halogeno)pyrazol-w-yl]-3-hydroxy-3-([substituted]-1H-1,2,4-triazol-3-yl)-propenone
(B-1465) 3-hydroxy-1-(q-(([substituted]heteroaryl)oxy)furan-w-yl)-3-([substituted]-2H-tetrazol-5-yl)-propenone
(B-1466) 1-[(q-(([substituted]heteroaryl)alkenyl)-z-alkyl)pyridin-w-yl]-3-hydroxy-3-([substituted]-1H-1,2,4-triazol-3-yl)-propenone
(B-1467) 4-[(q-(([substituted]heteroaryl)alkenyl)-z-halogeno)furan-w-yl]-2-hydroxy-4-oxo-2-butenoic acid
(B-1468) 3-hydroxy-1-(q-(1-hydroxy-([substituted]heteroaryl)methyl)pyridin-w-yl)-3-([substituted]-1H-1,2,4-triazol-3-yl)-propenone (B-1469) 4-[nH-(z-alkyl-q-(([substituted]aryl)carbonylamino))imidazol-w-yl]-2-hydroxy-4-oxo-2-butenoic acid
(B-1470) 1-[nH-(z-halogeno-q-(([substituted]aryl)oxycarbonyl))imidazol-w-yl]-3-hydroxy-3-([substituted]-1H-1,2,4-triazol-3-yl)-propenone
(B-1471) 1-[(z-alkyl-q-(([substituted]aryl)alkyl))oxazol-w-yl]-3-hydroxy-3-([substituted]-1H-1,2,4-triazol-3-yl)-propenone
(B-1472) 4-[(q-([substituted]aryl)-z-halogeno)pyridin-w-yl]-2-hydroxy-4-oxo-2-butenoic acid
(B-1473) 1-(nH-q-(([substituted]aryl)carboxy)imidazol-w-yl)-3-hydroxy-3-([substituted]-2H-tetrazol-5-yl)-propenone
(B-1474) 4-[(z-halogeno-q-(([substituted]heteroaryl)oxy))isoxazol-w-yl]-2-hydroxy-4-oxo-2-butenoic acid
(B-1475) 4-[(z-alkyl-q-(([substituted]aryl)carbonyl))isoxazol-w-yl]-2-hydroxy-4-oxo-2-butenoic acid
(B-1476) 1-(q-(([substituted]heteroaryl)aminosulfonyl)isoxazol-w-yl)-3-hydroxy-3-([substituted]-1H-1,2,4-triazol-3-yl)-propenone
(B-1477) 1-[(q-([substituted]aryl)-z-halogeno)pyridin-w-yl]-3-hydroxy-3-([substituted]-2H-tetrazol-5-yl)-propenone
(B-1478) 1-[(q-(([substituted]heteroaryl)amino)-z-halogeno)isoxazol-w-yl]-3-hydroxy-3-([substituted]-2H-tetrazol-5-yl)-propenone
(B-1479) 3-hydroxy-1-(q-(([substituted]heteroaryl)oxy)isoxazol-w-yl)-3-([substituted]-2H-tetrazol-5-yl)-propenone
(B-1480) 1-[(z-halogeno-q-(([substituted]heteroaryl)sulfinyl))pyrrol-w-yl]-3-hydroxy-3-([substituted]-2H-tetrazol-5-yl)-propenone
(B-1481) 1-[(z-halogeno-q-(([substituted]aryl)sulfonyl))furan-w-yl]-3-hydroxy-3-([substituted]-2H-tetrazol-5-yl)-propenone
(B-1482) 1-[(z-halogeno-q-(([substituted]aryl)oxycarbonyl))furan-w-yl]-3-hydroxy-3-([substituted]-1H-1,2,4-triazol-3-yl)-propenone
(B-1483) 4-(q-(([substituted]aryl)aminocarbonyl)thiazol-w-yl)-2-hydroxy-4-oxo-2-butenoic acid
(B-1484) 4-[(z-halogeno-q-(([substituted]heteroaryl)oxy))pyridin-w-yl]-2-hydroxy-4-oxo-2-butenoic acid
(B-1485) 1-[(z-halogeno-q-(([substituted]heteroaryl)oxycarbonyl))oxazol-w-yl]-3-hydroxy-3-([substituted]-2H-tetrazol-5-yl)-propenone
(B-1486) 1-[(z-halogeno-q-(1-hydroxy-([substituted]aryl)methyl))pyridin-w-yl]-3-hydroxy-3-([substituted]-1H-1,2,4-triazol-3-yl)-propenone
(B-1487) 4-[nH-(q-((([substituted]heteroaryl)carbonylamino)-z-halogeno)pyrazol-w-yl]-2-hydroxy-4-oxo-2-butenoic acid
(B-1488) 1-[(z-alkyl-q-(([substituted]aryl)sulfonylamino))oxazol-w-yl]-3-hydroxy-3-([substituted]-2H-tetrazol-5-yl)-propenone
(B-1489) 1-(nH-q-(([substituted]aryl)aminosulfonyl)imidazol-w-yl)-3-hydroxy-3-([substituted]-2H-tetrazol-5-yl)-propenone
(B-1490) 4-[(q-(([substituted]heteroaryl)amino)-z-halogeno)oxazol-w-yl]-2-hydroxy-4-oxo-2-butenoic acid
(B-1491) 1-[(q-([substituted]aryl)-z-halogeno)thiazol-w-yl]-3-hydroxy-3-([substituted]-1H-1,2,4-triazol-3-yl)-propenone
(B-1492) 1-[(q-(([substituted]heteroaryl)amino)-z-halogeno)pyrrol-w-yl]-3-hydroxy-3-([substituted]-2H-tetrazol-5-yl)-propenone
(B-1493) 1-[(z-alkyl-q-(([substituted]heteroaryl)aminosulfonyl))furan-w-yl]-3-hydroxy-3-([substituted]-2H-tetrazol-5-yl)-propenone
(B-1494) 4-(q-(([substituted]heteroaryl)amino)oxazol-w-yl)-2-hydroxy-4-oxo-2-butenoic acid
(B-1495) 1-[(z-alkyl-q-(([substituted]heteroaryl)sulfonyl))furan-w-yl]-3-hydroxy-3-([substituted]-1H-1,2,4-triazol-3-yl)-propenone
(B-1496) 3-hydroxy-1-(q-(([substituted]heteroaryl)oxycarbonyl)oxazol-w-yl)-3-([substituted]-1H-1,2,4-triazol-3-yl)-propenone
(B-1497) 1-[(z-alkyl-q-(([substituted]heteroaryl)carbonyl))oxazol-w-yl]-3-hydroxy-3-([substituted]-1H-1,2,4-triazol-3-yl)-propenone
(B-1498) 4-[(q-(([substituted]aryl)alkenyl)-z-halogeno)thiophen-w-yl]-2-hydroxy-4-oxo-2-butenoic acid
(B-1499) 1-(q-(([substituted]aryl)carbonylamino)isoxazol-w-yl)-3-hydroxy-3-([substituted]-2H-tetrazol-5-yl)-propenone
(B-1500) 1-[(q-(([substituted]aryl)amino)-z-halogeno)isoxazol-w-yl]-3-hydroxy-3-([substituted]-2H-tetrazol-5-yl)-propenone
(B-1501) 2-hydroxy-4-(q-(1-hydroxy-([substituted]aryl)methyl)pyridin-w-yl)-4-oxo-2-butenoic acid
(B-1502) 4-[(z-alkyl-q-(([substituted]heteroaryl)oxycarbonyl))thiophen-w-yl]-2-hydroxy-4-oxo-2-butenoic acid
(B-1503) 4-[(z-alkyl-q-(([substituted]aryl)sulfinyl))pyridin-w-yl]-2-hydroxy-4-oxo-2-butenoic acid
(B-1504) 1-[(z-alkyl-q-(([substituted]aryl)alkyl))pyrrol-w-yl]-3-hydroxy-3-([substituted]-2H-tetrazol-5-yl)-propenone
(B-1505) 4-[(q-(([substituted]aryl)aminosulfonyl)-z-halogeno)oxazol-w-yl]-2-hydroxy-4-oxo-2-butenoic acid
(B-1506) 4-[(z-alkyl-q-(([substituted]aryl)carbonyl))thiazol-w-yl]-2-hydroxy-4-oxo-2-butenoic acid
(B-1507) 1-(nH-q-(([substituted]aryl)amino)imidazol-w-yl)-3-hydroxy-3-([substituted]-1H-1,2,4-triazol-3-yl)-propenone
(B-1508) 3-hydroxy-1-(q-(([substituted]aryl)oxy)thiazol-w-yl)-3-([substituted]-2H-tetrazol-5-yl)-propenone
(B-1509) 3-hydroxy-1-(nH-q-(([substituted]aryl)oxycarbonyl)imidazol-w-yl)-3-([substituted]-2H-tetrazol-5-yl)-propenone
(B-1510) 1-[nH-(q-(([substituted]aryl)carbonylamino)-z-halogeno)pyrazol-w-yl]-3-hydroxy-3-([substituted]-2H-tetrazol-5-yl)-propenone
(B-1511) 1-[(z-alkyl-q-(([substituted]heteroaryl)carbonylamino))thiazol-w-yl]-3-hydroxy-3-([substituted]-2H-tetrazol-5-yl)-propenone
(B-1512) 1-[(z-alkyl-q-(([substituted]aryl)amino))pyridin-w-yl]-3-hydroxy-3-([substituted]-2H-tetrazol-5-yl)-propenone
(B-1513) 1-[(z-halogeno-q-(([substituted]heteroaryl)sulfinyl))pyridin-w-yl]-3-hydroxy-3-([substituted]-2H-tetrazol-5-yl)-propenone
(B-1514) 4-[nH-(q-(([substituted]heteroaryl)carboxy)-z-halogeno)pyrazol-w-yl]-2-hydroxy-4-oxo-2-butenoic acid
(B-1515) 3-hydroxy-1-(q-(([substituted]aryl)thio)furan-w-yl)-3-([substituted]-1H-1,2,4-triazol-3-yl)-propenone
(B-1516) 1-[(q-(([substituted]heteroaryl)alkyl)-z-halogeno)thiophen-w-yl]-3-hydroxy-3-([substituted]-1H-1,2,4-triazol-3-yl)-propenone
(B-1517) 1-[(z-halogeno-q-(([substituted]aryl)sulfinyl))thiophen-w-yl]-3-hydroxy-3-([substituted]-2H-tetrazol-5-yl)-propenone
(B-1518) 4-[nH-(q-(([substituted]aryl)carbonylamino)-z-halogeno)pyrazol-w-yl]-2-hydroxy-4-oxo-2-butenoic acid (B-1519) 2-hydroxy-4-oxo-4-(q-(([substituted]heteroaryl)carboxy)thiophen-w-yl)-2-butenoic acid
(B-1520) 3-hydroxy-1-(q-(1-hydroxy-([substituted]aryl)methyl)furan-w-yl)-3-([substituted]-2H-tetrazol-5-yl)-propenone
(B-1521) 1-(q-(([substituted]aryl)carbonylamino)thiophen-w-yl)-3-hydroxy-3-([substituted]-1H-1,2,4-triazol-3-yl)-propenone
(B-1522) 1-[nH-(z-alkyl-q-(([substituted]aryl)amino))pyrazol-w-yl]-3-hydroxy-3-([substituted]-2H-tetrazol-5-yl)-propenone
(B-1523) 2-hydroxy-4-oxo-4-(q-(([substituted]heteroaryl)sulfonyl)oxazol-w-yl)-2-butenoic acid
(B-1524) 3-hydroxy-3-([substituted]-2H-tetrazol-5-yl)-1-(q-(([substituted]aryl)thio)furan-w-yl)-propenone
(B-1525) 4-(q-([substituted]aryl)thiophen-w-yl)-2-hydroxy-4-oxo-2-butenoic acid
(B-1526) 1-[(q-(([substituted]heteroaryl)amino)-z-halogeno)oxazol-w-yl]-3-hydroxy-3-([substituted]-1H-1,2,4-triazol-3-yl)-propenone
(B-1527) 1-[(z-alkyl-q-(1-hydroxy-([substituted]aryl)methyl))oxazol-w-yl]-3-hydroxy-3-([substituted]-1H-1,2,4-triazol-3-yl)-propenone
(B-1528) 4-(q-(([substituted]heteroaryl)alkyl)furan-w-yl)-2-hydroxy-4-oxo-2-butenoic acid
(B-1529) 1-[(z-alkyl-q-(([substituted]hetoroaryl)alkyl))thiazol-w-yl]-3-hydroxy-3-([substituted]-1H-1,2,4-triazol-3-yl)-propenone
(B-1530) 4-(q-(([substituted]heteroaryl)carbonylamino)pyridin-w-yl)-2-hydroxy-4-oxo-2-butenoic acid
(B-1531) 4-[(z-alkyl-q-(([substituted]aryl)sulfonyl))thiazol-w-yl]-2-hydroxy-4-oxo-2-butenoic acid
(B-1532) 1-[(z-alkyl-q-(([substituted]aryl)sulfonylamino))thiazol-w-yl]-3-hydroxy-3-([substituted]-1H-1,2,4-triazol-3-yl)-propenone
(B-1533) 1-[(z-alkyl-q-(([substituted]heteroaryl)aminocarbonyl))isoxazol-w-yl]-3-hydroxy-3-([substituted]-2H-tetrazol-5-yl)-propenone
(B-1534) 1-[(z-alkyl-q-(([substituted]aryl)alkyl))isoxazol-w-yl]-3-hydroxy-3-([substituted]-1H-1,2,4-triazol-3-yl)-propenone
(B-1535) 4-[(q-(([substituted]aryl)alkyl)-z-halogeno)pyrrol-w-yl]-2-hydroxy-4-oxo-2-butenoic acid
(B-1536) 1-[(q-(([substituted]heteroaryl)carboxy)-z-halogeno)pyridin-w-yl]-3-hydroxy-3-([substituted]-2H-tetrazol-5-yl)-propenone
(B-1537) 1-(q-(([substituted]heteroaryl)amino)pyrrol-w-yl)-3-hydroxy-3-([substituted]-1H-1,2,4-triazol-3-yl)-propenone
(B-1538) 1-[nH-(q-(([substituted]aryl)carbonyl)-z-halogeno)pyrazol-w-yl]-3-hydroxy-3-([substituted]-2H-tetrazol-5-yl)-propenone
(B-1539) 4-[nH-(z-alkyl-q-(([substituted]aryl)sulfinyl))pyrazol-w-yl]-2-hydroxy-4-oxo-2-butenoic acid
(B-1540) 4-[(z-alkyl-q-(([substituted]heteroaryl)aminocarbonyl))pyrrol-w-yl]-2-hydroxy-4-oxo-2-butenoic acid
(B-1541) 3-hydroxy-1-(q-(1-hydroxy-([substituted]aryl)methyl)thiazol-w-yl)-3-([substituted]-1H-1,2,4-triazol-3-yl)-propenone
(B-1542) 2-hydroxy-4-oxo-4-(q-(([substituted]aryl)sulfinyl)isoxazol-w-yl)-2-butenoic acid
(B-1543) 1-[(z-alkyl-q-(([substituted]heteroaryl)oxy))pyrrol-w-yl]-3-hydroxy-3-([substituted]-1H-1,2,4-triazol-3-yl)-propenone
(B-1544) 4-[nH-(z-alkyl-q-(([substituted]heteroaryl)oxy))pyrazol-w-yl]-2-hydroxy-4-oxo-2-butenoic acid
(B-1545) 2-hydroxy-4-oxo-4-(q-(([substituted]heteroaryl)oxy)thiophen-w-yl)-2-butenoic acid
(B-1546) 2-hydroxy-4-oxo-4-(q-(([substituted]heteroaryl)carboxy)thiazol-w-yl)-2-butenoic acid
(B-1547) 4-(q-(([substituted]aryl)amino)isoxazol-w-yl)-2-hydroxy-4-oxo-2-butenoic acid
(B-1548) 1-[(q-(([substituted]heteroaryl)aminocarbonyl)-z-halogeno)thiazol-w-yl]-3-hydroxy-3-([substituted]-2H-tetrazol-5-yl)-propenone
(B-1549) 1-[(q-(([substituted]aryl)alkenyl)-z-alkyl)thiazol-w-yl]-3-hydroxy-3-([substituted]-1H-1,2,4-triazol-3-yl)-propenone
(B-1550) 1-[(q-(([substituted]aryl)aminocarbonyl)-z-halogeno)pyrrol-w-yl]-3-hydroxy-3-([substituted]-2H-tetrazol-5-yl)-propenone
(B-1551) 3-hydroxy-1-(q-(([substituted]heteroaryl)oxy)pyrrol-w-yl)-3-([substituted]-1H-1,2,4-triazol-3-yl)-propenone
(B-1552) 1-[nH-(z-alkyl-q-(([substituted]heteroaryl)amino))pyrazol-w-yl]-3-hydroxy-3-([substituted]-2H-tetrazol-5-yl)-propenone
(B-1553) 1-(nH-q-(([substituted]aryl)alkenyl)imidazol-w-yl)-3-hydroxy-3-([substituted]-2H-tetrazol-5-yl)-propenone
(B-1554) 1-(nH-q-(([substituted]heteroaryl)carboxy)imidazol-w-yl)-3-hydroxy-3-([substituted]-1H-1,2,4-triazol-3-yl)-propenone
(B-1555) 2-hydroxy-4-(q-(1-hydroxy-([substituted]heteroaryl)methyl)pyridin-w-yl)-4-oxo-2-butenoic acid
(B-1556) 4-[(q-(([substituted]aryl)aminosulfonyl)-z-halogeno)thiophen-w-yl]-2-hydroxy-4-oxo-2-butenoic acid
(B-1557) 1-[(z-alkyl-q-(([substituted]heteroaryl)amino))pyridin-w-yl]-3-hydroxy-3-([substituted]-2H-tetrazol-5-yl)-propenone
(B-1558) 1-(q-(([substituted]heteroaryl)alkyl)oxazol-w-yl)-3-hydroxy-3-([substituted]-2H-tetrazol-5-yl)-propenone
(B-1559) 1-[nH-(z-halogeno-q-(([substituted]heteroaryl)sulfonylamino))imidazol-w-yl]-3-hydroxy-3-([substituted]-2H-tetrazol-5-yl)-propenone
(B-1560) 4-[(z-alkyl-q-(([substituted]heteroaryl)alkyl))thiophen-w-yl]-2-hydroxy-4-oxo-2-butenoic acid
(B-1561) 3-hydroxy-1-(q-(([substituted]heteroaryl)sulfinyl)furan-w-yl)-3-([substituted]-2H-tetrazol-5-yl)-propenone
(B-1562) 1-[(z-halogeno-q-(([substituted]heteroaryl)sulfonylamino))isoxazol-w-yl]-3-hydroxy-3-([substituted]-1H-1,2,4-triazol-3-yl)-propenone
(B-1563) 1-[(z-halogeno-q-(([substituted]aryl)sulfonylamino))thiazol-w-yl]-3-hydroxy-3-([substituted]-2H-tetrazol-5-yl)-propenone
(B-1564) 4-[(z-alkyl-q-(([substituted]heteroaryl)sulfonyl))thiazol-w-yl]-2-hydroxy-4-oxo-2-butenoic acid
(B-1565) 1-[(z-alkyl-q-(([substituted]aryl)oxycarbonyl))oxazol-w-yl]-3-hydroxy-3-([substituted]-2H-tetrazol-5-yl)-propenone
(B-1566) 1-(q-([substituted]heteroaryl)isoxazol-w-yl)-3-hydroxy-3-([substituted]-1H-1,2,4-triazol-3-yl)-propenone
(B-1567) 4-(nH-q-(([substituted]aryl)alkyl)imidazol-w-yl)-2-hydroxy-4-oxo-2-butenoic acid
(B-1568) 3-hydroxy-1-(q-(([substituted]aryl)sulfonylamino)isoxazol-w-yl)-3-([substituted]-1H-1,2,4-triazol-3-yl)-propenone
(B-1569) 1-[(z-alkyl-q-(([substituted]heteroaryl)aminosulfonyl))thiazol-w-yl]-3-hydroxy-3-([substituted]-2H-tetrazol-5-yl)-propenone
(B-1570) 1-[(q-(([substituted]heteroaryl)carbonylamino)-z-halogeno)furan-w-yl]-3-hydroxy-3-([substituted]-1H-1,2,4-triazol-3-yl)-propenone (B-1571) 1-[(q-(([substituted]heteroaryl)alkyl)-z-halogeno)isoxazol-w-yl]-3-hydroxy-3-([substituted]-2H-tetrazol-5-yl)-propenone
(B-1572) 4-[(z-halogeno-q-(([substituted]heteroaryl)oxy))furan-w-yl]-2-hydroxy-4-oxo-2-butenoic acid
(B-1573) 1-[(z-halogeno-q-(1-hydroxy-([substituted]aryl)methyl))thiazol-w-yl]-3-hydroxy-3-([substituted]-2H-tetrazol-5-yl)-propenone
(B-1574) 1-[(q-(([substituted]heteroaryl)aminosulfonyl)-z-halogeno)thiophen-w-yl]-3-hydroxy-3-([substituted]-1H-1,2,4-triazol-3-yl)-propenone
(B-1575) 1-(q-(([substituted]heteroaryl)carbonyl)pyrrol-w-yl)-3-hydroxy-3-([substituted]-2H-tetrazol-5-yl)-propenone
(B-1576) 1-[(z-alkyl-q-(([substituted]aryl)carboxy))pyridin-w-yl]-3-hydroxy-3-([substituted]-1H-1,2,4-triazol-3-yl)-propenone
(B-1577) 1-[(z-halogeno-q-(([substituted]aryl)sulfinyl))furan-w-yl]-3-hydroxy-3-([substituted]-2H-tetrazol-5-yl)-propenone
(B-1578) 1-[(z-alkyl-q-(([substituted]aryl)sulfinyl))oxazol-w-yl]-3-hydroxy-3-([substituted]-2H-tetrazol-5-yl)-propenone
(B-1579) 1-[(z-alkyl-q-([substituted]aryl))thiazol-w-yl]-3-hydroxy-3-([substituted]-2H-tetrazol-5-yl)-propenone
(B-1580) 4-[(q-(([substituted]heteroaryl)aminocarbonyl)-z-halogeno)thiophen-w-yl]-2-hydroxy-4-oxo-2-butenoic acid
(B-1581) 1-(q-(([substituted]heteroaryl)aminosulfonyl)pyrrol-w-yl)-3-hydroxy-3-([substituted]-2H-tetrazol-5-yl)-propenone
(B-1582) 1-[(q-(([substituted]heteroaryl)alkyl)-z-halogeno)isoxazol-w-yl]-3-hydroxy-3-([substituted]-1H-1,2,4-triazol-3-yl)-propenone
(B-1583) 1-[(z-halogeno-q-(([substituted]aryl)sulfonyl))isoxazol-w-yl]-3-hydroxy-3-([substituted]-1H-1,2,4-triazol-3-yl)-propenone
(B-1584) 1-[(z-alkyl-q-(1-hydroxy-([substituted]aryl)methyl))thiazol-w-yl]-3-hydroxy-3-([substituted]-2H-tetrazol-5-yl)-propenone
(B-1585) 4-[nH-(z-alkyl-q-([substituted]heteroaryl))pyrazol-w-yl]-2-hydroxy-4-oxo-2-butenoic acid
(B-1586) 1-[(z-halogeno-q-(([substituted]heteroaryl)sulfonylamino))pyridin-w-yl]-3-hydroxy-3-([substituted]-1H-1,2,4-triazol-3-yl)-propenone
(B-1587) 4-(q-(([substituted]aryl)carbonylamino)pyrrol-w-yl)-2-hydroxy-4-oxo-2-butenoic acid
(B-1588) 1-[(z-alkyl-q-(([substituted]heteroaryl)thio))isoxazol-w-yl]-3-hydroxy-3-([substituted]-1H-1,2,4-triazol-3-yl)-propenone
(B-1589)) 1-[(q-(([substituted]aryl)aminocarbonyl)-z-halogeno)thiophen-w-yl]-3-hydroxy-3-([substituted]-1H-1,2,4-triazol-3-yl)-propenone
(B-1590) 4-(q-(([substituted]aryl)aminocarbonyl)isoxazol-w-yl)-2-hydroxy-4-oxo-2-butenoic acid
(B-1591) 4-(q-(([substituted]aryl)aminocarbonyl)oxazol-w-yl)-2-hydroxy-4-oxo-2-butenoic acid
(B-1592) 3-hydroxy-1-(q-(([substituted]heteroaryl)carboxy)oxazol-w-yl)-3-([substituted]-1H-1,2,4-triazol-3-yl)-propenone
(B-1593) 2-hydroxy-4-oxo-4-(nH-q-(([substituted]aryl)sulfonyl)pyrazol-w-yl)-2-butenoic acid
(B-1594) 4-[(q-(([substituted]heteroaryl)aminosulfonyl)-z-halogeno)oxazol-w-yl]-2-hydroxy-4-oxo-2-butenoic acid
(B-1595) 4-[nH-(z-halogeno-q-(1-hydroxy-([substituted]heteroaryl)methyl))imidazol-w-yl]-2-hydroxy-4-oxo-2-butenoic acid
(B-1596) 1-[nH-(z-halogeno-q-(([substituted]heteroaryl)sulfonyl))pyrazol-w-yl]-3-hydroxy-3-([substituted]-2H-tetrazol-5-yl)-propenone
(B-1597) 1-[(z-halogeno-q-(([substituted]heteroaryl)thio))isoxazol-w-yl]-3-hydroxy-3-([substituted]-2H-tetrazol-5-yl)-propenone
(B-1598) 1-[nH-(z-alkyl-q-(([substituted]aryl)sulfinyl))pyrazol-w-yl]-3-hydroxy-3-([substituted]-2H-tetrazol-5-yl)-propenone
(B-1599) 4-[(q-(([substituted]heteroaryl)carboxy)-z-alkyl)thiazol-w-yl]-2-hydroxy-4-oxo-2-butenoic acid
(B-1600) 1-[(z-alkyl-q-(([substituted]heteroaryl)alkyl))oxazol-w-yl]-3-hydroxy-3-([substituted]-1H-1,2,4-triazol-3-yl)-propenone
(B-1601) 1-[(q-(([substituted]aryl)carboxy)-z-halogeno)pyrrol-w-yl]-3-hydroxy-3-([substituted]-1H-1,2,4-triazol-3-yl)-propenone
(B-1602) 4-[(q-([substituted]aryl)-z-halogeno)oxazol-w-yl]-2-hydroxy-4-oxo-2-butenoic acid
(B-1603) 4-[(q-(([substituted]heteroaryl)carboxy)-z-halogeno)furan-w-yl]-2-hydroxy-4-oxo-2-butenoic acid
(B-1604) 1-[nH-(z-alkyl-q-(([substituted]aryl)aminosulfonyl))imidazol-w-yl]-3-hydroxy-3-([substituted]-1H-1,2,4-triazol-3-yl)-propenone
(B-1605) 3-hydroxy-1-(q-(([substituted]heteroaryl)carboxy)oxazol-w-yl)-3-([substituted]-2H-tetrazol-5-yl)-propenone
(B-1606) 1-(q-(([substituted]heteroaryl)carbonyl)thiazol-w-yl)-3-hydroxy-3-([substituted]-2H-tetrazol-5-yl)-propenone
(B-1607) 4-[(z-alkyl-q-(([substituted]heteroaryl)carbonyl))pyrrol-w-yl]-2-hydroxy-4-oxo-2-butenoic acid
(B-1608) 1-(q-(([substituted]aryl)aminosulfonyl)pyridin-w-yl)-3-hydroxy-3-([substituted]-2H-tetrazol-5-yl)-propenone
(B-1609) 3-hydroxy-3-([substituted]-2H-tetrazol-5-yl)-1-(q-(([substituted]aryl)thio)isoxazol-w-yl)-propenone
(B-1610) 1-[(q-(([substituted]heteroaryl)carbonylamino)-z-halogeno)oxazol-w-yl]-3-hydroxy-3-([substituted]-1H-1,2,4-triazol-3-yl)-propenone
(B-1611) 4-[(z-alkyl-q-(([substituted]heteroaryl)oxy))isoxazol-w-yl]-2-hydroxy-4-oxo-2-butenoic acid
(B-1612) 1-[(q-(([substituted]aryl)aminocarbonyl)-z-halogeno)pyridin-w-yl]-3-hydroxy-3-([substituted]-2H-tetrazol-5-yl)-propenone
(B-1613) 4-[(q-(([substituted]aryl)aminosulfonyl)-z-halogeno)furan-w-yl]-2-hydroxy-4-oxo-2-butenoic acid
(B-1614) 1-[(q-(([substituted]aryl)aminocarbonyl)-z-halogeno)thiazol-w-yl]-3-hydroxy-3-([substituted]-2H-tetrazol-5-yl)-propenone
(B-1615) 3-hydroxy-1-(q-(([substituted]heteroaryl)sulfinyl)isoxazol-w-yl)-3-([substituted]-1H-1,2,4-triazol-3-yl)-propenone
(B-1616) 1-(q-(([substituted]heteroaryl)carbonylamino)pyrrol-w-yl)-3-hydroxy-3-([substituted]-2H-tetrazol-5-yl)-propenone
(B-1617) 4-(nH-q-(([substituted]heteroaryl)carbonyl)imidazol-w-yl)-2-hydroxy-4-oxo-2-butenoic acid
(B-1618) 4-[(z-alkyl-q-([substituted]heteroaryl))thiophen-w-yl]-2-hydroxy-4-oxo-2-butenoic acid
(B-1619) 4-[(z-alkyl-q-(([substituted]aryl)aminosulfonyl))pyrrol-w-yl]-2-hydroxy-4-oxo-2-butenoic acid
(B-1620) 4-[(z-halogeno-q-(([substituted]aryl)thio))furan-w-yl]-2-hydroxy-4-oxo-2-butenoic acid
(B-1621) 1-(nH-q-(([substituted]aryl)aminocarbonyl)pyrazol-w-yl)-3-hydroxy-3-([substituted]-2H-tetrazol-5-yl)-propenone (B-1622) 1-[(z-alkyl-q-(([substituted]heteroaryl)aminosulfonyl))isoxazol-w-yl]-3-hydroxy-3-([substituted]-1H-1,2,4-triazol-3-yl)-propenone
(B-1623) 1-[(z-alkyl-q-(1-hydroxy-([substituted]aryl)methyl))thiophen-w-yl]-3-hydroxy-3-([substituted]-1H-1,2,4-triazol-3-yl)-propenone
(B-1624) 4-[(z-alkyl-q-(([substituted]aryl)carboxy))thiophen-w-yl]-2-hydroxy-4-oxo-2-butenoic acid
(B-1625) 2-hydroxy-4-(q-(1-hydroxy-([substituted]aryl)methyl)isoxazol-w-yl)-4-oxo-2-butenoic acid
(B-1626) 3-hydroxy-1-(q-(([substituted]heteroaryl)carboxy)pyrrol-w-yl)-3-([substituted]-1H-1,2,4-triazol-3-yl)-propenone
(B-1627) 1-[nH-(z-halogeno-q-(([substituted]heteroaryl)oxy))pyrazol-w-yl]-3-hydroxy-3-([substituted]-1H-1,2,4-triazol-3-yl)-propenone
(B-1628) 4-[nH-(z-alkyl-q-(([substituted]heteroaryl)sulfinyl))pyrazol-w-yl]-2-hydroxy-4-oxo-2-butenoic acid
(B-1629) 1-[nH-(z-halogeno-q-(([substituted]heteroaryl)oxycarbonyl))imidazol-w-yl]-3-hydroxy-3-([substituted]-2H-tetrazol-5-yl)-propenone
(B-1630) 1-[(z-alkyl-q-(1-hydroxy-([substituted]heteroaryl)methyl))isoxazol-w-yl]-3-hydroxy-3-([substituted]-1H-1,2,4-triazol-3-yl)-propenone
(B-1631) 1-[(q-(([substituted]aryl)carboxy)-z-halogeno)isoxazol-w-yl]-3-hydroxy-3-([substituted]-1H-1,2,4-triazol-3-yl)-propenone
(B-1632) 1-(q-(([substituted]heteroaryl)carboxy)furan-w-yl)-3-hydroxy-3-([substituted]-2H-tetrazol-5-yl)-propenone
(B-1633) 4-[(q-(([substituted]heteroaryl)aminosulfonyl)-z-halogeno)thiazol-w-yl]-2-hydroxy-4-oxo-2-butenoic acid
(B-1634) 1-[(z-halogeno-q-(([substituted]heteroaryl)thio)furan-w-yl]-3-hydroxy-3-([substituted]-1H-1,2,4-triazol-3-yl)-propenone
(B-1635) 1-[(z-alkyl-q-(([substituted]aryl)carbonylamino))furan-w-yl]-3-hydroxy-3-([substituted]-2H-tetrazol-5-yl)-propenone
(B-1636) 4-[nH-(z-halogeno-q-(([substituted]aryl)sulfinyl))imidazol-w-yl]-2-hydroxy-4-oxo-2-butenoic acid
(B-1637) 1-[(q-(([substituted]heteroaryl)carboxy)-z-alkyl)furan-w-yl]-3-hydroxy-3-([substituted]-2H-tetrazol-5-yl)-propenone
(B-1638) 1-[(q-([substituted]aryl)-z-halogeno)oxazol-w-yl]-3-hydroxy-3-([substituted]-1H-1,2,4-triazol-3-yl)-propenone
(B-1639) 1-(q-([substituted]aryl)thiophen-w-yl)-3-hydroxy-3-([substituted]-2H-tetrazol-5-yl)-propenone
(B-1640) 3-hydroxy-1-(q-(([substituted]heteroaryl)sulfonylamino)thiophen-w-yl)-3-([substituted]-2H-tetrazol-5-yl)-propenone
(B-1641) 3-hydroxy-1-(q-(([substituted]heteroaryl)sulfonyl)thiazol-w-yl)-3-([substituted]-2H-tetrazol-5-yl)-propenone
(B-1642) 4-[(z-halogeno-q-(([substituted]heteroaryl)oxycarbonyl))oxazol-w-yl]-2-hydroxy-4-oxo-2-butenoic acid
(B-1643) 1-[nH-(z-halogeno-q-(([substituted]heteroaryl)sulfonyl))imidazol-w-yl]-3-hydroxy-3-([substituted]-1H-1,2,4-triazol-3-yl)-propenone
(B-1644) 1-[nH-(q-(([substituted]aryl)alkenyl)-z-halogeno)pyrazol-w-yl]-3-hydroxy-3-([substituted]-1H-1,2,4-triazol-3-yl)-propenone
(B-1645) 1-[(z-halogeno-q-(([substituted]aryl)sulfonyl))thiophen-w-yl]-3-hydroxy-3-([substituted]-1H-1,2,4-triazol-3-yl)-propenone
(B-1646) 1-[(z-halogeno-q-(1-hydroxy-([substituted]heteroaryl)methyl))pyrrol-w-yl]-3-hydroxy-3-([substituted]-2H-tetrazol-5-yl)-propenone
(B-1647) 3-hydroxy-1-(q-(([substituted]aryl)sulfonylamino)thiazol-w-yl)-3-([substituted]-2H-tetrazol-5-yl)-propenone
(B-1648) 1-(q-(([substituted]aryl)alkyl)pyridin-w-yl)-3-hydroxy-3-([substituted]-1H-1,2,4-triazol-3-yl)-propenone
(B-1649) 2-hydroxy-4-oxo-4-(nH-q-(([substituted]heteroaryl)sulfonylamino)pyrazol-w-yl)-2-butenoic acid
(B-1650) 1-(q-(([substituted]heteroaryl)alkenyl)isoxazol-w-yl)-3-hydroxy-3-([substituted]-2H-tetrazol-5-yl)-propenone
(B-1651) 4-[(q-(([substituted]aryl)carboxy)-z-halogeno)oxazol-w-yl]-2-hydroxy-4-oxo-2-butenoic acid
(B-1652) 1-[(q-(([substituted]heteroaryl)amino)-z-halogeno)furan-w-yl]-3-hydroxy-3-([substituted]-2H-tetrazol-5-yl)-propenone
(B-1653) 4-(nH-q-([substituted]aryl)imidazol-w-yl)-2-hydroxy-4-oxo-2-butenoic acid
(B-1654) 4-[(z-halogeno-q-(([substituted]heteroaryl)sulfonyl))thiazol-w-yl]-2-hydroxy-4-oxo-2-butenoic acid
(B-1655) 1-[nH-(z-halogeno-q-(([substituted]aryl)thio))imidazol-w-yl]-3-hydroxy-3-([substituted]-1H-1,2,4-triazol-3-yl)-propenone
(B-1656) 2-hydroxy-4-oxo-4-(q-(([substituted]heteroaryl)oxycarbonyl)isoxazol-w-yl)-2-butenoic acid
(B-1657) 4-[(q-((2substituted]aryl)aminocarbonyl)-z-halogeno)pyrrol-w-yl]-2-hydroxy-4-oxo-2-butenoic acid
(B-1658) 1-[(z-halogeno-q-(([substituted]aryl)oxycarbonyl))thiazol-w-yl]-3-hydroxy-3-([substituted]-2H-tetrazol-5-yl)-propenone
(B-1659) 1-[(z-alkyl-q-(([substituted]aryl)sulfonyl))pyrrol-w-yl]-3-hydroxy-3-([substituted]-2H-tetrazol-5-yl)-propenone
(B-1660) 1-[(z-halogeno-q-(([substituted]heteroaryl)oxycarbonyl))pyridin-w-yl]-3-hydroxy-3-([substituted]-2H-tetrazol-5-yl)-propenone
(B-1661) 1-[nH-(q-(([substituted]aryl)aminosulfonyl)-z-halogeno)pyrazol-w-yl]-3-hydroxy-3-([substituted]-1H-1,2,4-triazol-3-yl)-propenone
(B-1662) 4-[(z-alkyl-q-(([substituted]heteroaryl)amino))thiophen-w-yl]-2-hydroxy-4-oxo-2-butenoic acid
(B-1663) 1-[(z-alkyl-q-(([substituted]heteroaryl)carbonyl))oxazol-w-yl]-3-hydroxy-3-([substituted]-2H-tetrazol-5-yl)-propenone
(B-1664) 3-hydroxy-1-(q-(([substituted]aryl)oxy)thiazol-w-yl)-3-([substituted]-1H-1,2,4-triazol-3-yl)-propenone
(B-1665) 1-[nH-(z-alkyl-q-([substituted]aryl))imidazol-w-yl]-3-hydroxy-3-([substituted]-2H-tetrazol-5-yl)-propenone
(B-1666) 1-[(z-alkyl-q-(([substituted]aryl)carboxy))pyridin-w-yl]-3-hydroxy-3-([substituted]-2H-tetrazol-5-yl)-propenone
(B-1667) 1-[nH-(q-(([substituted]aryl)carbonylamino)-z-halogeno)imidazol-w-yl]-3-hydroxy-3-([substituted]-1H-1,2,4-triazol-3-yl)-propenone
(B-1668) 2-hydroxy-4-oxo-4-(q-(([substituted]aryl)sulfonyl)pyrrol-w-yl)-2-butenoic acid
(B-1669) 3-hydroxy-1-(q-(([substituted]heteroaryl)oxy)pyrrol-w-yl)-3-([substituted]-2H-tetrazol-5-yl)-propenone
(B-1670) 1-[(z-alkyl-q-(([substituted]heteroaryl)thio))thiazol-w-yl]-3-hydroxy-3-([substituted]-1H-1,2,4-triazol-3-yl)-propenone
(B-1671) 1-[(z-alkyl-q-(([substituted]heteroaryl)alkyl))furan-w-yl]-3-hydroxy-3-([substituted]-1H-1,2,4-triazol-3-yl)-propenone
(B-1672) 1-[(z-alkyl-q-(([substituted]aryl)sulfonyl))pyridin-w-yl]-3-hydroxy-3-([substituted]-2H-tetrazol-5-yl)-propenone (B-1673) 1-[(z-halogeno-q-(([substituted]heteroaryl)oxy))furan-w-yl]-3-hydroxy-3-([substituted]-1H-1,2,4-triazol-3-yl)-propenone (B-1674) 4-[(q-(([substituted]aryl)carbonylamino)-z-halogeno)pyrrol-w-yl]-2-hydroxy-4-oxo-2-butenoic acid (B-1675) 1-[(q-(([substituted]heteroaryl)alkenyl)-z-alkyl)thiazol-w-yl]-3-hydroxy-3-([substituted]-1H-1,2,4-triazol-3-yl)-propenone (B-1676) 1-[nH-(z-halogeno-q-(([substituted]aryl)oxy))imidazol-w-yl]-3-hydroxy-3-([substituted]-2H-tetrazol-5-yl)-propenone (B-1677) 1-[(q-(([substituted]heteroaryl)carboxy)-z-halogeno)thiophen-w-yl]-3-hydroxy-3-([substituted]-1H-1,2,4-triazol-3-yl)-propenone (B-1678) 4-[nH-(q-(([substituted]heteroaryl)carboxy)-z-halogeno)imidazol-w-yl]-2-hydroxy-4-oxo-2-butenoic acid (B-1679) 1-[(z-alkyl-q-(([substituted]heteroaryl)sulfonyl))pyridin-w-yl]-3-hydroxy-3-([substituted]-1H-1,2,4-triazol-3-yl)-propenone (B-1680) 4-[(z-halogeno-q-(([substituted]heteroaryl)sulfinyl))oxazol-w-yl]-2-hydroxy-4-oxo-2-butenoic acid (B-1681) 1-[(z-alkyl-q-(([substituted]heteroaryl)aminocarbonyl))thiazol-w-yl]-3-hydroxy-3-([substituted]-1H-1,2,4-triazol-3-yl)-propenone (B-1682) 4-[(z-halogeno-q-(([substituted]aryl)sulfonyl))furan-w-yl]-2-hydroxy-4-oxo-2-butenoic acid (B-1683) 1-(nH-q-(([substituted]heteroaryl)carbonylamino)imidazol-w-yl)-3-hydroxy-3-([substituted]-1H-1,2,4-triazol-3-yl)-propenone (B-1684) 2-hydroxy-4-oxo-4-(q-(([substituted]aryl)sulfonyl)oxazol-w-yl)-2-butenoic acid (B-1685) 4-[(z-halogeno-q-(([substituted]aryl)sulfonylamino))oxazol-w-yl]-2-hydroxy-4-oxo-2-butenoic acid (B-1686) 4-(nH-q-(([substituted]heteroaryl)carbonylamino)pyrazol-w-yl)-2-hydroxy-4-oxo-2-butenoic acid (B-1687) 1-[(z-alkyl-q-(([substituted]aryl)aminosulfonyl))thiophen-w-yl]-3-hydroxy-3-([substituted]-1H-1,2,4-triazol-3-yl)-propenone (B-1688) 4-[nH-(z-halogeno-q-([substituted]heteroaryl))imidazol-w-yl]-2-hydroxy-4-oxo-2-butenoic acid (B-1689) 3-hydroxy-1-(nH-q-(([substituted]aryl)sulfinyl)pyrazol-w-yl)-3-([substituted]-1H-1,2,4-triazol-3-yl)-propenone (B-1690) 1-[(z-alkyl-q-(([substituted]aryl)sulfonylamino))pyridin-w-yl]-3-hydroxy-3-([substituted]-1H-1,2,4-triazol-3-yl)-propenone (B-1691) 1-[nH-(z-alkyl-q-(([substituted]aryl)sulfonylamino))imidazol-w-yl]-3-hydroxy-3-([substituted]-1H-1,2,4-triazol-3-yl)-propenone (B-1692) 4-(q-(([substituted]aryl)amino)thiophen-w-yl)-2-hydroxy-4-oxo-2-butenoic acid (B-1693) 1-[(z-halogeno-q-(([substituted]heteroaryl)sulfonylamino))oxazol-w-yl]-3-hydroxy-3-([substituted]-2H-tetrazol-5-yl)-propenone (B-1694) 4-[nH-(z-alkyl-q-(([substituted]heteroaryl)oxycarbonyl))pyrazol-w-yl]-2-hydroxy-4-oxo-2-butenoic acid (B-1695) 4-[(z-alkyl-q-(([substituted]heteroaryl)alkyl))pyridin-w-yl]-2-hydroxy-4-oxo-2-butenoic acid (B-1696) 4-[(z-alkyl-q-(([substituted]aryl)aminosulfonyl))thiazol-w-yl]-2-hydroxy-4-oxo-2-butenoic acid (B-1697) 1-[(z-halogeno-q-(([substituted]aryl)oxy))oxazol-w-yl]-3-hydroxy-3-([substituted]-2H-tetrazol-5-yl)-propenone (B-1698) 4-[nH-(z-alkyl-q-(1-hydroxy-([substituted]heteroaryl)methyl))imidazol-w-yl]-2-hydroxy-4-oxo-2-butenoic acid (B-1699) 1-(q-(([substituted]aryl)carbonyl)thiazol-w-yl)-3-hydroxy-3-([substituted]-2H-tetrazol-5-yl)-propenone (B-1700) 1-[(q-(([substituted]heteroaryl)carbonylamino)-z-halogeno)thiazol-w-yl]-3-hydroxy-3-([substituted]-2H-tetrazol-5-yl)-propenone (B-1701) 1-[(z-alkyl-q-(([substituted]aryl)thio))isoxazol-w-yl]-3-hydroxy-3-([substituted]-1H-1,2,4-triazol-3-yl)-propenone (B-1702) 1-[(z-alkyl-q-(([substituted]heteroaryl)sulfinyl))pyrrol-w-yl]-3-hydroxy-3-([substituted]-2H-tetrazol-5-yl)-propenone (B-1703) 1-[(z-alkyl-q-(([substituted]heteroaryl)thio))isoxazol-w-yl]-3-hydroxy-3-([substituted]-2H-tetrazol-5-yl)-propenone (B-1704) 1-[(z-halogeno-q-(([substituted]heteroaryl)oxycarbonyl))thiophen-w-yl]-3-hydroxy-3-([substituted]-2H-tetrazol-5-yl)-propenone (B-1705) 4-(nH-q-(([substituted]aryl)alkyl)pyrazol-w-yl)-2-hydroxy-4-oxo-2-butenoic acid (B-1706) 4-[(z-halogeno-q-(([substituted]aryl)sulfinyl))thiazol-w-yl]-2-hydroxy-4-oxo-2-butenoic acid (B-1707) 1-(nH-q-(([substituted]aryl)carboxy)pyrazol-w-yl)-3-hydroxy-3-([substituted]-1H-1,2,4-triazol-3-yl)-propenone (B-1708) 4-[(z-halogeno-q-(([substituted]aryl)sulfonyl))thiophen-w-yl]-2-hydroxy-4-oxo-2-butenoic acid (B-1709) 4-[(z-alkyl-q-(([substituted]heteroaryl)thio))pyridin-w-yl]-2-hydroxy-4-oxo-2-butenoic acid (B-1710) 1-[(q-(([substituted]heteroaryl)carbonylamino)-z-halogeno)pyrrol-w-yl]-3-hydroxy-3-([substituted]-2H-tetrazol-5-yl)-propenone (B-1711) 1-[(q-(([substituted]aryl)alkenyl)-z-alkyl)thiazol-w-yl]-3-hydroxy-3-([substituted]-2H-tetrazol-5-yl)-propenone (B-1712) 4-[nH-(z-halogeno-q-(([substituted]aryl)sulfonylamino))imidazol-w-yl]-2-hydroxy-4-oxo-2-butenoic acid (B-1713) 2-hydroxy-4-oxo-4-(nH-q-(([substituted]heteroaryl)sulfinyl)imidazol-w-yl)-2-butenoic acid (B-1714) 1-[(z-halogeno-q-(([substituted]aryl)sulfinyl))oxazol-w-yl]-3-hydroxy-3-([substituted]-2H-tetrazol-5-yl)-propenone (B-1715) 4-[(z-halogeno-q-(([substituted]heteroaryl)sulfonylamino))thiazol-w-yl]-2-hydroxy-4-oxo-2-butenoic acid (B-1716) 1-[(z-halogeno-q-(([substituted]heteroaryl)sulfonyl))oxazol-w-yl]-3-hydroxy-3-([substituted]-1H-1,2,4-triazol-3-yl)-propenone (B-1717) 4-[(q-(([substituted]heteroaryl)carboxy)-z-halogeno)pyridin-w-yl]-2-hydroxy-4-oxo-2-butenoic acid (B-1718) 1-[(z-halogeno-q-(([substituted]heteroaryl)sulfonyl))isoxazol-w-yl]-3-hydroxy-3-([substituted]-2H-tetrazol-5-yl)-propenone (B-1719) 4-[(z-halogeno-q-(([substituted]aryl)oxycarbonyl))pyrrol-w-yl]-2-hydroxy-4-oxo-2-butenoic acid (B-1720) 4-[nH-(z-halogeno-q-([substituted]heteroaryl))pyrazol-w-yl]-2-hydroxy-4-oxo-2-butenoic acid (B-1721) 1-[nH-(z-alkyl-q-(1-hydroxy-([substituted]heteroaryl)methyl))imidazol-w-yl]-3-hydroxy-3-([substituted]-1H-1,2,4-triazol-3-yl)-propenone (B-1722) 1-[(z-halogeno-q-(([substituted]heteroaryl)sulfonyl))furan-w-yl]-3-hydroxy-3-([substituted]-1H-1,2,4-triazol-3-yl)-propenone (B-1723) 4-[(q-(([substituted]heteroaryl)aminosulfonyl)-z-halogeno)pyridin-w-yl]-2-hydroxy-4-oxo-2-butenoic acid (B-1724) 4-[(z-halogeno-q-([substituted]heteroaryl))isoxazol-w-yl]-2-hydroxy-4-oxo-2-butenoic acid
(B-1725) 1-[nH-(z-halogeno-q-(([substituted]heteroaryl)thio))pyrazol-w-yl]-3-hydroxy-3-([substituted]-1H-1,2,4-triazol-3-yl)-propenone
(B-1726) 3-hydroxy-1-(q-(([substituted]aryl)thio)isoxazol-w-yl)-3-([substituted]-1H-1,2,4-triazol-3-yl)-propenone
(B-1727) 4-[(z-alkyl-q-(([substituted]aryl)carbonyl))pyrrol-w-yl]-2-hydroxy-4-oxo-2-butenoic acid
(B-1728) 1-[nH-(z-alkyl-q-(([substituted]aryl)thio))imidazol-w-yl]-3-hydroxy-3-([substituted]-1H-1,2,4-triazol-3-yl)-propenone
(B-1729) 1-[(z-alkyl-q-(([substituted]heteroaryl)carbonyl))pyrrol-w-yl]-3-hydroxy-3-([substituted]-2H-tetrazol-5-yl)-propenone
(B-1730) 3-hydroxy-1-(q-(([substituted]aryl)carbonyl)furan-w-yl)-3-([substituted]-1H-1,2,4-triazol-3-yl)-propenone
(B-1731) 4-[nH-(z-alkyl-q-(([substituted]aryl)alkyl))imidazol-w-yl]-2-hydroxy-4-oxo-2-butenoic acid
(B-1732) 1-[nH-(z-halogeno-q-(1-hydroxy-([substituted]heteroaryl)methyl))pyrazol-w-yl]-3-hydroxy-3-([substituted]-2H-tetrazol-5-yl)-propenone
(B-1733) 4-[(z-alkyl-q-(([substituted]aryl)carbonyl))pyridin-w-yl]-2-hydroxy-4-oxo-2-butenoic acid
(B-1734) 1-[(z-alkyl-q-(([substituted]aryl)carbonyl))furan-w-yl]-3-hydroxy-3-([substituted]-1H-1,2,4-triazol-3-yl)-propenone
(B-1735) 3-hydroxy-1-(q-(1-hydroxy-([substituted]aryl)methyl)thiazol-w-yl)-3-([substituted]-2H-tetrazol-5-yl)-propenone
(B-1736) 1-(q-(([substituted]aryl)carbonyl)thiophen-w-yl)-3-hydroxy-3-([substituted]-1H-1,2,4-triazol-3-yl)-propenone
(B-1737) 3-hydroxy-1-(q-(([substituted]heteroaryl)sulfonylamino)thiophen-w-yl)-3-([substituted]-1H-1,2,4-triazol-3-yl)-propenone
(B-1738) 4-[(z-alkyl-q-(([substituted]heteroaryl)sulfonyl))pyridin-w-yl]-2-hydroxy-4-oxo-2-butenoic acid
(B-1739) 1-[nH-(q-(([substituted]heteroaryl)carboxy)-z-alkyl)imidazol-w-yl]-3-hydroxy-3-([substituted]-2H-tetrazol-5-yl)-propenone
(B-1740) 4-[(z-halogeno-q-([substituted]heteroaryl))pyrrol-w-yl]-2-hydroxy-4-oxo-2-butenoic acid
(B-1741) 1-[nH-(z-alkyl-q-(([substituted]heteroaryl)sulfonylamino))pyrazol-w-yl]-3-hydroxy-3-([substituted]-1H-1,2,4-triazol-3-yl)-propenone
(B-1742) 1-[(z-halogeno-q-(1-hydroxy-([substituted]heteroaryl)methyl))thiophen-w-yl]-3-hydroxy-3-([substituted]-1H-1,2,4-triazol-3-yl)-propenone
(B-1743) 1-[(z-halogeno-q-(([substituted]aryl)thio))thiophen-w-yl]-3-hydroxy-3-([substituted]-2H-tetrazol-5-yl)-propenone
(B-1744) 3-hydroxy-1-(nH-q-(([substituted]aryl)sulfonyl)imidazol-w-yl)-3-([substituted]-2H-tetrazol-5-yl)-propenone
(B-1745) 4-[(z-halogeno-q-(([substituted]aryl)oxycarbonyl))pyridin-w-yl]-2-hydroxy-4-oxo-2-butenoic acid
(B-1746) 1-[(q-(([substituted]heteroaryl)aminocarbonyl)-z-halogeno)oxazol-w-yl]-3-hydroxy-3-([substituted]-1H-1,2,4-triazol-3-yl)-propenone
(B-1747) 4-[(q-(([substituted]heteroaryl)carbonyl)-z-halogeno)pyridin-w-yl]-2-hydroxy-4-oxo-2-butenoic acid
(B-1748) 3-hydroxy-1-(q-(1-hydroxy-([substituted]heteroaryl)methyl)thiazol-w-yl)-3-([substituted]-1H-1,2,4-triazol-3-yl)-propenone
(B-1749) 4-[(z-halogeno-q-(([substituted]heteroaryl)oxycarbonyl))pyridin-w-yl]-2-hydroxy-4-oxo-2-butenoic acid
(B-1750) 1-[(z-alkyl-q-(([substituted]aryl)oxycarbonyl))thiophen-w-yl]-3-hydroxy-3-([substituted]-2H-tetrazol-5-yl)-propenone
(B-1751) 2-hydroxy-4-oxo-4-(q-(([substituted]aryl)sulfonylamino)isoxazol-w-yl)-2-butenoic acid
(B-1752) 1-[(z-alkyl-q-(([substituted]heteroaryl)oxy))oxazol-w-yl]-3-hydroxy-3-([substituted]-1H-1,2,4-triazol-3-yl)-propenone
(B-1753) 1-[(z-halogeno-q-(1-hydroxy-([substituted]aryl)methyl))pyrrol-w-yl]-3-hydroxy-3-([substituted]-1H-1,2,4-triazol-3-yl)-propenone
(B-1754) 1-[nH-(z-alkyl-q-(([substituted]heteroaryl)carbonylamino))pyrazol-w-yl]-3-hydroxy-3-([substituted]-1H-1,2,4-triazol-3-yl)-propenone
(B-1755) 2-hydroxy-4-oxo-4-(q-(([substituted]aryl)thio)isoxazol-w-yl)-2-butenoic acid
(B-1756) 1-[(q-(([substituted]heteroaryl)aminocarbonyl)-z-halogeno)isoxazol-w-yl]-3-hydroxy-3-([substituted]-1H-1,2,4-triazol-3-yl)-propenone
(B-1757) 3-hydroxy-1-(q-(1-hydroxy-([substituted]heteroaryl)methyl)furan-w-yl)-3-([substituted]-1H-1,2,4-triazol-3-yl)-propenone
(B-1758) 1-[(z-alkyl-q-(([substituted]aryl)sulfonylamino))isoxazol-w-yl]-3-hydroxy-3-([substituted]-1H-1,2,4-triazol-3-yl)-propenone
(B-1759) 4-[(z-alkyl-q-(([substituted]heteroaryl)sulfonylamino))thiazol-w-yl]-2-hydroxy-4-oxo-2-butenoic acid
(B-1760) 1-[(z-halogeno-q-(([substituted]heteroaryl)sulfonyl))oxazol-w-yl]-3-hydroxy-3-([substituted]-2H-tetrazol-5-yl)-propenone
(B-1761) 1-[nH-(z-halogeno-q-(([substituted]aryl)sulfinyl))pyrazol-w-yl]-3-hydroxy-3-([substituted]-2H-tetrazol-5-yl)-propenone
(B-1762) 3-hydroxy-1-(nH-q-(([substituted]aryl)thio)pyrazol-w-yl)-3-([substituted]-1H-1,2,4-triazol-3-yl)-propenone
(B-1763) 1-(q-(([substituted]heteroaryl)alkenyl)thiazol-w-yl)-3-hydroxy-3-([substituted]-2H-tetrazol-5-yl)-propenone
(B-1764) 1-(q-(([substituted]heteroaryl)aminocarbonyl)isoxazol-w-yl)-3-hydroxy-3-([substituted]-2H-tetrazol-5-yl)-propenone
(B-1765) 4-(q-(([substituted]heteroaryl)amino)furan-w-yl)-2-hydroxy-4-oxo-2-butenoic acid
(B-1766) 1-[(q-(([substituted]aryl)amino)-z-halogeno)thiophen-w-yl]-3-hydroxy-3-([substituted]-2H-tetrazol-5-yl)-propenone
(B-1767) 2-hydroxy-4-oxo-4-(q-(([substituted]aryl)oxy)pyridin-w-yl)-2-butenoic acid
(B-1768) 1-(q-(([substituted]aryl)aminocarbonyl)pyrrol-w-yl)-3-hydroxy-3-([substituted]-1H-1,2,4-triazol-3-yl)-propenone
(B-1769) 1-(q-(([substituted]aryl)carbonylamino)thiazol-w-yl)-3-hydroxy-3-([substituted]-2H-tetrazol-5-yl)-propenone
(B-1770) 1-[nH-(z-alkyl-q-(([substituted]heteroaryl)sulfonyl))pyrazol-w-yl]-3-hydroxy-3-([substituted]-1H-1,2,4-triazol-3-yl)-propenone
(B-1771) 1-[(q-(([substituted]heteroaryl)alkenyl)-z-alkyl)oxazol-w-yl]-3-hydroxy-3-([substituted]-1H-1,2,4-triazol-3-yl)-propenone
(B-1772) 1-(q-(([substituted]heteroaryl)aminosulfonyl)thiazol-w-yl)-3-hydroxy-3-([substituted]-2H-tetrazol-5-yl)-propenone (B-1773) 1-(q-((([substituted]heteroaryl)alkenyl)thiazol-w-yl)-3-hydroxy-3-([substituted]-1H-1,2,4-triazol-3-yl)-propenone (B-1774) 1-[(q-((([substituted]heteroaryl)alkyl)-z-halogeno)pyrrol-w-yl]-3-hydroxy-3-([substituted]-1H-1,2,4-triazol-3-yl)-propenone (B-1775) 4-[(q-((([substituted]heteroaryl)carboxy)-z-alkyl)furan-w-yl]-2-hydroxy-4-oxo-2-butenoic acid (B-1776) 4-[nH-(z-alkyl-q-((([substituted]heteroaryl)carbonylamino))imidazol-w-yl]-2-hydroxy-4-oxo-2-butenoic acid (B-1777) 1-[(q-((([substituted]aryl)aminosulfonyl)-z-halogeno)pyrrol-w-yl]-3-hydroxy-3-([substituted]-1H-1,2,4-triazol-3-yl)-propenone (B-1778) 1-(q-(([substituted]heteroaryl)oxazol-w-yl)-3-hydroxy-3-([substituted]-1H-1,2,4-triazol-3-yl)-propenone (B-1779) 1-[(z-alkyl-q-((([substituted]heteroaryl)oxycarbonyl))isoxazol-w-yl]-3-hydroxy-3-([substituted]-1H-1,2,4-triazol-3-yl)-propenone (B-1780) 1-[(z-alkyl-q-((([substituted]aryl)sulfinyl))furan-w-yl]-3-hydroxy-3-([substituted]-1H-1,2,4-triazol-3-yl)-propenone (B-1781) 4-[(z-halogeno-q-((([substituted]heteroaryl)sulfinyl))pyrrol-w-yl]-2-hydroxy-4-oxo-2-butenoic acid (B-1782) 4-[(z-alkyl-q-((([substituted]aryl)oxycarbonyl))pyrrol-w-yl]-2-hydroxy-4-oxo-2-butenoic acid (B-1783) 1-(q-((([substituted]aryl)alkenyl)pyridin-w-yl)-3-hydroxy-3-([substituted]-1H-1,2,4-triazol-3-yl)-propenone (B-1784) 4-[(z-alkyl-q-((([substituted]heteroaryl)sulfonyl))isoxazol-w-yl]-2-hydroxy-4-oxo-2-butenoic acid (B-1785) 1-[(q-((([substituted]aryl)aminosulfonyl)-z-halogeno)isoxazol-w-yl]-3-hydroxy-3-([substituted]-2H-tetrazol-5-yl)-propenone (B-1786) 2-hydroxy-4-oxo-4-(q-((([substituted]aryl)sulfonylamino)thiazol-w-yl)-2-butenoic acid (B-1787) 1-[(z-halogeno-q-((([substituted]heteroaryl)thio))pyridin-w-yl]-3-hydroxy-3-([substituted]-1H-1,2,4-triazol-3-yl)-propenone (B-1788) 3-hydroxy-1-(q-((([substituted]aryl)oxy)thiophen-w-yl)-3-([substituted]-1H-1,2,4-triazol-3-yl)-propenone (B-1789) 1-(q-((([substituted]aryl)aminocarbonyl)thiophen-w-yl)-3-hydroxy-3-([substituted]-1H-1,2,4-triazol-3-yl)-propenone (B-1790) 1-[nH-(z-alkyl-q-((([substituted]aryl)carbonylamino))imidazol-w-yl]-3-hydroxy-3-([substituted]-1H-1,2,4-triazol-3-yl)-propenone (B-1791) 4-[(z-halogeno-q-((([substituted]heteroaryl)sulfinyl))isoxazol-w-yl]-2-hydroxy-4-oxo-2-butenoic acid (B-1792) 1-[nH-(z-alkyl-q-((([substituted]heteroaryl)carbonylamino))imidazol-w-yl]-3-hydroxy-3-([substituted]-1H-1,2,4-triazol-3-yl)-propenone (B-1793) 1-[(z-alkyl-q-((([substituted]aryl)aminocarbonyl))thiazol-w-yl]-3-hydroxy-3-([substituted]-1H-1,2,4-triazol-3-yl)-propenone (B-1794) 4-[(q-((([substituted]heteroaryl)carboxy)-z-alkyl)thiophen-w-yl]-2-hydroxy-4-oxo-2-butenoic acid (B-1795) 1-(nH-q-((([substituted]aryl)carbonylamino)pyrazol-w-yl)-3-hydroxy-3-([substituted]-2H-tetrazol-5-yl)-propenone (B-1796) 1-(q-((([substituted]heteroaryl)carbonylamino)isoxazol-w-yl)-3-hydroxy-3-([substituted]-2H-tetrazol-5-yl)-propenone (B-1797) 1-[nH-(z-alkyl-q-((([substituted]aryl)aminosulfonyl))imidazol-w-yl]-3-hydroxy-3-([substituted]-2H-tetrazol-5-yl)-propenone (B-1798) 4-[(z-halogeno-q-((([substituted]aryl)sulfinyl))thiophen-w-yl]-2-hydroxy-4-oxo-2-butenoic acid (B-1799) 1-[(q-((([substituted]aryl)carbonylamino)-z-halogeno)furan-w-yl]-3-hydroxy-3-([substituted]-2H-tetrazol-5-yl)-propenone (B-1800) 1-[(z-alkyl-q-((([substituted]heteroaryl)carbonyl))furan-w-yl]-3-hydroxy-3-([substituted]-2H-tetrazol-5-yl)-propenone (B-1801) 1-[(q-((([substituted]aryl)carbonyl)-z-halogeno)oxazol-w-yl]-3-hydroxy-3-([substituted]-2H-tetrazol-5-yl)-propenone (B-1802) 3-hydroxy-1-(q-((([substituted]heteroaryl)sulfonyl)furan-w-yl)-3-([substituted]-2H-tetrazol-5-yl)-propenone (B-1803) 4-[(q-((([substituted]heteroaryl)aminocarbonyl)-z-halogeno)furan-w-yl]-2-hydroxy-4-oxo-2-butenoic acid (B-1804) 4-[nH-(q-((([substituted]aryl)amino)-z-halogeno)pyrazol-w-yl]-2-hydroxy-4-oxo-2-butenoic acid (B-1805) 1-[(z-alkyl-q-((([substituted]heteroaryl)alkyl))pyrrol-w-yl]-3-hydroxy-3-([substituted]-2H-tetrazol-5-yl)-propenone (B-1806) 1-[nH-(q-((([substituted]aryl)aminosulfonyl)-z-halogeno)imidazol-w-yl]-3-hydroxy-3-([substituted]-1H-1,2,4-triazol-3-yl)-propenone (B-1807) 1-[(z-alkyl-q-((([substituted]aryl)amino))pyrrol-w-yl]-3-hydroxy-3-([substituted]-2H-tetrazol-5-yl)-propenone (B-1808) 3-hydroxy-1-(q-((([substituted]heteroaryl)sulfonylamino)furan-w-yl)-3-([substituted]-1H-1,2,4-triazol-3-yl)-propenone (B-1809) 1-[(z-halogeno-q-((([substituted]aryl)sulfonylamino))pyridin-w-yl]-3-hydroxy-3-([substituted]-2H-tetrazol-5-yl)-propenone (B-1810) 1-[nH-(z-alkyl-q-((([substituted]aryl)oxy))imidazol-w-yl]-3-hydroxy-3-([substituted]-1H-1,2,4-triazol-3-yl)-propenone (B-1811) 1-(q-((([substituted]heteroaryl)carbonyl)thiophen-w-yl)-3-hydroxy-3-([substituted]-1H-1,2,4-triazol-3-yl)-propenone (B-1812) 1-[nH-(z-halogeno-q-(1-hydroxy-([substituted]aryl)methyl))imidazol-w-yl]-3-hydroxy-3-([substituted]-1H-1,2,4-triazol-3-yl)-propenone (B-1813) 3-hydroxy-1-(nH-q-((([substituted]heteroaryl)sulfonyl)pyrazol-w-yl)-3-([substituted]-2H-tetrazol-5-yl)-propenone (B-1814) 3-hydroxy-1-(q-((([substituted]aryl)sulfinyl)pyrrol-w-yl)-3-([substituted]-2H-tetrazol-5-yl)-propenone (B-1815) 1-[nH-(z-halogeno-q-((([substituted]aryl)sulfonylamino))pyrazol-w-yl]-3-hydroxy-3-([substituted]-2H-tetrazol-5-yl)-propenone (B-1816) 2-hydroxy-4-oxo-4-(q-((([substituted]aryl)sulfonylamino)furan-w-yl)-2-butenoic acid (B-1817) 3-hydroxy-1-(q-((([substituted]heteroaryl)sulfonylamino)thiazol-w-yl)-3-([substituted]-1H-1,2,4-triazol-3-yl)-propenone (B-1818) 3-hydroxy-1-(q-((([substituted]aryl)oxy)pyridin-w-yl)-3-([substituted]-1H-1,2,4-triazol-3-yl)-propenone (B-1819) 1-[(q-((([substituted]aryl)alkenyl)-z-alkyl)isoxazol-w-yl]-3-hydroxy-3-([substituted]-1H-1,2,4-triazol-3-yl)-propenone (B-1820) 1-[nH-(z-alkyl-q-((([substituted]aryl)oxy))imidazol-w-yl]-3-hydroxy-3-([substituted]-2H-tetrazol-5-yl)-propenone (B-1821) 1-(nH-q-((([substituted]aryl)alkenyl)imidazol-w-yl)-3-hydroxy-3-([substituted]-1H-1,2,4-triazol-3-yl)-propenone (B-1822) 1-[(z-alkyl-q-(([substituted]heteroaryl)oxy))pyridin-w-yl]-3-hydroxy-3-([substituted]-1H-1,2,4-triazol-3-yl)-propenone (B-1823) 4-(q-(([substituted]aryl)carboxy)pyridin-w-yl)-2-hydroxy-4-oxo-2-butenoic acid (B-1824) 4-[(z-alkyl-q-(([substituted]aryl)alkyl))thiazol-w-yl]-2-hydroxy-4-oxo-2-butenoic acid (B-1825) 1-[(q-([substituted]aryl)-z-halogeno)pyridin-w-yl]-3-hydroxy-3-([substituted]-1H-1,2,4-triazol-3-yl)-propenone (B-1826) 2-hydroxy-4-oxo-4-(q-(([substituted]aryl)oxycarbonyl)thiazol-w-yl)-2-butenoic acid (B-1827) 4-[(q-(([substituted]heteroaryl)alkenyl)-z-halogeno)pyridin-w-yl]-2-hydroxy-4-oxo-2-butenoic acid (B-1828) 4-[nH-(z-alkyl-q-(1-hydroxy-([substituted]aryl)methyl))pyrazol-w-yl]-2-hydroxy-4-oxo-2-butenoic acid (B-1829) 1-[(z-alkyl-q-(([substituted]heteroaryl)carbonylamino))pyridin-w-yl]-3-hydroxy-3-([substituted]-2H-tetrazol-5-yl)-propenone (B-1830) 4-[(z-alkyl-q-([substituted]aryl))isoxazol-w-yl]-2-hydroxy-4-oxo-2-butenoic acid (B-1831) 1-[(z-alkyl-q-(([substituted]aryl)carbonyl))thiophen-w-yl]-3-hydroxy-3-([substituted]-1H-1,2,4-triazol-3-yl)-propenone (B-1832) 4-[(z-alkyl-q-(([substituted]heteroaryl)carbonylamino))thiophen-w-yl]-2-hydroxy-4-oxo-2-butenoic acid (B-1833) 1-((q-(([substituted]heteroaryl)aminocarbonyl)furan-w-yl)-3-hydroxy-3-([substituted]-1H-1,2,4-triazol-3-yl)-propenone (B-1834) 3-hydroxy-1-(nH-q-(([substituted]heteroaryl)thio)pyrazol-w-yl)-3-([substituted]-1H-1,2,4-triazol-3-yl)-propenone (B-1835) 1-[(q-(([substituted]heteroaryl)carbonyl)-z-halogeno)furan-w-yl]-3-hydroxy-3-([substituted]-2H-tetrazol-5-yl)-propenone (B-1836) 1-[(z-alkyl-q-(([substituted]heteroaryl)aminosulfonyl))pyridin-w-yl]-3-hydroxy-3-([substituted]-1H-1,2,4-triazol-3-yl)-propenone (B-1837) 1-(q-(([substituted]aryl)amino)furan-w-yl)-3-hydroxy-3-([substituted]-1H-1,2,4-triazol-3-yl)-propenone (B-1838) 4-[(z-alkyl-q-(([substituted]aryl)thio))isoxazol-w-yl]-2-hydroxy-4-oxo-2-butenoic acid (B-1839) 4-[(z-alkyl-q-(([substituted]heteroaryl)sulfinyl))thiophen-w-yl]-2-hydroxy-4-oxo-2-butenoic acid (B-1840) 1-[(q-(([substituted]heteroaryl)aminocarbonyl)-z-halogeno)pyridin-w-yl]-3-hydroxy-3-([substituted]-2H-tetrazol-5-yl)-propenone (B-1841) 2-hydroxy-4-oxo-4-(q-(([substituted]heteroaryl)sulfonylamino)isoxazol-w-yl)-2-butenoic acid (B-1842) 2-hydroxy-4-(q-(1-hydroxy-([substituted]aryl)methyl)thiazol-w-yl)-4-oxo-2-butenoic acid (B-1843) 1-[(z-halogeno-q-(1-hydroxy-([substituted]aryl)methyl))oxazol-w-yl]-3-hydroxy-3-([substituted]-1H-1,2,4-triazol-3-yl)-propenone (B-1844) 1-[(q-(([substituted]aryl)aminocarbonyl)-z-halogeno)oxazol-w-yl]-3-hydroxy-3-([substituted]-1H-1,2,4-triazol-3-yl)-propenone (B-1845) 1-[nH-(z-alkyl-q-(1-hydroxy-([substituted]aryl)methyl))pyrazol-w-yl]-3-hydroxy-3-([substituted]-1H-1,2,4-triazol-3-yl)-propenone (B-1846) 1-[(z-halogeno-q-(([substituted]aryl)thio)furan-w-yl]-3-hydroxy-3-([substituted]-2H-tetrazol-5-yl)-propenone (B-1847) 4-[nH-(z-alkyl-q-(([substituted]aryl)amino))imidazol-w-yl]-2-hydroxy-4-oxo-2-butenoic acid (B-1848) 1-[(z-alkyl-q-(([substituted]aryl)oxycarbonyl))pyridin-w-yl]-3-hydroxy-3-([substituted]-1H-1,2,4-triazol-3-yl)-propenone (B-1849) 4-[(z-alkyl-q-(([substituted]heteroaryl))oxazol-w-yl]-2-hydroxy-4-oxo-2-butenoic acid (B-1850) 1-[(q-(([substituted]aryl)alkyl)-z-halogeno)furan-w-yl]-3-hydroxy-3-([substituted]-1H-1,2,4-triazol-3-yl)-propenone (B-1851) 1-[(q-(([substituted]aryl)carbonylamino)-z-halogeno)furan-w-yl]-3-hydroxy-3-([substituted]-1H-1,2,4-triazol-3-yl)-propenone (B-1852) 1-[nH-(z-halogeno-q-(([substituted]heteroaryl)thio))imidazol-w-yl]-3-hydroxy-3-([substituted]-2H-tetrazol-5-yl)-propenone (B-1853) 1-[(z-alkyl-q-(([substituted]aryl)oxy))oxazol-w-yl]-3-hydroxy-3-([substituted]-2H-tetrazol-5-yl)-propenone (B-1854) 1-(q-(([substituted]heteroaryl)alkyl)isoxazol-w-yl)-3-hydroxy-3-([substituted]-2H-tetrazol-5-yl)-propenone (B-1855) 1-[(z-alkyl-q-([substituted]aryl))isoxazol-w-yl]-3-hydroxy-3-([substituted]-2H-tetrazol-5-yl)-propenone (B-1856) 4-[(q-(([substituted]heteroaryl)aminosulfonyl)-z-halogeno)pyrrol-w-yl]-2-hydroxy-4-oxo-2-butenoic acid (B-1857) 2-hydroxy-4-(q-(1-hydroxy-([substituted]aryl)methyl)furan-w-yl)-4-oxo-2-butenoic acid (B-1858) 2-hydroxy-4-oxo-4-(q-(([substituted]heteroaryl)oxycarbonyl)pyridin-w-yl)-2-butenoic acid (B-1859) 3-hydroxy-1-(q-(([substituted]aryl)sulfonyl)furan-w-yl)-3-([substituted]-2H-tetrazol-5-yl)-propenone (B-1860) 1-[(z-halogeno-q-(([substituted]aryl)thio))oxazol-w-yl]-3-hydroxy-3-([substituted]-2H-tetrazol-5-yl)-propenone (B-1861) 2-hydroxy-4-oxo-4-(q-(([substituted]heteroaryl)oxy)pyridin-w-yl)-2-butenoic acid (B-1862) 1-[nH-(q-(([substituted]aryl)carboxy)-z-halogeno)imidazol-w-yl]-3-hydroxy-3-([substituted]-1H-1,2,4-triazol-3-yl)-propenone (B-1863) 4-[(z-alkyl-q-(([substituted]aryl)aminocarbonyl))thiazol-w-yl]-2-hydroxy-4-oxo-2-butenoic acid (B-1864) 1-[(z-alkyl-q-(([substituted]aryl)aminocarbonyl))pyridin-w-yl]-3-hydroxy-3-([substituted]-2H-tetrazol-5-yl)-propenone (B-1865) 1-(q-(([substituted]aryl)aminocarbonyl)oxazol-w-yl)-3-hydroxy-3-([substituted]-2H-tetrazol-5-yl)-propenone (B-1866) 4-[nH-(z-alkyl-q-(([substituted]aryl)aminosulfonyl))pyrazol-w-yl]-2-hydroxy-4-oxo-2-butenoic acid (B-1867) 1-[(q-(([substituted]aryl)alkenyl)-z-alkyl)thiophen-w-yl]-3-hydroxy-3-([substituted]-2H-tetrazol-5-yl)-propenone (B-1868) 1-(q-([substituted]aryl)isoxazol-w-yl)-3-hydroxy-3-([substituted]-2H-tetrazol-5-yl)-propenone (B-1869) 1-[(z-alkyl-q-(([substituted]heteroaryl)sulfonyl))oxazol-w-yl]-3-hydroxy-3-([substituted]-1H-1,2,4-triazol-3-yl)-propenone (B-1870) 3-hydroxy-1-(q-(([substituted]heteroaryl)sulfinyl)pyridin-w-yl)-3-([substituted]-2H-tetrazol-5-yl)-propenone (B-1871) 1-(q-(([substituted]aryl)carbonyl)thiophen-w-yl)-3-hydroxy-3-([substituted]-2H-tetrazol-5-yl)-propenone (B-1872) 3-hydroxy-1-(q-(1-hydroxy-([substituted]heteroaryl)methyl)oxazol-w-yl)-3-([substituted]-2H-tetrazol-5-yl)-propenone (B-1873) 1-[(q-(([substituted]heteroaryl)aminosulfonyl)-z-halogeno)isoxazol-w-yl]-3-hydroxy-3-([substituted]-1H-1,2,4-triazol-3-yl)-propenone (B-1874) 4-[(q-(([substituted]heteroaryl)alkenyl)-z-halogeno)pyrrol-w-yl]-2-hydroxy-4-oxo-2-butenoic acid
(B-1875) 1-[(q-(([substituted]aryl)alkenyl)-z-alkyl)isoxazol-w-yl]-3-hydroxy-3-([substituted]-2H-tetrazol-5-yl)-propenone
(B-1876) 1-(nH-q-(([substituted]heteroaryl)amino)imidazol-w-yl)-3-hydroxy-3-([substituted]-2H-tetrazol-5-yl)-propenone
(B-1877) 1-[(z-alkyl-q-(([substituted]aryl)aminocarbonyl))pyridin-w-yl]-3-hydroxy-3-([substituted]-1H-1,2,4-triazol-3-yl)-propenone
(B-1878) 1-[(q-(([substituted]heteroaryl)carbonylamino)-z-halogeno)furan-w-yl]-3-hydroxy-3-([substituted]-2H-tetrazol-5-yl)-propenone
(B-1879) 4-(nH-q-(([substituted]heteroaryl)carbonylamino)imidazol-w-yl)-2-hydroxy-4-oxo-2-butenoic acid
(B-1880) 1-[(z-alkyl-q-(([substituted]heteroaryl)carbonyl))pyridin-w-yl]-3-hydroxy-3-([substituted]-2H-tetrazol-5-yl)-propenone
(B-1881) 1-[(q-(([substituted]aryl)amino)-z-halogeno)furan-w-yl]-3-hydroxy-3-([substituted]-1H-1,2,4-triazol-3-yl)-propenone
(B-1882) 3-hydroxy-1-(q-(([substituted]heteroaryl)sulfinyl)oxazol-w-yl)-3-([substituted]-1H-1,2,4-triazol-3-yl)-propenone
(B-1883) 2-hydroxy-4-oxo-4-(q-(([substituted]heteroaryl)thio)furan-w-yl)-2-butenoic acid
(B-1884) 1-[(z-halogeno-q-(1-hydroxy-([substituted]heteroaryl)methyl))isoxazol-w-yl]-3-hydroxy-3-([substituted]-2H-tetrazol-5-yl)-propenone
(B-1885) 1-[(z-alkyl-q-(([substituted]heteroaryl)alkyl))oxazol-w-yl]-3-hydroxy-3-([substituted]-2H-tetrazol-5-yl)-propenone
(B-1886) 1-[(z-halogeno-q-(([substituted]heteroaryl)oxy))thiophen-w-yl]-3-hydroxy-3-([substituted]-1H-1,2,4-triazol-3-yl)-propenone
(B-1887) 4-[(z-alkyl-q-(([substituted]aryl)oxy))thiophen-w-yl]-2-hydroxy-4-oxo-2-butenoic acid
(B-1888) 4-(q-(([substituted]heteroaryl)aminosulfonyl)pyrrol-w-yl)-2-hydroxy-4-oxo-2-butenoic acid
(B-1889) 4-[nH-(q-(([substituted]heteroaryl)alkyl)-z-halogeno)imidazol-w-yl]-2-hydroxy-4-oxo-2-butenoic acid
(B-1890) 4-(nH-q-(([substituted]aryl)carbonyl)imidazol-w-yl)-2-hydroxy-4-oxo-2-butenoic acid
(B-1891) 4-[(z-alkyl-q-(([substituted]aryl)sulfinyl))thiophen-w-yl]-2-hydroxy-4-oxo-2-butenoic acid
(B-1892) 1-[(q-(([substituted]aryl)alkenyl)-z-halogeno)oxazol-w-yl]-3-hydroxy-3-([substituted]-1H-1,2,4-triazol-3-yl)-propenone
(B-1893) 4-[nH-(z-halogeno-q-(1-hydroxy-([substituted]aryl)methyl))pyrazol-w-yl]-2-hydroxy-4-oxo-2-butenoic acid
(B-1894) 3-hydroxy-1-(q-(1-hydroxy-([substituted]heteroaryl)methyl)pyrrol-w-yl)-3-([substituted]-2H-tetrazol-5-yl)-propenone
(B-1895) 1-[(z-halogeno-q-(([substituted]aryl)sulfonyl))oxazol-w-yl]-3-hydroxy-3-([substituted]-2H-tetrazol-5-yl)-propenone
(B-1896) 1-(q-(([substituted]heteroaryl)alkenyl)oxazol-w-yl)-3-hydroxy-3-([substituted]-2H-tetrazol-5-yl)-propenone
(B-1897) 4-[(z-alkyl-q-(([substituted]heteroaryl)thio))thiazol-w-yl]-2-hydroxy-4-oxo-2-butenoic acid
(B-1898) 1-[(z-alkyl-q-(([substituted]aryl)oxycarbonyl))pyrrol-w-yl]-3-hydroxy-3-([substituted]-2H-tetrazol-5-yl)-propenone
(B-1899) 1-[(z-alkyl-q-(([substituted]heteroaryl)oxy))furan-w-yl]-3-hydroxy-3-([substituted]-2H-tetrazol-5-yl)-propenone
(B-1900) 4-[(z-alkyl-q-(([substituted]aryl)amino))isoxazol-w-yl]-2-hydroxy-4-oxo-2-butenoic acid
(B-1901) 4-[(q-(([substituted]aryl)amino)-z-halogeno)pyrrol-w-yl]-2-hydroxy-4-oxo-2-butenoic acid
(B-1902) 4-[(z-alkyl-q-(([substituted]heteroaryl)oxycarbonyl))isoxazol-w-yl]-2-hydroxy-4-oxo-2-butenoic acid
(B-1903) 1-[(z-halogeno-q-(([substituted]heteroaryl)oxy))furan-w-yl]-3-hydroxy-3-([substituted]-2H-tetrazol-5-yl)-propenone
(B-1904) 1-[nH-(z-alkyl-q-(([substituted]aryl)thio))imidazol-w-yl]-3-hydroxy-3-([substituted]-2H-tetrazol-5-yl)-propenone
(B-1905) 1-[(z-alkyl-q-(([substituted]aryl)carboxy))oxazol-w-yl]-3-hydroxy-3-([substituted]-2H-tetrazol-5-yl)-propenone
(B-1906) 1-[(q-(([substituted]heteroaryl)carboxy)-z-halogeno)furan-w-yl]-3-hydroxy-3-([substituted]-2H-tetrazol-5-yl)-propenone
(B-1907) 1-[(z-alkyl-q-(([substituted]aryl)carboxy))pyrrol-w-yl]-3-hydroxy-3-([substituted]-2H-tetrazol-5-yl)-propenone
(B-1908) 1-[(z-alkyl-q-(([substituted]heteroaryl)amino))thiazol-w-yl]-3-hydroxy-3-([substituted]-1H-1,2,4-triazol-3-yl)-propenone
(B-1909) 4-[(z-alkyl-q-(([substituted]aryl)amino))thiophen-w-yl]-2-hydroxy-4-oxo-2-butenoic acid
(B-1910) 1-(q-(([substituted]heteroaryl)aminosulfonyl)pyridin-w-yl)-3-hydroxy-3-([substituted]-2H-tetrazol-5-yl)-propenone
(B-1911) 1-[(z-alkyl-q-(([substituted]heteroaryl)carbonylamino))thiazol-w-yl]-3-hydroxy-3-([substituted]-1H-1,2,4-triazol-3-yl)-propenone
(B-1912) 4-[nH-(z-alkyl-q-([substituted]heteroaryl))imidazol-w-yl]-2-hydroxy-4-oxo-2-butenoic acid
(B-1913) 4-[(z-alkyl-q-([substituted]aryl))thiazol-w-yl]-2-hydroxy-4-oxo-2-butenoic acid
(B-1914) 1-[(z-alkyl-q-(([substituted]aryl)thio))pyridin-w-yl]-3-hydroxy-3-([substituted]-1H-1,2,4-triazol-3-yl)-propenone
(B-1915) 1-[(q-(([substituted]heteroaryl)amino)-z-halogeno)isoxazol-w-yl]-3-hydroxy-3-([substituted]-1H-1,2,4-triazol-3-yl)-propenone
(B-1916) 1-(q-(([substituted]heteroaryl)aminocarbonyl)thiazol-w-yl)-3-hydroxy-3-([substituted]-2H-tetrazol-5-yl)-propenone
(B-1917) 3-hydroxy-1-(nH-q-(1-hydroxy-([substituted]heteroaryl)methyl)pyrazol-w-yl)-3-([substituted]-1H-1,2,4-triazol-3-yl)-propenone
(B-1918) 4-(q-(([substituted]heteroaryl)carbonyl)thiophen-w-yl)-2-hydroxy-4-oxo-2-butenoic acid
(B-1919) 4-[(q-(([substituted]heteroaryl)alkenyl)-z-alkyl)pyridin-w-yl]-2-hydroxy-4-oxo-2-butenoic acid
(B-1920) 1-(q-(([substituted]aryl)carboxy)pyridin-w-yl)-3-hydroxy-3-([substituted]-2H-tetrazol-5-yl)-propenone
(B-1921) 2-hydroxy-4-oxo-4-(nH-q-(([substituted]heteroaryl)oxycarbonyl)pyrazol-w-yl)-2-butenoic acid
(B-1922) 1-[nH-(z-halogeno-q-(([substituted]heteroaryl)sulfonylamino))imidazol-w-yl]-3-hydroxy-3-([substituted]-1H-1,2,4-triazol-3-yl)-propenone
(B-1923) 1-(nH-q-(([substituted]aryl)carbonyl)pyrazol-w-yl)-3-hydroxy-3-([substituted]-1H-1,2,4-triazol-3-yl)-propenone
(B-1924) 1-(q-(([substituted]heteroaryl)alkenyl)isoxazol-w-yl)-3-hydroxy-3-([substituted]-1H-1,2,4-triazol-3-yl)-propenone (B-1925) 4-[(z-alkyl-q-(([substituted]heteroaryl)oxycarbonyl))furan-w-yl]-2-hydroxy-4-oxo-2-butenoic acid
(B-1926) 1-[(z-alkyl-q-(1-hydroxy-([substituted]aryl)methyl))pyrrol-w-yl]-3-hydroxy-3-([substituted]-1H-1,2,4-triazol-3-yl)-propenone
(B-1927) 1-[(z-alkyl-q-(([substituted]heteroaryl)aminocarbonyl))oxazol-w-yl]-3-hydroxy-3-([substituted]-2H-tetrazol-5-yl)-propenone
(B-1928) 4-[(z-alkyl-q-(([substituted]aryl)amino))pyrrol-w-yl]-2-hydroxy-4-oxo-2-butenoic acid
(B-1929) 1-[nH-(z-alkyl-q-(([substituted]heteroaryl)amino))imidazol-w-yl]-3-hydroxy-3-([substituted]-1H-1,2,4-triazol-3-yl)-propenone
(B-1930) 1-(q-(([substituted]aryl)carboxy)thiazol-w-yl)-3-hydroxy-3-([substituted]-2H-tetrazol-5-yl)-propenone
(B-1931) 4-[(z-halogeno-q-(1-hydroxy-([substituted]aryl)methyl))thiazol-w-yl]-2-hydroxy-4-oxo-2-butenoic acid
(B-1932) 3-hydroxy-1-(q-(([substituted]aryl)oxycarbonyl)pyrrol-w-yl)-3-([substituted]-1H-1,2,4-triazol-3-yl)-propenone
(B-1933) 1-(q-(([substituted]heteroaryl)aminosulfonyl)thiazol-w-yl)-3-hydroxy-3-([substituted]-1H-1,2,4-triazol-3-yl)-propenone
(B-1934) 4-[(q-(([substituted]aryl)alkenyl)-z-halogeno)furan-w-yl]-2-hydroxy-4-oxo-2-butenoic acid
(B-1935) 3-hydroxy-1-(nH-q-(([substituted]heteroaryl)oxy)imidazol-w-yl)-3-([substituted]-1H-1,2,4-triazol-3-yl)-propenone
(B-1936) 3-hydroxy-1-(q-(1-hydroxy-([substituted]aryl)methyl)thiophen-w-yl)-3-([substituted]-1H-1,2,4-triazol-3-yl)-propenone
(B-1937) 4-[(z-alkyl-q-(([substituted]aryl)carboxy))oxazol-w-yl]-2-hydroxy-4-oxo-2-butenoic acid
(B-1938) 1-[nH-(q-(([substituted]heteroaryl)aminocarbonyl)-z-halogeno)imidazol-w-yl]-3-hydroxy-3-([substituted]-2H-tetrazol-5-yl)-propenone
(B-1939) 1-(nH-q-([substituted]heteroaryl)imidazol-w-yl)-3-hydroxy-3-([substituted]-2H-tetrazol-5-yl)-propenone
(B-1940) 4-[(q-(([substituted]heteroaryl)aminocarbonyl)-z-halogeno)isoxazol-w-yl]-2-hydroxy-4-oxo-2-butenoic acid
(B-1941) 4-[(z-halogeno-q-(([substituted]aryl)thio))thiazol-w-yl]-2-hydroxy-4-oxo-2-butenoic acid
(B-1942) 1-(q-(([substituted]aryl)carboxy)oxazol-w-yl)-3-hydroxy-3-([substituted]-1H-1,2,4-triazol-3-yl)-propenone
(B-1943) 3-hydroxy-1-(q-(([substituted]heteroaryl)oxycarbonyl)thiazol-w-yl)-3-([substituted]-1H-1,2,4-triazol-3-yl)-propenone
(B-1944) 1-[(z-alkyl-q-(([substituted]aryl)oxycarbonyl))isoxazol-w-yl]-3-hydroxy-3-([substituted]-1H-1,2,4-triazol-3-yl)-propenone
(B-1945) 1-(nH-q-(([substituted]heteroaryl)aminosulfonyl)pyrazol-w-yl)-3-hydroxy-3-([substituted]-2H-tetrazol-5-yl)-propenone
(B-1946) 1-[nH-(z-alkyl-q-([substituted]heteroaryl))pyrazol-w-yl]-3-hydroxy-3-([substituted]-2H-tetrazol-5-yl)-propenone
(B-1947) 1-(q-(([substituted]heteroaryl)amino)thiophen-w-yl)-3-hydroxy-3-([substituted]-1H-1,2,4-triazol-3-yl)-propenone
(B-1948) 4-[(z-alkyl-q-(1-hydroxy-([substituted]heteroaryl)methyl))isoxazol-w-yl]-2-hydroxy-4-oxo-2-butenoic acid
(B-1949) 1-[(z-alkyl-q-(([substituted]heteroaryl)carbonylamino))thiophen-w-yl]-3-hydroxy-3-([substituted]-1H-1,2,4-triazol-3-yl)-propenone
(B-1950) 1-(nH-q-(([substituted]aryl)amino)pyrazol-w-yl)-3-hydroxy-3-([substituted]-1H-1,2,4-triazol-3-yl)-propenone
(B-1951) 4-(q-(([substituted]heteroaryl)aminosulfonyl)isoxazol-w-yl)-2-hydroxy-4-oxo-2-butenoic acid
(B-1952) 1-[nH-(z-alkyl-q-(([substituted]heteroaryl)thio))pyrazol-w-yl]-3-hydroxy-3-([substituted]-1H-1,2,4-triazol-3-yl)-propenone
(B-1953) 1-[(q-(([substituted]aryl)carboxy)-z-halogeno)oxazol-w-yl]-3-hydroxy-3-([substituted]-2H-tetrazol-5-yl)-propenone
(B-1954) 1-[nH-(q-(([substituted]heteroaryl)aminosulfonyl)-z-halogeno)imidazol-w-yl]-3-hydroxy-3-([substituted]-1H-1,2,4-triazol-3-yl)-propenone
(B-1955) 4-[(z-halogeno-q-(([substituted]heteroaryl)oxy))thiophen-w-yl]-2-hydroxy-4-oxo-2-butenoic acid
(B-1956) 1-[nH-(z-halogeno-q-(([substituted]aryl)sulfonylamino))imidazol-w-yl]-3-hydroxy-3-([substituted]-1H-1,2,4-triazol-3-yl)-propenone
(B-1957) 1-[(z-alkyl-q-(([substituted]heteroaryl)carbonyl))pyrrol-w-yl]-3-hydroxy-3-([substituted]-1H-1,2,4-triazol-3-yl)-propenone
(B-1958) 3-hydroxy-1-(q-(([substituted]aryl)sulfonyl)thiophen-w-yl)-3-([substituted]-2H-tetrazol-5-yl)-propenone
(B-1959) 1-[(z-halogeno-q-([substituted]heteroaryl))pyrrol-w-yl]-3-hydroxy-3-([substituted]-1H-1,2,4-triazol-3-yl)-propenone
(B-1960) 4-[nH-(q-(([substituted]aryl)alkenyl)-z-alkyl)imidazol-w-yl]-2-hydroxy-4-oxo-2-butenoic acid
(B-1961) 1-[(q-(([substituted]aryl)alkenyl)-z-halogeno)thiazol-w-yl]-3-hydroxy-3-([substituted]-2H-tetrazol-5-yl)-propenone
(B-1962) 1-[(z-halogeno-q-(([substituted]heteroaryl)oxycarbonyl))thiazol-w-yl]-3-hydroxy-3-([substituted]-2H-tetrazol-5-yl)-propenone
(B-1963) 3-hydroxy-1-(q-(([substituted]heteroaryl)sulfonylamino)pyridin-w-yl)-3-([substituted]-1H-1,2,4-triazol-3-yl)-propenone
(B-1964) 1-[nH-(z-alkyl-q-(([substituted]heteroaryl)carbonyl))pyrazol-w-yl]-3-hydroxy-3-([substituted]-1H-1,2,4-triazol-3-yl)-propenone
(B-1965) 3-hydroxy-1-nH-q-(([substituted]heteroaryl)sulfonylamino)pyrazol-w-yl)-3-([substituted]-2H-tetrazol-5-yl)-propenone
(B-1966) 1-[(z-alkyl-q-(([substituted]heteroaryl)sulfinyl))isoxazol-w-yl]-3-hydroxy-3-([substituted]-1H-1,2,4-triazol-3-yl)-propenone
(B-1967) 1-[(z-alkyl-q-(([substituted]heteroaryl)aminosulfonyl))pyrrol-w-yl]-3-hydroxy-3-([substituted]-1H-1,2,4-triazol-3-yl)-propenone
(B-1968) 1-[(z-halogeno-q-(([substituted]heteroaryl)sulfinyl))pyridin-w-yl]-3-hydroxy-3-([substituted]-1H-1,2,4-triazol-3-yl)-propenone
(B-1969) 1-[(z-alkyl-q-(([substituted]aryl)carboxy))isoxazol-w-yl]-3-hydroxy-3-([substituted]-2H-tetrazol-5-yl)-propenone
(B-1970) 1-[(q-(([substituted]aryl)carboxy)-z-halogeno)furan-w-yl]-3-hydroxy-3-([substituted]-2H-tetrazol-5-yl)-propenone
(B-1971) 1-[nH-(z-alkyl-q-(([substituted]heteroaryl)carbonyl))imidazol-w-yl]-3-hydroxy-3-([substituted]-2H-tetrazol-5-yl)-propenone
(B-1972) 1-(q-(([substituted]heteroaryl)amino)isoxazol-w-yl)-3-hydroxy-3-([substituted]-1H-1,2,4-triazol-3-yl)-propenone
(B-1973) 1-[(z-halogeno-q-(([substituted]aryl)oxycarbonyl))pyridin-w-yl]-3-hydroxy-3-([substituted]-2H-tetrazol-5-yl)-propenone (B-1974) 2-hydroxy-4-oxo-4-(q-(([substituted]heteroaryl)oxycarbonyl)oxazol-w-yl)-2-butenoic acid
(B-1975) 1-[(q-(([substituted]heteroaryl)alkyl)-z-halogeno)oxazol-w-yl]-3-hydroxy-3-([substituted]-1H-1,2,4-triazol-3-yl)-propenone
(B-1976) 4-[(z-halogeno-q-(([substituted]aryl)sulfonylamino))furan-w-yl]-2-hydroxy-4-oxo-2-butenoic acid
(B-1977) 1-[(z-halogeno-q-(([substituted]heteroaryl)thio))pyrrol-w-yl]-3-hydroxy-3-([substituted]-1H-1,2,4-triazol-3-yl)-propenone
(B-1978) 1-[(z-alkyl-q-(([substituted]aryl)carboxy))thiazol-w-yl]-3-hydroxy-3-([substituted]-1H-1,2,4-triazol-3-yl)-propenone
(B-1979) 1-[nH-(q-(([substituted]heteroaryl)carboxy)-z-halogeno)imidazol-w-yl]-3-hydroxy-3-([substituted]-2H-tetrazol-5-yl)-propenone
(B-1980) 4-[nH-(z-halogeno-q-(([substituted]heteroaryl)sulfonyl))pyrazol-w-yl]-2-hydroxy-4-oxo-2-butenoic acid
(B-1981) 1-[nH-(z-halogeno-q-(([substituted]aryl)oxy))pyrazol-w-yl]-3-hydroxy-3-([substituted]-1H-1,2,4-triazol-3-yl)-propenone
(B-1982) 1-[(z-alkyl-q-(([substituted]heteroaryl)carbonylamino))pyrrol-w-yl]-3-hydroxy-3-([substituted]-2H-tetrazol-5-yl)-propenone
(B-1983) 1-(q-(([substituted]heteroaryl)carbonyl)oxazol-w-yl)-3-hydroxy-3-([substituted]-2H-tetrazol-5-yl)-propenone
(B-1984) 1-[(q-(([substituted]aryl)carbonyl)-z-halogeno)pyrrol-w-yl]-3-hydroxy-3-([substituted]-1H-1,2,4-triazol-3-yl)-propenone
(B-1985) 4-[(z-halogeno-q-(([substituted]aryl)sulfinyl))pyrrol-w-yl]-2-hydroxy-4-oxo-2-butenoic acid
(B-1986) 1-[(z-alkyl-q-(([substituted]aryl)sulfonyl))furan-w-yl]-3-hydroxy-3-([substituted]-1H-1,2,4-triazol-3-yl)-propenone
(B-1987) 4-[nH-(z-halogeno-q-(1-hydroxy-([substituted]aryl)methyl))imidazol-w-yl]-2-hydroxy-4-oxo-2-butenoic acid
(B-1988) 4-[(z-halogeno-q-(([substituted]aryl)sulfinyl))isoxazol-w-yl]-2-hydroxy-4-oxo-2-butenoic acid
(B-1989) 1-[(z-alkyl-q-([substituted]heteroaryl))pyridin-w-yl]-3-hydroxy-3-([substituted]-1H-1,2,4-triazol-3-yl)-propenone
(B-1990) 1-[(z-alkyl-q-(([substituted]heteroaryl)amino))thiazol-w-yl]-3-hydroxy-3-([substituted]-2H-tetrazol-5-yl)-propenone
(B-1991) 3-hydroxy-3-([substituted]-2H-tetrazol-5-yl)-1-(q-(([substituted]heteroaryl)thio)furan-w-yl)-propenone
(B-1992) 4-[nH-(z-halogeno-q-(([substituted]heteroaryl)oxycarbonyl))pyrazol-w-yl]-2-hydroxy-4-oxo-2-butenoic acid
(B-1993) 3-hydroxy-1-(q-(([substituted]aryl)oxycarbonyl)oxazol-w-yl)-3-([substituted]-1H-1,2,4-triazol-3-yl)-propenone
(B-1994) 1-[(z-halogeno-q-(1-hydroxy-([substituted]heteroaryl)methyl))thiazol-w-yl]-3-hydroxy-3-([substituted]-1H-1,2,4-triazol-3-yl)-propenone
(B-1995) 4-[nH-(z-alkyl-q-(([substituted]aryl)amino))pyrazol-w-yl]-2-hydroxy-4-oxo-2-butenoic acid
(B-1996) 1-[(z-alkyl-q-(([substituted]aryl)carboxy))isoxazol-w-yl]-3-hydroxy-3-([substituted]-1H-1,2,4-triazol-3-yl)-propenone
(B-1997) 4-[(z-halogeno-q-(([substituted]heteroaryl)sulfonyl))pyridin-w-yl]-2-hydroxy-4-oxo-2-butenoic acid
(B-1998) 4-[(q-(([substituted]heteroaryl)carbonylamino)-z-halogeno)isoxazol-w-yl]-2-hydroxy-4-oxo-2-butenoic acid
(B-1999) 1-(q-(([substituted]heteroaryl)aminocarbonyl)furan-w-yl)-3-hydroxy-3-([substituted]-2H-tetrazol-5-yl)-propenone
(B-2000) 1-[(q-(([substituted]heteroaryl)carboxy)-z-halogeno)furan-w-yl]-3-hydroxy-3-([substituted]-1H-1,2,4-triazol-3-yl)-propenone
(B-2001) 1-[(z-halogeno-q-(([substituted]aryl)oxycarbonyl))furan-w-yl]-3-hydroxy-3-([substituted]-2H-tetrazol-5-yl)-propenone
(B-2002) 1-[(q-(([substituted]heteroaryl)carboxy)-z-alkyl)isoxazol-w-yl]-3-hydroxy-3-([substituted]-1H-1,2,4-triazol-3-yl)-propenone
(B-2003) 1-(nH-q-(([substituted]aryl)aminosulfonyl)imidazol-w-yl)-3-hydroxy-3-([substituted]-1H-1,2,4-triazol-3-yl)-propenone
(B-2004) 1-(q-(([substituted]aryl)amino)thiazol-w-yl)-3-hydroxy-3-([substituted]-1H-1,2,4-triazol-3-yl)-propenone
(B-2005) 1-[(z-halogeno-q-([substituted]heteroaryl))thiophen-w-yl]-3-hydroxy-3-([substituted]-2H-tetrazol-5-yl)-propenone
(B-2006) 1-[(z-halogeno-q-(([substituted]aryl)oxycarbonyl))oxazol-w-yl]-3-hydroxy-3-([substituted]-2H-tetrazol-5-yl)-propenone
(B-2007) 1-[(z-alkyl-q-(([substituted]aryl)oxy))thiophen-w-yl]-3-hydroxy-3-([substituted]-1H-1,2,4-triazol-3-yl)-propenone
(B-2008) 1-[(q-(([substituted]heteroaryl)aminosulfonyl)-z-halogeno)pyridin-w-yl]-3-hydroxy-3-([substituted]-1H-1,2,4-triazol-3-yl)-propenone
(B-2009) 3-hydroxy-1-(nH-q-(1-hydroxy-([substituted]aryl)methyl)imidazol-w-yl)-3-([substituted]-1H-1,2,4-triazol-3-yl)-propenone
(B-2010) 2-hydroxy-4-(q-(1-hydroxy-([substituted]heteroaryl)methyl)furan-w-yl)-4-oxo-2-butenoic acid
(B-2011) 3-hydroxy-1-(q-(([substituted]heteroaryl)sulfonylamino)thiazol-w-yl)-3-([substituted]-2H-tetrazol-5-yl)-propenone
(B-2012) 1-[(z-alkyl-q-(([substituted]aryl)oxycarbonyl))oxazol-w-yl]-3-hydroxy-3-([substituted]-1H-1,2,4-triazol-3-yl)-propenone
(B-2013) 1-[(q-((([substituted]aryl)alkenyl)-z-alkyl)thiophen-w-yl]-3-hydroxy-3-([substituted]-1H-1,2,4-triazol-3-yl)-propenone
(B-2014) 1-[(q-((([substituted]aryl)aminosulfonyl)-z-halogeno)thiophen-w-yl]-3-hydroxy-3-([substituted]-1H-1,2,4-triazol-3-yl)-propenone
(B-2015) 2-hydroxy-4-oxo-4-(q-(([substituted]aryl)oxycarbonyl)furan-w-yl)-2-butenoic acid
(B-2016) 3-hydroxy-1-(q-(([substituted]aryl)sulfinyl)pyrrol-w-yl)-3-([substituted]-1H-1,2,4-triazol-3-yl)-propenone
(B-2017) 1-(q-(([substituted]heteroaryl)carbonyl)oxazol-w-yl)-3-hydroxy-3-([substituted]-1H-1,2,4-triazol-3-yl)-propenone
(B-2018) 4-[(q-(([substituted]aryl)carbonyl)-z-halogeno)isoxazol-w-yl]-2-hydroxy-4-oxo-2-butenoic acid
(B-2019) 3-hydroxy-1-(q-(([substituted]heteroaryl)oxycarbonyl)thiophen-w-yl)-3-([substituted]-2H-tetrazol-5-yl)-propenone
(B-2020) 1-[(z-alkyl-q-(([substituted]heteroaryl)thio))furan-w-yl]-3-hydroxy-3-([substituted]-1H-1,2,4-triazol-3-yl)-propenone
(B-2021) 4-[(z-alkyl-q-([substituted]aryl))thiophen-w-yl]-2-hydroxy-4-oxo-2-butenoic acid
(B-2022) 1-(q-(([substituted]aryl)carboxy)thiazol-w-yl)-3-hydroxy-3-([substituted]-1H-1,2,4-triazol-3-yl)-propenone (B-2023) 1-[(z-alkyl-q-(([substituted]aryl)aminocarbonyl))isoxazol-w-yl]-3-hydroxy-3-([substituted]-1H-1,2,4-triazol-3-yl)-propenone (B-2024) 4-[nH-(z-alkyl-q-(([substituted]heteroaryl)sulfonylamino))imidazol-w-yl]-2-hydroxy-4-oxo-2-butenoic acid (B-2025) 1-[(q-(([substituted]heteroaryl)carbonylamino)-z-halogeno)pyridin-w-yl]-3-hydroxy-3-([substituted]-1H-1,2,4-triazol-3-yl)-propenone (B-2026) 2-hydroxy-4-oxo-4-(nH-q-(([substituted]heteroaryl)sulfinyl)pyrazol-w-yl)-2-butenoic acid (B-2027) 4-[(z-alkyl-q-(([substituted]heteroaryl)aminocarbonyl))pyridin-w-yl]-2-hydroxy-4-oxo-2-butenoic acid (B-2028) 1-(q-(([substituted]heteroaryl)carbonylamino)oxazol-w-yl)-3-hydroxy-3-([substituted]-1H-1,2,4-triazol-3-yl)-propenone (B-2029) 4-[(q-(([substituted]aryl)carboxy)-z-halogeno)furan-w-yl]-2-hydroxy-4-oxo-2-butenoic acid (B-2030) 4-[(z-alkyl-q-(([substituted]heteroaryl)aminosulfonyl))thiophen-w-yl]-2-hydroxy-4-oxo-2-butenoic acid (B-2031) 1-(nH-q-(([substituted]heteroaryl)aminocarbonyl)imidazol-w-yl)-3-hydroxy-3-([substituted]-1H-1,2,4-triazol-3-yl)-propenone (B-2032) 4-[nH-(z-alkyl-q-(([substituted]heteroaryl)aminocarbonyl))pyrazol-w-yl]-2-hydroxy-4-oxo-2-butenoic acid (B-2033) 1-[(z-alkyl-q-(1-hydroxy-([substituted]heteroaryl)methyl))thiazol-w-yl]-3-hydroxy-3-([substituted]-2H-tetrazol-5-yl)-propenone (B-2034) 1-(q-(([substituted]heteroaryl)amino)pyridin-w-yl)-3-hydroxy-3-([substituted]-2H-tetrazol-5-yl)-propenone (B-2035) 1-[nH-(z-alkyl-q-(([substituted]aryl)oxycarbonyl))pyrazol-w-yl]-3-hydroxy-3-([substituted]-1H-1,2,4-triazol-3-yl)-propenone (B-2036) 1-[(z-halogeno-q-(([substituted]aryl)oxycarbonyl))thiophen-w-yl]-3-hydroxy-3-([substituted]-2H-tetrazol-5-yl)-propenone (B-2037) 4-[(z-alkyl-q-(([substituted]heteroaryl)sulfonylamino))pyridin-w-yl]-2-hydroxy-4-oxo-2-butenoic acid (B-2038) 1-[(q-(([substituted]aryl)alkenyl)-z-alkyl)pyrrol-w-yl]-3-hydroxy-3-([substituted]-1H-1,2,4-triazol-3-yl)-propenone (B-2039) 1-(q-(([substituted]aryl)carboxy)pyrrol-w-yl)-3-hydroxy-3-([substituted]-1H-1,2,4-triazol-3-yl)-propenone (B-2040) 3-hydroxy-1-(q-(([substituted]heteroaryl)carboxy)isoxazol-w-yl)-3-([substituted]-2H-tetrazol-5-yl)-propenone (B-2041) 4-[(z-alkyl-q-(([substituted]heteroaryl)sulfinyl))thiazol-w-yl]-2-hydroxy-4-oxo-2-butenoic acid (B-2042) 1-[(z-alkyl-q-(([substituted]heteroaryl)sulfonylamino))isoxazol-w-yl]-3-hydroxy-3-([substituted]-2H-tetrazol-5-yl)-propenone (B-2043) 1-[(q-(([substituted]aryl)amino)-z-halogeno)oxazol-w-yl]-3-hydroxy-3-([substituted]-1H-1,2,4-triazol-3-yl)-propenone (B-2044) 2-hydroxy-4-(nH-q-(1-hydroxy-([substituted]heteroaryl)methyl)pyrazol-w-yl)-4-oxo-2-butenoic acid (B-2045) 4-[(q-(([substituted]heteroaryl)alkenyl)-z-halogeno)thiazol-w-yl]-2-hydroxy-4-oxo-2-butenoic acid (B-2046) 4-[(z-halogeno-q-(([substituted]aryl)oxycarbonyl))isoxazol-w-yl]-2-hydroxy-4-oxo-2-butenoic acid (B-2047) 3-hydroxy-1-(nH-q-(1-hydroxy-([substituted]aryl)methyl)imidazol-w-yl)-3-([substituted]-2H-tetrazol-5-yl)-propenone (B-2048) 4-[nH-(q-(([substituted]aryl)aminocarbonyl)-z-halogeno)imidazol-w-yl]-2-hydroxy-4-oxo-2-butenoic acid (B-2049) 1-[(q-(([substituted]aryl)carboxy)-z-halogeno)isoxazol-w-yl]-3-hydroxy-3-([substituted]-2H-tetrazol-5-yl)-propenone (B-2050) 3-hydroxy-1-(q-(([substituted]aryl)sulfonylamino)thiophen-w-yl)-3-([substituted]-1H-1,2,4-triazol-3-yl)-propenone (B-2051) 3-hydroxy-1-(q-(([substituted]aryl)sulfonyl)pyridin-w-yl)-3-([substituted]-2H-tetrazol-5-yl)-propenone (B-2052) 1-[(z-alkyl-q-(([substituted]aryl)thio))pyrrol-w-yl]-3-hydroxy-3-([substituted]-2H-tetrazol-5-yl)-propenone (B-2053) 4-[nH-(z-halogeno-q-(([substituted]aryl)oxy))pyrazol-w-yl]-2-hydroxy-4-oxo-2-butenoic acid (B-2054) 4-[(z-alkyl-q-(([substituted]heteroaryl)oxy))thiophen-w-yl]-2-hydroxy-4-oxo-2-butenoic acid (B-2055) 1-(nH-q-(([substituted]heteroaryl)alkenyl)imidazol-w-yl)-3-hydroxy-3-([substituted]-2H-tetrazol-5-yl)-propenone (B-2056) 4-(nH-q-(([substituted]heteroaryl)aminocarbonyl)imidazol-w-yl)-2-hydroxy-4-oxo-2-butenoic acid (B-2057) 4-[nH-(q-(([substituted]aryl)carbonyl)-z-halogeno)pyrazol-w-yl]-2-hydroxy-4-oxo-2-butenoic acid (B-2058) 1-[(q-(([substituted]heteroaryl)alkenyl)-z-alkyl)isoxazol-w-yl]-3-hydroxy-3-([substituted]-2H-tetrazol-5-yl)-propenone (B-2059) 4-[(q-(([substituted]heteroaryl)aminosulfonyl)-z-halogeno)thiophen-w-yl]-2-hydroxy-4-oxo-2-butenoic acid (B-2060) 4-[(q-(([substituted]aryl)alkenyl)-z-alkyl)pyridin-w-yl]-2-hydroxy-4-oxo-2-butenoic acid (B-2061) 1-(nH-q-(([substituted]aryl)carbonyl)imidazol-w-yl)-3-hydroxy-3-([substituted]-2H-tetrazol-5-yl)-propenone (B-2062) 1-[nH-(q-(([substituted]heteroaryl)alkenyl)-z-alkyl)pyrazol-w-yl]-3-hydroxy-3-([substituted]-1H-1,2,4-triazol-3-yl)-propenone (B-2063) 4-[nH-(z-alkyl-q-(([substituted]aryl)oxy))pyrazol-w-yl]-2-hydroxy-4-oxo-2-butenoic acid (B-2064) 4-[(z-alkyl-q-(1-hydroxy-([substituted]aryl)methyl))isoxazol-w-yl]-2-hydroxy-4-oxo-2-butenoic acid (B-2065) 1-[(z-alkyl-q-(([substituted]heteroaryl)carbonyl))thiophen-w-yl]-3-hydroxy-3-([substituted]-2H-tetrazol-5-yl)-propenone (B-2066) 3-hydroxy-1-(q-(([substituted]heteroaryl)sulfonyl)pyridin-w-yl)-3-([substituted]-2H-tetrazol-5-yl)-propenone (B-2067) 4-(q-(([substituted]heteroaryl)aminosulfonyl)thiazol-w-yl)-2-hydroxy-4-oxo-2-butenoic acid (B-2068) 1-[(q-(([substituted]heteroaryl)amino)-z-halogeno)furan-w-yl]-3-hydroxy-3-([substituted]-1H-1,2,4-triazol-3-yl)-propenone (B-2069) 1-[nH-(z-alkyl-q-(([substituted]aryl)amino))pyrazol-w-yl]-3-hydroxy-3-([substituted]-1H-1,2,4-triazol-3-yl)-propenone (B-2070) 2-hydroxy-4-oxo-4-(q-(([substituted]heteroaryl)sulfonyl)isoxazol-w-yl)-2-butenoic acid (B-2071) 1-[nH-(z-halogeno-q-(([substituted]aryl)sulfonylamino))imidazol-w-yl]-3-hydroxy-3-([substituted]-2H-tetrazol-5-yl)-propenone (B-2072) 1-[(z-alkyl-q-(([substituted]heteroaryl)sulfonylamino))oxazol-w-yl]-3-hydroxy-3-([substituted]-2H-tetrazol-5-yl)-propenone (B-2073) 1-(q-(([substituted]heteroaryl)alkyl)thiophen-w-yl)-3-hydroxy-3-([substituted]-2H-tetrazol-5-yl)-propenone (B-2074) 4-[(z-alkyl-q-(([substituted](heteroaryl)oxy))oxazol-w-yl]-2-hydroxy-4-oxo-2-butenoic acid (B-2075) 1-[(q-(([substituted]heteroaryl)alkenyl)-z-halogeno)pyridin-w-yl]-3-hydroxy-3-([substituted]-2H-tetrazol-5-yl)-propenone (B-2076) 4-[(q-(([substituted]heteroaryl)aminosulfonyl)-z-halogeno)furan-w-yl]-2-hydroxy-4-oxo-2-butenoic acid (B-2077) 1-[nH-(z-alkyl-q-((([substituted]aryl)aminocarbonyl))pyrazol-w-yl]-3-hydroxy-3-([substituted]-1H-1,2,4-triazol-3-yl)-propenone (B-2078) 4-[(z-alkyl-q-(([substituted]heteroaryl)sulfinyl))pyridin-w-yl]-2-hydroxy-4-oxo-2-butenoic acid (B-2079) 1-[(z-halogeno-q-(([substituted]aryl)sulfonyl))oxazol-w-yl]-3-hydroxy-3-([substituted]-1H-1,2,4-triazol-3-yl)-propenone (B-2080) 1-[nH-(z-alkyl-q-(([substituted]aryl)sulfinyl))imidazol-w-yl]-3-hydroxy-3-([substituted]-2H-tetrazol-5-yl)-propenone (B-2081) 4-(q-(([substituted]heteroaryl)aminocarbonyl)oxazol-w-yl)-2-hydroxy-4-oxo-2-butenoic acid (B-2082) 1-[nH-(z-alkyl-q-(([substituted]heteroaryl)sulfonyl))pyrazol-w-yl]-3-hydroxy-3-([substituted]-2H-tetrazol-5-yl)-propenone (B-2083) 1-[nH-(q-(([substituted]heteroaryl)alkyl)-z-halogeno)pyrazol-w-yl]-3-hydroxy-3-([substituted]-2H-tetrazol-5-yl)-propenone (B-2084) 2-hydroxy-4-oxo-4-(q-(([substituted]aryl)oxy)oxazol-w-yl)-2-butenoic acid (B-2085) 4-[nH-(z-alkyl-q-(([substituted]heteroaryl)sulfonyl))pyrazol-w-yl]-2-hydroxy-4-oxo-2-butenoic acid (B-2086) 2-hydroxy-4-oxo-4-(q-(([substituted]heteroaryl)sulfonylamino)thiophen-w-yl)-2-butenoic acid (B-2087) 2-hydroxy-4-(q-(1-hydroxy-([substituted]heteroaryl)methyl)thiophen-w-yl)-4-oxo-2-butenoic acid (B-2088) 1-[(z-alkyl-q-(([substituted]aryl)sulfonyl))thiophen-w-yl]-3-hydroxy-3-([substituted]-1H-1,2,4-triazol-3-yl)-propenone (B-2089) 1-[(z-halogeno-q-(([substituted]heteroaryl)sulfonylamino))isoxazol-w-yl]-3-hydroxy-3-([substituted]-2H-tetrazol-5-yl)-propenone (B-2090) 1-[(z-halogeno-q-(([substituted]heteroaryl)sulfinyl))oxazol-w-yl]-3-hydroxy-3-([substituted]-1H-1,2,4-triazol-3-yl)-propenone (B-2091) 4-[(z-halogeno-q-(([substituted]heteroaryl)sulfonylamino))oxazol-w-yl]-2-hydroxy-4-oxo-2-butenoic acid (B-2092) 4-[(q-(([substituted]aryl)amino)-z-halogeno)thiazol-w-yl]-2-hydroxy-4-oxo-2-butenoic acid (B-2093) 3-hydroxy-1-(q-(([substituted]aryl)sulfinyl)isoxazol-w-yl)-3-([substituted]-2H-tetrazol-5-yl)-propenone (B-2094) 1-(q-(([substituted]aryl)alkenyl)oxazol-w-yl)-3-hydroxy-3-([substituted]-2H-tetrazol-5-yl)-propenone (B-2095) 4-[(q-(([substituted]heteroaryl)alkenyl)-z-alkyl)oxazol-w-yl]-2-hydroxy-4-oxo-2-butenoic acid (B-2096) 1-[(z-alkyl-q-(([substituted]heteroaryl)oxycarbonyl))thiophen-w-yl]-3-hydroxy-3-([substituted]-1H-1,2,4-triazol-3-yl)-propenone (B-2097) 1-[(q-(([substituted]heteroaryl)carboxy)-z-halogeno)isoxazol-w-yl]-3-hydroxy-3-([substituted]-2H-tetrazol-5-yl)-propenone (B-2098) 1-(q-(([substituted]heteroaryl)amino)thiazol-w-yl)-3-hydroxy-3-([substituted]-2H-tetrazol-5-yl)-propenone (B-2099) 1-[nH-(q-(([substituted]heteroaryl)alkenyl)-z-alkyl)imidazol-w-yl]-3-hydroxy-3-([substituted]-1H-1,2,4-triazol-3-yl)-propenone (B-2100) 1-[(z-alkyl-q-(([substituted]heteroaryl)carbonylamino))furan-w-yl]-3-hydroxy-3-([substituted]-2H-tetrazol-5-yl)-propenone (B-2101) 1-[nH-(z-halogeno-q-(([substituted]heteroaryl)oxycarbonyl))imidazol-w-yl]-3-hydroxy-3-([substituted]-1H-1,2,4-triazol-3-yl)-propenone (B-2102) 1-[(z-alkyl-q-(1-hydroxy-([substituted]heteroaryl)methyl))thiophen-w-yl]-3-hydroxy-3-([substituted]-2H-tetrazol-5-yl)-propenone (B-2103) 4-(q-(([substituted]aryl)aminocarbonyl)pyrrol-w-yl)-2-hydroxy-4-oxo-2-butenoic acid (B-2104) 4-[(z-alkyl-q-(([substituted]heteroaryl)aminosulfonyl))isoxazol-w-yl]-2-hydroxy-4-oxo-2-butenoic acid (B-2105) 1-[nH-(z-halogeno-q-(([substituted]heteroaryl)oxy))imidazol-w-yl]-3-hydroxy-3-([substituted]-1H-1,2,4-triazol-3-yl)-propenone (B-2106) 1-[(z-halogeno-q-(([substituted]aryl)thio))pyridin-w-yl]-3-hydroxy-3-([substituted]-2H-tetrazol-5-yl)-propenone (B-2107) 3-hydroxy-1-(nH-q-(([substituted]heteroaryl)sulfonylamino)pyrazol-w-yl)-3-([substituted]-1H-1,2,4-triazol-3-yl)-propenone (B-2108) 4-(q-(([substituted]aryl)carboxy)pyrrol-w-yl)-2-hydroxy-4-oxo-2-butenoic acid (B-2109) 4-[(q-(([substituted]heteroaryl)carboxy)-z-halogeno)isoxazol-w-yl]-2-hydroxy-4-oxo-2-butenoic acid (B-2110) 1-(q-(([substituted]aryl)carbonylamino)furan-w-yl)-3-hydroxy-3-([substituted]-1H-1,2,4-triazol-3-yl)-propenone (B-2111) 4-[(q-([substituted]aryl)-z-halogeno)thiazol-w-yl]-2-hydroxy-4-oxo-2-butenoic acid (B-2112) 1-[(z-alkyl-q-(([substituted]heteroaryl)alkyl))thiophen-w-yl]-3-hydroxy-3-([substituted]-1H-1,2,4-triazol-3-yl)-propenone (B-2113) 3-hydroxy-3-([substituted]-2H-tetrazol-5-yl)-1-(nH-q-(([substituted]aryl)thio)imidazol-w-yl)-propenone (B-2114) 1-[(z-alkyl-q-(([substituted]heteroaryl)oxycarbonyl))furan-w-yl]-3-hydroxy-3-([substituted]-2H-tetrazol-5-yl)-propenone (B-2115) 1-(q-(([substituted]heteroaryl)carbonylamino)furan-w-yl)-3-hydroxy-3-([substituted]-1H-1,2,4-triazol-3-yl)-propenone (B-2116) 3-hydroxy-1-(q-(([substituted]heteroaryl)sulfonylamino)oxazol-w-yl)-3-([substituted]-2H-tetrazol-5-yl)-propenone (B-2117) 1-[(z-alkyl-q-(([substituted]aryl)sulfonylamino))thiazol-w-yl]-3-hydroxy-3-([substituted]-2H-tetrazol-5-yl)-propenone (B-2118) 1-(q-(([substituted]heteroaryl)carboxy)furan-w-yl)-3-hydroxy-3-([substituted]-1H-1,2,4-triazol-3-yl)-propenone (B-2119) 3-hydroxy-1-(q-(([substituted]heteroaryl)sulfonyl)oxazol-w-yl)-3-([substituted]-1H-1,2,4-triazol-3-yl)-propenone (B-2120) 1-[(z-alkyl-q-(([substituted]aryl)sulfonyl))thiazol-w-yl]-3-hydroxy-3-([substituted]-1H-1,2,4-triazol-3-yl)-propenone (B-2121) 4-[nH-(z-alkyl-q-(([substituted]aryl)carboxy))pyrazol-w-yl]-2-hydroxy-4-oxo-2-butenoic acid (B-2122) 4-[(z-alkyl-q-(([substituted]aryl)carbonyl))oxazol-w-yl]-2-hydroxy-4-oxo-2-butenoic acid
(B-2123) 1-[(q-(([substituted]aryl)alkyl)-z-halogeno)oxazol-w-yl]-3-hydroxy-3-([substituted]-1H-1,2,4-triazol-3-yl)-propenone
(B-2124) 4-[(q-(([substituted]aryl)aminocarbonyl)-z-halogeno)thiazol-w-yl]-2-hydroxy-4-oxo-2-butenoic acid
(B-2125) 1-[nH-(q-(([substituted]heteroaryl)carbonylamino)-z-halogeno)imidazol-w-yl]-3-hydroxy-3-([substituted]-2H-tetrazol-5-yl)-propenone
(B-2126) 3-hydroxy-1-(nH-q-(([substituted]heteroaryl)oxy)pyrazol-w-yl)-3-([substituted]-2H-tetrazol-5-yl)-propenone
(B-2127) 4-[(z-alkyl-q-(([substituted]heteroaryl)alkyl))isoxazol-w-yl]-2-hydroxy-4-oxo-2-butenoic acid
(B-2128) 3-hydroxy-1-(q-(([substituted]heteroaryl)carboxy)pyridin-w-yl)-3-([substituted]-1H-1,2,4-triazol-3-yl)-propenone
(B-2129) 4-(q-(([substituted]aryl)aminocarbonyl)furan-w-yl)-2-hydroxy-4-oxo-2-butenoic acid
(B-2130) 1-[(q-(([substituted]heteroaryl)alkenyl)-z-alkyl)pyridin-w-yl]-3-hydroxy-3-([substituted]-2H-tetrazol-5-yl)-propenone
(B-2131) 4-[(z-alkyl-q-([substituted]aryl))oxazol-w-yl]-2-hydroxy-4-oxo-2-butenoic acid
(B-2132) 4-[nH-(q-(([substituted]heteroaryl)alkyl)-z-halogeno)pyrazol-w-yl]-2-hydroxy-4-oxo-2-butenoic acid
(B-2133) 3-hydroxy-1-(nH-q-(([substituted]heteroaryl)sulfonylamino)imidazol-w-yl)-3-([substituted]-2H-tetrazol-5-yl)-propenone
(B-2134) 1-[(q-(([substituted]heteroaryl)alkenyl)-z-halogeno)thiophen-w-yl]-3-hydroxy-3-([substituted]-2H-tetrazol-5-yl)-propenone
(B-2135) 2-hydroxy-4-(q-(1-hydroxy-([substituted]heteroaryl)methyl)isoxazol-w-yl)-4-oxo-2-butenoic acid
(B-2136) 3-hydroxy-1-(nH-q-(([substituted]heteroaryl)sulfinyl)imidazol-w-yl)-3-([substituted]-2H-tetrazol-5-yl)-propenone
(B-2137) 4-[(z-alkyl-q-([substituted]aryl))furan-w-yl]-2-hydroxy-4-oxo-2-butenoic acid
(B-2138) 2-hydroxy-4-oxo-4-(q-(([substituted]heteroaryl)carboxy)pyrrol-w-yl)-2-butenoic acid
(B-2139) 1-[(z-alkyl-q-(([substituted]aryl)oxy))isoxazol-w-yl]-3-hydroxy-3-([substituted]-1H-1,2,4-triazol-3-yl)-propenone
(B-2140) 1-[(z-halogeno-q-(([substituted]heteroaryl)sulfonylamino))pyrrol-w-yl]-3-hydroxy-3-([substituted]-2H-tetrazol-5-yl)-propenone
(B-2141) 1-[(z-alkyl-q-(1-hydroxy-([substituted]aryl)methyl))oxazol-w-yl]-3-hydroxy-3-([substituted]-2H-tetrazol-5-yl)-propenone
(B-2142) 4-[(q-(([substituted]aryl)alkenyl)-z-alkyl)pyrrol-w-yl]-2-hydroxy-4-oxo-2-butenoic acid
(B-2143) 4-[nH-(z-alkyl-q-(([substituted]aryl)sulfonylamino))pyrazol-w-yl]-2-hydroxy-4-oxo-2-butenoic acid
(B-2144) 1-(q-(([substituted]aryl)carboxy)isoxazol-w-yl)-3-hydroxy-3-([substituted]-2H-tetrazol-5-yl)-propenone
(B-2145) 1-(q-(([substituted]aryl)alkyl)furan-w-yl)-3-hydroxy-3-([substituted]-1H-1,2,4-triazol-3-yl)-propenone
(B-2146) 4-[nH-(z-halogeno-q-(([substituted]aryl)thio))imidazol-w-yl]-2-hydroxy-4-oxo-2-butenoic acid
(B-2147) 1-[nH-(z-halogeno-q-(([substituted]aryl)oxy))imidazol-w-yl]-3-hydroxy-3-([substituted]-1H-1,2,4-triazol-3-yl)-propenone
(B-2148) 3-hydroxy-1-(q-(([substituted]heteroaryl)sulfonylamino)oxazol-w-yl)-3-([substituted]-1H-1,2,4-triazol-3-yl)-propenone
(B-2149) 1-[(z-halogeno-q-(([substituted]aryl)sulfonyl))pyridin-w-yl]-3-hydroxy-3-([substituted]-1H-1,2,4-triazol-3-yl)-propenone
(B-2150) 1-[(q-(([substituted]aryl)carbonylamino)-z-halogeno)thiophen-w-yl]-3-hydroxy-3-([substituted]-1H-1,2,4-triazol-3-yl)-propenone
(B-2151) 4-[(q-(([substituted]heteroaryl)alkenyl)-z-alkyl)furan-w-yl]-2-hydroxy-4-oxo-2-butenoic acid
(B-2152) 1-[nH-(z-halogeno-q-(([substituted]heteroaryl))pyrazol-w-yl]-3-hydroxy-3-([substituted]-2H-tetrazol-5-yl)-propenone
(B-2153) 3-hydroxy-1-(nH-q-(([substituted]heteroaryl)oxycarbonyl)imidazol-w-yl)-3-([substituted]-1H-1,2,4-triazol-3-yl)-propenone
(B-2154) 1-[(z-halogeno-q-(([substituted]aryl)oxy))thiophen-w-yl]-3-hydroxy-3-([substituted]-2H-tetrazol-5-yl)-propenone
(B-2155) 3-hydroxy-1-(q-(([substituted]heteroaryl)sulfonyl)furan-w-yl)-3-([substituted]-1H-1,2,4-triazol-3-yl)-propenone
(B-2156) 1-[(q-(([substituted]heteroaryl)carbonylamino)-z-halogeno)thiophen-w-yl]-3-hydroxy-3-([substituted]-2H-tetrazol-5-yl)-propenone
(B-2157) 1-[(z-halogeno-q-(([substituted]aryl)sulfinyl))thiazol-w-yl]-3-hydroxy-3-([substituted]-2H-tetrazol-5-yl)-propenone
(B-2158) 1-[(q-(([substituted]heteroaryl)aminocarbonyl)-z-halogeno)pyrrol-w-yl]-3-hydroxy-3-([substituted]-2H-tetrazol-5-yl)-propenone
(B-2159) 4-[(z-alkyl-q-(([substituted]aryl)sulfinyl))thiazol-w-yl]-2-hydroxy-4-oxo-2-butenoic acid
(B-2160) 4-[(z-alkyl-q-(([substituted]aryl)aminocarbonyl))thiophen-w-yl]-2-hydroxy-4-oxo-2-butenoic acid
(B-2161) 1-[(z-alkyl-q-(([substituted]aryl)amino))thiophen-w-yl]-3-hydroxy-3-([substituted]-2H-tetrazol-5-yl)-propenone
(B-2162) 4-[(z-halogeno-q-(([substituted]heteroaryl)sulfinyl))thiazol-w-yl]-2-hydroxy-4-oxo-2-butenoic acid
(B-2163) 1-[nH-(q-(([substituted]heteroaryl)carbonylamino)-z-halogeno)imidazol-w-yl]-3-hydroxy-3-([substituted]-1H-1,2,4-triazol-3-yl)-propenone
(B-2164) 1-(q-([substituted]heteroaryl)oxazol-w-yl)-3-hydroxy-3-([substituted]-2H-tetrazol-5-yl)-propenone
(B-2165) 1-(q-(([substituted]aryl)carbonyl)pyrrol-w-yl)-3-hydroxy-3-([substituted]-2H-tetrazol-5-yl)-propenone
(B-2166) 1-[nH-(z-alkyl-q-(([substituted]aryl)aminosulfonyl))pyrazol-w-yl]-3-hydroxy-3-([substituted]-1H-1,2,4-triazol-3-yl)-propenone
(B-2167) 1-[nH-(q-(([substituted]aryl)alkyl)-z-halogeno)pyrazol-w-yl]-3-hydroxy-3-([substituted]-2H-tetrazol-5-yl)-propenone
(B-2168) 1-[nH-(z-alkyl-q-(([substituted]aryl)thio))pyrazol-w-yl]-3-hydroxy-3-([substituted]-2H-tetrazol-5-yl)-propenone
(B-2169) 1-[nH-(q-(([substituted]aryl)carboxy)-z-halogeno)pyrazol-w-yl]-3-hydroxy-3-([substituted]-2H-tetrazol-5-yl)-propenone
(B-2170) 4-(nH-q-(([substituted]aryl)amino)pyrazol-w-yl)-2-hydroxy-4-oxo-2-butenoic acid
(B-2171) 4-[nH-(z-halogeno-q-(([substituted]heteroaryl)sulfonylamino))pyrazol-w-yl]-2-hydroxy-4-oxo-2-butenoic acid
(B-2172) 4-(q-(([substituted]heteroaryl)alkyl)thiophen-w-yl)-2-hydroxy-4-oxo-2-butenoic acid (B-2173) 1-(q-(([substituted]aryl)carboxy)pyridin-w-yl)-3-hydroxy-3-([substituted]-1H-1,2,4-triazol-3-yl)-propenone
(B-2174) 4-[(z-halogeno-q-(1-hydroxy-([substituted]heteroaryl)methyl))pyrrol-w-yl]-2-hydroxy-4-oxo-2-butenoic acid
(B-2175) 4-[nH-(z-halogeno-q-(([substituted]aryl)oxy))imidazol-w-yl]-2-hydroxy-4-oxo-2-butenoic acid
(B-2176) 4-(nH-q-(([substituted]aryl)carboxy)imidazol-w-yl)-2-hydroxy-4-oxo-2-butenoic acid
(B-2177) 1-[nH-(z-alkyl-q-(([substituted]aryl)amino))imidazol-w-yl]-3-hydroxy-3-([substituted]-2H-tetrazol-5-yl)-propenone
(B-2178) 4-[(z-alkyl-q-(([substituted]aryl)carbonylamino))pyridin-w-yl]-2-hydroxy-4-oxo-2-butenoic acid
(B-2179) 4-(q-(([substituted]aryl)alkenyl)thiophen-w-yl)-2-hydroxy-4-oxo-2-butenoic acid
(B-2180) 4-[(z-alkyl-q-(([substituted]heteroaryl)oxycarbonyl))pyridin-w-yl]-2-hydroxy-4-oxo-2-butenoic acid
(B-2181) 3-hydroxy-1-(q-(([substituted]heteroaryl)thio)pyrrol-w-yl)-3-([substituted]-1H-1,2,4-triazol-3-yl)-propenone
(B-2182) 1-[(q-(([substituted]heteroaryl)carboxy)-z-halogeno)isoxazol-w-yl]-3-hydroxy-3-([substituted]-1H-1,2,4-triazol-3-yl)-propenone
(B-2183) 2-hydroxy-4-oxo-4-(q-(([substituted]heteroaryl)oxycarbonyl)furan-w-yl)-2-butenoic acid
(B-2184) 4-[nH-(z-alkyl-q-(([substituted]aryl)thio))imidazol-w-yl]-2-hydroxy-4-oxo-2-butenoic acid
(B-2185) 1-[(q-(([substituted]aryl)carboxy-z-halogeno)thiazol-w-yl]-3-hydroxy-3-([substituted]-1H-1,2,4-triazol-3-yl)-propenone
(B-2186) 4-(q-(([substituted]heteroaryl)amino)isoxazol-w-yl)-2-hydroxy-4-oxo-2-butenoic acid
(B-2187) 1-[nH-(z-alkyl-q-(([substituted]aryl)alkyl))imidazol-w-yl]-3-hydroxy-3-([substituted]-2H-tetrazol-5-yl)-propenone
(B-2188) 4-(q-([substituted]aryl)thiazol-w-yl)-2-hydroxy-4-oxo-2-butenoic acid
(B-2189) 1-(q-(([substituted]heteroaryl)alkyl)pyridin-w-yl)-3-hydroxy-3-([substituted]-1H-1,2,4-triazol-3-yl)-propenone
(B-2190) 1-[nH-(q-(([substituted]heteroaryl)aminocarbonyl)-z-halogeno)pyrazol-w-yl]-3-hydroxy-3-([substituted]-2H-tetrazol-5-yl)-propenone
(B-2191) 3-hydroxy-3-([substituted]-2H-tetrazol-5-yl)-1-(q-(([substituted]heteroaryl)thio)pyrrol-w-yl)-propenone
(B-2192) 1-[(z-halogeno-q-(([substituted]aryl)thio))furan-w-yl]-3-hydroxy-3-([substituted]-1H-1,2,4-triazol-3-yl)-propenone
(B-2193) 3-hydroxy-1-(nH-q-(([substituted]heteroaryl)sulfonyl)imidazol-w-yl)-3-([substituted]-1H-1,2,4-triazol-3-yl)-propenone
(B-2194) 1-[(z-alkyl-q-(([substituted]aryl)aminocarbonyl))isoxazol-w-yl]-3-hydroxy-3-([substituted]-2H-tetrazol-5-yl)-propenone
(B-2195) 1-(q-(([substituted]heteroaryl)carbonylamino)thiophen-w-yl)-3-hydroxy-3-([substituted]-1H-1,2,4-triazol-3-yl)-propenone
(B-2196) 4-[nH-(z-halogeno-q-(([substituted]heteroaryl)oxy))imidazol-w-yl]-2-hydroxy-4-oxo-2-butenoic acid
(B-2197) 4-(q-(([substituted]heteroaryl)aminosulfonyl)furan-w-yl)-2-hydroxy-4-oxo-2-butenoic acid
(B-2198) 2-hydroxy-4-oxo-4-(q-(([substituted]aryl)oxycarbonyl)pyridin-w-yl)-2-butenoic acid
(B-2199) 1-(nH-q-(([substituted]heteroaryl)amino)imidazol-w-yl)-3-hydroxy-3-([substituted]-1H-1,2,4-triazol-3-yl)-propenone
(B-2200) 1-[(q-(([substituted]heteroaryl)carboxy)-z-halogeno)thiazol-w-yl]-3-hydroxy-3-([substituted]-1H-1,2,4-triazol-3-yl)-propenone
(B-2201) 1-[(z-alkyl-q-(([substituted]aryl))pyridin-w-yl]-3-hydroxy-3-([substituted]-1H-1,2,4-triazol-3-yl)-propenone
(B-2202) 4-[(z-alkyl-q-(([substituted]aryl)amino))furan-w-yl]-2-hydroxy-4-oxo-2-butenoic acid
(B-2203) 1-[(z-alkyl-q-(([substituted]aryl)carboxy))thiophen-w-yl]-3-hydroxy-3-([substituted]-2H-tetrazol-5-yl)-propenone
(B-2204) 1-[(z-alkyl-q-(([substituted]aryl)sulfinyl))isoxazol-w-yl]-3-hydroxy-3-([substituted]-1H-1,2,4-triazol-3-yl)-propenone
(B-2205) 1-[(z-halogeno-q-(([substituted]heteroaryl)sulfonylamino))pyrrol-w-yl]-3-hydroxy-3-([substituted]-1H-1,2,4-triazol-3-yl)-propenone
(B-2206) 1-(q-(([substituted]heteroaryl)carbonyl)thiazol-w-yl)-3-hydroxy-3-([substituted]-1H-1,2,4-triazol-3-yl)-propenone
(B-2207) 4-(q-(([substituted]heteroaryl)alkenyl)furan-w-yl)-2-hydroxy-4-oxo-2-butenoic acid
(B-2208) 4-[(z-halogeno-q-(([substituted]aryl)sulfonylamino))thiazol-w-yl]-2-hydroxy-4-oxo-2-butenoic acid
(B-2209) 1-(q-(([substituted]aryl)alkenyl)pyrrol-w-yl)-3-hydroxy-3-([substituted]-2H-tetrazol-5-yl)-propenone
(B-2210) 1-(q-(([substituted]heteroaryl)amino)oxazol-w-yl)-3-hydroxy-3-([substituted]-2H-tetrazol-5-yl)-propenone
(B-2211) 1-[(q-(([substituted]aryl)aminocarbonyl)-z-halogeno)pyridin-w-yl]-3-hydroxy-3-([substituted]-1H-1,2,4-triazol-3-yl)-propenone
(B-2212) 1-[nH-(q-(([substituted]aryl)alkenyl)-z-alkyl)imidazol-w-yl]-3-hydroxy-3-([substituted]-1H-1,2,4-triazol-3-yl)-propenone
(B-2213) 1-(q-(([substituted]heteroaryl)aminosulfonyl)isoxazol-w-yl)-3-hydroxy-3-([substituted]-2H-tetrazol-5-yl)-propenone
(B-2214) 1-[(z-alkyl-q-(1-hydroxy-([substituted]heteroaryl)methyl))pyrrol-w-yl]-3-hydroxy-3-([substituted]-2H-tetrazol-5-yl)-propenone
(B-2215) 3-hydroxy-1-(nH-q-(([substituted]aryl)sulfonylamino)imidazol-w-yl)-3-([substituted]-1H-1,2,4-triazol-3-yl)-propenone
(B-2216) 4-[nH-(q-(([substituted]heteroaryl)alkenyl)-z-halogeno)imidazol-w-yl]-2-hydroxy-4-oxo-2-butenoic acid
(B-2217) 1-[(z-alkyl-q-(([substituted]heteroaryl)aminosulfonyl))thiophen-w-yl]-3-hydroxy-3-([substituted]-1H-1,2,4-triazol-3-yl)-propenone
(B-2218) 1-[(z-alkyl-q-(([substituted]heteroaryl)amino))oxazol-w-yl]-3-hydroxy-3-([substituted]-1H-1,2,4-triazol-3-yl)-propenone
(B-2219) 1-(nH-q-(([substituted]aryl)alkenyl)pyrazol-w-yl)-3-hydroxy-3-([substituted]-2H-tetrazol-5-yl)-propenone
(B-2220) 2-hydroxy-4-(q-(1-hydroxy-([substituted]heteroaryl)methyl)oxazol-w-yl)-4-oxo-2-butenoic acid
(B-2221) 1-[nH-(q-(([substituted]heteroaryl)aminosulfonyl)-z-halogeno)pyrazol-w-yl]-3-hydroxy-3-([substituted]-2H-tetrazol-5-yl)-propenone
(B-2222) 4-[(z-halogeno-q-(([substituted]heteroaryl)sulfonyl))furan-w-yl]-2-hydroxy-4-oxo-2-butenoic acid
(B-2223) 1-[(z-alkyl-q-(([substituted]aryl)carbonyl))isoxazol-w-yl]-3-hydroxy-3-([substituted]-2H-tetrazol-5-yl)-propenone (B-2224) 1-[(z-alkyl-q-(([substituted]heteroaryl)thio))pyridin-w-yl]-3-hydroxy-3-([substituted]-1H-1,2,4-triazol-3-yl)-propenone
(B-2225) 4-[(z-alkyl-q-(([substituted]heteroaryl)thio))oxazol-w-yl]-2-hydroxy-4-oxo-2-butenoic acid
(B-2226) 1-[(z-alkyl-q-(([substituted]aryl)aminosulfonyl))thiophen-w-yl]-3-hydroxy-3-([substituted]-2H-tetrazol-5-yl)-propenone
(B-2227) 4-(q-(([substituted]heteroaryl)amino)pyridin-w-yl)-2-hydroxy-4-oxo-2-butenoic acid
(B-2228) 1-(q-([substituted]heteroaryl)isoxazol-w-yl)-3-hydroxy-3-([substituted]-2H-tetrazol-5-yl)-propenone
(B-2229) 1-[(z-alkyl-q-(([substituted]heteroaryl)alkyl))pyridin-w-yl]-3-hydroxy-3-([substituted]-2H-tetrazol-5-yl)-propenone
(B-2230) 1-[(z-halogeno-q-(1-hydroxy-([substituted]heteroaryl)methyl))pyridin-w-yl]-3-hydroxy-3-([substituted]-2H-tetrazol-5-yl)-propenone
(B-2231) 1-[(q-(([substituted]aryl)amino)-z-halogeno)thiazol-w-yl]-3-hydroxy-3-([substituted]-1H-1,2,4-triazol-3-yl)-propenone
(B-2232) 1-[(q-([substituted]aryl)-z-halogeno)isoxazol-w-yl]-3-hydroxy-3-([substituted]-2H-tetrazol-5-yl)-propenone
(B-2233) 4-[(z-halogeno-q-(1-hydroxy-([substituted]aryl)methyl))oxazol-w-yl]-2-hydroxy-4-oxo-2-butenoic acid
(B-2234) 4-[nH-(z-halogeno-q-(([substituted]heteroaryl)oxycarbonyl))imidazol-w-yl]-2-hydroxy-4-oxo-2-butenoic acid
(B-2235) 1-[(z-halogeno-q-(([substituted]heteroaryl)oxy))pyridin-w-yl]-3-hydroxy-3-([substituted]-1H-1,2,4-triazol-3-yl)-propenone
(B-2236) 4-[(z-halogeno-q-(([substituted]heteroaryl)sulfonylamino))furan-w-yl]-2-hydroxy-4-oxo-2-butenoic acid
(B-2237) 1-[nH-(z-halogeno-q-(([substituted]heteroaryl)sulfonylamino))pyrazol-w-yl]-3-hydroxy-3-([substituted]-2H-tetrazol-5-yl)-propenone
(B-2238) 1-[nH-(z-alkyl-q-(([substituted]aryl)sulfinyl))pyrazol-w-yl]-3-hydroxy-3-([substituted]-1H-1,2,4-triazol-3-yl)-propenone
(B-2239) 1-[(z-halogeno-q-(([substituted]aryl)oxy))pyrrol-w-yl]-3-hydroxy-3-([substituted]-2H-tetrazol-5-yl)-propenone
(B-2240) 1-(nH-q-(([substituted]aryl)carboxy)imidazol-w-yl)-3-hydroxy-3-([substituted]-1H-1,2,4-triazol-3-yl)-propenone
(B-2241) 1-[(z-alkyl-q-([substituted]aryl))oxazol-w-yl]-3-hydroxy-3-([substituted]-2H-tetrazol-5-yl)-propenone
(B-2242) 4-(q-(([substituted]heteroaryl)aminosulfonyl)oxazol-w-yl)-2-hydroxy-4-oxo-2-butenoic acid
(B-2243) 4-[(z-alkyl-q-(([substituted]aryl)thio))pyridin-w-yl]-2-hydroxy-4-oxo-2-butenoic acid
(B-2244) 1-(nH-q-(([substituted]heteroaryl)amino)pyrazol-w-yl)-3-hydroxy-3-([substituted]-1H-1,2,4-triazol-3-yl)-propenone
(B-2245) 3-hydroxy-1-(nH-q-(([substituted]heteroaryl)sulfinyl)imidazol-w-yl)-3-([substituted]-1H-1,2,4-triazol-3-yl)-propenone
(B-2246) 3-hydroxy-1-(q-(([substituted]aryl)sulfinyl)oxazol-w-yl)-3-([substituted]-2H-tetrazol-5-yl)-propenone
(B-2247) 1-[nH-(z-alkyl-q-(([substituted]aryl))pyrazol-w-yl]-3-hydroxy-3-([substituted]-1H-1,2,4-triazol-3-yl)-propenone
(B-2248) 1-[(z-alkyl-q-(([substituted]aryl)alkyl))thiophen-w-yl]-3-hydroxy-3-([substituted]-1H-1,2,4-triazol-3-yl)-propenone
(B-2249) 1-(q-(([substituted]heteroaryl)alkyl)thiophen-w-yl)-3-hydroxy-3-([substituted]-1H-1,2,4-triazol-3-yl)-propenone
(B-2250) 1-[nH-(z-alkyl-q-(([substituted]aryl)carbonyl))pyrazol-w-yl]-3-hydroxy-3-([substituted]-2H-tetrazol-5-yl)-propenone
(B-2251) 1-[nH-(z-alkyl-q-(([substituted]heteroaryl)amino))pyrazol-w-yl]-3-hydroxy-3-([substituted]-1H-1,2,4-triazol-3-yl)-propenone
(B-2252) 4-[(z-alkyl-q-(([substituted]heteroaryl)amino))pyridin-w-yl]-2-hydroxy-4-oxo-2-butenoic acid
(B-2253) 4-[(z-alkyl-q-(([substituted]aryl)sulfinyl))furan-w-yl]-2-hydroxy-4-oxo-2-butenoic acid
(B-2254) 4-[(z-alkyl-q-(([substituted]heteroaryl)carbonyl))oxazol-w-yl]-2-hydroxy-4-oxo-2-butenoic acid
(B-2255) 1-[nH-(z-alkyl-q-(1-hydroxy-([substituted]heteroaryl)methyl))pyrazol-w-yl]-3-hydroxy-3-([substituted]-2H-tetrazol-5-yl)-propenone
(B-2256) 4-[(q-(([substituted]heteroaryl)carbonylamino)-z-halogeno)pyrrol-w-yl]-2-hydroxy-4-oxo-2-butenoic acid
(B-2257) 4-(q-(([substituted]aryl)amino)pyridin-w-yl)-2-hydroxy-4-oxo-2-butenoic acid
(B-2258) 4-[(z-halogeno-q-(([substituted]heteroaryl)thio))oxazol-w-yl]-2-hydroxy-4-oxo-2-butenoic acid
(B-2259) 4-[(z-halogeno-q-(([substituted]heteroaryl)sulfonyl))isoxazol-w-yl]-2-hydroxy-4-oxo-2-butenoic acid
(B-2260) 1-(q-(([substituted]aryl)amino)thiophen-w-yl)-3-hydroxy-3-([substituted]-2H-tetrazol-5-yl)-propenone
(B-2261) 1-[(z-alkyl-q-(([substituted]aryl)alkyl))pyridin-w-yl]-3-hydroxy-3-([substituted]-2H-tetrazol-5-yl)-propenone
(B-2262) 3-hydroxy-1-(q-(([substituted]heteroaryl)sulfonyl)pyrrol-w-yl)-3-([substituted]-1H-1,2,4-triazol-3-yl)-propenone
(B-2263) 3-hydroxy-1-(q-(([substituted]aryl)sulfinyl)pyridin-w-yl)-3-([substituted]-2H-tetrazol-5-yl)-propenone
(B-2264) 3-hydroxy-1-(nH-q-(([substituted]aryl)thio)imidazol-w-yl)-3-([substituted]-1H-1,2,4-triazol-3-yl)-propenone
(B-2265) 1-[(z-alkyl-q-(([substituted]aryl)sulfonylamino))thiophen-w-yl]-3-hydroxy-3-([substituted]-1H-1,2,4-triazol-3-yl)-propenone
(B-2266) 1-[(z-alkyl-q-(([substituted]heteroaryl)sulfinyl))thiazol-w-yl]-3-hydroxy-3-([substituted]-2H-tetrazol-5-yl)-propenone
(B-2267) 1-[(q-(([substituted]aryl)carbonylamino)-z-halogeno)oxazol-w-yl]-3-hydroxy-3-([substituted]-2H-tetrazol-5-yl)-propenone
(B-2268) 3-hydroxy-1-(q-(([substituted]heteroaryl)oxycarbonyl)isoxazol-w-yl)-3-([substituted]-2H-tetrazol-5-yl)-propenone
(B-2269) 4-[(z-halogeno-q-([substituted]heteroaryl))oxazol-w-yl]-2-hydroxy-4-oxo-2-butenoic acid
(B-2270) 1-[(z-halogeno-q-(([substituted]aryl)oxycarbonyl))pyridin-w-yl]-3-hydroxy-3-([substituted]-1H-1,2,4-triazol-3-yl)-propenone
(B-2271) 4-[(z-alkyl-q-(([substituted]aryl)oxycarbonyl))furan-w-yl]-2-hydroxy-4-oxo-2-butenoic acid
(B-2272) 2-hydroxy-4-oxo-4-(nH-q-(([substituted]heteroaryl)carboxy)pyrazol-w-yl)-2-butenoic acid
(B-2273) 4-[nH-(z-alkyl-q-(([substituted]heteroaryl)thio))imidazol-w-yl]-2-hydroxy-4-oxo-2-butenoic acid
(B-2274) 1-[nH-(q-(([substituted]heteroaryl)carboxy)-z-halogeno)pyrazol-w-yl]-3-hydroxy-3-([substituted]-2H-tetrazol-5-yl)-propenone (B-2275) 2-hydroxy-4-oxo-4-(nH-q-(([substituted]heteroaryl)sulfonyl)imidazol-w-yl)-2-butenoic acid
(B-2276) 1-(q-(([substituted]heteroaryl)carbonyl)pyrrol-w-yl)-3-hydroxy-3-([substituted]-1H-1,2,4-triazol-3-yl)-propenone
(B-2277) 4-[nH-(z-alkyl-q-(([substituted]aryl)aminocarbonyl))imidazol-w-yl]-2-hydroxy-4-oxo-2-butenoic acid
(B-2278) 1-[(z-halogeno-q-(([substituted]aryl)sulfinyl))thiazol-w-yl]-3-hydroxy-3-([substituted]-1H-1,2,4-triazol-3-yl)-propenone
(B-2279) 4-[(q-(([substituted]heteroaryl)alkyl)-z-halogeno)thiazol-w-yl]-2-hydroxy-4-oxo-2-butenoic acid
(B-2280) 4-(nH-q-(([substituted]heteroaryl)aminocarbonyl)pyrazol-w-yl)-2-hydroxy-4-oxo-2-butenoic acid
(B-2281) 4-(q-(([substituted]heteroaryl)carbonylamino)isoxazol-w-yl)-2-hydroxy-4-oxo-2-butenoic acid
(B-2282) 1-[(z-halogeno-q-(([substituted]aryl)sulfinyl))pyridin-w-yl]-3-hydroxy-3-([substituted]-1H-1,2,4-triazol-3-yl)-propenone
(B-2283) 1-[(z-alkyl-q-(([substituted]aryl)sulfonyl))oxazol-w-yl]-3-hydroxy-3-([substituted]-1H-1,2,4-triazol-3-yl)-propenone
(B-2284) 3-hydroxy-1-(q-(([substituted]heteroaryl)oxycarbonyl)thiazol-w-yl)-3-([substituted]-2H-tetrazol-5-yl)-propenone
(B-2285) 1-(nH-q-(([substituted]heteroaryl)alkyl)imidazol-w-yl)-3-hydroxy-3-([substituted]-1H-1,2,4-triazol-3-yl)-propenone
(B-2286) 4-[(z-alkyl-q-(([substituted]heteroaryl)carbonyl))isoxazol-w-yl]-2-hydroxy-4-oxo-2-butenoic acid
(B-2287) 3-hydroxy-1-(q-(1-hydroxy-([substituted]aryl)methyl)oxazol-w-yl)-3-([substituted]-2H-tetrazol-5-yl)-propenone
(B-2288) 1-[nH-(z-alkyl-q-([substituted]aryl))imidazol-w-yl]-3-hydroxy-3-([substituted]-1H-1,2,4-triazol-3-yl)-propenone
(B-2289) 1-[nH-(q-(([substituted]aryl)alkyl)-z-halogeno)pyrazol-w-yl]-3-hydroxy-3-([substituted]-1H-1,2,4-triazol-3-yl)-propenone
(B-2290) 1-[nH-(q-(([substituted]heteroaryl)carbonylamino)-z-halogeno)pyrazol-w-yl]-3-hydroxy-3-([substituted]-1H-1,2,4-triazol-3-yl)-propenone
(B-2291) 1-[(q-(([substituted]aryl)aminosulfonyl)-z-halogeno)oxazol-w-yl]-3-hydroxy-3-([substituted]-2H-tetrazol-5-yl)-propenone
(B-2292) 3-hydroxy-1-(q-(([substituted]aryl)thio)oxazol-w-yl)-3-([substituted]-1H-1,2,4-triazol-3-yl)-propenone
(B-2293) 4-(q-(([substituted]aryl)amino)oxazol-w-yl)-2-hydroxy-4-oxo-2-butenoic acid
(B-2294) 4-[(z-alkyl-q-([substituted]heteroaryl))furan-w-yl]-2-hydroxy-4-oxo-2-butenoic acid
(B-2295) 4-(nH-q-(([substituted]aryl)aminocarbonyl)imidazol-w-yl)-2-hydroxy-4-oxo-2-butenoic acid
(B-2296) 1-[(z-halogeno-q-(1-hydroxy-([substituted]aryl)methyl))isoxazol-w-yl]-3-hydroxy-3-([substituted]-2H-tetrazol-5-yl)-propenone
(B-2297) 1-[(z-alkyl-q-(([substituted]heteroaryl)oxycarbonyl))pyridin-w-yl]-3-hydroxy-3-([substituted]-1H-1,2,4-triazol-3-yl)-propenone
(B-2298) 4-[(z-alkyl-q-(([substituted]aryl)oxycarbonyl))thiazol-w-yl]-2-hydroxy-4-oxo-2-butenoic acid
(B-2299) 1-(q-(([substituted]heteroaryl)alkyl)furan-w-yl)-3-hydroxy-3-([substituted]-1H-1,2,4-triazol-3-yl)-propenone
(B-2300) 1-(nH-q-(([substituted]heteroaryl)carboxy)imidazol-w-yl)-3-hydroxy-3-([substituted]-2H-tetrazol-5-yl)-propenone
(B-2301) 1-[(z-alkyl-q-(([substituted]heteroaryl)aminocarbonyl))thiophen-w-yl]-3-hydroxy-3-([substituted]-1H-1,2,4-triazol-3-yl)-propenone
(B-2302) 3-hydroxy-3-([substituted]-2H-tetrazol-5-yl)-1-(nH-q-(([substituted]heteroaryl)thio)pyrazol-w-yl)-propenone
(B-2303) 4-[(z-alkyl-q-(([substituted]aryl)carboxy))furan-w-yl]-2-hydroxy-4-oxo-2-butenoic acid
(B-2304) 4-[nH-(z-alkyl-q-(([substituted]heteroaryl)aminosulfonyl))pyrazol-w-yl]-2-hydroxy-4-oxo-2-butenoic acid
(B-2305) 2-hydroxy-4-oxo-4-(q-(([substituted]heteroaryl)thio)thiazol-w-yl)-2-butenoic acid
(B-2306) 1-[(q-(([substituted]heteroaryl)carboxy)-z-alkyl)thiophen-w-yl]-3-hydroxy-3-([substituted]-1H-1,2,4-triazol-3-yl)-propenone
(B-2307) 2-hydroxy-4-(nH-q-(1-hydroxy-([substituted]aryl)methyl)pyrazol-w-yl)-4-oxo-2-butenoic acid
(B-2308) 4-[(q-(([substituted]heteroaryl)aminocarbonyl)-z-halogeno)pyridin-w-yl]-2-hydroxy-4-oxo-2-butenoic acid
(B-2309) 4-[(z-alkyl-q-(([substituted]heteroaryl)aminosulfonyl))furan-w-yl]-2-hydroxy-4-oxo-2-butenoic acid
(B-2310) 1-[(z-halogeno-q-([substituted]heteroaryl))pyridin-w-yl]-3-hydroxy-3-([substituted]-2H-tetrazol-5-yl)-propenone
(B-2311) 4-(q-([substituted]aryl)furan-w-yl)-2-hydroxy-4-oxo-2-butenoic acid
(B-2312) 1-[(z-alkyl-q-(([substituted]aryl)sulfonylamino))oxazol-w-yl]-3-hydroxy-3-([substituted]-1H-1,2,4-triazol-3-yl)-propenone
(B-2313) 1-[(z-alkyl-q-(([substituted]heteroaryl)amino))pyrrol-w-yl]-3-hydroxy-3-([substituted]-2H-tetrazol-5-yl)-propenone
(B-2314) 1-[(q-(([substituted]aryl)carbonylamino)-z-halogeno)pyrrol-w-yl]-3-hydroxy-3-([substituted]-1H-1,2,4-triazol-3-yl)-propenone
(B-2315) 4-[nH-(z-alkyl-q-(([substituted]heteroaryl)carbonyl))pyrazol-w-yl]-2-hydroxy-4-oxo-2-butenoic acid
(B-2316) 4-[(q-(([substituted]heteroaryl)alkyl)-z-halogeno)pyridin-w-yl]-2-hydroxy-4-oxo-2-butenoic acid
(B-2317) 4-[(z-alkyl-q-(([substituted]heteroaryl)sulfonylamino))pyrrol-w-yl]-2-hydroxy-4-oxo-2-butenoic acid
(B-2318) 1-[(q-(([substituted]aryl)alkenyl)-z-alkyl)furan-w-yl]-3-hydroxy-3-([substituted]-2H-tetrazol-5-yl)-propenone
(B-2319) 1-[(q-(([substituted]aryl)carboxy)-z-halogeno)thiophen-w-yl]-3-hydroxy-3-([substituted]-2H-tetrazol-5-yl)-propenone
(B-2320) 1-[(z-alkyl-q-([substituted]heteroaryl))pyrrol-w-yl]-3-hydroxy-3-([substituted]-1H-1,2,4-triazol-3-yl)-propenone
(B-2321) 1-[(z-halogeno-q-(([substituted]heteroaryl)sulfinyl))furan-w-yl]-3-hydroxy-3-([substituted]-2H-tetrazol-5-yl)-propenone
(B-2322) 1-[(q-(([substituted]heteroaryl)alkyl)-z-halogeno)thiazol-w-yl]-3-hydroxy-3-([substituted]-2H-tetrazol-5-yl)-propenone
(B-2323) 1-[nH-(z-halogeno-q-(([substituted]aryl)oxy))pyrazol-w-yl]-3-hydroxy-3-([substituted]-2H-tetrazol-5-yl)-propenone
(B-2324) 1-[(z-alkyl-q-(([substituted]aryl)oxy))furan-w-yl]-3-hydroxy-3-([substituted]-1H-1,2,4-triazol-3-yl)-propenone (B-2325) 1-(nH-q-(([substituted]heteroaryl)aminocarbonyl)pyrazol-w-yl)-3-hydroxy-3-([substituted]-1H-1,2,4-triazol-3-yl)-propenone (B-2326) 4-[(z-alkyl-q-([substituted]aryl))pyrrol-w-yl]-2-hydroxy-4-oxo-2-butenoic acid (B-2327) 1-[nH-(z-halogeno-q-([substituted]heteroaryl))imidazol-w-yl]-3-hydroxy-3-([substituted]-1H-1,2,4-triazol-3-yl)-propenone (B-2328) 2-hydroxy-4-oxo-4-(q-(([substituted]heteroaryl)sulfinyl)pyridin-w-yl)-2-butenoic acid (B-2329) 1-(nH-q-(([substituted]aryl)carbonylamino)pyrazol-w-yl)-3-hydroxy-3-([substituted]-1H-1,2,4-triazol-3-yl)-propenone (B-2330) 4-(q-(([substituted]heteroaryl)carbonyl)oxazol-w-yl)-2-hydroxy-4-oxo-2-butenoic acid (B-2331) 1-[(z-halogeno-q-([substituted]heteroaryl))isoxazol-w-yl]-3-hydroxy-3-([substituted]-1H-1,2,4-triazol-3-yl)-propenone (B-2332) 2-hydroxy-4-oxo-4-(nH-q-(([substituted]heteroaryl)oxy)imidazol-w-yl)-2-butenoic acid (B-2333) 1-[(z-alkyl-q-(([substituted]heteroaryl)thio))oxazol-w-yl]-3-hydroxy-3-([substituted]-1H-1,2,4-triazol-3-yl)-propenone (B-2334) 1-(q-(([substituted]aryl)amino)oxazol-w-yl)-3-hydroxy-3-([substituted]-1H-1,2,4-triazol-3-yl)-propenone (B-2335) 4-[(z-alkyl-q-(([substituted]heteroaryl)thio))pyrrol-w-yl]-2-hydroxy-4-oxo-2-butenoic acid (B-2336) 3-hydroxy-3-([substituted]-2H-tetrazol-5-yl)-1-(q-((([substituted]heteroaryl)thio)pyridin-w-yl)-propenone (B-2337) 1-(q-(([substituted]heteroaryl)carbonylamino)isoxazol-w-yl)-3-hydroxy-3-([substituted]-1H-1,2,4-triazol-3-yl)-propenone (B-2338) 1-[(z-alkyl-q-(([substituted]heteroaryl)sulfonylamino))thiazol-w-yl]-3-hydroxy-3-([substituted]-2H-tetrazol-5-yl)-propenone (B-2339) 4-[(q-(([substituted]heteroaryl)aminocarbonyl)-z-halogeno)thiazol-w-yl]-2-hydroxy-4-oxo-2-butenoic acid (B-2340) 1-[(q-([substituted]aryl)-z-halogeno)thiophen-w-yl]-3-hydroxy-3-([substituted]-2H-tetrazol-5-yl)-propenone (B-2341) 1-[(q-(([substituted]heteroaryl)carboxy)-z-halogeno)oxazol-w-yl]-3-hydroxy-3-([substituted]-2H-tetrazol-5-yl)-propenone (B-2342) 1-[(z-alkyl-q-(([substituted]heteroaryl)sulfonyl))isoxazol-w-yl]-3-hydroxy-3-([substituted]-1H-1,2,4-triazol-3-yl)-propenone (B-2343) 1-[(q-(([substituted]heteroaryl)amino)-z-halogeno)pyrrol-w-yl]-3-hydroxy-3-([substituted]-1H-1,2,4-triazol-3-yl)-propenone (B-2344) 4-(q-(([substituted]heteroaryl)carbonylamino)pyrrol-w-yl)-2-hydroxy-4-oxo-2-butenoic acid (B-2345) 1-[(z-halogeno-q-(([substituted]heteroaryl)oxycarbonyl))pyridin-w-yl]-3-hydroxy-3-([substituted]-1H-1,2,4-triazol-3-yl)-propenone (B-2346) 3-hydroxy-1-(nH-q-(1-hydroxy-([substituted]heteroaryl)methyl)pyrazol-w-yl)-3-([substituted]-2H-tetrazol-5-yl)-propenone (B-2347) 1-[nH-(q-(([substituted]aryl)alkenyl)-z-alkyl)imidazol-w-yl]-3-hydroxy-3-([substituted]-2H-tetrazol-5-yl)-propenone (B-2348) 1-[(z-alkyl-q-(([substituted]heteroaryl)carbonylamino))furan-w-yl]-3-hydroxy-3-([substituted]-1H-1,2,4-triazol-3-yl)-propenone (B-2349) 4-[nH-(z-halogeno-q-(([substituted]heteroaryl)oxy))pyrazol-w-yl]-2-hydroxy-4-oxo-2-butenoic acid (B-2350) 4-[nH-(z-alkyl-q-(([substituted]aryl)aminocarbonyl))pyrazol-w-yl]-2-hydroxy-4-oxo-2-butenoic acid (B-2351) 1-[nH-(z-alkyl-q-(([substituted]aryl)alkyl))pyrazol-w-yl]-3-hydroxy-3-([substituted]-1H-1,2,4-triazol-3-yl)-propenone (B-2352) 1-[(q-(([substituted]aryl)aminocarbonyl)-z-halogeno)thiazol-w-yl]-3-hydroxy-3-([substituted]-1H-1,2,4-triazol-3-yl)-propenone (B-2353) 4-[(q-(([substituted]aryl)carbonylamino)-z-halogeno)furan-w-yl]-2-hydroxy-4-oxo-2-butenoic acid (B-2354) 2-hydroxy-4-oxo-4-(q-(([substituted]heteroaryl)sulfonylamino)oxazol-w-yl)-2-butenoic acid (B-2355) 1-(nH-q-(([substituted]aryl)alkyl)imidazol-w-yl)-3-hydroxy-3-([substituted]-1H-1,2,4-triazol-3-yl)-propenone (B-2356) 1-[(q-(([substituted]heteroaryl)alkyl)-z-halogeno)pyridin-w-yl]-3-hydroxy-3-([substituted]-2H-tetrazol-5-yl)-propenone (B-2357) 3-hydroxy-1-(nH-q-(([substituted]aryl)sulfinyl)imidazol-w-yl)-3-([substituted]-1H-1,2,4-triazol-3-yl)-propenone (B-2358) 1-[nH-(z-alkyl-q-(([substituted]heteroaryl)oxycarbonyl))pyrazol-yl]-3-hydroxy-3-([substituted]-2H-tetrazol-5-yl)-propenone (B-2359) 1-(q-(([substituted]aryl)carbonylamino)pyrrol-w-yl)-3-hydroxy-3-([substituted]-1H-1,2,4-triazol-3-yl)-propenone (B-2360) 4-[(z-halogeno-q-(([substituted]aryl)oxy))furan-w-yl]-2-hydroxy-4-oxo-2-butenoic acid (B-2361) 1-[(q-(([substituted]aryl)alkenyl)-z-halogeno)pyridin-w-yl]-3-hydroxy-3-([substituted]-2H-tetrazol-5-yl)-propenone (B-2362) 1-(q-(([substituted]aryl)aminocarbonyl)pyridin-w-yl)-3-hydroxy-3-([substituted]-1H-1,2,4-triazol-3-yl)-propenone (B-2363) 3-hydroxy-1-(q-(1-hydroxy-([substituted]aryl)methyl)isoxazol-w-yl)-3-([substituted]-2H-tetrazol-5-yl)-propenone (B-2364) 4-[nH-(z-halogeno-q-(([substituted]aryl)sulfonyl))imidazol-w-yl]-2-hydroxy-4-oxo-2-butenoic acid (B-2365) 4-(q-(([substituted]heteroaryl)carbonyl)isoxazol-w-yl)-2-hydroxy-4-oxo-2-butenoic acid (B-2366) 1-[(q-(([substituted]heteroaryl)alkenyl)-z-alkyl)thiophen-w-yl]-3-hydroxy-3-([substituted]-2H-tetrazol-5-yl)-propenone (B-2367) 3-hydroxy-1-(q-(([substituted]heteroaryl)oxy)oxazol-w-yl)-3-([substituted]-2H-tetrazol-5-yl)-propenone (B-2368) 4-[(q-(([substituted]aryl)carbonyl)-z-halogeno)oxazol-w-yl]-2-hydroxy-4-oxo-2-butenoic acid (B-2369) 2-hydroxy-4-oxo-4-(q-(([substituted]heteroaryl)oxycarbonyl)thiophen-w-yl)-2-butenoic acid (B-2370) 1-[(q-(([substituted]heteroaryl)alkenyl)-z-halogeno)oxazol-w-yl]-3-hydroxy-3-([substituted]-2H-tetrazol-5-yl)-propenone (B-2371) 1-[(z-alkyl-q-(([substituted]aryl)alkyl))pyrrol-w-yl]-3-hydroxy-3-([substituted]-1H-1,2,4-triazol-3-yl)-propenone (B-2372) 4-[(q-(([substituted]aryl)aminosulfonyl)-z-halogeno)isoxazol-w-yl]-2-hydroxy-4-oxo-2-butenoic acid (B-2373) 4-[(z-alkyl-q-(([substituted]aryl)aminocarbonyl))pyridin-w-yl]-2-hydroxy-4-oxo-2-butenoic acid (B-2374) 4-(q-(([substituted]heteroaryl)carbonylamino)oxazol-w-yl)-2-hydroxy-4-oxo-2-butenoic acid (B-2375) 4-(nH-q-(([substituted]heteroaryl)amino)imidazol-w-yl)-2-hydroxy-4-oxo-2-butenoic acid (B-2376) 2-hydroxy-4-oxo-4-(q-(([substituted]heteroaryl)sulfonyl)furan-w-yl)-2-butenoic acid (B-2377) 1-[(z-alkyl-q-(([substituted]aryl)carbonyl))pyridin-w-yl]-3-hydroxy-3-([substituted]-2H-tetrazol-5-yl)-propenone (B-2378) 1-[(q-(([substituted]aryl)carboxy)-z-halogeno)pyridin-w-yl]-3-hydroxy-3-([substituted]-2H-tetrazol-5-yl)-propenone (B-2379) 3-hydroxy-1-(nH-q-(([substituted]aryl)sulfonyl)pyrazol-w-yl)-3-([substituted]-1H-1,2,4-triazol-3-yl)-propenone (B-2380) 2-hydroxy-4-oxo-4-(q-(([substituted]heteroaryl)sulfinyl)isoxazol-w-yl)-2-butenoic acid (B-2381) 1-[(z-halogeno-q-(([substituted]aryl)thio))thiazol-w-yl]-3-hydroxy-3-([substituted]-2H-tetrazol-5-yl)-propenone (B-2382) 4-[(z-alkyl-q-(([substituted]aryl)sulfonylamino))pyrrol-w-yl]-2-hydroxy-4-oxo-2-butenoic acid (B-2383) 1-[(z-alkyl-q-(([substituted]aryl)sulfonyl))isoxazol-w-yl]-3-hydroxy-3-([substituted]-1H-1,2,4-triazol-3-yl)-propenone (B-2384) 1-[(z-alkyl-q-(([substituted]aryl)alkyl))thiophen-w-yl]-3-hydroxy-3-([substituted]-2H-tetrazol-5-yl)-propenone (B-2385) 1-(q-(([substituted]aryl)alkyl)oxazol-w-yl)-3-hydroxy-3-([substituted]-1H-1,2,4-triazol-3-yl)-propenone (B-2386) 1-[(q-(([substituted]heteroaryl)carbonyl)-z-halogeno)pyrrol-w-yl]-3-hydroxy-3-([substituted]-2H-tetrazol-5-yl)-propenone (B-2387) 1-[(q-(([substituted]heteroaryl)carboxy)-z-halogeno)pyrrol-w-yl]-3-hydroxy-3-([substituted]-1H-1,2,4-triazol-3-yl)-propenone (B-2388) 1-[nH-(z-halogeno-q-(([substituted]aryl)sulfonyl))pyrazol-w-yl]-3-hydroxy-3-([substituted]-1H-1,2,4-triazol-3-yl)-propenone (B-2389) 1-(q-(([substituted]aryl)alkenyl)pyridin-w-yl)-3-hydroxy-3-([substituted]-2H-tetrazol-5-yl)-propenone (B-2390) 4-[(z-alkyl-q-(([substituted]heteroaryl)carbonyl))pyridin-w-yl]-2-hydroxy-4-oxo-2-butenoic acid (B-2391) 1-[(z-halogeno-q-(([substituted]aryl)sulfonylamino))isoxazol-w-yl]-3-hydroxy-3-([substituted]-1H-1,2,4-triazol-3-yl)-propenone (B-2392) 4-[(z-halogeno-q-([substituted]heteroaryl))pyridin-w-yl]-2-hydroxy-4-oxo-2-butenoic acid (B-2393) 1-[(z-alkyl-q-(1-hydroxy-([substituted]aryl)methyl))isoxazol-w-yl]-3-hydroxy-3-([substituted]-1H-1,2,4-triazol-3-yl)-propenone (B-2394) 3-hydroxy-1-(q-(([substituted]aryl)oxy)isoxazol-w-yl)-3-([substituted]-2H-tetrazol-5-yl)-propenone (B-2395) 1-[(q-(([substituted]heteroaryl)alkenyl)-z-halogeno)isoxazol-w-yl]-3-hydroxy-3-([substituted]-2H-tetrazol-5-yl)-propenone (B-2396) 4-[(z-halogeno-q-(([substituted]aryl)oxycarbonyl))oxazol-w-yl]-2-hydroxy-4-oxo-2-butenoic acid (B-2397) 1-[nH-(q-(([substituted]aryl)amino)-z-halogeno)pyrazol-w-yl]-3-hydroxy-3-([substituted]-1H-1,2,4-triazol-3-yl)-propenone (B-2398) 1-[nH-(z-alkyl-q-(([substituted]aryl)sulfonyl))imidazol-w-yl]-3-hydroxy-3-([substituted]-2H-tetrazol-5-yl)-propenone (B-2399) 1-[(z-alkyl-q-(([substituted]heteroaryl)oxycarbonyl))thiophen-w-yl]-3-hydroxy-3-([substituted]-2H-tetrazol-5-yl)-propenone (B-2400) 1-[(z-alkyl-q-(([substituted]aryl)carboxy))furan-w-yl]-3-hydroxy-3-([substituted]-2H-tetrazol-5-yl)-propenone (B-2401) 1-[nH-(q-(([substituted]aryl)carbonylamino)-z-halogeno)pyrazol-w-yl]-3-hydroxy-3-([substituted]-1H-1,2,4-triazol-3-yl)-propenone (B-2402) 1-[(z-alkyl-q-(([substituted]aryl)sulfinyl))pyrrol-w-yl]-3-hydroxy-3-([substituted]-1H-1,2,4-triazol-3-yl)-propenone (B-2403) 3-hydroxy-1-(q-(([substituted]aryl)thio)thiazol-w-yl)-3-([substituted]-1H-1,2,4-triazol-3-yl)-propenone (B-2404) 4-(q-(([substituted]heteroaryl)aminocarbonyl)thiophen-w-yl)-2-hydroxy-4-oxo-2-butenoic acid (B-2405) 1-[(q-(([substituted]heteroaryl)amino)-z-halogeno)oxazol-w-yl]-3-hydroxy-3-([substituted]-2H-tetrazol-5-yl)-propenone (B-2406) 4-[nH-(z-alkyl-q-(([substituted]heteroaryl)thio))pyrazol-w-yl]-2-hydroxy-4-oxo-2-butenoic acid (B-2407) 1-(q-([substituted]aryl)pyridin-w-yl)-3-hydroxy-3-([substituted]-2H-tetrazol-5-yl)-propenone (B-2408) 3-hydroxy-1-(q-(([substituted]aryl)oxycarbonyl)furan-w-yl)-3-([substituted]-1H-1,2,4-triazol-3-yl)-propenone (B-2409) 1-(q-(([substituted]aryl)aminocarbonyl)pyrrol-w-yl)-3-hydroxy-3-([substituted]-2H-tetrazol-5-yl)-propenone (B-2410) 3-hydroxy-1-(q-(([substituted]heteroaryl)oxy)pyridin-w-yl)-3-([substituted]-2H-tetrazol-5-yl)-propenone (B-2411) 1-[(q-(([substituted]aryl)aminosulfonyl)-z-halogeno)furan-w-yl]-3-hydroxy-3-([substituted]-2H-tetrazol-5-yl)-propenone (B-2412) 1-(q-(([substituted]heteroaryl)carbonylamino)thiazol-w-yl)-3-hydroxy-3-([substituted]-1H-1,2,4-triazol-3-yl)-propenone (B-2413) 1-[(q-(([substituted]heteroaryl)amino)-z-halogeno)thiophen-w-yl]-3-hydroxy-3-([substituted]-2H-tetrazol-5-yl)-propenone (B-2414) 1-[(z-halogeno-q-(([substituted]heteroaryl)oxycarbonyl))thiophen-w-yl]-3-hydroxy-3-([substituted]-1H-1,2,4-triazol-3-yl)-propenone (B-2415) 1-[(z-alkyl-q-(1-hydroxy-([substituted]aryl)methyl))pyridin-w-yl]-3-hydroxy-3-([substituted]-2H-tetrazol-5-yl)-propenone (B-2416) 3-hydroxy-1-(q-(([substituted]aryl)sulfonylamino)furan-w-yl)-3-([substituted]-1H-1,2,4-triazol-3-yl)-propenone (B-2417) 1-[nH-(q-(([substituted]aryl)amino)-z-halogeno)pyrazol-w-yl]-3-hydroxy-3-([substituted]-2H-tetrazol-5-yl)-propenone (B-2418) 1-[(z-alkyl-q-(([substituted]aryl)sulfonylamino))pyrrol-w-yl]-3-hydroxy-3-([substituted]-1H-1,2,4-triazol-3-yl)-propenone (B-2419) 1-(q-(([substituted]heteroaryl)aminosulfonyl)furan-w-yl)-3-hydroxy-3-([substituted]-2H-tetrazol-5-yl)-propenone (B-2420) 1-[(q-(([substituted]heteroaryl)alkenyl)-z-halogeno)oxazol-w-yl]-3-hydroxy-3-([substituted]-1H-1,2,4-triazol-3-yl)-propenone (B-2421) 1-[(q-(([substituted]heteroaryl)carbonyl)-z-halogeno)thiazol-w-yl]-3-hydroxy-3-([substituted]-2H-tetrazol-5-yl)-propenone (B-2422) 1-[(z-alkyl-q-(([substituted]aryl)oxycarbonyl))thiophen-w-yl]-3-hydroxy-3-([substituted]-1H-1,2,4-triazol-3-yl)-propenone (B-2423) 1-[nH-(z-alkyl-q-(([substituted]heteroaryl)amino))imidazol-w-yl]-3-hydroxy-3-([substituted]-2H-tetrazol-5-yl)-propenone (B-2424) 3-hydroxy 1-(q-(([substituted]aryl)sulfinyl)thiazol-w-yl)-3-([substituted]-1H-1,2,4-triazol-3-yl)-propenone (B-2425) 1-[(q-(([substituted]heteroaryl)alkenyl)-z-halogeno)thiazol-w-yl]-3-hydroxy-3-([substituted]-2H-tetrazol-5-yl)-propenone (B-2426) 4-[(z-halogeno-q-(([substituted]aryl)sulfonylamino))isoxazol-w-yl]-2-hydroxy-4-oxo-2-butenoic acid (B-2427) 1-[nH-(z-alkyl-q-(([substituted]heteroaryl)carbonyl))imidazol-w-yl]-3-hydroxy-3-([substituted]-1H-1,2,4-triazol-3-yl)-propenone (B-2428) 1-[nH-(q-(([substituted]aryl)aminocarbonyl)-z-halogeno))imidazol-w-yl]-3-hydroxy-3-([substituted]-1H-1,2,4-triazol-3-yl)-propenone (B-2429) 1-[(z-halogeno-q-(([substituted]heteroaryl)sulfinyl))thiophen-w-yl]-3-hydroxy-3-([substituted]-2H-tetrazol-5-yl)-propenone (B-2430) 2-hydroxy-4-oxo-4-(q-(([substituted]aryl)thio)oxazol-w-yl)-2-butenoic acid (B-2431) 4-[(z-alkyl-q-(([substituted]aryl)carbonyl))furan-w-yl]-2-hydroxy-4-oxo-2-butenoic acid (B-2432) 1-[nH-(z-alkyl-q-(([substituted]aryl)carbonyl))imidazol-w-yl]-3-hydroxy-3-([substituted]-1H-1,2,4-triazol-3-yl)-propenone (B-2433) 1-[(q-(([substituted]aryl)carbonyl)-z-halogeno)thiazol-w-yl]-3-hydroxy-3-([substituted]-1H-1,2,4-triazol-3-yl)-propenone (B-2434) 1-[(z-alkyl-q-(([substituted]heteroaryl)carbonylamino))pyridin-w-yl]-3-hydroxy-3-([substituted]-1H-1,2,4-triazol-3-yl)-propenone (B-2435) 1-[nH-(q-(([substituted]aryl)alkenyl)-z-halogeno)imidazol-w-yl]-3-hydroxy-3-([substituted]-2H-tetrazol-5-yl)-propenone (B-2436) 1-[(z-alkyl-q-(([substituted]heteroaryl)carbonylamino))pyrrol-w-yl]-3-hydroxy-3-([substituted]-1H-1,2,4-triazol-3-yl)-propenone (B-2437) 1-[nH-(q-(([substituted]aryl)aminosulfonyl)-z-halogeno)imidazol-w-yl]-3-hydroxy-3-([substituted]-2H-tetrazol-5-yl)-propenone (B-2438) 2-hydroxy-4-oxo-4-(q-(([substituted]aryl)oxy)thiazol-w-yl)-2-butenoic acid (B-2439) 4-[(z-alkyl-q-(([substituted]aryl)sulfonyl))oxazol-w-yl]-2-hydroxy-4-oxo-2-butenoic acid (B-2440) 2-hydroxy-4-oxo-4-(q-(([substituted]aryl)sulfonyl)pyridin-w-yl)-2-butenoic acid (B-2441) 4-[nH-(q-(([substituted]heteroaryl)aminosulfonyl)-z-halogeno)pyrazol-w-yl]-2-hydroxy-4-oxo-2-butenoic acid (B-2442) 4-[(z-alkyl-q-(([substituted]aryl)sulfonylamino))thiophen-w-yl]-2-hydroxy-4-oxo-2-butenoic acid (B-2443) 1-[nH-(q-(([substituted]heteroaryl)carboxy)-z-halogeno)pyrazol-w-yl]-3-hydroxy-3-([substituted]-1H-1,2,4-triazol-3-yl)-propenone (B-2444) 1-(q-(([substituted]heteroaryl)amino)pyridin-w-yl)-3-hydroxy-3-([substituted]-1H-1,2,4-triazol-3-yl)-propenone (B-2445) 1-(q-(([substituted]aryl)carboxy)isoxazol-w-yl)-3-hydroxy-3-([substituted]-1H-1,2,4-triazol-3-yl)-propenone (B-2446) 3-hydroxy-1-(q-(1-hydroxy-([substituted]heteroaryl)methyl)thiophen-w-yl)-3-([substituted]-2H-tetrazol-5-yl)-propenone (B-2447) 1-[(z-halogeno-q-(([substituted]heteroaryl)sulfonyl))thiophen-w-yl]-3-hydroxy-3-([substituted]-1H-1,2,4-triazol-3-yl)-propenone (B-2448) 1-(q-(([substituted]heteroaryl)aminosulfonyl)pyrrol-w-yl)-3-hydroxy-3-([substituted]-1H-1,2,4-triazol-3-yl)-propenone (B-2449) 1-[nH-(z-alkyl-q-(1-hydroxy-([substituted]aryl)methyl))imidazol-w-yl]-3-hydroxy-3-([substituted]-1H-1,2,4-triazol-3-yl)-propenone (B-2450) 1-[nH-(z-alkyl-q-(([substituted]aryl)carboxy))pyrazol-w-yl]-3-hydroxy-3-([substituted]-2H-tetrazol-5-yl)-propenone (B-2451) 3-hydroxy-1-(q-(([substituted]heteroaryl)sulfinyl)pyrrol-w-yl)-3-([substituted]-2H-tetrazol-5-yl)-propenone (B-2452) 2-hydroxy-4-oxo-4-(q-(([substituted]aryl)sulfinyl)pyridin-w-yl)-2-butenoic acid (B-2453) 3-hydroxy-1-(q-(([substituted]aryl)oxy)oxazol-w-yl)-3-([substituted]-1H-1,2,4-triazol-3-yl)-propenone (B-2454) 1-[(z-alkyl-q-(([substituted]aryl)sulfinyl))pyridin-w-yl]-3-hydroxy-3-([substituted]-1H-1,2,4-triazol-3-yl)-propenone (B-2455) 4-[nH-(q-(([substituted]aryl)alkyl)-z-halogeno)pyrazol-w-yl]-2-hydroxy-4-oxo-2-butenoic acid (B-2456) 4-[(z-alkyl-q-(([substituted]aryl)oxy))isoxazol-w-yl]-2-hydroxy-4-oxo-2-butenoic acid (B-2457) 4-[nH-(z-alkyl-q-(1-hydroxy-([substituted]aryl)methyl))thiazol-w-yl]-2-hydroxy-4-oxo-2-butenoic acid (B-2458) 1-[nH-(q-(([substituted]heteroaryl)carbonyl)-z-halogeno)imidazol-w-yl]-3-hydroxy-3-([substituted]-1H-1,2,4-triazol-3-yl)-propenone (B-2459) 1-[nH-(q-(([substituted]heteroaryl)alkenyl)-z-halogeno)imidazol-w-yl]-3-hydroxy-3-([substituted]-1H-1,2,4-triazol-3-yl)-propenone (B-2460) 1-(q-(([substituted]heteroaryl)aminosulfonyl)oxazol-w-yl)-3-hydroxy-3-([substituted]-1H-1,2,4-triazol-3-yl)-propenone (B-2461) 1-[nH-(q-(([substituted]heteroaryl)amino)-z-halogeno)imidazol-w-yl]-3-hydroxy-3-([substituted]-2H-tetrazol-5-yl)-propenone (B-2462) 2-hydroxy-4-oxo-4-(q-(([substituted]aryl)sulfinyl)oxazol-w-yl)-2-butenoic acid (B-2463) 3-hydroxy-1-(q-(([substituted]heteroaryl)oxy)isoxazol-w-yl)-3-([substituted]-1H-1,2,4-triazol-3-yl)-propenone (B-2464) 4-[(z-alkyl-q-(([substituted]aryl)aminocarbonyl))furan-w-yl]-2-hydroxy-4-oxo-2-butenoic acid (B-2465) 4-[nH-(z-alkyl-q-(([substituted]aryl)sulfonyl))pyrazol-w-yl]-2-hydroxy-4-oxo-2-butenoic acid (B-2466) 4-[nH-(z-alkyl-q-(([substituted]aryl)carbonyl))imidazol-w-yl]-2-hydroxy-4-oxo-2-butenoic acid (B-2467) 1-[nH-(z-alkyl-q-(([substituted]heteroaryl)oxy))imidazol-w-yl]-3-hydroxy-3-([substituted]-2H-tetrazol-5-yl)-propenone (B-2468) 4-[(z-alkyl-q-(([substituted]heteroaryl)sulfonylamino))furan-w-yl]-2-hydroxy-4-oxo-2-butenoic acid (B-2469) 4-[(z-halogeno-q-([substituted]heteroaryl))furan-w-yl]-2-hydroxy-4-oxo-2-butenoic acid (B-2470) 3-hydroxy-3-([substituted]-2H-tetrazol-5-yl)-1-(q-(([substituted]heteroaryl)thio)isoxazol-w-yl)-propenone (B-2471) 3-hydroxy-1-(q-(([substituted]aryl)oxy)pyrrol-w-yl)-3-([substituted]-2H-tetrazol-5-yl)-propenone (B-2472) 3-hydroxy-1(nH-q-(([substituted]aryl)oxy)pyrazol-w-yl)-3-([substituted]-1H-1,2,4-triazol-3-yl)-propenone (B-2473) 4-(q-(([substituted]aryl)alkyl)pyridin-w-yl)-2-hydroxy-4-oxo-2-butenoic acid (B-2474) 3-hydroxy-1-(q-(1-hydroxy-([substituted]aryl)methyl)pyrrol-w-yl)-3-([substituted]-1H-1,2,4-triazol-3-yl)-propenone (B-2475) 1-[(q-(([substituted]heteroaryl)carboxy)-z-alkyl)thiazol-w-yl]-3-hydroxy-3-([substituted]-2H-tetrazol-5-yl)-propenone (B-2476) 4-[nH-(q-(([substituted]heteroaryl)carbonyl)-z-halogeno)imidazol-w-yl]-2-hydroxy-4-oxo-2-butenoic acid
(B-2477) 1-[(z-alkyl-q-(([substituted]heteroaryl)thio))pyridin-w-yl]-3-hydroxy-3-([substituted]-2H-tetrazol-5-yl)-propenone
(B-2478) 3-hydroxy-1-(q-(([substituted]heteroaryl)oxy)thiophen-w-yl)-3-([substituted]-1H-1,2,4-triazol-3-yl)-propenone
(B-2479) 1-[(q-(([substituted]aryl)alkyl)-z-halogeno)oxazol-w-yl]-3-hydroxy-3-([substituted]-2H-tetrazol-5-yl)-propenone
(B-2480) 1-[(z-alkyl-q-(([substituted]heteroaryl)carbonyl))furan-w-yl]-3-hydroxy-3-([substituted]-1H-1,2,4-triazol-3-yl)-propenone
(B-2481) 1-[(z-alkyl-q-(([substituted]heteroaryl)sulfonylamino))pyridin-w-yl]-3-hydroxy-3-([substituted]-2H-tetrazol-5-yl)-propenone
(B-2482) 1-[(z-alkyl-q-(([substituted]aryl)oxy))thiophen-w-yl]-3-hydroxy-3-([substituted]-2H-tetrazol-5-yl)-propenone
(B-2483) 4-[nH-(z-alkyl-q-(([substituted]heteroaryl)sulfinyl))imidazol-w-yl]-2-hydroxy-4-oxo-2-butenoic acid
(B-2484) 4-(q-(([substituted]aryl)carbonyl)isoxazol-w-yl)-2-hydroxy-4-oxo-2-butenoic acid
(B-2485) 1-(q-(([substituted]aryl)carbonylamino)furan-w-yl)-3-hydroxy-3-([substituted]-2H-tetrazol-5-yl)-propenone
(B-2486) 4-[nH-(q-(([substituted]heteroaryl)carbonylamino)-z-halogeno)imidazol-w-yl]-2-hydroxy-4-oxo-2-butenoic acid
(B-2487) 4-(q-(([substituted]aryl)aminocarbonyl)pyridin-w-yl)-2-hydroxy-4-oxo-2-butenoic acid
(B-2488) 2-hydroxy-4-oxo-4-(nH-q-(([substituted]aryl)sulfonyl)imidazol-w-yl)-2-butenoic acid
(B-2489) 4-[z-alkyl-q-(([substituted]aryl)sulfonylamino))isoxazol-w-yl]-2-hydroxy-4-oxo-2-butenoic acid
(B-2490) 1-(q-(([substituted]aryl)carboxy)oxazol-w-yl)-3-hydroxy-3-([substituted]-2H-tetrazol-5-yl)-propenone
(B-2491) 4-[nH-(q-(([substituted]aryl)carboxy)-z-halogeno)pyrazol-w-yl]-2-hydroxy-4-oxo-2-butenoic acid
(B-2492) 1-(nH-q-(([substituted]heteroaryl)alkenyl)imidazol-w-yl)-3-hydroxy-3-([substituted]-1H-1,2,4-triazol-3-yl)-propenone
(B-2493) 1-[(z-halogeno-q-(([substituted]aryl)oxycarbonyl))isoxazol-w-yl]-3-hydroxy-3-([substituted]-1H-1,2,4-triazol-3-yl)-propenone
(B-2494) 1-[(z-alkyl-q-(([substituted]heteroaryl)amino))thiophen-w-yl]-3-hydroxy-3-([substituted]-1H-1,2,4-triazol-3-yl)-propenone
(B-2495) 1-[(q-(([substituted]heteroaryl)alkenyl)-z-halogeno)furan-w-yl]-3-hydroxy-3-([substituted]-2H-tetrazol-5-yl)-propenone
(B-2496) 1-[(q-(([substituted]aryl)alkenyl)-z-alkyl)oxazol-w-yl]-3-hydroxy-3-([substituted]-1H-1,2,4-triazol-3-yl)-propenone
(B-2497) 3-hydroxy-1-(q-(([substituted]aryl)sulfonyl)furan-w-yl)-3-([substituted]-1H-1,2,4-triazol-3-yl)-propenone
(B-2498) 4-[(z-halogeno-q-(([substituted]aryl)sulfonyl))thiazol-w-yl]-2-hydroxy-4-oxo-2-butenoic acid
(B-2499) 1-(q-(([substituted]heteroaryl)alkenyl)furan-w-yl)-3-hydroxy-3-([substituted]-2H-tetrazol-5-yl)-propenone
(B-2500) 1-(nH-q-(([substituted]aryl)aminocarbonyl)imidazol-w-yl)-3-hydroxy-3-([substituted]-1H-1,2,4-triazol-3-yl)-propenone
(B-2501) 1-[(q-(([substituted]aryl)alkenyl)-z-halogeno)thiazol-w-yl]-3-hydroxy-3-([substituted]-1H-1,2,4-triazol-3-yl)-propenone
(B-2502) 1-[nH-(z-alkyl-q-(([substituted]aryl)carboxy))imidazol-w-yl]-3-hydroxy-3-([substituted]-1H-1,2,4-triazol-3-yl)-propenone
(B-2503) 1-(q-(([substituted]aryl)alkyl)thiophen-w-yl)-3-hydroxy-3-([substituted]-1H-1,2,4-triazol-3-yl)-propenone
(B-2504) 2-hydroxy-4-oxo-4-(nH-q-(([substituted]aryl)oxycarbonyl)imidazol-w-yl)-2-butenoic acid
(B-2505) 4-[(q-(([substituted]aryl)-z-halogeno)pyrrol-w-yl]-2-hydroxy-4-oxo-2-butenoic acid
(B-2506) 4-[(z-alkyl-q-(([substituted]heteroaryl)aminosulfonyl))oxazol-w-yl]-2-hydroxy-4-oxo-2-butenoic acid
(B-2507) 1-(q-(([substituted]heteroaryl)carbonylamino)thiazol-w-yl)-3-hydroxy-3-([substituted]-2H-tetrazol-5-yl)-propenone
(B-2508) 4-[(q-(([substituted]aryl)aminocarbonyl)-z-halogeno)furan-w-yl]-2-hydroxy-4-oxo-2-butenoic acid
(B-2509) 3-hydroxy-1-(q-(1-hydroxy-([substituted]heteroaryl)methyl)pyridin-w-yl)-3-([substituted]-2H-tetrazol-5-yl)-propenone
(B-2510) 4-[(q-(([substituted]heteroaryl)carbonyl)-z-halogeno)thiazol-w-yl]-2-hydroxy-4-oxo-2-butenoic acid
(B-2511) 1-[(z-alkyl-q-(([substituted]aryl)oxycarbonyl))furan-w-yl]-3-hydroxy-3-([substituted]-2H-tetrazol-5-yl)-propenone
(B-2512) 4-[(q-(([substituted]heteroaryl)alkenyl)-z-alkyl)thiophen-w-yl]-2-hydroxy-4-oxo-2-butenoic acid
(B-2513) 1-[(z-halogeno-q-(([substituted]aryl)sulfonylamino))pyridin-w-yl]-3-hydroxy-3-([substituted]-1H-1,2,4-triazol-3-yl)-propenone
(B-2514) 4-[nH-(z-alkyl-q-(([substituted]heteroaryl)amino))pyrazol-w-yl]-2-hydroxy-4-oxo-2-butenoic acid
(B-2515) 3-hydroxy-3-([substituted]-2H-tetrazol-5-yl)-1-(q-(([substituted]aryl)thio)pyrrol-w-yl)-propenone
(B-2516) 1-[(q-(([substituted]heteroaryl)carbonylamino)-z-halogeno)thiazol-w-yl]-3-hydroxy-3-([substituted]-1H-1,2,4-triazol-3-yl)-propenone
(B-2517) 1-(q-(([substituted]aryl)alkenyl)thiophen-w-yl)-3-hydroxy-3-([substituted]-1H-1,2,4-triazol-3-yl)-propenone
(B-2518) 1-[(z-alkyl-q-(([substituted]heteroaryl)sulfonylamino))pyrrol-w-yl]-3-hydroxy-3-([substituted]-1H-1,2,4-triazol-3-yl)-propenone
(B-2519) 1-[(z-halogeno-q-(([substituted]aryl)sulfonyl))pyrrol-w-yl]-3-hydroxy-3-([substituted]-1H-1,2,4-triazol-3-yl)-propenone
(B-2520) 4-(q-(([substituted]aryl)aminosulfonyl)furan-w-yl)-2-hydroxy-4-oxo-2-butenoic acid
(B-2521) 2-hydroxy-4-oxo-4-(q-(([substituted]heteroaryl)sulfonylamino)furan-w-yl)-2-butenoic acid
(B-2522) 2-hydroxy-4-oxo-4-(q-(([substituted]aryl)oxy)isoxazol-w-yl)-2-butenoic acid
(B-2523) 1-[(z-halogeno-q-(([substituted]heteroaryl)oxycarbonyl))pyrrol-w-yl]-3-hydroxy-3-([substituted]-1H-1,2,4-triazol-3-yl)-propenone
(B-2524) 4-(q-(([substituted]aryl)amino)thiazol-w-yl)-2-hydroxy-4-oxo-2-butenoic acid
(B-2525) 1-(q-(([substituted]heteroaryl)carbonylamino)pyridin-w-yl)-3-hydroxy-3-([substituted]-2H-tetrazol-5-yl)-propenone
(B-2526) 4-[(z-alkyl-q-(([substituted]aryl)carbonylamino))oxazol-w-yl]-2-hydroxy-4-oxo-2-butenoic acid
(B-2527) 2-hydroxy-4-(q-(1-hydroxy-([substituted]aryl)methyl)oxazol-w-yl)-4-oxo-2-butenoic acid (B-2528) 4-(nH-q-(([substituted]heteroaryl)alkyl)imidazol-w-yl)-2-hydroxy-4-oxo-2-butenoic acid
(B-2529) 1-[(q-(([substituted]heteroaryl)carboxy)-z-alkyl)oxazol-w-yl]-3-hydroxy-3-([substituted]-2H-tetrazol-5-yl)-propenone
(B-2530) 1-(q-(([substituted]aryl)carbonylamino)pyridin-w-yl)-3-hydroxy-3-([substituted]-2H-tetrazol-5-yl)-propenone
(B-2531) 4-[(q-(([substituted]heteroaryl)aminosulfonyl)-z-halogeno)isoxazol-w-yl]-2-hydroxy-4-oxo-2-butenoic acid
(B-2532) 2-hydroxy-4-oxo-4-(nH-q-(([substituted]heteroaryl)thio)pyrazol-w-yl)-2-butenoic acid
(B-2533) 1-[(z-halogeno-q-(([substituted]heteroaryl)thio))pyrrol-w-yl]-3-hydroxy-3-([substituted]-2H-tetrazol-5-yl)-propenone
(B-2534) 4-[(z-halogeno-q-(([substituted]aryl)thio))oxazol-w-yl]-2-hydroxy-4-oxo-2-butenoic acid
(B-2535) 2-hydroxy-4-oxo-4-(nH-q-(([substituted]aryl)oxy)pyrazol-w-yl)-2-butenoic acid
(B-2536) 1-[(z-halogeno-q-(([substituted]heteroaryl)sulfonylamino))furan-w-yl]-3-hydroxy-3-([substituted]-1H-1,2,4-triazol-3-yl)-propenone
(B-2537) 1-[nH-(z-alkyl-q-([substituted]aryl))pyrazol-w-yl]-3-hydroxy-3-([substituted]-2H-tetrazol-5-yl)-propenone
(B-2538) 1-[nH-(q-(([substituted]aryl)alkenyl)-z-halogeno)pyrazol-w-yl]-3-hydroxy-3-([substituted]-2H-tetrazol-5-yl)-propenone
(B-2539) 1-[(z-alkyl-q-(([substituted]heteroaryl)carbonylamino))thiophen-w-yl]-3-hydroxy-3-([substituted]-2H-tetrazol-5-yl)-propenone
(B-2540) 4-[(q-(([substituted]aryl)alkyl)-z-halogeno)furan-w-yl]-2-hydroxy-4-oxo-2-butenoic acid
(B-2541) 1-[(z-alkyl-q-(([substituted]heteroaryl)oxy))thiazol-w-yl]-3-hydroxy-3-([substituted]-1H-1,2,4-triazol-3-yl)-propenone
(B-2542) 1-[(q-(([substituted]aryl)carboxy)-z-halogeno)pyrrol-w-yl]-3-hydroxy-3-([substituted]-2H-tetrazol-5-yl)-propenone
(B-2543) 1-[(z-halogeno-q-(([substituted]heteroaryl)oxycarbonyl))thiazol-w-yl]-3-hydroxy-3-([substituted]-1H-1,2,4-triazol-3-yl)-propenone
(B-2544) 4-(q-([substituted]aryl)oxazol-w-yl)-2-hydroxy-4-oxo-2-butenoic acid
(B-2545) 2-hydroxy-4-oxo-4-(q-(([substituted]heteroaryl)sulfinyl)furan-w-yl)-2-butenoic acid
(B-2546) 4-[(z-alkyl-q-(([substituted]aryl)oxycarbonyl))pyridin-w-yl]-2-hydroxy-4-oxo-2-butenoic acid
(B-2547) 1-[nH-(q-(([substituted]heteroaryl)aminosulfonyl)-z-halogeno)pyrazol-w-yl]-3-hydroxy-3-([substituted]-1H-1,2,4-triazol-3-yl)-propenone
(B-2548) 1-[nH-(z-alkyl-q-(([substituted]heteroaryl)oxycarbonyl))pyrazol-w-yl]-3-hydroxy-3-([substituted]-1H-1,2,4-triazol-3-yl)-propenone
(B-2549) 3-hydroxy-1-(nH-q-(([substituted]aryl)sulfonylamino)pyrazol-w-yl)-3-([substituted]-2H-tetrazol-5-yl)-propenone
(B-2550) 1-[(q-(([substituted]heteroaryl)aminosulfonyl)-z-halogeno)thiazol-w-yl]-3-hydroxy-3-([substituted]-2H-tetrazol-5-yl)-propenone
(B-2551) 1-[(q-(([substituted]aryl)carbonylamino)-z-halogeno)oxazol-w-yl]-3-hydroxy-3-([substituted]-1H-1,2,4-triazol-3-yl)-propenone
(B-2552) 1-[(q-(([substituted]aryl)carboxy)-z-halogeno)oxazol-w-yl]-3-hydroxy-3-([substituted]-1H-1,2,4-triazol-3-yl)-propenone
(B-2553) 3-hydroxy-1-(q-(([substituted]heteroaryl)thio)isoxazol-w-yl)-3-([substituted]-1H-1,2,4-triazol-3-yl)-propenone
(B-2554) 4-[(z-halogeno-q-(([substituted]aryl)oxycarbonyl))furan-w-yl]-2-hydroxy-4-oxo-2-butenoic acid
(B-2555) 1-(q-(([substituted]heteroaryl)aminosulfonyl)pyridin-w-yl)-3-hydroxy-3-([substituted]-1H-1,2,4-triazol-3-yl)-propenone
(B-2556) 1-[(z-halogeno-q-(([substituted]heteroaryl)sulfonylamino))thiazol-w-yl]-3-hydroxy-3-([substituted]-2H-tetrazol-5-yl)-propenone
(B-2557) 3-hydroxy-1-(q-(1-hydroxy-([substituted]heteroaryl)methyl)thiophen-w-yl)-3-([substituted]-1H-1,2,4-triazol-3-yl)-propenone
(B-2558) 1-[(q-(([substituted]aryl)aminosulfonyl)-z-halogeno)pyridin-w-yl]-3-hydroxy-3-([substituted]-1H-1,2,4-triazol-3-yl)-propenone
(B-2559) 1-[nH-(q-(([substituted]aryl)carboxy)-z-halogeno)pyrazol-w-yl]-3-hydroxy-3-([substituted]-1H-1,2,4-triazol-3-yl)-propenone
(B-2560) 1-[(q-(([substituted]heteroaryl)aminocarbonyl)-z-halogeno)pyrrol-w-yl]-3-hydroxy-3-([substituted]-1H-1,2,4-triazol-3-yl)-propenone
(B-2561) 1-(q-([substituted]aryl)pyrrol-w-yl)-3-hydroxy-3-([substituted]-1H-1,2,4-triazol-3-yl)-propenone
(B-2562) 1-[(z-alkyl-q-(([substituted]heteroaryl)sulfonyl))furan-w-yl]-3-hydroxy-3-([substituted]-2H-tetrazol-5-yl)-propenone
(B-2563) 1-(q-(([substituted]aryl)alkyl)thiazol-w-yl)-3-hydroxy-3-([substituted]-2H-tetrazol-5-yl)-propenone
(B-2564) 1-[(z-halogeno-q-(([substituted]heteroaryl)thio))thiazol-w-yl]-3-hydroxy-3-([substituted]-1H-1,2,4-triazol-3-yl)-propenone
(B-2565) 3-hydroxy-1-(q-(([substituted]aryl)oxy)pyrrol-w-yl)-3-([substituted]-1H-1,2,4-triazol-3-yl)-propenone
(B-2566) 3-hydroxy-1-(q-(([substituted]heteroaryl)sulfinyl)isoxazol-w-yl)-3-([substituted]-2H-tetrazol-5-yl)-propenone
(B-2567) 4-[(z-alkyl-q-(([substituted]aryl)amino))oxazol-w-yl]-2-hydroxy-4-oxo-2-butenoic acid
(B-2568) 1-[(z-alkyl-q-(([substituted]aryl)aminosulfonyl))pyrrol-w-yl]-3-hydroxy-3-([substituted]-1H-1,2,4-triazol-3-yl)-propenone
(B-2569) 2-hydroxy-4-oxo-4-(q-(([substituted]aryl)oxy)pyrrol-w-yl)-2-butenoic acid
(B-2570) 4-[(z-halogeno-q-(([substituted]aryl)sulfonylamino))pyrrol-w-yl]-2-hydroxy-4-oxo-2-butenoic acid
(B-2571) 4-[nH-(z-halogeno-q-(([substituted]aryl)sulfonyl))pyrazol-w-yl]-2-hydroxy-4-oxo-2-butenoic acid
(B-2572) 1-(q-(([substituted]aryl)aminocarbonyl)furan-w-yl)-3-hydroxy-3-([substituted]-1H-1,2,4-triazol-3-yl)-propenone
(B-2573) 4-[(z-alkyl-q-(([substituted]aryl)sulfonylamino))thiazol-w-yl]-2-hydroxy-4-oxo-2-butenoic acid
(B-2574) 1-[(z-alkyl-q-(([substituted]aryl)aminosulfonyl))oxazol-w-yl]-3-hydroxy-3-([substituted]-2H-tetrazol-5-yl)-propenone
(B-2575) 1-[(q-(([substituted]aryl)alkenyl)-z-alkyl)furan-w-yl]-3-hydroxy-3-([substituted]-1H-1,2,4-triazol-3-yl)-propenone
(B-2576) 4-[(z-halogeno-q-(1-hydroxy-([substituted]heteroaryl)methyl))oxazol-w-yl]-2-hydroxy-4-oxo-2-butenoic acid
(B-2577) 1-[(z-alkyl-q-(([substituted]heteroaryl)oxycarbonyl))pyrrol-w-yl]-3-hydroxy-3-([substituted]-2H-tetrazol-5-yl)-propenone (B-2578) 4-[(q-(([substituted]aryl)carboxy)-z-halogeno)pyrrol-w-yl]-2-hydroxy-4-oxo-2-butenoic acid
(B-2579) 1-[(z-halogeno-q-(([substituted]aryl)thio))isoxazol-w-yl]-3-hydroxy-3-([substituted]-1H-1,2,4-triazol-3-yl)-propenone
(B-2580) 1-[nH-(z-alkyl-q-(([substituted]heteroaryl)sulfinyl))pyrazol-w-yl]-3-hydroxy-3-([substituted]-2H-tetrazol-5-yl)-propenone
(B-2581) 4-[(z-alkyl-q-(([substituted]aryl)carboxy))pyrrol-w-yl]-2-hydroxy-4-oxo-2-butenoic acid
(B-2582) 4-[(z-halogeno-q-([substituted]heteroaryl))thiophen-w-yl]-2-hydroxy-4-oxo-2-butenoic acid
(B-2583) 1-[(z-alkyl-q-(1-hydroxy-([substituted]heteroaryl)methyl))pyridin-w-yl]-3-hydroxy-3-([substituted]-1H-1,2,4-triazol-3-yl)-propenone
(B-2584) 4-[(z-halogeno-q-(([substituted]heteroaryl)thio))isoxazol-w-yl]-2-hydroxy-4-oxo-2-butenoic acid
(B-2585) 4-[(z-alkyl-q-(([substituted]aryl)oxy))oxazol-w-yl]-2-hydroxy-4-oxo-2-butenoic acid (B-2586) 1-[nH-(q-(([substituted]heteroaryl)alkenyl)-z-halogeno)imidazol-w-yl]-3-hydroxy-3-([substituted]-2H-tetrazol-5-yl)-propenone
(B-2587) 1-[(z-alkyl-q-(([substituted]heteroaryl)carbonyl))thiophen-w-yl]-3-hydroxy-3-([substituted]-1H-1,2,4-triazol-3-yl)-propenone
(B-2588) 4-[(z-halogeno-q-(([substituted]aryl)sulfinyl))oxazol-w-yl]-2-hydroxy-4-oxo-2-butenoic acid
(B-2589) 1-[(z-alkyl-q-(([substituted]aryl)aminocarbonyl))furan-w-yl]-3-hydroxy-3-([substituted]-1H-1,2,4-triazol-3-yl)-propenone
(B-2590) 1-[(z-alkyl-q-(([substituted]aryl)amino))furan-w-yl]-3-hydroxy-3-([substituted]-1H-1,2,4-triazol-3-yl)-propenone
(B-2591) 1-(q-(([substituted]heteroaryl)aminocarbonyl)pyrrol-w-yl)-3-hydroxy-3-([substituted]-1H-1,2,4-triazol-3-yl)-propenone
(B-2592) 3-hydroxy-1-(q-(([substituted]aryl)oxy)furan-w-yl)-3-([substituted]-2H-tetrazol-5-yl)-propenone A most preferable embodiment of the compound (II) is a compound wherein $A^1$ is furyl, pyrrolyl or oxazolyl; X is hydroxy; Y is —COOH, 2H-tetrazol-5-yl, 1H-1,2,4-triazol-3-yl, 5-methyl-1H-1,2,4-triazol-3-yl, 6-carboxypyridin-2-yl, 5-carboxypyridin-2-yl, 4carboxypyridin-2-yl, pyridin-2-yl or pyrimidin-2-yl; $Z^1$ and $Z^3$ each is a bond; $Z^2$ is a bond, —CO—, —O—, —S—, —SO$_2$— or lower alkylene (especially, —CH$_2$—, —(CH$_2$)$_2$—); $R^1$ is phenyl optionally substituted with a substituent(s) (especially, halogen); and p is 0. Particularly preferred is a compound which is substituted with the group of the formula: -$Z^1$-$Z^2$-$Z^3$-$R^1$ at 5-position of furan-2-yl or pyrrol-2-yl, or at 2-position of oxazol-5-yl. More preferred is a compound wherein $R^1$ is phenyl substituted with a fluorine atom (especially, 4-fluorophenyl).

The compound of the present invention is usually at the following chemical equilibrium in a solution or the like. The equilibrium is illustrated with the compound (I).

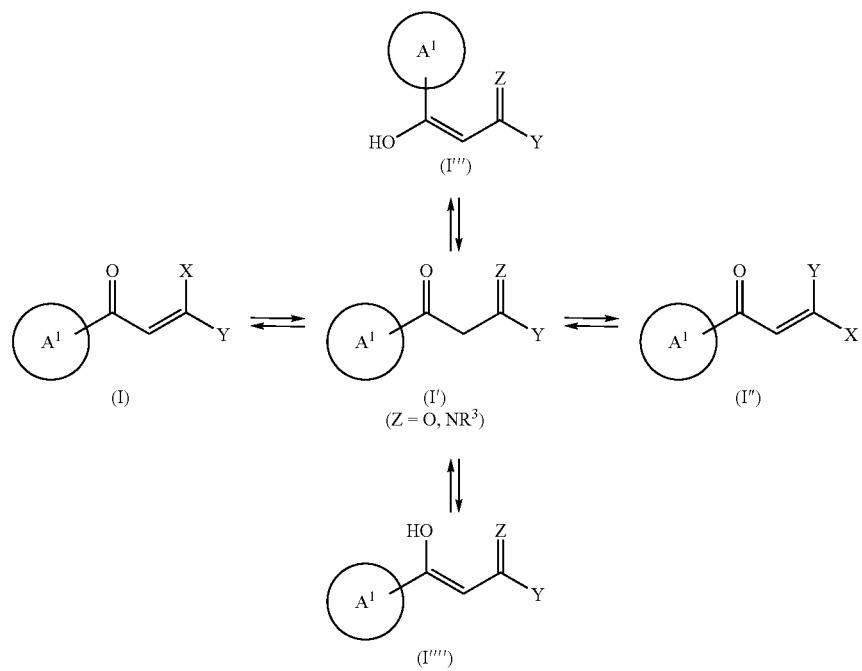

wherein $A^1$ is optionally substituted heteroaryl, provided that indol-3-yl is excluded; X is hydroxy, protected hydroxy or optionally substituted amino; Y is —COOR$^A$ wherein R$^A$ is hydrogen or ester residue, —CONR$^B$R$^C$ wherein R$^B$ and R$^C$ each is independently hydrogen or amide residue, optionally substituted aryl or optionally substituted heteroaryl; and R$^3$ is hydrogen or a substituent on the imino group.

In the chemical equilibrium shown above, the compound (I', wherein Z=O) is the diketone derivative of the compound (I, wherein X=OH), and the compound (I") and the compound (I) are cis-trans isomers with respect to the olefin part of the group of the formula: —(C=O)—CH=C(X)Y. Moreover, the compound of the present invention may form a tautomer such as the compound (I''') and the compound (II''''). All theoretically possible tautomers and isomers of the compound (I) including these compounds are in the scope of the present invention. In the specification, the compound (I), its all tautomers and isomers may be referred to as "the compound (I)". Though the compounds of the present invention may exist as the above tautomers upon the NMR (CDCl₃, d-DMSO) determination, most of them are of (I) form. Thus, most of N.M.R. data in the following examples correspond to the above-described form (I).

Furthermore, heteroaryl includes various tautomers and is not limited to the specific structure. Examples of triazolyl, tetrazolyl and hydroxypyridyl are illustrated below. Other heteroaryl may be illustrated as well.

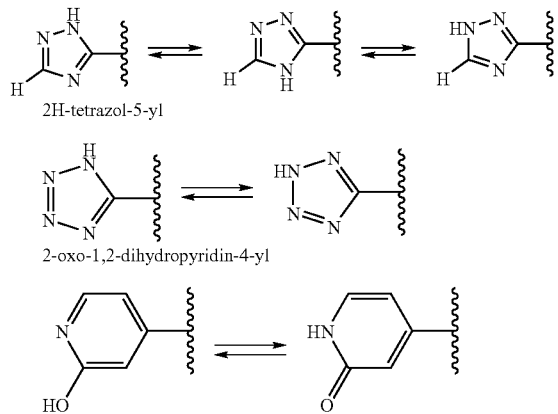

A prodrug is a derivative of the compound of the present invention having a group which can be decomposed chemically or metabolically, and such prodrug is converted to a pharmaceutically active compound of the present invention by means of solvolysis or by placing the compound in vivo under a physiological condition. Therefore, a prodrug itself may not possess an anti-integrase activity, so long as it can be converted to the active compound of the present invention. Method for the selection and process of an appropriate prodrug derivative are described in the literature such as Design of Prodrugs, Elsevier, Amsterdam 1985.

When the compound of the present invention has a carboxyl group, an ester derivative prepared by reacting a basal acid compound with a suitable alcohol or an amide derivative prepared by reacting a basal acid compound with a suitable amine is exemplified as a prodrug. A particularly preferred ester derivative as an prodrug is methyl ester, ethyl ester, n-propyl ester, isopropyl ester, n-butyl ester, isobutyl ester, tert-butyl ester, morpholinoethyl ester, N,N-diethylglycolamido ester or the like. A particularly preferred amide derivative as a prodrug is amide, N-methyl amide, N-ethyl amide, N-benzyl amide or the like.

When the compound of the present invention has a hydroxy group, an acyloxy derivative prepared by reacting with a suitable acyl halide (e.g., acid chloride, halogenated acid) or a suitable acid anhydride (e.g., mixed acid anhydride) is exemplified as a prodrug. A particularly preferred acyloxy derivative as a prodrug is —OCOC₂H₅, —OCO(tert-Bu), —OCOC₁₅H₃₁, —OCO(m-COONa—Ph), —OCOCH₂CH₂COONa, —OCOCH(NH₂)CH₃, and —OCOCH₂N(CH₃)₂ or the like.

When the compound of the present invention has an amino group, an amide derivative prepared by reacting with a suitable acid halide or a suitable acid anhydride is exemplified as a prodrug. A particularly preferred amide derivative as a prodrug is —NHCO(CH₂)₂₀CH₃, —NHCOCH(NH₂)CH₃ or the like.

As shown below, the compound of the formula pre-(I) or pre-(II) is one of the useful prodrugs of the compound of the formula (I) or (II). The compound of the formula pre-(I) or pre-(II) is converted to the compound of the formula (I) or (II) by hydrolysis of the dioxofuryl group (particularly, 4,5-dioxo-4,5-dihydrofuran-2-yl) in vivo.

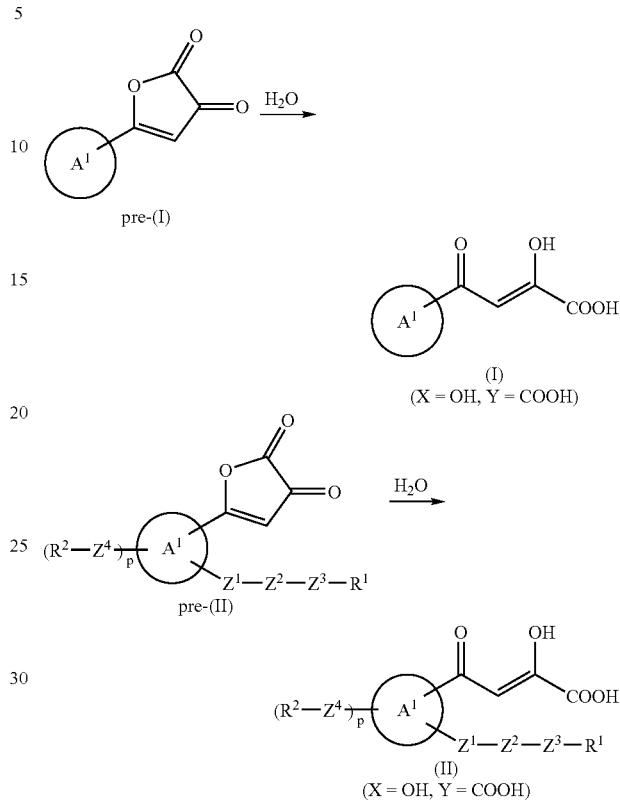

As a salt of the compound of the present invention, any of pharmaceutically acceptable salts can be used, including base addition salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aryl lower alkyl amine salts such as N,N-dibenzylethylenediamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltrimethylammonium salts, benzyltributylammonium salts, methyltrioctylammonium salts or tetrabutylammonium salts; and basic amino acid salts such as arginine salts or lysine salts. Acid addition salts include, for example, mineral acid salts such as hydrochlorides salts, sulfates salts, nitrate salts, phosphates salts, carbonates salts, hydrogen carbonates salts or perchlorates salts; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

Furthermore, various hydrates and solvates of the compound of the present invention, for example, monohydrate, dihydrate and the like, are in the scope of the present invention. The compound of the present invention may involve residual water.

The term "inhibit" means that the compound of the present invention suppresses the action of integrase. The term "pharmaceutically acceptable" means harmless with respect to the prevention and the treatment.

The general method for the preparation of the compound of the present invention (route [A] to [I]) is explained below.

The compounds of the present invention are novel heteroaromatic derivatives. $A^1$ of the compound of the present invention includes monocyclic heteroaryl such as furyl, thienyl, pyrrolyl, imidazolyl, pyrazolyl, triazolyl, tetrazolyl, oxazolyl, isoxazolyl, thiazolyl, isothiazolyl, pyridyl, pyridazinyl, pyrimidinyl, furazanyl, pyrazinyl, thiadiazolyl, oxadiazolyl or the like, and fused heteroaryl such as benzofuryl, benzothienyl, benzimidazolyl, benzothiazolyl, indolyl (provided that indol-3-yl is excluded), dibenzofuryl, quinolinyl, isoquinolinyl, cinnolinyl, quinazolinyl, quinoxalinyl, phthalazinyl, purinyl, pteridinyl, carbazolyl, phenanthridinyl, acridinyl, phenazinyl, 1,10-phenanthrolinyl, isoindolyl, 1H-indazolyl, indolidinyl or the like.

Various functional groups can be introduced to these heteroaromatic compounds through the reaction known in the field of the aromatic compound or the specific reaction depending on each heteroaromatic ring. Heteroaromatic compounds having a desired substituent(s) can be prepared. For example, the following documents can be referred to as the general organic synthesis of various kinds of heteroaromatic compounds: (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS and the like. The compounds of the present invention can be easily prepared from the commercially available heteroaromatic compounds or derivatives thereof through well-known reactions as shown below.

Introduction of the group of the formula: —C(=O)—CH=C(X)Y to the heteroaromatic compound can be performed in accordance with the following synthetic routes [A1] to [A4].

(1) Preparation of the Compound of the Formula (I) or (II) wherein X is OH

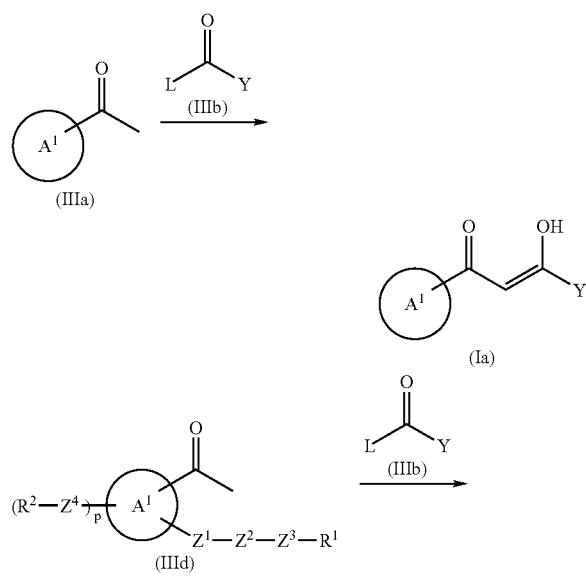

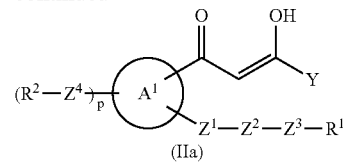

wherein $A^1$ is optionally substituted heteroaryl, provided that optionally substituted indol-3-yl is excluded, Y is —COOR$^4$ wherein R$^4$ is hydrogen or ester residue, optionally substituted aryl or optionally substituted heteroaryl; $Z^1$ and $Z^3$ each is independently a bond, lower alkylene or lower alkenylene; $Z^2$ and $Z^4$ each is independently a bond, lower alkylene, lower alkenylene, —CH(OH)—, —S—, —SO—, —SO$_2$—, —SO$_2$NR$^{21}$—, —NR$^{21}$SO$_2$—, —O—, —NR$^{21}$—, —NR$^{21}$CO—, —CONR$^{21}$—, —C(=O)—O—, —O—C(=O)— or —CO—; R$^{21}$ is hydrogen, lower alkyl or lower alkenyl; R$^1$ is optionally substituted aryl, optionally substituted heteroaryl, optionally substituted cycloalkyl, optionally substituted cycloalkenyl or optionally substituted heterocycle; R$^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercapto, optionally substituted amino, nitro or halogen; p is 0 or 1; and L is a leaving group such as halogen, —OR$^4$ wherein R$^4$ is lower alkyl or the like, or the like.

The heteroaromatic derivative of the formula (IIIa) or (IIId) having an acetyl group can be obtained as follows; 1) use of a commercially available compound, 2) introduction of an acetyl group to heteroaromatic compound through Friedel-Crafts reaction or 3) Grignard reaction of ester derivative, amide derivative or the like by using methyl magnesium bromide or the like.

For example, the compound of the formula (Ia) or (IIa) can be prepared by reacting the compound of the formula (IIIa) or (IIId) with the compound of the formula (IIIb), preferably in the presence of a base.

A solvent to be used is tetrahydrofuran (THF), dioxane, diethylether or the like. A base to be used is sodium ethoxide, potasium tert-butoxide, lithiumbistrimethylsilylamide (LHMDS) or the like. A reaction temperature is approximately −100° C. to 100° C., preferably −70° C. to 60° C.

The compound of the formula (IIIb) includes, for example, oxalic acid dimethyl ester (oxalic acid diethyl ester), methyl oxalylchloride, ethyl oxalylchloride, anhydrous phthalic acid, orthomethoxybenzoylchloride, 2-trityl-2H-tetrazol-5-carboxylic acid ethyl ester, 1-trityl-1H-1,2,4-triazol-3-carboxylic acid ethyl ester, 1-trityl-5-methyl-1H-1,2,4-triazol-3-carboxylic acid ethyl ester, 1-tritylimidazole-2-carboxylic acid ethyl ester, 2-trityl-2H-tetrazol-5-carboxylic acid methyl ester, 1-trityl-1H-1,2,4-triazole-3-carboxylic acid methyl ester, 1-tritylimidazole-2-carboxylic acid methyl ester, 2-(tetrahydropyran-2-yl)-2H-tetrazole-5-carboxylic acid ethyl ester, 1-(tetrahydropyran-2-yl)-1H-1,2,4-triazole-3-carboxylic acid ethyl ester, 1-(tetrahydropyran-2-yl)imidazole-2-carboxylic acid ethyl ester, 2-(tetrahydropyran-2-yl)-2H-tetrazole-5-carboxylic acid methyl ester, 1-(tetrahydropyran-2-yl)-1H-1,2,4-triazole-3-carboxylic acid methyl ester, 1-(tetrahydropyran-2-yl)-imidazole-2-carboxylic acid methyl ester, 2-methoxymethyl-2H-tetrazol-5-carboxylic acid ethyl ester, 1-methoxymethyl-1H-1,2,4-triazol-3-carboxylic acid ethyl ester, 1-methoxymethyl-imidazole-2-carboxylic acid ethyl ester, 2-methoxymethyl-2H-tetrazol-5-carboxylic acid methyl ester, 1-methoxymethyl-1H-1,2,4-triazol-3-carboxylic acid methyl ester, 1-methoxymethyl-imidazole-2-carboxylic acid methyl ester or the like.

Instead of the above shown procedure, the compound of the formula (Ia) can be prepared through the following method.

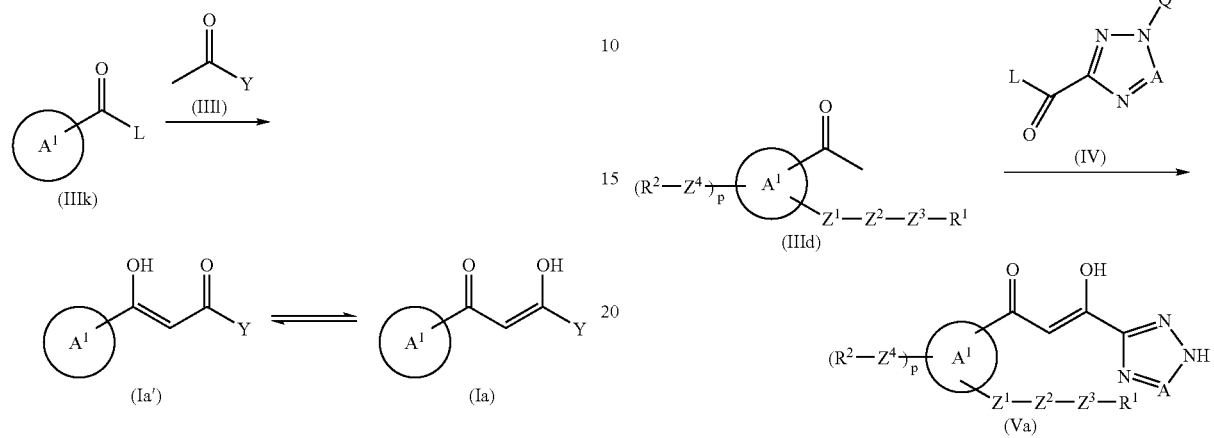

wherein $A^1$, Y and L are as defined above.

The compound of the formula (I'a) or (Ia) can be prepared by reacting the compound of the formula (IIIk) with the compound of the formula (IIII) in the presence of a base, if desired, following the deprotection. A base to be used is the same as that used in the above shown procedure.

The compound of the formula (IIIk) includes 2-furancarboxylic acid chloride, 5-benzyl-2-furancarboxylic acid chloride, 5-(4-fluorobenzyl)-2-furancarboxylic acid chloride, 3-furancarboxylic acid chloride, 5-benzyl-3-furan carboxylic acid chloride, 5-(4-fluorobenzyl)-3-furan carboxylic acid chloride, 5-(4-fluorobenzyl)-2-furan carboxylic acid bromide, 5-(4-fluorobenzyl)-3-furan carboxylic acid bromide, 2-furan carboxylic acid methyl ester, 5-benzyl-2-furan carboxylic acid methyl ester, 5-(4-fluorobenzyl)-2-furan carboxylic acid methyl ester, 5-(4-fluorobenzyl)-2-furan carboxylic acid ethyl ester or the like.

The compound of the formula (IIII) includes 1-Boc-2-acetylpyrrole, 2-acetylpyridine, 3-acetyl-1-Boc-1,2,4-triazole, 5-acetyl-2-Boc-tetrazole, 2-acetylpyrimidine, 1-trityl-2-acetylpyrrole, 2-acetylpyridine, 3-acetyl-1-trityl-1,2,4-triazole, 5-acetyl-2-trityl-tetrazole or the like.

The protective group of the compound of the formula (IIII), if necessary, can be selected as the case may be. Especially preferred is Boc(tert-butoylcarbonyl) or trityl, which can be eliminated under an acidic condition.

A more preferred embodiment of the process is shown as follows.

Synthetic route [A2]

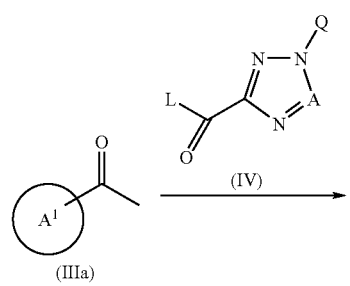

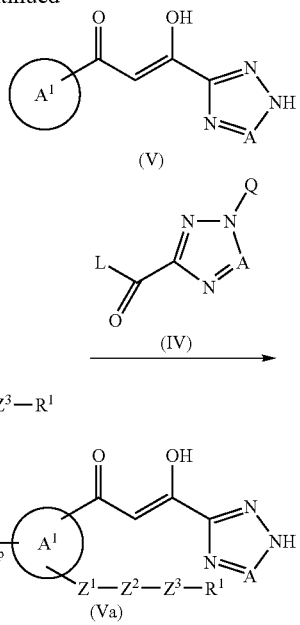

wherein $A^1$, $Z^1$, $Z^2$, $Z^3$, $Z^4$, $R^1$, $R^2$ and p are as defined above; A is C—W wherein W is hydrogen, lower alkyl, lower haloalkyl or halogen, or N; Q is a protective group; and L is a leaving group.

The compound of the formula (V) or (Va) can be prepared by reacting the compound of the formula (IIIa) and (IIId) with the compound of the formula (IV) in the presence of a base and following the deprotection of Q.

Concretely, to a solution cooled at −78 to −30° C., preferably −78 to −50° C. of the compound of the formula (IIIa) or (IIId) in an aprotic solvent such as tetrahydrofuran, dioxane, diethylether or the like is added dropwise a base such as sodium ethoxide, potasium tert-butoxide, lithium-bistrimethylsilylamide or an aprotic solvent containing them, under the temperature kept during the addition.

Subsequently, the reaction solution is warmed up to −20 to 10° C., preferably −10 to 0° C. and cooled down again to −78 to −30° C., preferably −78 to −50° C. To the solution is added dropwise the compound of the formula (IV) or in the above aprotic solvent thereof. The reaction mixture is warmed up to room temperature after the addition and further stirred for 0.5 to 10 hours, preferably 1 to 5 hours. The reaction mixture is poured into a saturated aqueous solution of an inorganic salt such as ammonium chloride, sodium chloride or the like, extracted with an organic solvent such as dichloromethane, CHCl$_3$, ethylacetate or the like, if desired, washed with saturated brine, dried over desiccant such as anhydrous sodium sulfate, anhydrous magnesium sulphate or the like and evaporated.

Next, the above-obtained residue may be treated for the elimination of a protective group Q under an acidic condition such as hydrochloric acid, diluted hydrochloric acid, sulfuric acid, trifluoroacetic acid or the like, a neutral condition such as tetrabutylammonium fluoride, BBr$_3$ or the like, or a basic condition such as sodium hydroxide, sodium methoxide, sodium ethoxide, potassium carbonate or the like. The deprotection condition may be selected depending on the kind of the protective group Q, as the case may be. For example, when a protective group is trityl, tetrahydropyran-2-yl, methoxymethyl, dialkoxy methyl or the like, the deprotection can be performed by using hydrochloric acid or the like. When a protective group is acyl, N,N-dimethylsulfamoyl or the like, the deprotection can be performed by using sodium hydroxide or the like. When a protective group is trimethylsilyl or the like, the deprotection can be performed by using tetrabutyl ammoniumfluoride or the like.

A preferable embodiment of the compound of the formula (IIId) is a compound of the formula (VI):

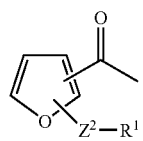

(VI)

wherein $Z^2$ is a bond, —CO—, —O—, —S—, —SO$_2$—, —CH$_2$— or —(CH$_2$)$_2$— and $R^1$ is optionally substituted phenyl. More preferred is a compound wherein $Z^2$ is —SO$_2$—, —CH$_2$— or —(CH$_2$)$_2$— and $R^1$ is phenyl optionally substituted with halogen.

Examples of a compound of the formula (IIIa) and (IIId) is 2-acetylfuran, 2-acetyl-5-benzylfuran, 2-acetyl-5-(4-methylbenzyl)furan, 2-acetyl-5-(4-methoxybenzyl)furan, 2-acetyl-5-(4-fluorobenzyl)furan, 2-acetyl-5-(4-chlorobenzyl)furan, 2-acetyl -5-(3-methylbenzyl)furan, 2-acetyl-5-(3-methoxybenzyl)furan, 2-acetyl-5-(3-fluorobenzyl)furan, 2-acetyl-5-(3-chlorobenzyl)furan, 3-acetylfuran, 3-acetyl-1-benzyl-5-ethoxycarbonylpyrrole, 2-acetyl-1-(4-fluorobenzyl)pyrrole, 3-acetyl-1-(4-fluorobenzyl)pyrrole, 3-acetyl-1-benzyl-5-(2-methoxycarbonylvinyl)pyrrole, 2-acetyl-1-benzyl-(2-carboxy ethyl)pyrrole, 3-acetyl-1-benzenesulfonyl-4-(4-fluorobenzyl)pyrrole, 3-acetyl-1-benzylpyrrole, 2-acetyl-5-(4-fluorobenzyl)pyrrole or the like.

Examples of a compound of the formula (IV) is 2-trityl-2H-tetrazol-5-carboxylic acid ethyl ester, 1-trityl-1H-1,2,4-triazol-3-carboxylic acid ethyl ester, 1-trityl-5-methyl-1H-1,2,4-triazol-3-carboxylic acid ethyl ester, 2-trityl-2H-tetrazol-5-carboxylic acid methyl ester, 1-trityl-1H-1,2,4-triazol-3-carboxylic acid methyl ester, 2-(tetrahydropyran-2-yl)-2H-tetrazol-5-carboxylic acid ethyl ester, 1-(tetrahydropyran-2-yl)-1H-1,2,4-triazol-3-carboxylic acid ethyl ester, 2-(tetrahydropyran-2-yl)-2H-tetrazol-5-carboxylic acid methyl ester, 1-(tetrahydropyran-2-yl)-1H-1,2,4-triazol-3-carboxylic acid methyl ester, 2-methoxymethyl-2H-tetrazol-5-carboxylic acid ethyl ester, 1-methoxymethyl-1H-1,2,4-triazol-3-carboxylic acid ethyl ester, 2-methoxymethyl-2H-tetrazol-5-carboxylic acid methyl ester, 1-methoxymethyl-1H-1,2,4-triazol-3-carboxylic acid methyl ester or the like, preferably trazol-5-carboxylic acid ethyl ester, 1-trityl-1H-1,2,4-triazol-3-carboxylic acid ethyl ester, 1-trityl-5-methyl-1H-1,2,4-triazol-3-carboxylic acid ethyl ester, 1-trityl-5-chloro-1H-1,2,4-triazol-3-carboxylic acid ethyl ester, 1-trityl-5-methoxymethyl-1H-1,2,4-triazol-3-carboxylic acid ethyl ester, 1-trityl-5-ethyl-1H-1,2,4-triazol-3-carboxylic acid ethyl ester, 1-trityl-5-n-propyl-1H-1,2,4-triazol-3-carboxylic acid ethyl ester, 1-trityl-5-isopropyl-1H-1,2,4-triazol-3-carboxylic acid ethyl ester, 1-trityl-5-trifluoromethyl-1H-1,2,4-triazol-3-carboxylic acid ethyl ester or the like.

A protective group Q is not limited to the specific groups and can be selected from the protective groups which are suitable for a process of the compound of the present invention. For example, N protective group described in Section "Protection for The Amino Group" of "Protective groups in Organic Synthesis" can be used. Examples of protective group Q include methoxymethyl, dialkoxy methyl, tert-butoylcarbonyl, 9-fluorenylmethoxycarbonyl, tosyl, trityl, acyl, formyl, tetrahydropyran-2-yl, (1-methoxy-1-methyl)ethyl, 1-ethoxyethyl, hydroxymethyl, trimethylsilyl, N,N-dimethylsulfamoyl or the like, preferably methoxymethyl, ethoxymethyl, trityl, tetrahydropyran-2-yl.

A leaving group L is not limited to a specific one and can be selected from the leaving groups which are suitable for a process of the compound of the present invention. Examples of the leaving group L include alkoxy (e.g., methoxy, ethoxy, isopropoxy, tert-butoyl, biphenylmethoxy or the like), heteroaryl (e.g., imidazolyl, tetrazolyl), cyano or the like. Preferred is methoxy or ethoxy.

(2) Preparation of a Compound of the Formula (I) or (II) wherein X is NHR$^5$

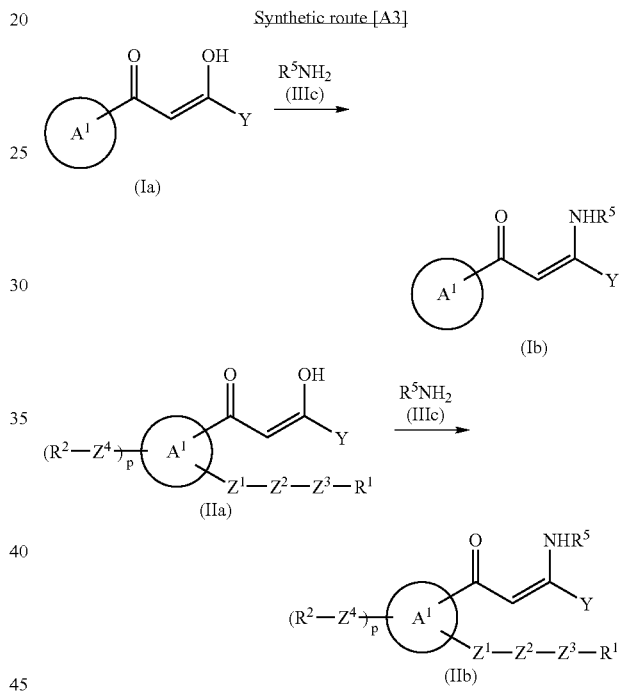

Synthetic route [A3]

wherein $A^1$, Y, $Z^1$, $Z^2$, $Z^3$, $Z^4$, $R^1$, $R^2$ and p are as defined above; $R^5$ is hydrogen or a substituent on the amino group.

The compound of the formula (Ib) or (IIb) can be prepared by reacting the compound of the formula (Ia) or (IIa) with a compound of the formula (IIIc) or its acid addition salt.

A solvent to be used is, for example, methanol, ethanol or the like. A reaction temperature is approximately −10 to 100° C., preferably room temperature to 100° C.

(3) Preparation of the Compound of the Formula (I) or (II) wherein Y is —COOR$^A$ or —CONR$^B$R$^C$ Synthetic route [A4]

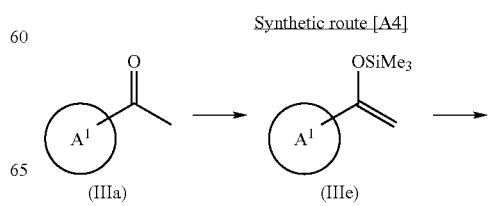

-continued

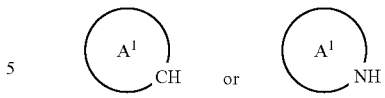

(IIIg)

(IIIi)

(IIId)

(IIIf)

(IIIh)

(IIIj)

wherein $A^1$, $Z^1$, $Z^2$, $Z^3$, $Z^4$, $R^1$, $R^2$ and p are as defined above; $R^A$ is hydrogen or ester residue; $R^B$ and $R^C$ each is independently hydrogen or amide residue.

Illustrated above is a process for producing a compound of the formula (IIIi) or (IIIj), that is a compound of the formula (I) or (II) wherein Y is —COOR$^A$ or —CONR$^B$R$^C$ wherein $R^A$ is hydrogen or ester residue, $R^B$ and $R^C$ each is independently hydrogen or amide residue, from a compound of the formula (IIIa) or (IIId).

First, silyl enol ether is prepared by reacting a compound of the formula (IIIa) or (IIId) with trimethylsilyl acetic acid ethyl ester or the like in an aprotic solvent. The obtained compound of the formula (IIIe) or (IIIf) is reacted with oxalylchloride for introducing a dioxofuryl group (in detail, 4,5-dioxo-4,5-dihydrofuran-2-yl) to produce a compound of the formula (IIIg) or (IIIh). Subsequently, a compound of the formula (IIIi) or (IIIj) can be prepared by reacting the above compound with water, aqueous ammonia, various alcohols, various amines (e.g., R$^A$OH, R$^B$R$^C$NH).

Introduction of a group of the formula: -$Z^1$-$Z^2$-$Z^3$-$R^1$ wherein $Z^1$, $Z^2$, $Z^3$ and $R^1$ each is as defined above or a group of the formula: -$Z^4$-$R^2$ wherein $Z^4$ and $R^2$ each is as defined above into the heteroaromatic compound can be carried out in accordance with the following synthetic routes [B] to [I] or the like.

The ring of the formula:

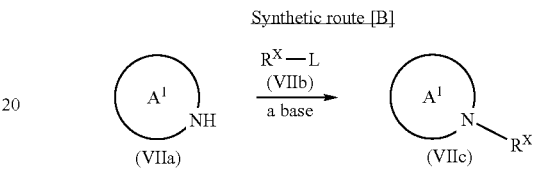

is heteroaromatic or heteroaryl group optionally substituted with a group of the formula: —C(=O)—CH=C(X)Y. The group of the formula: -$Z^1$-$Z^2$-$Z^3$-$R^1$ or -$Z^4$-$R^2$ may be introduced before or after introducing the group of the formula: —C(=O)—CH=C(X)Y. In the above-illustrated formula, "CH" and "NH" are a carbon atom and a nitrogen atom which constitutes heteroaromatic ring and bonds to a hydrogen atom, respectively.

Synthetic route [B]

(VIIa) → (VIIc)

$R^X$—L (VIIb), a base wherein $A^1$ is optionally substituted heteroaryl, provided that optionally substituted indol-3-yl is excluded; a group of the formula: —$R^X$ is a group of the formula: -$Z^1$-$Z^2$-$Z^3$-$R^1$ wherein $Z^1$ and $Z^3$ each is independently a bond, lower alkylene or lower alkenylene; $Z^2$ is a bond, lower alkylene, lower alkenylene, —CH(OH)—, —S—, —SO—, —SO$_2$—, —SO$_2$NR$^{21}$—, —NR$^{21}$SO$_2$—, —O—, —NR$^{21}$, —NR$^{21}$CO—, —CONR$^{21}$—, —C(=O)—O—, —O—C(=O)— or —CO—; $R^{21}$ is hydrogen, lower alkyl or lower alkenyl; $R^1$ is optionally substituted aryl, optionally substituted heteroaryl, optionally substituted cycloalkyl, optionally substituted cycloalkenyl or optionally substituted heterocyclic, or a group of the formula: -$Z^4$-$R^3$ wherein $Z^4$ is a bond, lower alkylene, lower alkenylene, —CH(OH)—, —S—, —SO—, —SO$_2$—, —SO$_2$NR$^{21}$—, —NR$^{21}$SO$_2$—, —O—, —NR$^{21}$—, —NR$^{21}$CO—, —CONR$^{21}$—, —C(=O)—O—, —O—C(=O)— or —CO—; $R^{21}$ is hydrogen, lower alkyl or lower alkenyl; $R^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercapto, optionally substituted amino, nitro or halogen; and L is a leaving group (e.g., halogen or the like).

A compound of the formula (VIIc) can be prepared by reacting a compound of the formula (VIIa) with a compound of the formula (VIIb), or isocyanate derivative or the like which can be used for introducing a group of the formula: —$R^X$.

A base to be used is, for example, NaH, K$_2$CO$_3$ or the like. A solvent to be used is for example, tetrahydrofuran (THF), dioxane or the like.

A compound of the formula (VIIb) is, for example, various sulfonylhalides (e.g., (substituted) benzenesulfonylchloride, 2-thiophensulfonylchloride, (substituted) amino sulfonylchloride, alkylsulfonylchloride or the like), alkylhalide (e.g., methyl iodide, butyl bromide, cyclopropyl bromide or the like), aryl(lower)alkylhalide (e.g., (substituted) benzylchloride, picolylchloride, naphthylmethylchloride, biphenylmethylchloride or the like), carbamoyl chloride (e.g., dimethylcarbamoyl chloride or the like), halogenated acyl (e.g., 4-fluorobenzoylchloride or the like) or the like.

Isocyanate derivative is, for example, (substituted) arylisocyanate (e.g, phenylisocyanate or the like) or the like.

A reaction temperature is approximately −100 to 100° C., preferably −20 to 60° C.

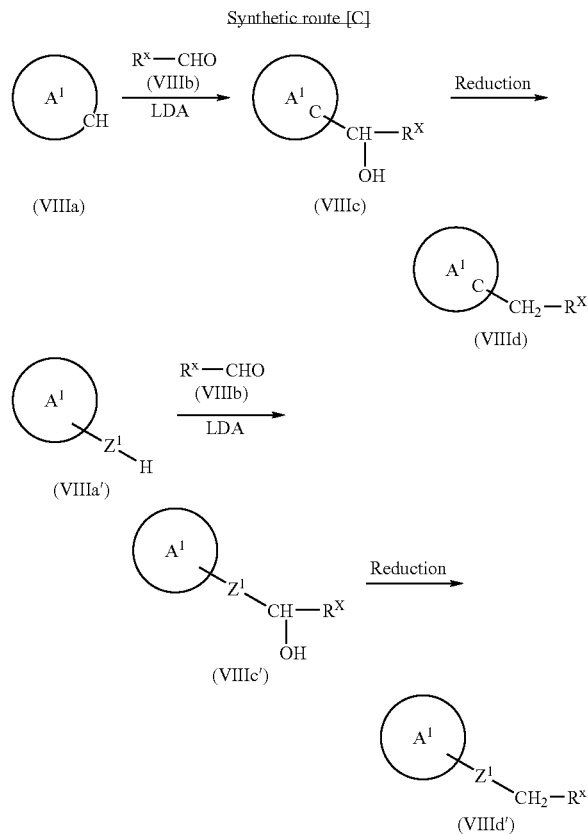

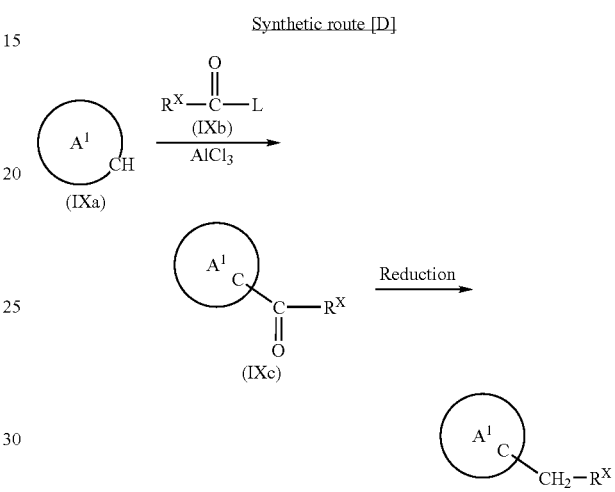

wherein $A^1$ is as defined above; a group of the formula: —CH(OH)—$R^X$, a group of the formula: —CH$_2$—$R^X$, a group of the formula: -$Z^1$-CH(OH)—$R^X$ and a group of the formula: -$Z^1$-CH$_2$—$R^X$ each is independently a group of the formula: -$Z^1$-$Z^2$-$Z^3$-$R^1$ wherein $Z^1$, $Z^2$, $Z^3$ and $R^1$ are as defined above or a group of the formula: -$Z^4$-$R^2$ wherein $Z^4$ and $R^2$ are as defined above.

A compound of the formula (VIIIc) or (VIIIc') can be prepared by lithiation of a compound of the formula (VIIIa) or (VIIIa') with a base (e.g., n-BuLi, LDA or the like), followed by reacting the above obtained compound with an aldehyde of the formula (VIIIb), as shown in Tetrahedron Letters, 1979, 5, p469. LDA may be commercially available or prepared from n-BuLi and (i-Pr)$_2$NH upon the reaction.

A solvent to be used is, for example, tetrahydrofuran (THF), dioxane, diethylether or the like. A compound of the formula (VIIIb) is, for example, (substituted) benzaldehyde (e.g., benzaldehyde, 4-fluorobenzaldehyde, 4-chlorobenzaldehyde, 2,4-difluorobenzaldehyde, 4-trifluoromethylbenzaldehyde or the like), alkanal (e.g., formaldehyde, acetaldehyde, isovaleraldehyde or the like), furfural, 3-furaldehyde, 2-thiophenecarbaldehyde, 3-thiophenecarbaldehyde or the like. A reaction temperature is approximately −100 to 100° C., preferably −70 to 50° C.

A compound of the formula (VIIId) or (VIIId') can be prepared from a compound of the formula (VIIIc) or (VIIIc') by reduction reaction. Such reduction reaction is, for example, 1) reacting the above compound with trimethylchlorosilane and sodium iodide at −20 to 50° C. as shown in Tetrahedron, 1995, 51, p11043, 2) reacting the above compound with phenylchlorothionoformate to produce thio ester derivative, and radically reducing the above obtained compound by tributyltin hydride and AIBN (azodiisobutyronitrile) in a solution such as toluene or the like under heating as shown in J. Org. Chem., 1993, 58, p2552, or the like.

A ketone (e.g.; a compound of the formula: $R_X$—(C═O)—Me or the like) can be used in place of an aldehyde of the formula (VIIIb). In such a case, a group of the formula: —C(OH)Me—$R^X$ or —CHMe—$R^X$ can be introduced into the above shown compound of the formula (VIIIc), (VIIIc'), (VIIId) or (VIIId') in place of a group of the formula: —C(OH)H—$R^X$ or —CH$_2$—$R^X$.

wherein $A^1$ is as defined above; a group of the formula: —C(═O)—$R^X$ and a group of the formula: —CH$_2$—$R^X$ each is independently a group of the formula: -$Z^1$-$Z^2$-$Z^3$-$R^1$ wherein $Z^1$, $Z^2$, $Z^3$ and $R^1$ are as defined above or the formula: -$Z^4$-$R^2$ wherein $Z^4$ and $R^2$ are as defined above; and L is a leaving group (e.g., halogen, —O(C═O)$R^4$ wherein $R^4$ is lower alkyl or the like) or the like.

A compound of the formula (IXc) can be prepared by Friedel-Crafts reaction of a compound of the formula (IXa) with a compound of the formula (IXb). In general, Friedel-Crafts reaction can be carried out in the presence of Lewis acid. A group of the formula: —(C═O)—$R^X$ can be introduced at a desired position depending on the kind of Lewis acid. For example, when $A^1$ is pyrrole, an acyl group can be introduced at the 3-position of pyrrole by using aluminum chloride and at the 2-position by using BF$_3$/ether as Lewis Acid. A compound of the formula (IXb) is, for example, acetylchloride, acetic anhydride, cyclohexylcarbonylchloride, (substituted) benzoylchloride (e.g., 4-fluorobenzoylchloride, 4-fluorobenzoylbromide, 4-chlorobenzoylchloride, 2,4-difluorobenzoylchloride, 4-trifluoromethylbenzoylchloride or the like) or the like. A solvent to be used is, for example, carbon disulfide, methylene chloride, dichloroethane or the like. A reaction temperature is approximately −100 to 100° C., preferably −50 to 50° C., more preferably −20 to 30° C.

A compound of the formula (IXd) can be prepared from a compound of the formula (IXc) by reduction reaction. Such reduction reaction is, for example, 1) reacting the above compound with triethylsilane (Et$_3$SiH) as shown in J. Org. Chem., 1978, 43, p374, 2) reducing a compound of the formula (XIc) with borane/tert-butylamine complex in the presence of aluminum chloride, or the like.

A solvent to be used is, for example, methylene chloride, ethers or the like. A reaction temperature is approximately −100 to 100° C., preferably −30 to 30° C.

Synthetic route [E]

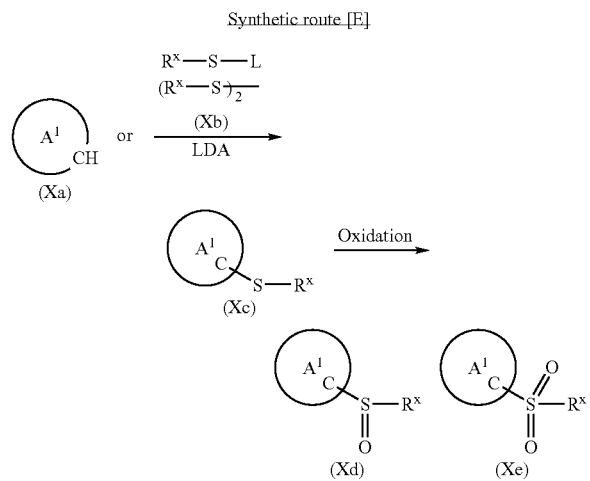

wherein $A^1$ is as defined above; a group of the formula: —S—$R^X$, a group of the formula: —SO—$R^X$ and a group of the formula: —SO$_2$—$R^X$ each is independently a group of the formula: -$Z^1$-$Z^2$-$Z^3$-$R^1$ wherein $Z^1$, $Z^2$, $Z^3$ and $R^1$ are as defined above or a group of the formula: -$Z^4$-$R^2$ wherein $Z^4$ and $R^2$ are as defined above; and L is halogen or the like.

As well as synthetic route [C], a heteroaromatic compound is lithiated and reacted with a compound of the formula (Xb) to give a sulfenyl derivative of the formula (Xc). A solvent to be used is, for example, tetrahydrofuran (THF), dioxane or the like. A reaction temperature is approximately −100 to 100° C., preferably −70 to 50° C. A compound of the formula (Xb) is disulfide (e.g., (substituted) diphenyldisulfide, dimethyldisulfide or the like), (substituted) phenylsulfenylchloride (e.g., 4-fluorophenylsulfenylchloride or the like) or the like.

Oxidation of the obtained sulfenyl derivative of the formula (Xc) produces two types of oxide: a sulfinyl derivative of the formula (Xd) and sulfonyl derivative of the formula (Xe). An oxidizing agent to be used is oxone, m-chloroperbenzoic acid or the like. A solvent to be used is methylene chloride, chloroform or the like. A reaction temperature is approximately −100 to 100° C., preferably −50 to 50° C., and more preferably −20 to 30° C.

Synthetic route [F]

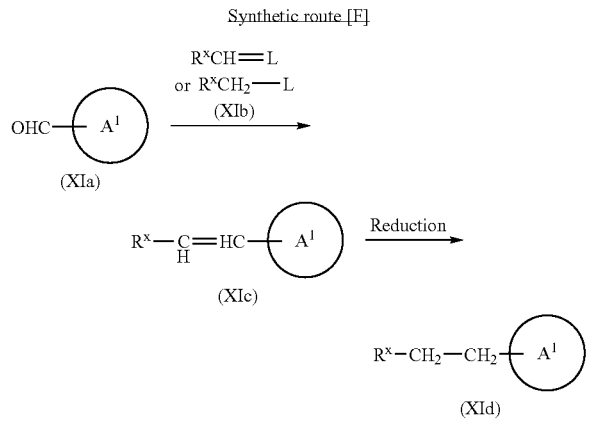

wherein $A^1$ is as defined above; a group of the formula: —CH=CH—$R^X$ and a group of the formula: —C$_2$H$_4$—$R^X$ each is independently a group of the formula: -$Z^1$-$Z^2$-$Z^3$-$R^1$ wherein $Z^1$, $Z^2$, $Z^3$ and $R^1$ are as defined above or a group of the formula: -$Z^4$-$R^2$ wherein $Z^4$ and $R^2$ are as defined above; and L is —P(=O)(OEt)$_2$, =PPh$_3$ or the like.

A heteroaromatic derivative having a formyl group, shown of the formula (XIa), can be obtained as follows: 1) use of a commercially available compound or 2) introduction of a formyl group to heteroaromatic compound through Vilsmeier reaction, Reimer-Tiemann reaction or the like.

An olefin derivative of the formula (XIc) can be prepared by Wittig reaction or Horner-Emmons reaction of a compound of the formula (XIa) with a compound of the formula (XIb), if desired, in the presence of a base.

A compound of the formula (XIb) is, for example, an ylide derivative (e.g., (carbethoxy)triphenylphospholan or the like), phosphoryl derivative (e.g., methyl diethylphosphono acetate, diethylbenzyl phosphonate or the like) or the like. A solvent to be used is, for example, dimethylformamide (DMF), tetrahydrofuran (THF), dioxane or the like. A reaction temperature is approximately −100 to 150° C., preferably −20 to 100° C.

A compound of the formula (XId) can be prepared by reducing an olefin derivative of the formula (XIc). Hydrogenation or the like can be used as reduction reaction. A catalyst to be used is, for example, palladium-carbon or the like. A solvent to be used is, for example, tetrahydrofuran (THF), ethanol or the like, preferably mixed solvent with ethanol and tetrahydrofuran. A reaction temperature is approximately −100 to 100° C., preferably −20 to 30° C.

Synthetic route [G]

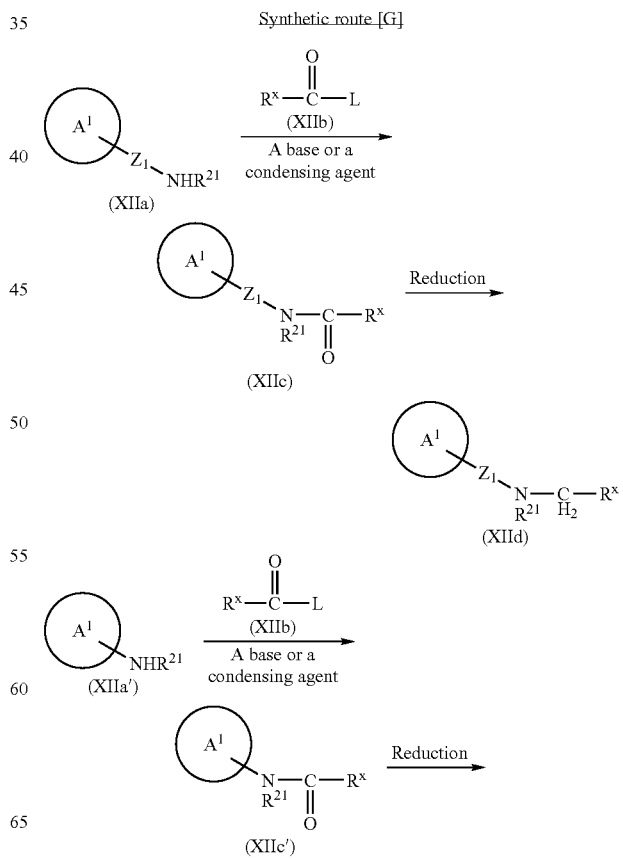

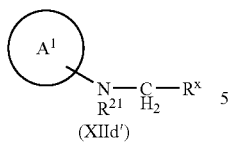

(XIId')

wherein $A^1$ and $Z^1$ are as defined above; a group of the formula: —$R^X$ and a group of the formula: —$CH_2$—$R^X$ each is independently a group of the formula: -$Z^3$-$R^1$ wherein $Z^3$ and $R^1$ are as defined above or a group of the formula: —$R^2$ wherein $R^2$ is as defined above; and L is a leaving group (e.g., halogen, hydroxy, —O(C=O)$R^4$ wherein $R^4$ is lower alkyl or the like, or the like).

A compound of the formula (II) wherein $Z^2$ and $Z^4$ each is independently —$NR^{21}CO$— or —$NR^{21}$— wherein $R^{21}$ is as defined above can be prepared as illustrated above.

A heteroaromatic derivative having amino group of the formula (XIIa) or (XIIa'), is easily prepared by 1) obtaining a commercially available compound, 2) reacting the corresponding halogen derivative with $R^{21}NH_2$, or 3) reducing a nitro derivative prepared by nitration.

For example, a compound of the formula (XIIc) or (XIIc') can be prepared by reacting a compound of the formula (XIIa) or (XIIa') with a compound of the formula (XIIb), preferably in the presence of a base, as shown in shin-jikkenn kagakukouza, Vol. 14, 1978, page 1787; Synthesis, 1986, p852–854; shin-jikkenn kagakukouza, Vol. 22, 1992, page 155. When a compound of the formula (XIIb) is carboxylic acid, a compound of the formula (XIIc) or (XIIc') can be prepared by condensation reaction using a condensing agent.

A solvent to be used is, for example, tetrahydrofuran (THF), dioxane or the like. A base to be used is, for example, pyridine, dimethylamino pyridine or the like. A condensing agent to be used is, for example, DCC (dicyclohexylcarbodiimide), EDC or the like. A reaction temperature is approximately −100 to 100° C., preferably −70 to 60° C.

A compound of the formula (XIId) or (XIId') can be prepared by reducing a compound of the formula (XIIc) or (XIIc'). Reduction reaction is carried out by using lithium aluminum hydride, borane methylsulfide complex or the like.

In the above shown synthetic route [G], a sulfonamide derivative of the formula (II) wherein $Z^2$ or $Z^4$ is —$NR^{21}SO_2$—, can be prepared by using a compound of the formula: $R^X(SO_2)L$ wherein $R^X$ is as defined above and L is halogen or the like in place of a compound of the formula: $R^X(C=O)L$. When a heteroaromatic compound having a carboxy group or the like, shown as a compound of the formula (XIIa) or (XIIa') wherein a group of the formula: —$NHR^{21}$ is a group of the formula: —COL wherein L is a leaving group (e.g., halogen, hydroxy, —O(C=O)$R^4$ wherein $R^4$ is lower alkyl or the like, or the like), can be obtained or prepared as a starting material, an amide derivative of the formula (II) wherein $Z^2$ or $Z^4$ is —$CONR^{21}$—, can be prepared by condensation reaction using a compound of the formula: $R^XNH_2$ in place of a compound of the (XIIb) as well as the above shown synthetic route [G]. On the other hand, when a heteroaromatic compound having a group of the formula: —$(SO_2)L$ wherein L is halogen or the like can be obtained or prepared as a starting material, an sulfonamide derivative of the formula (II) wherein $Z^2$ or $Z^4$ is —$SO_2NR^{21}$—, can be prepared by using a compound of the formula: $R^XNH_2$.

Synthetic route [H]

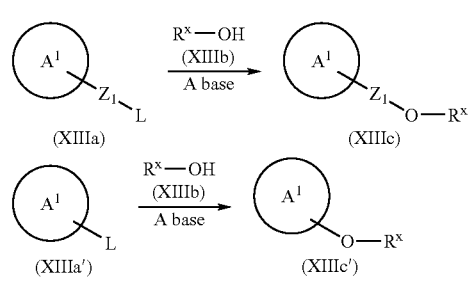

wherein $A^1$ and $Z^1$ are as defined above; L is halogen; and a group of the formula: —$R^X$ is a group of the formula: -$Z^3$-$R^1$ wherein $Z^3$ and $R^1$ are as defined above or a group of the formula: —$R^2$ wherein $R^2$ is as defined above.

A compound of the formula (II) wherein $Z^2$ or $Z^4$ is —O— can be prepared as illustrated above.

A compound of the formula (XIIIa) or (XIIIa') is, for example, 2-bromofuran-5-carboxylic acid ethyl ester, 2-chlorofuran-5-carboxylic acid ethyl ester, 2-bromofuran-5-carboxylic acid methyl ester, 2-chlorofuran-5-carboxylic acid methyl ester, 2-acetyl-5-bromofuran, 2-acetyl-5-chlorofuran, 2-bromothiophene-5-carboxylic acid ethyl ester, 2-chlorothiophene-5-carboxylic acid ethyl ester, 2-bromothiophene-5-carboxylic acid methyl ester, 2-chlorothiophene-5-carboxylic acid methyl ester, 2-acetyl-5-bromothiophene, 2-acetyl-5-chlorothiophene, 2-bromopyrrole-5-carboxylic acid ethyl ester, 2-chloropyrrole-5-carboxylic acid ethyl ester, 2-bromopyrrole-5-carboxylic acid methyl ester, 2-chloropyrrole-5-carboxylic acid methyl ester, 2-acetyl-5-bromopyrrole, 2-acetyl-5-chloropyrrole, 2-bromomethylfuran-5-carboxylic acid ethyl ester, 2-chloromethylfuran-5-carboxylic acid ethyl ester, 2-bromomethylfuran-5-carboxylic acid methyl ester, 2-chloromethylfuran-5-carboxylic acid methyl ester, 2-acetyl-5-bromomethylfuran, 2-acetyl-5-chloromethylfuran or the like.

A base to be used is, for example, NaH, NaOH, LiH or the like.

A reaction temperature is room temperature to 100° C. A solvent to be used is, for example, DMF or the like.

Examples of a compound of the formula (XIIIb) include, for example, alcohols, phenols (e.g., phenol, 4-fluorophenol, 4-chlorophenol, 4-bromophenol, 2,4-difluorophenol, 4-trifluoromethylphenol or the like) or the like.

A compound of the formula: $R^X$—SH wherein $R^X$ is as defined above (e.g., thiol, thiophenol (e.g., 4-fluorothiophenol, 4-chlorothiophenol, 4-bromothiophenol, 2,4-difluorothiophenol, 4-trifluoromethylthiophenol or the like) or the like) can be used in place of a compound of the formula (XIIIb). In such a case, a compound of the formula (II) wherein $Z^2$ or $Z^4$ is —S— can be prepared.

When heteroaromatic ring ($A^1$) has a group of the formula: -$Z^1$-OH wherein $Z^1$ is as defined above or a group of the formula: —OH, a compound of the formula (XIIIc) or (XIIIc') can be prepared by using a compound of the formula: $R^X$—L wherein $R^X$ is as defined above in place of a compound of the formula (XIIIb).

Synthetic route [I]

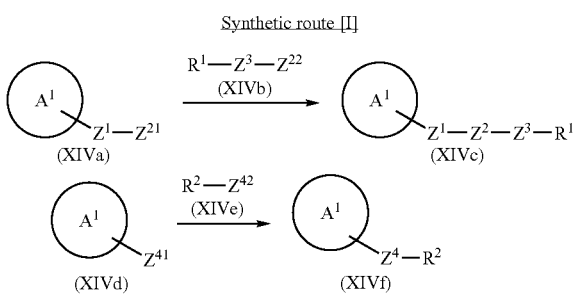

wherein $A^1$, $Z^1$, $Z^2$, $Z^3$, $Z^4$, $R^1$ and $R^2$ are as defined above; $Z^{21}$, $Z^{22}$, $Z^{41}$ and $Z^{42}$ each is independently —CHO, —SH, —SO$_2$L, —MgL, —Li, —NHR$^{21}$, —OH, —L, —COOH, —COL, —B(OH)$_2$, —OTf or the like; and L is halogen or the like.

Whereas the above shown synthetic routes [B] to [H] mainly relate to direct insertion of a substituent(s) into the heteroaromatic ring, this synthetic route [I] can provide a compound of the formula (XIVc) or (XIVf) by further reacting a functional group attached to the heteroaromatic ring (e.g, a group of the formula: -Z$^1$-Z$^{21}$, a group of the formula: -Z$^{41}$).

For example, a combination of $Z^{21}$ and $Z^{22}$ or a combination of $Z^{41}$ and $Z^{42}$ forms $Z^2$ as shown below (-Z$^{21}$+-Z$^{22}$→-Z$^2$-; -Z$^{41}$+-Z$^{42}$→-Z$^2$—).

—CHO+—MgL→—CH(OH)—
—CHO+—Li→—CH(OH)—
—CH(OH)—→—CO—
—CH(OH)—→—CH$_2$—
—SH+—L—→—S—→—SO—→—SO$_2$—
—OH+—L→—O—
—NHR$^{21}$+—L→—NR$^{21}$—
—SO$_2$L+—NHR$^{21}$→—SO$_2$NR$^{21}$— or —NR$^{21}$SO$_2$—
—COL+—NHR$^{21}$→—CONR$^{21}$— or —NR$^{21}$CO—
—COOH+—NHR$^{21}$→—CONR$^{21}$— or —NR$^{21}$CO—
—COL+—OH→—C(=O)—O— or —O—C(=O)—
—COOH+—OH→—C(=O)—O— or —O—C(=O)—
—B(OH)$_2$+—L→— (a bond)
—OTf+—L→— (a bond)

These reactions are well known in organic chemistry and can be performed in accordance with an usual public method and condition such as reaction temperature, solvent or the like.

The procedure of the above-shown reactions [A] to [I] can be modified according to the character of heteroaromatic derivative, the introduction position of the substituent or the like. Protection of functional groups and the deprotection, if desired, may be performed in accordance with a well known method. The example includes protection of carbonyl group with acetal, protection of carboxylic acid with ester residue or the like.

Method for use of the compound of the present invention is explained below.

The compound of the present invention is useful as a pharmaceutical composition such as an antiviral agent or the like. The compound of the present invention has an outstanding inhibitory activity against integrase of viruses (especially, lentivirus, retrovirus). Therefore, the compound of the present invention is expected to prevent or treat various diseases caused by viruses producing integrase to grow in animal cells upon infection, and is useful as, for example, an integrase inhibitor against retroviruses (e.g., HIV-1, HIV-2, HTLV-1, SIV, FIV or the like), especially, an anti-HIV agent or the like.

The compound of the present invention can be used to prepare an anti-HIV medical mixture, by the combination with an anti-HIV agent possessing other inhibitory mechanism such as an adsorption inhibitor (e.g., dextran sulfate, curdlan sulfate, soluble CD4, TAK-779, T22 or the like), a TAT inhibitor (Ro 24-7429 or the like), a REV inhibitor, a reverse transcriptase inhibitor (e.g., AZT, DDI, 3TC, DDC, D4T, S-1153, Nevirapine, HEPT derivatives, TIBO, Abacavir sulfate, efavirenz or the like), a protease inhibitor (e.g., Saquinqvir, Ritonavir, Nelfinavir, Indinavir, Anprenavir, KNI-272 or the like) or the like. The compound of the present invention can be used in combination therapy. Since any integrase inhibitor has not been on sale yet, it is useful to use the compound of the present invention in combination therapy, associated with the above anti-HIV agent showing other inhibitory mechanism. The compound of the present invention can be used in cocktail therapy or the like as a concomitant agent showing synergy effect, such as enhancing the activity of the other anti-HIV agent.

The compound of the present invention can be used to suppress the spread of the retrovirus infection over non-target tissues in the gene therapy using a retrovirus vector derived from HIV or MLV. Specially, in the case that cells and the like are infected by such a vector in vitro and then are put back in a body, a previous administeration of the compound of the present invention prevents an unnecessary infection. The compound of the present invention is useful in the field of the gene therapy, which seems to be developed furthermore.

The compounds of the present invention can be administered orally or parenterally. For oral administration, the compounds of the present invention can be used in any form of usual formulations, for example, solid formulations such as tablets, powders, granules, capsules; aqueous formulations; oleaginous suspensions; solutions such as syrup or elixir. For parenteral administration, the compounds of the present invention can be used as an aqueous or oleaginous suspension injection, or nose drops. In the preparation of such formulations, conventional excipients, binding agents, lubricants, aqueous solvents, oleaginous solvents, emulsifying agents, suspending agents, preservatives, stabilizers, and the like can be optionally used.

A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In the case of manufacturing a pharmaceutical composition according to the present invention, an active ingredient is admixed or diluted with a carrier, or they are contained in a carrier in the form of capsule, sacheier, paper, or another container. In the case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound of the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. Example of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

Although an appropriate dosage of the compound of the present invention varies depending on the administration route, age, body weight, conditions of the patient, and kind of disease, in the case of oral administration, the daily dosage can be between approximately 0.05–3000 mg, preferably approximately 0.1–1000 mg, for an adult. The daily dosage can be administered in divisions. In the case of parenteral administration, the daily dosage for an adult can be between approximately 0.01–1000 mg, preferably approximately 0.05–500 mg.

Furthermore, all kinds of heteroaromatic derivatives having the group of the formula: —C(=O)—CH=C(X)Y wherein X and Y are as defined above can be used as pharmaceutical compositions such as antiviral agents, as well as the compound of the present invention. In said heteroaromatic derivatives, a wide variety of substituents can be introduced as partial structures other than —C(=O)—CH=C(X)Y, as far as they do not have a negative effect on the pharmacological activity. These compounds can be prepared in accordance with the above preparations of the compound of the present invention.

The compound of the present invention is useful as an intermediate or a starting material for preparing medicines or the like. For example, the compound of the present invention wherein $R^4$ defined in Y is an ester residue can be easily derived to the compound wherein $R^4$ is hydrogen by deprotection.

EXAMPLE

Examples of the present invention are shown below. Reactions are usually carried out under nitrogen atmosphere, and reaction solvents are used as dried over molecular sieve and the like. Extracts are dried over sodium sulfate or magnesium sulfate and the like.

(Abbreviation)

MeOH=methanol; EtOH=ethanol; DMF=N,N-dimethylformamide; THF=tetrahydrofuran; DMSO=dimethylsulfoxide; Bn=benzyl; Ph=phenyl; Tr=trityl; MOM=methoxymethyl

REFERENCE EXAMPLE

2-Trityl-2H-tetrazol-5-carboxylic acid ethyl ester, 1-trityl-1H-1,2,4-triazol-3-carboxylic acid ethyl ester and 2-trityl-2H-1,2,4-triazol-3-carboxylic acid ethyl ester to be used in the present invention were prepared in accordance with methods (A) to (C) described below. Additionally, 1-trityl-1H-1,2,4-triazol-3-carboxylic acid ethyl ester and 2-trityl-2H-1,2,4-triazol-3-carboxylic acid ethyl ester have a protective group (trityl) at different position, but both of them can be used in the preparation of the compound of the present invention.

(A) 2-Trityl-2H-tetrazol-5-carboxylic acid ethyl ester (1) To a solution of trimethyltinazide (6.17 g, 30 mmol) in pyridine (20 ml) was added dropwise ethyl cyanoformate (3.30 g, 33 mmol) for 15 minutes at room temperature. The temperature of the reaction solution became approximately 45° C. The reaction mixture was gradually cooled down to room temperature and stirred for 1 hour, heated at 60° C. and then stirred for 18 hours. After cooling, the reaction mixture was concentrated under reduced pressure. To the residue was added concentrated hydrochloric acid (5 ml). After stirring for 15 minutes at room temperature, saturated brine (20 ml) was added thereto. The mixture was twice extracted with ethylacetate, washed with saturated brine and dried. The solvent was evaporated. The obtained crystal was washed with hexane to give 1H-tetrazol-5-carboxylic acid ethyl ester (3.47 g). Yield: 81%.

(2) To a solution of 1H-tetrazol-5-carboxylic acid ethyl ester (3.47 g, 24.4 mmol) in THF (20 ml) were added triethylamine (3.70 g, 36.6 mmol) and tritylchloride (7.14 g, 25.6 mmol) successively. The reaction mixture was stirred for 1 hour at room temperature and concentrated under reduced pressure. The residue was partitioned between ethylacetate and water. The ethylacetate layer was washed with an aqueous saturated sodium bicarbonate, washed with water and dried. The solvent was evaporated. The obtained crystal was washed with hexane to give the titled compound (8.15 g). Yield: 87%.

M.p.: 162° C. (decomposition) NMR(CDCl$_3$) δ: 1.43(3H, t,J=7.2 Hz), 4.50(2H, q, J=7.2 Hz), 7.08–7.12(6H, m), 7.29–7.41(9H, m).

(B) 1-Trityl-1H-1,2,4-triazol-3-carboxylic acid ethyl ester (1) A mixture of ethyl thioxamate (10.55 g, 79.2 mmol) and formylhydrazine (5.00 g, 83.2 mmol) was heated at 65° C. for 30 minutes and stirred in accordance with a method described in Collect. Czech Chem. Commun., 1984, 49, p 2492. After cooling, the precipitated crystal was collected by filteration and washed with ethanol to give (N-formylhydrazino)-imino acetic acid ethyl ester (9.62 g). Yield: 76%.

(2) A suspension of (N-Formylhydrazino)-imino acetic acid ethyl ester (9.62 g, 60.4 mmol) in diglyme (40 ml) was refluxed for 30 minutes. After cooling, the precipitated crystal was collected by filtration and washed with hexane to give 1H-1,2,4-triazol-3-carboxylic acid ethyl ester (7.28 g). Yield: 85%.

(3) To a solution of 1H-1,2,4-triazol-3-carboxylic acid ethyl ester (7.62 g, 54 mmol) in DMF (60 ml) was added at room temperature N,N-diisopropylethylamine (14 g, 108 mmol) and tritylchloride (15.8 g, 56.7 mmol), successively. The mixture was stirred for 2 hours. The reaction mixture was mixed with water (300 ml) and ethylacetate (300 ml). The crystal was collected by filteration, dissolved in CHCl$_3$ (150 ml), washed with water and dried. The solvent was evaporated. The residue was crystallized from ether to give the titled compound (8.91 g). Additionally, ethylacetate layer was washed with water and dried. The solvent was evaporated. The residue was crystallized from ether to give the titled compound (4.73 g). Total amount of the titled compound: 13.64 g. Yield: 66%.

NMR(CDCl$_3$) δ: 1.41(3H, t,J=7.2 Hz), 4.45(2H, q, J=7.2 Hz), 7.11–7.13(6H, m), 7.32–7.36(9H, m), 8.01(1H, s).

(C) 2-Trityl-2H-1,2,4-triazol-3-carboxylic acid ethyl ester (1) Sodium hydride (60% dispersion in mineral oil, 13.8 g, 345 mmol) was washed with hexane and suspended in DMF (150 ml). At an ice bath temperature, 1,2,4-triazole (total; 20.7 g, 300 mmol) was added thereto in four divisions. After stirring for 30 minutes, to the mixture was added tritylchloride (total; 83.7 g, 300 mmol) in seven divisions and additionally added DMF (50 ml). After stirring for 1.5 hours at room temperature, to the reaction mixture was added water (600 ml). The precipitated crystal was collected by filteration, washed with water, dissolved in CHCl$_3$ (800 ml) and dried. The solvent was evaporated. The obtained residue was chromatographed on silica gel (ethylacetate:CHCl$_3$=1:2, v/v). The fraction of the objective was concentrated to give 1-trityl-1H-1,2,4-triazole (43.9 g). Yield: 47%.

(2) A solution of 1-Trityl-1H-1,2,4-triazole (10.5 g, 33.6 mmol) in THF (300 ml) was cooled under −70° C. To the solution was added at −72 to −68° C. a solution of n-butyllithium in hexane (1.54 M solution, 24 ml, 36.9 mmol). The reaction solution was gradually warmed up to −25° C. and cooled down to −60° C. again. To the mixture was added dropwise a solution of chloroethylformate (7.29 g, 67.2 mmol) in THF (15 ml). The reaction mixture was warmed up to room temperature, stirred for 1.5 hours, concentrated under reduced pressure and mixed with ethylacetate (700 ml). The precipitated crystal was collected by filteration, washed with water, dissolved in THF (200 ml) and dried. The solvent was evaporated. The obtained crystal was washed with ethylacetate to give the titled compound (2.90 g). The ethylacetate layer was washed with 2% aqueous ammonia, washed with water and dried. The solvent was evaporated. The obtained residue was chromatographed on silica gel (hexane:ethylacetate:CHCl$_3$=2:1:2, v/v/v) to give the titled compound (3.65 g). Total of the titled compound: 6.55 g. Yield: 51%.

NMR(CDCl$_3$) δ: 1.02(3H, t,J=7.2 Hz), 3.76(2H, q, J=7.2 Hz), 7.12–7.14(6H, m), 7.28–7.33(9H, m), 7.99(1H, s).

Preparation of a Compound wherein Heteroaryl (A$^1$) is Pyrrolyl (Compound No. I-1-41)

Example 1

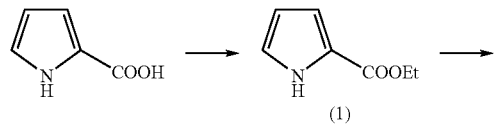

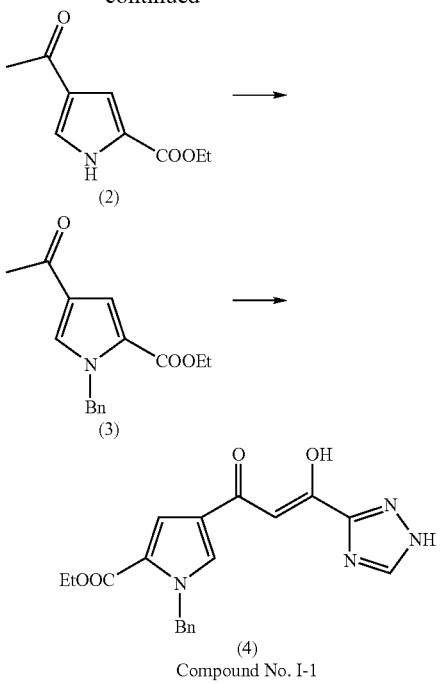

Compound No. I-1

1-[(1-Benzyl-5-ethoxycarbonyl)pyrrol-3-yl]-3-hydroxy-3-(1H-1,2,4-triazol-3-yl)-propenone (Compound No. I-1)

(1) To pyrrole-2-carboxylic acid (2.2 g, 20 mmol) were added at room temperature thionylchloride (2 ml, 27.4 mmol) and DMF (0.5 ml). The mixture was heated at 50° C. for 30 minutes. An excess of thionyl chloride was evaporated under reduced pressure. The residue was dissolved in toluene (5 ml) and evaporated under reduced pressure again. This procedure was performed three times. After that, the residue was dissolved in chloroform (10 ml), and the solution was added dropwise at room temperature to ethanol (20 ml) and stirred for 30 minutes. The reaction mixture was concentrated. The residue was chromatographed on silica gel (hexane:ethylacetate=1:1 v/v). The fraction of the objective was concentrated to give 2-ethoxycarbonylpyrrole (2.9 g) as an oil quantitatively.

NMR(CDCl$_3$) δ: 1.36(3H, t, J=7.0 Hz), 4.33(2H, q, J=7.0 Hz), 6.22–6.31(1H, m), 6.89–6.98(2H, m), 9.20(1H, brs).

(2) To a suspension of aluminum chloride (5.7 g, 43 mmol) in dichloroethane (60 ml) was added dropwise at an ice bath temperature a solution of acetylchloride (3.38 g, 43 mmol) in dichloroethane (10 ml). The solution was stirred at 10° C. for 30 minutes and ice-cooled again. To the solution was added dropwise a solution of the above-obtained compound (2.9 g, 20.8 mmol) in dichloroethane (5 ml). After stirring for 1 hour, the reaction mixture was poured into ice-water, extracted with ethylacetate. The ethylacetate was washed with water and dried. The solvent was evaporated to give 4-acetyl-2-ethoxycarbonylpyrrole (3.34 g) as an oil. Yield: 88%.

NMR(CDCl$_3$) δ:1.38(3H, t, J=7.0 Hz), 4.35(2H, q, J=7.0 Hz), 7.24–7.31(1H, m), 7.54–7.55(1H, m), 9.52(1H, brs).

(3) To a suspension of sodium hydride (60% dispersion in mineral oil, 440 mg, 11 mmol) in DMF (15 ml) was added dropwise at an ice bath temperature a solution of the above-obtained compound (1.8 g, 10 mmol) in DMF (5 ml).

After stirring at room temperature for 15 minutes, the solution was cooled at an ice bath temperture and mixed with a solution of benzylbromide (1.88 g, 11 mmol) in DMF (2 ml). After stirring at room temperature for 30 minutes, the mixture was poured into ice-water and extracted with ethylacetate. The ethyl acetate was washed with water and dried. The solvent was evaporated. The obtained white crystal was washed with hexane to give 3-acetyl-1-benzyl-5-ethoxycarbonylpyrrole (2.4 g). Yield: 88%.

NMR(CDCl$_3$) δ:1.32(3H, t, J=7.2 Hz), 2.41(3H, s), 4.26 (2H, q, J=7.2 Hz), 5.57(2H, s), 7.06–7.18(1H, m), 7.24–7.44 (4H, m).

(4) To a solution of the above-obtained compound (271 mg, 1 mmol) in THF (10 ml) was added at −65° C. a solution of lithiumbistrimethylsilylamide in THF (1 M solution. 2 ml, 2 mmol). The reaction solution was gradually warmed up to 0° C. and cooled down to −70° C. again. To the solution was added dropwise a solution of 1-trityl-1H-[1,2,4-triazol]-3-carboxylic acid ethyl ester (767 mg, 2 mmol) in THF (10 ml). The reaction solution was warmed to room temperature and stirred for additional 2 hours. The mixture was poured into excess of aqueous ammonium chloride and extracted with ethylacetate. The ethyl acetate was washed with water and dried. The solvent was evaporated. The obtained residue was mixed with dioxane (10 ml) and 2 N HCl (2 ml) and stirred at 70° C. for 30 minutes. Dioxane was evaporated under reduced pressure. The residue was partitioned between ethylacetate and water. The ethylacetate layer was washed with water and dried. The solvent was evaporated. The obtained yellow crude crystal was recrystallized from isopropylether-chloroform to give the titled compound (300 mg). Yield: 82%. M.p.: 204–206° C.

Elemental analysis for C$_{19}$H$_{18}$N$_4$O$_4$ Calcd. (%): C, 62.29; H, 4.95; N, 15.29. Found. (%): C, 61.94; H, 5.03; N; 15.02. NMR(d$_6$-DMSO) δ: 1.24(3H, t, J=7.2 Hz), 4.20(2H, q, J=7.2 Hz), 5.61(2H, s), 6.97(1H, s), 7.12–7.42(6H, m), 8.32(1H, s), 8.77(1H, s).

Example 2

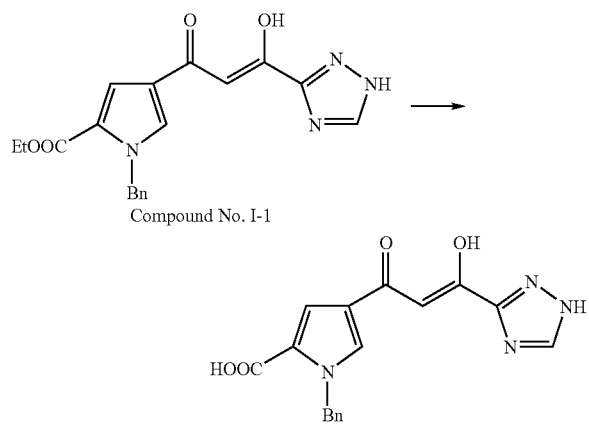

Compound No. I-1

Compound No. I-2

1-[(1-Benzyl-5-carboxy)pyrrol-3-yl]-3-hydroxy-3-(1H-1,2,4-triazol-3-yl)-propenone (Compound No. I-2)

(1) To a solution of 1-[(1-benzyl-5-ethoxycarbonyl) pyrrol-3-yl]-3-hydroxy-3-(1H-1,2,4-triazol-3-yl)-propenone (150 mg, 0.41 mmol) obtained in Example 1 in dioxane (10 ml) was added 2 N NaOH (1 ml). The solution was stirred at 50° C. for 30 minutes. The reaction mixture was concentrated under reduced pressure. The residue was partitioned between ether (10 ml) and water (10 ml). The water layer was separated and washed with ether, and then acidified with 2 N HCl. The extract with ethylacetate was washed with water and dried. The solvent was evaporated. The obtained yellow powder was recrystallized from ethylacetate to give the titled compound (100 mg) Yield: 74%.

M.p.: 264–265° C. Elemental analysis for C$_{17}$H$_{14}$N$_4$O$_4$ 0.3 H$_2$O Calcd. (%): C, 59.40; H, 4.28; N, 16.30. Found. (%): C, 59.21; H, 4.30; N, 16.20. NMR(d$_6$-DMSO) δ: 5.63(2H, s), 6.95(1H, s), 7.16–7.40(6H, m), 8.27(1H, d, J=1.8 Hz), 8.69(1H, brs), 12.8(1H, brs).

Example 3

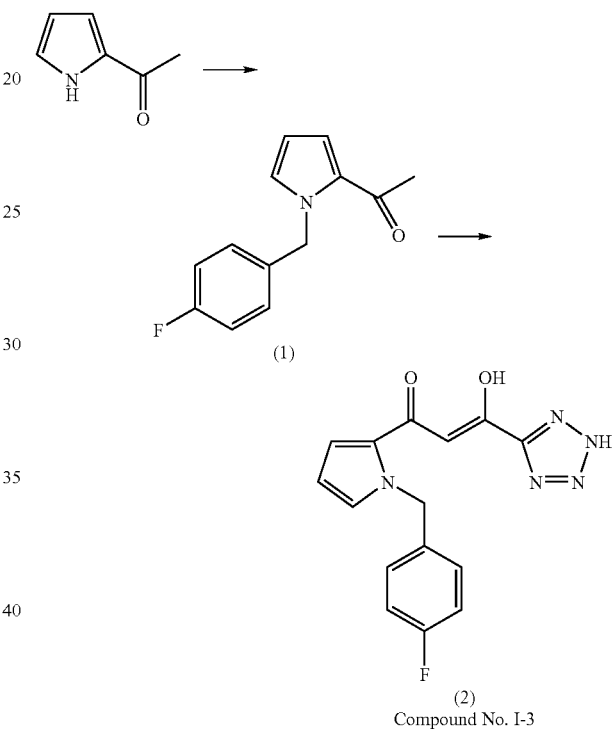

Compound No. I-3

1-[1-(4-Fluorobenzyl)pyrrol-2-yl]-3-hydroxy-3-(2H-tetrazol-5-yl)-propenone (Compound No. I-3)

(1) To a suspension of sodium hydride (60% in mineral oil, 1.32 g, 33 mmol) in DMF (30 ml) was added at an ice bath temperature a solution of 2-acetylpyrrole (3.27 g, 30 mmol) in DMF (5 ml). The mixture was stirred at room temperature for 15 minutes and cooled again. To the solution was added dropwise a solution of 4-fluorobenzylbromide (6.24 g, 33 mmol) in DMF (2 ml). The reaction solution was stirred at room temperature for 1 hour and poured into ice-water, and then extracted with ethylacetate. The ethyl acetate was washed with water and dried. The solvent was evaporated to give 2-acetyl-1-(4-fluorobenzyl)pyrrole (6.5 g) as an oil quantitatively.

NMR(CDCl$_3$) δ: 2.41(3H, s), 5.53(2H, s), 6.18–6.22(1H, m), 6.88–7.14(6H, m).

(2) To a solution of the above-obtained compound (1.1 g, 5 mmol) in THF (20 ml) was added under −65° C. a solution of lithiumbistrimethylsilylamide in THF (1 M solution, 10 ml, 10 mmol). The reaction solvent was gradually warmed up to 0° C. and cooled again to −70° C. To the mixture was added dropwise a solution of 2-trityl-2H-tetrazol-5-carboxylic acid ethyl ester (2.3 g, 6 mmol) in THF (15 ml). The reaction mixture was gradually warmed up to room temperature and stirred for 1.5 hours, and poured into an excess amount of aqueous ammonium chloride, and then extracted with ethylacetate. The extract was washed with brine and dried. The solvent was evaporated. To the obtained residue was added dioxane (15 ml) and 2 N HCl (5 ml). The mixture was stirred for 30 minutes at 70° C. Dioxane was evaporated under reduced pressure. The residue was partitioned between ethylacetate and water. The ethylacetate layer was washed with water and dried. The solvent was evaporated. The residue was dissolved in ether and extracted with 1 N NaOH (6 ml) three times. The alkaline extract was washed with ether twice and neutralized with 1 N HCl, and extracted with ethylacetate. The extract was washed with water and brine, and then dried. The solvent was evaporated. The obtained yellow crude crystal was washed with a small amount of ethylacetate. Recrystallization from ethylacetate gave the titled compound (1.3 g). Yield: 83%. M.p.: 147–150° C.

Elemental analysis for $C_{15}H_{12}FN_5O_2$ 0.2 $H_2O$ Calcd. (%): C, 56.85; H, 3.94; N, 22.10; F, 6.00. Found. (%): C, 56.68; H, 4.02; N, 22.47; F, 5.72. NMR($d_6$-DMSO) δ: 5.65(2H, s), 6.37(1H, dd, J=3.0, 2.7 Hz), 7.05–7.20(5H, m), 7.47–7.58 (2H, m).

Example 4

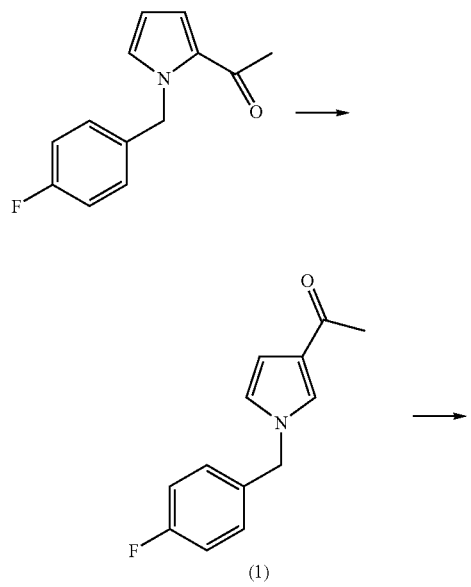

Compound No. I-4

1-[1-(4-fluorobenzyl)pyrrol-3-yl]-3-hydroxy-3-(2H-tetrazol-5-yl)-propenone (Compound No. I-4)

(1) 2-Acetyl-(4-fluorobenzyl)pyrrole (542 mg, 2.5 mmol) obtained in accordance with the method described in Example 3 (1) was dissolved in trifluoroacetic acid (5 ml). The mixture was stirred for 1.5 hours at 80° C. After cooling to room temperature, the mixture was poured to ice-water and neutralized with 4 N NaOH, and then extracted with ethylacetate. The extract was washed with water and dried. The solvent was evaporated. The obtained residue was chlomatographed on silica gel (hexane:ethylacetate=3:1 v/v). The fraction of the objective was concentrated to give 3-acetyl-1-(4-fluorobenzyl)pyrrole (480 mg) as an oil. Yield: 88%.

NMR(CDCl$_3$) δ: 2.38(3H, s), 5.04(2H, s), 6.60–6.64(2H, m), 7.00–7.09(2H, m), 7.10–7.17(2H, m), 7.26–7.30(1H, m).

(2) To a solution of the above-obtained compound (180 mg, 0.83 mmol) in THF (15 ml) was added dropwise under −65° C. a solution of lithium bistrimethylsilylamide in THF (1 M solution, 1.7 ml, 1.7 mmol). The reaction mixture was warmed up to 0° C. and cooled down to −70° C. again. To the mixture was added dropwise a solution of 2-trityl-2H-tetrazol-5-carboxylic acid ethyl ester (653 mg, 1.7 mmol) in THF (5 ml). The mixture was warmed up to room temperature and stirred for 1.5 hours. The reaction mixture was poured to an excess amount of aqueous ammonium chloride and extracted with ethylacetate. The extract was washed with brine and dried. The solvent was evaporated. The obtained residue in dioxane (5 ml) and 2 N HCl (2 ml) was stirred for 30 minutes at 70° C. The dioxane was evaporated under reduced pressure. The residue was partitioned between ethylacetate and water. The ethylacetate layer was washed with water, dried and evaporated. The residue dissolved in ether was extracted with 1 N NaOH (6 ml) three times. The alkaline extract was washed with ether twice and neutralized with 1 N HCl, and then extracted with ethylacetate. The extract was washed with water and brine, and dried. The solvent was evaporated. The obtained pale yellow crude crystal was washed with a small amount of chloroform and recrystallized from chloroform to give the titled compound (91 mg). Yield: 35%. M.p.: 168–170° C.

Elemental analysis for $C_{15}H_{12}FN_5O_2$ 0.6 $H_2O$ Calcd. (%): C, 53.75; H, 3.79; N. 20.90; F, 5.67. Found. (%): C, 53.83; H, 3.73; N, 21.20; F, 5.50. NMR($d_6$-DMSO) δ: 5.20(2H, s), 6.68(1H, dd, J=3.0, 1.8 Hz), 6.96(1H, s), 7.02–7.08(1H, s), 7.16–7.26(2H, m), 7.34–7.44(2H, m), 8.02–8.08(1H, m).

Example 5

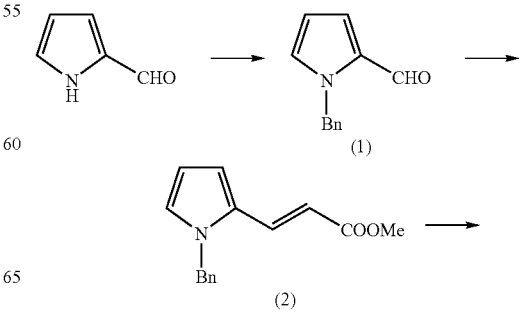

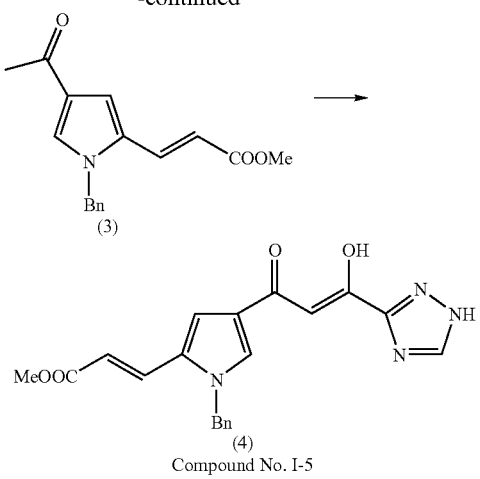

Compound No. I-5

1-[[1-Benzyl-5-(2-methoxycarbonylvinyl)]pyrrol-3-yl]-3-hydroxy-3-(1H-1,2,4-triazol-3-yl)-propenone (Compound No. I-5)

(1) To a suspension of sodium hydride (60% in mineral oil, 4.8 g, 120 mmol) in DMF (100 ml) was added dropwise at an ice bath temperature a solution of 2-formylpyrrole (9.5 g, 100 mmol) in DMF (10 ml). The mixture was stirred for 15 minutes at room temperature and cooled again. To the mixture was added dropwise a solution of benzylbromide (20.5 g, 120 mmol) in DMF (10 ml). The reaction mixture was stirred for 60 minutes at room temperature and poured to ice-water, and extracted with ethylacetate. The extract was washed with water and dried. The solvent was evaporated to give 1-benzyl-2-formylpyrrole (18.0 g) as an oil quantitatively.

NMR(CDCl$_3$) δ: 5.57(2H, s), 6.27(1H, t, J=3.0 Hz), 6.97(2H, d, J=3.0 Hz), 7.12–7.18(2H, m), 7.24–7.36(5H, m), 9.58(1H, s).

(2) To a suspension of sodium hydride (60% in mineral oil, 960 mg, 24 mmol) in DMF (20 ml) was added dropwise at an ice bath temperature a solution of diethyl (methoxycarbonylmethyl)phosphonate (5.04 g, 24 mmol) in DMF (1 ml). The mixture was stirred for 15 minutes at room temperature and cooled again. To the mixture was added dropwise a solution of 1-benzyl-2-formylpyrrole (3.7 g, 20 mmol) in DMF (2 ml). The reaction mixture was stirred for 4 hours at room temperature and poured into ice-water and extracted with ethylacetate. The extract was washed with water and dried. The solvent was evaporated. The obtained white crystal was washed with isopropylether to give 1-benzyl-2-(2-methoxycarbonylvinyl)pyrrole (3.14 g). Yield. 65%.

NMR(CDCl$_3$) δ: 3.73(3H, s), 5.21(2H, s), 6.13(1H, d, J=15.9 Hz), 6.23–6.27(1H, m), 6.72–6.75(1H, m), 6.82–6.86 (1H, m), 7.00–7.07(2H, m), 7.22–7.36(3H, m), 7.55(1H, d, J=15.9 Hz).

(3) To a suspension of alminium chloride (4.0 g, 30 mmol) in dichloromethane (30 ml) was added dropwise at an ice bath temperature a solution of acetic anhydride (1.23 g, 12 mmol) in dichloromethane (10 ml). The mixture was stirred for 30 minutes at room temperature and cooled again. To the mixture was added dropwise a solution of the above compound (2.43 g, 10 mmol) in dichloromethane (5 ml). The reaction mixture was stirred for 1 hour at room temperature and poured into ice-water, and extracted with ethylacetate.

The extract was washed with water and dried. The solvent was evaporated to give 3-acetyl-1-benzyl-5-(2-methoxycarbonylvinyl)pyrrole (1.8 g) as a white crystal. Yield: 64%.

NMR(CDCl$_3$) δ: 2.41(3H, s), 3.75(3H, s), 5.21(2H, s), 6.24(1H, d, J=15.9 Hz), 7.04–7.12(3H, m), 7.30–7.40(4H, m), 7.50(1H, d, J=15.9 Hz).

(4) To a solution of the above-obtained compound (283 mg, 1 mmol) in THF (15 ml) was added dropwise under −65° C. a solution of lithium bistrimethylsilylamide in THF (1 M solution, 1.2 ml, 1.2 mmol). The reaction mixture was warmed to −10° C. and cooled again. To the mixture was added dropwise a solution of 1-trityl-1H-1,2,4-triazol-3-carboxylic acid ethyl ester (575 mg, 1.5 mmol) in THF (7 ml). The reaction mixture was stirred for 2 hours and poured into an excess of aqueous ammonium chloride, and extracted with ethylacetate. The extract was washed with brine and dried. The solvent was evaporated. The obtained residue in dioxane (10 ml) and 2 N HCl (2 ml) was stirred for 30 minutes at 70° C. The dioxane was evaporated under reduced pressure. The residue was partitioned between ethylacetate and water. The ethylacetate layer was washed with water and dried. The solvent was evaporated. The obtained yellow crude crystal was recrystallized from isopropylether-ethylacetate-chloroform to give the titled compound (186 mg). Yield: 49%.

M.p.: 238–240° C. Elemental analysis for C$_{20}$H$_{18}$N$_4$O$_4$ 0.4H$_2$O Calcd. (%): C, 62.30; H, 4.91; N, 14.53. Found. (%): C, 62.18; H, 4.74; N, 14.53. NMR(d$_6$-DMSO) δ: 3.64(3H, s), 5.42(2H, s), 6.36(1H, d, J=15.9 Hz), 6.95(1H, s), 7.02–7.58(7H, m), 8.17(1H, s), 8.76(1H, s).

Example 6

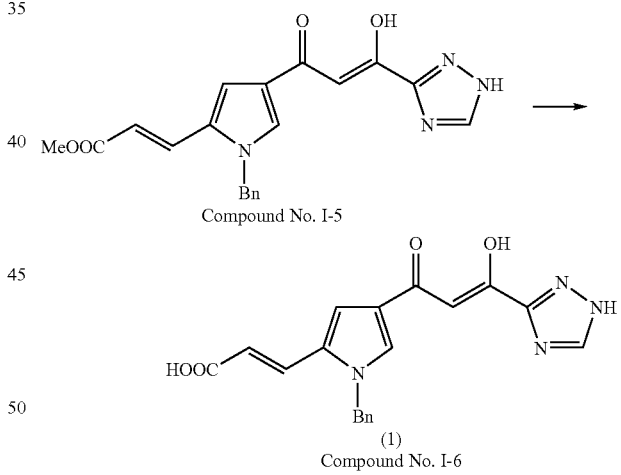

1-[[1-Benzyl-5-(2-carboxyvinyl)]pyrrol-3-yl]-3-hydroxy-3-(1H-1,2,4-triazol-3-yl)-propenone (Compound No. I-6)

(1) To a solution of 1-[[1-benzyl-5-(2-methoxycarbonylvinyl)]pyrrol-3-yl]-3-hydroxy-3-(1H-1,2,4-triazol-3-yl)-propenone (70 mg, 0.19 mmol), obtained in Example 5, in dioxane (10 ml) was added 2 N NaOH (1 ml). The mixture was stirred for 30 minutes at 50° C. The reaction mixture was concentrated under reduced pressure and partitioned between ether (10 ml) and water (10 ml). Water layer was separated and washed with Et$_2$O, and acidified with 2 N HCl, and then extracted with ethylacetate.

The extract was washed with water and dried. The solvent was evaporated. The obtained yellow powder was recrystallized from ethylacetate to give the titled compound (35 mg). Yield: 51%. M.p.: 263–265° C.

Elemental analysis for $C_{19}H_{16}N_4O_4$ $0.6H_2O$ Calcd. (%): C, 60.83; H, 4.62; N, 14.93. Found. (%): C, 60.88; H, 4.74; N, 14.88. NMR($d_6$-DMSO) δ: 5.45(2H, s), 6.36(1H, d, J=15.6 Hz), 7.10–7.48(8H, m), 8.17(1H, s), 8.76(1H, s).

Example 7

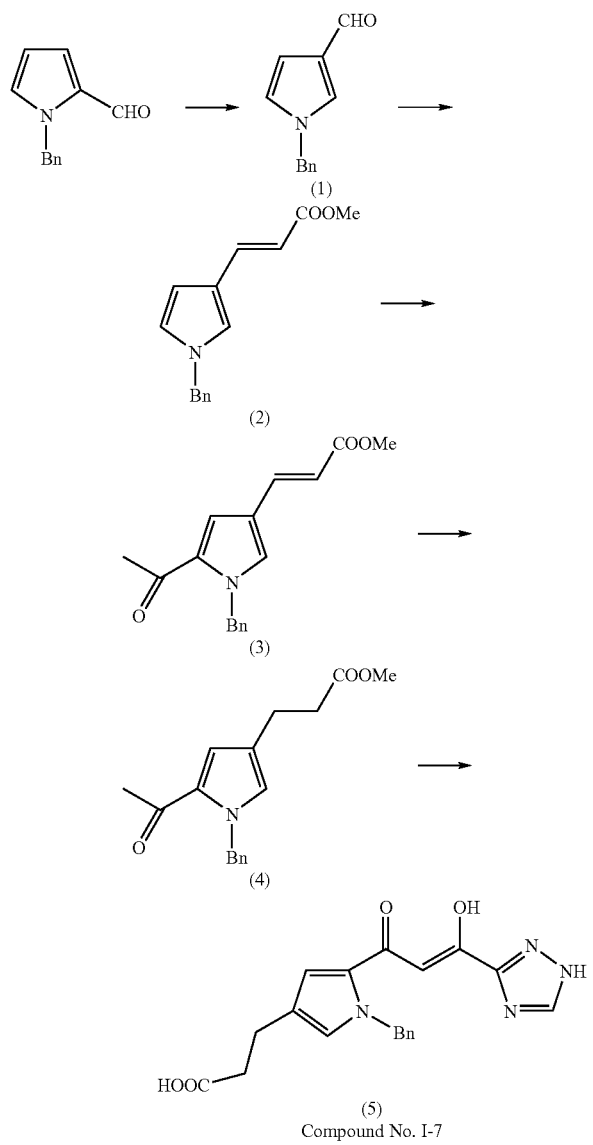

1-[[1-Benzyl-4-(2-carboxyethyl)]pyrrol-2-yl]-3-hydroxy-3-(1H-1,2,4-triazol-3-yl)-propenone (Compound No. I-7)

(1) To a solution of 1-benzyl-2-formylpyrrole (3.7 g, 20 mmol), obtained in accordance with the method described in Example 5 (1), in $CHCl_3$ (17 ml) was added at room temperature trifluoromethanesulfonic acid (14 ml, 158 mmol). The reaction mixture was stirred for 6 hours at 80° C. The mixture was cooled to room temperature, neutralized with aqueous sodium acetate, extracted with chloroform. The extract was washed with aqueous potassium carbonate and brine, and then dried. The solvent was evaporated. The obtained oil was chromatographed on silica gel (hexane:ethylacetate=3:1 v/v). The fraction of the objective was concentrated to give 1-benzyl-3-formylpyrrole (1.25 g) as a crystal. Yield: 33.7%.

NMR($CDCl_3$) δ: 5.10(2H, s), 6.64–6.72(2H, m), 7.12–7.20(2H, m), 7.28–7.40(4H, m), 9.74(1H, s).

(2) To a suspension of sodium hydride (60% in mineral oil, 311 mg, 7.8 mmol) in DMF (15 ml) was added dropwise at an ice bath temperature a solution of diethyl (methoxycarbonylmethyl)phosphonate (1.64 g, 7.8 mmol) in DMF (3 ml). The mixture was stirred for 30 minutes at room temperature and cooled again. To the mixture was added dropwise a solution of 1-benzyl-3-formylpyrrole (1.2 g, 6.5 mmol) in DMF (2 ml). The reaction mixture was stirred for 12 hours at room temperature and poured into ice-water, and extracted with ethylacetate. The extract was washed with water and dried. The solvent was evaporated. The obtained white crystal was washed with i-$Pr_2O$ to give 1-benzyl-3-(2-methoxycarbonylvinyl)pyrrole (1.3 g). Yield: 83%.

NMR($CDCl_3$) δ: 3.75(3H, s), 5.04(2H, s), 6.09(1H, m), 6.38–6.44(1H, m), 6.62–6.70(1H, m), 6.86–6.94(1H, m), 7.08–7.20(2H, m), 7.28–7.40(3H, m), 7.61(1H, d, J=15.9 Hz).

(3) To a solution of acetic anhydride (250 mg, 2.5 mmol) in dichloromethane (10 ml) was added dropwise a solution of boron trifluoride diethyletherate (937 mg, 6.6 mmol) in dichloromethane (2 ml). The reaction mixture was stirred for 30 minutes at room temperature and cooled again. To the mixture was added dropwise a solution of the above-obtained compound (540 mg, 2.2 mmol) in dichloromethane (5 ml). The mixture was stirred for 30 minutes and poured into ice-water, and extracted with ethylacetate. The extract was washed with water and dried. The solvent was evaporated. The obtained crude crystal was chromatographed on silica gel (hexane:ethylacetate=5:1 v/v). The fraction of the objective was concentrated to give 2-acetyl-1-benzyl-4-(2-methoxycarboxyvinyl)pyrrole (300 mg) as a crystal. Yield: 48%.

NMR($CDCl_3$) δ: 2.44(3H, s), 3.77(3H, s), 5.56(2H, s), 6.19(1H, d, J=15.9 Hz), 7.01–7.18(4H, m), 7.24–7.35(3H, m), 7.54(1H, d, J=15.9 Hz).

(4) To a solution of the above-obtained compound (156 mg, 0.55 mmol) in THF (3 ml) and EtOH (3 ml) was added at an ice bath temperature 10% palladium-carbon (15.6 mg). The mixture was treated under $H_2$ atmosphere for 30 minutes at room temperature. The mixture was filtered. The filtrate was evaporated under reduced pressure to give 2-acetyl-1-benzyl-4-(2-methoxycarbonylethyl)pyrrole (153 mg) quantitatively.

NMR($CDCl_3$) δ: 2.38(3H, s), 2.57(2H, t, J=7.2 Hz), 2.78(2H, t, J=7.2 Hz), 3.66(3H, s), 5.52(2H, s), 6.75–6.84 (2H, m), 7.07–7.12(2H, m), 7.20–7.38(3H, m).

(5) To a solution of the above-obtained compound (153 mg, 0.54 mmol) in THF (10 ml) was added dropwise under −65° C. a solution of lithium bistrimethylsilylamide in THF (1 M solution, 0.65 ml, 0.65 mmol). The reaction mixture was warmed up to −30° C. and cooled down to −70° C. again. To the mixture was added dropwise a solution of 1-trityl-1H-1,2,4-triazole-3-carboxylic acid ethyl ester (248 g, 0.65 mmol) in THF (5 ml). The reaction mixture was warmed to 0° C. The mixture was mixed with an excess amount of aqueous ammonium chloride and extracted with ethylacetate. The extract was washed with brine and dried.

The solvent was evaporated. The obtained residue was partitioned between dioxane (5 ml) and 2 N HCl (1 ml), and heated at 70° C. for 1 hour with stirring. The dioxane was evaporated under reduced pressure, and the residue was partitioned between ethylacetate and water. The ethylacetate layer was washed with water and dried. The solvent was evaporated. The obtained yellow crude crystal was recrystallized from ethylacetate to give the titled compound (42 mg). Yield: 21.2%. M.p.: 207–209° C.

Elemental analysis for $C_{19}H_{18}N_4O_4$ 0.6 $H_2O$ Calcd. (%): C, 60.50; H, 5.13; N, 14.85. Found. (%): C, 60.46; H, 5.12; N, 15.11. NMR($d_6$-DMSO) δ: 2.46–2.57(2H, m), 2.66(2H, dd, J=7.2, 8.4 Hz), 5.60(2H, s), 6.89(1H, s), 7.04–7.35(7H, m), 8.64(1H, brs).

Example 8

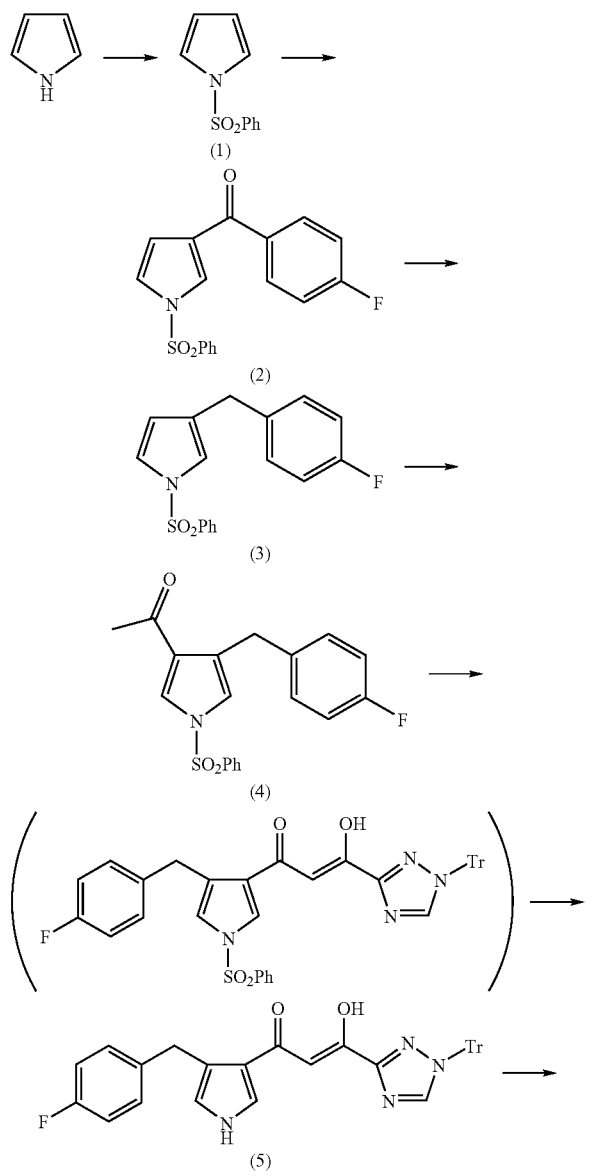

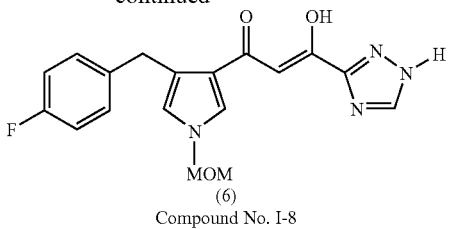

Compound No. I-8

1-[[4-(4-Fluorobenzyl)-1-methoxymethyl]pyrrol-3-yl]-3-hydroxy-3-(1H-1,2,4-triazol-3-yl)-propenone (Compound No. I-8)

(1) To a suspension of sodium hydride (60% in mineral oil, 2.4 g, 60 mmol) in DMF (100 ml) was added dropwise at an ice bath temperature a solution of pyrrole (3.35 g, 50 mmol) in DMF (5 ml). The mixture was stirred for 30 minutes at room temperature and cooled again. To the mixture was added dropwise a soluton of benzenesulfonylchloride (9.7 g, 5.5 mmol) in DMF (3 ml). The mixture was stirred for 30 minutes at room temperature and poured into ice-water, and extracted with ethylacetate. The extract was washed with water and dried. The solvent was evaporated. The obtained crystal was washed with hexane to give 1-benzenesulfonylpyrrole (8.4 g). Yield: 81%.

NMR(CDCl$_3$) δ: 7.30–7.42(5H, m), 7.58–7.68(4H, m).

(2) To a suspension of aluminum chloride (3.2 g, 24 mmol) in dichloromethane (30 ml) was added dropwise a solution of 4-fluorobenzoylchloride (3.49 g, 22 mmol) in dichloromethane (3 ml). The mixture was stirred for 10 hours. To the mixture was added at an ice bath temperature a solution of the above-obtained compound (4.15 g, 20 mmol) in dichloromethane (10 ml). The mixture was stirred for 30 minutes and poured into ice-water, and extracted with ethylacetate. The extract was washed with water and dried. The solvent was evaporated to give 1-benzenesulfonyl-3-(4-fluorobenzoyl)pyrrole (4.8 g) as a crystal. Yield: 73%.

NMR(CDCl$_3$) δ: 6.77–6.80(1H, m), 7.12–7.24(3H, m), 7.52–7.60(2H, m), 7.62–7.70(2H, m), 7.82–7.94(4H, s).

(3) To a suspension of aluminum chloride (4.0 g, 30 mmol) in dichloromethane (50 ml) was added a crystal of boran tert-butylamine complex (5.2 g, 60 mmol). The mixture was stirred for 30 minutes. To the mixture was added dropwise a solution of the above-obtained compound (3.3 g, 10 mmol) in dichloromethane (10 ml). The mixture was stirred for 10 minutes and poured into ice-water, and then partitioned between ethylacetate and water. The ethylacetate layer was washed with 2 N HCl (50 ml), aqueous sodium bicarbonate and water, successively and dried. The solvent was evaporated to give 1-benzenesulfonyl-3-(4-fluorobenzyl)pyrrole (3.47 g) as an oil quantitatively.

NMR(CDCl$_3$) δ: 3.70(2H, s), 6.08–6.12(1H, m), 6.86–6.98(3H, m), 7.04–7.10(3H, m), 7.46–7.54(2H, m), 7.56–7.64(1H, m), 7.80–7.85(2H, m).

(4) To a suspension of aluminum chloride (2.93 g, 22 mmol) in dichloromethane (40 ml) was added dropwise a solution of acetic anhydride (1.11 g, 11 mmol) in dichloromethane (2 ml). The mixture was stirred for 30 minutes and then cooled. To the mixture was added dropwise a solution of the above-obtained compound (3.15 g, 10 mmol) in dichloromethane (4 ml). The mixture was stirred for 10 minutes and poured into ice-water, and extracted with ethylacetate. The extract was washed with water and dried. The solvent was evaporated. The obtained crystal was washed with isopropylether to give 3-acetyl-1-benzenesulfonyl-4-(4-fluorobenzyl)pyrrole (880 mg) as a white crystal. The filtrate was concentrated and chromatographed on silica gel (hexane:ethylacetate=4:1 v/v). The fraction of the objective was concentrated to give 3-acetyl-1-benzenesulfonyl-4-(4-fluorobenzyl)pyrrole (1.1 g). Yield: 56%.

NMR(CDCl$_3$) δ: 2.39(3H, s), 3.98(2H, s), 6.68–6.70(1H, m), 6.86–7.02(2H, m), 7.06–7.18(2H, m), 7.48–7.74(4H, m), 7.83–7.92(2H, m).

(5) To a solution of the above-obtained compound (357 mg, 1 mmol) in THF (20 ml) was added dropwise under −65° C. a solution of lithium bistrimethylsilylamide in THF (1 M solution, 1.5 ml, 1.5 mmol). The reaction mixture was warmed up to 0° C. and cooled down to −70° C. To the solution was added a solution of 1-trityl-1H-1,2,4-triazole-3-carboxylic acid ethyl ester (575 mg, 1.5 mmol) in THF (7 ml). The mixture was warmed to room temperature and stirred for 2 hours. The mixture was added to an excess amount of aqueous ammonium chloride and extracted with ethylacetate. The extract was washed with brine and dried. The solvent was evaporated. The obtained residue was partitioned between dioxane (5 ml) and 4 N LiOH (1 ml) and heated at 70° C. with stirring for 1 hour. The dioxane was evaporated. The residue was extracted with ethylacetate after acidification with aqueous HCl. The extract was washed with water and saturated brine, and dried. The solvent was evaporated. The obtained pale yellow crude crystal was recrystallized from ethylacetate and hexane to give 1-[4-(4-fluorobenzyl)pyrrol-3-yl]-3-hydroxy-3-(1H-1-trityl-1,2,4-triazol-3-yl)-propenone (120 mg). Yield: 22%.

NMR(d$_6$-DMSO) δ: 4.04(2H, s), 6.58(1H, s), 6.83(1H, s), 6.94–7.28(10H, m), 7.30–7.50(10H, m), 7.80(1H, s), 8.34(1H, s).

(6) To a suspension of sodium hydride (60% in mineral oil, 20 mg, 0.5 mmol) in THF (10 ml) was added dropwise at an ice bath temperature a solution of the above-obtained compound (110 mg, 0.2 mmol) in THF (5 ml). The reaction mixture was stirred for 15 minutes at room temperature and cooled again. To the mixture was added dropwise a solution of methoxymethylchloride (19.3 mg, 0.24 mmol) in THF (1 ml). The reaction mixture was stirred for 2 hours and poured into ice-water, and then extracted with ethylacetate. The extract was washed with water and dried. The solvent was evaporated. The obtained residue was partitioned between dioxane (5 ml) and 2 N HCl (1 ml) and stirred at 70° C. for 30 minutes. The dioxane was evaporated. The residue was partitioned between ethylacetate and water. The ethylacetate layer was washed with water and dried. The solvent was evaporated. The obtained pale yellow crude crystal was recrystallized from isopropylether-chloroform-ethylacetate to the titled compound (15 mg). Yield: 21%.

M.p.: 189–191° C. Elemental analysis for C$_{18}$H$_{17}$FN$_4$O$_3$ 0.2 C$_4$H$_8$O$_2$ Calcd. (%): C, 60.38; H, 5.01; N, 14.98; F, 5.04. Found. (%): C, 60.53; H, 4.79; N, 14.71; F, 5.05. NMR(d$_6$-DMSO) δ: 3.20(3H, s), 5.20(2H, s), 6.68(1H, s), 6.88(1H, s), 7.02–7.25(2H, m), 7.32–7.42(2H, m), 8.05(1H, brs), 8.75(1H, brs).

Example 9

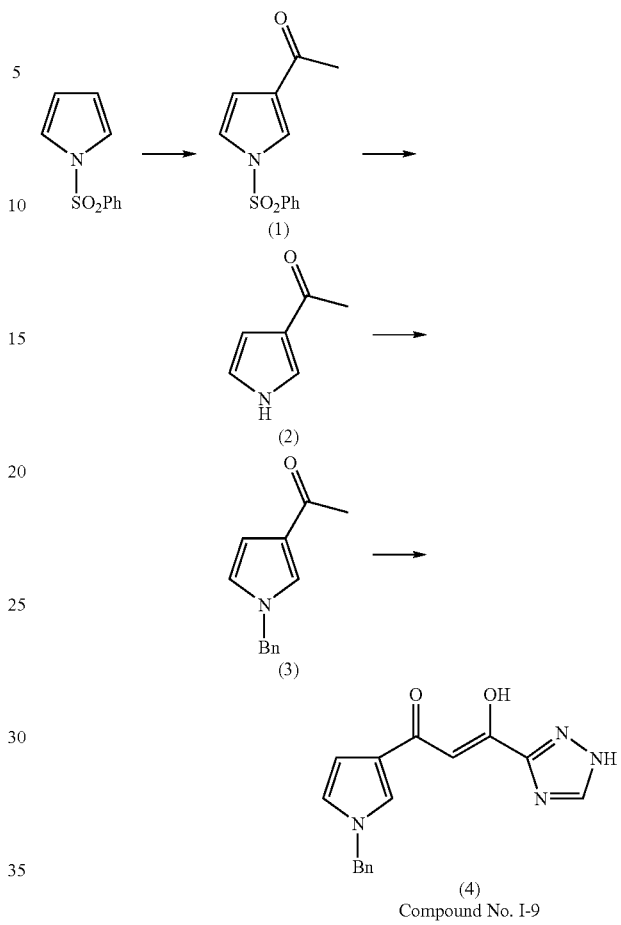

Compound No. I-9

1-(1-Benzylpyrrol-3-yl)-3-hydroxy-3-(1H-1,2,4-triazol-3-yl)-propenone (Compound No. I-9)

(1) 1-Benzenesulfonylpyrrole (2.07 g, 10 mmol) obtained in accordance with a method described in Example 8 (1) was reacted with acetic anhydride in accordance with a method described in Tetrahedron Letters, 1981, 22, p 4901. The obtained crude crystal was washed with a mixture of hexane and ether to give 3-acetyl-1-benzenesulfonylpyrrole (2.39 g). Yield: 96%.

NMR(CDCl$_3$) δ: 2.41(33H, s), 6.68–6.71(1H, m), 7.14–7.16(1H, m), 7.52–7.67(3H, m), 7.72–7.74(1H, m), 7.90–7.95(2H, m).

(2) To the above-obtained compound (1.25 g, 5 mmol) were added dioxane (5 ml) and 1 N LiOH (10 ml). The mixture was refluxed for 2 hours. After cooling, the mixture was neutralized with hydrochloric acid. Subsequently, the dioxane was evaporated under reduced pressure. The residue was extracted with ethylacetate and washed with water and dried. The solvent was evaporated. The obtained residue was crystallized from hexane to give 3-acetyl pyrrole (0.47 g). Yield: 86%.

NMR(CDCl$_3$) δ: 2.44(3H, s), 6.67–6.68(1H, m), 6.78–6.79(1H, m), 7.42–7.43(1H, m), 8.65(1H, brs).

(3) The above-obtained compound (0.38 g, 3.5 mmol) was reacted with benzylbromide in accordance with a method described in J. Heterocycl. Chem., 1994, p 1715. The obtained crude oily residue was chromatographed on silica gel (hexane:ethylacetate=1:1 v/v). The fraction of the objective was concentrated to give 3-acetyl-1-benzylpyrrole (0.59 g). Yield: 85%.

NMR(CDCl$_3$) δ:2.38(3H, s), 5.07(2H, s), 6.61–6.65(2H, m), 7.13–7.17(2H, m), 7.30–7.36(4H, m).

(4) To a solution of the above-obtained compound (0.50 g, 2.5 mmol) and 2-trityl-2H-1,2,4-triazol-3-carboxylic acid ethyl ester (1.44 g, 3.75 mmol) in THF (10 ml) was added at an ice bath temperature potassium tert-butoxide (0.56 g, 5 mmol). The reaction mixture was warmed up to room temperature and stirred for 1.5 hours. The reaction mixture was poured to an excess of aqueous ammonium chloride and extracted with ethylacetate. The extract was washed with brine and dried. The solvent was evaporated. The obtained residue was crystallized from ether and washed. The crude crystal was partitioned between dioxane (10 ml) and 1 N HCl (10 ml). The mixture was stirred for 1 hour at room temperature. Subsequently, the dioxane was evaporated under reduced pressure. The residue was partitioned between ethylacetate and water. The ethylacetate layer was washed with water and dried. The solvent was evaporated. The residue was crystallized from ether and washed. The obtained pale yellow crude crystal was recrystallized from chloroform to give the titled compound (0.15 g). Yield: 20%. M.p.: 216–217° C.

Elemental analysis for C$_{16}$H$_{14}$N$_4$O$_2$ 0.05 CHCl$_3$ 0.2 H$_2$O Calcd. (%): C, 63.44; H, 4.79; N, 18.44. Found. (%): C, 63.47; H, 4.79; N, 18.39. NMR(d$_6$-DMSO) δ: 5.20(2H, s), 6.60–6.62(1H, m), 6.84(1H, s), 7.00–7.02(1H, m), 7.29–7.40(5H, m), 7.92–7.93(1H, m), 8.69(1H, brs), 14.61 (1H, brs).

Example 10

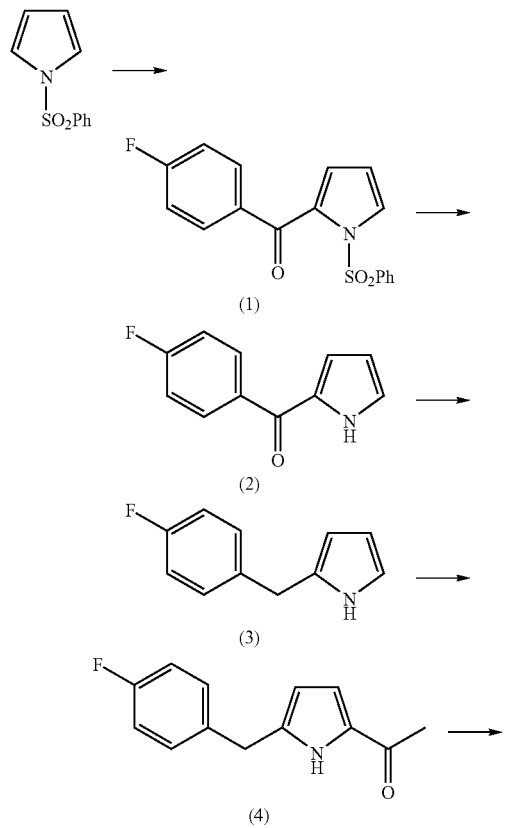

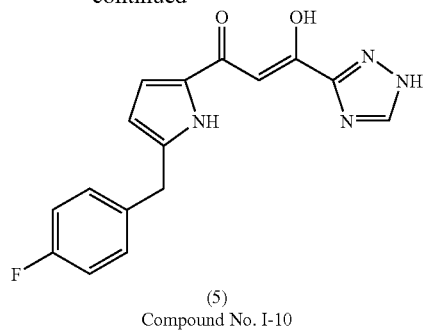

Compound No. I-10

1-[5-(4-Fluorobenzyl)pyrrol-2-yl]-3-hydroxy-3-(1H-1,2,4-triazol-3-yl)-propenone (Compound No. I-10)

(1) To a solution of 4-fluorobenzoylchloride (1.74 g, 11 mmol) in dichloromethane (2ml) was added dropwise a solution of boron trifluoride diethyletherate (3.4 ml, 27.6 mmol) in dichloromethane (20 ml). The mixture was stirred for 10 minutes at room temperature. Subsequently, to the mixture was added dropwise a solution of 1-benzenesulfonylpyrrole (1.9 g, 9.2 mmol) in accordance with a method described in Example 8 (1) in dichloromethane (5 ml). The mixture was stirred for 12 hours. The reaction mixture was poured into ice-water and extracted with ethylacetate. The extract was washed with water and dried. The solvent was evaporated. The obtained crude crystal was recrystallized from isopropylether to give 1-benzenesulfonyl-2-(4-fluorobenzoyl)pyrrole (1.0 g) as a crystal.

Yield: 19.8%. NMR(CDCl$_3$) δ: 6.36(1H, t, J=3.3 Hz), 6.68–6.72(1H, m), 7.08–7.16(2H, m), 7.54–7.70(3H, m), 7.76–7.80(1H, m), 7.81–7.88(2H, m), 8.09–8.14(2H, m).

(2) To a solution of the above-obtained compound (1.0 g, 3 mmol) in dioxane (10 ml) was added 4 N LiOH (2 ml). The mixture was stirred for 6 hours at 80° C. and concentrated under reduced pressure. The residue was extracted with ethylacetate and washed water and dried. The solvent was evaporated to give 2-(4-fluorobenzoyl)pyrrole (600 mg) as an oil quantitatively.

NMR(CDCl$_3$) δ: 6.34–6.38(1H, m), 6.84–6.90(1H, m), 7.11–7.18(3H, m), 7.90–7.98(2H, m), 9.58(1H, brs).

(3) To a suspension of aluminum chloride (1.27 g, 9.5 mmol) in dichloromethane (20 ml) was added a crystal of borane tert-butylamine complex (1.65 g, 19 mmol). The mixture was stirred for 15 minutes. To the mixture was added dropwise at an ice bath temperature a solution of the above-obtained compound (600 mg, 3 mmol) in dichloromethane (4 ml). The mixture was stirred for 1.5 hours at room temperature, and poured into ice-water, and partitioned between ethylacetate and water. The ethylacetate layer was washed with 2 N HCl (50 ml), aqueous saturated sodium bicarbonate and water, successively and then dried. The solvent was evaporated. The residue was chromatographed on silica gel (hexane:ethylacetate=5:1 v/v). The fraction of the objective was concentrated to give 2-(4-fluorobenzyl)pyrrole (419 mg) as an oil. Yield: 80%.

NMR(CDCl$_3$) δ: 3.95(2H, s), 5.92–6.00(1H, m), 6.12–6.18(1H, m), 6.60–6.70(1H, m), 6.94–7.04(2H, m), 7.12–7.20(2H, m), 7.80(1H, brs).

(4) To dimethylacetoamide (209 mg, 2.4 mmol) was added dropwise phosphorus oxychloride (890 mg, 5.8 mmol). The mixture was stirred for 30 minutes at room temperature. To the mixture was added dropwise a solution of the above-obtained compound (419 mg, 2.4 mmol) in dichloromethane (2 ml). After stirring for 6 hours, the reaction mixture was poured into ice-water, and extracted with ethylacetate. The extract was washed with water and dried. The solvent was evaporated. The obtained residue was chromatographed on silica gel (hexane:ethylacetate=4:1 v/v). The fraction of the objective was concentrated to give 2-acetyl-5-(4-fluorobenzyl)pyrrole (140 mg) as an oil.

Yield: 26.9%. NMR(CDCl$_3$) δ: 2.37(3H, s), 3.95(2H, s), 5.98–6.04(1H, m), 6.80–6.86(1H, m), 6.94–7.06(2H, m), 7.10–7.20(2H, m), 9.05(1H, brs).

(5) A solution of the above-obtained compound (130 mg, 0.6 mmol) in THF (10 ml) was added dropwise under −65° C. a solution of lithium bistrimethylsilylamide in THF (1 M solution, 1.8 ml, 1.8 mmol). Subsequently, the reaction mixture was gradually warmed up to 0° C. and cooled down to −70° C. again. To the reaction mixture was added dropwise a solution of 1-trityl-1H-1,2,4-triazole-3-carboxylic acid ethyl ester (346 mg, 0.9 mmol) in THF (5 ml). The reaction mixture was gradually warmed and stirred at −20° C. for 20 minutes, and then warmed up to room temperature. The reaction mixture was added to an excess amount of aqueous ammonium chloride and extracted with ethylacetate. The extract was washed with brine and dried. The solvent was evaporated. The obtained residue was partitioned between dioxane (5 ml) and 2 N HCl (1 ml) and stirred for 30 minutes at 70° C. The dioxane was evaporated under reduced pressure. To the residue was added ethylacetate and water. The ethylacetate layer was washed with water and dried. The solvent was evaporated and dried. The obtained crude yellow crystal was recrystallized from isopropylether-chloroform to give the titled compound (35 mg). Yield: 18.7%. M.p.: 180–183° C.

Elemental analysis for C$_{16}$H$_{13}$FN$_4$O$_2$ 0.2 H$_2$O Calcd. (%): C, 60.83; H, 4.28; N, 17.74; F, 6.01. Found. (%): C, 60.61; H, 4.24; N, 17.61; F, 5.82. NMR(d$_6$-DMSO) δ: 3.97(2H, s), 6.04(1H,s), 6.89(1H, s), 7.01–7.18(6H, m), 8.72(1H, brs).

Example 11–41

The following compounds were prepared as well as the above-shown compound.

1-[1-(4-Fluorobenzyl)pyrrol-2-yl]-3-hydroxy-3-(1H-1,2,4-triazol-3-yl)-propenone (Compound No. I-11)

M.p.: 170–173° C. Recrystallized from ethylacetate Elemental analysis for C$_{16}$H$_{13}$FN$_4$O$_2$ 0.2 HCl Calcd. (%): C, 60.13; H, 4.16; N, 17.53; F, 5.94. Found. (%): C, 60.21; H, 4.12; N, 17.41; F, 5.62. NMR(d$_6$-DMSO) δ: 5.65(2H, s), 6.30–6.36(1H, m), 6.94(1H, m), 7.04–7.50(6H, m), 8.65(1H, brs).

3-Hydroxy-1-[1-(pyridin-4-ylmethyl)pyrrol-2-yl]-3-(1H-1,2,4-triazol-3-yl)-propenone (Compound No. I-12)

M.p.: 189–191° C. Recrystallized from ethylacetate-isopropylether Elemental analysis for C$_{15}$H$_{13}$N$_5$O$_2$ 0.1 H$_2$O 0.6 C$_4$H$_8$O$_2$ 0.1 C$_2$H$_6$O Calcd. (%): C, 59.10; H, 5.16; N, 19.81. Found. (%): C, 59.11; H, 4.92; N, 19.60. NMR(d$_6$-DMSO) δ: 5.70(2H, s), 6.37(1H, s), 6.98(2H, d, J=3.0 Hz), 7.29–7.50(3H, m), 8.42–8.54(2H, m), 8.65(1H, brs).

3-Hydroxy-1-(pyrrol-3-yl)-3-(1H-1,2,4-triazol-3-yl)-propenone (Compound No. I-13)

M.p.: 121–124° C. Recrystallized from CHCl$_3$ NMR(d$_6$-DMSO) δ: 6.60(1H, m), 6.87(1H, s), 6.92(1H, m), 7.77(1H, m), 8.74(1H, brs), 11.7(1H, brs), 14.6(1H, brs).

1-[4-(4-Fluorobenzyl)pyrrol-3-yl]-3-hydroxy-3-(1H-1,2,4-triazol-3-yl)-propenone (Compound No. I-14)

M.p.: 210–213° C. Recrystallized from ethylacetate-hexane Elemental analysis for C$_{16}$H$_{13}$FN$_4$O$_2$ 0.2 H$_2$O, 0.2 C$_2$H$_6$O Calcd. (%): C, 60.59; H, 4.53; N, 17.23; F, 5.84. Found. (%): C, 60.62; H, 4.45; N, 16.95; F, 5.69. NMR(d$_6$-DMSO) δ: 4.07(2H, s), 6.59(1H, s), 6.87(1H, s), 7.02–7.11 (2H, m), 7.16–7.30(2H, m), 7.83(1H, s), 8.70(1H, brs), 11.5(1H, s), 14.6(1H, brs).

1-(1-Benzenesulfonylpyrrol-3-yl)-3-hydroxy-3-(1H-1,2,4-triazol-3-yl)-propenone (Compound No. I-15)

M.p.: 258–264° C. Recrystallized from CHCl$_3$ Elemental analysis for C$_{15}$H$_{12}$N$_4$O$_4$S Calcd. (%): C, 52.32; H, 3.51; N, 16.27; S, 9.31. Found. (%): C, 52.26; H, 3.60; N, 16.05; S, 9.22. NMR(d$_6$-DMSO) δ: 6.85(1H, m), 7.03(1H, s), 7.53 (1H, m), 7.67–7.74(2H, m), 7.78–7.84(1H, m), 8.08–8.15 (2H, m), 8.37(1H, m), 8.65(1H, brs).

1-(1-Benzenesulfonylpyrrol-2-yl)-3-hydroxy-3-(2H-tetrazol-5-yl)-propenone (Compound No. I-16)

M.p.: 87–89° C. Recrystallized from ether-hexane Elemental analysis for C$_{14}$H$_{11}$N$_5$O$_4$S 0.2 H$_2$O Calcd. (%): C, 48.19; H, 3.29; N, 20.07; S, 9.19. Found. (%): C, 48.26; H, 3.42; N, 20.05; S, 9.21.

NMR(CDCl$_3$) δ: 6.46(1H, m), 7.07(1H, s), 7.28(1H, m), 7.53–7.58(2H, m), 7.62–7.67(1H, m), 7.91(1H, m), 7.99–8.02(2H, m).

3-Hydroxy-1-(pyrrol-3-yl)-3-(2H-tetrazol-5-yl)-propenone (Compound No. I-17)

M.p.: >230° C. Recrystallized from ethylacetate Elemental analysis for C$_8$H$_7$N$_5$O$_2$ Calcd. (%): C, 46.83; H, 3.44; N, 34.13. Found. (%): C, 46.95; H, 3.52; N, 33.34. NMR(d$_6$-DMSO) δ: 6.66–6.67(1H, m), 6.95–6.97(1H, m), 7.01(1H, s), 7.90–7.91(1H, m), 11.8(1H, brs).

1-(1-Benzylpyrrol-3-yl)-3-hydroxy-3-(2H-tetrazol-5-yl)-propenone (Compound No. I-18)

M.p.: 188–189° C. Recrystallized from ethylacetate Elemental analysis for C$_{15}$H$_{13}$N$_5$O$_2$ 0.2 H$_2$O Calcd. (%): C, 60.27; H, 4.52; N, 23.43. Found. (%): C, 60.39; H, 4.51; N, 23.39. NMR(d$_6$-DMSO) δ: 5.22(2H, s), 6.68–6.69(1H, m), 6.97(1H, s), 7.05(1H, m), 7.31–7.40(5H, m), 8.06(1H, m).

1-(1-Benzenesulfonylpyrrol-3-yl)-3-hydroxy-3-(2H-tetrazol-5-yl)-propenone (Compound No. I-19)

M.p.: 203–204° C. Recrystallized from ethylacetate Elemental analysis for C$_{14}$H$_{11}$N$_5$O$_4$S 0.75 H$_2$O Calcd. (%): C, 46.86; H, 3.51; N, 19.52; F, 8.94. Found. (%): C, 47.22; H, 3.48; N, 19.32; F, 8.95. NMR(d$_6$-DMSO) δ: 6.89–6.92 (1H, m), 7.21(1H, s), 7.56–7.57(1H, m), 7.68–7.73(2H, m), 7.80–7.84(1H, m), 8.12–8.15(2H, m), 8.52–8.53(1H, m).

1-[1-(4-Chlorobenzenesulfonyl)pyrrol-3-yl]-3-hydroxy-3-(2H-tetrazol-5-yl)-propenone (Compound No. I-20)

M.p.: 213–214° C. Recrystallized from ethylacetate Elemental analysis for C$_{14}$H$_{10}$ClN$_5$O$_4$S Calcd. (%): C, 44.28; H, 2.65; N, 18.44; Cl, 9.34; S, 8.44. Found. (%): C, 44.44; H, 2.72; N, 18.34; Cl, 9.06; S, 8.39. NMR($d_6$-DMSO) δ: 6.92(1H, m), 7.20(1H, s), 7.57–7.58(1H, m), 7.79(2H, d, J=8.7 Hz), 8.16(2H, d, J=8.7 Hz), 8.53(1H,m).

1-[1-(4-Fluorobenzenesulfonyl)pyrrol-3-yl]-3-hydroxy-3-(2H-tetrazol-5-yl)-propenone (Compound No. I-21)

M.p.: >97° C. (decomposition), Recrystallized from ether Elemental analysis for $C_{14}H_{10}FN_5O_4S$ 0.25 $H_2O$ 0.5 $C_4H_{10}O$ Calcd. (%): C, 47.46; H, 3.86; N, 17.30; F, 4.69; S, 7.92. Found. (%): C, 47.48; H, 4.11; N, 17.10; F, 4.49; S, 7.98. NMR($d_6$-DMSO) δ: 6.90–6.92(1H, m), 7.20(1H, s), 7.53–7.59(3H, m), 8.22–8.27(2H, m), 8.52–8.53(1H, m).

2-Hydroxy-4-oxo-4-(pyrrol-3-yl)-2-butenoic acid (Compound No. I-22)

M.p.: 185–192° C. Recrystallized from ethylacetate Elemental analysis for $C_8H_7NO_4$ Calcd. (%): C, 53.04; H, 3.90; N, 7.73. Found. (%): C, 52.95; H, 4.03; N, 7.58. NMR($d_6$-DMSO) δ: 6.60–6.61(1H, m), 6.78(1H, s), 6.92–6.93(1H, m), 7.88–7.89(1H, m), 11.8(1H,brs).

4-(1-Benzenesulfonylpyrrol-3-yl)-2-hydroxy-4-oxo-2-butenoic acid (Compound No. I-23)

M.p.: 186–188° C. Recrystallized from ethylacetate Elemental analysis for $C_{14}H_{11}NO_6S$ Calcd. (%): C, 52.33; H, 3.45; N, 4.36; S, 9.98. Found. (%): C, 51.71; H, 3.50; N, 4.31; S, 9.86. NMR($d_6$-DMSO) δ: 6.83(1H, m), 6.92(1H, brs), 7.51–7.53(1H, m), 7.66–7.82(3H, m), 8.11–8.15(2H, m), 8.53(1H, m).

1-[(4-Benzoyl-1-(4-fluorobenzyl))pyrrol-2-yl]-3-hydroxy-3-(2H-tetrazol-5-yl)-propenone (Compound No. I-24)

M.p.: 160–163° C. Recrystallized from ethylacetate Elemental analysis for $C_{22}H_{16}F_2N_5O_3$ 0.3 $H_2O$ Calcd. (%): C, 62.50; H, 3.96; N, 16.56; F, 4.49 Found. (%): C, 62.54; H, 4.02; N, 16.41; F, 4.22. NMR($d_6$-DMSO) δ: 5.72(2H, s), 6.90–7.32(4H, m), 7.52–7.70(3H, m), 7.78–7.90(3H, m), 8.23(1H, d, J=1.5 Hz).

3-Hydroxy-1-[(4-(2-phenylethyl))pyrrol-3-yl]-3-(2H-tetrazol-5-yl)-propenone (Compound No. I-25)

M.p.: 228–230° C. Recrystallized from ether Elemental analysis for $C_{16}H_{15}N_5O_2$ 0.16 $C_2H_4O_2$ Calcd. (%): C, 61.46; 1H, 4.94; N, 21.96. Found. (%): C, 61.74; H, 4.88; N, 21.67. NMR($d_6$-DMSO) δ: 2.84–3.02(4H, m), 6.74(1H, m), 7.04 (1H, s), 7.17–7.32(5H, m), 7.96(1H, m), 11.6(1H, brs).

1-[(1-Benzyl-5-n-propyl)pyrrol-3-yl]-3-hydroxy-3-(2H-tetrazol-5-yl)-propenone (Compound No. I-26)

M.p.: 156–158° C. Recrystallized from ethylacetate-hexane Elemental analysis for $C_{18}H_{19}N_5O_2$ 0.1 $C_4H_8O_2$ Calcd. (%): C, 63.84; H, 5.77; N, 20.23. Found. (%): C, 63.93; H, 5.76; N, 20.23. NMR($d_6$-DMSO) δ: 0.89(3H, t, J=7.8 Hz), 1.42–1.60(2H, m), 2.42(2H, t, J=7.8 Hz), 5.23 (2H, s), 6.47(1H, s), 6.95(1H, s), 7.10–7.18(2H, m), 7.26–7.40(3H, m), 7.99(1H, s).

1-[(1-Benzyl-5-n-butyl)pyrrol-3-yl]-3-hydroxy-3-(2H-tetrazol-5-yl)-propenone (Compound No. I-27)

M.p.: 118–120° C. Recrystallized from ether-hexane-ethylacetate Elemental analysis for $C_{19}H_{21}N_5O_2$ 0.2 $C_4H_8O_2$ Calcd. (%): C, 64.44; H, 6.17; N, 18.98. Found. (%): C, 64.60; H, 6.02; N, 18.97. NMR(CDCl$_3$) δ: 0.91(3H, t, J=7.2 Hz), 1.30–1.44(2H, m), 1.52–1.68(2H, m), 2.46(2H, t, J=7.2 Hz), 5.09(2H, s), 6.50(1H, s), 7.04–7.10(2H, m), 7.30–7.50(3H, m).

1-[(1-Benzyl-5-n-octyl)pyrrol-3-yl]-3-hydroxy-3-(2H-tetrazol-5-yl)-propenone (Compound No. I-28)

M.p.: 130–135° C. Recrystallized from hexane Elemental analysis for $C_{23}H_{29}FN_5O_2$ 0.4 $H_2O$ Calcd. (%): C, 66.61; H, 7.24; N, 16.89. Found. (%): C, 66.34; H, 7.01; N, 17.37. NMR($d_6$-DMSO) δ: 0.80–0.95(3H, m), 1.10–1.40(10H, m), 1.40–1.62(2H, m), 2.34–2.50(2H, m), 5.23(2H, s), 6.47(1H, s), 6.96(1H,m), 7.05–7.50(5H, m), 8.02(1H, s).

1-[(1-Benzyl-5-ethoxycarbonyl)pyrrol-3-yl]-3-hydroxy-3-(2H-tetrazol-5-yl)-propenone (Compound No. I-29)

M.p.: 85–90° C. Recrystallized from ethylacetate NMR ($d_6$-DMSO) δ: 1.36(3H, t, J=6.9 Hz), 4.30(2H, q,J=6.9 Hz), 5.62(2H, s), 7.04(1H, s), 7.16–7.62(5H, m).

1-[(1-Benzenesulfonyl-4-ethyl)pyrrol-3-yl]-3-hydroxy-3-(2H-tetrazol-5-yl)-propenone (Compound No. I-30)

M.p.: 178–180° C. Recrystallized from ethylacetate NMR ($d_6$-DMSO) δ: 1.19(3H, t, J=7.6 Hz), 2.73(2H, qd, J=7.6, 1.2 Hz), 6.96–7.04(2H, m), 7.48–7.78(3H, m), 7.90–8.02(3H, m).

1-[[1-Benzenesulfonyl-4-(2-phenylethyl)]pyrrol-3-yl]-3-hydroxy-3-(2H-tetrazol-5-yl)-propenone (Compound No. I-31)

M.p.: 178–181° C. Recrystallized from ether Elemental analysis for $C_{22}H_{19}N_5O_4S$ Calcd. (%): C, 58.79; H, 4.26; N, 15.58; S, 7.13. Found. (%): C, 59.24; H, 4.37; N, 15.75; S, 6.61. NMR($d_6$-DMSO) δ: 2.81–2.98(4H, m), 7.11–7.30(7H, m), 7.68–7.73(2H, m), 7.80–7.86(1H, m), 8.07–7.10(2H, m), 8.64(1H, d, J=2.4 Hz),

1-[[1-Benzyl-4-(2-methoxycarbonylvinyl)]pyrrol-3-yl]-3-hydroxy-3-(1H-1,2,4-triazol-3-yl)-propenone (Compound No. I-32)

M.p.: 207–210° C. Recrystallized from ethylacetate-CHCl$_3$ Elemental analysis for $C_{20}H_{18}FN_4O_4$ 0.1 $H_2O$ 0.1 $C_4H_8O_2$ Calcd. (%): C, 62.99; H, 4.92; N, 14.40. Found. (%): C, 62.87; H, 4.76; N, 14.31. NMR($d_6$-DMSO) δ: 3.69(3H, s), 5.19(2H,s), 6.37(1H, d, J=15.9 Hz), 6.91(1H, s), 7.28–7.42(6H, m), 7.76(1H, d, J=2.1 Hz), 7.37(1H, s), 8.67(1H, brs).

1-[[1-Benzyl-4-(2-carboxyvinyl)]pyrrol-3-yl]-3-hydroxy-3-(1H-1,2,4-triazol-3-yl)-propenone (Compound No. I-33)

M.p.: 226–228° C. Recrystallized from ethylacetate-hexane Elemental analysis for $C_{19}H_{16}N_4O_4$ 0.1 $C_4H_8O_2$ Calcd. (%): C, 62.44; H, 4.54; N, 15.01. Found. (%): C, 62.06; H, 4.61; N, 14.82. NMR($d_6$-DMSO) δ: 5.19(2H, s), 6.25(1H, d, J=16.2 Hz), 6.90(1H, s), 7.28–7.44(5H, m), 7.72(1H, s), 8.12–8.20(2H, m), 8.63(1H, brs).

1-[1,4-Di-(4-fluorobenzyl)pyrrol-3-yl]-3-hydroxy-3-(1H-1,2,4-triazol-3-yl)-propenone (Compound No. I-34)

M.p.: 166–168° C. Recrystallized from ethylacetate Elemental analysis for $C_{23}H_{18}F_2N_4O_2$ Calcd. (%): C, 65.71;

H, 4.32; N, 13.33; F, 9.04. Found. (%): C, 65.82; H, 4.33; N, 13.03; F, 8.78. NMR($d_6$-DMSO) δ: 4.03(2H, s), 5.10(2H, s), 6.65(1H, s), 6.84(1H, s), 7.00–7.40(8H, m), 8.04(1H, s), 8.58(1H, brs).

1-[[4-(4-Fluorobenzyl)-1-n-propyl]pyrrol-3-yl]-3-hydroxy-3-(1H-1,2,4-triazol-3-yl)-propenone (Compound No. I-35)

M.p.: 210–211° C. Recrystallized from chloroform Elemental analysis for $C_{19}H_{19}FN_4O_2$ Calcd. (%): C, 64.40; H, 5.40; N, 15.81; F, 5.36. Found. (%): C, 64.28; H, 5.37; N, 15.61; F, 5.23. NMR($d_6$-DMSO) δ: 0.81(3H, t, J=7.2 Hz), 1.60–1.82(2H, m), 3.68–3.96(2H, m), 4.05(2H, s), 6.57(1H, d, J=1.8 Hz), 6.80–7.36(4H, m), 7.91(1H, d, J=1.8 Hz), 8.57(1H, brs).

1-[[1-Benzyl-4-(2-methoxycarbonylvinyl)]pyrrol-2-yl]-3-hydroxy-3-(1H-1,2,4-triazol-3-yl)-propenone (Compound No. I-36)

M.p.: 212–214° C. Recrystallized from ethylacetate-chloroform-isopropylether Elemental analysis for $C_{20}H_{18}N_4O_4$ 0.04 $CHCl_3$ Calcd. (%): C, 62.82; H, 4.75; N, 14.62. Found. (%): C, 62.76; H, 4.46; N, 14.44. NMR($d_6$-DMSO) δ: 3.69(3H, s), 5.19(2H, s), 6.37(1H, d, J=15.9 Hz), 6.91(1H, s), 7.30–7.42(6H, m), 7.77(1H, s), 8.20(1H, s), 8.66(1H, brs).

1-[[1-Benzyl-4-(2-carboxyvinyl)]pyrrol-2-yl]-3-hydroxy-3-(1H-1,2,4-triazol-3-yl)-propenone (Compound No. I-37)

M.p.: 215–218° C. Recrystallized from chloroform Elemental analysis for $C_{19}H_{16}N_4O_4$ Calcd. (%): C, 62.63; H, 4.43; N, 15.38. Found. (%): C, 62.29; H, 4.69; N, 15.11. NMR($d_6$-DMSO) δ: 5.19(2H, s), 6.25(1H, d, J=16.5 Hz), 6.90(1H, s), 7.30–7.43(5H, m), 7.72(1H, s), 8.12–8.22(2H, m), 8.62(1H, brs).

1-[[1-Benzyl-5-(2-methoxycarbonylvinyl)]pyrrol-3-yl]-3-hydroxy-3-(2H-tetrazol-5-yl)-propenone (Compound No. I-38)

M.p.: 223–225° C. Recrystallized from ethylacetate-hexane. Elemental analysis for $C_{19}H_{17}N_5O_4$ 0.1 $C_4H_8O_2$ Calcd. (%): C, 60.03; H, 4.62; N, 18.04. Found. (%): C, 60.26; H, 4.57; N, 17.91. NMR($d_6$-DMSO) δ: 3.66(3H, s), 5.48(2H, s), 6.49(1H, d, J=15.6 Hz), 7.08(1H, s), 7.10–7.60 (7H, m), 8.30(1H, s).

1-[[1-Benzyl-5-(2-carboxyvinyl)]pyrrol-3-yl]-3-hydroxy-3-(2H-tetrazol-5-yl)-propenone (Compound No. I-39)

M.p.: 234–236° C. (decomposition). Recrystallized from ethylacetate. Elemental analysis for $C_{18}H_{15}N_5O_4$ 0.3 $C_4H_8O_2$ Calcd. (%): C, 58.86; H, 4.48; N, 17.88. Found. (%): C, 58.94; H, 4.45; N, 17.51. NMR($d_6$-DMSO) δ: 5.46(2H, s), 6.38(1H, d, J=15.9 Hz), 7.07(1H, s), 7.10–7.18 (2H, m), 7.26–7.54(5H, m), 8.27(1H, s).

1-[[1-Benzyl-5-(2-methoxycarbonylethyl)]pyrrol-3-yl]-3-hydroxy-3-(2H-tetrazol-5-yl)-propenone (Compound No. I-40)

M.p.: 178–180° C. Recrystallized from ethylacetate-hexane-ether. Elemental analysis for $C_{19}H_{19}N_5O_4$ Calcd. (%): C, 59.84; H, 5.02; N, 18.36. Found. (%): C, 59.38; H, 5.07; N, 18.03. NMR($CDCl_3$) δ: 2.50–2.70(2H, m), 2.75–2.88(2H, m), 3.72(3H, s), 5.10(2H, s), 6.48(1H, s), 6.95(1H, s), 7.02–7.10(2H, m), 7.28–7.48(4H, s).

1-[[1-Benzyl-5-(2-methoxycarbonylvinyl)]pyrrol-3-yl]-3-hydroxy-3-(furan-2-yl)-propenone (Compound No. I-41)

M.p.: 121–122° C. Recrystallized from ether-hexane. Elemental analysis for $C_{22}H_{19}NO_5$ Calcd. (%): C, 70.02; H, 5.07; N, 3.71. Found. (%): C, 69.90; H, 4.99; N, 3.87. NMR($d_6$-DMSO) δ: 3.66(3H, s), 5.45(2H, s), 6.41(1H, d, J=15.6 Hz), 6.67(1H, s), 6.76–6.80(1H, m), 7.12(2H, d, J=8.1 Hz), 7.22–7.40(4H, m), 7.44–7.54(2H, m), 8.00–8.20 (2H, m).

Preparation of a Compound wherein Heteroaryl ($A^1$) is Furyl (Compound No. I-42 to 139)

Example 42

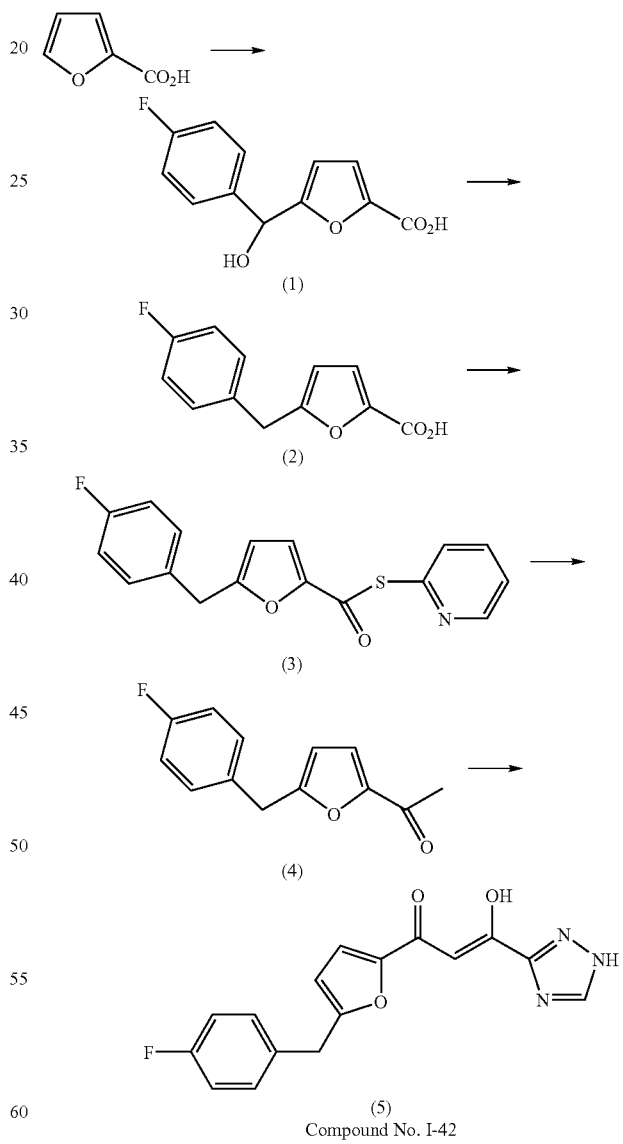

1-[5-(4-fluorobenzyl)furan-2-yl]-3-hydroxy-3-(1H-1,2,4-triazol-3-yl)-propenone (Compound No. I-42)

(1) Furan-2-carboxylic acid (5.6 g, 50 mmol) was reacted with 4-fluorobenzaldehyde (6.8 g, 55 mmol) in accordance with a method described in Tetrahedron Letters, 1979, 5, p 469. The obtained crude crystal was washed with isopropylether to give 5-[[1-(4-fluorophenyl)-1-hydroxy]methyl]-furan-2-carboxylic acid (8.1 g). Yield 69%. M.p.: 139–140° C. (decomposition)

NMR(CDCl$_3$) δ: 5.88(1H, s), 6.28(1H, d, J=3.6 Hz), 7.07(2H, t, J=8.7 Hz), 7.25(1H, d, J=3.6 Hz), 7.39–7.44(2H, m).

(2) The above-obtained compound (4.72 g, 20 mmol) was reduced with trimethylchlorosilane (10.8 g, 100 mmol) and sodium iodide (15 g, 100 mmol) in accordance with a method described in Tetrahedron, 1995, 51, p 11043 to give 5-(4-fluorobenzyl)-furan-2-carboxylic acid (3.52 g) as a crystal. Yield 80%.

NMR(d$_6$-DMSO) δ: 4.05(2H, s), 6.31(1H, d, J=3.3 Hz), 7.12–7.18(3H, m), 7.27–7.32(2H, m), 12.9(1H, brs).

(3) The above-obtained compound (3.52 g, 16 mmol) was reacted with dipyridyldisulfide (4.2 g, 19.2 mmol) and triphenylphosphine (5.04 g, 19.2 mmol) in accordance with a method described in Bull. Chem. Soc. Japan., 1974, 47, p 1777 to give 5-(4-fluorobenzyl)-furan-2-carboxylic acid 2-pyridylthio ester (3.7 g). Yield 77%. M.p.: 88–89° C.

NMR(CDCl$_3$) δ: 4.04(2H, s), 6.15(1H, d, J=3.3 Hz), 7.03(2H, t, J=8.7 Hz), 7.22(1H, d, J=3.3 Hz), 7.22–7.26(2H, m), 7.29–7.34(1H, m), 7.70–7.79(2H, m), 8.63–8.66(1H, m).

(4) The above-obtained compound (3.7 g, 12.4 mmol) was reacted with methylmagnesiumbromide in THF solution (1 M, 14 ml) in accordance with a method described in Bull. Chem. Soc. Japan., 1974, 47, p 1777 to give 2-acetyl-5-(4-fluorobenzyl)-furan (2.7 g) as an oil quantitatively.

NMR(CDCl$_3$) δ: 2.43(3H, s), 4.01(2H, s), 6.10(1H, d, J=3.6 Hz), 7.01(2H, t, J=9.0 Hz), 7.10(1H, d, J=3.6 Hz), 7.18–7.23(2H, m).

(5) To a solution of the above-obtained compound (1.31 g, 6 mmol) in THF (18 ml) was added at −70 to −65° C. a solution of lithiumbistrimethylsilylamide in THF (1 M solution, 7.8 ml, 7.8 mmol). Subsequently, the reaction mixture was gradually warmed up to −10° C., and cooled down to −70° C. again. To the mixture was added 1-trityl-1H-1,2,4-triazole-3-carboxylic acid ethyl ester (2.99 g, 7.8 mmol) in THF (30 ml). The reaction solution was warmed up gradually to room temperature and stirred for 1.5 hours. The reaction solution was poured into an excess amount of aqueous ammonium chloride and extracted with ethylacetate. The extract was washed with brine and dried. The solvent was evaporated. The obtained residue was partitioned between dioxane (75 ml) and 1 N HCl (20 ml) and stirred for 0.5 hour for 80° C. The dioxane was evaporated under reduced pressure. The residue was partitioned between ethylacetate and water. The ethylacetate layer was washed with water and dried, and then evaporated. The residue was dissolved in ether and extracted with 1 N NaOH (6 ml) three times. The alkaline extract was washed with ether twice and neutralized with 1 N HCl, and then extracted with ethylacetate. The extract was washed with water and saturated brine. The solvent was dried and evaporated. The obtained crude crystal was washed with a small amount of ethylacetate and recrystallized from ethylacetate to give the titled compound (1.15 g). Yield 61%. M.p.: 183–185° C.

Elemental analysis for C$_{16}$H$_{12}$FN$_3$O$_3$ Calcd. (%): C, 61.34; H, 3.86; N, 13.41; F, 6.06. Found. (%): C, 61.22; H, 3.72; N, 13.41; F, 6.03. NMR(d$_6$-DMSO) δ: 4.15(2H, s), 6.47(1H, d, J=3.3 Hz), 6.93(1H, s), 7.17(2H, t, J=9.0 Hz), 7.31–7.37(2H, m), 7.50(1H, d, J=3.3 Hz), 8.70(1H, brs).

Example 43 to 132

The following compounds were prepared in accordance with the above-mentioned method.

1-(5-Benzenesulfonylfuran-2-yl)-3-hydroxy-3-(1H-1,2,4-triazol-3-yl)-propenone (Compound No. I-43)

M.p.: 207–210° C. Recrystallized from ethylacetate. Elemental analysis for C$_{15}$H$_{11}$N$_3$O$_5$S 1.2 H$_2$O Calcd. (%): C, 49.10; H, 3.68; N, 11.45; S, 8.74. Found. (%): C, 48.84; H, 3.68; N, 11.67; S, 9.05. NMR(d$_6$-DMSO) δ: 7.02(1H, s), 7.62–7.86(5H, m), 8.02–8.08(2H, m), 8.82(1H, brs).

3-Hydroxy-1-(5-phenylthiofuran-2-yl)-3-(1H-1,2,4-triazol-3-yl)-propenone (Compound No. I-44)

M.p.: 144–147° C. Recrystallized from ethylacetate. Elemental analysis for C$_{15}$H$_{11}$N$_3$O$_3$S 0.3 H$_2$O Calcd. (%): C, 56.52; H, 3.67; N, 13.18; S, 10.06. Found. (%): C, 56.85; H, 3.71; N, 13.56; S, 9.48. NMR(d$_6$-DMSO) δ: 6.97(1H, s), 7.12(1H, d, J=3.6 Hz), 7.30–7.44(5H, m), 7.65(1H, d, J=3.6 Hz), 8.74(1H, brs).

1-[3-(4-Fluorobenzyl)furan-2-yl]-3-hydroxy-3-(1H-1,2,4-triazol-3-yl)-propenone (Compound No. I-45)

M.p.: 221–223° C. Recrystallized from ether. Elemental analysis for C$_{16}$H$_{12}$FN$_3$O$_3$ Calcd. (%): C, 61.34; H, 3.86; N, 13.41; F, 6.06. Found. (%): C, 61.04; H, 3.98; N, 13.28; F, 5.87. NMR(d$_6$-DMSO) δ: 4.23(2H, s), 6.65(1H, d, J=1.8 Hz), 7.03(1H, s), 7.10–7.16(2H, m), 7.31–7.36(2H, m), 7.97(1H, d, J=1.8 Hz), 8.74(1H, brs), 14.7(1H, brs).

1-[3-(4-Fluorobenzyl)furan-2-yl]-3-hydroxy-3-(2H-tetrazol-5-yl)-propenone (Compound No. I-46)

M.p.: 171–174° C. Recrystallized from ether. Elemental analysis for C$_{15}$H$_{11}$FN$_4$O$_3$ Calcd. (%): C, 57.33; H, 3.53; N, 17.86; F, 6.05. Found. (%): C, 57.05; H, 3.61; N, 17.74; F, 5.82. NMR(d$_6$-DMSO) δ: 4.24(2H, s), 6.70(1H, d, J=1.8 Hz), 7.09(1H, s), 7.10–7.17(2H, m), 7.32–7.37(2H, m), 8.04(1H, d, J=1.8 Hz).

1-(5-n-Butylfuran-2-yl)-3-hydroxy-3-(2H-tetrazol-5-yl)-propenone (Compound No. I-47)

M.p.: 124–125° C. Recrystallized from ether-hexane. Elemental analysis for C$_{12}$H$_{14}$N$_4$O$_3$ Calcd. (%): C, 54.96; H, 5.38; N, 21.36. Found. (%): C, 55.02; H, 5.43; N, 21.09. NMR(CDCl$_3$) δ: 0.95(3H, t, J=7.8 Hz), 1.37–1.45(2H, m), 1.65–1.73(2H, m), 2.76(2H, t, J=7.8 Hz), 6.30(1H, d, J=3.6 Hz), 7.23(1H, s), 7.39(1H, d, J=3.6 Hz).

1-(5-n-Butylfuran-2-yl)-3-hydroxy-3-(1H-1,2,4-triazol-3-yl)-propenone (Compound No. I-48)

M.p.: 72–73° C. Recrystallized from ether. Elemental analysis for C$_{13}$H$_{15}$N$_3$O$_3$ 0.25 H$_2$O Calcd. (%): C, 58.75; H, 5.88; N, 15.81. Found. (%): C, 58.10; H, 5.65; N, 15.81. NMR(CDCl$_3$) δ: 0.96(3H, t, J=7.5 Hz), 1.35–1.42(2H, m), 1.65–1.75(2H, m), 2.74(2H, t, J=7.5 Hz), 6.25(1H, d, J=3.6 Hz), 7.12(1H, s), 7.29(1H, d, J=3.6 Hz).8.44(1H, s).

1-[2-(4-Fluorobenzyl)furan-3-yl]-3-hydroxy-3-(1H-1,2,4-triazol-3-yl)-propenone (Compound No. I-49)

M.p.: 170–177° C. Recrystallized from ethylacetate. Elemental analysis for C$_{16}$H$_{12}$FN$_3$O$_3$ 0.1 H$_2$O Calcd. (%): C, 60.99; H, 3.90; N, 13.34; F, 6.03. Found. (%): C, 61.01; H, 4.07; N, 13.47; F, 5.99. NMR(d$_6$-DMSO) δ: 4.41(2H, s), 6.92(1H, s), 7.04(1H, d, J=1.8 Hz), 7.14(2H, t, J=9.3 Hz), 7.28–7.33(2H, m), 7.72(1H, d, J=1.8 Hz), 8.70(1H, brs).

1-[4-(4-Fluorobenzyl)furan-3-yl]-3-hydroxy-3-(1H-1,2,4-triazol-3-yl)-propenone (Compound No. I-50)

M.p.: 217–220° C. Recrystallized from ethylacetate. Elemental analysis for C$_{16}$H$_{12}$FN$_3$O$_3$ Calcd. (%): C, 61.34; H, 3.86; N, 13.41; F, 6.06. Found. (%): C, 61.19; H, 4.04; N, 13.16; F, 5.90. NMR(d$_6$-DMSO) δ: 4.02(2H, s), 6.93(1H, s), 7.09(2H, t, J=9.0 Hz), 7.25–7.31(2H, m), 7.56(1H, s), 8.66 (1H, brs), 8.80(1H, s).

1-[5-(4-Fluorobenzyl)furan-3-yl]-3-hydroxy-3-(1H-1,2,4-triazol-3-yl)-propenone (Compound No. I-51)

M.p.: 176–179° C. Recrystallized from ethylacetate. Elemental analysis for C$_{16}$H$_{12}$FN$_3$O$_3$ Calcd. (%): C, 61.34; H, 3.86; N, 13.41; F, 6.06. Found. (%): C, 61.19; H, 3.81; N, 13.52; F, 6.19. NMR(d$_6$-DMSO) δ: 4.03(2H, s), 6.62(1H, d, J=0.9 Hz), 6.90(1H, s), 7.15(2H, t, J=9.0 Hz), 7.29–7.34(2H, m), 8.60(1H, d, J=0.9 Hz), 8.67(1H, brs).

1-[2-(4-Fluorobenzyl)furan-3-yl]-3-hydroxy-3-(2H-tetrazol-5-yl)-propenone (Compound No. I-52)

M.p.: 150–153° C. Recrystallized from ether. Elemental analysis for C$_{15}$H$_{11}$FN$_4$O$_3$ Calcd. (%): C, 57.33; H, 3.53; N, 17.83; F, 6.04. Found. (%): C, 57.29; H, 3.72; N, 17.74; F, 5.84. NMR(CDCl$_3$) δ: 4.40(2H, s), 6.75(1H, d, J=2.1 Hz), 6.99(2H, t, J=8.7 Hz), 7.01(1H, s), 7.24–7.29(2H, m), 7.39 (1H, d, J=2.1 Hz).

4-[5-(4-Fluorobenzyl)furan-2-yl]-2-hydroxy-4-oxo-2-butenoic acid methyl ester (Compound No. I-53)

M.p.: 102–104° C. Recrystallized from ether. Elemental analysis for C$_{16}$H$_{13}$FO$_5$ Calcd. (%): C, 63.16; H, 4.31; F, 6.24. Found. (%): C, 62.96; H, 4.16; F, 6.14. NMR(CDCl$_3$) δ: 3.93(3H, s), 4.05(2H, s), 6.20(1H, d, J=3.6 Hz), 6.87(1H, s), 7.03(2H, t, J=8.7 Hz), 7.19–7.25(2H, m), 7.28(1H, d, J=3.6 Hz).

4-[5-(4-Fluorobenzyl)furan-2-yl]-2-hydroxy-4-oxo-2-butenoic acid (Compound No. I-54)

M.p.: 145–148° C. Recrystallized from ether. Elemental analysis for C$_{15}$H$_{11}$FO$_5$ Calcd. (%): C, 62.07; H, 3.82; F, 6.55. Found. (%): C, 61.90; H, 3.86; F, 6.45. NMR(d$_6$-DMSO) δ: 4.14(2H, s), 6.48(1H, d, J=3.6 Hz), 6.80(1H, s), 7.17(2H, t, J=8.7 Hz), 7.30–7.35(2H, m), 7.67(1H, d, J=3.6 Hz).

1-[5-(4-Fluorobenzyl)furan-2-yl]-3-hydroxy-3-(2H-tetrazol-5-yl)-propenone (Compound No. I-55)

M.p.: 121–123° C. Recrystallized from ether. Elemental analysis for C$_{15}$H$_{11}$FN$_4$O$_3$ Calcd. (%): C, 57.33; H, 3.53; N, 17.83; F, 6.04. Found. (%): C, 57.25; H, 3.58; N, 17.53; F, 5.81. NMR(d$_6$-DMSO) δ: 4.16(2H, s), 6.51(1H, d, J=3.6 Hz), 7.05(1H, s), 7.18(2H, t, J=8.7 Hz), 7.32–7.38(2H, m), 7.65(1H, d, J=3.6 Hz).

1-[4-(4-Fluorobenzyl)furan-2-yl]-3-hydroxy-3-(1H-1,2,4-triazol-3-yl)-propenone (Compound No. I-56)

M.p.: 187–191° C. Recrystallized from ethylacetate. Elemental analysis for C$_{16}$H$_{12}$FN$_3$O$_3$ Calcd. (%): C, 61.34; H, 3.86; N, 13.41; F, 6.06. Found. (%): C, 61.08; H, 3.87; N, 13.72; F, 6.08. NMR(d$_6$-DMSO) δ: 3.81(2H, s), 6.97(1H, s), 7.14(2H, t, J=9.0 Hz), 7.30–7.35(2H, m), 7.45(1H, s), 7.92 (1H, s), 8.75(1H, brs).

1-(5-Benzylfuran-2-yl)-3-hydroxy-3-(1H-1,2,4-triazol-3-yl)-propenone (Compound No. I-57)

M.p.: 176–179° C. Recrystallized from ethylacetate. Elemental analysis for C$_{16}$H$_{13}$N$_3$O$_3$ 0.15 C$_4$H$_8$O$_2$ Calcd. (%): C, 64.63; H, 4.64; N, 13.62. Found. (%): C, 64.41; H, 4.40; N, 13.42. NMR(d$_6$-DMSO) δ: 4.14(2H, s), 6.48(1H, d, J=3.6 Hz), 6.93(1H, s), 7.24–7.38(5H, m), 7.51(1H, d, J=3.6 Hz), 8.72(1H, brs), 14.7(1H, brs).

1-[5-(4-Fluorobenzoyl)furan-2-yl]-3-hydroxy-3-(1H-1,2,4-triazol-3-yl)-propenone (Compound No. I-58)

M.p.: 240–242° C. Recrystallized from 95% ethanol. Elemental analysis for C$_{16}$H$_{10}$FN$_3$O$_4$ Calcd. (%): C, 58.71; H, 3.09; N, 12.84; F, 5.81. Found. (%): C, 58.68; H, 3.11; N, 12.68; F, 5.64. NMR(d$_6$-DMSO) δ: 7.16(1H, s), 7.45(2H, t, J=8.7 Hz), 7.57(1H, d, J=3.9 Hz), 7.72(1H, d, J=3.9 Hz), 8.06–8.11(2H, m), 8.76(1H, s).

1-[5-(4-Chlorobenzyl)furan-2-yl]-3-hydroxy-3-(1H-1,2,4-triazol-3-yl)-propenone (Compound No. I-59)

M.p.: 96–99° C. Recrystallized from ethanol. Elemental analysis for C$_{16}$H$_{12}$ClN$_3$O$_3$ Calcd. (%): C, 58.28; H, 3.67; N, 12.74; Cl, 10.75. Found. (%): C, 58.16; H, 3.80; N, 12.40; Cl, 10.50. NMR(d$_6$-DMSO) δ: 4.16(2H, s), 6.49(1H, d, J=3.6 Hz), 6.93(1H, s), 7.30–7.43(4H, m), 7.52(1H, d, J=3.6 Hz), 8.75(1H, brs).

1-[5-(4-Fluorobenzyl)furan-2-yl]-3-hydroxy-3-(5-methyl-1H-1,2,4-triazol-3-yl)-propenone (Compound No. I-60)

M.p.: 179–182° C. Recrystallized from ethylacetate. Elemental analysis for C$_{17}$H$_{14}$FN$_3$O$_3$ Calcd. (%): C, 62.38; H, 4.31; N, 12.84; F, 5.80. Found. (%): C, 62.29; H, 4.16; N, 11.65; F, 5.78. NMR(d$_6$-DMSO) δ: 2.43(3H, s), 4.14(2H, s), 6.46(1H, d, J=3.3 Hz), 6.88(1H, s), 7.15–7.20(2H, m), 7.31–7.36(2H, m), 7.49(1H, d, J=3.3 Hz), 14.3(1H, brs).

1-[[5-(4-Fluorobenzyl)-3-methyl]furan-2-yl]-3-hydroxy-3-(1H-1,2,4-triazol-3-yl)-propenone (Compound No. I-61)

M.p.: 191–192° C. Recrystallized from ethylacetate. Elemental analysis for C$_{17}$H$_{14}$FN$_3$O$_3$ Calcd. (%): C, 62.38; H, 4.31; N, 12.84; F, 5.80. Found. (%): C, 62.23; H, 4.29; N, 12.79; F, 5.79. NMR(d$_6$-DMSO) δ: 2.36(3H, s), 4.10(2H, s), 6.34(1H, s), 6.89(1H, s), 7.18(2H, t, J=9.0 Hz), 7.32–7.37 (2H, m), 8.70(1H, brs).

3-Hydroxy-1-[5-(4-methoxybenzyl)furan-2-yl]-3-(1H-1,2,4-triazol-3-yl)-propenone (Compound No. I-62)

M.p.: 114–116° C. Recrystallized from ethylacetate. Elemental analysis for C$_{17}$H$_{15}$N$_3$O$_4$ Calcd. (%): C, 62.76; H, 4.65; N, 12.92. Found. (%): C, 62.90; H, 4.57; N, 12.26. NMR(d$_6$-DMSO) δ: 3.73(3H, s), 4.07(2H, s), 6.44(1H, d, J=3.3 Hz), 6.91(2H, d, J=8.7 Hz), 6.92(1H, s), 7.22(2H, d, J=8.7 Hz), 7.50(1H, d, J=3.3 Hz), 8.77(1H, brs).

1-[5-(4-Fluorophenoxy)furan-2-yl]-3-hydroxy-3-(1H-1,2,4-triazol-3-yl)-propenone (Compound No. I-63)

M.p.: 187–191° C. Recrystallized from ethanol-ether. Elemental analysis for C$_{15}$H$_{10}$FN$_3$O$_4$ 0.5 H$_2$O Calcd. (%): C, 55.56; H, 3.42; N, 12.96; F, 5.86. Found. (%): C, 55.88; H, 3.15; N, 13.09; F, 5.79. NMR(d$_6$-DMSO) δ: 5.86(1H, d, J=3.9 Hz), 6.85(1H, s), 7.25–7.40(4H, m), 7.65(1H, d, J=3.9 Hz), 8.63(1H, brs).

3-Hydroxy-3-(1H-1,2,4-triazol-3-yl)-1-[5-(4-trifluoromethylbenzyl)furan-2-yl]-propenone (Compound No. I-64)

M.p.: 177–178° C. Recrystallized from ethylacetate. Elemental analysis for $C_{17}H_{12}F_3N_3O_3$ 0.25 $H_2O$ 0.1 $C_4H_8O_2$ Calcd. (%): C, 55.49; H, 3.56; N, 11.16; F, 15.13. Found. (%): C, 55.54; H, 3.59; N, 11.04; F, 15.21. NMR ($d_6$-DMSO) δ: 4.27(2H, s), 6.54(1H, d, J=3.3 Hz), 6.94(1H, s), 7.53(2H, d, J=7.8 Hz), 7.53(1H, d, J=3.3 Hz), 7.72(2H, d, J=7.8 Hz), 8.76(1H, brs).

1-[5-(3-Fluorobenzyl)furan-2-yl]-3-hydroxy-3-(1H-1,2,4-triazol-3-yl)-propenone (Compound No. I-65)

M.p.: 140–143° C. Recrystallized from ethanol. Elemental analysis for $C_{16}H_{12}FN_3O_3$ Calcd. (%): C, 61.34; H, 3.86; N, 13.41; F, 6.06. Found. (%): C, 61.41; H, 3.84; N, 13.05; F, 5.97. NMR($d_6$-DMSO) δ: 4.19(2H, s), 6.52(1H, d, J=3.3 Hz), 6.95(1H, s), 7.10–7.18(3H, m), 7.36–7.41(1H, m), 7.52(1H, d, J=3.3 Hz), 8.77(1H, brs), 14.7(1H, brs).

1-[5-(2-Fluorobenzyl)furan-2-yl]-3-hydroxy-3-(1H-1,2,4-triazol-3-yl)-propenone (Compound No. I-66)

M.p.: 182–184° C. Recrystallized from ethanol-ether. Elemental analysis for $C_{16}H_{12}FN_3O_3$ Calcd. (%): C, 61.34; H, 3.86; N, 13.41; F, 6.06. Found. (%): C, 61.47; H, 3.90; N, 13.04; F, 5.99. NMR($d_6$-DMSO) δ: 4.18(2H, s), 6.46(1H, d, J=3.3 Hz), 6.94(1H, s), 7.17–7.26(2H, m), 7.32–7.40(2H, m), 7.51(1H, d, J=3.3 Hz), 8.79(1H, brs).

1-[5-(4-Fluorophenyl)furan-2-yl]-3-hydroxy-3-(1H-1,2,4-triazol-3-yl)-propenone (Compound No. I-67)

M.p.: 128–129° C. Recrystallized from ethylacetate-ether. Elemental analysis for $C_{15}H_{10}FN_3O_3$ 0.5 $H_2O$ Calcd. (%): C, 58.44; H, 3.60; N, 13.63; F, 6.16. Found. (%): C, 58.13; H, 3.66; N, 13.96; F, 6.12. NMR($d_6$-DMSO) δ: 7.10(1H, s), 7.31(1H, d, J=3.9 Hz), 7.39(2H, t, J=9.0 Hz), 7.70(1H, d, J=3.9 Hz), 7.96(1H, dd, J=9.0, 5.4 Hz), 8.76(1H, brs).

1-[5-(4-Fluorophenylthio)furan-2-yl]-3-hydroxy-3-(1H-1,2,4-triazol-3-yl)-propenone (Compound No. I-68)

M.p.: 150–152° C. Recrystallized from ethylacetate. Elemental analysis for $C_{15}H_{10}FN_3O_3S$ 0.2 $H_2O$ Calcd. (%): C, 53.79; H, 3.13; N, 12.55; F, 5.67; S, 9.57. Found. (%): C, 53.95; H, 3.06; N, 12.75; F, 5.37; S, 9.33. NMR($d_6$-DMSO) δ: 6.97(1H, s), 7.09(1H, d, J=3.6 Hz), 7.22–7.33(2H, m), 7.42–7.52(2H, m), 7.65(1H, d, J=3.6 Hz), 8.75(1H, brs), 14.7(1H, brs).

1-[5-(4-Bromophenylthio)furan-2-yl]-3-hydroxy-3-(1H-1,2,4-triazol-3-yl)-propenone (Compound No. I-69)

M.p.: 155–158° C. Recrystallized from ethanol. Elemental analysis for $C_{15}H_{10}BrN_3O_3S$ 0.6 $H_2O$ 0.2$C_2H_6O$ Calcd. (%): C, 44.87; H, 3.03; N, 10.19; Br, 19.38; S, 7.78. Found. (%): C, 44.56; H, 2.86; N, 10.61; Br, 19.13; S, 7.86. NMR($d_6$-DMSO) δ: 6.98(1H, s), 7.18(1H, d, J=3.6 Hz), 7.22–7.32(2H, m), 7.52–7.64(2H, m), 7.67(1H, d, J=3.6 Hz), 8.76(1H, brs).

1-[5-(2,4-Difluorophenylthio)furan-2-yl]-3-hydroxy-3-(1H-1,2,4-triazol-3-yl)-propenone (Compound No. I-70)

M.p.: 158–160° C. Recrystallized from ethylacetate-ethanol. NMR($d_6$-DMSO) δ: 6.95(1H, s), 7.06(1H, d, J=3.6 Hz), 7.10–7.24(1H, m), 7.38–7.59(2H, m), 7.62(1H, d, J=3.6 Hz), 8.79(1H, brs).

1-[5-(4-Biphenyl)furan-2-yl]-3-hydroxy-3-(1H-1,2,4-triazol-3-yl)-propenone (Compound No. I-71)

M.p.: 278–279° C. Recrystallized from ethylacetate-ether. Elemental analysis for $C_{21}H_{15}N_3O_3$ Calcd. (%): C, 70.58; H, 4.23; N, 11.76. Found. (%): C, 70.59; H, 4.31; N, 11.27. NMR($d_6$-DMSO) δ: 7.13(1H, s), 7.38(1H, d, J=3.6 Hz), 7.43(1H, d, J=7.5 Hz), 7.51(2H, t, J=7.5 Hz), 7.70–7.90(5H, m), 7.99(2H, d, J=8.4 Hz), 8.80(1H, brs).

3-Hydroxy-1-[5-(4-methylbenzyl)furan-2-yl]-3-(1H-1,2,4-triazol-3-yl)-propenone (Compound No. I-72)

M.p.: 166–167° C. Recrystallized from ethylacetate. Elemental analysis for $C_{17}H_{15}N_3O_3$ 0.1 $C_4H_8O_2$ Calcd. (%): C, 65.69; H, 5.01; N, 13.21. Found. (%): C, 65.45; H, 4.93; N, 13.37. NMR($d_6$-DMSO) δ: 2.28(3H, s), 4.09(2H, s), 6.46(1H, d, J=3.6 Hz), 6.93(1H, s), 7.13–7.18(4H, m), 7.51(1H, d, J=3.6 Hz), 8.76(1H, brs), 14.7(1H, brs).

3-Hydroxy-1-[5-(4-methylphenyl)furan-2-yl]-3-(1H-1,2,4-triazol-3-yl)-propenone (Compound No. I-73)

M.p.: 227–228° C. Recrystallized from ethylacetate-ether. Elemental analysis for $C_{16}H_{13}N_3O_3$ 0.1 $H_2O$ Calcd. (%): C, 64.68; H, 4.48; N, 14.14. Found. (%): C, 64.58; H, 4.41; N, 14.17. NMR($d_6$-DMSO) δ: 2.37(3H, s), 7.08(1H, s), 7.25 (1H, d, J=3.9 Hz), 7.34(2H, d, J=8.4 Hz), 7.68(1H, d, J=3.9 Hz), 7.79(2H, d, J=8.4 Hz), 8.73(1H, brs).

1-[5-(2,4-Difluorobenzyl)furan-2-yl]-3-hydroxy-3-(1H-1,2,4-triazol-3-yl)-propenone (Compound No. I-74)

M.p.: 171–173° C. Recrystallized from ethylacetate-isopropylether. Elemental analysis for $C_{16}H_{11}F_2N_3O_3$ Calcd. (%): C, 58.01; H, 3.35; N, 12.68; F, 11.47. Found. (%): C, 57.97; H, 3.34; N, 12.64; F, 11.19. NMR($d_6$-DMSO) δ: 4.17(2H, s), 6.45(1H, s), 6.94(1H, s), 7.10–7.51(4H, m), 8.78(1H, s), 14.6(1H, brs).

1-[5-(2,6-Difluorobenzyl)furan-2-yl]-3-hydroxy-3-(1H-1,2,4-triazol-3-yl)-propenone (Compound No. I-75)

M.p.: 187–189° C. Recrystallized from ethylacetate. Elemental analysis for $C_{16}H_{11}F_2N_3O_3$ 0.2 $H_2O$ Calcd. (%): C, 57.39; H, 3.43; N, 12.55; F, 11.35. Found. (%): C, 57.34; H, 3.30; N, 12.47; F, 11.22. NMR($d_6$-DMSO) δ: 4.18(2H, s), 6.44(1H, d, J=3.3 Hz), 6.93(1H, s), 7.14–7.51(4H, m), 8.79(1H, s), 13.7(1H, brs).

1-[5-(3,4-Difluorobenzyl)furan-2-yl]-3-hydroxy-3-(1H-1,2,4-triazol-3-yl)-propenone (Compound No. I-76)

M.p.: 164–166° C. Recrystallized from ethylacetate. Elemental analysis for $C_{16}H_{11}F_2N_3O_3$ Calcd. (%): C, 58.01; H, 3.35; N, 12.68; F, 11.47. Found. (%): C, 57.95; H, 3.38; N, 12.66; F, 11.56. NMR($d_6$-DMSO) δ: 4.17(2H, s), 6.50 (1H, d, J=3.3 Hz), 6.95(1H, s), 7.14–7.46(3H, m), 7.52(1H, d, J=3.3 Hz), 8.77(1H, brs), 14.7(1H, brs).

1-[5-(2,5-Difluorobenzyl)furan-2-yl]-3-hydroxy-3-(1H-1,2,4-triazol-3-yl)-propenone (Compound No. I-77)

M.p.: 161–163° C. Recrystallized from ethylacetate. Elemental analysis for $C_{16}H_{11}F_2N_3O_3$ Calcd. (%): C, 58.01;

H, 3.35; N, 12.68; F, 11.47. Found. (%): C, 57.62; H, 3.26; N, 12.74; F, 11.37. NMR(d$_6$-DMSO) δ: 4.19(2H, s), 6.49 (1H, d, J=3.3 Hz), 6.95(1H, s), 7.17–7.34(3H, m), 7.52(1H, d, J=3.3 Hz), 8.75(1H, brs), 14.3(1H, brs).

3-Hydroxy-1-(5-phenethylfuran-2-yl)-3-(1H-1,2,4-triazol-3-yl)-propenone (Compound No. I-78)

M.p.: 207–209° C. Recrystallized from ethylacetate. Elemental analysis for C$_{17}$H$_{15}$N$_3$O$_3$ Calcd. (%): C, 66.01; H, 4.89; N, 13.58. Found. (%) C, 65.57; H, 4.98; N, 13.18. NMR(d$_3$-DMSO) δ: 2.96–3.12(4H, m), 5.45(1H, d, J=3.3 Hz), 6.96(1H, s), 7.16–7.34(5H, m), 7.47(1H, d, J=3.3 Hz), 8.77(1H, brs), 14.7(1H, brs).

3-Hydroxy-3-(1H-1,2,4-triazol-3-yl)-1-[5-(3-trifluoromethylbenzyl)furan-2-yl]-propenone (Compound No. I-79)

M.p.: 146–148° C. Recrystallized from ethylacetate-isopropryether. Elemental analysis for C$_{17}$H$_{12}$F$_3$N$_3$O$_3$ Calcd. (%): C, 56.20; H, 3.33; N, 11.57; F, 15.69. Found. (%): C, 56.21; H, 3.30; N, 11.73; F, 15.66. NMR(d$_6$-DMSO) δ: 4.28(2H, s), 5.51(1H, d, J=3.3 Hz), 6.95(1H, s), 7.50(1H, d, J=3.3 Hz), 7.56–7.70(4H, m), 8.74(1H, brs), 14.7(1H, brs).

1-[5-(2-Chlorobenzyl)furan-2-yl]-3-hydroxy-3-(1H-1,2,4-triazol-3-yl)-propenone (Compound No. I-80)

M.p.: 169–171° C. Recrystallized from ethylacetate-isopropylether. Elemental analysis for C$_{16}$H$_{12}$ClN$_3$O$_3$ Calcd. (%): C, 58.28; H, 3.67; N, 12.74; Cl, 10.75. Found. (%): C, 58.08; H, 3.63; N, 12.59; Cl, 10.68. NMR(d$_6$-DMSO) δ: 4.26(2H, s), 6.42(1H, d, J=3.3 Hz), 6.94(1H, s), 7.33–7.51(5H, m), 8.77(1H, brs), 14.7(1H, brs).

3-Hydroxy-1-[5-(4-hydroxybenzyl)furan-2-yl]-3-(1H-1,2,4-triazol-3-yl)-propenone (Compound No. I-81)

M.p.: 229–233° C. Recrystallized from ether. Elemental analysis for C$_{16}$H$_{13}$N$_3$O$_4$ Calcd. (%): C, 61.73; H, 4.21; N, 13.50. Found. (%): C, 61.95; H, 4.15; N, 11.93. NMR(d$_6$-DMSO) δ: 4.01(2H, s), 6.42(1H, d, J=3.6 Hz), 6.72(2H, d, J=8.7 Hz), 6.93(1H, s), 7.08(2H, d, J=8.7 Hz), 7.49(1H, d, J=3.6 Hz), 8.77(1H, brs), 9.31(1H,s), 14.7(1H, brs).

1-[5-(4-Fluorobenzyl)furan-2-yl]-3-hydroxy-3-(2-methyl-2H-1,2,4-triazol-3-yl)-propenone (Compound No. I-82)

M.p.: 58° C. Recrystallized from ether. Elemental analysis for C$_{17}$H$_{14}$FN$_3$O$_3$ Calcd. (%): C, 62.38; H, 4.31; N, 12.84; F, 5.80. Found. (%): C, 62.32; H, 4.34; N, 13.11; F, 5.65. NMR(d$_6$-DMSO) δ: 4.15(2H, s), 4.18(3H, s), 6.49(1H, d, J=3.3 Hz), 6.95(1H, s), 7.14–7.20(2H, m), 7.32–7.37(2H, m), 7.52(1H, d, J=3.3 Hz), 8.14(1H, s).

3-Hydroxy-1-[[5-(thiophen-2-yl)methyl]furan-2-yl]-3-(1H-1,2,4-triazol-3-yl)-propenone (Compound No. I-83)

M.p.: 207–208° C. Recrystallized from ethylacetate-ether. Elemental analysis for C$_{14}$H$_{11}$N$_3$O$_3$S Calcd. (%): C, 55.81; H, 3.68; N, 13.95; S, 10.64. Found. (%): C, 55.83; H, 3.75; N, 13.36; S, 10.74. NMR(d$_6$-DMSO) δ: 4.39(2H, s), 6.54 (1H, d, J=3.3 Hz), 6.97(1H, s), 7.00–7.10(2H, m), 7.41–7.43 (1H, m), 7.51(1H, brs), 8.78(1H, brs).

1-[[5-(Furan-3-yl)methyl]furan-2-yl]-3-hydroxy-3-(1H-1,2,4-triazol-3-yl)-propenone (Compound No. I-84)

M.p.: 173–174° C. Recrystallized from ethylacetate-ether. Elemental analysis for C$_{14}$H$_{11}$N$_3$O$_4$ Calcd. (%): C, 58.95; H, 3.89; N, 14.73. Found. (%): C, 58.90; H, 3.89; N, 14.42. NMR(d$_6$-DMSO) δ: 3.96(2H, s), 6.46(2H, brs), 6.96(1H, s), 7.50(1H, d, J=2.7 Hz), 7.62(1H, brs), 7.64(1H, brs), 8.77 (1H, brs).

3-Hydroxy-1-[[5-(thiophen-3-yl)methyl]furan-2-yl]-3-(1H-1,2,4-triazol-3-yl)-propenone (Compound No. I-85)

M.p.: 210–211° C. Recrystallized from ethylacetate-ether. Elemental analysis for C$_{14}$H$_{11}$N$_3$O$_3$S Calcd. (%): C, 55.81; H, 3.68; N, 13.95; S, 10.64. Found. (%): C, 55.66; H, 3.79; N, 13.77; S, 10.47. NMR(d$_6$-DMSO) δ: 4.15(2H, s), 6.47 (1H, d, J=3.3 Hz), 6.95(1H, s), 7.05(1H, dd, J=5.1, 1.2 Hz), 7.34(1H, m), 7.46–7.56(2H, m), 8.75(1H, brs).

1-[4-Chloro-5-(4-fluorobenzyl)furan-2-yl]-3-hydroxy-3-(1H-1,2,4-triazol-3-yl)-propenone (Compound No. I-86)

M.p.: 203–204° C. Recrystallized from ethylacetate-isopropylether. Elemental analysis for C$_{16}$H$_{11}$ClFN$_3$O$_3$ Calcd. (%): C, 55.27; H, 3.19; N, 12.08; Cl, 10.20, F, 5.46. Found. (%): C, 55.07; H, 3.16; N, 12.16; Cl, 9.81, F, 5.19. NMR(d$_6$-DMSO) δ: 4.18(2H, s), 6.95(1H, s), 7.15–7.33(4H, m), 7.79(1H, s), 8.77(1H, brs), 14.7(1H, brs).

1-(5-Cyclohexylmethylfuran-2-yl)-3-hydroxy-3-(1H-1,2,4-triazol-3-yl)-propenone (Compound No. I-87)

M.p.: 146–148° C. Recrystallized from ether. Elemental analysis for C$_{16}$H$_{19}$N$_3$O$_3$ Calcd. (%): C, 63.77; H, 6.35; N, 13.94. Found. (%): C, 63.72; H, 6.32; N, 13.91. NMR(d$_6$-DMSO) δ: 0.92–1.30(5H, m), 1.60–1.70(6H, m), 2.64(2H, d, J=6.3 Hz), 6.48(1H, d, J=3.3 Hz), 6.95(1H, s), 7.49(1H, d, J=3.3 Hz), 8.76(1H, brs), 14.7(1H, brs).

3-Hydroxy-1-[5-(3-methylbutyl)furan-2-yl]-3-(1H-1,2,4-triazol-3-yl)-propenone (Compound No. I-88)

M.p.: 137–138° C. Recrystallized from ethylacetate-hexane. Elemental analysis for C$_{14}$H$_{17}$N$_3$O$_3$ Calcd. (%): C, 61.08; H, 6.22; N, 15.26. Found. (%): C, 60.94; H, 6.17; N, 15.12. NMR(d$_6$-DMSO) δ: 0.92(6H, d, J=6.3 Hz), 1.50–1.70 (3H, m), 2.74–2.79(2H, m), 6.49(1H, d, J=3.6 Hz), 6.95(1H, s), 7.49(1H, d, J=3.6 Hz), 8.74(1H, brs), 14.7(1H, brs).

3-Hydroxy-1-[[5-(tetrahydropyran-4-yl)methyl]furan-2-yl]-3-(1H-1,2,4-triazol-3-yl)-propenone (Compound No. I-89)

M.p.: 145–147° C. Recrystallized from ethylacetate-hexane. Elemental analysis for C$_{15}$H$_{17}$N$_3$O$_4$ Calcd. (%) C, 59.40; H, 5.65; N, 13.85. Found. (%): C, 59.20; H, 5.59; N, 13.84. NMR(d$_6$-DMSO) δ: 1.24–1.32(2H, m), 1.50–1.58 (2H, m), 1.91(1H, m), 2.70(2H, d, J=7.2 Hz), 3.25–3.30(2H, m), 3.80–4.04(2H, m), 6.50(1H, d, J=3.3 Hz), 6.96(1H, s), 7.50(1H, d, J=3.3 Hz), 8.76(1H, brs), 14.7(1H, brs).

1-[5-(2-Cyclopentylethyl)furan-2-yl]-3-hydroxy-3-(1H-1,2,4-triazol-3-yl)-propenone (Compound No. I-90)

M.p.: 161–162° C. Recrystallized from ethylacetate-hexane. Elemental analysis for C$_{16}$H$_{19}$N$_3$O$_3$ 0.2H$_2$O Calcd. (%): C, 63.02; H, 6.41; N, 13.78. Found. (%): C, 62.66; H, 6.35; N, 13.34. NMR(d$_6$-DMSO) δ: 1.13–1.15(2H, m), 1.50–1.76(9H, m), 2.76(2H, t, J=7.8 Hz), 6.49(1H, d, J=3.3 Hz), 6.95(1H, s), 7.49(1H, d, J=3.3 Hz), 8.76(1H, brs), 14.7(1H, brs).

1-[[5-(2-Chlorothiophen-3-yl)methyl]furan-2-yl]-3-hydroxy-3-(1H-1,2,4-triazol-3-yl)-propenone (Compound No. I-91)

M.p.: 105–106° C. Recrystallized from ethylacetate-ether. MS: m/z=336(M+H) NMR(d$_6$-DMSO) δ: 4.11(2H, s), 6.46 (1H, d, J=3.3 Hz), 6.95(1H, s), 6.99(1H, d, J=5.7 Hz), 7.47(1H, d, J=5.4 Hz), 7.50–7.60(1H, m), 8.78(1H, brs).

1-(5-Cyclopropylmethylfuran-2-yl)-3-hydroxy-3-(1H-1,2,4-triazol-3-yl)-propenone (Compound No. I-92)

M.p.: 135–137° C. Recrystallized from ethylacetate. Elemental analysis for C$_{13}$H$_{13}$N$_3$O$_3$ Calcd. (%): C, 60.23; H, 5.05; N, 16.21. Found. (%): C, 60.07; H, 5.09; N, 16.16. NMR(d$_6$-DMSO) δ: 0.22–0.24(2H, m), 0.51–0.55(2H, m), 1.05(1H, m), 2.68(2H, d, J=6.9 Hz), 6.54(1H, d, J=3.6 Hz), 6.97(1H, s), 7.51(1H, d, J=3.6 Hz), 8.75(1H, brs), 14.2(1H, brs).

1-(5-Acetylfuran-2-yl)-3-hydroxy-3-(1H-1,2,4-triazol-3-yl)-propenone (Compound No. I-93)

M.p.: 206–208° C. Recrystallized from ethylacetate-ether. Elemental analysis for C$_{11}$H$_9$N$_3$O$_4$ 0.5 H$_2$O Calcd. (%): C, 51.57; H, 3.93; N, 16.40. Found. (%): C, 51.95; H, 3.82; N, 16.33. NMR(d$_6$-DMSO) δ: 2.53(3H, s), 7.12(1H, s), 7.63 (2H,brs), 8.81(1H, brs).

1-[5-(4-Fluorophenyl-hydroxy-methyl)furan-2-yl]-3-hydroxy-3-(1H-1,2,4-triazol-3-yl)-propenone (Compound No. I-94)

M.p.: 191–192° C. (decomposition). Recrystallized from ethylacetate. Elemental analysis for C$_{16}$H$_{12}$FN$_3$O$_4$ Calcd. (%): C, 58.35; H, 3.68; N, 12.76; F, 5.77. Found. (%): C, 58.31; H, 3.68; N, 12.68; F, 5.67. NMR(d$_6$-DMSO) δ: 5.84(1H, d, J=4.8 Hz), 6.38(1H, d, J=4.8 Hz), 6.50(1H, d, J=3.3 Hz), 6.94(1H, s), 7.20(2H, t, J=8.7 Hz), 7.45–7.50(3H, m), 8.70(1H, brs).

1-[5-(4-Fluorobenzyl)furan-2-yl]-3-(furan-2-yl)-3-hydroxy-propenone (Compound No. I-95)

M.p.: 44–45° C. Recrystallized from isopropylether-hexane. Elemental analysis for C$_{18}$H$_{13}$FO$_4$ Calcd. (%): C, 69.23; H, 4.20; F, 6.08. Found. (%): C, 69.16; H, 4.11; F, 6.18. NMR(CDCl$_3$) δ: 4.04(2H, s), 6.15(1H, d, J=3.6 Hz), 6.56(1H, s), 6.58(1H, d, J=1.8 Hz), 7.03(2H, t, J=8.7 Hz), 7.13(1H, d, J=3.6 Hz), 7.19–7.28(3H, m), 7.58–7.62(1H, m).

1-[5-(4-Fluorobenzyl)furan-2-yl]-3-hydroxy-3-(2-methylthiazol-4-yl)-propenone (Compound No. I-96)

M.p.: 96–98° C. Recrystallized from isopropylether. Elemental analysis for C$_{18}$H$_{14}$FNO$_3$S Calcd. (%): C, 62.96; H, 4.11; N, 4.00; F, 5.53; S, 9.34. Found. (%): C, 62.84; H, 4.16; N, 4.04; F, 5.36; S, 9.15. NMR(CDCl$_3$) δ: 2.78(3H, s), 4.05(2H, s), 6.13(1H, d, J=3.6 Hz), 6.95(1H, s), 7.02(2H, t, J=8.7 Hz), 7.19–7.26(3H, m), 7.94(1H, s).

1-[5-(4-Fluorobenzyl)furan-2-yl]-3-hydroxy-3-(5-methoxymethyl-1H-1,2,4-triazol-3-yl)-propenone (Compound No. I-97)

M.p.: 167–168° C. Recrystallized from ethylacetate-ether. Elemental analysis for C$_{18}$H$_{16}$FN$_3$O$_4$ 0.1H$_2$O Calcd. (%): C, 60.20; H, 4.55; N, 11.70; F, 5.29. Found. (%): C, 60.00; H, 4.51; N, 11.66; F, 5.02. NMR(d$_6$-DMSO) δ: 3.35(3H, s), 4.15(2H, s), 4.59(2H, s), 6.47(1H, d, J=3.6 Hz), 6.91(1H, s), 7.17(2H, t, J=8.7 Hz), 7.25–7.40(2H, m), 7.52(1H, d, J=3.6 Hz).

3-(5-Ethyl-1H-1,2,4-triazol-3-yl)-1-[5-(4-fluorobenzyl)furan-2-yl]-3-hydroxy-propenone (Compound No. I-98)

M.p.: 204–205° C. Recrystallized from ethylacetate-ether. Elemental analysis for C$_{18}$H$_{16}$FN$_3$O$_3$ 0.25H$_2$O Calcd. (%): C, 62.51; H, 4.81; N, 12.15; F, 5.49. Found. (%): C, 62.57; H, 4.68; N, 12.25; F, 5.30. NMR(d$_6$-DMSO) δ: 1.27(3H, t, J=7.8 Hz), 2.79(2H, q, J=7.8 Hz), 4.15(2H, s), 6.45(1H, d, J=3.6 Hz), 6.88(1H, s), 7.17(2H, t, J=9.3 Hz), 7.25–7.40(2H, m), 7.49(1H, d, J=3.6 Hz).

1-[5-(4-Fluorobenzyl)furan-2-yl]-3-hydroxy-3-(5-isopropyl-1H-1,2,4-triazol-3-yl)-propenone (Compound No. I-99)

M.p.: 146–147° C. Recrystallized from ethylacetate-ether. Elemental analysis for C$_{19}$H$_{18}$FN$_3$O$_3$ 0.25H$_2$O Calcd. (%): C, 63.41; H, 5.18; N, 11.68; F, 5.28. Found. (%): C, 63.47; H, 5.09; N, 12.43; F, 4.85. NMR(d$_6$-DMSO) δ: 1.30(6H, d, J=6.9 Hz, 3.00–3.20(1H, m), 4.15(2H, s), 6.45(1H, d, J=3.6 Hz), 6.87(1H, s), 7.17(2H, t, J=9.3 Hz), 7.25–7.40(2H, m), 7.48(1H, d, J=3.6 Hz).

1-[5-(4-Fluorobenzyl)furan-2-yl]-3-hydroxy-3-(1-methyl-1H-imidazol-2-yl)-propenone (Compound No. I-100)

M.p.: 56–57° C. Recrystallized from isopropylether-hexane. Elemental analysis for C$_{18}$H$_{15}$FN$_2$O$_3$ 0.5H$_2$O Calcd. (%): C, 64.47; H, 4.81; N, 8.35; F, 5.67. Found. (%): C, 64.68; H, 4.80; N, 8.47; F, 5.49. NMR(CDCl$_3$) δ: 4.01 (2H, s), 4.08(3H, s), 6.12(1H, d, J=3.6 Hz), 6.98–7.23(7H, m).

1-[5-(4-Fluorobenzyl)furan-2-yl]-3-hydroxy-3-(1H-imidazol-2-yl)-propenone hydrochloride (Compound No. I-101)

M.p.: 186–191° C. Recrystallized from ethanol-ethylacetate. Elemental analysis for C$_{17}$H$_{13}$FN$_2$O$_3$ HCl 1.8H$_2$O Calcd. (%): C, 53.57; H, 4.65; N, 7.35; Cl, 9.30; F, 4.98. Found. (%): C, 53.34; H, 4.13; N, 7.36; Cl, 9.62; F, 5.06. NMR(d$_6$-DMSO) δ: 4.15(2H, s), 6.51(1H, d, J=3.6 Hz), 7.15–7.51(6H, m), 7.72(2H, s).

1-[5-(4-Fluorobenzyl)furan-2-yl]-3-(furan-3-yl)-3-hydroxy-propenone (Compound No. I-102)

M.p.: 53–55° C. Recrystallized from isopropylether-hexane. Elemental analysis for C$_{18}$H$_{13}$FO$_4$ Calcd. (%): C, 69.23; H, 4.20; F, 6.08. Found. (%): C, 69.24; H, 4.06; F, 5.96. NMR(CDCl$_3$) δ: 4.04(2H, s), 6.12–6.16(1H, m), 6.31 (1H, s), 6.72–6.76(1H, m), 7.03(2H, t, J=8.7 Hz), 7.13(1H, d, J=3.6 Hz), 7.16–7.28(2H, m), 7.46–7.50(1H, m), 8.04–8.07(1H, m).

1-[5-(4-Fluorobenzyl)furan-2-yl]-3-(thiophen-2-yl)-3-hydroxy-propenone (Compound No. I-103)

M.p.: 50–52° C. Recrystallized from hexane-ethylacetate. Elemental analysis for C$_{18}$H$_{13}$FO$_3$S Calcd. (%): C, 65.84; H, 3.99; F, 5.79; S, 9.76. Found. (%): C, 65.61; H, 3.93; F, 5.63; S, 9.72. NMR(CDCl$_3$) δ: 4.05(2H, s), 6.15(1H, d, J=3.3 Hz), 6.52(1H, s), 7.03(2H, t, J=8.4 Hz), 7.11(1H, d, J=3.3 Hz), 7.12–7.19(1H, m), 7.20–7.30(2H, m), 7.61(1H, dd, J=5.1, 0.8 Hz), 7.77(1H, dd, J=5.1, 0.8 Hz).

1-[5-(4-Fluorobenzyl)furan-2-yl]-3-hydroxy-3-(thiazol-2-yl)-propenone (Compound No. I-104)

M.p.: amorphous. Elemental analysis for $C_{17}H_{12}FNO_3S$ Calcd. (%): C, 62.00; H, 3.67; N, 4.25; F, 5.77; S, 9.74. Found. (%): C, 62.02; H, 3.68; N, 4.22; F, 5.56; S, 8.94. NMR(CDCl$_3$) δ: 4.04(2H, s), 6.17(1H, d, J=3.3 Hz), 7.02 (2H, d, J=8.4 Hz), 7.10(1H, s), 7.12–7.30(3H, m), 7.67(1H, brs), 8.03(1H, brs).

1-[5-(4-Fluorobenzyl)furan -2-yl]-3-hydroxy-3-(isoxazol-3-yl)-propenone (Compound No. I-105)

M.p.: 50–62° C. Recrystallized from hexane. Elemental analysis for $C_{17}H_{12}FNO_4$ Calcd. (%): C, 65.18; H, 3.86; N, 4.47; F, 6.06. Found. (%): C, 65.04: H, 3.76; N, 4.40; F, 5.95. NMR(CDCl$_3$) δ: 4.04(2H, s), 6.18(1H, d, J=3.3 Hz), 6.82 (1H, d, J=1.8 Hz), 6.92(1H, s), 7.03(2H, t, J=8.7 Hz), 7.15–7.30(3H, m), 8.52(1H, d, J=1.8 Hz).

1-[5-(4-Fluorobenzyl)furan-2-yl]-3-hydroxy-3-(pyridin-2-yl)-propenone (Compound No. I-106)

M.p.: 84–85° C. Recrystallized from ether-hexane. Elemental analysis for $C_{19}H_{14}FNO_3 \cdot 0.2H_2O$ Calcd. (%): C, 69.80; H, 4.44; N, 4.28; F, 5.81. Found. (%): C, 69.76; H, 4.34; N, 4.34; F, 5.73. NMR(CDCl$_3$) δ: 4.06(2H, s), 6.16 (1H, d, J=3.3 Hz), 7.03(2H, t, J=8.4 Hz), 7.20–7.30(3H, m), 7.32(1H, s), 7.40–7.48(1H, m), 7.87(1H, dt, J=1.5, 7.5 Hz), 8.11(1H, d, J=7.5 Hz), 8.68–8.74(1H, m).

1-[5-(4-Fluorobenzyl)furan-2-yl]-3-hydroxy-3-(5-methylisoxazol-3-yl)-propenone (Compound No. I-107)

M.p.: 95–97° C. Recrystallized from isopropanol. Elemental analysis for $C_{18}H_{14}FNO_4$ Calcd. (%): C, 66.05; H, 4.31; N, 4.28; F, 5.80. Found. (%): C, 66.12; H, 4.29; N, 4.48; F, 5.65. NMR(CDCl$_3$) δ: 2.51(3H, s), 4.04(2H, s), 6.16(1H, d, J=3.6 Hz), 6.43(1H, s), 6.86(1H, s), 7.02(2H, t, J=8.4 Hz), 7.18–7.24(3H, m).

1-[5-(4-Fluorobenzyl)furan-2-yl]-3-hydroxy-3-(3-methylisoxazol-5-yl)-propenone (Compound No. I-108)

M.p.: 106–107° C. Recrystallized from isopropanol. Elemental analysis for $C_{18}H_{14}FNO_4$ Calcd. (%): C, 66.05; H, 4.31; N, 4.28; F, 5.80. Found. (%): C, 66.09; H, 4.18; N, 4.53; F, 5.57. NMR(CDCl$_3$) δ: 2.39(3H, s), 4.06(2H, s), 6.19(1H, d, J=3.3 Hz), 6.72(1H, d, J=3.3 Hz), 6.73(1H, s), 7.03(2H, t, J=8.7 Hz), 7.21–7.26(2H, m).

1-[5-(4-Fluorobenzyl)furan-2-yl]-3-hydroxy-3-(5-methyl-[1,3,4]-oxadiazol-2-yl)-propenone (Compound No. I-109)

M.p.: 147–149° C. Recrystallized from isopropylether. Elemental analysis for $C_{17}H_{13}FN_2O_4 \cdot 0.2H_2O$ Calcd. (%): C, 61.52; H, 4.07; N, 8.44; F, 5.72. Found. (%): C, 61.66; H, 3.94; N, 8.70; F, 5.55. NMR(CDCl$_3$) δ: 2.67(3H, s), 4.05 (2H, s), 6.21(1H, d, J=3.6 Hz), 7.00–7.20(3H, m), 7.35–7.70 (3H, m).

1-[5-(4-Fluorobenzyl)furan-2-yl]-3-[5-(4-fluorobenzyl)-[1,3,4]-oxadiazol-2-yl]-3-hydroxy-propenone (Compound No. I-110)

M.p.: 88–90° C. Recrystallized from isopropylether. Calcd. (%): C, 64.85; H, 3.88; N, 6.58; F, 8.92. Found. (%): C, 64.89; H, 3.80; N, 6.79; F, 8.81. NMR(CDCl$_3$) δ: 4.05 (2H, s), 4.28(2H, s), 6.20(1H, d, J=3.6 Hz), 7.0–7.09(5H, m), 7.18–7.36(5H, m).

1-[5-(4-Fluorobenzyl)furan-2-yl]-3-hydroxy-3-(pyrazin-2-yl)-propenone (Compound No. I-111)

M.p.: 127–129° C. Recrystallized from ethylacetate. Elemental analysis for $C_{18}H_{13}FN_2O_3$ Calcd. (%): C, 66.66; H, 4.04; N, 8.64; F, 5.86. Found. (%): C, 66.73; H, 4.05; N, 8.63; F, 5.61. NMR(CDCl$_3$) δ: 4.07(2H, s), 6.18(1H, d, J=3.4 Hz), 7.03(2H, t, J=8.8 Hz), 7.20–7.30(4H, m), 8.65–8.75(2H, m), 9.25(1H, s).

1-[5-(4-Fluorobenzyl)furan-2-yl]-3-hydroxy-3-(5-propyl-1H-1,2,4-triazol-3-yl)-propenone (Compound No. I-112)

M.p.: 167–168° C. Recrystallized from ethylacetate-ether. Elemental analysis for $C_{19}H_{18}FN_3O_3$ Calcd. (%): C, 64.22; H, 5.11; N, 11.82; F, 5.35. Found. (%): C, 64.05; H., 5.07; N, 11.80; F, 5.13. NMR(d$_6$-DMSO) δ: 0.92(3H, t, J=7.5 Hz), 1.60–1.80(2H, m), 2.73(2H, q, J=7.5 Hz), 4.15(2H, s), 6.45(1H, d, J=3.6 Hz), 6.88(1H, s), 7.17(2H, t, J=9.3 Hz), 7.25–7.40(2H, m), 7.49(1H, d, J=3.6 Hz).

1-[5-(4-Fluorobenzyl)furan-2-yl]-3-hydroxy-3-phenyl-propenone (Compound No. I-113)

M.p.: 70–72° C. Recrystallized from hexane-ethylacetate. Elemental analysis for $C_{20}H_{15}FO_3$ Calcd. (%): C, 74.52; H, 4.69; F, 5.89. Found. (%): C, 74.30; H, 4.66; F, 5.81. NMR(CDCl$_3$) δ: 4.06(2H, s), 6.16(1H, d, J=3.3 Hz), 6.67 (1H, s), 7.03(2H, t, J=8.4 Hz), 7.16–7.28(3H, m), 7.42–7.58 (3H, m), 7.90–7.98(2H, m).

3-(6-carboxypyridin-2-yl)-1-[5-(4-fluorobenzyl) furan-2-yl]-3-hydroxy-propenone (Compound No. I-114)

M.p.: 135–137° C. Recrystallized from ethylacetate. Elemental analysis for $C_{20}H_{14}FNO_6$ Calcd. (%): C, 65.40; H, 3.84; N, 3.81; F, 5.17. Found. (%): C, 65.13; H, 3.80; N, 3.93; F, 5.09. NMR(CDCl$_3$) δ: 4.10(2H, s), 6.21(1H, d, J=3.6 Hz), 7.05(2H, t, J=8.7 Hz), 7.21–7.30(4H, m), 8.15 (1H, t, J=7.8 Hz), 8.36–8.40(2H, m).

3-(6-ethoxycarbonylpyridin-2-yl)-1-[5-(4-fluorobenzyl)furan-2-yl]-3-hydroxy-propenone (Compound No. I-115)

M.p.: 83–84° C. Recrystallized from ether-hexane. Elemental analysis for $C_{22}H_{18}FNO_5$ Calcd. (%): C, 66.83; H, 4.59; N, 3.54; F, 4.81. Found. (%): C, 66.72; H, 4.50; N, 3.69; F, 4.73. NMR(CDCl$_3$) δ: 1.48(3H, t, J=7.2 Hz), 4.07(2H, s), 4.51(2H, q, J=7.2 Hz), 6.17(1H, d, J=3.6 Hz), 7.03(2H, t, J=8.4 Hz), 7.20–7.30(3H, m), 7.40(1H, s), 8.00 (1H, t, J=7.5 Hz), 8.18–8.28(2H, m).

1-[5-(4-Fluorobenzyl)furan-2-yl]-3-hydroxy-3-(isoquinolin-3-yl)-propenone (Compound No. I-116)

M.p.: 154–156° C. Recrystallized from ethylacetate. Elemental analysis for $C_{23}H_{16}FNO_3 \cdot 0.1H_2O$ Calcd. (%): C, 73.63; H, 4.35; N, 3.73; F, 5.06. Found. (%): C, 73.38; H, 4.32; N, 3.80; F, 5.11. NMR(CDCl$_3$) δ: 4.08(2H, s), 6.16 (1H, d, J=3.6 Hz), 7.03(2H, t, J=9.0 Hz), 7.20–7.30(3H, m), 7.44(1H, s), 7.70–7.82(2H, m), 7.95–8.15(2H, m), 8.52(1H, s), 9.29(1H, s).

1-[5-(4-Fluorobenzyl)furan-2-yl]-3-hydroxy-3-(6-methylpyridin-2-yl)-propenone (Compound No. I-117)

M.p.: 67–69° C. Recrystallized from isopropylether. Elemental analysis for $C_{20}H_{16}FNO_3$ Calcd. (%): C, 71.21;

H, 4.78; N, 4.15; F, 5.63. Found. (%): C, 70.93; H, 4.75; N, 4.24; F, 5.41. NMR(CDCl$_3$) δ: 2.65(3H, s), 4.07(2H, s), 6.14(1H, d, J=3.6 Hz), 7.03(2H, t, J=8.8 Hz), 7.20–7.32(5H, m), 7.72(1H, t, J=8.0 Hz), 7.84–7.92(1H, m).

3-(1-Benzenesulfonylpyrrol-2-yl)-1-[5-(4-fluorobenzyl)furan-2-yl]-3-hydroxy-propenone (Compound No. I-118)

M.p.: 97–98° C. Recrystallized from ether. Elemental analysis for C$_{24}$H$_{18}$FNO$_5$S Calcd. (%): C, 63.85; H, 4.02; N, 3.10; F, 4.21; S, 7.10. Found. (%): C, 63.76; H, 4.17; N, 3.15; F, 4.12; S, 7.04. NMR(CDCl$_3$) δ: 4.00(2H, s), 6.12(1H, d, J=3.6 Hz), 6.30–6.40(2H, m), 6.95–7.08(4H, m), 7.10–7.20(2H, m), 7.45–7.65(3H, m), 7.75–7.85(1H, m), 7.95–8.05(2H, m).

1-[5-(4-Fluorobenzyl)furan-2-yl]-3-hydroxy-3-(1-methylpyrrol-2-yl)-propenone (Compound No. I-119)

M.p.: 75–76° C. Recrystallized from isopropylether. Elemental analysis for C$_{19}$H$_{16}$FNO$_3$ Calcd. (%): C, 70.14; H, 4.96; N, 4.31; F, 5.84. Found. (%): C, 69.94; H, 4.95; N, 4.25; F, 5.67. NMR(CDCl$_3$) δ: 4.00(3H, s), 4.03(2H, s), 4.21(2H, s), 6.08–6.20(2H, m), 6.80–6.85(1H, m), 6.95–7.05(4H, m), 7.05–7.35(2H, m). Keto form.

Example 120

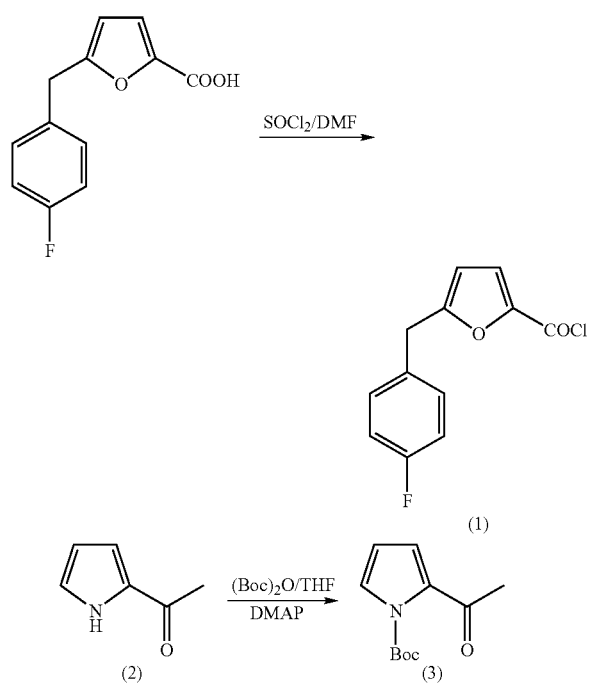

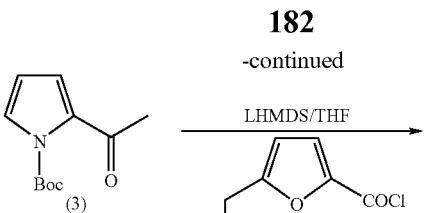

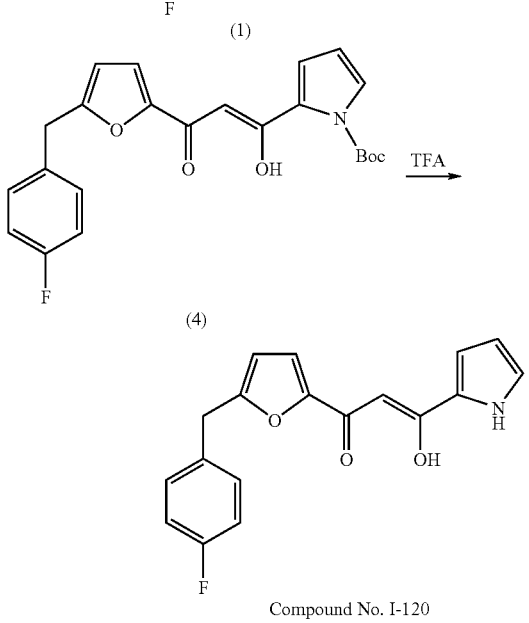

Compound No. I-120

1-[5-(4-Fluorobenzyl)furan-2-yl]-3-hydroxy-3-(pyrrol-2-yl)-propenone (Compound No. I-120)

(1) To 5-(4-fluorobenzyl)-2-furan carboxylic acid (450 mg, 2 mmol) were added thionylchloride (1 ml, 13.7 mmol) and DMF (0.025 ml). The mixture was stirred for 30 minutes at room temperature. The excess amount of thionylchloride was evaporated. The precipitated residue was washed with n-hexane to give crude 5-(4-fluorobenzyl)-2-furan carboxylic acid chloride (480 mg). NMR(CDCl$_3$) δ: 4.03(2H, s), 6.20(1H, d, J=3.6 Hz), 7.03(2H, t, J=8.7 Hz), 7.19–7.24(2H, m), 7.42(1H, d, J=3.6 Hz).

(2) To a solution of 2-acetylpyrrole (1.09 g, 10 mmol) in THF (15 ml) was added dropwise at an ice bath temperature a solution of di-tert-butyldicarbonate (2.58 g, 12 mmol) in THF (5 ml). Subsequently, to the reaction mixture was added a crystal of 4-dimethylaminopyridine (122 mg, 1 mmol). The reaction mixture was stirred at room temperature for 30 minutes. The reaction solvent was evaporated, mixed with ice-water, extracted with ethylacetate, washed with water and dried. The solvent was evaporated to give 2-acetyl-1-tert-butoylcarbonylpyrrole (2.1 g) as a pale yellow oil. NMR(CDCl$_3$) δ: 1.58(9H, s), 2.45(3H, s), 6.17(1H, t, J=3.0 Hz), 6.85–6.89(1H, m), 7.30–7.34(1H, m).

(3) To a solution of 2-acetyl-1-tert-butoylcarbonylpyrrole (313.7 mg, 1.5 mmol) in THF (10 ml) was added dropwise under −65° C., a solution of lithiumbistrimethylsilylamide in THF (1 M solution, 2 ml, 2 mmol). Subsequently, the reaction mixture was gradually warmed up to 0° C., cooled down to −70° C. again and mixed dropwise with a solution of 5-(4-fluorobenzyl)-furan carboxylic acid chloride (358 mg, 1.5 mmol) in THF (5 ml). The reaction mixture was gradually warmed up to room temperature and stirred for 30 minutes. The reaction solution was poured into an excess amount of ammonium chloride aqueous solution, extracted with ethylacetate, washed with brine and dried. The solvent was evaporated. To the obtained yellow oil was added trifluoroacetic acid (2 ml) and stirred for 30 minutes at room temperature. Trifluoroacetic acid was evaporated under reduced pressure. The residue was extracted with ethylacetate, washed with aqueous sodium hydrogencarbonate, washed with brine and dried. The solvent was evaporated. The obtained residue was recrystallized from n-hexane-isopropylether to give the titled compound (200 mg) as a yellow crystal. Yield 43%.

M.p.: 96–98° C. Recrystallized from hexane-isopropylether. Elemental analysis for $C_{18}H_{14}FNO_3$ $0.1H_2O$ Calcd. (%): C, 69.05; H, 4.57; N, 4.47; F, 6.07. Found. (%): C, 68.91; H, 4.51; N, 4.53; F, 5.71. NMR(CDCl$_3$) δ: 4.04 (2H, s), 6.12(1H, m), 6.25–6.35(1H, m), 6.39(1H, s), 6.95–7.10(4H, m), 7.15–7.30(3H, m), 9.10–9.25(1H, brs).

1-[5-(4-Fluorobenzyl)furan-2-yl]-3-hydroxy-3-(pyridin-3-yl)-propenone (Compound No. I-121)

M.p.: 53–54° C. Recrystallized from isopropylether. Elemental analysis for $C_{19}H_{14}FNO_3$ $0.1H_2O$ Calcd. (%): C, 70.19; H, 4.40; N, 4.31; F, 5.84. Found. (%): C, 70.25; H, 4.30; N, 4.44; F, 5.72. NMR(CDCl$_3$) δ: 4.07(2H, s), 6.19 (1H, d, J=3.6 Hz), 6.68(1H, s), 7.04(2H, t, J=8.4 Hz), 7.20–7.30(3H, m), 7.38–7.50(1H, m), 8.22(1H, d, J=8.4 Hz), 8.65–8.82(1H, brs), 9.05–9.20(2H, brs).

1-[5-(4-Fluorobenzyl)furan-2-yl]-3-hydroxy-3-(pyridin-4-yl)-propenone (Compound No. I-122)

M.p.: 90–92° C. Recrystallized from isopropylether. Elemental analysis for $C_{19}H_{14}FNO_3$ $0.1H_2O$ Calcd. (%): C, 70.19; H, 4.40; N, 4.31; F, 5.84. Found. (%): C, 70.07; H, 4.33; N, 4.47; F, 5.74. NMR(CDCl$_3$) δ: 4.07(2H, s), 6.20 (1H, d, J=3.6 Hz), 6.70(1H, s), 7.04(2H, t, J=8.4 Hz), 7.20–7.28(3H, m), 7.75(2H, d, J=5.7 Hz), 8.70–8.90(2H, brs).

1-[5-(4-Fluorobenzyl)furan-2-yl]-3-hydroxy-3-(5-methoxycarbonylpyridin-2-yl)-propenone (Compound No. I-123)

M.p.: 147–150° C. Recrystallized from isopropylether. Elemental analysis for $C_{21}H_{16}FNO_5$ $0.5H_2O$ Calcd. (%): C, 64.61; H, 4.39; N, 3.59; F, 4.87. Found. (%): C, 64.85; H, 4.19; N, 3.93; F, 4.60. NMR(CDCl$_3$) δ: 3.99(3H, s), 4.07 (2H, s), 6.17(1H, d, J=3.6 Hz), 7.03(2H, t, J=9.0 Hz), 7.20–7.30(3H, m), 7.35(1H, s), 8.15(1H, d, J=8.4 Hz), 8.43(1H, dd, J=8.4, 2.1 Hz), 9.26(1H, brs).

3-(5-Carboxypyridin-2-yl)-1-[5-(4-fluorobenzyl)furan-2-yl]-3-hydroxy-propenone (Compound No. I-124)

M.p.: 196–198° C. Recrystallized from isopropylether. Elemental analysis for $C_{20}H_{14}FNO_5$ $0.2H_2O$ Calcd. (%): C, 64.76; H, 3.91; N, 3.78; F, 5.12. Found. (%): C, 64.95; H, 3.73; N, 3.93; F, 4.99. NMR(CDCl$_3$) δ: 4.08(2H, s), 6.18 (1H, d, J=3.6 Hz), 7.03(2H, t, J=9.0 Hz), 7.20–7.32(3H, m), 7.37(1H, s), 8.20(1H, d, J=8.4 Hz), 8.51(1H, dd, J=8.4, 1.8 Hz), 9.34(1H, brs).

1-[5-(4-Fluorobenzyl)furan-2-yl]-3-hydroxy-3-(4-methoxycarbonylpyridin-2-yl)-propenone (Compound No. I-125)

M.p.: 109–110° C. Recrystallized from isopropylether. Elemental analysis for $C_{21}H_{16}FNO_5$ Calcd. (%): C, 66.14; H, 4.23; N, 3.67; F, 4.98. Found. (%): C, 66.07; H, 4.22; N, 3.75; F, 5.00. NMR(CDCl$_3$) δ: 4.00(3H, s), 4.06(2H, s), 6.16(1H, d, J=3.3 Hz), 7.03(2H, t, J=8.4 Hz), 7.20–7.28(3H, m), 7.31(1H, s), 7.97(1H, dd, J=4.8, 1.5 Hz), 8.61(1H, brs), 8.85(1H, d, J=4.8 Hz).

3-(4-carboxypyridin-2-yl)-1-[5-(4-fluorobenzyl)furan-2-yl]-3-hydroxy-propenone (Compound No. I-126)

Elemental analysis for $C_{20}H_{14}FNO_5$ M.p.: 208–210° C. Recrystallized from isopropylether. Calcd. (%): C, 65.40; H, 3.84; N, 3.81; F, 5.17. Found. (%): C, 65.14; H, 3.79; N, 3.90; F, 4.95. NMR(CDCl$_3$) δ: 4.09(2H, s), 6.25(1H, d, J=3.6 Hz), 7.03(2H, t, J=8.4 Hz), 7.21–7.32(3H, m), 7.65 (1H, s), 7.96–8.02(1H, m), 8.56(1H, brs), 8.85(1H, d, J=5.1 Hz).

1-[5-(4-Fluorobenzyl)furan-2-yl]-3-hydroxy-3-(pyrimidin-2-yl)-propenone (Compound No. I-127)

M.p.: 77–80° C. Recrystallized from ethylacetate-chloroform. Elemental analysis for $C_{18}H_{13}FNO_3$ $0.2H_2O$ $0.2C_4H_8O_2$ $0.03CHCl_3$ Calcd. (%): C, 64.78; H, 4.34; N, 8.02; F, 5.44. Found. (%): C, 65.04; H, 4.04; N, 7.77; F, 5.56. NMR(CDCl$_3$) δ: 4.07(2H, s), 6.18(1H, d, J=3.2 Hz), 7.03 (2H, t, J=8.8 Hz), 7.18–7.22(3H, m), 7.39(1H, s), 7.39(1H, t, J=4.8 Hz), 8.92(2H, d, J=4.8 Hz).

3-(3-Carboxypyridin-2-yl)-1-[5-(4-fluorobenzyl)furan-2-yl]-3-hydroxy-propenone (Compound No. I-128)

M.p.: 127–130° C. Recrystallized from ethylacetate. Elemental analysis for $C_{20}H_{14}FNO_5$ $0.2H_2O$ Calcd. (%): C, 64.76; H, 3.91; N, 3.78; F, 5.12. Found. (%): C, 65.56; H, 3.71; N, 3.88; F, 5.02. NMR(CDCl$_3$) δ: 3.99(2H, s), 6.15 (1H, d, J=3.3 Hz), 6.24(1H, s), 6.92–7.06(2H, m), 7.10–7.26 (3H, m), 7.60–7.70(1H, m), 7.90–8.04(1H, m), 8.64–8.70 (1H, m).

1-[5-(4-Fluorobenzyl)furan-2-yl]-3-hydroxy-3-(5-trifluoromethyl-1H-1,2,4-triazol-3-yl)-propenone (Compound No. I-129)

M.p.: 154–155° C. Recrystallized from hexane-isopropylether. Elemental analysis for $C_{17}H_{11}F_4N_3O_3$ Calcd. (%): C, 53.55; H, 2.91; N, 11.02; F, 19.93. Found. (%): C, 53.88; H, 3.00; N, 10.72; F, 19.69. NMR(d$_6$-DMSO) δ: 4.16(2H, s), 6.51(1H, d, J=3.6 Hz), 6.96(1H, s), 7.18(2H, t, J=8.7 Hz), 7.26–7.40(2H, m), 7.69(1H, d, J=3.6 Hz).

1-[5-(4-Fluorobenzyl)furan-2-yl]-3-hydroxy-3-(5-methyloxazol-2-yl)-propenone (Compound No. I-130)

M.p.: 87–88° C. Recrystallized from isopropylether. Elemental analysis for $C_{18}H_{14}FNO_4$ $0.2H_2O$ Calcd. (%): C, 65.33; H, 4.39; N, 4.39; F, 5.74. Found. (%): C, 65.14; H, 4.20; N, 4.34; F, 5.42. NMR(CDCl$_3$) δ: 2.45(3H, s), 4.04 (2H, s), 6.17(1H, d, J=3.6 Hz), 6.91(1H, s), 6.99(1H, s), 7.02(2H, t, J=8.4 Hz), 7.18–7.25(3H, m).

3-(5-Chloro-1H-1,2,4-triazol-3-yl)-1-[5-(4-fluorobenzyl)furan-2-yl]-3-hydroxy-propenone (Compound No. I-131)

M.p.: 129–130° C. Recrystallized from ethylacetate-hexane. Elemental analysis for $C_{16}H_{11}ClFN_3O_3$ $0.17C_6H_{14}$ Calcd. (%): C, 56.39; H, 3.71; N, 11.60; Cl, 9.79; F, 5.25. Found. (%): C, 56.19; H, 3.37; N, 11.38; Cl, 8.84; F, 5.30. NMR($d_6$-DMSO) δ: 4.15(2H, s), 6.50(1H, d, J=3.6 Hz), 6.89(1H, s), 7.17(2H, t, J=8.7 Hz), 7.40–7.60(2H, m), 7.63 (1H, d, J=3.6 Hz).

1-[5-(4-Fluorobenzyl)furan-2-yl]-3-hydroxy-3-([1,3,4]thiadiazol-2-yl)-propenone (Compound No. I-132)

oil Elemental analysis for $C_{16}H_{11}FN_2O_3S$ $0.2C_6H_{12}O$ $0.05CHCl_3$ $0.2H_2O$ Calcd. (%): C, 57.56; H, 3.88; N, 7.78; F, 5.28; S, 8.91. Found. (%): C, 57.54; H, 3.46; N, 7.44; F, 5.68; S, 8.53. NMR(CDCl$_3$) δ: 4.06(2H, s), 6.21(1H, d, J=3.3 Hz), 7.03(2H, t, J=8.7 Hz), 7.15–7.325(4H, m), 9.31 (1H, s).

Example 133–139

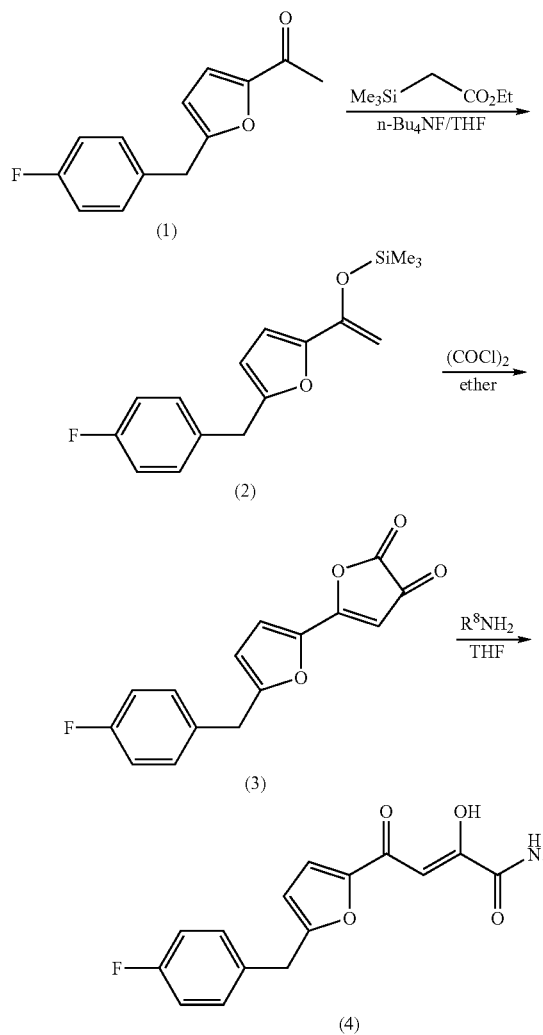

| | | |
|---|---|---|
| $R^B$ = ◁ | | Comp. No. I-133 |
| $R^B$ = H | | Comp. No. I-134 |
| $R^B$ = pyridyl | | Comp. No. I-135 |
| $R^B$ = thiazolyl | | Comp. No. I-136 |
| $R^B$ = phenyl | | Comp. No. I-137 |
| $R^B$ = triazolyl-NH | | Comp. No. I-138 |
| $R^B$ = thiadiazolyl | | Comp. No. I-139 |

4-[5-(4-Fluorobenzyl)furan-2-yl]-2-hydroxy-4-oxo-2-butenoic acid cyclopropylamide (Compound No. I-133)

(1) A solution of 2-acetyl-5-(4-fluorobenzyl)furan (10 g, 46 mmol) and trimethylsilylacetic acid ethyl ester (10.9 g, 68 mmol) in anhydrous THF (30 ml) was cooled at −20° C. To a solution was added anhydrous tetrabutylammoniumfluoride (0.2 g). The reaction mixture was gradually warmed up to room temperature and stirred for 15 minutes at 50° C. The THF was evaporated under reduced pressure. The residue was distilled under reduced pressure. The fraction showing b.p. 130° C. (0.5 mmHg) was collected to give [1-[5-(4-fluorobenzyl)furan-2-yl]vinyloxy]-trimethylsilane (11.7 g). Yield 88%.

(2) To a solution of the above-obtained compound (9.0 g, 31 mmol) in anhydrous ether (45 ml) was added dropwise at an ice bath temperature oxalylchloride (2.0 g, 16 mmol). The reaction mixture was stirred for 30 minutes at room temperature. The precipitated crystal was collected by filtration and washed with anhydrous ether-hexane (1:1, v/v) to give 5'-(4-fluorobenzyl)-[2,2']bifranyl-4,5-dione (1.8 g). Yield 21%.

M.p.: 113–114° C. (decomposition). Elemental analysis for $C_{15}H_9FO_4$ $0.2H_2O$ Calcd. (%): C, 65.32; H, 3.44; F, 6.89. Found. (%): C, 65.23; H, 3.47; F, 6.85. NMR($d_6$-DMSO) δ: 4.10(2H, s), 6.17(1H, s), 6.33(1H, d, J=3.6 Hz), 7.02–7.25 (4H, m), 7.34(1H, d, J=3.6 Hz).

(3) To a solution of the above-obtained compound (100 mg, 0.37 mmol) in anhydrous THF (2 ml) was added at an ice bath temperature cyclopropylamine (63 mg, 1.1 mmol). The reaction mixture was stirred for 15 minutes at room temperature. The THF was evaporated. The residue was dissolved in acetone and treated with activated carbon. The solution was filtered and concentrated. The obtained crystal was washed with isopropylether to give a titled compound (71 mg). Yield 59%.

M.p.: 116–117° C. Elemental analysis for $C_{18}H_{16}FNO_4$ Calcd. (%): C, 65.65; H, 4.90; N, 4.25; F, 5.77. Found. (%): C, 65.27; H, 4.84; N, 4.35; F, 5.74. NMR($d_6$-DMSO) δ: 0.5–0.70(4H, m), 2.81(1H, m), 4.14(2H, s), 6.48(1H, d, J=3.6 Hz), 6.74(1H, s), 7.13–7.36(4H, m), 7.60(1H, d, J=3.6 Hz), 8.79(1H, d, J=5.4 Hz).

The following compounds were prepared in accordance with the preparation of the compound of Example 133.

4-[5-(4-Fluorobenzyl)furan-2-yl]-2-hydroxy-4-oxo-2-butenoic acid amide (Compound No. I-134)

M.p.: 113–115° C. Recrystallized from isopropylether. Elemental analysis for $C_{15}H_{12}FNO_4$ Calcd. (%): C, 62.28;

H, 4.18; N, 4.84; F, 6.57. Found. (%): C, 62.02; H, 4.14; N, 4.96; F, 6.33. NMR($d_6$-DMSO) δ: 4.13(2H, s), 6.47(1H, d, J=3.6 Hz), 6.75(1H, s), 7.13–7.35(4H, m), 7.57(1H, d, J=3.6 Hz), 7.91(1H, s), 8.08(1H, s).

4-[5-(4-Fluorobenzyl)furan-2-yl]-2-hydroxy-4-oxo-2-butenoic acid pyridin-2-yl amide (Compound No. I-135)

M.p.: >250° C. Recrystallized from ether. Elemental analysis for $C_{20}H_{16}FN_2O_4$ Calcd. (%): C, 65.57; H, 4.13; N, 7.65; F, 5.19. Found. (%): C, 65.30; H, 3.88; N, 7.72; F, 5.26. NMR($d_6$-DMSO) δ: 3.96(2H, s), 6.27(1H, d, J=3.6 Hz), 6.59–6.55(1H, m), 7.08–7.56(8H, m), 7.90–8.27(2H, m).

4-[5-(4-Fluorobenzyl)furan-2-yl]-2-hydroxy-4-oxo-2-butenoic acid thiazol-2-yl amide (Compound No. I-136)

M.p.: 198° C. (decomposition), Recrystallized from ether. Elemental analysis for $C_{18}H_{13}FN_2O_4S$ Calcd. (%): C, 58.06; H, 3.52; N, 7.52; F, 5.10; S, 8.61. Found. (%): C, 58.12; H, 3.45; N, 7.49; F, 4.98; S, 8.63. NMR($d_6$-DMSO) δ: 4.15(2H, s), 6.52(1H, d, J=3.6 Hz), 6.97(1H, s), 7.15–7.38(5H, m), 7.60(1H, d, J=3.6 Hz), 7.68(1H, d, J=3.6 Hz).

4-[5-(4-Fluorobenzyl)furan-2-yl]-2-hydroxy-4-oxo-2-butenoic acid phenyl amide (Compound No. I-137)

M.p.: 132–134° C. Recrystallized from isopropylether. Elemental analysis for $C_{21}H_{16}FNO_4$ Calcd. (%): C, 69.04; H, 4.41; N, 3.83; F, 5.20. Found. (%): C, 68.92; H, 4.34; N, 3.91; F, 5.03. NMR($d_6$-DMSO) δ: 4.16(2H, s), 6.52(1H, d, J=3.6 Hz), 6.90(1H, s), 7.15–7.39(7H, m), 7.66(1H, d, J=3.6 Hz), 7.77–7.83(2H, m), 10.6(1H, s).

4-[5-(4-Fluorobenzyl)furan-2-yl]-2-hydroxy-4-oxo-2-butenoic acid (1H-1,2,4-triazol-3-yl)amide (Compound No. I-138)

M.p.: 250° C. (decomposition), Recrystallized from methanol-chloroform. Elemental analysis for $C_{17}H_{13}FN_4O_4$ Calcd. (%): C, 57.30; H, 3.68; N, 15.72; F, 5.33. Found. (%): C, 57.32; H, 3.57; N, 15.72; F, 5.18. NMR($d_6$-DMSO) δ: 4.15(2H, s), 6.51(1H, d, J=3.6 Hz), 6.89(1H, s), 7.13–7.37 (4H, m), 7.68(1H, d, J=3.6 Hz), 8.50(1H, brs), 10.9(1H, brs), 13.7(1H, brs).

4-[5-(4-Fluorobenzyl)furan-2-yl]-2-hydroxy-4-oxo-2-butenoic acid ([1,3,4]thiadiazol-2-yl)amide (Compound No. I-139)

M.p.: 199–201° C. (decomposition), Recrystallized from ether. Elemental analysis for $C_{17}H_{12}FN_3O_4S$ Calcd. (%): C, 54.69; H, 3.24; N, 11.25; F, 5.09; S, 8.59. Found. (%): C, 54.37; H, 3.17; N, 11.08; F, 4.83; S, 8.43. NMR($d_6$-DMSO) δ: 4.16(2H, s), 6.53(1H, d, J=3.3 Hz), 6.99(1H, s), 7.12–7.37 (4H, m), 7.71(1H, d, J=3.3 Hz), 9.30(1H, s), 13.3(1H, brs).

Preparation of a Compound wherein Heteroaryl ($A^1$) is Thienyl (Compound No. I-140)

Example 140

1-[5-(4-Fluorobenzyl)thiophen-2-yl]-3-hydroxy-3-(1H-1,2,4-triazol-3-yl)-propenone (Compound No. I-140)

M.p.: 185–187° C. Recrystallized from ethylacetate. Elemental analysis for $C_{16}H_{12}FN_3O_2S$ 0.3 $H_2O$ Calcd. (%): C, 57.41; H, 3.79; N, 12.55; F, 5.68; S, 9.58. Found. (%): C, 57.58; H, 3.82; N, 12.77; F, 5.49; S, 9.31. NMR($d_6$-DMSO) δ: 4.25(2H, s), 7.04–7.40(6H, m), 7.98(1H, d, J=3.8 Hz), 8.77(1H, brs), 13.8(1H, brs).

Preparation of a Compound wherein Heteroaryl ($A^1$) is Imidazolyl (Compound No. I-141–145)

Example 141–145

1-[1H-(1-Benzyl-2-methoxymethyl)imidazol-4-yl]-3-hydroxy-3-(2H-tetrazol-5-yl)-propenone (Compound No. I-141)

M.p.: 179–181° C. Recrystallized from ethylacetate-isopropylether. Elemental analysis for $C_{16}H_{16}N_6O_3$ Calcd. (%): C, 56.47; H, 4.74; N, 24.69. Found. (%): C, 56.44; H, 4.82; N, 24.71. NMR($d_6$-DMSO) δ: 3.27(3H, s), 4.53(2H, s), 5.34(2H, s), 7.18(1H, s), 7.29–7.41(5H, m), 8.24(1H, s).

3-Hydroxy-1-[1H-(2-methoxymethyl)imidazol-4-yl]-3-(2H-tetrazol-5-yl)-propenone hydrochloride hydrate (Compound No. I-142)

M.p.: 135–140° C. Recrystallized from methanol-ethylacetate. Elemental analysis for $C_9H_{10}N_6O_3$ 1.85 HCl 2.5 $H_2O$ Calcd. (%): C, 29.80; H, 4.68; N, 23.17; Cl, 18.08. Found. (%): C, 30.33; H, 4.82; N, 22.85; Cl, 18.08. NMR($d_6$-DMSO) δ: 3.35(3H, s), 4.60(2H, s), 7.24(1H, s), 8.37(1H, s).

1-(1H-1-Benzylimidazol-4-yl)-3-hydroxy-3-(2H-tetrazol-5-yl)-propenone (Compound No. I-143)

M.p.: 205° C. (decomposition), Recrystallized from ethylacetate-isopropylether. Elemental analysis for $C_{14}H_{12}N_6O_2$ 0.3 $H_2O$ Calcd. (%): C, 55.74; H, 4.21; N, 27.86. Found. (%): C, 55.89; H, 4.37; N, 27.50. NMR($d_6$-DMSO) δ: 5.33(2H, s), 7.14(1H, s), 7.38(5H, m), 8.15(1H, s), 8.26(1H, s).

1-[1H-(1-Benzyl-2-phenoxymethyl)imidazol-4-yl]-3-hydroxy-3-(2H-tetrazol-5-yl)-propenone (Compound No. I-144)

M.p.: 177–178° C. Recrystallized from ethylacetate. Elemental analysis for $C_{21}H_{18}N_6O_3$ Calcd. (%): C, 62.68; H, 4.51; N, 20.88. Found. (%): C, 62.87; H, 4.70; N, 20.60. NMR($d_6$-DMSO) δ: 5.22(2H, s), 5.40(2H, s), 6.95–7.34 (10H, m), 8.31(1H, s).

1-[2-(4-Fluorobenzyl)-1H-imidazol-4-yl]-3-hydroxy-3-(1H-1,2,4-triazol-3-yl)-propenone hydrochloride hydrate (Compound No. I-145)

M.p.: 200–203° C. Recrystallized from ethylacetate-ethanol. Elemental analysis for $C_{15}H_{12}FN_5O_2$ 1.85 HCl $H_2O$ 0.2 $C_4H_8O_2$ Calcd. (%): C, 45.58; H, 4.22; N, 16.82; Cl, 15.75; F, 4.56. Found. (%): C, 45.62; H, 4.10; N, 16.95; Cl, 15.84; F, 4.48. NMR($d_6$-DMSO) δ: 4.40(2H, s), 7.18(1H, s), 7.10–7.20(2H, m), 7.36–7.43(2H, m), 8.40(1H, s), 8.69 (1H, s).

Preparation of a Compound wherein Heteroaryl ($A^1$) is Pyrazolyl (Compound No. I-146–147)

Example 146–147

1-[2H-2-(4-Fluorobenzyl)pyrazol-3-yl]-3-hydroxy-3-(2H-tetrazol-5-yl)-propenone (Compound No. I-146)

M.p.: 195–197° C. Recrystallized from ether. Elemental analysis for $C_{14}H_{11}FN_6O_2$ Calcd. (%): C, 53.50; H, 3.53; N, 26.74; F, 6.04. Found. (%): C, 53.65; H, 3.53; N, 26.71; F, 5.92. NMR($d_6$-DMSO) δ: 5.79(2H, s), 7.12–7.26(6H, m), 7.47(1H, d, J=2.1 Hz), 7.74(1H, d, J=2.1 Hz).

1-[1H-1-(4-Fluorobenzyl)pyrazol-4-yl]-3-hydroxy-3-(1H-1,2,4-triazol-3-yl)-propenone (Compound No. I-147)

M.p.: 203–206° C. Recrystallized from ethylacetate. Elemental analysis for $C_{16}H_{16}FN_5O_2$ Calcd. (%): C, 57.51; H, 3.86; N, 22.35; F, 6.06. Found. (%): C, 57.10; H, 3.89; N, 22.23; F, 5.79. NMR($d_6$-DMSO) δ: 5.39(2H, s), 6.92(1H, s), 7.17–7.41(4H, m), 8.14(1H, s), 8.66(1H, brs), 8.76(1H, s), 14.3(1H, brs).

Preparation of a Compound wherein Heteroaryl ($A^1$) is Pyridyl (Compound No. I-148)

Example 148

1-[6-(4-Fluorobenzyl)pyridin-2-yl]-3-hydroxy-3-(1H-1,2,4-triazol-3-yl)-propenone (Compound No. I-148)

M.p.: 155–159° C. Recrystallized from ethylacetate-ether. Elemental analysis for $C_{17}H_{13}FN_4O_2$ 0.4 $H_2O$ Calcd. (%): C, 61.59; H, 4.20; N, 16.90; F, 5.73. Found. (%): C, 61.86; H, 4.11; N, 16.97; F, 5.45. NMR($d_6$-DMSO) δ: 4.23(2H, s), 7.15(1H, s), 7.00–7.98(7H, m), 8.90(1H, brs).

Preparation of a Compound wherein Heteroaryl ($A^1$) is Thiazolyl (Compound No. I-149)

Example 149

1-[5-(4-Fluorobenzyl)thiazol-2-yl]-3-hydroxy-3-(1H-1,2,4-triazol-3-yl)-propenone (Compound No. I-149)

M.p.: 184–188° C. Recrystallized from ethylacetate-ether. Elemental analysis for $C_{15}H_{11}FN_4O_2S$ 0.75 $H_2O$ 0.1 $C_4H_8O_2$ Calcd. (%): C, 52.46; H, 3.80; N, 15.89; F, 5.39; S, 9.09. Found. (%): C, 52.24; H, 3.34; N, 15.66; F, 5.33; S, 9.03. NMR($d_6$-DMSO) δ: 4.33(2H, s), 7.14–7.40(5H, m), 8.00(1H, s), 8.76(1H, brs), 14.7(1H, brs).

Preparation of a Compound wherein Heteroaryl ($A^1$) is Oxazolyl (Compound No. I-150–152)

Example 150–152

1-[2-(4-Fluorobenzyl)oxazol-5-yl]-3-hydroxy-3-(1H-1,2,4-triazol-3-yl)-propenone (Compound No. I-150)

M.p.: 200–203° C. Recrystallized from ethylacetate. Elemental analysis for $C_{15}H_{11}FN_4O_3$ 0.1 $H_2O$ Calcd. (%): C, 57.00; H, 3.57; N, 17.73; F, 6.01. Found. (%): C, 56.74; H, 3.51; N, 17.66; F, 5.82. NMR($d_6$-DMSO) δ: 4.31(2H, s), 6.96(1H, s), 7.14–7.42(4H, m), 8.20(1H, s), 8.78(1H, brs).

1-[2-(4-Fluorobenzyl)oxazol-5-yl]-3-hydroxy-3-(pyridin-2-yl)-propenone (Compound No. I-151)

M.p.: 108–109° C. Recrystallized from ethylacetate-isopropylether. Elemental analysis for $C_{18}H_{13}FN_2O_3$ Calcd. (%): C, 66.66; H, 4.04; N, 8.64; F, 5.86. Found. (%): C, 66.64; H, 3.96; N, 8.66; F, 5.59. NMR(CDCl$_3$) δ: 4.19(2H, s), 7.02–7.07(2H, m), 7.26–7.34(3H, m), 7.45–7.48(1H, m), 7.80(1H, s), 7.86–7.91(1H, m), 8.12(1H, d, J=7.8 Hz), 8.72(1H, d, J=4.5 Hz).

1-[2-(4-Fluorobenzyl)oxazol-5-yl]-3-hydroxy-3-(pyrimidin-2-yl)-propenone (Compound No. I-152)

M.p.: 97–100° C. Recrystallized from ethylacetate-isopropylether. Elemental analysis for $C_{17}H_{12}FN_3O_3$ 0.4$H_2O$ Calcd. (%): C, 61.41; H, 3.88; N, 12.64; F, 5.71. Found. (%): C, 61.76; H, 3.58; N, 12.21; F, 5.84. NMR($d_6$-DMSO) δ: 4.28(2H, s), 7.15–7.21(3H, m), 7.36–7.40(2H, m), 7.64(1H, brs), 8.11(1H, brs), 8.98–9.02(2H, m).

Preparation of a Compound wherein Heteroaryl ($A^1$) is Isoxazolyl (Compound No. I-153)

Example 153

3-Hydroxy-1-(5-phenylisoxazol-3-yl)-3-(1H-1,2,4-triazol-3-yl)-propenone (Compound No. I-153)

M.p.: 238–240° C. Recrystallized from ethylacetate-ether. Elemental analysis for $C_{14}H_{10}N_4O_3$ 0.2 $H_2O$ Calcd. (%): C, 58.82; H, 3.67; N, 19.60. Found. (%i): C, 58.87; H, 3.58; N, 19.43. NMR($d_6$-DMSO) δ: 7.27(1H, s), 7.51–7.64(4H, m), 7.95–8.02(2H, m), 8.82(1H, brs).

Preparation of a Compound wherein Heteroaryl ($A^1$) is Benzofuryl (Compound No. I-154–157)

Example 154–157

1-(Benzofuran-3-yl)-3-hydroxy-3-(2H-tetrazol-5-yl)-propenone (Compound No. I-154)

M.p.: 201–202° C. Recrystallized from ethylacetate. Elemental analysis for $C_{12}H_8N_4O_3$ Calcd. (%): C, 56.25; H, 3.15; N, 21.87. Found. (%): C, 56.05; H, 3.26; N, 21.63. NMR($d_6$-DMSO) δ: 7.34(1H, s), 7.46–7.50(2H, m), 7.76–7.79(1H, m), 8.16–8.19(1H, m), 9.37(1H, s).

1-(2-Benzylbenzofuran-3-yl)-3-hydroxy-3-(2H-tetrazol-5-yl)-propenone (Compound No. I-155)

M.p.: 181–183° C. Recrystallized from chloroform. Elemental analysis for $C_{19}H_{14}N_4O_3$ 0.25 $H_2O$ Calcd. (%): C, 65.04; H, 4.17; N, 15.97. Found. (%): C, 65.02; H, 3.96; N, 16.10. NMR($d_6$-DMSO) δ: 4.61(2H, s), 7.17(1H, s), 7.26–7.47(7H, m), 7.68–7.70(1H, m), 7.95–7.98(1H, m).

1-[2-(4-Fluorobenzyl)benzofuran-3-yl]-3-hydroxy-3-(2H-tetrazol-5-yl)-propenone (Compound No. I-156)

M.p.: 164–168° C. Recrystallized from ether-hexane Elemental analysis for $C_{19}H_{13}FN_4O_3$ 0.2 $C_4H_{10}O$ Calcd. (%): C, 62.72; H, 3.99; N, 14.78; F, 5.01. Found. (%): C, 62.43; H, 3.74; N, 14.74; F, 4.76. NMR(CDCl$_3$) δ: 4.53(2H, s), 6.98–7.04(2H, m), 7.26(1H, s), 7.34–7.41(4H, m), 7.49–7.52(1H, m), 7.95–7.98(1H, m).

1-[2-(4-Fluorobenzyl)benzofuran-3-yl]-3-hydroxy-3-(1H-1,2,4-triazol-3-yl)-propenone (Compound No. I-157)

M.p.: 122–124° C. Recrystallized from ether-n-hexane. Elemental analysis for $C_{20}H_{14}FN_3O_3$ 0.25 $H_2O$ Calcd. (%): C, 65.30; H, 3.97; N, 11.42; F, 5.16. Found. (%): C, 65.50; H, 3.99; N, 11.24; F, 4.99. NMR(CDCl$_3$) δ: 4.54(2H, s), 6.98–7.04(2H, m), 7.26(1H, s), 7.34–7.41(4H, m), 7.47–7.50(1H, m), 7.96–7.99(1H, m), 8.38(1H, s).

Preparation of a Compound wherein Heteroaryl ($A^1$) is Benzothienyl (Compound No. I-158)

Example 158

1-[2-(4-Fluorobenzyl)benzothiophen-3-yl]-3-hydroxy-3-(1H-1,2,4-triazol-3-yl)-propenone (Compound No. I-158)

M.p.: 190–195° C. Recrystallized from ether. Elemental analysis for $C_{20}H_{14}FN_3O_2S$ Calcd. (%): C, 63.31; H, 3.72;

N, 11.08; F, 5.01; S, 8.45. Found. (%): C, 63.08; H, 3.82; N, 11.28; F, 4.84; S, 8.46. NMR(CDCl$_3$) δ: 4.53(2H, s), 7.01 (2H, t, J=8.7 Hz), 7.11(1H, s), 7.26–7.48(4H, m), 7.75(1H, d, J=7.8 Hz), 8.10(1H, d, J=7.5 Hz), 8.43(1H, brs).

Preparation of a Compound wherein Heteroaryl (A$^1$) is Benzimidazolyl (Compound No. I-159)

Example 159

1-(1H-1-Benzylbenzimidazol-2-yl)-3-hydroxy-3-(2H-tetrazol-5-yl)-propenone (Compound No. I-159)

M.p.: 234° C. (decomposition), Recrystallized from ethylacetate-isopropylether. Elemental analysis for C$_{18}$H$_{14}$N$_6$O$_2$ Calcd. (%): C, 62.42; H, 4.07; N, 24.26. Found. (%): C, 62.45; H, 4.34; N, 23.82. NMR(d$_6$-DMSO) δ: 6.05(2H, s), 7.22–7.98(10H, m).

Preparation of a Compound wherein Heteroaryl (A$^1$) is Quinolinyl (Compound No. I-160–161)

Example 160–161

3-Hydroxy-1-(quinolin-3-yl)-3-(2H-tetrazol-5-yl)-propenone (Compound No. I-160)

M.p.: 232° C. (decomposition). Recrystallized from ether. NMR(d$_6$-DMSO) δ: 7.60(1H, s), 7.73–8.28(4H, m), 9.26 (1H, m), 9.47(1H, m).

1-(2-Benzylquinolin-3-yl)-3-hydroxy-3-(2H-tetrazol-5-yl)-propenone (Compound No. I-161)

M.p.: 167–169° C. (decomposition). Recrystallized from ether. Elemental analysis for C$_{20}$H$_{15}$N$_5$O$_2$ Calcd. (%): C, 67.22; H, 4.23; N, 19.60. Found. (%): C, 66.63; H, 4.55; N, 19.50. NMR(d$_6$-DMSO) δ: 4.57(2H, s), 7.02(1H, s), 7.10–7.21(5H, m), 7.64–8.15(4H, m), 8.82(1H, s).

Preparation of a Compound wherein Heteroaryl (A$^1$) is Indolidinyl (Compound No. I-162)

Example 162

1-[3-(4-Fluorobenzyl)indolidin-1-yl]-3-hydroxy-3-(1H-1,2,4-triazol-3-yl)-propenone (Compound No. I-162)

M.p.: 235–240° C. Recrystallized from ethylacetate. Elemental analysis for C$_{20}$H$_{15}$FN$_4$O$_2$ Calcd. (%): C, 66.29; H, 4.17; N, 15.46: F, 5.24. Found. (%): C, 66.13; H, 4.14; N, 15.24; F, 5.05. NMR(d$_6$-DMSO) δ: 4.31(2H, s), 6.91(1H, s), 7.00–7.40(7H, m), 8.31(1H, d, J=6.6 Hz), 8.37(1H, d, J=9.0 Hz), 8.54(1H, brs).

The following compounds are prepared as the compounds or the present invention.
(1) 1-(5-(4-Chlorophenoxy)furan-2-yl)-3-hydroxy-3-(1H-1,2,4-triazol-3-yl)-propenone
(2) 3-Hydroxy-1-(4-(4-methoxyphenylthio)furan-2-yl)-3-(1H-1,2,4-triazol-3-yl)-propenone
(3) 3-Hydroxy-1-[(5-phenoxymethyl-1-phenylthio)pyrrol-3-yl]-3-(1H-1,2,4-triazol-3-propenone
(4) 3-Hydroxy-1-(5-(4-methylbenzyl)furan-3-yl)-3-(2H-tetrazol-5-yl)-propenone
(5) 4-(5-(4-Acetylbenzyl)furan-3-yl)-2-hydroxy-4-oxo-2-butenoic acid
(6) 1-[(2-Benzenesulfonyl-5-(2-phenylethyl))furan-3-yl]-3-hydroxy-3-(1H-1,2,4-triazol-3-yl)-propenone
(7) 1-[(1-Benzyl-4-carboxy)pyrrol-2-yl]-3-hydroxy-3-(2H-tetrazol-5-yl)-propenone
(8) 1-(4-(4-Chlorobenzenesulfonyl)thiophen-2-yl)-3-hydroxy-3-(2H-tetrazol-5-yl)-propenone
(9) 3-Hydroxy-1-(5-(3-methoxyphenoxy)furan-2-yl)-3-(1H-1,2,4-triazol-3-yl)-propenone
(10) 1-(1-(4-Fluorobenzenesulfonyl)pyrrol-2-yl)-3-hydroxy-3-(2H-tetrazol-5-yl)-propenone
(11) 1-[(3-Benzenesulfonyl-5-methyl)furan-2-yl]-3-hydroxy-3-(1H-1,2,4-triazol-3-yl)-propenone
(12) 1-[(3-Benzenesulfonyl-4-fluoro)furan-2-yl]-3-hydroxy-3-(1H-1,2,4-triazol-3-yl)-propenone
(13) 2-Hydroxy-4-oxo-4-(4-(pyridin-4-ylmethyl)thiophen-3-yl)-2-butenoic acid
(14) 3-Hydroxy-1-(1-(4-methoxybenzyl)pyrrol-3-yl)-3-(1H-1,2,4-triazol-3-yl)-propenone
(15) 3-Hydroxy-1-(4-(4-methylbenzyl)thiophen-2-yl)-3-(1H-1,2,4-triazol-3-yl)-propenone
(16) 2-Hydroxy-4-(4-(4-methoxybenzyl)furan-3-yl)-4-oxo-2-butenoic acid (17) 3-Hydroxy-1-[(5-n-octyl-1-(pyridin-2-ylmethyl))pyrrol-3-yl]-3-(1H-1,2,4-triazol-3-yl)-propenone
(18) 4-(5-(2-Fluorobenzyl)pyrrol-2-yl)-2-hydroxy-4-oxo-2-butenoic acid
(19) 1-[(2-Benzenesulfonyl-4-(2-phenylethyl))furan-3-yl]-3-hydroxy-3-(1H-1,2,4-triazol-3-yl)-propenone
(20) 3-Hydroxy-1-(4-(3-methoxybenzyl)furan-3-yl)-3-(1H-1,2,4-triazol-3-yl)-propenone
(21) 1-[(1-Benzyl-5-n-butyl)pyrrol-3-yl]-3-hydroxy-3-(1H-1,2,4-triazol-3-yl)-propenone
(22) 1-(2H-2-(2-Fluorobenzyl)pyrazol-3-yl)-3-hydroxy-3-(1H-1,2,4-triazol-3-yl)-propenone
(23) 4-(5-(4-Aminobenzyl)furan-3-yl)-2-hydroxy-4-oxo-2-butenoic acid
(24) 4-(4-(4-Aminobenzyl)pyrrol-2-yl)-2-hydroxy-4-oxo-2-butenoic acid
(25) 1-[(1-(4-Acetylbenzyl)-5-ethoxycarbonyl)pyrrol-3-yl]-3-hydroxy-3-(2H-tetrazol-5-yl)-propenone
(26) 3-Hydroxy-1-[(1-(4-methoxybenzyl)-5-phenoxymethyl)pyrrol-3-yl]-3-(2H-tetrazol-5-yl)-propenone
(27) 1-[(1-(4-Aminobenzyl)-5-benzoyl)pyrrol-3-yl]-3-hydroxy-3-(1H-1,2,4-triazol-3-yl)-propenone
(28) 1-(2-(4-Aminobenzyl)thiazol-4-yl)-3-hydroxy-3-(1H-1,2,4-triazol-3-yl)-propenone
(29) 3-Hydroxy-1-[(5-(2-phenylethyl)-2-(pyridin-4-ylmethyl))furan-3-yl]-3-(1H-1,2,4-triazol-3-yl)-propenone
(30) 1-(4-(4-Fluorobenzenesulfonyl)pyrrol-3-yl)-3-hydroxy-3-(2H-tetrazol-5-yl)-propenone
(31) 3-Hydroxy-1-[(5-n-octyl-1-(pyridin-4-ylmethyl))pyrrol-3-yl]-3-(2H-tetrazol-5-yl)-propenone
(32) 1-[(4-Benzoyl-1-(3-fluorobenzyl))pyrrol-2-yl]-3-hydroxy-3-(2H-tetrazol-5-yl)-propenone
(33) 1-[(1-(4-Aminobenzyl)-5-n-butyl)pyrrol-3-yl]-3-hydroxy-3-(2H-tetrazol-5-yl)-propenone
(34) 1-(3-(4-Fluorobenzyl)pyrrol-2-yl)-3-hydroxy-3-(2H-tetrazol-5-yl)-propenone
(35) 1-(1H-1-(3-Fluorobenzyl)pyrazol-4-yl)-3-hydroxy-3-(2H-tetrazol-5-yl)-propenone
(36) 4-(1H-1-(4-Chlorobenzenesulfonyl)pyrazol-4-yl)-2-hydroxy-4-oxo-2-butenoic acid
(37) 4-(2-Benzenesulfonylpyrrol-3-yl)-2-hydroxy-4-oxo-2-butenoic acid
(38) 1-(5-(4-Aminobenzyl)pyrrol-3-yl)-3-hydroxy-3-(1H-1,2,4-triazol-3-yl)-propenone
(39) 1-[(4-Chloro-5-(pyridin-4-ylmethyl))furan-3-yl]-3-hydroxy-3-(1H-1,2,4-triazol-3-yl)-propenone

(40) 1-(3-(4-Fluorobenzyl)thiophen-2-yl)-3-hydroxy-3-(1H-1,2,4-triazol-3-yl)-propenone
(41) 2-Hydroxy-4-(1-(4-methylbenzyl)pyrrol-2-yl)-4-oxo-2-butenoic acid
(42) 1-(5-(4-Chlorobenzenesulfonyl)pyrrol-3-yl)-3-hydroxy-3-(2H-tetrazol-5-yl)-propenone
(43) 1-[(1-(4-Chlorobenzenesulfonyl)-5-ethoxycarbonyl)pyrrol-3-yl]-3-hydroxy-3-(2H)-tetrazol-5-yl)-propenone
(44) 3-Hydroxy-1-[(1-(4-methoxybenzyl)-4-(2-phenylethyl))pyrrol-3-yl]-3-(2H-tetrazol-5-yl)-propenone
(45) 1-[(5-n-Butyl-1-phenylthio)pyrrol-3-yl]-3-hydroxy-3-(2H-tetrazol-5-yl)-propenone
(46) 2-Hydroxy-4-(5-(4-methoxybenzyl)pyrrol-3-yl)-4-oxo-2-butenoic acid
(47) 2-Hydroxy-4-(5-(4-methylbenzyl)furan-3-yl)-4-oxo-2-butenoic acid
(48) 4-(5-(4-Fluorobenzyl)pyrrol-2-yl)-2-hydroxy-4-oxo-2-butenoic acid
(49) 3-Hydroxy-1-[(4-methyl-5-phenyl)furan-2-yl]-3-(1H-1,2,4-triazol-3-yl)-propenone
(50) 3-Hydroxy-1-(4-phenylthiopyrrol-2-yl)-3-(2H-tetrazol-5-yl)-propenone
(51) 4-(4-(4-Fluorobenzenesulfonyl)thiophen-2-yl)-2-hydroxy-4-oxo-2-butenoic acid
(52) 3-Hydroxy-1-[(2-methyl-5-phenyl)furan-2-yl]-3-(1H-1,2,4-triazol-3-yl)-propenone
(53) 1-(2H-5-(4Acetylbenzyl)pyrazol-3-yl)-3-hydroxy-3-(1H-1,2,4-triazol-3-yl)-propenone
(54) 2-Hydroxy-4-oxo-4-(5-(pyridin-4-ylmethyl)furan-2-yl)-2-butenoic acid
(55) 1-(4-(4-Fluorobenzyl)thiophen-2-yl)-3-hydroxy-3-(2H-tetrazol-5-yl)-propenone
(56) 4-(2-(4-Chlorobenzenesulfonyl)thiazol-4-yl)-2-hydroxy-4-oxo-2-butenoic acid
(57) 1-[(1-(4-Aminobenzyl)-5-phenoxymethyl)pyrrol-3-yl]-3-hydroxy-3-(2H-tetrazol-5-yl)-propenone
(58) 1-[(2-Fluoro-5-(pyridin-4-ylmethyl))furan-3-yl]-3-hydroxy-3-(1H-1,2,4-triazol-3-yl)-propenone
(59) 1-(5-(4-Fluorobenzyl)thiophen-3-yl)-3-hydroxy-3-(1H-1,2,4-triazol-3-yl)-propenone
(60) 1-(4-(4-Aminobenzyl)thiophen-3-yl)-3hydroxy-3-(2H-tetrazol-5-yl)-propenone
(61) 1-[(1-Benzyl-4-(2-phenylethyl))pyrrol-3-yl]-3-hydroxy-3-(1H-1,2,4-triazol-3-yl)-propenone
(62) 1-[(1-Benzyl-5-methoxymethyl)pyrrol-3-yl]-3-hydroxy-3-(1H-1,2,4-triazol-3-yl)-propenone
(63) 1-[(1-(4-Chlorobenzenesulfonyl)-5-phenoxymethyl)pyrrol-3-yl]-3-hydroxy-3-(2H)-tetrazol-5-yl)-propenone
(64) 3-Hydroxy-1-(3-(pyridin-2-ylmethyl)pyrrol-2-yl)-3-(2H-tetrazol-5-yl)-propenone
(65) 2-Hydroxy-4-oxo-4-(4-phenylthiofuran-3-yl)-2-butenoic acid
(66) 4-(2H-5-(4-Fluorobenzyl)pyrazol-3-yl)-2-hydroxy-4-oxo-2-butenoic acid
(67) 3-Hydroxy-1-(1H-1-phenylthiopyrazol-4-yl)-3-(1H-1,2,4-triazol-3-yl)-propenone
(68) 3-Hydroxy-1-(3-(pyridin-4-ylmethyl)furan-2-yl)-3-(2H-tetrazol-5-yl)-propenone
(69) 4-(3-(4-Acetylbenzyl)pyrrol-2-yl)-2-hydroxy-4-oxo-2-butenoic acid
(70) 1-[(1-(4-Chlorobenzenesulfonyl)-5-methoxymethyl)pyrrol-3-yl]-3-hydroxy-3-(2H-tetrazol-5-yl)-propenone
(71) 3-Hydroxy-1-(2H-2-(pyridin-2-ylmethyl)pyrazol-4-yl)-3-(1H-1,2,4-triazol-3-yl)-propenone
(72) 2-Hydroxy-4-oxo-4-(4-phenylthiothiazol-2-yl)-2-butenoic acid
(73) 3-Hydroxy-1-(2H-4-(pyridin-4-ylmethyl)pyrazol-3-yl)-3-(1H-1,2,4-triazol-3-yl)-propenone
(74) 1-[(5-Carboxy-1-phenylthio)pyrrol-3-yl]-3-hydroxy-3-(1H-1,2,4-triazol-3-yl)-propenone
(75) 1-[(4-Fluoro-3-phenyl)furan-2-yl]-3-hydroxy-3-(1H-1,2,4-triazol-3-yl)-propenone
(76) 2-Hydroxy-4-oxo-4-(2-(pyridin-2-ylmethyl)thiazol-4-yl)-2-butenoic acid
(77) 3-Hydroxy-1-(3-(4-methylphenylthio)furan-2-yl)-3-(1H-1,2,4-triazol-3-yl)-propenone
(78) 3-Hydroxy-3-(1H-1,2,4-triazol-3-yl)-1-(2-(4-trifluoromethylphenylthio)furan-3-yl)-propenone
(79) 3-Hydroxy-1-(2H-5-(4-methylbenzyl)pyrazol-3-yl)-3-(2H-tetrazol-5-yl)-propenone
(80) 1-[(4-Benzoyl-1-(pyridin-4-ylmethyl))pyrrol-2-yl]-3-hydroxy-3-(1H-1,2,4-triazol-3-yl)-propenone
(81) 2-Hydroxy-4-oxo-4-(5-(pyridin-4-ylmethyl)pyrrol-2-yl)-2-butenoic acid
(82) 1-[(1-(4-Acetylbenzyl)-5-benzoyl)pyrrol-3-yl]-3-hydroxy-3-(2H-tetrazol-5-yl)-propenone
(83) 1-[(5-Fluoro-4-phenyl)furan-2-yl]-3-hydroxy-3-(1H-1,2,4-triazol-3-yl)-propenone
(84) 1-[(5-Benzoyl-1-(3-fluorobenzyl))pyrrol-3-yl]-3-hydroxy-3-(2H-tetrazol-5-yl)-propenone
(85) 1-[(1-(4-Acetylbenzyl)-4-carboxy)pyrrol-2-yl]-3-hydroxy-3-(2H-tetrazol-5-yl)-propenone
(86) 3-Hydroxy-1-(2H-2-(4-methylbenzyl)pyrazol-3-yl)-3-(1H-1,2,4-triazol-3-yl)-propenone
(87) 3-Hydroxy-1-(4-(pyridin-4-ylmethyl)thiazol-2-yl)-3-(1H-1,2,4-triazol-3-yl)-propenone
(88) 1-[(3-Chloro-4-(pyridin-4-ylmethyl))furan-2-yl]-3-hydroxy-3-(1H-1,2,4-triazol-3-yl)-propenone
(89) 1-[(1-(2-Fluorobenzyl)-4-phenoxymethyl)pyrrol-2-yl]-3-hydroxy-3-(2H-tetrazol-5-yl)-propenone
(90) 1-(2-(2-Fluorobenzyl)thiophen-3-yl)-3-hydroxy-3-(1H-1,2,4-triazol-3-yl)-propenone
(91) 1-(2-(2-Fluorobenzyl)thiophen-3-yl)-3-hydroxy-3-(2H-tetrazol-5-yl)-propenone
(92) 4-(2-(4-Fluorobenzyl)furan-3-yl)-2-hydroxy-4-oxo-2-butenoic acid
(93) 3-Hydroxy-1-[(4-n-octyl-1-(pyridin-4-ylmethyl))pyrrol-2-yl]-3-(2H-tetrazol-5-yl)-propenone
(94) 3-Hydroxy-1-(4-(4-methylbenzyl)pyrrol-2-yl)-3-(1H-1,2,4-triazol-3-yl)-propenone
(95) 1-(3-(4-Chlorophenylthio)furan-2-yl)-3-hydroxy-3-(1H-1,2,4-triazol-3-yl)-propenone
(96) 3-Hydroxy-1-(3-(4-methylbenzyl)pyrrol-2-yl)-3-(2H-tetrazol-5-yl)-propenone
(97) 4-(5-(4-Chlorobenzenesulfonyl)pyrrol-3-yl)-2-hydroxy-4-oxo-2-butenoic acid
(98) 1-(2-(4-Fluorobenzenesulfonyl)thiazol-4-yl)-3-hydroxy-3-(2H-tetrazol-5-yl)-propenone
(99) 1-[(4-(4-Fluorobenzyl)-5-methyl)furan-2-yl]-3-hydroxy-3-(1H-1,2,4-triazol-3-yl)-propenone
(100) 1-[(4-Fluoro-2-(pyridin-4-ylmethyl))furan-3-yl]-3-hydroxy-3-(1H-1,2,4-triazol-3-yl)-propenone
(101) 1-(4-(4-Fluorobenzyl)pyrrol-2-yl)-3-hydroxy-3-(2H-tetrazol-5-yl)-propenone
(102) 1-[(1-(4-Acetylbenzyl)-5-n-butyl)pyrrol-3-yl]-3-hydroxy-3-(2H-tetrazol-5-yl)-propenone
(103) 1-(2-Benzenesulfonylthiazol-4-yl)-3-hydroxy-3-(1H-1,2,4-triazol-3-yl)-propenone
(104) 3-Hydroxy-1-[(3-methyl-5-(pyridin-4-ylmethyl))furan-2-yl]-3-(1H-1,2,4-triazol-3-yl)-propenone
(105) 2-Hydroxy-4-oxo-4-(1-phenylthiopyrrol-3-yl)-2-butenoic acid
(106) 3-Hydroxy-1-[(4-methyl-2-(pyridin-4-ylmethyl))furan-3-yl]-3-(1H-1,2,4-triazol-3-yl)-propenone
(107) 1-(5-(4-Chlorobenzenesulfonyl)thiophen-2-yl)-3-hydroxy-3-(1H-1,2,4-triazol-3-yl)-propenone (108) 1-[(4-Fluoro-3-(pyridin-4-ylmethyl))furan-2-yl]-3-hydroxy-3-(1H-1,2,4-triazol-3-yl)-propenone
(109) 1-(3-(4-Chlorobenzenesulfonyl)furan-2-yl)-3-hydroxy-3-(2H-tetrazol-5-yl)-propenone
(110) 1-[(4-Benzenesulfonyl-2-(2-phenylethyl))furan-3-yl]-3-hydroxy-3-(1H-1,2,4-triazol-3-yl)-propenone
(111) 4-(4-(4-Chlorobenzenesulfonyl)furan-2-yl)-2-hydroxy-4-oxo-2-butenoic acid
(112) 1-(3-Benzenesulfonylfuran-2-yl)-3-hydroxy-3-(1H-1,2,4-triazol-3-yl)-propenone
(113) 3-Hydroxy-1-(5-(4-methylphenylthio)furan-3-yl)-3-(1H-1,2,4-triazol-3-yl)-propenone
(114) 1-(5-(4-Fluorobenzyl)thiophen-3-yl)-3-hydroxy-3-(2H-tetrazol-5-yl)-propenone
(115) 3-Hydroxy-1-(1H-1-(4-methoxybenzyl)pyrazol-3-yl)-3-(2H-tetrazol-5-yl)-propenone
(116) 1-(3-(4-Chlorobenzenesulfonyl)pyrrol-2-yl)-3-hydroxy-3-(1H-1,2,4-triazol-3-yl)-propenone
(117) 4-(4-(4-Fluorobenzyl)furan-2-yl)-2-hydroxy-4-oxo-2-butenoic acid
(118) 1-(2-(3-Chlorophenoxy)furan-3-yl)-3-hydroxy-3-(1H-1,2,4-triazol-3-yl)-propenone
(119) 2-Hydroxy-4-oxo-4-(4-phenylthiopyrrol-3-yl)-2-butenoic acid
(120) 3-Hydroxy-1-[(2-(2-phenylethyl)-4-(pyridin-4-ylmethyl))furan-3-yl]-3-(1H-1,2,4-triazol-3-yl)-propenone
(121) 4-(4-(4-Aminobenzyl)furan-2-yl)-2-hydroxy-4-oxo-2-butenoic acid
(122) 4-(2H-2-(4-Aminobenzyl)pyrazol-3-yl)-2-hydroxy-4-oxo-2-butenoic acid
(123) 1-(3-(4-Acetylbenzyl)thiophen-2-yl)-3-hydroxy-3-(2H-tetrazol-5-yl)-propenone
(124) 1-[(1-(4-Acetylbenzyl)-5-carboxy)pyrrol-3-yl]-3-hydroxy-3-(1H-1,2,4-triazol-3-yl)-propenone
(125) 1-[(1-(4-Acetylbenzyl)-4-ethyl)pyrrol-3-yl]-3-hydroxy-3-(1H-1,2,4-triazol-3-yl)-propenone
(126) 1-[(1(4-Fluorobenzyl)-4-methoxymethyl)pyrrol-2-yl]-3-hydroxy-3-(1H-1,2,4-triazol-3-yl)-propenone
(127) 2-Hydroxy-4-oxo-4-(5-(pyridin-4-ylmethyl)furan-3-yl)-2-butenoic acid
(128) 3-Hydroxy-1-(1H-1-(pyridin-2-ylmethyl)pyrazol-4-yl)-3-(1H-1,2,4-triazol-3-yl)-propenone
(129) 1-[(4-Ethyl-1-(4-fluorobenzyl))pyrrol-2-yl]-3-hydroxy-3-(2H-tetrazol-5-yl)-propenone
(130) 1-[(4-Carboxy-1-(2-fluorobenzyl))pyrrol-2-yl]-3-hydroxy-3-(1H-1,2,4-triazol-3-yl)-propenone
(131) 3-Hydroxy-3-(1H-1,2,4-triazol-3-yl)-1-(5-(4-trifluoromethylphenylthio)furan-3-yl)-propenone
(132) 1-(2H-4-(4-Fluorobenzyl)pyrazol-3-yl)-3-hydroxy-3-(1H-1,2,4-triazol-3-yl)-propenone
(133) 1-(1H-1-(2-Fluorobenzyl)pyrazol-3-yl)-3-hydroxy-3-(1H-1,2,4-triazol-3-yl)-propenone
(134) 1-[(1-Benzyl-4-n-propyl)pyrrol-2-yl]-3-hydroxy-3-(2H-tetrazol-5-yl)-propenone
(135) 1-[(1-(4-Fluorobenzyl)-5-methoxymethyl)pyrrol-3-yl]-3-hydroxy-3-(2H-tetrazol-5-yl)-propenone
(136) 4-(4-(3-Fluorobenzyl)furan-2-yl)-2-hydroxy-4-oxo-2-butenoic acid
(137) 1-[(4-Ethyl-1-(4-fluorobenzenesulfonyl))pyrrol-3-yl]-3-hydroxy-3-(2H-tetrazol-5-yl)-propenone
(138) 1-(4-(4-Fluorobenzenesulfonyl)thiazol-2-yl)-3-hydroxy-3-(2H-tetrazol-5-yl)-propenone
(139) 1-(1-(4-Chlorobenzenesulfonyl)pyrrol-3-yl)-3-hydroxy-3-(1H-1,2,4-triazol-3-yl)-propenone
(140) 1-(5-(4-Amino phenylthio)furan-3-yl)-3-hydroxy-3-(1H-1,2,4-triazol-3-yl)-propenone
(141) 1-(1-(4-Aminobenzyl)pyrrol-2-yl)-3-hydroxy-3-(1H-1,2,4-triazol-3-yl)-propenone
(142) 1-(5-(3-Chlorobenzyl)furan-2-yl)-3-hydroxy-3-(1H-1,2,4-triazol-3-yl)-propenone
(143) 4-(3-(4-Aminobenzyl)pyrrol-2-yl)-2-hydroxy-4-oxo-2-butenoic acid
(144) 1-[(4-Benzoyl-1-phenylthio)pyrrol-2-yl]-3-hydroxy-3-(2H-tetrazol-5-yl)-propenone
(145) 4-(5-(4-Aminobenzyl)furan-2-yl)-2-hydroxy-4-oxo-2-butenoic acid
(146) 1-(2H-2-(4-Fluorobenzenesulfonyl)pyrazol-4-yl)-3-hydroxy-3-(1H-1,2,4-triazol-3-yl)-propenone
(147) 3-Hydroxy-1-(4-phenylthiopyrrol-3-yl)-3-(2H-tetrazol-5-yl)-propenone
(148) 2-Hydroxy-4-(4-(4-methoxybenzyl)thiophen-3-yl)-4-oxo-2-butenoic acid
(149) 1-[(1-(4-Acetylbenzyl)-5-n-octyl)pyrrol-3-yl]-3-hydroxy-3-(2H-tetrazol-5-yl)-propenone
(150) 1-(3-(4-Aminobenzyl)pyrrol-2-yl)-3-hydroxy-3-(2H-tetrazol-5-yl)-propenone
(151) 1-(1-(4-Fluorobenzenesulfonyl)pyrrol-2-yl)-3-hydroxy-3-(1H-1,2,4-triazol-3-yl)-propenone
(152) 1-(4-(4-Aminobenzyl)thiophen-2-yl)-3-hydroxy-3-(2H-tetrazol-5-yl)-propenone
(153) 1-[(5-(4-Fluorobenzyl)-4-(2-phenylethyl))furan-2-yl]-3-hydroxy-3-(1H-1,2,4-triazol-3-yl)-propenone
(154) 1-(3-(4-Amino phenylthio)furan-2-yl)-3-hydroxy-3-(1H-1,2,4-triazol-3-yl)-propenone
(155) 1-[(1-(4-Fluorobenzenesulfonyl)-5-n-octyl)pyrrol-3-yl]-3-hydroxy-3-(1H-1,2,4-triazol-3-yl)-propenone
(156) 3-Hydroxy-1-(3-phenylthiofuran-2-yl)-3-(2H-tetrazol-5-yl)-propenone
(157) 2-Hydroxy-4-(5-(4-methylbenzyl)pyrrol-2-yl)-4-oxo-2-butenoic acid
(158) 3-Hydroxy-1-(2H-4-(4-methoxybenzyl)pyrazol-3-yl)-3-(2H-tetrazol-5-yl)-propenone
(159) 4-(2H-5-(3-Fluorobenzyl)pyrazol-3-yl)-2-hydroxy-4-oxo-2-butenoic acid
(160) 1-(5-(4-Fluorobenzenesulfonyl)thiophen-2-yl)-3-hydroxy-3-(1H-1,2,4-triazol-3-yl)-propenone
(161) 1-(4-(4-Aminobenzyl)furan-2-yl)-3-hydroxy-3-(1H-1,2,4-triazol-3-yl)-propenone
(162) 1-[(5-Chloro-4-(4-fluorobenzyl))furan-2-yl]-3-hydroxy-3-(1H-1,2,4-triazol-3-yl)-propenone
(163) 4-(5-(4-Aminobenzyl)thiophen-3-yl)-2-hydroxy-4-oxo-2-butenoic acid
(164) 1-[(1-(3-Fluorobenzyl)-5-n-octyl)pyrrol-3-yl]-3-hydroxy-3-(1H-1,2,4-triazol-3-yl)-propenone
(165) 1-[(5-n-Butyl-1-(pyridin-4-ylmethyl))pyrrol-3-yl]-3-hydroxy-3-(1H-1,2,4-triazol-3-yl)-propenone
(166) 1-(5-(4-Chlorobenzenesulfonyl)furan-3-yl)-3-hydroxy-3-(2H-tetrazol-5-yl)-propenone
(167) 1-(1-(4-Aminobenzyl)pyrrol-3-yl)-3-hydroxy-3-(2H-tetrazol-5-yl)-propenone
(168) 3-Hydroxy-1-[(1-(4-methoxybenzyl)-4-phenoxymethyl)pyrrol-2-yl]-3-(1H-1,2,4,-triazol-3-yl)-propenone
(169) 1-(4-(4-Aminophenoxy)furan-3-yl)-3-hydroxy-3-(1H-1,2,4-triazol-3-yl)-propenone
(170) 3-Hydroxy-1-(4-(pyridin-2-ylmethyl)thiophen-3-yl)-3-(1H-1,2,4-triazol-3-yl)-propenone
(171) 1-[(2-Benzenesulfonyl-5-chloro)furan-3-yl]-3-hydroxy-3-(1H-1,2,4-triazol-3-yl)-propenone
(172) 3-Hydroxy-1-[(1-(4-methoxybenzyl)-4-n-octyl)pyrrol-2-yl]-3-(1H-1,2,4-triazol-3-yl)-propenone
(173) 1-[(4-Benzoyl-1-(4-fluorobenzenesulfonyl))pyrrol-2-yl]-3-hydroxy-3-(1H-1,2,4-triazol-3-yl)-propenone (174) 1-(4-(4-Fluorobenzenesulfonyl)furan-2-yl)-3-hydroxy-3-(2H-tetrazol-5-yl)-propenone
(175) 1-[(1-(3-Fluorobenzyl)-4-methoxymethyl)pyrrol-2-yl]-3-hydroxy-3-(2H-tetrazol-5-yl)-propenone
(176) 1-[(4-Ethoxycarbonyl-1-phenylthio)pyrrol-2-yl]-3-hydroxy-3-(2H-tetrazol-5-yl)-propenone
(177) 1-(1H-1-(4-Acetylbenzyl)pyrazol-4-yl)-3-hydroxy-3-(1H-1,2,4-triazol-3-yl)-propenone
(178) 4-(3-(3-Fluorobenzyl)furan-2-yl)-2-hydroxy-4-oxo-2-butenoic acid
(179) 1-[(1-Benzyl-4-phenoxymethyl)pyrrol-2-yl]-3-hydroxy-3-(1H-1,2,4-triazol-3-yl)-propenone
(180) 1-[(3-Chloro-5-(pyridin-4-ylmethyl))furan-2-yl]-3-hydroxy-3-(1H-1,2,4-triazol-3-yl)-propenone
(181) 1-[(5-Benzoyl-1-benzyl)pyrrol-3-yl]-3-hydroxy-3-(2H-tetrazol-5-yl)-propenone
(182) 1-[(1-(4-Acetylbenzyl)-4-n-propyl)pyrrol-2-yl]-3-hydroxy-3-(1H-1,2,4-triazol-3-yl)-propenone
(183) 1-[(4-Ethoxycarbonyl-1-(4-methylbenzyl))pyrrol-2-yl]-3-hydroxy-3-(2H-tetrazol-5-yl)-propenone
(184) 1-(3-Benzylfuran-2-yl)-3-hydroxy-3-(2H-tetrazol-5-yl)-propenone
(185) 1-(5-(3-Fluorobenzyl)pyrrol-3-yl)-3-hydroxy-3-(2H-tetrazol-5-yl)-propenone
(186) 1-(3-(4-Fluorobenzyl)thiophen-2-yl)-3-hydroxy-3-(2H-tetrazol-5-yl)-propenone
(187) 3-Hydroxy-1-[(4-phenoxymethyl-1-phenylthio)pyrrol-2-yl]-3-(2H-tetrazol-5-yl)-propenone
(188) 1-(4-Benzylfuran-3-yl)-3-hydroxy-3-(2H-tetrazol-5-yl)-propenone
(189) 1-(2H-4-(3-Fluorobenzyl)pyrazol-3-yl)-3-hydroxy-3-(1H-1,2,4-triazol-3-yl)-propenone
(190) 1-(4-(4-Chlorobenzenesulfonyl)thiazol-2-yl)-3-hydroxy-3-(2H-tetrazol-5-yl)-propenone
(191) 4-(5-Benzylfuran-2-yl)-2-hydroxy-4-oxo-2-butenoic acid
(192) 3-Hydroxy-1-(1-(pyridin-2-ylmethyl)pyrrol-2-yl)-3-(1H-1,2,4-triazol-3-yl)-propenone
(193) 1-[(5-n-Butyl-1-(pyridin-2-ylmethyl))pyrrol-3-yl]-3-hydroxy-3-(1H-1,2,4-triazol-3-yl)-propenone
(194) 1-[(1-(4-Fluorobenzenesulfonyl)-5-phenoxymethyl)pyrrol-3-yl]-3-hydroxy-3-(1H-1,2,4-triazol-3-yl)-propenone
(195) 1-[(4-Benzoyl-1-(4-methoxybenzyl))pyrrol-2-yl]-3-hydroxy-3-(1H-1,2,4-triazol-3-yl)-propenone
(196) 1-(3-(2-Fluorobenzyl)furan-2-yl)-3-hydroxy-3-(1H-1,2,4-triazol-3-yl)-propenone
(197) 2-Hydroxy-4-oxo-4-(2H-2-(pyridin-4-ylmethyl)pyrazol-3-yl)-2-butenoic acid
(198) 3-Hydroxy-1-(2-(pyridin-4-ylmethyl)furan-3-yl)-3-(2H-tetrazol-5-yl)-propenone
(199) 1-[(1-(2-Fluorobenzyl)-4-methoxymethyl)pyrrol-2-yl]-3-hydroxy-3-(1H-1,2,4-triazol-3-yl)-propenone
(200) 4-(2H-4-(3-Fluorobenzyl)pyrazol-3-yl)-2-hydroxy-4-oxo-2-butenoic acid
(201) 1-(4-(4-Fluorobenzyl)furan-2-yl)-3-hydroxy-3-(2H-tetrazol-5-yl)-propenone
(202) 3-Hydroxy-1-[(2-phenyl-5-(2-phenylethyl))furan-3-yl]-3-(1H-1,2,4-triazol-3-yl)-propenone
(203) 1-(5-(2-Fluorobenzyl)thiophen-2-yl)-3-hydroxy-3-(1H-1,2,4-triazol-3-yl)-propenone
(204) 4-(4-Benzenesulfonylthiazol-2-yl)-2-hydroxy-4-oxo-2-butenoic acid
(205) 2-Hydroxy-4-oxo-4-(2-(pyridin-4-ylmethyl)thiazol-4-yl)-2-butenoic acid
(206) 2-Hydroxy-4-oxo-4-(5-(pyridin-2-ylmethyl)thiophen-3-yl)-2-butenoic acid
(207) 1-[(4-Chloro-5-(pyridin-4-ylmethyl))furan-2-yl]-3-hydroxy-3-(1H-1,2,4-triazol-3-yl)-propenone
(208) 1-[(4-Ethoxycarbonyl-1-(4-fluorobenzenesulfonyl))pyrrol-2-yl]-3-hydroxy-3-(1H-1,2,4-triazol-3-yl)-propenone
(209) 4-(5-Benzenesulfonylthiophen-3-yl)-2-hydroxy-4-oxo-2-butenoic acid
(210) 4-(1H-1-Benzylpyrazol-3-yl)-2-hydroxy-4-oxo-2-butenoic acid
(211) 4-(3-Benzenesulfonylpyrrol-2-yl)-2-hydroxy-4-oxo-2-butenoic acid
(212) 4-(2-Benzylthiophen-3-yl)-2-hydroxy-4-oxo-2-butenoic acid
(213) 3-Hydroxy-1-(5-(3-methoxyphenoxy)furan-3-yl)-3-(1H-1,2,4-triazol-3-yl)-propenone
(214) 3-Hydroxy-3-(1H-1,2,4-triazol-3-yl)-1-(5-(4-trifluoromethylphenoxy)furan-2-yl)-propenone
(215) 4-(4-(4-Fluorobenzyl)thiophen-2-yl)-2-hydroxy-4-oxo-2-butenoic acid
(216) 1-[(4-Carboxy-1-(3-fluorobenzyl))pyrrol-2-yl]-3-hydroxy-3-(2H-tetrazol-5-yl)-propenone
(217) 3-Hydroxy-1-[(5-methyl-4-phenyl)furan-3-yl]-3-(1H-1,2,4-triazol-3-yl)-propenone
(218) 4-(5-(4-Aminobenzyl)pyrrol-3-yl)-2-hydroxy-4-oxo-2-butenoic acid
(219) 1-(3-Benzenesulfonylthiophen-2-yl)-3-hydroxy-3-(2H-tetrazol-5-yl)-propenone
(220) 4-(2-(4-Fluorobenzyl)pyrrol-3-yl)-2-hydroxy-4-oxo-2-butenoic acid
(221) 1-(5-(4-Aminobenzyl)thiophen-3-yl)-3-hydroxy-3-(1H-1,2,4-triazol-3-yl)-propenone
(222) 3-Hydroxy-1-(2-(pyridin-4-ylmethyl)pyrrol-3-yl)-3-(2H-tetrazol-5-yl)-propenone
(223) 3-Hydroxy-1-(5-(pyridin-4-ylmethyl)furan-3-yl)-3-(1H-1,2,4-triazol-3-yl)-propenone
(224) 1-(2-(4-Acetylbenzyl)thiophen-3-yl)-3-hydroxy-3-(2H-tetrazol-5-yl)-propenone
(225) 1-(2H-2-Benzenesulfonylpyrazol-3-yl)-3-hydroxy-3-(1H-1,2,4-triazol-3-yl)-propenone
(226) 3-Hydroxy-1-(3-phenoxyfuran-2-yl)-3-(1H-1,2,4-triazol-3-yl)-propenone
(227) 3-Hydroxy-1-[(5-phenoxymethyl-1-(pyridin-4-ylmethyl))pyrrol-3-yl]-3-(1H-1,2,4-triazol-3-yl)-propenone
(228) 3-Hydroxy-1-(4-phenoxyfuran-3-yl)-3-(1H-1,2,4-triazol-3-yl)-propenone
(229) 3-Hydroxy-1-(2H-2-phenylthiopyrazol-3-yl)-3-(1H-1,2,4-triazol-3-yl)-propenone
(230) 2-Hydroxy-4-oxo-4-(2H-5-phenylthiopyrazol-3-yl)-2-butenoic acid
(231) 1-(2H-5-(3-Fluorobenzyl)pyrazol-3-yl)-3-hydroxy-3-(1H-1,2,4-triazol-3-yl)-propenone
(232) 2-Hydroxy-4-oxo-4-(4-(pyridin-4-ylmethyl)furan-2-yl)-2-butenoic acid
(233) 4-(2H-2-Benzylpyrazol-4-yl)-2-hydroxy-4-oxo-2-butenoic acid
(234) 1-(2H-5-(2-Fluorobenzyl)pyrazol-3-yl)-3-hydroxy-3-(1H-1,2,4-triazol-3-yl)-propenone
(235) 1-(4-Benzenesulfonylpyrrol-2-yl)-3-hydroxy-3-(2H-tetrazol-5-yl)-propenone
(236) 1-[(1-(4-Acetylbenzyl)-4-(2-phenylethyl))pyrrol-2-yl]-3-hydroxy-3(1H-1,2,4-triazol-3-yl)-propenone
(237) 1-[(4-Carboxy-1-(3-fluorobenzyl))pyrrol-2-yl]-3-hydroxy-3-(1H-1,2,4-triazol-3-yl)-propenone
(238) 1-[(1-Benzyl-4-methoxymethyl)pyrrol-2-yl]-3-hydroxy-3-(2H-tetrazol-5-yl)-propenone
(239) 1-[(1-(4-Chlorobenzenesulfonyl)-5-phenoxymethyl)pyrrol-3-yl]-3-hydroxy-3-(1H-1,2,4-triazol-3-yl)-propenone (240) 1-[(4-Fluoro-3-(4-fluorobenzyl))furan-2-yl]-3-hydroxy-3-(1H-1,2,4-triazol-3-yl)-propenone
(241) 4-(4-(4-Fluorobenzyl)thiazol-2-yl)-2-hydroxy-4-oxo-2-butenoic acid
(242) 3-Hydroxy-1-(5-(pyridin-4-ylmethyl)furan-2-yl)-3-(2H-tetrazol-5-yl)-propenone
(243) 3-Hydroxy-1-[(2-(2-phenylethyl)-5-(pyridin-4-ylmethyl))furan-3-yl]-3-(1H-1,2,4-triazol-3-yl)-propenone
(244) 1-(2-(4-Fluorobenzyl)thiazol-4-yl)-3-hydroxy-3-(2H-tetrazol-5-yl)-propenone
(245) 1-[(5-Carboxy-1-(pyridin-2-ylmethyl))pyrrol-3-yl]-3-hydroxy-3-(2H-tetrazol-5-yl)-propenone
(246) 3-Hydroxy-1-(2-(pyridin-2-ylmethyl)thiophen-3-yl)-3-(2H-tetrazol-5-yl)-propenone
(247) 2-Hydroxy-4-oxo-4-(2H-4-(pyridin-2-ylmethyl)pyrazol-3-yl)-2-butenoic acid
(248) 1-[(5-Carboxy-1-(4-fluorobenzyl))pyrrol-3-yl]-3-hydroxy-3-(1H-1,2,4-triazol-3-yl)-propenone
(249) 3-Hydroxy-1-(4-(pyridin-2-ylmethyl)thiophen-2-yl)-3-(2H-tetrazol-5-yl)-propenone
(250) 3-Hydroxy-1-(4-phenylthiofuran-2-yl)-3-(1H-1,2,4-triazol-3-yl)-propenone
(251) 3-Hydroxy-1-(5-(4-methoxybenzyl)furan-3-yl)-3-(1H-1,2,4-triazol-3-yl)-propenone
(252) 1-(2-(4-Aminophenoxy)furan-3-yl)-3-hydroxy-3-(1H-1,2,4-triazol-3-yl)-propenone
(253) 3-Hydroxy-1-(1H-1-phenylthiopyrazol-4-yl)-3-(2H-tetrazol-5-yl)-propenone
(254) 3-Hydroxy-3-(1H-1,2,4-triazol-3-yl)-1-(4-(2-trifluoromethylbenzyl)furan-2-yl)-propenone
(255) 3-Hydroxy-3-(1H-1,2,4-triazol-3-yl)-1-(4-(2-trifluoromethylbenzyl)furan-3-yl)-propenone
(256) 4-(4-(3-Fluorobenzyl)pyrrol-2-yl)-2-hydroxy-4-oxo-2-butenoic acid
(257) 1-[(1-(4-Aminobenzyl)-5-n-propyl)pyrrol-3-yl]-3-hydroxy-3-(2H-tetrazol-5-yl)-propenone
(258) 1-(4-Benzylfuran-2-yl)-3-hydroxy-3-(1H-1,2,4-triazol-3-yl)-propenone
(259) 1-(2-Benzenesulfonylfuran-3-yl)-3-hydroxy-3-(2H-tetrazol-5-yl)-propenone
(260) 3-Hydroxy-1-(5-(pyridin-2-ylmethyl)furan-2-yl)-3-(2H-tetrazol-5-yl)-propenone
(261) 3-Hydroxy-1-(4-(pyridin-4-ylmethyl)thiophen-3-yl)-3-(2H-tetrazol-5-yl)-propenone
(262) 3-Hydroxy-1-(5-(4-methylbenzyl)thiophen-3-yl)-3-(2H-tetrazol-5-yl)-propenone
(263) 1-(2H-2-Benzylpyrazol-4-yl)-3-hydroxy-3-(2H-tetrazol-5-yl)-propenone
(264) 1-[(5-n-Butyl-1-(4-fluorobenzyl))pyrrol-3-yl]-3-hydroxy-3-(1H-1,2,4-triazol-3-yl)-propenone
(265) 1-(5-Benzylthiophen-3-yl)-3-hydroxy-3-(2H-tetrazol-5-yl)-propenone
(266) 3-Hydroxy-1-[(4-n-octyl-1-phenylthio)pyrrol-2-yl]-3-(2H-tetrazol-5-yl)-propenone
(267) 1-(4-(4-Chlorobenzenesulfonyl)furan-2-yl)-3-hydroxy-3-(1H-1,2,4-triazol-3-yl)-propenone
(268) 1-(5-(4-Aminobenzyl)thiophen-2-yl)-3-hydroxy-3-(2H-tetrazol-5-yl)-propenone
(269) 1-[(4-Ethyl-1-(pyridin-4-ylmethyl))pyrrol-2-yl]-3-hydroxy-3-(1H-1,2,4-triazol-3-yl)-propenone
(270) 1-(4-(2-Fluorobenzyl)pyrrol-3-yl)-3-hydroxy-3-(1H-1,2,4-triazol-3-yl)-propenone
(271) 3-Hydroxy-1-[(1-(4-methoxybenzyl)-5-methoxymethyl)pyrrol-3-yl]-3-(1H-1,2,4-triazol-3-yl)-propenone
(272) 3-Hydroxy-1-[(5-methyl-4-(pyridin-4-ylmethyl))furan-3-yl]-3-(1H-1,2,4-triazol-3-yl)-propenone
(273) 3-Hydroxy-1-(2H-5-(4-methoxybenzyl)pyrazol-3-yl)-3-(2H-tetrazol-5-yl)-propenone
(274) 3-Hydroxy-1-(4-(4-methoxyphenylthio)furan-3-yl)-3-(1H-1,2,4-triazol-3-yl)-propenone
(275) 1-(3-Benzylpyrrol-2-yl)-3-hydroxy-3-(1H-1,2,4-triazol-3-yl)-propenone
(276) 1-[(1-(4-Aminobenzyl)-4-ethyl)pyrrol-3-yl]-3-hydroxy-3-(2H-tetrazol-5-yl)-propenone
(277) 3-Hydroxy-3-(1H-1,2,4-triazol-3-yl)-1-(2-(3-trifluoromethylbenzyl)furan-3-yl)-propenone
(278) 1-(2H-5-(4-Fluorobenzenesulfonyl)pyrazol-3-yl)-3-hydroxy-3-(1H-1,2,4-triazol-3-yl)-propenone
(279) 3-Hydroxy-1-(4-(pyridin-4-ylmethyl)thiazol-2-yl)-3-(2H-tetrazol-5-yl)-propenone
(280) 2-Hydroxy-4-(4-(4-methylbenzyl)furan-3-yl)-4-oxo-2-butenoic acid
(281) 1-(3-(3-Fluorobenzyl)thiophen-2-yl)-3-hydroxy-3-(2H-tetrazol-5-yl)-propenone
(282) 4-(1-(2-Fluorobenzyl)pyrrol-3-yl)-2-hydroxy-4-oxo-2-butenoic acid
(283) 4-(2-(3-Fluorobenzyl)furan-3-yl)-2-hydroxy-4-oxo-2-butenoic acid
(284) 1-(1-(4-Acetylbenzyl)pyrrol-3-yl)-3-hydroxy-3-(2H-tetrazol-5-yl)-propenone
(285) 4-(5-(3-Fluorobenzyl)thiophen-2-yl)-2-hydroxy-4-oxo-2-butenoic acid
(286) 3-Hydroxy-3-(1H-1,2,4-triazol-3-yl)-1-(5-(3-trifluoromethylphenylthio)furan-2-yl)-propenone
(287) 3-Hydroxy-3-(1H-1,2,4-triazol-3-yl)-1-(4-(3-trifluoromethylphenoxy)furan-2-yl)-propenone
(288) 3-Hydroxy-1-(4-(4-methylbenzyl)thiazol-2-yl)-3-(2H-tetrazol-5-yl)-propenone
(289) 1-[(2-(2-Fluorobenzyl)-5-n-propyl)pyrrol-3-yl]-3-hydroxy-3-(1H-1,2,4-triazol-3-yl)-propenone
(290) 3-Hydroxy-1-[(1-phenylthio-4-n-propyl)pyrrol-2-yl]-3-(2H-tetrazol-5-yl)-propenone
(291) 1-[(5-Benzenesulfonyl-2-chloro)furan-3-yl]-3-hydroxy-3-(1H-1,2,4-triazol-3-yl)-propenone
(292) 2-Hydroxy-4-(1H-1-(4-methylbenzyl)pyrazol-3-yl)-4-oxo-2-butenoic acid
(293) 3-Hydroxy-1-(5-(pyridin-2-ylmethyl)thiophen-3-yl)-3-(2H-tetrazol-5-yl)-propenone
(294) 1-[(1-Benzenesulfonyl-5-carboxy)pyrrol-3-yl]-3-hydroxy-3-(1H-1,2,4-triazol-3-yl)-propenone
(295) 3-Hydroxy-1-(4-(4-methoxybenzyl)pyrrol-2-yl)-3-(1H-1,2,4-triazol-3-yl)-propenone
(296) 1-(2H-5-Benzenesulfonylpyrazol-3-yl)-3-hydroxy-3-(1H-1,2,4-triazol-3-yl)-propenone
(297) 1-(5-(2-Fluorobenzyl)furan-2-yl)-3-hydroxy-3-(2H-tetrazol-5-yl)-propenone
(298) 3-Hydroxy-1-(4-(3-methoxyphenoxy)furan-3-yl)-3-(1H-1,2,4-triazol-3-yl)-propenone
(299) 1-[(1-(3-Fluorobenzyl)-5-methoxymethyl)pyrrol-3-yl]-3-hydroxy-3-(1H-1,2,4-triazol-3-yl)-propenone
(300) 3-Hydroxy-3-(1H-1,2,4-triazol-3-yl)-1-(4-(3-trifluoromethylbenzyl)furan-3-yl)-propenone
(301) 2-Hydroxy-4-oxo-4-(5-phenylthiothiophen-2-yl)-2-butenoic acid
(302) 1-(1H-1-Benzylpyrazol-3-yl)-3-hydroxy-3-(2H-tetrazol-5-yl)-propenone
(303) 4-(1H-1-Benzenesulfonylpyrazol-4-yl)-2-hydroxy-4-oxo-2-butenoic acid
(304) 3-Hydroxy-1-[(4-methoxymethyl-1-phenylthio)pyrrol-2-yl]-3-(1H-1,2,4-triazol-3-yl)-propenone
(305) 1-[(5-(4-Fluorobenzyl)-3-(2-phenylethyl))furan-2-yl]-3-hydroxy-3-(1H-1,2,4-triazol-3-yl)-propenone
(306) 1-[(4-Benzenesulfonyl-5-methyl)furan-3-yl]-3-hydroxy-3-(1H-1,2,4-triazol-3-yl)-propenone (307) 3-Hydroxy-1-[(5-n-propyl-1-(pyridin-4-ylmethyl))pyrrol-3-yl]-3-(2H-tetrazol-5-yl)-propenone
(308) 1-(3-(3-Fluorobenzyl)furan-2-yl)-3-hydroxy-3-(2H-tetrazol-5-yl)-propenone
(309) 2-Hydroxy-4-(4-(4-methylbenzyl)thiazol-2-yl)-4-oxo-2-butenoic acid
(310) 1-[(1-(3-Fluorobenzyl)-4-(2-phenylethyl))pyrrol-2-yl]-3-hydroxy-3-(2H-tetrazol-5-yl)-propenone
(311) 3-Hydroxy-1-(5-phenylthiofuran-3-yl)-3-(2H-tetrazol-5-yl)-propenone
(312) 1-[(4-Benzoyl-1-(4-chlorobenzenesulfonyl))pyrrol-2-yl]-3-hydroxy-3-(2H-tetrazol-5-yl)-propenone
(313) 1-(5-Benzenesulfonylpyrrol-2-yl)-3-hydroxy-3-(2H-tetrazol-5-yl)-propenone
(314) 1-(5-(4-Aminobenzyl)furan-2-yl)-3-hydroxy-3-(1H-1,2,4-triazol-3-yl)-propenone
(315) 1-[(1-(4-Fluorobenzyl)-4-(2-phenylethyl))pyrrol-3-yl]-3-hydroxy-3-(2H-tetrazol-5-yl)-propenone
(316) 1-(3-(2-fluorobenzyl)thiophen-2-yl)-3-hydroxy-3-(2H-tetrazol-5-yl)-propenone
(317) 3-Hydroxy-1-(2-(4-methylbenzyl)furan-3-yl)-3-(1H-1,2,4-triazol-3-yl)-propenone
(318) 1-(5-(3-Fluorobenzyl)furan-3-yl)-3-hydroxy-3-(1H-1,2,4-triazol-3-yl)-propenone
(319) 1-(4-(4-Aminobenzyl)pyrrol-3-yl)-3-hydroxy-3-(1H-1,2,4-triazol-3-yl)-propenone
(320) 3-Hydroxy-1-(2H-2-(pyridin-4-ylmethyl)pyrazol-3-yl)-3-(2H-tetrazol-5-yl)-propenone
(321) 3-Hydroxy-1-(4-(4-methoxybenzyl)thiophen-2-yl)-3-(2H-tetrazol-5-yl)-propenone
(322) 1-(5-(4-Chlorobenzyl)furan-3-yl)-3-hydroxy-3-(1H-1,2,4-triazol-3-yl)-propenone
(323) 1-(4-(2-Fluorobenzyl)thiophen-2-yl)-3-hydroxy-3-(2H-tetrazol-5-yl)-propenone
(324) 3-Hydroxy-3-(1H-1,2,4-triazol-3-yl)-1-(3-(3-trifluoromethylphenoxy)furan-2-yl)-propenone
(325) 1-(4-Benzenesulfonylfuran-2-yl)-3-hydroxy-3-(2H-tetrazol-5-yl)-propenone
(326) 3-Hydroxy-1-[(5-n-octyl-1-(pyridin-2-ylmethyl))pyrrol-3-yl]-3-(2H-tetrazol-5-yl)-propenone
(327) 4-(2H-2-(4-aminobenzyl)pyrazol-4-yl)-2-hydroxy-4-oxo-2-butenoic acid
(328) 1-(5-(4-Chlorobenzenesulfonyl)furan-2-yl)-3-hydroxy-3-(1H-1,2,4-triazol-3-yl)-propenone
(329) 1-(2-Benzylthiazol-4-yl)-3-hydroxy-3-(2H-tetrazol-5-yl)-propenone
(330) 3-Hydroxy-1-(5-(3-methoxyphenylthio)furan-3-yl)-3-(1H-1,2,4-triazol-3-yl)-propenone
(331) 1-(2H-5-(2-fluorobenzyl)pyrazol-3-yl)-3-hydroxy-3-(2H-tetrazol-5-yl)-propenone
(332) 1-(5-(4-Amino phenylthio)furan-2-yl)-3-hydroxy-3-(1H-1,2,4-triazol-3-yl)-propenone
(333) 1-(5-Benzenesulfonylthiophen-2-yl)-3-hydroxy-3-(2H-tetrazol-5-yl)-propenone
(334) 1-(2-(4-Chlorobenzenesulfonyl)furan-3-yl)-3-hydroxy-3-(2H-tetrazol-5-yl)-propenone
(335) 3-Hydroxy-1-[(5-phenyl-2-(2-phenylethyl))furan-3-yl]-3-(1H-1,2,4-triazol-3-yl)-propenone
(336) 3-Hydroxy-1-(1-phenylthiopyrrol-2-yl)-3-(2H-tetrazol-5-yl)-propenone
(337) 1-[(1-(4-Chlorobenzenesulfonyl)-4-(2-phenylethyl))pyrrol-3-yl]-3-hydroxy-3-(2H-tetrazol-5-yl)-propenone
(338) 1-(2H-2-(4-Acetylbenzyl)pyrazol-4-yl)-3-hydroxy-3-(2H-tetrazol-5-yl)-propenone
(339) 3-Hydroxy-1-[(3-methyl-5-phenyl)furan-2-yl]-3-(1H-1,2,4-triazol-3-yl)-propenone
(340) 3-Hydroxy-1-(4-(pyridin-4-ylmethyl)thiophen-3-yl)-3-(1H-1,2,4-triazol-3-yl)-propenone
(341) 1-[(5-Carboxy-1-(pyridin-4-ylmethyl))pyrrol-3-yl]-3-hydroxy-3-(1H-1,2,4-triazol-3-yl)-propenone
(342) 1-[(5-Benzenesulfonyl-4-(2-phenylethyl))furan-2-yl]-3-hydroxy-3-(1H-1,2,4-triazol-3-yl)-propenone
(343) 1-(2-Benzenesulfonylthiophen-3-yl)-3-hydroxy-3-(1H-1,2,4-triazol-3-yl)-propenone
(344) 1-(4-(3-Fluorobenzyl)thiophen-2-yl)-3-hydroxy-3-(2-tetrazol-5-yl)-propenone
(345) 1-[(1-(2-Fluorobenzyl)-4-phenoxymethyl)pyrrol-2-yl]-3-hydroxy-3-(1H-1,2,4-triazol-3-yl)-propenone
(346) 1-[(1-(4-Acetylbenzyl)-4-benzoyl)pyrrol-2-yl]-3-hydroxy-3-(1H-1,2,4-triazol-3-yl)-propenone
(347) 1-(5-(4-Aminobenzyl)pyrrol-3-yl)-3-hydroxy-3-(2H-tetrazol-5-yl)-propenone
(348) 3-Hydroxy-3-(1H-1,2,4-triazol-3-yl)-1-(2-(4-trifluoromethylphenoxy)furan-3-yl)-propenone
(349) 3-Hydroxy-1-(1H-1-(pyridin-2-ylmethyl)pyrazol-3-yl)-3-(1H-1,2,4-triazol-3-yl)-propenone
(350) 1-[(1-(4-Aminobenzyl)-5-n-propyl)pyrrol-3-yl]-3-hydroxy-3-(1H-1,2,4-triazol-3-yl)-propenone
(351) 4-(3-(4-Aminobenzyl)thiophen-2-yl)-2-hydroxy-4-oxo-2-butenoic acid
(352) 3-Hydroxy-3-(1H-1,2,4-triazol-3-yl)-1-(2-(3-trifluoromethylphenoxy)furan-3-yl)-propenone
(353) 2-Hydroxy-4-oxo-4-(4-phenylthiopyrrol-2-yl)-2-butenoic acid
(354) 3-Hydroxy-1-(4-(pyridin-2-ylmethyl)thiophen-3-yl)-3-(2H-tetrazol-5-yl)-propenone
(355) 2-Hydroxy-4-oxo-4-(2H-4-(pyridin-4-ylmethyl)pyrazol-3-yl)-2-butenoic acid
(356) 2-Hydroxy-4-(4-(4-methylbenzyl)pyrrol-2-yl)-4-oxo-2-butenoic acid
(357) 4-(1H-1-(4-Acetylbenzyl)pyrazol-3-yl)-2-hydroxy-4-oxo-2-butenoic acid
(358) 1-[(1-Benzenesulfonyl-5-benzoyl)pyrrol-3-yl]-3-hydroxy-3-(2H-tetrazol-5-yl)-propenone
(359) 1-[(1-(4-Fluorobenzyl)-4-n-propyl)pyrrol-2-yl]-3-hydroxy-3-(2H-tetrazol-5-yl)-propenone
(360) 4-(2H-4-benzenesulfonylpyrazol-3-yl)-2-hydroxy-4-oxo-2-butenoic acid
(361) 3-Hydroxy-1-[(1-(4-methoxybenzyl)-5-n-octyl)pyrrol-3-yl]-3-(1H-1,2,4triazol-3-yl)-propenone
(362) 1-(4-Benzylthiazol-2-yl)-3-hydroxy-3-(2H-tetrazol-5-yl)-propenone
(363) 1-(2H-2-(4-Acetylbenzyl)pyrazol-3-yl)-3-hydroxy-3-(1H-1,2,4-triazol-3-yl)-propenone
(364) 1-(3-Benzenesulfonylpyrrol-2-yl)-3-hydroxy-3-(1H-1,2,4-triazol-3-yl)-propenone
(365) 1-[(4-Carboxy-1-(4-methoxybenzyl))pyrrol-2-yl]-3-hydroxy-3-(2H-tetrazol-5-yl)-propenone
(366) 4-(4-Benzylpyrrol-3-yl)-2-hydroxy-4-oxo-2-butenoic acid
(367) 3-Hydroxy-3-(1H-1,2,4-triazol-3-yl)-1-(5-(4-trifluoromethylphenylthio)furan-2-yl)-propenone
(368) 1-[(1-(4-Aminobenzyl)-4-benzoyl)pyrrol-2-yl]-3-hydroxy-3-(1H-1,2,4-triazol-3-yl)-propenone
(369) 1-[(5-(4-Fluorobenzyl)-4-methyl)furan-3-yl]-3-hydroxy-3-(1H-1,2,4-triazol-3-yl)-propenone
(370) 3-Hydroxy-1-[(1-(4-methoxybenzyl)-4-n-propyl)pyrrol-2-yl]-3-(1H-1,2,4-triazol-3-yl)-propenone
(371) 1-(1-(4-fluorobenzyl)pyrrol-3-yl)-3-hydroxy-3-(1H-1,2,4-triazol-3-yl)-propenone
(372) 1-[(1-(3-Fluorobenzyl)-4-n-propyl)pyrrol-2-yl]-3-hydroxy-3-(1H-1,2,4-triazol-3-yl)-propenone
(373) 1-(5-(3-Fluorophenyl)furan-3-yl)-3-hydroxy-3-(1H-1,2,4-triazol-3-yl)-propenone
(374) 1-[(1-Benzyl-4-methoxymethyl)pyrrol-2-yl]-3-hydroxy-3-(1H-1,2,4-triazol-3-yl)-propenone (375) 3-Hydroxy-1-(1-(4-methylbenzyl)pyrrol-3-yl)-3-(1H-1,2,4-triazol-3-yl)-propenone
(376) 1-(5-Benzylthiophen-2-yl)-3-hydroxy-3-(2H-tetrazol-5-yl)-propenone
(377) 1-[(4-Benzoyl-1-(4-methylbenzyl))pyrrol-2-yl]-3-hydroxy-3-(2H-tetrazol-5-yl)-propenone
(378) 1-[(1-(4-Chlorobenzenesulfonyl)-4-(2-phenylethyl))pyrrol-2-yl]-3-hydroxy-3-(1H-1,2,4-triazol-3-yl)-propenone
(379) 2-Hydroxy-4-oxo-4-(2H-5-(pyridin-4-ylmethyl)pyrazol-3-yl)-2-butenoic acid
(380) 4-(2-(2-fluorobenzyl)thiophen-3-yl)-2-hydroxy-4-oxo-2-butenoic acid
(381) 2-Hydroxy-4-oxo-4-(5-(pyridin-2-ylmethyl)pyrrol-2-yl)-2-butenoic acid
(382) 1-(2-(4-Fluorobenzyl)thiophen-3-yl)-3-hydroxy-3-(1H-1,2,4-triazol-3-yl)-propenone
(383) 1-[(1-(4-Acetylbenzyl)-4-n-propyl)pyrrol-2-yl]-3-hydroxy-3-(2H-tetrazol-5-yl)-propenone
(384) 2-Hydroxy-4-oxo-4-(1-(pyridin-4-ylmethyl)pyrrol-3-yl)-2-butenoic acid
(385) 2-Hydroxy-4-oxo-4-(1H-1-(pyridin-4-ylmethyl)pyrazol-3-yl)-2-butenoic acid
(386) 1-[(5-Ethoxycarbonyl-1-(4-methoxybenzyl))pyrrol-3-yl]-3-hydroxy-3-(1H-1,2,4-triazol-3-yl)-propenone
(387) 4-(4-(4-Aminobenzyl)thiophen-3-yl)-2-hydroxy-4-oxo-2-butenoic acid
(388) 4-(5-(4-Aminobenzyl)thiophen-2-yl)-2-hydroxy-4-oxo-2-butenoic acid
(389) 1-[(2-Chloro-5-(4-fluorobenzyl))furan-3-yl]-3-hydroxy-3-(1H-1,2,4-triazol-3-yl)-propenone
(390) 1-(4-(4-Fluorobenzenesulfonyl)thiazol-2-yl)-3-hydroxy-3-(1H-1,2,4-triazol-3-yl)-propenone
(391) 3-Hydroxy-1-(2H-5-(pyridin-2-ylmethyl)pyrazol-3-yl)-3-(2H-tetrazol-5-yl)-propenone
(392) 1-(4-(2-Chlorobenzyl)furan-3-yl)-3-hydroxy-3-(1H-1,2,4-triazol-3-yl)-propenone
(393) 1-(2-(3-Fluorobenzyl)thiophen-3-yl)-3-hydroxy-3-(1H-1,2,4-triazol-3-yl)-propenone
(394) 1-[(1-(4-Chlorobenzenesulfonyl)-5-n-propyl)pyrrol-3-yl]-3-hydroxy-3-(2H-tetrazol-5-yl)-propenone
(395) 3-Hydroxy-1-[(4-(2-phenylethyl)-5-(pyridin-4-ylmethyl))furan-2-yl]-3-(1H-1,2,4-triazol-3-yl)-propenone
(396) 1-[(4-Chloro-2-phenyl)furan-3-yl]-3-hydroxy-3-(1H-1,2,4-triazol-3-yl)-propenone
(397) 1-[(1-(4-Acetylbenzyl)-4-ethoxycarbonyl)pyrrol-2-yl]-3-hydroxy-3-(2H-tetrazol-5-yl)-propenone
(398) 4-(3-benzenesulfonylfuran-2-yl)-2-hydroxy-4-oxo-2-butenoic acid
(399) 4-(2H-4-(2-fluorobenzyl)pyrazol-3-yl)-2-hydroxy-4-oxo-2-butenoic acid
(400) 1-[(1-(4-Fluorobenzyl)-4-phenoxymethyl)pyrrol-2-yl]-3-hydroxy-3-(1H-1,2,4-triazol-3-yl)-propenone
(401) 1-(1-benzylpyrrol-2-yl)-3-hydroxy-3-(1H-1,2,4-triazol-3-yl)-propenone
(402) 1-[(4-Ethyl-1-(pyridin-2-ylmethyl))pyrrol-2-yl]-3-hydroxy-3-(1H-1,2,4-triazol-3-yl)-propenone
(403) 3-Hydroxy-1-(2H-4-(4-methylbenzyl)pyrazol-3-yl)-3-(2H-tetrazol-5-yl)-propenone
(404) 1-(5-(4-Fluorobenzenesulfonyl)furan-2-yl)-3-hydroxy-3-(2H-tetrazol-5-yl)-propenone
(405) 1-(5-(4-Acetylbenzyl)furan-3-yl)-3-hydroxy-3-(1H-1,2,4-triazol-3-yl)-propenone
(406) 1-(2H-2-(4-fluorobenzyl)pyrazol-3-yl)-3-hydroxy-3-(1H-1,2,4-triazol-3-yl)-propenone
(407) 1-[(4-Benzoyl-1-benzyl)pyrrol-2-yl]-3-hydroxy-3-(2H-tetrazol-5-yl)-propenone
(408) 3-Hydroxy-1-(5-(pyridin-4-ylmethyl)thiophen-3-yl)-3-(2H-tetrazol-5-yl)-propenone
(409) 1-[(4-Benzoyl-1-(4-fluorobenzyl))pyrrol-2-yl]-3-hydroxy-3-(1H-1,2,4-triazol-3-yl)-propenone
(410) 1-[(4-Ethoxycarbonyl-1-(3-fluorobenzyl))pyrrol-2-yl]-3-hydroxy-3-(2H-tetrazol-5-yl)-propenone
(411) 1-[(5-Ethoxycarbonyl-1-(pyridin-2-ylmethyl))pyrrol-3-yl]-3-hydroxy-3-(2H-tetrazol-5-yl)-propenone
(412) 1-[(1-(4-Aminobenzyl)-4-methoxymethyl)pyrrol-2-yl]-3-hydroxy-3-(2H-tetrazol-5-yl)-propenone
(413) 1-(2H-2-(4-fluorobenzenesulfonyl)pyrazol-3-yl)-3-hydroxy-3-(2H-tetrazol-5-yl)-propenone
(414) 4-(2H-2-(4-fluorobenzenesulfonyl)pyrazol-4-yl)-2-hydroxy-4-oxo-2-butenoic acid
(415) 1-[(5-Fluoro-2-(pyridin-4-ylmethyl))furan-3-yl]-3-hydroxy-3-(1H-1,2,4-triazol-3-yl)-propenone
(416) 1-[(1-Benzenesulfonyl-4-n-butyl)pyrrol-2-yl]-3-hydroxy-3-(1H-1,2,4-triazol-3-yl)-propenone
(417) 3-Hydroxy-1-(4-(4-methylbenzyl)thiophen-3-yl)-3-(2H-tetrazol-5-yl)-propenone
(418) 1-[(4-Carboxy-1-(4-fluorobenzyl))pyrrol-2-yl]-3-hydroxy-3-(1H-1,2,4-triazol-3-yl)-propenone
(419) 1-[(3-Chloro-5-(4-fluorobenzyl))furan-2-yl]-3-hydroxy-3-(1H-1,2,4-triazol-3-yl)-propenone
(420) 1-[(4-Carboxy-1-(4-fluorobenzenesulfonyl))pyrrol-2-yl]-3-hydroxy-3-(1H-1,2,4-triazol-3-yl)-propenone
(421) 3-Hydroxy-1-(2H-4-(4-methoxybenzyl)pyrazol-3-yl)-3-(1H-1,2,4-triazol-3-yl)-propenone
(422) 4-(4-(4-Fluorobenzyl)pyrrol-2-yl)-2-hydroxy-4-oxo-2-butenoic acid
(423) 4-(2H-4-benzylpyrazol-3-yl)-2-hydroxy-4-oxo-2-butenoic acid
(424) 3-Hydroxy-1-(4-(4-methylphenylthio)furan-2-yl)-3-(1H-1,2,4-triazol-3-yl)-propenone
(425) 2-Hydroxy-4-(2-(4-methoxybenzyl)thiazol-4-yl)-4-oxo-2-butenoic acid
(426) 4-(5-(4-Fluorobenzyl)thiophen-2-yl)-2-hydroxy-4-oxo-2-butenoic acid
(427) 3-Hydroxy-1-(1-(pyridin-2-ylmethyl)pyrrol-3-yl)-3-(2H-tetrazol-5-yl)-propenone
(428) 1-[(5-Benzoyl-1-(4-chlorobenzenesulfonyl))pyrrol-3-yl]-3-hydroxy-3-(2H-tetrazol-5-yl)-propenone
(429) 1-(2-(4-Fluorobenzenesulfonyl)thiophen-3-yl)-3-hydroxy-3-(1H-1,2,4-triazol-3-yl)-propenone
(430) 3-Hydroxy-1-(2-phenylthiopyrrol-3-yl)-3-(1H-1,2,4-triazol-3-yl)-propenone
(431) 1-[(5-Benzoyl-1-(pyridin-2-ylmethyl))pyrrol-3-yl]-3-hydroxy-3-(2H-tetrazol-5-yl)-propenone
(432) 2-Hydroxy-4-(4-(4-methylbenzyl)thiophen-3-yl)-4-oxo-2-butenoic acid
(433) 2-Hydroxy-4-oxo-4-(5-phenylthiofuran-2-yl)-2-butenoic acid
(434) 1-(1H-1-(2-fluorobenzyl)pyrazol-4-yl)-3-hydroxy-3-(1H-1,2,4-triazol-3-yl)-propenone
(435) 1-[(4-Ethyl-1-phenylthio)pyrrol-2-yl]-3-hydroxy-3-(1H-1,2,4-triazol-3-yl)-propenone
(436) 1-(2H-5-(3-fluorobenzyl)pyrazol-3-yl)-3-hydroxy-3-(2H-tetrazol-5-yl)-propenone
(437) 1-[(1-Benzenesulfonyl-5-n-butyl)pyrrol-3-yl]-3-hydroxy-3-(1H-1,2,4-triazol-3-yl)-propenone
(438) 1-(4-(2-Fluorobenzyl)thiophen-2-yl)-3-hydroxy-3-(1H-1,2,4-triazol-3-yl)-propenone
(439) 3-Hydroxy-3-(1H-1,2,4-triazol-3-yl)-1-(4-(3-trifluoromethylbenzyl)furan-2-yl)-propenone
(440) 3-Hydroxy-1-(2H-4-(pyridin-2-ylmethyl)pyrazol-3-yl)-3-(2H-tetrazol-5-yl)-propenone
(441) 1-[(4-(4-Fluorobenzyl)-3-methyl)furan-2-yl]-3-hydroxy-3-(1H-1,2,4-triazol-3-yl)-propenone (442) 1-[(4-n-Butyl-1-(pyridin-2-ylmethyl))pyrrol-2-yl]-3-hydroxy-3-(2H-tetrazol-5-yl)-propenone
(443) 2-Hydroxy-4-oxo-4-(4-pyridin-2-ylmethyl)pyrrol-3-yl)-2-butenoic acid
(444) 4-(4-Benzylpyrrol-2-yl)-2-hydroxy-4-oxo-2-butenoic acid
(445) 1-(5-(4-Chlorophenoxy)furan-3-yl)-3-hydroxy-3-(1H-1,2,4-triazol-3-yl)-propenone
(446) 1-(5-(2-chlorophenylthio)furan-2-yl)-3-hydroxy-3-(1H-1,2,4-triazol-3-yl)-propenone
(447) 3-Hydroxy-1-(1H-1-(pyridin-2-ylmethyl)pyrazol-4-yl)-3-(2H-tetrazol-5-yl)-propenone
(448) 3-Hydroxy-1-[(2-methyl-4-phenyl)furan-3-yl]-3-(1H-1,2,4-triazol-3-yl)-propenone
(449) 1-[(1-Benzyl-4-n-octyl)pyrrol-2-yl]-3-hydroxy-3-(2H-tetrazol-5-yl)-propenone
(450) 1-(1H-1-(2-fluorobenzyl)pyrazol-3-yl)-3-hydroxy-3-(2H-tetrazol-5-yl)-propenone
(451) 2-Hydroxy-4-oxo-4-(4-(pyridin-2-ylmethyl)furan-3-yl)-2-butenoic acid
(452) 1-[(5-Fluoro-3-(4-fluorobenzyl))furan-2-yl]-3-hydroxy-3-(1H-1,2,4-triazol-3-yl)-propenone
(453) 1-[(1-(4-Chlorobenzenesulfonyl)-4-ethoxycarbonyl)pyrrol-2-yl]-3-hydroxy-3-(1H-1,2,4-triazol-3-yl)-propenone
(454) 1-(4-(3-Fluorobenzyl)pyrrol-3-yl)-3-hydroxy-3-(2H-tetrazol-5-yl)-propenone
(455) 3-Hydroxy-1-[(4-phenoxymethyl-1-(pyridin-2-ylmethyl))pyrrol-2-yl]-3-(1H-1,2,4-triazol-3-yl)-propenone
(456) 4-(2H-4-(4-fluorobenzenesulfonyl)pyrazol-3-yl)-2-hydroxy-4-oxo-2-butenoic acid
(457) 3-Hydroxy-1-[(4-n-octyl-1-(pyridin-2-ylmethyl))pyrrol-2-yl]-3-(1H-1,2,4-triazol-3-yl)-propenone
(458) 3-Hydroxy-1-(2H-5-(pyridin-4-ylmethyl)pyrazol-3-yl)-3-(2H-tetrazol-5-yl)-propenone
(459) 1-(2-Benzylthiophen-3-yl)-3-hydroxy-3-(2H-tetrazol-5-yl)-propenone
(460) 3-Hydroxy-1-[(4-methyl-3-(pyridin-4-ylmethyl))furan-2-yl]-3-(1H-1,2,4-triazol-3-yl)-propenone
(461) 1-(4-(2-methoxybenzyl)furan-2-yl)-3-hydroxy-3-(1H-1,2,4-triazol-3-yl)-propenone
(462) 4-(1-(4-Fluorobenzyl)pyrrol-2-yl)-2-hydroxy-4-oxo-2-butenoic acid
(463) 1-[(5-Ethoxycarbonyl-1-(3-fluorobenzyl))pyrrol-3-yl]-3-hydroxy-3-(1H-1,2,4-triazol-3-yl)-propenone
(464) 1-[(3-(4-fluorobenzyl)-5-methyl)furan-2-yl]-3-hydroxy-3-(1H-1,2,4-triazol-3-yl)-propenone
(465) 1-[(5-Benzoyl-1-(4-chlorobenzenesulfonyl))pyrrol-3-yl]-3-hydroxy-3-(1H-1,2,4-triazol-3-yl)-propenone
(466) 3-Hydroxy-1-(1-phenylthiopyrrol-3-yl)-3-(2H-tetrazol-5-yl)-propenone
(467) 1-(1H-1-benzenesulfonylpyrazol-4-yl)-3-hydroxy-3-(1H-1,2,4-triazol-3-yl)-propenone
(468) 3-Hydroxy-1-(5-(pyridin-4-ylmethyl)furan-2-yl)-3-(1H-1,2,4-triazol-3-yl)-propenone
(469) 1-[(5-Benzoyl-1-(4-fluorobenzyl))pyrrol-3-yl]-3-hydroxy-3-(2H-tetrazol-5-yl)-propenone
(470) 3-Hydroxy-1-(5-(pyridin-4-ylmethyl)thiophen-2-yl)-3-(2H-tetrazol-5-yl)-propenone
(471) 4-(2H-2-(4-Acetylbenzyl)pyrazol-4-yl)-2-hydroxy-4-oxo-2-butenoic acid
(472) 3-Hydroxy-1-(5-phenylthiothiophen-2-yl)-3-(2H-tetrazol-5-yl)-propenone
(473) 3-Hydroxy-1-(4-(4-methylphenylthio)furan-3-yl)-3-(1H-1,2,4-triazol-3-yl)-propenone
(474) 1-(2-(4-Acetylbenzyl)furan-3-yl)-3-hydroxy-3-(2H-tetrazol-5-yl)-propenone
(475) 1-[(4-n-Butyl-1-phenylthio)pyrrol-2-yl]-3-hydroxy-3-(1H-1,2,4-triazol-3-yl)-propenone
(476) 4-(5-Benzylfuran-3-yl)-2-hydroxy-4-oxo-2-butenoic acid
(477) 4-(5-(4-Fluorobenzenesulfonyl)furan-3-yl)-2-hydroxy-4-oxo-2-butenoic acid
(478) 1-(3-(3-Chlorobenzyl)furan-2-yl)-3-hydroxy-3-(1H-1,2,4-triazol-3-yl)-propenone
(479) 3-Hydroxy-1-[(4-methyl-3-phenyl)furan-2-yl]-3-(1H-1,2,4-triazol-3-yl)-propenone
(480) 3-Hydroxy-1-(3-(4-methylbenzyl)furan-2-yl)-3-(2H-tetrazol-5-yl)-propenone
(481) 1-(2-(2-Chlorophenylthio)furan-3-yl)-3-hydroxy-3-(1H-1,2,4-triazol-3-yl)-propenone
(482) 4-(5-(4-Acetylbenzyl)pyrrol-3-yl)-2-hydroxy-4-oxo-2-butenoic acid
(483) 1-(4-(3-Fluorobenzyl)thiophen-2-yl)-3-hydroxy-3-(1H-1,2,4-triazol-3-yl)-propenone
(484) 1-[(1-(4-Fluorobenzyl)-4-methoxymethylpyrrol-2-yl]-3-hydroxy-3-(2H-tetrazol-5-yl)-propenone
(485) 3-Hydroxy-1-(4-phenylthiofuran-3-yl)-3-(1H-1,2,4-triazol-3-yl)-propenone
(486) 1-(4-Benzylthiophen-3-yl)-3-hydroxy-3-(1H-1,2,4-triazol-3-yl)-propenone
(487) 1-(2H-2-(4-chlorobenzenesulfonyl)pyrazol-3-yl)-3-hydroxy-3-(1H-1,2,4-triazol-3-yl)-propenone
(488) 2-Hydroxy-4-oxo-4-(1-phenylthiopyrrol-2-yl)-2-butenoic acid
(489) 1-(5-(4-Acetylbenzyl)furan-3-yl)-3-hydroxy-3-(2H-tetrazol-5-yl)-propenone
(490) 2-Hydroxy-4-oxo-4-(3-(pyridin-2-ylmethyl)thiophen-2-yl)-2-butenoic acid
(491) 2-Hydroxy-4-(3-(4-methylbenzyl)furan-2-yl)-4-oxo-2-butenoic acid
(492) 4-(2-(4-Fluorobenzyl)thiazol-4-yl)-2-hydroxy-4-oxo-2-butenoic acid
(493) 1-(2H-4-(4-Fluorobenzenesulfonyl)pyrazol-3-yl)-3-hydroxy-3-(1H-1,2,4-triazol-3-yl)-propenone
(494) 3-Hydroxy-1-[(5-phenyl-4-(2-phenylethyl))furan-2-yl]-3-(1H-1,2,4-triazol-3-yl)-propenone
(495) 3-Hydroxy-1-(4-(4-methylbenzyl)pyrrol-3-yl)-3-(1H-1,2,4-triazol-3-yl)-propenone
(496) 1-[(5-n-Butyl-1-(3-fluorobenzyl))pyrrol-3-yl]-3-hydroxy-3-(1H-1,2,4-triazol-3-yl)-propenone
(497) 1-(3-(2-chlorobenzyl)furan-2-yl)-3-hydroxy-3-(1H-1,2,4-triazol-3-yl)-propenone
(498) 1-(4-(4-Chlorophenylthio)furan-2-yl)-3-hydroxy-3-(1H-1,2,4-triazol-3-yl)-propenone
(499) 1-(4-(2-Chlorophenoxy)furan-2-yl)-3-hydroxy-3-(1H-1,2,4-triazol-3-yl)-propenone
(500) 1-[(1-(4-Fluorobenzyl)-5-n-propyl)pyrrol-3-yl]-3-hydroxy-3-(1H-1,2,4-triazol-3-yl)-propenone
(501) 1-(3-Benzylfuran-2-yl)-3-hydroxy-3-(1H-1,2,4-triazol-3-yl)-propenone
(502) 3-Hydroxy-1-[(5-phenoxymethyl-1-(pyridin-4-ylmethyl))pyrrol-3-yl]-3-(2H-tetrazol-5-yl)-propenone
(503) 4-(3-(4-Fluorobenzenesulfonyl)furan-2-yl)-2-hydroxy-4-oxo-2-butenoic acid
(504) 4-(5-n-Butylfuran-2-yl)-2-hydroxy-4-oxo-2-butenoic acid
(505) 2-Hydroxy-4-(2-(4-methoxybenzyl)thiophen-3-yl)-4-oxo-2-butenoic acid
(506) 1-[(4-Benzoyl-1-(2-fluorobenzyl))pyrrol-2-yl]-3-hydroxy-3-(1H-1,2,4-triazol-3-yl)-propenone
(507) 1-(4-Benzenesulfonylthiophen-3-yl)-3-hydroxy-3-(2H-tetrazol-5-yl)-propenone
(508) 1-[(1-Benzyl-4-ethoxycarbonyl)pyrrol-2-yl]-3-hydroxy-3-(2H-tetrazol-5-yl)-propenone (509) 3-Hydroxy-1-[(5-methyl-4-phenyl)furan-2-yl]-3-(1H-1,2,4-triazol-3-yl)-propenone
(510) 3-Hydroxy-1-(3-(3-methoxyphenylthio)furan-2-yl)-3-(1H-1,2,4-triazol-3-yl)-propenone
(511) 1-[(4-Benzenesulfonyl-5-fluoro)furan-2-yl]-3-hydroxy-3-(1H-1,2,4-triazol-3-yl)-propenone
(512) 4-(4-(4-Aminobenzyl)thiophen-2-yl)-2-hydroxy-4-oxo-2-butenoic acid
(513) 3-Hydroxy-1-(5-(pyridin-4-ylmethyl)pyrrol-3-yl)-3-(2H-tetrazol-5-yl)-propenone
(514) 3-Hydroxy-1-(2H-2-(4-methylbenzyl)pyrazol-4-yl)-3-(1H-1,2,4-triazol-3-yl)-propenone
(515) 3-Hydroxy-1-(4-(4-methylbenzyl)thiophen-3-yl)-3-(1H-1,2,4-triazol-3-yl)-propenone
(516) 2-Hydroxy-4-oxo-4-(1H-1-(pyridin-2-ylmethyl)pyrazol-4-yl)-2-butenoic acid
(517) 1-[(1-(2-Fluorobenzyl)-4-n-propyl)pyrrol-2-yl]-3-hydroxy-3-(1H-1,2,4-triazol-3-yl)-propenone
(518) 1-(2H-2-(4-chlorobenzenesulfonyl)pyrazol-3-yl)-3-hydroxy-3-(2H-triazol-5-yl)-propenone
(519) 1-(5-(4-Fluorophenyl)furan-3-yl)-3-hydroxy-3-(1H-1,2,4-triazol-3-yl)-propenone
(520) 1-[(5-Carboxy-1-(4-methylbenzyl))pyrrol-3-yl]-3-hydroxy-3-(1H-1,2,4-triazol-3-yl)-propenone
(521) 1-[(5-n-Butyl-1-(4-chlorobenzenesulfonyl))pyrrol-3-yl]-3-hydroxy-3-(2H-tetrazol-5-yl)-propenone
(522) 1-[(4-n-Butyl-1-(3-fluorobenzyl))pyrrol-2-yl]-3-hydroxy-3-(1H-1,2,4-triazol-3-yl)-propenone
(523) 1-[(1-(4-Chlorobenzenesulfonyl)-4-phenoxymethyl)pyrrol-2-yl]-3-hydroxy-3-(2H-tetrazol-5-yl)-propenone
(524) 1-(5-(2-methoxybenzyl)furan-3-yl)-3-hydroxy-3-(1H-1,2,4-triazol-3-yl)-propenone
(525) 4-(4-(4-Fluorobenzenesulfonyl)pyrrol-2-yl)-2-hydroxy-4-oxo-2-butenoic acid
(526) 1-[(4-Benzoyl-1-(4-fluorobenzenesulfonyl))pyrrol-2-yl]-3-hydroxy-3-(2H-tetrazol-5-yl)-propenone
(527) 1-(4-(4-Chlorobenzenesulfonyl)pyrrol-2-yl)-3-hydroxy-3-(1H-1,2,4-triazol-3-yl)-propenone
(528) 1-(2-(4-Acetylbenzyl)furan-3-yl)-3-hydroxy-3-(1H-1,2,4-triazol-3-yl)-propenone
(529) 1-(4-(3-Fluorobenzyl)thiophen-3-yl)-3-hydroxy-3-(2H-tetrazol-5-yl)-propenone
(530) 1-(1-benzylpyrrol-2-yl)-3-hydroxy-3-(2H-tetrazol-5-yl)-propenone
(531) 1-[(2-(4-Fluorobenzyl)-5-(2-phenylethyl))furan-3-yl]-3-hydroxy-3-(1H-1,2,4-triazol-3-yl)-propenone
(532) 1-(2H-4-benzylpyrazol-3-yl)-3-hydroxy-3-(1H-1,2,4-triazol-3-yl)-propenone
(533) 3-Hydroxy-1-(5-phenoxyfuran-2-yl)-3-(1H-1,2,4-triazol-3-yl)-propenone
(534) 1-(4-n-Butylfuran-3-yl)-3-hydroxy-3-(2H-tetrazol-5-yl)-propenone
(535) 1-[(4-Chloro-2-(4-fluorobenzyl))furan-3-yl]-3-hydroxy-3-(1H-1,2,4-triazol-3-yl)-propenone
(536) 3-Hydroxy-1-(5-(2-methoxyphenylthio)furan-3-yl)-3-(1H-1,2,4-triazol-3-yl)-propenone
(537) 1-(2H-2-(4-aminobenzyl)pyrazol-3-yl)-3-hydroxy-3-(1H-1,2,4-triazol-3-yl)-propenone
(538) 1-(2H-2-(4-fluorobenzenesulfonyl)pyrazol-3-yl)-3-hydroxy-3-(1H-1,2,4-triazol-3-yl)-propenone
(539) 1-(3-(4-Aminobenzyl)furan-2-yl)-3-hydroxy-3-(2H-tetrazol-5-yl)-propenone
(540) 1-(5-(2-Fluorobenzyl)pyrrol-2-yl)-3-hydroxy-3-(2H-tetrazol-5-yl)-propenone
(541) 3-Hydroxy-1-(3-(pyridin-4-ylmethyl)thiophen-2-yl)-3-(1H-1,2,4-triazol-3-yl)-propenone
(542) 4-(2-(4-Fluorobenzenesulfonyl)thiazol-4-yl)-2-hydroxy-4-oxo-2-butenoic acid
(543) 3-Hydroxy-1-(4-(4-methylbenzyl)furan-2-yl)-3-(1H-1,2,4-triazol-3-yl)-propenone
(544) 3-Hydroxy-1-(2-phenylthiothiophen-3-yl)-3-(1H-1,2,4-triazol-3-yl)-propenone
(545) 1-(4-Benzylpyrrol-2-yl)-3-hydroxy-3-(1H-1,2,4-triazol-3-yl)-propenone
(546) 1-(4-(2-Fluorophenyl)furan-3-yl)-3-hydroxy-3-(1H-1,2,4-triazol-3-yl)-propenone
(547) 1-(5-(4-Chlorobenzenesulfonyl)thiophen-2-yl)-3-hydroxy-3-(2H-tetrazol-5-yl)-propenone
(548) 1-(5-(4-Fluorobenzenesulfonyl)pyrrol-2-yl)-3-hydroxy-3-(2H-tetrazol-5-yl)-propenone
(549) 3-Hydroxy-3-(1H-1,2,4-triazol-3-yl)-1-(4-(4-trifluoromethylphenoxy)furan-2-yl)-propenone
(550) 3-Hydroxy-1-(5-phenylthiopyrrol-2-yl)-3-(2H-tetrazol-5-yl)-propenone
(551) 3-Hydroxy-3-(1H-1,2,4-triazol-3-yl)-1-(2-(3-trifluoromethylphenylthio)furan-3-yl)-propenone
(552) 1-(4-(4-Chlorobenzenesulfonyl)pyrrol-3-yl)-3-hydroxy-3-(1H-1,2,4-triazol-3-yl)-propenone
(553) 3-Hydroxy-1-[(4-phenyl-5-(2-phenylethyl))furan-2-yl]-3-(1H-1,2,4-triazol-3-yl)-propenone
(554) 1-[(5-Benzoyl-1-benzyl)pyrrol-3-yl]-3-hydroxy-3-(1H-1,2,4-triazol-3-yl)-propenone
(555) 1-[(1-Benzyl-5-n-propyl)pyrrol-3-yl]-3-hydroxy-3-(1H-1,2,4-triazol-3-yl)-propenone
(556) 1-(2-Benzenesulfonylfuran-3-yl)-3-hydroxy-3-(1H-1,2,4-triazol-3-yl)-propenone
(557) 1-(4-(3-Chlorophenoxy)furan-3-yl)-3-hydroxy-3-(1H-1,2,4-triazol-3-yl)-propenone
(558) 1-[(1-Benzenesulfonyl-4-ethyl)pyrrol-3-yl]-3-hydroxy-3-(1H-1,2,4-triazol-3-yl)-propenone
(559) 2-Hydroxy-4-oxo-4-(2H-2-(pyridin-2-ylmethyl)pyrazol-3-yl)-2-butenoic acid
(560) 3-Hydroxy-1-[(5-methoxymethyl-1-phenylthio)pyrrol-3-yl]-3-(1H-1,2,4-triazol-3-yl)-propenone
(561) 1-(5-(4-Fluorobenzenesulfonyl)furan-3-yl)-3-hydroxy-3-(2H-tetrazol-5-yl)-propenone
(562) 1-[(4-Ethyl-1-(3-fluorobenzyl))pyrrol-2-yl]-3-hydroxy-3-(2H-tetrazol-5-yl)-propenone
(563) 1-[(5-Fluoro-4-(pyridin-4-ylmethyl))furan-2-yl]-3-hydroxy-3-(1H-1,2,4-triazol-3-yl)-propenone
(564) 2-Hydroxy-4-(1-(4-methoxybenzyl)pyrrol-3-yl)-4-oxo-2-butenoic acid
(565) 1-(2H-2-(2-fluorobenzyl)pyrazol-4-yl)-3-hydroxy-3-(1H-1,2,4-triazol-3-yl)-propenone
(566) 3-Hydroxy-1-(3-(4-methylbenzyl)furan-2-yl)-3-(1H-1,2,4-triazol-3-yl)-propenone
(567) 1-(3-(4-Chlorobenzyl)furan-2-yl)-3-hydroxy-3-(1H-1,2,4-triazol-3-yl)-propenone
(568) 1-(2-(3-Fluorobenzyl)furan-3-yl)-3-hydroxy-3-(1H-1,2,4-triazol-3-yl)-propenone
(569) 1-(2-(4-Chlorobenzenesulfonyl)furan-3-yl)-3-hydroxy-3-(1H-1,2,4-triazol-3-yl)-propenone
(570) 3-Hydroxy-1-(4-(4-methoxybenzyl)furan-3-yl)-3-(2H-tetrazol-5-yl)-propenone
(571) 1-[(1-(4-Acetylbenzyl)-5-ethoxycarbonyl)pyrrol-3-yl]-3-hydroxy-3-(1H-1,2,4-triazol-3-yl)-propenone
(572) 3-Hydroxy-1-(2H-4-phenylthiopyrazol-3-yl)-3-(1H-1,2,4-triazol-3-yl)-propenone
(573) 1-[(1-(4-Aminobenzyl)-5-ethoxycarbonyl)pyrrol-3-yl]-3-hydroxy-3-(2H-tetrazol-5-yl)-propenone
(574) 4-(3-(4-Fluorobenzyl)pyrrol-2-yl)-2-hydroxy-4-oxo-2-butenoic acid
(575) 3-Hydroxy-3-(1H-1,2,4-triazol-3-yl)-1-(5-(2-trifluoromethylbenzyl)furan-3-yl)-propenone
(576) 3-Hydroxy-1-(2H-2-(pyridin-2-ylmethyl)pyrazol-4-yl)-3-(2H-tetrazol-5-yl)-propenone (577) 4-(4-Benzylthiophen-2-yl)-2-hydroxy-4-oxo-2-butenoic acid
(578) 3-Hydroxy-3-(1H-1,2,4-triazol-3-yl)-1-(4-(3-trifluoromethylphenylthio)furan-2-yl)-propenone
(579) 1-[(4-Chloro-5-(4-fluorobenzyl))furan-3-yl]-3-hydroxy-3-(1H-1,2,4-triazol-3-yl)-propenone
(580) 2-Hydroxy-4-oxo-4-(4-(pyridin-4-ylmethyl)thiazol-2-yl)-2-butenoic acid
(581) 4-(2-(4-Chlorobenzenesulfonyl)pyrrol-3-yl)-2-hydroxy-4-oxo-2-butenoic acid
(582) 4-(1-(4-Fluorobenzenesulfonyl)pyrrol-3-yl)-2-hydroxy-4-oxo-2-butenoic acid
(583) 1-(4-Benzylpyrrol-2-yl)-3-hydroxy-3-(2H-tetrazol-5-yl)-propenone
(584) 1-(2-(4-Chlorobenzenesulfonyl)thiazol-4-yl)-3-hydroxy-3-(1H-1,2,4-triazol-3-yl)-propenone
(585) 3-Hydroxy-1-(4-(4-methoxybenzyl)thiazol-2-yl)-3-(2H-tetrazol-5-yl)-propenone
(586) 3-Hydroxy-1-(5-phenylthiopyrrol-3-yl)-3-(1H-1,2,4-triazol-3-yl)-propenone
(587) 1-[(1-(3-Fluorobenzyl)-4-n-octyl)pyrrol-2-yl]-3-hydroxy-3-(2H-tetrazol-5-yl)-propenone
(588) 3-Hydroxy-1-(2-(4-methoxybenzyl)thiophen-3-yl)-3-(2H-tetrazol-5-yl)-propenone
(589) 3-Hydroxy-1-[(2-methyl-5-(pyridin-4-ylmethyl))furan-3-yl]-3-(1H-1,2,4-triazol-3-yl)-propenone
(590) 4-(5-(3-Fluorobenzyl)furan-3-yl)-2-hydroxy-4-oxo-2-butenoic acid
(591) 3-Hydroxy-1-(5-phenylthiothiophen-3-yl)-3-(2H-tetrazol-5-yl)-propenone
(592) 3-Hydroxy-1-(2-(4-methoxyphenylthio)furan-3-yl)-3-(1H-1,2,4-triazol-3-yl)-propenone
(593) 1-[(5-Benzoyl-1-(pyridin-4-ylmethyl))pyrrol-3-yl]-3-hydroxy-3-(1H-1,2,4-triazol-3-yl)-propenone
(594) 1-[(4-(4-Fluorobenzyl)-5-(2-phenylethyl))furan-3-yl]-3-hydroxy-3-(1H-1,2,4-triazol-3-yl)-propenone
(595) 4-(3-(4-Chlorobenzenesulfonyl)furan-2-yl)-2-hydroxy-4-oxo-2-butenoic acid
(596) 1-[(4-Ethoxycarbonyl-1-(4-fluorobenzyl))pyrrol-2-yl]-3-hydroxy-3-(2H-tetrazol-5-yl)-propenone
(597) 1-[(5-Benzoyl-1-(4-methylbenzyl))pyrrol-3-yl]-3-hydroxy-3-(1H-1,2,4-triazol-3-yl)-propenone
(598) 1-[(2-Chloro-4-(pyridin-4-ylmethyl))furan-3-yl]-3-hydroxy-3-(1H-1,2,4-triazol-3-yl)-propenone
(599) 3-Hydroxy-1-[(3-(2-phenylethyl)-5-(pyridin-4-ylmethyl))furan-2-yl]-3-(1H-1,2,4-triazol-3-yl)-propenone
(600) 4-(4-Benzenesulfonylpyrrol-2-yl)-2-hydroxy-4-oxo-2-butenoic acid
(601) 1-(2-(2-Fluorobenzyl)furan-3-yl)-3-hydroxy-3-(2H-tetrazol-5-yl)-propenone
(602) 1-(4-(4-Chlorobenzenesulfonyl)thiophen-3-yl)-3-hydroxy-3-(2H-tetrazol-5-yl)-propenone
(603) 2-Hydroxy-4-oxo-4-(2H-2-(pyridin-4-ylmethyl)pyrazol-4-yl)-2-butenoic acid
(604) 1-[(4-(4-Fluorobenzyl)-5-methyl)furan-3-yl]-3-hydroxy-3-(1H-1,2,4-triazol-3-yl)-propenone
(605) 1-[(4-Carboxy-1-(pyridin-2-ylmethyl))pyrrol-2-yl]-3-hydroxy-3-(1H-1,2,4-triazol-3-yl)-propenone
(606) 3-Hydroxy-1-(3-(4-methoxybenzyl)pyrrol-2-yl)-3-(2H-tetrazol-5-yl)-propenone
(607) 3-Hydroxy-1-[(4-methoxymethyl-1-(pyridin-2-ylmethyl))pyrrol-2-yl]-3-(2H-tetrazol-5-yl)-propenone
(608) 1-(1-(4-Acetylbenzyl)pyrrol-3-yl)-3-hydroxy-3-(1H-1,2,4-triazol-3-yl)-propenone
(609) 1-(5-(3-Fluorobenzyl)furan-3-yl)-3-hydroxy-3-(2H-tetrazol-5-yl)-propenone
(610) 1-[(4-Benzenesulfonyl-3-methyl)furan-2-yl]-3-hydroxy-3-(1H-1,2,4-triazol-3-yl)-propenone
(611) 1-[(5-Benzenesulfonyl-2-methyl)furan-3-yl]-3-hydroxy-3-(1H-1,2,4-triazol-3-yl)-propenone
(612) 3-Hydroxy-1-(2-(4-methylbenzyl)thiophen-3-yl)-3-(1H-1,2,4-triazol-3-yl)-propenone
(613) 3-Hydroxy-3-(1H-1,2,4-triazol-3-yl)-1-(5-(4-trifluoromethylphenoxy)furan-3-yl)-propenone
(614) 1-(2H-2-benzenesulfonylpyrazol-4-yl)-3-hydroxy-3-(1H-1,2,4-triazol-3-yl)-propenone
(615) 1-[(5-Chloro-3-(4-fluorobenzyl))furan-2-yl]-3-hydroxy-3-(1H-1,2,4-triazol-3-yl)-propenone
(616) 1-(5-(2-Fluorobenzyl)furan-3-yl)-3-hydroxy-3-(1H-1,2,4-triazol-3-yl)-propenone
(617) 1-(4-n-Butylfuran-3-yl)-3-hydroxy-3-(1H-1,2,4-triazol-3-yl)-propenone
(618) 1-[(4-Ethyl-1-(pyridin-4-ylmethyl))pyrrol-3-yl]-3-hydroxy-3-(1H-1,2,4-triazol-3-yl)-propenone
(619) 1-[(4-Benzenesulfonyl-5-chloro)furan-3-yl]-3-hydroxy-3-(1H-1,2,4-triazol-3-yl)-propenone
(620) 1-[(1-(2-Fluorobenzyl)-5-n-propyl)pyrrol-3-yl]-3-hydroxy-3-(2H-tetrazol-5-yl)-propenone
(621) 1-(1H-1-(4-chlorobenzenesulfonyl)pyrazol-4-yl)-3-hydroxy-3-(1H-1,2,4-triazol-3-yl)-propenone
(622) 1-[(4-Fluoro-5-phenyl)furan-2-yl]-3-hydroxy-3-(1H-1,2,4-triazol-3-yl)-propenone
(623) 4-(1H-1-(4-fluorobenzyl)pyrazol-3-yl)-2-hydroxy-4-oxo-2-butenoic acid
(624) 1-(4-(4-Acetylbenzyl)pyrrol-3-yl)-3-hydroxy-3-(1H-1,2,4-triazol-3-yl)-propenone
(625) 4-(2-benzenesulfonylfuran-3-yl)-2-hydroxy-4-oxo-2-butenoic acid
(626) 3-Hydroxy-1-(1-(4-methylbenzyl)pyrrol-3-yl)-3-(2H-tetrazol-5-yl)-propenone
(627) 4-(4-(2-Fluorobenzyl)pyrrol-3-yl)-2-hydroxy-4-oxo-2-butenoic acid
(628) 1-(4-(3-Fluorobenzyl)furan-3-yl)-3-hydroxy-3-(2H-tetrazol-5-yl)-propenone
(629) 1-(4-(3-Fluorobenzyl)furan-3-yl)-3-hydroxy-3-(1H-1,2,4-triazol-3-yl)-propenone
(630) 1-(5-(4-Chlorophenylthio)furan-2-yl)-3-hydroxy-3-(1H-1,2,4-triazol-3-yl)-propenone
(631) 1-[(5-Benzenesulfonyl-3-fluoro)furan-2-yl]-3-hydroxy-3-(1H-1,2,4-triazol-3-yl)-propenone
(632) 1-(2-(4-Chlorobenzenesulfonyl)thiophen-3-yl-3-hydroxy-3-(1H-1,2,4-triazol-3-yl)-propenone
(633) 3-Hydroxy-1-(4-(3-methoxybenzyl)furan-2-yl)-3-(1H-1,2,4-triazol-3-yl)-propenone
(634) 1-[(1-(4-Acetylbenzyl)-4-(2-phenylethyl))pyrrol-3-yl]-3-hydroxy-3-(2H-tetrazol-5-yl)-propenone
(635) 4-(1-(4-Acetylbenzyl)pyrrol-3-yl)-2-hydroxy-4-oxo-2-butenoic acid
(636) 1-[(1-(4-Chlorobenzenesulfonyl)-5-n-octyl)pyrrol-3-yl]-3-hydroxy-3-(2H-tetrazol-5-yl)-propenone
(637) 2-Hydroxy-4-oxo-4-(2-(pyridin-4-ylmethyl)furan-3-yl)-2-butenoic acid
(638) 1-[(4-Ethyl-1-(3-fluorobenzyl))pyrrol-2-yl]-3-hydroxy-3-(1H-1,2,4-triazol-3-yl)-propenone
(639) 1-[(1-(4-Acetylbenzyl)-4-n-octyl)pyrrol-2-yl]-3-hydroxy-3-(2H-tetrazol-5-yl)-propenone
(640) 1-(2-n-Butylfuran-3-yl)-3-hydroxy-3-(1H-1,2,4-triazol-3-yl)-propenone
(641) 4-(4-(3-Fluorobenzyl)thiophen-3-yl)-2-hydroxy-4-oxo-2-butenoic acid
(642) 1-[(1-(4-Chlorobenzenesulfonyl)-5-methoxymethyl)pyrrol-3-yl]-3-hydroxy-3-(1H-1,2,4-triazol-3-yl)-propenone (643) 1-(4-(3-Chlorophenoxy)furan-2-yl)-3-hydroxy-3-(1H-1,2,4-triazol-3-yl)-propenone
(644) 1-[(1-(4-Aminobenzyl)-5-n-butyl)pyrrol-3-yl]-3-hydroxy-3-(1H-1,2,4-triazol-3-yl)-propenone
(645) 1-[(4-Benzenesulfonyl-3-(2-phenylethyl))furan-2-yl]-3-hydroxy-3-(1H-1,2,4-triazol-3-yl)-propenone
(646) 3-Hydroxy-1-(4-(4-methoxybenzyl)thiophen-3-yl)-3-(2H-tetrazol-5-yl)-propenone
(647) 1-[(1-(4-Aminobenzyl)-4-n-butyl)pyrrol-2-yl]-3-hydroxy-3-(1H-1,2,4-triazol-3-yl)-propenone
(648) 1-[(1-Benzyl-4-n-propyl)pyrrol-2-yl]-3-hydroxy-3-(1H-1,2,4-triazol-3-yl)-propenone
(649) 1-[(1-Benzyl-4-ethyl)pyrrol-2-yl]-3-hydroxy-3-(1H-1,2,4-triazol-3-yl)-propenone
(650) 3-Hydroxy-1-[(5-methyl-2-phenyl)furan-3-yl]-3-(1H-1,2,4-triazol-3-yl)-propenone
(651) 4-(1-(4-Chlorobenzenesulfonyl)pyrrol-3-yl)-2-hydroxy-4-oxo-2-butenoic acid
(652) 1-(4-(3-Fluorobenzyl)pyrrol-2-yl)-3-hydroxy-3-(2H-tetrazol-5-yl)-propenone
(653) 3-Hydroxy-1-(1-(pyridin-2-ylmethyl)pyrrol-2-yl)-3-(2H-tetrazol-5-yl)-propenone
(654) 2-Hydroxy-4-(5-(4-methoxybenzyl)thiophen-3-yl)-4-oxo-2-butenoic acid
(655) 1-(4-(4-Chlorophenoxy)furan-3-yl)-3-hydroxy-3-(1H-1,2,4-triazol-3-yl)-propenone
(656) 1-(4-(4-Acetylbenzyl)furan-2-yl)-3-hydroxy-3-(1H-1,2,4-triazol-3-yl)-propenone
(657) 1-[(2-Chloro-5-(pyridin-4-ylmethyl))furan-3-yl]-3-hydroxy-3-(1H-1,2,4-triazol-3-yl)-propenone
(658) 2-Hydroxy-4-(4-(4-methylbenzyl)thiophen-2-yl)-4-oxo-2-butenoic acid
(659) 3-Hydroxy-1-(2H-2-(4-methoxybenzyl)pyrazol-4-yl)-3-(2H-tetrazol-5-yl)-propenone
(660) 1-(2H-2-benzylpyrazol-3-yl)-3-hydroxy-3-(1H-1,2,4-triazol-3-yl)-propenone
(661) 2-Hydroxy-4-oxo-4-(2-(pyridin-2-ylmethyl)thiophen-3-yl)-2-butenoic acid
(662) 4-(2-n-Butylfuran-3-yl)-2-hydroxy-4-oxo-2-butenoic acid
(663) 1-(5-Benzylpyrrol-2-yl)-3-hydroxy-3-(1H-1,2,4-triazol-3-yl)-propenone
(664) 1-[(1-(3-Fluorobenzyl)-5-n-octyl)pyrrol-3-yl]-3-hydroxy-3-(2H-tetrazol-5-yl)-propenone
(665) 1-(1H-1-benzylpyrazol-3-yl)-3-hydroxy-3-(1H-1,2,4-triazol-3-yl)-propenone
(666) 3-Hydroxy-3-(1H-1,2,4-triazol-3-yl)-1-(5-(2-trifluoromethylphenylthio)furan-3-yl)-propenone
(667) 1-[(1-(3-Fluorobenzyl)-5-n-propyl)pyrrol-3-yl]-3-hydroxy-3-(2H-tetrazol-5-yl)-propenone
(668) 1-[(5-Fluoro-3-phenyl)furan-2-yl]-3-hydroxy-3-(1H-1,2,4-triazol-3-yl)-propenone
(669) 3-Hydroxy-1-(2-phenylthiothiazol-4-yl)-3-(1H-1,2,4-triazol-3-yl)-propenone
(670) 3-Hydroxy-1-(3-(pyridin-2-ylmethyl)pyrrol-2-yl)-3-(1H-1,2,4-triazol-3-yl)-propenone
(671) 1-(3-(4-Acetylbenzyl)pyrrol-2-yl)-3-hydroxy-3-(1H-1,2,4-triazol-3-yl)-propenone
(672) 1-(4-(4-Chlorophenoxy)furan-2-yl)-3-hydroxy-3-(1H-1,2,4-triazol-3-yl)-propenone
(673) 1-[(1-(4-Chlorobenzenesulfonyl)-4-ethyl)pyrrol-2-yl]-3-hydroxy-3-(1H-1,2,4-triazol-3-yl)-propenone
(674) 3-Hydroxy-1-(2H-2-(4-methoxybenzyl)pyrazol-3-yl)-3-(2H-tetrazol-5-yl)-propenone
(675) 1-[(5-Benzenesulfonyl-4-chloro)furan-3-yl]-3-hydroxy-3-(1H-1,2,4-triazol-3-yl)-propenone
(676) 4-(3-(4-Chlorobenzenesulfonyl)thiophen-2-yl)-2-hydroxy-4-oxo-2-butenoic acid
(677) 1-(2-(4-Acetylbenzyl)thiazol-4-yl)-3-hydroxy-3-(2H-tetrazol-5-yl)-propenone
(678) 4-(1H-1-(2-fluorobenzyl)pyrazol-4-yl)-2-hydroxy-4-oxo-2-butenoic acid
(679) 1-(4-(4-Aminobenzyl)furan-3-yl)-3-hydroxy-3-(2H-tetrazol-5-yl)-propenone
(680) 1-[(4-Fluoro-5-phenyl)furan-3-yl]-3-hydroxy-3-(1H-1,2,4-triazol-3-yl)-propenone
(681) 1-[(5-n-Butyl-1-(pyridin-2-ylmethyl))pyrrol-3-yl]-3-hydroxy-3-(2H-tetrazol-5-yl)-propenone
(682) 1-[(1-(3-Fluorobenzyl)-5-n-propyl)pyrrol-3-yl]-3-hydroxy-3-(1H-1,2,4-triazol-3-yl)-propenone
(683) 1-(4-(4-Amino phenylthio)furan-2-yl)-3-hydroxy-3-(1H-1,2,4-triazol-3-yl)-propenone
(684) 2-Hydroxy-4-oxo-4-(5-phenylthiopyrrol-2-yl)-2-butenoic acid
(685) 1-(5-(3-Fluorobenzyl)thiophen-2-yl)-3-hydroxy-3-(1H-1,2,4-triazol-3-yl)-propenone
(686) 1-(4-Benzenesulfonylpyrrol-2-yl)-3-hydroxy-3-(1H-1,2,4-triazol-3-yl)-propenone
(687) 3-Hydroxy-1-(3-phenylthiopyrrol-2-yl)-3-(2H-tetrazol-5-yl)-propenone
(688) 1-[(3-Benzenesulfonyl-5-fluoro)furan-2-yl]-3-hydroxy-3-(1H-1,2,4-triazol-3-yl)-propenone
(689) 1-(3-(4-Acetylbenzyl)pyrrol-2-yl)-3-hydroxy-3-(2H-tetrazol-5-yl)-propenone
(690) 1-(4-(4-Acetylbenzyl)thiazol-2-yl)-3-hydroxy-3-(1H-1,2,4-triazol-3-yl)-propenone
(691) 3-Hydroxy-1-(2-phenylthiofuran-3-yl)-3-(2H-tetrazol-5-yl)-propenone
(692) 3-Hydroxy-1-[(1-(4-methylbenzyl)-4-phenoxymethyl)pyrrol-2-yl]-3-(1H-1,2,4-triazol-3-yl)-propenone
(693) 4-(5-(2-Fluorobenzyl)thiophen-2-yl)-2-hydroxy-4-oxo-2-butenoic acid
(694) 1-[(4-Benzenesulfonyl-3-fluoro)furan-2-yl]-3-hydroxy-3-(1H-1,2,4-triazol-3-yl)-propenone
(695) 1-(5-(4-Acetylphenoxy)furan-3-yl)-3-hydroxy-3-(1H-1,2,4-triazol-3-yl)-propenone
(696) 1-[(4-Ethyl-1-(4-fluorobenzyl))pyrrol-2-yl]-3-hydroxy-3-(1H-1,2,4-triazol-3-yl)-propenone
(697) 3-Hydroxy-1-(1H-1-(4-methylbenzyl)pyrazol-4-yl)-3-(1H-1,2,4-triazol-3-yl)-propenone
(698) 2-Hydroxy-4-(4-(4-methoxybenzyl)pyrrol-2-yl)-4-oxo-2-butenoic acid
(699) 1-[(2-Fluoro-4-(4-fluorobenzyl))furan-3-yl]-3-hydroxy-3-(1H-1,2,4-triazol-3-yl)-propenone
(700) 3-Hydroxy-1-(3-phenylthiothiophen-2-yl)-3-(2H-tetrazol-5-yl)-propenone
(701) 3-Hydroxy-1-(5-(4-methoxybenzyl)furan-3-yl)-3-(2H-tetrazol-5-yl)-propenone
(702) 3-Hydroxy-1-(4-phenylthiofuran-3-yl)-3-(2H-tetrazol-5-yl)-propenone
(703) 1-(4-(2-Fluorobenzyl)furan-2-yl)-3-hydroxy-3-(2H-tetrazol-5-yl)-propenone
(704) 2-Hydroxy-4-(4-(4-methoxybenzyl)furan-2-yl)-4-oxo-2-butenoic acid
(705) 4-(4-Benzenesulfonylfuran-2-yl)-2-hydroxy-4-oxo-2-butenoic acid
(706) 4-(5-Benzenesulfonylpyrrol-2-yl)-2-hydroxy-4-oxo-2-butenoic acid
(707) 1-(3-Benzylthiophen-2-yl)-3-hydroxy-3-(2H-tetrazol-5-yl)-propenone
(708) 1-[(4-Ethyl-1-phenylthio)pyrrol-3-yl]-3-hydroxy-3-(2H-tetrazol-5-yl)-propenone
(709) 1-(1-(4-Chlorobenzenesulfonyl)pyrrol-2-yl)-3-hydroxy-3-(2H-tetrazol-5-yl)-propenone (710) 1-(2-(4-Chlorobenzenesulfonyl)thiophen-3-yl)-3-hydroxy-3-(2H-tetrazol-5-yl)-propenone
(711) 1-(2-(4-Chlorobenzenesulfonyl)thiazol-4-yl)-3-hydroxy-3-(2H-tetrazol-5-yl)-propenone
(712) 1-[(5-Ethoxycarbonyl-1-(pyridin-4-ylmethyl))pyrrol-3-yl]-3-hydroxy-3-(1H-1,2,4-triazol-3-yl)-propenone
(713) 1-[(4-n-Butyl-1-(4-methoxybenzyl))pyrrol-2-yl]-3-hydroxy-3-(2H-tetrazol-5-yl)-propenone
(714) 1-(5-Benzylpyrrol-2-yl)-3-hydroxy-3-(2H-tetrazol-5-yl)-propenone
(715) 1-(5-(3-Fluorobenzyl)pyrrol-2-yl)-3-hydroxy-3-(1H-1,2,4-triazol-3-yl)-propenone
(716) 1-[(1-(4-Fluorobenzenesufonyl)-4-n-octyl)pyrrol-2-yl]-3-hydroxy-3-(1H-1,2,4-triazol-3-yl)-propenone
(717) 3-Hydroxy-1-[(4-methoxymethyl-1-(pyridin-2-ylmethyl))pyrrol-2-yl]-3-(1H-1,2,4-triazol-3-yl)-propenone
(718) 1-[(1-(3-Fluorobenzyl)-4-(2-phenylethyl))pyrrol-3-yl]-3-hydroxy-3-(1H-1,2,4-triazol-3-yl)-propenone
(719) 2-Hydroxy-4-oxo-4-(4-(pyridin-4-ylmethyl)pyrrol-3-yl)-2-butenoic acid
(720) 3-Hydroxy-1-(1-(pyridin-4-ylmethyl)pyrrol-3-yl)-3-(2H-tetrazol-5-yl)-propenone
(721) 1-(5-n-Butylfuran-3-yl)-3-hydroxy-3-(1H-1,2,4-triazol-3-yl)-propenone
(722) 1-(4-(4-Fluorobenzyl)pyrrol-3-yl)-3-hydroxy-3-(2H-tetrazol-5-yl)-propenone
(723) 3-Hydroxy-1-(2H-5-(pyridin-4-ylmethyl)pyrazol-3-yl)-3-(1H-1,2,4-triazol-3-yl)-propenone
(724) 3-Hydroxy-1-(5-phenylthiopyrrol-2-yl)-3-(1H-1,2,4-triazol-3-yl)-propenone
(725) 3-Hydroxy-1-(3-(4-methylbenzyl)thiophen-2-yl)-3-(1H-1,2,4-triazol-3-yl)-propenone
(726) 3-Hydroxy-1-(5-(4-methoxybenzyl)pyrrol-2-yl)-3-(2H-tetrazol-5-yl)-propenone
(727) 4-(1-Benzenesulfonylpyrrol-2-yl)-2-hydroxy-4-oxo-2-butenoic acid
(728) 1-(5-Benzenesulfonylfuran-2-yl)-3-hydroxy-3-(2H-tetrazol-5-yl)-propenone
(729) 1-(2H-4-(4-chlorobenzenesulfonyl)pyrazol-3-yl)-3-hydroxy-3-(1H-1,2,4-triazol-3-yl)-propenone
(730) 3-Hydroxy-1-[(1-(4-methylbenzyl)-5-n-octyl)pyrrol-3-yl]-3-(1H-1,2,4-triazol-3-yl)-propenone
(731) 2-Hydroxy-4-oxo-4-(4-(pyridin-4-ylmethyl)furan-3-yl)-2-butenoic acid
(732) 1-[(1-Benzenesulfonyl-4-ethoxycarbonyl)pyrrol-2-yl]-3-hydroxy-3-(1H-1,2,4-triazol-3-yl)-propenone
(733) 3-Hydroxy-3-(1H-1,2,4-triazol-3-yl)-1-(5-(2-trifluoromethylphenoxy)furan-3-yl)-propenone
(734) 4-(4-Benzylthiophen-3-yl)-2-hydroxy-4-oxo-2-butenoic acid
(735) 4-(1H-1-(2-fluorobenzyl)pyrazol-3-yl)-2-hydroxy-4-oxo-2-butenoic acid
(736) 1-[(5-(4-Fluorobenzyl)-4-(2-phenylethyl))furan-3-yl]-3-hydroxy-3-(1H-1,2,4-triazol-3-yl)-propenone
(737) 1-[(4-n-Butyl-1-(4-fluorobenzenesulfonyl))pyrrol-2-yl]-3-hydroxy-3-(2H-tetrazol-5-yl)-propenone
(738) 1-[(4-Chloro-5-phenyl)furan-3-yl]-3-hydroxy-3-(1H-1,2,4-triazol-3-yl)-propenone
(739) 1-(2H-2-(3-fluorobenzyl)pyrazol-4-yl)-3-hydroxy-3-(2H-tetrazol-5-yl)-propenone
(740) 3-Hydroxy-1-[(5-(2-phenylethyl)-4-(pyridin-4-ylmethyl))furan-2-yl]-3-(1H-1,2,4-triazol-3-yl)-propenone
(741) 1-(5-(4-Chlorobenzenesulfonyl)thiophen-3-yl)-3-hydroxy-3-(1H-1,2,4-triazol-3-yl)-propenone
(742) 3-Hydroxy-1-(2-(pyridin-4-ylmethyl)pyrrol-3-yl)-3-(1H-1,2,4-triazol-3-yl)-propenone
(743) 1-[(4-Ethyl-1-(3-fluorobenzyl))pyrrol-3-yl]-3-hydroxy-3-(1H-1,2,4-triazol-3-yl)-propenone
(744) 3-Hydroxy-3-(1H-1,2,4-triazol-3-yl)-1-(5-(3-trifluoromethylbenzyl)furan-3-yl)-propenone
(745) 3-Hydroxy-1-[(5-methyl-2-(pyridin-4-ylmethyl))furan-3-yl]-3-(1H-1,2,4-triazol-3-yl)-propenone
(746) 1-[(4-Ethoxycarbonyl-1-(3-fluorobenzyl))pyrrol-2-yl]-3-hydroxy-3-(1H-1,2,4-triazol-3-yl)-propenone
(747) 1-(4-(4-Fluorobenzenesulfonyl)thiophen-2-yl)-3-hydroxy-3-(2H-tetrazol-5-yl)-propenone
(748) 3-Hydroxy-1-[(4-(2-phenylethyl)-1-phenylthio)pyrrol-3-yl]-3-(2H-tetrazol-5-yl)-propenone
(749) 3-Hydroxy-1-(2H-2-(pyridin-2-ylmethyl)pyrazol-3-yl)-3-(1H-1,2,4-triazol-3-yl)-propenone
(750) 4-(2H-5-(2-fluorobenzyl)pyrazol-3-yl)-2-hydroxy-4-oxo-2-butenoic acid
(751) 1-[(1-Benzenesulfonyl-5-n-butyl)pyrrol-3-yl]-3-hydroxy-3-(2H-tetrazol-5-yl)-propenone
(752) 2-Hydroxy-4-(2-(4-methoxybenzyl)pyrrol-3-yl)-4-oxo-2-butenoic acid
(753) 4-(1-(4-Fluorobenzenesulfonyl)pyrrol-2-yl)-2-hydroxy-4-oxo-2-butenoic acid
(754) 1-(3-(4-Aminobenzyl)thiophen-2-yl)-3-hydroxy-3-(1H-1,2,4-triazol-3-yl)-propenone
(755) 3-Hydroxy-1-[(5-n-octyl-1-phenylthio)pyrrol-3-yl]-3-(2H-tetrazol-5-yl)-propenone
(756) 1-[(4-Ethoxycarbonyl-1-(2-fluorobenzyl))pyrrol-2-yl]-3-hydroxy-3-(1H-1,2,4-triazol-3-yl)-propenone
(757) 1-(4-(4-Acetylbenzyl)pyrrol-2-yl)-3-hydroxy-3-(1H-1,2,4-triazol-3-yl)-propenone
(758) 3-Hydroxy-3-(1H-1,2,4-triazol-3-yl)-1-(5-(2-trifluoromethylphenoxy)furan-2-yl)-propenone
(759) 3-Hydroxy-1-(4-phenylthiothiophen-3-yl)-3-(1H-1,2,4-triazol-3-yl)-propenone
(760) 1-[(4-Fluoro-2-(4-fluorobenzyl))furan-3-yl]-3-hydroxy-3-(1H-1,2,4-triazol-3-yl)-propenone
(761) 4-(4-(4-Acetylbenzyl)thiazol-2-yl)-2-hydroxy-4-oxo-2-butenoic acid
(762) 1-(4-(3-Fluorobenzyl)thiophen-3-yl)-3-hydroxy-3-(1H-1,2,4-triazol-3-yl)-propenone
(763) 2-Hydroxy-4-(3-(4-methoxybenzyl)thiophen-2-yl)-4-oxo-2-butenoic acid
(764) 3-Hydroxy-1-(2H-4-(4-methylbenzyl)pyrazol-3-yl)-3-(1H-1,2,4-triazol-3-yl)-propenone
(765) 4-(2H-2-(4-chlorobenzenesulfonyl)pyrazol-4-yl)-2-hydroxy-4-oxo-2-butenoic acid
(766) 1-(5-Benzylpyrrol-3-yl)-3-hydroxy-3-(2H-tetrazol-5-yl)-propenone
(767) 1-[(3-Chloro-4-(4-fluorobenzyl))furan-2-yl]-3-hydroxy-3-(1H-1,2,4-triazol-3-yl)-propenone
(768) 3-Hydroxy-1-(4-(4-methylbenzyl)thiophen-2-yl)-3-(2H-tetrazol-5-yl)-propenone
(769) 3-Hydroxy-1-[(4-(2-phenylethyl)-5-(pyridin-4-ylmethyl))furan-3-yl]-3-(1H-1,2,4-triazol-3-yl)-propenone
(770) 4-(2-(4-Fluorobenzenesulfonyl)pyrrol-3-yl)-2-hydroxy-4-oxo-2-butenoic acid
(771) 4-(5-(2-Fluorobenzyl)furan-2-yl)-2-hydroxy-4-oxo-2-butenoic acid
(772) 1-(2-(4-Fluorobenzyl)pyrrol-3-yl)-3-hydroxy-3-(1H-1,2,4-triazol-3-yl)-propenone
(773) 1-(2-(4-Acetylbenzyl)thiazol-4-yl)-3-hydroxy-3-(1H-1,2,4-triazol-3-yl)-propenone
(774) 1-(4-Benzenesulfonylthiophen-2-yl)-3-hydroxy-3-(1H-1,2,4-triazol-3-yl)-propenone
(775) 1-(5-(4-Acetylbenzyl)pyrrol-3-yl)-3-hydroxy-3-(1H-1,2,4-triazol-3-yl)-propenone (776) 1-[(1-(4-Aminobenzyl)-4-ethyl)pyrrol-2-yl]-3-hydroxy-3-(2H-tetrazol-5-yl)-propenone
(777) 1-(5-Benzenesulfonylfuran-3-yl)-3-hydroxy-3-(1H-1,2,4-triazol -3-yl)-propenone
(778) 4-(5-(4-Chlorobenzenesulfonyl)pyrrol-2-yl)-2-hydroxy-4-oxo-2-butenoic acid
(779) 2-Hydroxy-4-oxo-4-(5-phenylthiopyrrol-3-yl)-2-butenoic acid
(780) 1-(2H-2-(3-fluorobenzyl)pyrazol-4-yl)-3-hydroxy-3-(1H-1,2,4-triazol-3-yl)-propenone
(781) 1-[(1-(4-Aminobenzyl)-4-carboxy)pyrrol-2-yl]-3-hydroxy-3-(1H-1,2,4-triazol-3-yl)-propenone
(782) 1-[(4-Ethoxycarbonyl-1-phenylthio)pyrrol-2-yl]-3-hydroxy-3-(1H-1,2,4-triazol-3-yl)-propenone
(783) 3-Hydroxy-1-(5-(4-methylbenzyl)pyrrol-2-yl)-3-(2H-tetrazol-5-yl)-propenone
(784) 1-(5-(4-Acetylphenylthio)furan-3-yl)-3-hydroxy-3-(1H-1,2,4-triazol-3-yl)-propenone
(785) 3-Hydroxy-1-(5-(pyridin-2-ylmethyl)thiophen-2-yl)-3-(2H-tetrazol-5-yl)-propenone
(786) 4-(3-(4-Acetylbenzyl)thiophen-2-yl)-2-hydroxy-4-oxo-2-butenoic acid
(787) 3-Hydroxy-1-[(5-phenoxymethyl-1-(pyridin-2-ylmethyl))pyrrol-3-yl]-3-(2H-tetrazol-5-yl)-propenone
(788) 3-Hydroxy-1-(2H-2-(4-methylbenzyl)pyrazol-3-yl)-3-(2H-tetrazol-5-yl)-propenone
(789) 1-[(1-Benzenesulfonyl-4-(2-phenylethyl))pyrrol-2-yl]-3-hydroxy-3-(2H-tetrazol-5-yl)-propenone
(790) 1-[(5-Benzenesulfonyl-4-fluoro)furan-2-yl]-3-hydroxy-3-(1H-1,2,4-triazol-3-yl)-propenone
(791) 4-(2H-4-(4-fluorobenzyl)pyrazol-3-yl)-2-hydroxy-4-oxo-2-butenoic acid
(792) 4-(4-(4-Aminobenzyl)furan-3-yl)-2-hydroxy-4-oxo-2-butenoic acid
(793) 3-Hydroxy-3-(1H-1,2,4-triazol-3-yl)-1-(4-(2-trifluoromethylphenylthio)furan-2-yl)-propenone
(794) 4-(2-(4-Acetylbenzyl)thiophen-3-yl)-2-hydroxy-4-oxo-2-butenoic acid
(795) 1-[(4-Ethoxycarbonyl-1-(pyridin-2-ylmethyl))pyrrol-2-yl]-3-hydroxy-3-(2H-tetrazol-5-yl)-propenone
(796) 1-(1H-1-(4-fluorobenzenesulfonyl)pyrazol-3-yl)-3-hydroxy-3-(1H-1,2,4-triazol-3-yl)-propenone
(797) 1-(3-(4-Fluorobenzenesulfonyl)pyrrol-2-yl)-3-hydroxy-3-(1H-1,2,4-triazol-3-yl)-propenone
(798) 1-[(4-Ethyl-1-(4-methoxybenzyl))pyrrol-3-yl]-3-hydroxy-3-(2H-tetrazol-5-yl)-propenone
(799) 1-(5-(2-Fluorophenyl)furan-3-yl)-3-hydroxy-3-(1H-1,2,4-triazol-3-yl)-propenone
(800) 1-(2H-2-(4-Aminobenzyl)pyrazol-4-yl)-3-hydroxy-3-(2H-tetrazol-5-yl)-propenone
(801) 1-[(5-Fluoro-3-(pyridin-4-ylmethyl))furan-2-yl]-3-hydroxy-3-(1H-1,2,4-triazol-3-yl)-propenone
(802) 1-[(4-Ethyl-1-(4-fluorobenzyl))pyrrol-2-yl]-3-hydroxy-3-(2H-tetrazol-5-yl)-propenone
(803) 1-[(1-Benzyl-4-(2-phenylethyl))pyrrol-2-yl]-3-hydroxy-3-(2H-tetrazol-5-yl)-propenone
(804) 1-[(4-Carboxy-1-(4-chlorobenzenesulfonyl))pyrrol-2-yl]-3-hydroxy-3-(2H-tetrazol-5-yl)-propenone
(805) 1-(2-(4-Acetylbenzyl)pyrrol-3-yl)-3-hydroxy-3-(2H-tetrazol-5-yl)-propenone
(806) 4-(4-(3-Fluorobenzyl)pyrrol-3-yl)-2-hydroxy-4-oxo-2-butenoic acid
(807) 4-(4-(4-Fluorobenzyl)thiophen-3-yl)-2-hydroxy-4-oxo-2-butenoic acid
(808) 1-[(3-Benzenesulfonyl-4-methyl)furan-2-yl]-3-hydroxy-3-(1H-1,2,4-triazol-4-yl)-propenone
(809) 4-(5-(4-Chlorobenzenesulfonyl)thiophen-2-yl)-2-hydroxy-4-oxo-2-butenoic acid
(810) 1-(4-Benzenesulfonylfuran-3-yl)-3-hydroxy-3-(1H-1,2,4-triazol-3-yl)-propenone
(811) 1-(4-(2-Chlorophenylthio)furan-2-yl)-3-hydroxy-3-(1H-1,2,4-triazol-3-yl)-propenone
(812) 1-[(4-Ethyl-1-(2-fluorobenzyl))pyrrol-2-yl]-3-hydroxy-3-(2H-tetrazol-5-yl)-propenone
(813) 1-(4-(3-Fluorobenzyl)pyrrol-2-yl)-3-hydroxy-3-(1H-1,2,4-triazol-3-yl)-propenone
(814) 2-Hydroxy-4-oxo-4-(2H-5-(pyridin-2-ylmethyl)pyrazol-3-yl)-2-butenoic acid
(815) 1-[(1-Benzenesulfonyl-4-(2-phenylethyl))pyrrol-2-yl]-3-hydroxy-3-(1H-1,2,4-triazol-3-yl)-propenone
(816) 1-[(5-Benzenesulfonyl-4-methyl)furan-3-yl]-3-hydroxy-3-(1H-1,2,4-triazol-3-yl)-propenone
(817) 3-Hydroxy-3-(1H-1,2,4-triazol-3-yl)-1-(4-(4-trifluoromethylbenzyl)furan-2-yl)-propenone
(818) 3-Hydroxy-1-(4-phenylfuran-2-yl)-3-(1H-1,2,4-triazol-3-yl)-propenone
(819) 1-[(5-Ethoxycarbonyl-1-(4-fluorobenzenesulfonyl))pyrrol-3-yl]-3-hydroxy-3-(1H-1,2,4-triazol-3-yl)-propenone
(820) 1-(2-Benzenesulfonylthiophen-3-yl)-3-hydroxy-3-(2H-tetrazol-5-yl)-propenone
(821) 4-(5-Benzylthiophen-3-yl)-2-hydroxy-4-oxo-2-butenoic acid
(822) 3-Hydroxy-1-[(5-methoxymethyl-1-phenylthio)pyrrol-3-yl]-3-(2H-tetrazol-5-yl)-propenone
(823) 3-Hydroxy-1-(5-(pyridin-2-ylmethyl)pyrrol-3-yl)-3-(2H-tetrazol-5-yl)-propenone
(824) 1-[(5-Ethoxycarbonyl-1-(4-fluorobenzyl))pyrrol-3-yl]-3-hydroxy-3-(1H-1,2,4-triazol-3-yl)-propenone
(825) 1-(2H-4-(3-fluorobenzyl)pyrazol-3-yl)-3-hydroxy-3-(2H-tetrazol-5-yl)-propenone
(826) 4-(4-(2-Fluorobenzyl)furan-2-yl)-2-hydroxy-4-oxo-2-butenoic acid
(827) 4-(4-(4-Acetylbenzyl)furan-2-yl)-2-hydroxy-4-oxo-2-butenoic acid
(828) 1-[(1-(4-Fluorobenzenesulfonyl)-4-methoxymethyl)pyrrol-2-yl]-3-hydroxy-3-(1H-1,2,4-triazol-3-yl)-propenone
(829) 4-(3-(4-Fluorobenzenesulfonyl)thiophen-2-yl)-2-hydroxy-4-oxo-2-butenoic acid
(830) 1-[(5-Fluoro-2-phenyl)furan-3-yl]-3-hydroxy-3-(1H-1,2,4-triazol-3-yl)-propenone
(831) 1-(1H-1-benzylpyrazol-4-yl)-3-hydroxy-3-(2H-tetrazol-5-yl)-propenone
(832) 1-[(4-Ethyl-1-phenylthio)pyrrol-2-yl]-3-hydroxy-3-(2H-tetrazol-5-yl)-propenone
(833) 1-(4-(4-Acetylphenylthio)furan-2-yl)-3-hydroxy-3-(1H-1,2,4-triazol-3-yl)-propenone
(834) 1-[(1-Benzenesulfonyl-4-phenoxymethyl)pyrrol-2-yl]-3-hydroxy-3-(1H-1,2,4-triazol-3-yl)-propenone
(835) 1-[(3-fluoro-4-(pyridin-4-ylmethyl))furan-2-yl]-3-hydroxy-3-(1H-1,2,4-triazol-3-yl)-propenone
(836) 1-(4-(4-Chlorobenzenesulfonyl)furan-2-yl)-3-hydroxy-3-(2H-tetrazol-5-yl)-propenone
(837) 1-[(5-Carboxy-1-(4-methoxybenzyl))pyrrol-3-yl]-3-hydroxy-3-(2H-tetrazol-5-yl)-propenone
(838) 3-Hydroxy-1-(3-(2-methoxyphenylthio)furan-2-yl)-3-(1H-1,2,4-triazol-3-yl)-propenone
(839) 1-(5-(4-Fluorobenzyl)pyrrol-2-yl)-3-hydroxy-3-(2H-tetrazol-5-yl)-propenone
(840) 1-[(5-Benzoyl-1-(2-fluorobenzyl))pyrrol-3-yl]-3-hydroxy-3-(1H-1,2,4-triazol-3-yl)-propenone
(841) 1-[(4-(4-Fluorobenzyl)-2-methyl)furan-3-yl]-3-hydroxy-3-(1H-1,2,4-triazol-3-yl)-propenone
(842) 1-[(5-Benzoyl-1-(4-methoxybenzyl))pyrrol-3-yl]-3-hydroxy-3-(2H-tetrazol-5-yl)-propenone (843) 1-(4-Benzylthiophen-3-yl)-3-hydroxy-3-(2H-tetrazol-5-yl)-propenone
(844) 1-(5-(2-Fluorobenzyl)furan-3-yl)-3-hydroxy-3-(2H-tetrazol-5-yl)-propenone
(845) 3-Hydroxy-1-[(5-methoxymethyl-1-(pyridin-4-ylmethyl))pyrrol-3-yl]-3-(2H-tetrazol-5-yl)-propenone
(846) 4-(4-Benzenesulfonylfuran-3-yl)-2-hydroxy-4-oxo-2-butenoic acid
(847) 4-(5-Benzenesulfonylfuran-2-yl)-2-hydroxy-4-oxo-2-butenoic acid
(848) 1-(4-(4-Fluorobenzyl)thiazol-2-yl)-3-hydroxy-3-(1H-1,2,4-triazol-3-yl)-propenone
(849) 3-Hydroxy-1-[(4-methoxymethyl-1-(pyridin-4-ylmethyl))pyrrol-2-yl]-3-(1H-1,2,4-triazol-3-yl)-propenone
(850) 1-(4-(4-Acetylphenylthio)furan-3-yl)-3-hydroxy-3-(1H-1,2,4-triazol-3-yl)-propenone
(851) 1-(2-(3-Fluorobenzyl)thiazol-4-yl)-3-hydroxy-3-(2H-tetrazol-5-yl)-propenone
(852) 4-(2-(3-fluorobenzyl)thiazol-4-yl)-2-hydroxy-4-oxo-2-butenoic acid
(853) 1-(2H-2-(4-Fluorobenzenesulfonyl)pyrazol-4-yl)-3-hydroxy-3-(2H-tetrazol-5-yl)-propenone
(854) 1-[(4-Ethyl-1-(pyridin-2-ylmethyl))pyrrol-3-yl]-3-hydroxy-3-(1H-1,2,4-triazol-3-yl)-propenone
(855) 1-[(1-(4-Aminobenzyl)-4-n-octyl)pyrrol-2-yl]-3-hydroxy-3-(2H-tetrazol-5-yl)-propenone
(856) 1-(5-(2-Chlorophenylthio)furan-3-yl)-3-hydroxy-3-(1H-1,2,4-triazol-3-yl)-propenone
(857) 1-[(4-Ethyl-1-(pyridin-2-ylmethyl))pyrrol-2-yl]-3-hydroxy-3-(2H-tetrazol-5-yl)-propenone
(858) 1-[(2-Fluoro-4-(pyridin-4-ylmethyl))furan-3-yl]-3-hydroxy-3-(1H-1,2,4-triazol-3-yl)-propenone
(859) 1-(2H-2-Benzenesulfonylpyrazol-3-yl)-3-hydroxy-3-(2H-tetrazol-5-yl)-propenone
(860) 1-[(3-Fluoro-5-(4-fluorobenzyl))furan-2-yl]-3-hydroxy-3-(1H-1,2,4-triazol-3-yl)-propenone
(861) 3-Hydroxy-1-[(5-phenoxymethyl-1-(pyridin-2-ylmethyl))pyrrol-3-yl]-3-(1H-1,2,4-triazol-3-yl)-propenone
(862) 4-(3-(3-Fluorobenzyl)pyrrol-2-yl)-2-hydroxy-4-oxo-2-butenoic acid
(863) 3-Hydroxy-1-(5-(4-methoxybenzyl)pyrrol-3-yl)-3-(1H-1,2,4-triazol-3-yl)-propenone
(864) 1-(5-(4-Aminobenzyl)furan-2-yl)-3-hydroxy-3-(2H-tetrazol-5-yl)-propenone
(865) 2-Hydroxy-4-oxo-4-(4-(pyridin-4-ylmethyl)thiophen-2-yl)-2-butenoic acid
(866) 4-(2H-2-(3-Fluorobenzyl)pyrazol-3-yl)-2-hydroxy-4-oxo-2-butenoic acid
(867) 3-Hydroxy-1-(4-(pyridin-2-ylmethyl)pyrrol-3-yl)-3-(1H-1,2,4-triazol-3-yl)-propenone
(868) 4-(2-(4-Aminobenzyl)furan-3-yl)-2-hydroxy-4-oxo-2-butenoic acid
(869) 1-(1H-1-(2-Fluorobenzyl)pyrazol-4-yl)-3-hydroxy-3-(2H-tetrazol-5-yl)-propenone
(870) 2-Hydroxy-4-(5-(4-methylbenzyl)thiophen-2-yl)-4-oxo-2-butenoic acid
(871) 3-Hydroxy-1-(4-(pyridin-2-ylmethyl)thiophen-2-yl)-3-(1H-1,2,4-triazol-3-yl)-propenone
(872) 1-[(3-Fluoro-5-(pyridin-4-ylmethyl))furan-2-yl]-3-hydroxy-3-(1H-1,2,4-triazol-3-yl)-propenone
(873) 3-Hydroxy-1-(2-phenylfuran-3-yl)-3-(1H-1,2,4-triazol-3-yl)-propenone
(874) 1-(5-Benzylfuran-3-yl)-3-hydroxy-3-(1H-1,2,4-triazol-3-yl)-propenone
(875) 1-(2-(4-Acetylphenoxy)furan-3-yl)-3-hydroxy-3-(1H-1,2,4-triazol-3-yl)-propenone
(876) 1-(3-(4-Acetylbenzyl)furan-2-yl)-3-hydroxy-3-(2H-tetrazol-5-yl)-propenone
(877) 1-(1H-1-(3-Fluorobenzyl)pyrazol-3-yl)-3-hydroxy-3-(1H-1,2,4-triazol-3-yl)-propenone
(878) 1-(4-(4-Chlorophenylthio)furan-3-yl)-3-hydroxy-3-(1H-1,2,4-triazol-3-yl)-propenone
(879) 3-Hydroxy-1-(5-(pyridin-2-ylmethyl)pyrrol-3-yl)-3-(2H-tetrazol-5-yl)-propenone
(880) 1-[(5-Ethoxycarbonyl-1-(4-fluorobenzenesulfonyl))pyrrol-3-yl]-3-hydroxy-3-(2H-tetrazol-5-yl)-propenone
(881) 1-(4-(4-Fluorobenzenesulfonyl)furan-3-yl)-3-hydroxy-3-(2H-tetrazol-5-yl)-propenone
(882) 3-Hydroxy-1-[(5-n-propyl-1-(pyridin-2-ylmethyl))pyrrol-3-yl]-3-(2H-tetrazol-5-yl)-propenone
(883) 2-Hydroxy-4-(2H-4-(4-methoxybenzyl)pyrazol-3-yl)-4-oxo-2-butenoic acid
(884) 1-(1-(4-Chlorobenzenesulfonyl)pyrrol-2-yl)-3-hydroxy-3-(1H-1,2,4-triazol-3-yl)-propenone
(885) 1-[(1-(3-Fluorobenzyl)-4-phenoxymethyl)pyrrol-2-yl]-3-hydroxy-3-(2H-tetrazol-5-yl)-propenone
(886) 1-[(4-Fluoro-5-(pyridin-4-ylmethyl))furan-2-yl]-3-hydroxy-3-(1H-1,2,4-triazol-3-yl)-propenone
(887) 3-Hydroxy-1-(3-(4-methylbenzyl)thiophen-2-yl)-3-(2H-tetrazol-5-yl)-propenone
(888) 1-[(1-(4-Aminobenzyl)-4-benzoyl)pyrrol-2-yl]-3-hydroxy-3-(2H-tetrazol-5-yl)-propenone
(889) 1-(2H-4-(4-Fluorobenzenesulfonyl)pyrazol-3-yl)-3-hydroxy-3-(2H-tetrazol-5-yl)-propenone
(890) 1-[(1-Benzyl-4-n-butyl)pyrrol-2-yl]-3-hydroxy-3-(2H-tetrazol-5-yl)-propenone
(891) 1-(4-(4-Fluorobenzyl)thiazol-2-yl)-3-hydroxy-3-(2H-tetrazol-5-yl)-propenone
(892) 2-Hydroxy-4-oxo-4-(3-(pyridin-4-ylmethyl)pyrrol-2-yl)-2-butenoic acid
(893) 3-Hydroxy-1-(5-(4-methylbenzyl)thiophen-2-yl)-3-(2H-tetrazol-5-yl)-propenone
(894) 1-(3-n-butylfuran-2-yl)-3-hydroxy-3-(2H-tetrazol-5-yl)-propenone
(895) 1-[(4-Carboxy-1-(4-fluorobenzenesulfonyl))pyrrol-2-yl]-3-hydroxy-3-(2H-tetrazol-5-yl)-propenone
(896) 1-(5-(3-Fluorobenzyl)pyrrol-3-yl)-3-hydroxy-3-(1H-1,2,4-triazol-3-yl)-propenone
(897) 3-Hydroxy-1-(5-(pyridin-4-ylmethyl)pyrrol-2-yl)-3-(1H-1,2,4-triazol-3-yl)-propenone
(898) 1-[(1-(4-Chlorobenzenesulfonyl)-4-methoxymethyl)pyrrol-2-yl]-3-hydroxy-3-(1H-1,2,4-triazol-3-yl)-propenone
(899) 1-(4-(4-Acetylbenzyl)thiophen-2-yl)-3-hydroxy-3-(1H-1,2,4-triazol-3-yl)-propenone
(900) 1-(4-(4-Fluorobenzenesulfonyl)furan-2-yl)-3-hydroxy-3-(1H-1,2,4-triazol-3-yl)-propenone
(901) 4-(2-(4-Acetylbenzyl)pyrrol-3-yl)-2-hydroxy-4-oxo-2-butenoic acid
(902) 4-(3-(3-Fluorobenzyl)thiophen-2-yl)-2-hydroxy-4-oxo-2-butenoic acid
(903) 2-Hydroxy-4-(3-(4-methylbenzyl)pyrrol-2-yl)-4-oxo-2-butenoic acid
(904) 1-[(4-n-Butyl-1-(3-fluorobenzyl))pyrrol-2-yl]-3-hydroxy-3-(2H-tetrazol-5-yl)-propenone
(905) 1-[(4-Benzoyl-1-(4-methylbenzyl))pyrrol-2-yl]-3-hydroxy-3-(1H-1,2,4-triazol-3-yl)-propenone
(906) 1-(4-(3-Fluorobenzyl)thiazol-2-yl)-3-hydroxy-3-(2H-tetrazol-5-yl)-propenone
(907) 1-(4-(4-Acetylbenzyl)furan-3-yl)-3-hydroxy-3-(1H-1,2,4-triazol-3-yl)-propenone
(908) 3-Hydroxy-3-(1H-1,2,4-triazol-3-yl)-1-(3-(2-trifluoromethylphenoxy)furan-2-yl)-propenone (909) 1-[(3-Benzenesulfonyl-5-chloro)furan-2-yl]-3-hydroxy-3-(1H-1,2,4-triazol-3-yl)-propenone
(910) 1-[(5-Benzenesulfonyl-3-(2-phenylethyl))furan-2-yl]-3-hydroxy-3-(1H-1,2,4-triazol-3-yl)-propenone
(911) 1-(5-(4-Fluorobenzyl)thiophen-2-yl)-3-hydroxy-3-(2H-tetrazol-5-yl)-propenone
(912) 1-(3-(4-Fluorobenzenesulfonyl)furan-2-yl)-3-hydroxy-3-(2H-tetrazol-5-yl)-propenone
(913) 1-(5-(3-Fluorobenzyl)thiophen-2-yl)-3-hydroxy-3-(2H-tetrazol-5-yl)-propenone
(914) 4-(3-(2-Fluorobenzyl)furan-2-yl)-2-hydroxy-4-oxo-2-butenoic acid
(915) 1-[(1-(4-Acetylbenzyl)-4-carboxy)pyrrol-2-yl]-3-hydroxy-3-(1H-1,2,4-triazol-3-yl)-propenone
(916) 1-(4-(2-methoxybenzyl)furan-3-yl)-3-hydroxy-3-(1H-1,2,4-triazol-3-yl)-propenone
(917) 1-(4-(4-Aminobenzyl)furan-2-yl)-3-hydroxy-3-(2H-tetrazol-5-yl)-propenone
(918) 1-[(1-(4-Fluorobenzenesulfonyl)-5-methoxymethyl)pyrrol-3-yl]-3-hydroxy-3-(1H-1,2,4-triazol-3-yl)-propenone
(919) 3-Hydroxy-3-(1H-1,2,4-triazol-3-yl)-1-(2-(2-trifluoromethylbenzyl)furan-3-yl)-propenone
(920) 1-(4-(2-Chlorophenoxy)furan-3-yl)-3-hydroxy-3-(1H-1,2,4-triazol-3-yl)-propenone
(921) 1-[(4-n-Butyl-1-(4-fluorobenzenesulfonyl))pyrrol-2-yl]-3-hydroxy-3-(1H-1,2,4-triazol-3-yl)-propenone
(922) 3-Hydroxy-1-(4-(pyridin-2-ylmethyl)furan-2-yl)-3-(1H-1,2,4-triazol-3-yl)-propenone
(923) 1-[(1-(4-Acetylbenzyl)-5-methoxymethyl)pyrrol-3-yl]-3-hydroxy-3-(1H-1,2,4-triazol-3-yl)-propenone
(924) 1-[(1-(4-Acetylbenzyl)-4-ethyl)pyrrol-2-yl]-3-hydroxy-3-(2H-tetrazol-5-yl)-propenone
(925) 3-Hydroxy-1-[(1-(4-methoxybenzyl)-4-methoxymethyl)pyrrol-2-yl]-3-(2H-tetrazol-5-yl)-propenone
(926) 1-[(1-(4-Aminobenzyl)-5-ethoxycarbonyl)pyrrol-3-yl]-3-hydroxy-3-(1H-1,2,4-triazol-3-yl)-propenone
(927) 1-[(1-(4-Acetylbenzyl)-4-phenoxymethyl)pyrrol-2-yl]-3-hydroxy-3-(1H-1,2,4-triazol-3-yl)-propenone
(928) 3-Hydroxy-1-[(4-methyl-5-(pyridin-4-ylmethyl))furan-2-yl]-3-(1H-1,2,4-triazol-3-yl)-propenone
(929) 4-(1-(4-Aminobenzyl)pyrrol-2-yl)-2-hydroxy-4-oxo-2-butenoic acid
(930) 1-[(1-(4-Aminobenzyl)-5-carboxy)pyrrol-3-yl]-3-hydroxy-3-(1H-1,2,4-triazol-3-yl)-propenone
(931) 1-[(4-Carboxy-1-(4-fluorobenzyl))pyrrol-2-yl]-3-hydroxy-3-(2H-tetrazol-5-yl)-propenone
(932) 2-Hydroxy-4-oxo-4-(1H-1-(pyridin-4-ylmethyl)pyrazol-4-yl)-2-butenoic acid
(933) 1-(1H-1-(4-Fluorobenzyl)pyrazol-3-yl)-3-hydroxy-3-(2H-tetrazol-5-yl)-propenone
(934) 1-[(1-(4-Fluorobenzyl)-5-phenoxymethyl)pyrrol-3-yl]-3-hydroxy-3-(1H-1,2,4-triazol-3-yl)-propenone
(935) 4-(5-(4-Acetylbenzyl)pyrrol-2-yl)-2-hydroxy-4-oxo-2-butenoic acid
(936) 1-[(1-Benzyl-4-carboxy)pyrrol-2-yl]-3-hydroxy-3-(1H-1,2,4-triazol-3-yl)-propenone
(937) 3-Hydroxy-1-(2H-2-(pyridin-4-ylmethyl)pyrazol-4-yl)-3-(1H-1,2,4-triazol-3-yl)-propenone
(938) 4-(4-(3-Fluorobenzyl)furan-3-yl)-2-hydroxy-4-oxo-2-butenoic acid
(939) 1-(4-(4-Acetylphenoxy)furan-3-yl)-3-hydroxy-3-(1H-1,2,4-triazol-3-yl)-propenone
(940) 1-(5-(3-Chlorobenzyl)furan-3-yl)-3-hydroxy-3-(1H-1,2,4-triazol-3-yl)-propenone
(941) 1-[(4-Ethyl-1-(2-fluorobenzyl))pyrrol-2-yl]-3-hydroxy-3-(1H-1,2,4-triazol-3-yl)-propenone
(942) 1-[(5-n-Butyl-1-(2-fluorobenzyl))pyrrol-3-yl]-3-hydroxy-3-(2H-tetrazol-5-yl)-propenone
(943) 1-(3-(4-Fluorophenyl)furan-2-yl)-3-hydroxy-3-(1H-1,2,4-triazol-3-yl)-propenone
(944) 1-[(1-(4-Fluorobenzenesulfonyl)-4-phenoxymethyl)pyrrol-2-yl]-3-hydroxy-3-(1H-1,2,4-triazol-3-yl)-propenone
(945) 1-[(1-Benzenesulfonyl-4-methoxymethyl)pyrrol-2-yl]-3-hydroxy-3-(2H-tetrazol-5-yl)-propenone
(946) 1-[(1-(4-Aminobenzyl)-4-(2-phenylethyl))pyrrol-2-yl]-3-hydroxy-3-(1H-1,2,4-triazol-3-yl)-propenone
(947) 1-(5-(4-Fluorobenzyl)pyrrol-3-yl)-3-hydroxy-3-(2H-tetrazol-5-yl)-propenone
(948) 3-Hydroxy-1-(5-(4-methylbenzyl)pyrrol-3-yl)-3-(1H-1,2,4-triazol-3-yl)-propenone
(949) 1-[(1-Benzenesulfonyl-4-(2-phenylethyl))pyrrol-3-yl]-3-hydroxy-3-(1H-1,2,4-triazol-3-yl)-propenone
(950) 1-(4-(2-Fluorobenzyl)pyrrol-3-yl)-3-hydroxy-3-(2H-tetrazol-5-yl)-propenone
(951) 2-Hydroxy-4-oxo-4-(3-(pyridin-2-ylmethyl)furan-2-yl)-2-butenoic acid
(952) 3-Hydroxy-1-(2-(pyridin-4-ylmethyl)furan-3-yl)-3-(1H-1,2,4-triazol-3-yl)-propenone
(953) 1-(2H-2-(4-Acetylbenzyl)pyrazol-4-yl)-3-hydroxy-3-(1H-1,2,4-triazol-3-yl)-propenone
(954) 3-Hydroxy-1-[(1-(4-methoxybenzyl)-5-n-propyl)pyrrol-3-yl]-3-(2H-tetrazol-5-yl)-propenone
(955) 1-[(1-Benzenesulfonyl-4-ethyl)pyrrol-2-yl]-3-hydroxy-3-(2H-tetrazol-5-yl)-propenone
(956) 1-[(1-Benzenesulfonyl-5-carboxy)pyrrol-3-yl]-3-hydroxy-3-(2H-tetrazol-5-yl)-propenone
(957) 4-(3-Benzylthiophen-2-yl)-2-hydroxy-4-oxo-2-butenoic acid
(958) 1-[(5-Ethoxycarbonyl-1-(4-methoxybenzyl))pyrrol-3-yl]-3-hydroxy-3-(2H-tetrazol-5-yl)-propenone
(959) 3-Hydroxy-1-(4-phenylthiofuran-2-yl)-3-(2H-tetrazol-5-yl)-propenone
(960) 3-Hydroxy-1-[(5-n-octyl-1-(pyridin-4-ylmethyl))pyrrol-3-yl]-3-(1H-1,2,4-triazol-3-yl)-propenone
(961) 1-(1H-1-(4-aminobenzyl)pyrazol-4-yl)-3-hydroxy-3-(1H-1,2,4-triazol-3-yl)-propenone
(962) 1-(5-(3-Fluorobenzyl)thiophen-3-yl)-3-hydroxy-3-(2H-tetrazol-5-yl)-propenone
(963) 4-(4-(4-Fluorobenzenesulfonyl)furan-3-yl)-2-hydroxy-4-oxo-2-butenoic acid
(964) 3-Hydroxy-1-(4-(pyridin-2-ylmethyl)furan-3-yl)-3-(2H-tetrazol-5-yl)-propenone
(965) 4-(4-Benzylthiazol-2-yl)-2-hydroxy-4-oxo-2-butenoic acid
(966) 1-(5-(4-Aminobenzyl)furan-3-yl)-3-hydroxy-3-(1H-1,2,4-triazol-3-yl)-propenone
(967) 1-[(4-Ethoxycarbonyl-1-(4-methoxybenzyl))pyrrol-2-yl]-3-hydroxy-3-(2H-tetrazol-5-yl)-propenone
(968) 1-[(5-Benzoyl-1-phenylthio)pyrrol-3-yl]-3-hydroxy-3-(1H-1,2,4-triazol-3-yl)-propenone
(969) 3-Hydroxy-1-[(5-methyl-3-(pyridin-4-ylmethyl))furan-2-yl]-3-(1H-1,2,4-triazol-3-yl)-propenone
(970) 1-[(5-Benzenesulfonyl-4-methyl)furan-2-yl]-3-hydroxy-3-(1H-1,2,4-triazol-3-yl)-propenone
(971) 3-Hydroxy-1-[(4-(2-phenylethyl)-1-(pyridin-2-ylmethyl))pyrrol-2-yl]-3-(2H-tetrazol-5-yl)-propenone
(972) 1-(5-(4-Fluorobenzenesulfonyl)pyrrol-3-yl)-3-hydroxy-3-(1H-1,2,4-triazol-3-yl)-propenone
(973) 3-Hydroxy-1-(2-phenylthiothiophen-3-yl)-3-(2H-tetrazol-5-yl)-propenone
(974) 1-(5-Benzenesulfonylfuran-3-yl)-3-hydroxy-3-(2H-tetrazol-5-yl)-propenone (975) 1-[(4-Benzenesulfonyl-2-methyl)furan-3-yl]-3-hydroxy-3-(1H-1,2,4-triazol-3-yl)-propenone
(976) 1-[(5-Fluoro-4-(pyridin-4-ylmethyl))furan-3-yl]-3-hydroxy-3-(1H-1,2,4-triazol-3-yl)-propenone
(977) 1-[(1-Benzyl-4-ethyl)pyrrol-3-yl]-3-hydroxy-3-(2H-tetrazol-5-yl)-propenone
(978) 1-[(4-Ethyl-1-(pyridin-4-ylmethyl))pyrrol-3-yl]-3-hydroxy-3-(2H-tetrazol-5-yl)-propenone
(979) 1-[(1-(4-Fluorobenzyl)-5-phenoxymethyl)pyrrol-3-yl]-3-hydroxy-3-(2H-tetrazol-5-yl)-propenone
(980) 3-Hydroxy-1-(5-(3-methoxybenzyl)furan-2-yl)-3-(1H-1,2,4-triazol-3-yl)-propenone
(981) 1-[(5-Carboxy-1-(4-chlorobenzenesulfonyl))pyrrol-3-yl]-3-hydroxy-3-(2H-tetrazol-5-yl)-propenone
(982) 1-(5-(4-Chlorophenylthio)furan-3-yl)-3-hydroxy-3-(1H-1,2,4-triazol-3-yl)-propenone
(983) 3-Hydroxy-1-[(4-phenyl-3-(2-phenylethyl))furan-2-yl]-3-(1H-1,2,4-triazol-3-yl)-propenone
(984) 4-(2-(2-fluorobenzyl)thiazol-4-yl)-2-hydroxy-4-oxo-2-butenoic acid
(985) 3-Hydroxy-1-(2H-2-(4-methylbenzyl)pyrazol-4-yl)-3-(2H-tetrazol-5-yl)-propenone
(986) 1-(3-(2-fluorobenzyl)pyrrol-2-yl)-3-hydroxy-3-(1H-1,2,4-triazol-3-yl)-propenone
(987) 1-(5-(4-Chlorobenzenesulfonyl)furan-3-yl)-3-hydroxy-3-(1H-1,2,4-triazol-3-yl)-propenone
(988) 1-[(4-Benzoyl-1-(3-fluorobenzyl))pyrrol-2-yl]-3-hydroxy-3-(1H-1,2,4-triazol-3-yl)-propenone
(989) 1-(3-(3-Fluorobenzyl)furan-2-yl)-3-hydroxy-3-(1H-1,2,4-triazol-3-yl)-propenone
(990) 1-[(4-(4-Fluorobenzyl)-3-(2-phenylethyl))furan-2-yl]-3-hydroxy-3-(1H-1,2,4-triazol-3-yl)-propenone
(991) 1-(3-Benzylthiophen-2-yl)-3-hydroxy-3-(1H-1,2,4-triazol-3-yl)-propenone
(992) 3-Hydroxy-1-(2-(3-methoxyphenoxy)furan-3-yl)-3-(1H-1,2,4-triazol-3-yl)-propenone
(993) 2-Hydroxy-4-(5-(4-methoxybenzyl)furan-2-yl)-4-oxo-2-butenoic acid
(994) 1-[(5-Fluoro-4-phenyl)furan-3-yl]-3-hydroxy-3-(1H-1,2,4-triazol-3-yl)-propenone
(995) 3-Hydroxy-1-(1H-1-(pyridin-2-ylmethyl)pyrazol-3-yl)-3-(2H-tetrazol-5-yl)-propenone
(996) 4-(4-(4-chlorobenzenesulfonyl)furan-3-yl)-2-hydroxy-4-oxo-2-butenoic acid
(997) 1-(5-(4-Aminophenoxy)furan-2-yl)-3-hydroxy-3-(1H-1,2,4-triazol-3-yl)-propenone
(998) 1-(2H-5-(4-Fluorobenzyl)pyrazol-3-yl)-3-hydroxy-3-(2H-tetrazol-5-yl)-propenone
(999) 3-Hydroxy-1-[(1-phenylthio-5-n-propyl)pyrrol-3-yl]-3-(2H-tetrazol-5-yl)-propenone
(1000) 1-[(5-Ethoxycarbonyl-1-(3-fluorobenzyl))pyrrol-3-yl]-3-hydroxy-3-(2H-tetrazol-5-yl)-propenone
(1001) 1-[(4-Ethoxycarbonyl-1-(pyridin-4-ylmethyl))pyrrol-2-yl]-3-hydroxy-3-(1H-1,2,4-triazol-3-yl)-propenone
(1002) 1-[(4-Benzoyl-1-phenylthio)pyrrol-2-yl]-3-hydroxy-3-(1H-1,2,4-triazol-3-yl)-propenone
(1003) 1-(4-(3-Fluorophenyl)furan-2-yl)-3-hydroxy-3-(1H-1,2,4-triazol-3-yl)-propenone
(1004) 4-(2-(4-Aminobenzyl)thiophen-3-yl)-2-hydroxy-4-oxo-2-butenoic acid
(1005) 3-Hydroxy-1-(2-(pyridin-2-ylmethyl)thiazol-4-yl)-3-(2H-tetrazol-5-yl)-propenone
(1006) 3-Hydroxy-1-[(4-methyl-5-(pyridin-4-ylmethyl))furan-3-yl]-3-(1H-1,2,4-triazol-3-yl)-propenone
(1007) 1-(3-(3-Fluorobenzyl)pyrrol-2-yl)-3-hydroxy-3-(2H-tetrazol-5-yl)-propenone
(1008) 4-(3-(2-Fluorobenzyl)thiophen-2-yl)-2-hydroxy-4-oxo-2-butenoic acid
(1009) 1-(4-n-Butylfuran-2-yl)-3-hydroxy-3-(1H-1,2,4-triazol-3-yl)-propenone
(1010) 3-Hydroxy-3-(1H-1,2,4-triazol-3-yl)-1-(5-(2-trifluoromethylbenzyl)furan-2-yl)-propenone
(1011) 1-[(5-Carboxy-1-phenylthio)pyrrol-3-yl]-3-hydroxy-3-(2H-tetrazol-5-yl)-propenone
(1012) 1-[(1-(4-Aminobenzyl)-5-methoxymethyl)pyrrol-3-yl]-3-hydroxy-3-(2H-tetrazol-5-yl)-propenone
(1013) 3-Hydroxy-1-(5-(4-methoxyphenylthio)furan-2-yl)-3-(1H-1,2,4-triazol-3-yl)-propenone
(1014) 1-(5-(2-Fluorobenzyl)thiophen-3-yl)-3-hydroxy-3-(2H-tetrazol-5-yl)-propenone
(1015) 3-Hydroxy-1-(2-(pyridin-2-ylmethyl)pyrrol-3-yl)-3-(2H-tetrazol-5-yl)-propenone
(1016) 1-[(1-Benzyl-4-ethoxycarbonyl)pyrrol-2-yl]-3-hydroxy-3-(1H-1,2,4-triazol-3-yl)-propenone
(1017) 1-[(4-Benzoyl-1-(pyridin-4-ylmethyl))pyrrol-2-yl]-3-hydroxy-3-(2H-tetrazol-5-yl)-propenone
(1018) 1-(1H-1-(4-Chlorobenzenesulfonyl)pyrazol-4-yl)-3-hydroxy-3-(2H-tetrazol-5-yl)-propenone
(1019) 1-[(4-Carboxy-1-(pyridin-4-ylmethyl))pyrrol-2-yl]-3-hydroxy-3-(1H-1,2,4-triazol-3-yl)-propenone
(1020) 4-(4-(4-Acetylbenzyl)thiophen-2-yl)-2-hydroxy-4-oxo-2-butenoic acid
(1021) 1-[(4-n-Butyl-1-phenylthio)pyrrol-2-yl]-3-hydroxy-3-(2H-tetrazol-5-yl)-propenone
(1022) 1-(2H-4-(4-Acetylbenzyl)pyrazol-3-yl)-3-hydroxy-3-(1H-1,2,4-triazol-3-yl)-propenone
(1023) 1-[(1-Benzenesulfonyl-4-carboxy)pyrrol-2-yl]-3-hydroxy-3-(2H-tetrazol-5-yl)-propenone
(1024) 3-Hydroxy-1-(4-(4-methoxybenzyl)furan-3-yl)-3-(1H-1,2,4-triazol-3-yl)-propenone
(1025) 1-[(1-(3-Fluorobenzyl)-5-methoxymethyl)pyrrol-3-yl]-3-hydroxy-3-(2H-tetrazol-5-yl)-propenone
(1026) 1-[(4-n-Butyl-1-(pyridin-2-ylmethyl))pyrrol-2-yl]-3-hydroxy-3-(1H-1,2,4-triazol-3-yl)-propenone
(1027) 1-[(5-Carboxy-1-(4-fluorobenzyl))pyrrol-3-yl]-3-hydroxy-3-(2H-tetrazol-5-yl)-propenone
(1028) 1-[(1-(4-Chlorobenzenesulfonyl)-4-ethyl)pyrrol-3-yl]-3-hydroxy-3-(1H-1,2,4-triazol-3-yl)-propenone
(1029) 1-[(1-(4-Acetylbenzyl)-4-n-butyl)pyrrol-2-yl]-3-hydroxy-3-(1H-1,2,4-triazol-3-yl)-propenone
(1030) 1-[(5-Ethoxycarbonyl-1-phenylthio)pyrrol-3-yl]-3-hydroxy-3-(2H-tetrazol-5-yl)-propenone
(1031) 1-(2-(3-Fluorobenzyl)furan-3-yl)-3-hydroxy-3-(2H-tetrazol-5-yl)-propenone
(1032) 1-[(1-Benzenesulfonyl-5-methoxymethyl)pyrrol-3-yl]-3-hydroxy-3-(2H-tetrazol-5-yl)-propenone
(1033) 3-Hydroxy-1-(4-(pyridin-4-ylmethyl)pyrrol-3-yl)-3-(1H-1,2,4-triazol-3-yl)-propenone
(1034) 4-(2-(2-Fluorobenzyl)furan-3-yl)-2-hydroxy-4-oxo-2-butenoic acid
(1035) 2-Hydroxy-4-(2H-5-(4-methylbenzyl)pyrazol-3-yl)-4-oxo-2-butenoic acid
(1036) 4-(2-(4-Chlorobenzenesulfonyl)thiophen-3-yl)-2-hydroxy-4-oxo-2-butenoic acid
(1037) 3-Hydroxy-1-[(5-n-propyl-1-(pyridin-2-ylmethyl))pyrrol-3-yl]-3-(1H-1,2,4-triazol-3-yl)-propenone
(1038) 1-[(5-Carboxy-1-(4-fluorobenzenesulfonyl))pyrrol-3-yl]-3-hydroxy-3-(2H-tetrazol-5-yl)-propenone
(1039) 1-[(5-Chloro-4-(pyridin-4-ylmethyl))furan-2-yl]-3-hydroxy-3-(1H-1,2,4-triazol-3-yl)-propenone
(1040) 3-Hydroxy-1-(5-(4-methylphenylthio)furan-3-yl)-3-(1H-1,2,4-triazol-3-yl)-propenone
(1041) 1-(2-Benzylpyrrol-3-yl)-3-hydroxy-3-(2H-tetrazol-5-yl)-propenone (1042) 4-(5-(2-Fluorobenzyl)thiophen-3-yl)-2-hydroxy-4-oxo-2-butenoic acid
(1043) 3-Hydroxy-1-(5-phenylfuran-2-yl)-3-(1H-1,2,4-triazol-3-yl)-propenone
(1044) 1-(2-Benzylthiazol-4-yl)-3-hydroxy-3-(1H-1,2,4-triazol-3-yl)-propenone
(1045) 4-(4-(4-Fluorobenzyl)furan-3-yl)-2-hydroxy-4-oxo-2-butenoic acid
(1046) 1-(4-(4-Fluorobenzenesulfonyl)thiophen-2-yl)-3-hydroxy-3-(1H-1,2,4-triazol-3-yl)-propenone
(1047) 1-(5-(4-Aminobenzyl)furan-3-yl)-3-hydroxy-3-(2H-tetrazol-5-yl)-propenone
(1048) 3-Hydroxy-1-[(4-methoxymethyl-1-(4-methylbenzyl))pyrrol-2-yl]-3-(1H-1,2,4-triazol-3-yl)-propenone
(1049) 1-[(1-Benzyl-4-ethyl)pyrrol-2-yl]-3-hydroxy-3-(2H-tetrazol-5-yl)-propenone
(1050) 3-Hydroxy-1-[(1-(4-methoxybenzyl)-4-n-propyl)pyrrol-2-yl]-3-(2H-tetrazol-5-yl)-propenone
(1051) 4-(1H-1-(3-Fluorobenzyl)pyrazol-3-yl)-2-hydroxy-4-oxo-2-butenoic acid
(1052) 1-(1-(2-Fluorobenzyl)pyrrol-2-yl)-3-hydroxy-3-(2H-tetrazol-5-yl)-propenone
(1053) 1-(4-Benzenesulfonylthiazol-2-yl)-3-hydroxy-3-(2H-tetrazol-5-yl)-propenone
(1054) 3-Hydroxy-1-(1-(4-methoxybenzyl)pyrrol-2-yl)-3-(1H-1,2,4-triazol-3-yl)-propenone
(1055) 1-(4-(4-Chlorobenzyl)furan-2-yl)-3-hydroxy-3-(1H-1,2,4-triazol-3-yl)-propenone
(1056) 1-[(4-Fluoro-5-(4-fluorobenzyl))furan-3-yl]-3-hydroxy-3-(1H-1,2,4-triazol-3-yl)-propenone
(1057) 4-(1-(4-Acetylbenzyl)pyrrol-2-yl)-2-hydroxy-4-oxo-2-butenoic acid
(1058) 4-(5-Benzylpyrrol-2-yl)-2-hydroxy-4-oxo-2-butenoic acid
(1059) 3-Hydroxy-1-(2-(4-methoxybenzyl)thiophen-3-yl)-3-(1H-1,2,4-triazol-3-yl)-propenone
(1060) 1-(4-Benzenesulfonylthiazol-2-yl)-3-hydroxy-3-(1H-1,2,4-triazol-3-yl)-propenone
(1061) 1-[(1-(2-Fluorobenzyl)-4-(2-phenylethyl))pyrrol-3-yl]-3-hydroxy-3-(2H-tetrazol-5-yl)-propenone
(1062) 4-(4-(3-Fluorobenzyl)thiophen-2-yl)-2-hydroxy-4-oxo-2-butenoic acid
(1063) 1-(2H-4-(2-Fluorobenzyl)pyrazol-3-yl)-3-hydroxy-3-(2H-tetrazol-5-yl)-propenone
(1064) 1-[(5-Chloro-3-(pyridin-4-ylmethyl))furan-2-yl]-3-hydroxy-3-(1H-1,2,4-triazol-3-yl)-propenone
(1065) 3-Hydroxy-1-[(1-(4-methylbenzyl)-5-n-octyl)pyrrol-3-yl]-3-(2H-tetrazol-5-yl)-propenone
(1066) 1-[(5-Benzoyl-1-phenylthio)pyrrol-3-yl]-3-hydroxy-3-(2H-tetrazol-5-yl)-propenone
(1067) 2-Hydroxy-4-(5-(4-methylbenzyl)thiophen-3-yl)-4-oxo-2-butenoic acid
(1068) 1-(4-(3-Fluorobenzyl)pyrrol-3-yl)-3-hydroxy-3-(1H-1,2,4-triazol-3-yl)-propenone
(1069) 2-Hydroxy-4-oxo-4-(5-phenylthiofuran-3-yl)-2-butenoic acid
(1070) 1-[(1-(2-Fluorobenzyl)-4-n-octyl)pyrrol-2-yl]-3-hydroxy-3-(1H-1,2,4-triazol-3-yl)-propenone
(1071) 1-(2H-4-(4-Acetylbenzyl)pyrazol-3-yl)-3-hydroxy-3-(2H-tetrazol-5-yl)-propenone
(1072) 2-Hydroxy-4-(4-(4-methylbenzyl)furan-2-yl)-4-oxo-2-butenoic acid
(1073) 4-(2H-2-(4-Fluorobenzyl)pyrazol-4-yl)-2-hydroxy-4-oxo-2-butenoic acid
(1074) 4-(5-(3-Fluorobenzyl)pyrrol-2-yl)-2-hydroxy-4-oxo-2-butenoic acid
(1075) 3-Hydroxy-1-(5-(4-methylbenzyl)thiophen-3-yl)-3-(1H-1,2,4-triazol-3-yl)-propenone
(1076) 1-[(5-Chloro-4-(4-fluorobenzyl))furan-3-yl]-3-hydroxy-3-(1H-1,2,4-triazol-3-yl)-propenone
(1077) 1-[(4-Benzenesulfonyl-5-fluoro)furan-3-yl]-3-hydroxy-3-(1H-1,2,4-triazol-3-yl)-propenone
(1078) 3-Hydroxy-1-[(4-(2-phenylethyl)-1-(pyridin-4-ylmethyl))pyrrol-2-yl]-3-(2H-tetrazol-5-yl)-propenone
(1079) 1-[(5-Ethoxycarbonyl-1-(4-fluorobenzyl))pyrrol-3-yl]-3-hydroxy-3-(2H-tetrazol-5-yl)-propenone
(1080) 4-(2-(4-Aminobenzyl)thiazol-4-yl)-2-hydroxy-4-oxo-2-butenoic acid
(1081) 3-Hydroxy-1-(3-(4-methoxyphenylthio)furan-2-yl)-3-(1H-1,2,4-triazol-3-yl)-propenone
(1082) 1-[(1-(4-Chlorobenzenesulfonyl)-4-n-octyl)pyrrol-2-yl]-3-hydroxy-3-(1H-1,2,4-triazol-3-yl)-propenone
(1083) 4-(5-Benzenesulfonylpyrrol-2-yl)-2-hydroxy-4-oxo-2-butenoic acid
(1084) 1-[(1-Benzenesulfonyl-4-ethyl)pyrrol-2-yl]-3-hydroxy-3-(1H-1,2,4-triazol-3-yl)-propenone
(1085) 1-[(1-(4-Fluorobenzenesulfonyl)-5-n-propyl)pyrrol-3-yl]-3-hydroxy-3-(2H-tetrazol-5-yl)-propenone
(1086) 4-(3-Benzylfuran-2-yl)-2-hydroxy-4-oxo-2-butenoic acid
(1087) 1-[(3-Chloro-4-phenyl)furan-2-yl]-3-hydroxy-3-(1H-1,2,4-triazol-3-yl)-propenone
(1088) 3-Hydroxy-1-[(4-n-octyl-1-(pyridin-2-ylmethyl))pyrrol-2-yl]-3-(2H-tetrazol-5-yl)-propenone
(1089) 1-(2H-4-(4-Aminobenzyl)pyrazol-3-yl)-3-hydroxy-3-(1H-1,2,4-triazol-3-yl)-propenone
(1090) 1-(3-(3-Fluorobenzyl)thiophen-2-yl)-3-hydroxy-3-(1H-1,2,4-triazol-3-yl)-propenone
(1091) 1-(4-(2-Chlorobenzyl)furan-2-yl)-3-hydroxy-3-(1H-1,2,4-triazol-3-yl)-propenone
(1092) 1-(2-(3-Fluorobenzyl)thiazol-4-yl)-3-hydroxy-3-(1H-1,2,4-triazol-3-yl)-propenone
(1093) 1-[(1-(4-Aminobenzyl)-4-n-octyl)pyrrol-2-yl]-3-hydroxy-3-(1H-1,2,4-triazol-3-yl)-propenone
(1094) 1-(2-(3-Fluorophenyl)furan-3-yl)-3-hydroxy-3-(1H-1,2,4-triazol-3-yl)-propenone
(1095) 4-(4-n-Butylfuran-3-yl)-2-hydroxy-4-oxo-2-butenoic acid
(1096) 1-(1-(4-Fluorobenzenesulfonyl)pyrrol-3-yl)-3-hydroxy-3-(1H-1,2,4-triazol-3-yl)-propenone
(1097) 1-[(4-Ethoxycarbonyl-1-(pyridin-2-ylmethyl))pyrrol-2-yl]-3-hydroxy-3-(1H-1,2,4-triazol-3-yl)-propenone
(1098) 1-(2-(4-Aminobenzyl)pyrrol-3-yl)-3-hydroxy-3-(1H-1,2,4-triazol-3-yl)-propenone
(1099) 1-(2H-4-(4-Chlorobenzenesulfonyl)pyrazol-3-yl)-3-hydroxy-3-(2H-tetrazol-5-yl)-propenone
(1100) 2-Hydroxy-4-oxo-4-(1-(pyridin-4-ylmethyl)pyrrol-2-yl)-2-butenoic acid
(1101) 1-(4-(2-Fluorobenzyl)furan-2-yl)-3-hydroxy-3-(1H-1,2,4-triazol-3-yl)-propenone
(1102) 1-[(1-(3-Fluorobenzyl)-4-(2-phenylethyl))pyrrol-2-yl]-3-hydroxy-3-(1H-1,2,4-triazol-3-yl)-propenone
(1103) 1-[(5-Chloro-4-phenyl)furan-3-yl]-3-hydroxy-3-(1H-1,2,4-triazol-3-yl)-propenone
(1104) 1-(5-(3-Chlorophenylthio)furan-3-yl)-3-hydroxy-3-(1H-1,2,4-triazol-3-yl)-propenone
(1105) 1-(2-(4-Chlorobenzenesulfonyl)pyrrol-3-yl)-3-hydroxy-3-(2H-tetrazol-5-yl)-propenone
(1106) 1-(1-Benzenesulfonylpyrrol-2-yl)-3-hydroxy-3-(1H-1,2,4-triazol-3-yl)-propenone
(1107) 1-(4-(4-Aminobenzyl)thiazol-2-yl)-3-hydroxy-3-(2H-tetrazol-5-yl)-propenone (1108) 1-(2H-5-Benzylpyrazol-3-yl)-3-hydroxy-3-(1H-1,2,4-triazol-3-yl)-propenone
(1109) 4-(4-(4-Acetylbenzyl)pyrrol-2-yl)-2-hydroxy-4-oxo-2-butenoic acid
(1110) 1-[(1-(4-Aminobenzyl)-5-carboxy)pyrrol-3-yl]-3-hydroxy-3-(2H-tetrazol-5-yl)-propenone
(1111) 3-Hydroxy-1-[(4-n-propyl-1-(pyridin-4-ylmethyl))pyrrol-2-yl]-3-(2H-tetrazol-5-yl)-propenone
(1112) 1-(4-(2-Fluorophenyl)furan-2-yl)-3-hydroxy-3-(1H-1,2,4-triazol-3-yl)-propenone
(1113) 3-Hydroxy-1-[(4-(2-phenylethyl)-3-(pyridin-4-ylmethyl))furan-2-yl]-3-(1H-triazol-3-yl)-propenone
(1114) 1-[(4-Benzoyl-1-(pyridin-2-ylmethyl))pyrrol-2-yl]-3-hydroxy-3-(1H-1,2,4-triazol-3-yl)-propenone
(1115) 3-Hydroxy-1-[(5-methoxymethyl-1-(4-methylbenzyl))pyrrol-3-yl]-3-(1H-1,2,4-triazol-3-yl)-propenone
(1116) 2-Hydroxy-4-oxo-4-(5-(pyridin-4-ylmethyl)thiophen-3-yl)-2-butenoic acid
(1117) 1-[(1-(4-Chlorobenzenesulfonyl)-4-n-propyl)pyrrol-2-yl]-3-hydroxy-3-(2H-tetrazol-5-yl)-propenone
(1118) 1-(5-(4-Fluorobenzenesulfonyl)thiophen-3-yl)-3-hydroxy-3-(1H-1,2,4-triazol-3-yl)-propenone
(1119) 1-[(1-(4-Fluorobenzyl)-4-(2-phenylethyl))pyrrol-2-yl]-3-hydroxy-3-(2H-tetrazol-5-yl)-propenone
(1120) 3-Hydroxy-1-(5-(3-methoxyphenylthio)furan-2-yl)-3-(1H-1,2,4-triazol-3-yl)-propenone
(1121) 1-(4-(4-Aminobenzyl)pyrrol-2-yl)-3-hydroxy-3-(1H-1,2,4-triazol-3-yl)-propenone
(1122) 1-[(5-Ethoxycarbonyl-1-(pyridin-2-ylmethyl))pyrrol-3-yl]-3-hydroxy-3-(1H-1,2,4-triazol-3-yl)-propenone
(1123) 3-Hydroxy-1-(2-(pyridin-4-ylmethyl)thiophen-3-yl)-3-(2H-tetrazol-5-yl)-propenone
(1124) 1-[(5-n-Butyl-1-phenylthio)pyrrol-3-yl]-3-hydroxy-3-(1H-1,2,4-triazol-3-yl)-propenone
(1125) 1-(3-(2-Fluorobenzyl)pyrrol-2-yl)-3-hydroxy-3-(2H-tetrazol-5-yl)-propenone
(1126) 3-Hydroxy-1-(2H-2-(pyridin-2-ylmethyl)pyrazol-3-yl)-3-(2H-tetrazol-5-yl)-propenone
(1127) 3-Hydroxy-1-[(1-(4-methylbenzyl)-4-(2-phenylethyl))pyrrol-3-yl]-3-(2H-tetrazol-5-yl)-propenone
(1128) 1-(4-(3-Fluorobenzyl)thiazol-2-yl)-3-hydroxy-3-(1H-1,2,4-triazol-3-yl)-propenone
(1129) 3-Hydroxy-1-(5-(pyridin-4-ylmethyl)thiophen-2-yl)-3-(1H-1,2,4-triazol-3-yl)-propenone
(1130) 4-(2-(4-Aminobenzyl)pyrrol-3-yl)-2-hydroxy-4-oxo-2-butenoic acid
(1131) 3-Hydroxy-1-[(4-n-propyl-1-pyridin-4-ylmethyl))pyrrol-2-yl]-3-(1H-1,2,4-triazol-3-yl)-propenone
(1132) 1-(5-(4-Aminophenoxy)furan-3-yl)-3-hydroxy-3-(1H-1,2,4-triazol-3-yl)-propenone
(1133) 1-(2H-2-Benzenesulfonylpyrazol-4-yl)-3-hydroxy-3-(2H-tetrazol-5-yl)-propenone
(1134) 1-[(1-(4-Aminobenzyl)-4-ethyl)pyrrol-2-yl]-3-hydroxy-3-(1H-1,2,4-triazol-3-yl)-propenone
(1135) 1-(5-(4-Fluorobenzenesulfonyl)furan-3-yl)-3-hydroxy-3-(1H-1,2,4-triazol-3-yl)-propenone
(1136) 3-Hydroxy-1-(5-(4-methoxybenzyl)thiophen-3-yl)-3-(2H-tetrazol-5-yl)-propenone
(1137) 1-(1-(3-Fluorobenzyl)pyrrol-2-yl)-3-hydroxy-3-(1H-1,2,4-triazol-3-yl)-propenone
(1138) 3-Hydroxy-1-(4-(4-methylbenzyl)furan-3-yl)-3-(2H-tetrazol-5-yl)-propenone
(1139) 1-[(4-Ethoxycarbonyl-1-(4-methylbenzyl))pyrrol-2-yl]-3-hydroxy-3-(1H-1,2,4-triazol-3-yl)-propenone
(1140) 3-Hydroxy-3-(1H-1,2,4-triazol-3-yl)-1-(5-(3-trifluoromethylphenoxy)furan-3-yl)-propenone
(1141) 1-[(4-n-Butyl-1-(2-fluorobenzyl))pyrrol-2-yl]-3-hydroxy-3-(2H-tetrazol-5-yl)-propenone
(1142) 1-[(1-(4-Aminobenzyl)-4-ethoxycarbonyl)pyrrol-2-yl]-3-hydroxy-3-(1H-1,2,4-triazol-3-yl)-propenone
(1143) 1-[(1-(4-Chlorobenzenesulfonyl)-4-methoxymethyl)pyrrol-2-yl]-3-hydroxy-3-(2H-tetrazol-5-yl)-propenone
(1144) 1-[(3-Benzenesulfonyl-5-(2-phenylethyl))furan-2-yl]-3-hydroxy-3-(1H-1,2,4-triazol-3-yl)-propenone
(1145) 3-Hydroxy-1-(4-(4-methoxybenzyl)pyrrol-2-yl)-3-(2H-tetrazol-5-yl)-propenone
(1146) 1-[(1-(4-Aminobenzyl)-4-(2-phenylethyl))pyrrol-3-yl]-3-hydroxy-3-(1H-1,2,4-triazol-3-yl)-propenone
(1147) 4-(3-(4-Fluorobenzyl)furan-2-yl)-2-hydroxy-4-oxo-2-butenoic acid
(1148) 1-[(4-Ethyl-1-(pyridin-2-ylmethyl))pyrrol-3-yl]-3-hydroxy-3-(2H-tetrazol-5-yl)-propenone
(1149) 1-(2H-2-Benzylpyrazol-3-yl)-3-hydroxy-3-(2H-tetrazol-5-yl)-propenone
(1150) 1-(4-(4-Acetylbenzyl)furan-3-yl)-3-hydroxy-3-(2H-tetrazol-5-yl)-propenone
(1151) 1-[(1-(4-Chlorobenzenesulfonyl)-5-ethoxycarbonyl)pyrrol-3-yl]-3-hydroxy-3-(1H-1,2,4-triazol-3-yl)-propenone
(1152) 3-Hydroxy-1-(4-phenylthiothiazol-2-yl)-3-(2H-tetrazol-5-yl)-propenone
(1153) 2-Hydroxy-4-oxo-4-(4-(pyridin-4-ylmethyl)pyrrol-2-yl)-2-butenoic acid
(1154) 4-(5-(4-Fluorobenzenesulfonyl)thiophen-3-yl)-2-hydroxy-4-oxo-2-butenoic acid
(1155) 1-[(1-(4-Chlorobenzenesulfonyl)-4-n-octyl)pyrrol-2-yl]-3-hydroxy-3-(2H-tetrazol-5-yl)-propenone
(1156) 1-(3-(3-Chlorophenoxy)furan-2-yl)-3-hydroxy-3-(1H-1,2,4-triazol-3-yl)-propenone
(1157) 1-[(4-n-Butyl-1-(4-methylbenzyl))pyrrol-2-yl]-3-hydroxy-3-(2H-tetrazol-5-yl)-propenone
(1158) 1-[(1-(4-Fluorobenzyl)-5-methoxymethyl)pyrrol-3-yl]-3-hydroxy-3-(1H-1,2,4-triazol-3-yl)-propenone
(1159) 1-(4-Benzenesulfonylfuran-2-yl)-3-hydroxy-3-(1H-1,2,4-triazol-3-yl)-propenone
(1160) 1-[(1-(4-Aminobenzyl)-4-ethyl)pyrrol-3-yl]-3-hydroxy-3-(1H-1,2,4-triazol-3-yl)-propenone
(1161) 4-(4-(2-Fluorobenzyl)pyrrol-2-yl)-2-hydroxy-4-oxo-2-butenoic acid
(1162) 1-(3-(4-Acetylbenzyl)furan-3-yl)-3-hydroxy-3-(1H-1,2,4-triazol-3-yl)-propenone
(1163) 1-[(4-n-Butyl-1-(pyridin-4-ylmethyl))pyrrol-3-yl]-3-hydroxy-3-(2H-tetrazol-5-yl)-propenone
(1164) 1-[(1-(4-Chlorobenzenesulfonyl)-5-n-propyl)pyrrol-3-yl]-3-hydroxy-3-(1H-1,2,4-triazol-3-yl)-propenone
(1165) 1-(1-(3-fluorobenzyl)pyrrol-3-yl)-3-hydroxy-3-(2H-tetrazol-5-yl)-propenone
(1166) 3-Hydroxy-1-(5-phenylthiothiophen-2-yl)-3-(1H-1,2,4-triazol-3-yl)-propenone
(1167) 1-(2-(4-Aminobenzyl)thiophen-3-yl)-3-hydroxy-3-(2H-tetrazol-5-yl)-propenone
(1168) 1-[(1-(4-Aminobenzyl)-4-phenoxymethyl)pyrrol-2-yl]-3-hydroxy-3-(1H-1,2,4-triazol-3-yl)-propenone
(1169) 1-(4-Benzylpyrrol-3-yl)-3-hydroxy-3-(1H-1,2,4-triazol-3-yl)-propenone
(1170) 1-(5-(4-Chlorobenzonesulfonyl)pyrrol-2-yl)-3-hydroxy-3-(2H-tetrazol-5-yl)-propenone
(1171) 3-Hydroxy-1-(3-phenylthiofuran-2-yl)-3-(1H-1,2,4-triazol-3-yl)-propenone
(1172) 4-(4-(4-Acetylbenzyl)thiophen-3-yl)-2-hydroxy-4-oxo-2-butenoic acid
(1173) 3-Hydroxy-1-[(4-(2-phenylethyl)-1-phenylthio)pyrrol-2-yl]-3-(1H-1,2,4-triazol-3-yl)-propenone (1174) 1-[(1-(4-Acetylbenzyl)-4-(2-phenylethyl))pyrrol-3-yl]-3-hydroxy-3-(1H-1,2,4-triazol-3-yl)-propenone
(1175) 1-[(2-Benzenesulfonyl-4-methyl)furan-3-yl]-3-hydroxy-3-(1H-1,2,4-triazol-3-yl)-propenone
(1176) 1-(5-(4-Acetylbenzyl)pyrrol-3-yl)-3-hydroxy-3-(2H-tetrazol-5-yl)-propenone
(1177) 2-Hydroxy-4-oxo-4-(1H-1-phenylthiopyrazol-4-yl)-2-butenoic acid
(1178) 4-(4-(4-chlorobenzenesulfonyl)thiophen-3-yl)-2-hydroxy-4-oxo-2-butenoic acid
(1179) 3-Hydroxy-3-(1H-1,2,4-triazol-3-yl)-1-(3-(3-trifluoromethylphenylthio)furan-2-yl)-propenone
(1180) 4-(4-(4-Chlorobenzenesulfonyl)thiazol-2-yl)-2-hydroxy-4-oxo-2-butenoic acid
(1181) 1-(4-(4-Chlorobenzenesulfonyl)pyrrol-2-yl)-3-hydroxy-3-(2H-tetrazol-5-yl)-propenone
(1182) 3-Hydroxy-1-(4-(pyridin-4-ylmethyl)pyrrol-2-yl)-3-(1H-1,2,4-triazol-3-yl)-propenone
(1183) 1-(2-(4-Fluorophenyl)furan-3-yl)-3-hydroxy-3-(1H-1,2,4-triazol-3-yl)-propenone
(1184) 1-[(1-(3-Fluorobenzyl)-5-phenoxymethyl)pyrrol-3-yl]-3-hydroxy-3-(1H-1,2,4-triazol-3-yl)-propenone
(1185) 4-(4-(4-Chlorobenzenesulfonyl)pyrrol-2-yl)-2-hydroxy-4-oxo-2-butenoic acid
(1186) 3-Hydroxy-3-(1H-1,2,4-triazol-3-yl)-1-(4-(4-trifluoromethylphenoxy)furan-3-yl)-propenone
(1187) 4-(2H-5-(4-Chlorobenzenesulfonyl)pyrazol-3-yl)-2-hydroxy-4-oxo-2-butenoic acid
(1188) 1-[(1-(3-Fluorobenzyl)-4-n-propyl)pyrrol-2-yl]-3-hydroxy-3-(2H-tetrazol-5-yl)-propenone
(1189) 1-[(1-(4-Acetylbenzyl)-4-methoxymethyl)pyrrol-2-yl]-3-hydroxy-3-(1H-1,2,4-triazol-3-yl)-propenone
(1190) 3-Hydroxy-1-(2H-2-(pyridin-4-ylmethyl)pyrazol-3-yl)-3-(1H-1,2,4-triazol-3-yl)-propenone
(1191) 2-Hydroxy-4-oxo-4-(2-phenylthiopyrrol-3-yl)-2-butenoic acid
(1192) 1-[(1-(2-Fluorobenzyl)-5-methoxymethyl)pyrrol-3-yl]-3-hydroxy-3-(1H-1,2,4-triazol-3-yl)-propenone
(1193) 3-Hydroxy-1-[(5-phenoxymethyl-1-phenylthio)pyrrol-3-yl]-3-(2H-tetrazol-5-yl)-propenone
(1194) 1-[(1-(2-Fluorobenzyl)-5-methoxymethyl)pyrrol-3-yl]-3-hydroxy-3-(2H-tetrazol-5-yl)-propenone
(1195) 3-Hydroxy-1-[(4-n-propyl-1-(pyridin-2-ylmethyl))pyrrol-2-yl]-3-(1H-1,2,4-triazol-3-yl)-propenone
(1196) 2-Hydroxy-4-oxo-4-(2H-2-(pyridin-2-ylmethyl)pyrazol-4-yl)-2-butenoic acid
(1197) 1-(5-Benzylfuran-2-yl)-3-hydroxy-3-(2H-tetrazol-5-yl)-propenone
(1198) 1-[(5-Carboxy-1-(3-fluorobenzyl))pyrrol-3-yl]-3-hydroxy-3-(1H-1,2,4-triazol-3-yl)-propenone
(1199) 1-[(5-Benzenesulfonyl-2-fluoro)furan-3-yl]-3-hydroxy-3-(1H-1,2,4-triazol-3-yl)-propenone
(1200) 1-[(5-Ethoxycarbonyl-1-(4-methylbenzyl))pyrrol-3-yl]-3-hydroxy-3-(2H-tetrazol-5-yl)-propenone
(1201) 1-(5-Benzenesulfonylthiophen-3-yl)-3-hydroxy-3-(1H-1,2,4-triazol-3-yl)-propenone
(1202) 3-Hydroxy-3-(1H-1,2,4-triazol-3-yl)-1-(2-(4-trifluoromethylbenzyl)furan-3-yl)-propenone
(1203) 1-(5-(2-Chlorophenoxy)furan-2-yl)-3-hydroxy-3-(1H-1,2,4-triazol-3-yl)-propenone
(1204) 3-Hydroxy-1-(2H-2-(4-methoxybenzyl)pyrazol-4-yl)-3-(1H-1,2,4-triazol-3-yl)-propenone
(1205) 1-(4-(4-Chlorobenzenesulfonyl)thiophen-3-yl)-3-hydroxy-3-(1H-1,2,4-triazol-3-yl)-propenone
(1206) 3-Hydroxy-1-(5-(pyridin-2-ylmethyl)furan-3-yl)-3-(2H-tetrazol-5-yl)-propenone
(1207) 1-[(1-Benzyl-5-methoxymethyl)pyrrol-3-yl]-3-hydroxy-3-(2H-tetrazol-5-yl)-propenone
(1208) 3-Hydroxy-3-(1H-1,2,4-triazol-3-yl)-1-(3-(2-trifluoromethylbenzyl)furan-2-yl)-propenone
(1209) 1-(2-(4-Fluorobenzyl)pyrrol-3-yl)-3-hydroxy-3-(2H-tetrazol-5-yl)-propenone
(1210) 4-(1H-1-(4-Acetylbenzyl)pyrazol-4-yl)-2-hydroxy-4-oxo-2-butenoic acid
(1211) 4-(2-(4-Acetylbenzyl)furan-3-yl)-2-hydroxy-4-oxo-2-butenoic acid
(1212) 2-Hydroxy-4-oxo-4-(4-(pyridin-2-ylmethyl)pyrrol-2-yl)-2-butenoic acid
(1213) 1-[(1-(4-Fluorobenzenesulfonyl)-4-n-octyl)pyrrol-2-yl]-3-hydroxy-3-(2H-tetrazol-5-yl)-propenone
(1214) 1-(2H-5-(4-Fluorobenzenesulfonyl)pyrazol-3-yl)-3-hydroxy-3-(2H-tetrazol-5-yl)-propenone
(1215) 1-[(1-Benzyl-4-(2-phenylethyl))pyrrol-2-yl]-3-hydroxy-3-(1H-1,2,4-triazol-3-yl)-propenone
(1216) 1-(5-(4-Acetylbenzyl)thiophen-2-yl)-3-hydroxy-3-(2H-tetrazol-5-yl)-propenone
(1217) 3-Hydroxy-1-(3-(3-methoxyphenoxy)furan-2-yl)-3-(1H-1,2,4-triazol-3-yl)-propenone
(1218) 1-[(3-(4-Fluorobenzyl)-4-(2-phenylethyl))furan-2-yl]-3-hydroxy-3-(1H-1,2,4-triazol-3-yl)-propenone
(1219) 1-[(1-Benzenesulfonyl-4-n-propyl)pyrrol-2-yl]-3-hydroxy-3-(2H-tetrazol-5-yl)-propenone
(1220) 3-Hydroxy-1-(3-(4-methoxyphenoxy)furan-2-yl)-3-(1H-1,2,4-triazol-3-yl)-propenone
(1221) 3-Hydroxy-1-(5-(4-methoxybenzyl)pyrrol-2-yl)-3-(1H-1,2,4-triazol-3-yl)-propenone
(1222) 3-Hydroxy-1-[(4-phenoxymethyl-1-(pyridin-4-ylmethyl))pyrrol-2-yl]-3-(1H-1,2,4-triazol-3-yl)-propenone
(1223) 3-Hydroxy-1-(2H-2-(pyridin-4-ylmethyl)pyrazol-4-yl)-3-(2H-tetrazol-5-yl)-propenone
(1224) 3-Hydroxy-1-[(1-(4-methoxybenzyl)-5-phenoxymethyl)pyrrol-3-yl]-3-(1H-1,2,4-triazol-3-yl)-propenone
(1225) 1-[(4-Ethoxycarbonyl-1-(pyridin-4-ylmethyl))pyrrol-2-yl]-3-hydroxy-3-(2H-tetrazol-5-yl)-propenone
(1226) 2-Hydroxy-4-oxo-4-(2-(pyridin-2-ylmethyl)pyrrol-3-yl)-2-butenoic acid
(1227) 4-(2H-2-(2-Fluorobenzyl)pyrazol-3-yl)-2-hydroxy-4-oxo-2-butenoic acid
(1228) 1-(2-(2-Fluorophenyl)furan-3-yl)-3-hydroxy-3-(1H-1,2,4-triazol-3-yl)-propenone
(1229) 3-Hydroxy-1-(4-(2-methoxyphenoxy)furan-3-yl)-3-(1H-1,2,4-triazol-3-yl)-propenone
(1230) 3-Hydroxy-1-[(1-(4-methylbenzyl)-5-n-propyl)pyrrol-3-yl]-3-(2H-tetrazol-5-yl)-propenone
(1231) 3-Hydroxy-1-[(4-n-octyl-1-phenylthio)pyrrol-2-yl]-3-(1H-1,2,4-triazol-3-yl)-propenone
(1232) 1-[(3-Fluoro-5-phenyl)furan-2-yl]-3-hydroxy-3-(1H-1,2,4-triazol-3-yl)-propenone
(1233) 4-(5-(4-Acetylbenzyl)thiophen-3-yl)-2-hydroxy-4-oxo-2-butenoic acid
(1234) 1-(1H-1-(4-Acetylbenzyl)pyrazol-3-yl)-3-hydroxy-3-(2H-tetrazol-3-yl)-propenone
(1235) 3-Hydroxy-1-(5-(3-methoxybenzyl)furan-3-yl)-3-(1H-1,2,4-triazol-3-yl)-propenone
(1236) 1-[(5-Carboxy-1-(pyridin-2-ylmethyl))pyrrol-3-yl]-3-hydroxy-3-(1H-1,2,4-triazol-3-yl)-propenone
(1237) 1-(1-(4-Acetylbenzyl)pyrrol-2-yl)-3-hydroxy-3-(1H-1,2,4-triazol-3-yl)-propenone
(1238) 1-[(1-(4-Acetylbenzyl)-4-n-butyl)pyrrol-2-yl]-3-hydroxy-3-(2H-tetrazol-5-yl)-propenone
(1239) 1-[(5-n-Butyl-1-(4-fluorobenzenesulfonyl))pyrrol-3-yl]-3-hydroxy-3-(2H-tetrazol-5-yl)-propenone
(1240) 1-(2-(4-Acetylphenylthio)furan-3-yl)-3-hydroxy-3-(1H-1,2,4-triazol-3-yl)-propenone (1241) 1-[(1-Benzenesulfonyl-5-phenoxymethyl)pyrrol-3-yl]-3-hydroxy-3-(1H-1,2,4-triazol-3-yl)-propenone
(1242) 1-(4-(4-Fluorobenzyl)thiophen-2-yl)-3-hydroxy-3-(1H-1,2,4-triazol-3-yl)-propenone
(1243) 1-(2H-2-(3-fluorobenzyl)pyrazol-3-yl)-3-hydroxy-3-(1H-1,2,4-triazol-3-yl)-propenone
(1244) 1-(4-(4-Acetylbenzyl)thiophen-3-yl)-3-hydroxy-3-(2H-tetrazol-5-yl)-propenone
(1245) 1-(3-(4-Chlorobenzenesulfonyl)pyrrol-2-yl)-3-hydroxy-3-(2H-tetrazol-5-yl)-propenone
(1246) 1-[(1-(4-Acetylbenzyl)-5-methoxymethyl)pyrrol-3-yl]-3-hydroxy-3-(2H-tetrazol-5-yl)-propenone
(1247) 3-Hydroxy-1-(4-phenoxyfuran-2-yl)-3-(1H-1,2,4-triazol-3-yl)-propenone
(1248) 1-(3-(4-Aminobenzyl)furan-2-yl)-3-hydroxy-3-(1H-1,2,4-triazol-3-yl)-propenone
(1249) 3-Hydroxy-1-(4-(2-methoxyphenoxy)furan-2-yl)-3-(1H-1,2,4-triazol-3-yl)-propenone
(1250) 1-(5-(3-Fluorobenzyl)pyrrol-2-yl)-3-hydroxy-3-(2H-tetrazol-5-yl)-propenone
(1251) 3-Hydroxy-1-(2H-4-phenylthiopyrazol-3-yl)-3-(2H-tetrazol-5-yl)-propenone
(1252) 4-(4-(3-Fluorobenzyl)thiazol-2-yl)-2-hydroxy-4-oxo-2-butenoic acid
(1253) 2-Hydroxy-4-oxo-4-(3-phenylthiopyrrol-2-yl)-2-butenoic acid
(1254) 1-[(4-Ethyl-1-(4-methylbenzyl))pyrrol-2-yl]-3-hydroxy-3-(1H-1,2,4-triazol-3-yl)-propenone
(1255) 1-[(4-Fluoro-5-(pyridin-4-ylmethyl))furan-3-yl]-3-hydroxy-3-(1H-1,2,4-triazol-3-yl)-propenone
(1256) 3-Hydroxy-1-[(5-n-octyl-1-phenylthio)pyrrol-3-yl]-3-(1H-1,2,4-triazol-3-yl)-propenone
(1257) 1-[(2-Chloro-4-(4-fluorobenzyl))furan-3-yl]-3-hydroxy-3-(1H-1,2,4-triazol-3-yl)-propenone
(1258) 4-(1H-1-(4-aminobenzyl)pyrazol-3-yl)-2-hydroxy-4-oxo-2-butenoic acid
(1259) 2-Hydroxy-4-oxo-4-(5-phenylthiothiophen-3-yl)-2-butenoic acid
(1260) 2-Hydroxy-4-oxo-4-(5-(pyridin-4-ylmethyl)thiophen-2-yl)-2-butenoic acid
(1261) 3-Hydroxy-1-[(4-(2-phenylethyl)-1-phenylthio)pyrrol-3-yl]-3-(1H-1,2,4-triazol-3-yl)-propenone
(1262) 1-(3-(4-Fluorobenzenesulfonyl)furan-2-yl)-3-hydroxy-3-(1H-1,2,4-triazol-3-yl)-propenone
(1263) 1-(5-(3-Chlorophenylthio)furan-2-yl)-3-hydroxy-3-(1H-1,2,4-triazol-3-yl)-propenone
(1264) 1-(4-(2-Fluorobenzyl)thiophen-3-yl)-3-hydroxy-3-(2H-tetrazol-5-yl)-propenone
(1265) 3-Hydroxy-1-(2-phenylthiofuran-3-yl)-3-(1H-1,2,4-triazol-3-yl)-propenone
(1266) 3-Hydroxy-1-(4-phenylthiothiophen-2-yl)-3-(2H-tetrazol-5-yl)-propenone
(1267) 1-[(5-Carboxy-1-(4-methoxybenzyl))pyrrol-3-yl]-3-hydroxy-3-(1H-1,2,4-triazol-3-yl)-propenone
(1268) 2-Hydroxy-4-(4-(4-methylbenzyl)pyrrol-3-yl)-4-oxo-2-butenoic acid
(1269) 3-Hydroxy-1-(2-phenylthiothiazol-4-yl)-3-(2H-tetrazol-5-yl)-propenone
(1270) 4-(1-(4-Aminobenzyl)pyrrol-3-yl)-2-hydroxy-4-oxo-2-butenoic acid
(1271) 3-Hydroxy-1-(5-(pyridin-2-ylmethyl)thiophen-2-yl)-3-(1H-1,2,4-triazol-3-yl)-propenone
(1272) 1-(2-(4-Fluorobenzenesulfonyl)pyrrol-3-yl)-3-hydroxy-3-(2H-tetrazol-5-yl)-propenone
(1273) 1-[(4-n-Butyl-1-(4-fluorobenzyl))pyrrol-2-yl]-3-hydroxy-3-(1H-1,2,4-triazol-3-yl)-propenone
(1274) 3-Hydroxy-1-(3-phenylthiopyrrol-2-yl)-3-(1H-1,2,4-triazol-3-yl)-propenone
(1275) 4-(3-(4-Aminobenzyl)furan-2-yl)-2-hydroxy-4-oxo-2-butenoic acid
(1276) 1-[(2-Fluoro-5-(4-fluorobenzyl))furan-3-yl]-3-hydroxy-3-(1H-1,2,4-triazol-3-yl)-propenone
(1277) 3-Hydroxy-1-(2-phenoxyfuran-3-yl)-3-(1H-1,2,4-triazol-3-yl)-propenone
(1278) 3-Hydroxy-3-(1H-1,2,4-triazol-3-yl)-1-(4-(4-trifluoromethylphenylthio)furan-3-yl)-propenone
(1279) 1-(2-(4-Fluorobenzyl)thiophen-3-yl)-3-hydroxy-3-(2H-tetrazol-5-yl)-propenone
(1280) 1-(1H-1-(4-fluorobenzenesulfonyl)pyrazol-4-yl)-3-hydroxy-3-(1H-1,2,4-triazol-3-yl)-propenone
(1281) 2-Hydroxy-4-oxo-4-(4-(pyridin-2-ylmethyl)thiazol-2-yl)-2-butenoic acid
(1282) 3-Hydroxy-1-[(4-n-octyl-1-(pyridin-4-ylmethyl))pyrrol-2-yl]-3-(1H-1,2,4-triazol-3-yl)-propenone
(1283) 1-[(5-Benzoyl-1-(4-fluorobenzenesulfonyl))pyrrol-3-yl]-3-hydroxy-3-(2H-tetrazol-5-yl)-propenone
(1284) 1-(4-(4-Acetylbenzyl)thiophen-2-yl)-3-hydroxy-3-(2H-tetrazol-5-yl)-propenone
(1285) 1-[(1-(3-Fluorobenzyl)-4-(2-phenylethyl))pyrrol-3-yl]-3-hydroxy-3-(2H-tetrazol-5-yl)-propenone
(1286) 1-[(4-Benzenesulfonyl-5-chloro)furan-2-yl]-3-hydroxy-3-(1H-1,2,4-triazol-3-yl)-propenone
(1287) 3-Hydroxy-3-(1H-1,2,4-triazol-3-yl)-1-(5-(3-trifluoromethylphenylthio)furan-3-yl)-propenone
(1288) 1-[(1-(4-Chlorobenzenesulfonyl)-4-phenoxymethyl)pyrrol-2-yl]-3-hydroxy-3-(1H-1,2,4-triazol-3-yl)-propenone
(1289) 3-Hydroxy-1-(5-(4-methylbenzyl)furan-3-yl)-3-(1H-1,2,4-triazol-3-yl)-propenone
(1290) 1-[(1-(2-Fluorobenzyl)-4-n-octyl)pyrrol-2-yl]-3-hydroxy-3-(2H-tetrazol-5-yl)-propenone
(1291) 3-Hydroxy-1-(5-phenylthiofuran-2-yl)-3-(2H-tetrazol-5-yl)-propenone
(1292) 1-(2-(4-Aminobenzyl)furan-3-yl)-3-hydroxy-3-(1H-1,2,4-triazol-3-yl)-propenone
(1293) 3-Hydroxy-1-(4-phenylthiopyrrol-3-yl)-3-(1H-1,2,4-triazol-3-yl)-propenone
(1294) 3-Hydroxy-1-[(1-(4-methoxybenzyl)-4-(2-phenylethyl))pyrrol-2-yl]-3-(2H-tetrazol-5-yl)-propenone
(1295) 1-[(4-Ethyl-1-phenylthio)pyrrol-3-yl]-3-hydroxy-3-(1H-1,2,4-triazol-3-yl)-propenone
(1296) 2-Hydroxy-4-(3-(4-methoxybenzyl)pyrrol-2-yl)-4-oxo-2-butenoic acid
(1297) 2-Hydroxy-4-(2-(4-methylbenzyl)furan-3-yl)-4-oxo-2-butenoic acid
(1298) 3-Hydroxy-3-(1H-1,2,4-triazol-3-yl)-1-(5-(3-trifluoromethylphenoxy)furan-2-yl)-propenone
(1299) 4-(2H-2-(4-Fluorobenzenesulfonyl)pyrazol-3-yl)-2-hydroxy-4-oxo-2-butenoic acid
(1300) 1-(1H-1-Benzenesulfonylpyrazol-3-yl)-3-hydroxy-3-(2H-tetrazol-5-yl)-propenone
(1301) 1-(2-n-Butylfuran-3-yl)-3-hydroxy-3-(2H-tetrazol-5-yl)-propenone
(1302) 1-[(1-(4-Fluorobenzenesulfonyl)-4-n-propyl)pyrrol-2-yl]-3-hydroxy-3-(1H-1,2,4-triazol-3-yl)-propenone
(1303) 1-(4-(4-Fluorobenzyl)thiophen-3-yl)-3-hydroxy-3-(1H-1,2,4-triazol-3-yl)-propenone
(1304) 2-Hydroxy-4-oxo-4-(2-pyridin-2-ylmethyl)furan-3-yl)-2-butenoic acid
(1305) 1-(5-(4-Chlorobenzenesulfonyl)pyrrol-2-yl)-3-hydroxy-3-(1H-1,2,4-triazol-3-yl)-propenone
(1306) 3-Hydroxy-1-(4-phenylfuran-3-yl)-3-(1H-1,2,4-triazol-3-yl)-propenone
(1307) 3-Hydroxy-1-(1H-1-(4-methylbenzyl)pyrazol-4-yl)-3-(2H-tetrazol-5-yl)-propenone (1308) 3-Hydroxy-1-(1-(pyridin-4-ylmethyl)pyrrol-2-yl)-3-(2H-tetrazol-5-yl)-propenone (1309) 3-Hydroxy-1-(1H-1-(4-methoxybenzyl)pyrazol-4-yl)-3-(2H-tetrazol-5-yl)-propenone (1310) 1-[(4-Ethyl-1-(4-fluorobenzenesulfonyl))pyrrol-2-yl]-3-hydroxy-3-(2H-tetrazol-5-yl)-propenone (1311) 1-[(5-Carboxy-1-(4-fluorobenzenesulfonyl))pyrrol-3-yl]-3-hydroxy-3-(1H-1,2,4-triazol-3-yl)-propenone (1312) 3-Hydroxy-1-(5-(4-methoxyphenoxy)furan-3-yl)-3-(1H-1,2,4-triazol-3-yl)-propenone (1313) 2-Hydroxy-4-(2H-2-(4-methylbenzyl)pyrazol-3-yl)-4-oxo-2-butenoic acid (1314) 3-Hydroxy-1-(1-(4-methoxybenzyl)pyrrol-2-yl)-3-(2H-tetrazol-5-yl)-propenone (1315) 3-Hydroxy-3-(1H-1,2,4-triazol-3-yl)-1-(3-(2-trifluoromethylphenylthio)furan-2-yl)-propenone (1316) 3-Hydroxy-1-(4-(pyridin-2-ylmethyl)thiazol-2-yl)-3-(1H-1,2,4-triazol-3-yl)-propenone (1317) 1-(2H-4-benzenesulfonylpyrazol-3-yl)-3-hydroxy-3-(2H-tetrazol-5-yl)-propenone (1318) 4-(1-Benzylpyrrol-3-yl)-2-hydroxy-4-oxo-2-butenoic acid (1319) 1-(5-Benzenesulfonylthiophen-2-yl)-3-hydroxy-3-(1H-1,2,4-triazol-3-yl)-propenone (1320) 1-[(1-(4-Acetylbenzyl)-5-phenoxymethyl)pyrrol-3-yl]-3-hydroxy-3-(2H-tetrazol-5-yl)-propenone (1321) 1-(5-(4-Acetylphenylthio)furan-2-yl)-3-hydroxy-3-(1H-1,2,4-triazol-3-yl)-propenone (1322) 1-(4-(4-Aminobenzyl)pyrrol-2-yl)-3-hydroxy-3-(2H-tetrazol-5-yl)-propenone (1323) 1-(4-(4-Chlorobenzyl)furan-3-yl)-3-hydroxy-3-(1H-1,2,4-triazol-3-yl)-propenone (1324) 1-(5-(2-Fluorophenyl)furan-2-yl)-3-hydroxy-3-(1H-1,2,4-triazol-3-yl)-propenone (1325) 3-Hydroxy-1-(3-(4-methoxybenzyl)furan-2-yl)-3-(2H-tetrazol-5-yl)-propenone (1326) 3-Hydroxy-3-(1H-1,2,4-triazol-3-yl)-1-(4-(4-trifluoromethylphenylthio)furan-2-yl)-propenone (1327) 3-Hydroxy-1-[(4-(2-phenylethyl)-1-(pyridin-2-ylmethyl))pyrrol-2-yl]-3-(1H-1,2,4-triazol-3-yl)-propenone (1328) 4-(5-(2-Fluorobenzyl)pyrrol-3-yl)-2-hydroxy-4-oxo-2-butenoic acid (1329) 3-Hydroxy-1-(5-phenylfuran-3-yl)-3-(1H-1,2,4-triazol-3-yl)-propenone (1330) 1-[(1-(4-Acetylbenzyl)-4-ethoxycarbonyl)pyrrol-2-yl]-3-hydroxy-3-(1H-1,2,4-triazol-3-yl)-propenone (1331) 1-[(1-(4-Acetylbenzyl)-4-ethyl)pyrrol-3-yl]-3-hydroxy-3-(2H-tetrazol-5-yl)-propenone (1332) 3-Hydroxy-1-(2-(4-methylbenzyl)thiazol-4-yl)-3-(2H-tetrazol-5-yl)-propenone (1333) 1-(1H-1-(4-chlorobenzenesulfonyl)pyrazol-3-yl)-3-hydroxy-3-(1H-1,2,4-triazol-3-yl)-propenone (1334) 2-Hydroxy-4-(5-(4-methoxybenzyl)thiophen-2-yl)-4-oxo-2-butenoic acid (1335) 1-(1H-1-benzenesulfonylpyrazol-4-yl)-3-hydroxy-3-(2H-tetrazol-5-yl)-propenone (1336) 3-Hydroxy-1-(4-phenylthiothiazol-2-yl)-3-(1H-1,2,4-triazol-3-yl)-propenone (1337) 3-Hydroxy-1-(2-(pyridin-2-ylmethyl)pyrrol-3-yl)-3-(1H-1,2,4-triazol-3-yl)-propenone (1338) 1-[(1-(4-Fluorobenzenesulfonyl)-5-phenoxymethyl)pyrrol-3-yl]-3-hydroxy-3-(2H-tetrazol-5-yl)-propenone (1339) 1-[(1-(2-Fluorobenzyl)-4-(2-phenylethyl))pyrrol-2-yl]-3-hydroxy-3-(2H-tetrazol-5-yl)-propenone (1340) 1-(1H-1-(4-fluorobenzenesulfonyl)pyrazol-4-yl)-3-hydroxy-3-(2H-tetrazol-5-yl)-propenone (1341) 1-(4-(4-Amino phenylthio)furan-3-yl)-3-hydroxy-3-(1H-1,2,4-triazol-3-yl)-propenone (1342) 1-[(5-n-Butyl-1-(4-methoxybenzyl))pyrrol-3-yl]-3-hydroxy-3-(1H-1,2,4-triazol-3-yl)-propenone (1343) 1-(1-(4-Acetylbenzyl)pyrrol-2-yl)-3-hydroxy-3-(2H-tetrazol-5-yl)-propenone (1344) 4-(2-(3-fluorobenzyl)thiophen-3-yl)-2-hydroxy-4-oxo-2-butenoic acid (1345) 1-(1H-1-(4-fluorobenzyl)pyrazol-3-yl)-3-hydroxy-3-(1H-1,2,4-triazol-3-yl)-propenone (1346) 1-(2-(4-Fluorobenzenesulfonyl)pyrrol-3-yl)-3-hydroxy-3-(1H-1,2,4-triazol-3-yl)-propenone (1347) 1-[(1-Benzyl-5-carboxy)pyrrol-3-yl]-3-hydroxy-3-(2H-tetrazol-5-yl)-propenone (1348) 4-(2-(4-Fluorobenzenesulfonyl)thiophen-3-yl)-2-hydroxy-4-oxo-2-butenoic acid (1349) 4-(4-(2-Fluorobenzyl)thiazol-2-yl)-2-hydroxy-4-oxo-2-butenoic acid (1350) 1-(4-(4-Fluorobenzenesulfonyl)furan-3-yl)-3-hydroxy-3-(1H-1,2,4-triazol-3-yl)-propenone (1351) 1-(3-(4-Aminobenzyl)thiophen-2-yl)-3-hydroxy-3-(2H-tetrazol-5-yl)-propenone (1352) 1-(2H-5-(4-chlorobenzenesulfonyl)pyrazol-3-yl)-3-hydroxy-3-(2H-tetrazol-5-yl)-propenone (1353) 1-(3-(3-Fluorophenyl)furan-2-yl)-3-hydroxy-3-(1H-1,2,4-triazol-3-yl)-propenone (1354) 3-Hydroxy-1-(5-(4-methoxybenzyl)thiophen-3-yl)-3-(1H-1,2,4-triazol-3-yl)-propenone (1355) 3-Hydroxy-1-(4-(pyridin-4-ylmethyl)furan-3-yl)-3-(2H-tetrazol-5-yl)-propenone (1356) 1-(5-(4-Fluorobenzenesulfonyl)thiophen-2-yl)-3-hydroxy-3-(2H-tetrazol-5-yl)-propenone (1357) 4-(1-(4-Chlorobenzenesulfonyl)pyrrol-2-yl)-2-hydroxy-4-oxo-2-butenoic acid (1358) 1-(1H-1-(4-Acetylbenzyl)pyrazol-3-yl)-3-hydroxy-3-(1H-1,2,4-triazol-3-yl)-propenone (1359) 1-[(5-Carboxy-1-(4-chlorobenzenesulfonyl))pyrrol-3-yl]-3-hydroxy-3-(1H-1,2,4-triazol-3-yl)-propenone (1360) 3-Hydroxy-1-[(5-methoxymethyl-1-(pyridin-2-ylmethyl))pyrrol-3-yl]-3-(2H-tetrazol-5-yl)-propenone (1361) 3-Hydroxy-1-(1H-1-phenylthiopyrazol-3-yl)-3-(1H-1,2,4-triazol-3-yl)-propenone (1362) 1-[(1-Benzenesulfonyl-5-n-propyl)pyrrol-3-yl]-3-hydroxy-3-(2H-tetrazol-5-yl)-propenone (1363) 1-[(2-benzenesulfonyl-4-chloro)furan-3-yl]-3-hydroxy-3-(1H-1,2,4-triazol-3-yl)-propenone (1364) 1-[(1-(4-Chlorobenzenesulfonyl)-4-n-propyl)pyrrol-2-yl]-3-hydroxy-3-(1H-1,2,4-triazol-3-yl)-propenone (1365) 2-Hydroxy-4-oxo-4-(1H-1-phenylthiopyrazol-3-yl)-2-butenoic acid (1366) 3-Hydroxy-1-[(1-(4-methylbenzyl)-4-(2-phenylethyl))pyrrol-3-yl]-3-(1H-1,2,4-triazol-3-yl)-propenone (1367) 3-Hydroxy-1-(5-(4-methylbenzyl)pyrrol-3-yl)-3-(2H-tetrazol-5-yl)-propenone (1368) 1-(2H-5-(4-chlorobenzenesulfonyl)pyrazol-3-yl)-3-hydroxy-3-(1H-1,2,4-triazol-3-yl)-propenone (1369) 1-[(5-n-Butyl-1-(pyridin-4-ylmethyl))pyrrol-3-yl]-3-hydroxy-3-(2H-tetrazol-5-yl)-propenone (1370) 3-Hydroxy-1-(5-phenylthiopyrrol-3-yl)-3-(2H-tetrazol-5-yl)-propenone (1371) 1-(3-(2-fluorobenzyl)thiophen-2-yl)-3-hydroxy-3-(1H-1,2,4-triazol-3-yl)-propenone (1372) 2-Hydroxy-4-(5-(4-methoxybenzyl)pyrrol-2-yl)-4-oxo-2-butenoic acid (1373) 3-Hydroxy-1-(3-(pyridin-2-ylmethyl)furan-2-yl)-3-(2H-tetrazol-5-yl)-propenone (1374) 3-Hydroxy-1-[(1-(4-methylbenzyl)-4-n-propyl)pyrrol-2-yl]-3-(1H-1,2,4-triazol-3-yl)-propenone (1375) 1-(4-Benzylfuran-3-yl)-3-hydroxy-3-(1H-1,2,4-triazol-3-yl)-propenone (1376) 3-Hydroxy-1-(2-phenylthiopyrrol-3-yl)-3-(2H-tetrazol-5-yl)-propenone (1377) 4-(4-(4-Fluorobenzenesulfonyl)pyrrol-3-yl)-2-hydroxy-4-oxo-2-butenoic acid (1378) 1-(3-(4-Acetylphenoxy)furan-2-yl)-3-hydroxy-3-(1H-1,2,4-triazol-3-yl)-propenone (1379) 1-(1H-1-(4-aminobenzyl)pyrazol-4-yl)-3-hydroxy-3-(2H-tetrazol-5-yl)-propenone (1380) 1-[(1-(4-Aminobenzyl)-5-n-octyl)pyrrol-3-yl]-3-hydroxy-3-(1H-1,2,4-triazol-3-yl)-propenone (1381) 3-Hydroxy-1-(1H-1-(pyridin-4-ylmethyl)pyrazol-4-yl)-3-(2H-tetrazol-5-yl)-propenone (1382) 1-(5-(4-Acetylbenzyl)thiophen-2-yl)-3-hydroxy-3-(1H-1,2,4-triazol-3-yl)-propenone (1383) 3-Hydroxy-1-(4-(4-methylbenzyl)pyrrol-2-yl)-3-(2H-tetrazol-5-yl)-propenone (1384) 2-Hydroxy-4-oxo-4-(4-(pyridin-2-ylmethyl)furan-2-yl)-2-butenoic acid (1385) 1-(5-(2-chlorobenzyl)furan-3-yl)-3-hydroxy-3-(1H-1,2,4-triazol-3-yl)-propenone (1386) 3-Hydroxy-1-(1-(4-methylbenzyl)pyrrol-2-yl)-3-(2H-tetrazol-5-yl)-propenone (1387) 1-(3-(4-Chlorobenzenesulfonyl)thiophen-2-yl)-3-hydroxy-3-(1H-1,2,4-triazol-3-yl)-propenone (1388) 1-(4-(3-Fluorobenzyl)furan-2-yl)-3-hydroxy-3-(1H-1,2,4-triazol-3-yl)-propenone (1389) 1-(4-(4-Chlorobenzenesulfonyl)thiophen-2-yl)-3-hydroxy-3-(1H-1,2,4-triazol-3-yl)-propenone (1390) 3-Hydroxy-1-[(4-(2-phenylethyl)-1-phenylthio)pyrrol-2-yl]-3-(2H-tetrazol-5-yl)-propenone (1391) 4-(4-Benzenesulfonylpyrrol-3-yl)-2-hydroxy-4-oxo-2-butenoic acid (1392) 1-(3-(4-Aminophenoxy)furan-2-yl)-3-hydroxy-3-(1H-1,2,4-triazol-3-yl)-propenone (1393) 3-Hydroxy-1-(2-(2-methoxyphenoxy)furan-3-yl)-3-(1H-1,2,4-triazol-3-yl)-propenone (1394) 1-[(1-(3-Fluorobenzyl)-5-phenoxymethyl)pyrrol-3-yl]-3-hydroxy-3-(2H-tetrazol-5-yl)-propenone (1395) 1-[(5-Carboxy-1-(3-fluorobenzyl))pyrrol-3-yl]-3-hydroxy-3-(2H-tetrazol-5-yl)-propenone (1396) 1-[(1-(4-Acetylbenzyl)-5-n-butyl)pyrrol-3-yl]-3-hydroxy-3-(1H-1,2,4-triazol-3-yl)-propenone (1397) 3-Hydroxy-1-(5-(4-methoxybenzyl)pyrrol-3-yl)-3-(2H-tetrazol-5-yl)-propenone (1398) 1-[(1-Benzyl-4-n-octyl)pyrrol-2-yl]-3-hydroxy-3-(1H-1,2,4-triazol-3-yl)-propenone (1399) 1-[(1-(4-Fluorobenzenesulfonyl)-4-(2-phenylethyl))pyrrol-2-yl]-3-hydroxy-3-(1H-1,2,4-triazol-3-yl)-propenone (1400) 1-[(3-Benzenesulfonyl-4-(2-phenylethyl))furan-2-yl]-3-hydroxy-3-(1H-1,2,4-triazol-3-yl)-propenone (1401) 1-(5-(4-Fluorobenzenesulfonyl)furan-2-yl)-3-hydroxy-3-(1H-1,2,4-triazol-3-yl)-propenone (1402) 1-[(4-Carboxy-1-(pyridin-2-ylmethyl))pyrrol-2-yl]-3-hydroxy-3-(2H-tetrazol-5-yl)-propenone (1403) 1-(4-(4-Chlorobenzenesulfonyl)pyrrol-3-yl)-3-hydroxy-3-(2H-tetrazol-5-yl)-propenone (1404) 1-(5-Benzenesulfonylthiophen-3-yl)-3-hydroxy-3-(2H-tetrazol-5-yl)-propenone (1405) 1-(5-(2-methoxybenzyl)furan-2-yl)-3-hydroxy-3-(1H-1,2,4-triazol-3-yl)-propenone (1406) 1-(2H-4-benzenesulfonylpyrazol-3-yl)-3-hydroxy-3-(1H-1,2,4-triazol-3-yl)-propenone (1407) 1-(1-(2-fluorobenzyl)pyrrol-2-yl)-3-hydroxy-3-(1H-1,2,4-triazol-3-yl)-propenone (1408) 3-Hydroxy-1-[(4-(2-phenylethyl)-1-(pyridin-4-ylmethyl))pyrrol-3-yl]-3-(1H-1,2,4-triazol-3-yl)-propenone (1409) 1-(5-(4-Aminobenzyl)pyrrol-2-yl)-3-hydroxy-3-(2H-tetrazol-5-yl)-propenone (1410) 4-(4-Benzenesulfonylthiophen-3-yl)-2-hydroxy-4-oxo-2-butenoic acid (1411) 1-[(1-(4-Fluorobenzyl)-4-n-octyl)pyrrol-2-yl]-3-hydroxy-3-(2H-tetrazol-5-yl)-propenone (1412) 1-(2-(2-Fluorobenzyl)pyrrol-3-yl)-3-hydroxy-3-(2H-tetrazol-5-yl)-propenone (1413) 3-Hydroxy-1-(5-(pyridin-2-ylmethyl)pyrrol-2-yl)-3-(1H-1,2,4-triazol-3-yl)-propenone (1414) 2-Hydroxy-4-(2H-2-(4-methylbenzyl)pyrazol-4-yl)-4-oxo-2-butenoic acid (1415) 3-Hydroxy-1-(4-(pyridin-2-ylmethyl)pyrrol-2-yl)-3-(1H-1,2,4-triazol-3-yl)-propenone (1416) 3-Hydroxy-1-(2-(4-methoxybenzyl)pyrrol-3-yl)-3-(2H-tetrazol-5-yl)-propenone (1417) 1-(5-(4-Fluorobenzenesulfonyl)pyrrol-3-yl)-3-hydroxy-3-(2H-tetrazol-5-yl)-propenone (1481) 1-[(1-(4-Chlorobenzenesulfonyl)-4-(2-phenylethyl))pyrrol-2-yl]-3-hydroxy-3-(2H-tetrazol-5-yl)-propenone (1419) 1-[(4-n-Butyl-1-(4-methoxybenzyl))pyrrol-2-yl]-3-hydroxy-3-(1H-1,2,4-triazol-3-yl)-propenone (1420) 4-(1-(2-fluorobenzyl)pyrrol-2-yl)-2-hydroxy-4-oxo-2-butenoic acid (1421) 3-Hydroxy-1-[(5-methyl-4-(pyridin-4-ylmethyl))furan-2-yl]-3-(1H-1,2,4-triazol-3-yl)-propenone (1422) 3-Hydroxy-1-[(5-(2-phenylethyl)-4-(pyridin-4-ylmethyl))furan-3-yl]-3-(1H-1,2,4-triazol-3-yl)-propenone (1423) 1-[(4-Chloro-3-(4-fluorobenzyl))furan-2-yl]-3-hydroxy-3-(1H-1,2,4-triazol-3-yl)-propenone (1424) 3-Hydroxy-1-(5-(2-methoxyphenylthio)furan-2-yl)-3-(1H-1,2,4-triazol-3-yl)-propenone (1425) 1-[(1-Benzyl-5-phenoxymethyl)pyrrol-3-yl]-3-hydroxy-3-(2H-tetrazol-5-yl)-propenone (1426) 1-[(2-Chloro-4-phenyl)furan-3-yl]-3-hydroxy-3-(1H-1,2,4-triazol-3-yl)-propenone (1427) 2-Hydroxy-4-oxo-4-(3-(pyridin-4-ylmethyl)thiophen-2-yl)-2-butenoic acid (1428) 4-(5-(4-Fluorobenzenesulfonyl)furan-2-yl)-2-hydroxy-4-oxo-2-butenoic acid (1429) 4-(2-Fluorobenzyl)thiophen-3-yl)-2-hydroxy-4-oxo-2-butenoic acid (1430) 1-(4-(2-Fluorobenzyl)thiophen-3-yl)-3-hydroxy-3-(1H-1,2,4-triazol-3-yl)-propenone (1431) 1-[(4-Ethoxycarbonyl-1-(4-fluorobenzyl))pyrrol-2-yl]-3-hydroxy-3-(1H-1,2,4-triazol-3-yl)-propenone (1432) 1-(2H-2-(2-Fluorobenzyl)pyrazol-3-yl)-3-hydroxy-3-(2H-tetrazol-5-yl)-propenone (1433) 2-Hydroxy-4-oxo-4-(2-(pyridin-4-ylmethyl)thiophen-3-yl)-2-butenoic acid (1434) 4-(2H-2-Benzenesulfonylpyrazol-4-yl)-2-hydroxy-4-oxo-2-butenoic acid (1435) 3-Hydroxy-1-(5-(4-methoxyphenylthio)furan-3-yl)-3-(1H-1,2,4-triazol-3-yl)-propenone (1436) 4-(2H-5-Benzylpyrazol-3-yl)-2-hydroxy-4-oxo-2-butenoic acid (1437) 1-[(1-(4-Aminobenzyl)-5-methoxymethyl)pyrrol-3-yl]-3-hydroxy-3-(1H-1,2,4-triazol-3-yl)-propenone (1438) 1-[(4-Ethyl-1-(pyridin-4-ylmethyl))pyrrol-2-yl]-3-hydroxy-3-(2H-tetrazol-5-yl)-propenone (1439) 3-Hydroxy-1-[(5-methoxymethyl-1-(pyridin-2-ylmethyl))pyrrol-3-yl]-3-(1H-1,2,4-triazol-3-yl)-propenone (1440) 4-(5-Benzylpyrrol-3-yl)-2-hydroxy-4-oxo-2-butenoic acid
(1441) 3-Hydroxy-1-(1H-1-(pyridin-4-ylmethyl)pyrazol-3-yl)-3-(2H-tetrazol-5-yl)-propenone
(1442) 2-Hydroxy-4-(1-(4-methoxybenzyl)pyrrol-2-yl)-4-oxo-2-butenoic acid
(1443) 1-(5-(4-Fluorobenzenesulfonyl)thiophen-3-yl)-3-hydroxy-3-(2H-tetrazol-5-yl)-propenone
(1444) 1-(4-(2-Fluorobenzyl)furan-3-yl)-3-hydroxy-3-(2H-tetrazol-5-yl)-propenone
(1445) 1-[(5-Carboxy-1-(4-methylbenzyl))pyrrol-3-yl]-3-hydroxy-3-(2H-tetrazol-5-yl)-propenone
(1446) 1-(3-(2-Fluorobenzyl)furan-2-yl)-3-hydroxy-3-(2H-tetrazol-5-yl)-propenone
(1447) 1-[(2-Benzenesulfonyl-4-fluoro)furan-3-yl]-3-hydroxy-3-(1H-1,2,4-triazol-3-yl)-propenone
(1448) 1-(2-(4-Fluorobenzenesulfonyl)thiazol-4-yl)-3-hydroxy-3-(1H-1,2,4-triazol-3-yl)-propenone
(1449) 1-[(5-n-Butyl-1-(2-fluorobenzyl))pyrrol-3-yl]-3-hydroxy-3-(1H-1,2,4-triazol-3-yl)-propenone
(1450) 1-[(1-(4-Aminobenzyl)-5-phenoxymethyl)pyrrol-3-yl]-3-hydroxy-3-(1H-1,2,4-triazol-3-yl)-propenone
(1451) 1-(2-(3-Fluorobenzyl)pyrrol-3-yl)-3-hydroxy-3-(2H-tetrazol-5-yl)-propenone
(1452) 1-(5-(3-Fluorophenyl)furan-2-yl)-3-hydroxy-3-(1H-1,2,4-triazol-3-yl)-propenone
(1453) 1-(2-(4-Fluorobenzyl)thiazol-4-yl)-3-hydroxy-3-(1H-1,2,4-triazol-3-yl)-propenone
(1454) 4-(5-(4-Fluorobenzenesulfonyl)pyrrol-2-yl)-2-hydroxy-4-oxo-2-butenoic acid
(1455) 1-[(2-Benzenesulfonyl-5-methyl)furan-3-yl]-3-hydroxy-3-(1H-1,2,4-triazol-3-yl)-propenone
(1456) 1-(2-(4-Aminobenzyl)thiazol-4-yl)-3-hydroxy-3-(2H-tetrazol-5-yl)-propenone
(1457) 4-(2-(4-Fluorobenzyl)thiophen-3-yl)-2-hydroxy-4-oxo-2-butenoic acid
(1458) 4-(4-(4-Chlorobenzenesulfonyl)pyrrol-3-yl)-2-hydroxy-4-oxo-2-butenoic acid
(1459) 1-[(1-(2-Fluorobenzyl)-4-n-propyl)pyrrol-2-yl]-3-hydroxy-3-(2H-tetrazol-5-yl)-propenone
(1460) 1-[(1-Benzenesulfonyl-5-n-octyl)pyrrol-3-yl]-3-hydroxy-3-(2H-tetrazol-5-yl)-propenone
(1461) 1-(4-(3-Chlorobenzyl)furan-3-yl)-3-hydroxy-3-(1H-1,2,4-triazol-3-yl)-propenone
(1462) 1-(5-n-Butylfuran-3-yl)-3-hydroxy-3-(2H-tetrazol-5-yl)-propenone
(1463) 1-(2H-2-(4-Fluorobenzyl)pyrazol-4-yl)-3-hydroxy-3-(2H-tetrazol-5-yl)-propenone
(1464) 1-[(4-Ethyl-1-(4-methoxybenzyl))pyrrol-2-yl]-3-hydroxy-3-(2H-tetrazol-5-yl)-propenone
(1465) 3-Hydroxy-1-(2-(pyridin-2-ylmethyl)thiazol-4-yl)-3-(1H-1,2,4-triazol-3-yl)-propenone
(1466) 4-(3-(4-Acetylbenzyl)furan-2-yl)-2-hydroxy-4-oxo-2-butenoic acid
(1467) 1-[(4-Benzenesulfonyl-2-chloro)furan-3-yl]-3-hydroxy-3-(1H-1,2,4-triazol-3-yl)-propenone
(1468) 2-Hydroxy-4-oxo-4-(1H-1-(pyridin-2-ylmethyl)pyrazol-3-yl)-2-butenoic acid
(1469) 1-(5-(4-Acetylbenzyl)thiophen-3-yl)-3-hydroxy-3-(1H-1,2,4-triazol-3-yl)-propenone
(1470) 1-(2-(2-Chlorobenzyl)furan-3-yl)-3-hydroxy-3-(1H-1,2,4-triazol-3-yl)-propenone
(1471) 2-Hydroxy-4-oxo-4-(4-(pyridin-2-ylmethyl)thiophen-2-yl)-2-butenoic acid
(1472) 1-[(1-(4-Fluorobenzyl))-5-n-octyl]pyrrol-3-yl]-3-hydroxy-3-(1H-1,2,4-triazol-3-yl)-propenone
(1473) 4-(5-(3-Fluorobenzyl)thiophen-3-yl)-2-hydroxy-4-oxo-2-butenoic acid
(1474) 1-[(1-(3-Fluorobenzyl)-4-phenoxymethyl)pyrrol-2-yl]-3-hydroxy-3-(1H-1,2,4-triazol-3-yl)-propenone
(1475) 3-Hydroxy-1-(2H-5-(4-methylbenzyl)pyrazol-3-yl)-3-(1H-1,2,4-triazol-3-yl)-propenone
(1476) 1-[(1-(4-Aminobenzyl)-5-n-octyl)pyrrol-3-yl]-3-hydroxy-3-(2H-tetrazol-5-yl)-propenone
(1477) 1-(2H-2-Benzylpyrazol-4-yl)-3-hydroxy-3-(1H-1,2,4-triazol-3-yl)-propenone
(1478) 3-Hydroxy-1-(5-(pyridin-2-ylmethyl)thiophen-3-yl)-3-(1H-1,2,4-triazol-3-yl)-propenone
(1479) 1-[(1-Benzenesulfonyl-4-n-octyl)pyrrol-2-yl]-3-hydroxy-3-(1H-1,2,4-triazol-3-yl)-propenone
(1480) 1-(2H-2-(4-Chlorobenzenesulfonyl)pyrazol-4-yl)-3-hydroxy-3-(1H-1,2,4-triazol-3-yl)-propenone
(1481) 1-[(5-Fluoro-2-(4-fluorobenzyl))furan-3-yl]-3-hydroxy-3-(1H-1,2,4-triazol-3-yl)-propenone
(1482) 3-Hydroxy-1-[(1-(4-methoxybenzyl)-4-methoxymethyl)pyrrol-2-yl]-3-(1H-1,2,4-triazol-3-yl)-propenone
(1483) 3-Hydroxy-1-(1-(pyridin-4-ylmethyl)pyrrol-3-yl)-3-(1H-1,2,4-triazol-3-yl)-propenone
(1484) 1-(4-(4-Aminobenzyl)furan-3-yl)-3-hydroxy-3-(1H-1,2,4-triazol-3-yl)-propenone
(1485) 3-Hydroxy-1-[(4-(2-phenylethyl)-1-(pyridin-2-ylmethyl))pyrrol-3-yl]-3-(1H-1,2,4-triazol-3-yl)-propenone
(1486) 1-[(1-Benzenesulfonyl-4-benzoyl)pyrrol-2-yl]-3-hydroxy-3-(1H-1,2,4-triazol-3-yl)-propenone
(1487) 1-[(4-Carboxy-1-(4-methylbenzyl))pyrrol-2-yl]-3-hydroxy-3-(2H-tetrazol-5-yl)-propenone
(1488) 1-(3-(4-Fluorobenzyl)pyrrol-2-yl)-3-hydroxy-3-(1H-1,2,4-triazol-3-yl)-propenone
(1489) 3-Hydroxy-1-(4-phenylthiopyrrol-2-yl)-3-(1H-1,2,4-triazol-3-yl)-propenone
(1490) 1-(4-(4-Acetylphenoxy)furan-2-yl)-3-hydroxy-3-(1H-1,2,4-triazol-3-yl)-propenone
(1491) 1-[(5-Benzoyl-1-(3-fluorobenzyl))pyrrol-3-yl]-3-hydroxy-3-(1H-1,2,4-triazol-3-yl)-propenone
(1492) 1-[(1-(4-Fluorobenzenesulfonyl)-4-phenoxymethyl)pyrrol-2-yl]-3-hydroxy-3-(2H-tetrazol-5-yl)-propenone
(1493) 4-(5-(4-Fluorobenzenesulfonyl)pyrrol-3-yl)-2-hydroxy-4-oxo-2-butenoic acid
(1494) 4-(2H-4-(4-Chlorobenzenesulfonyl)pyrazol-3-yl)-2-hydroxy-4-oxo-2-butenoic acid
(1495) 3-Hydroxy-1-3-(pyridin-2-ylmethyl)thiophen-2-yl)-3-(2H-tetrazol-5-yl)-propenone
(1496) 3-Hydroxy-1-(2-(pyridin-2-ylmethyl)thiophen-3-yl)-3-(1H-1,2,4-triazol-3-yl)-propenone
(1497) 1-(5-(3-Chlorophenoxy)furan-2-yl)-3-hydroxy-3-(1H-1,2,4-triazol-3-yl)-propenone
(1498) 1-[(1-(2-Fluorobenzyl)-4-(2-phenylethyl))pyrrol-3-yl]-3-hydroxy-3-(1H-1,2,4-triazol-3-yl)-propenone
(1499) 1-[(1-Benzenesulfonyl-4-n-propyl)pyrrol-2-yl]-3-hydroxy-3-(1H-1,2,4-triazol-3-yl)-propenone
(1500) 4-(5-(2-Fluorobenzyl)furan-3-yl)-2-hydroxy-4-oxo-2-butenoic acid
(1501) 1-[(1-(4-Aminobenzyl)-4-n-butyl)pyrrol-2-yl]-3-hydroxy-3-(2H-tetrazol-5-yl)-propenone
(1502) 1-[(4-Carboxy-1-phenylthio)pyrrol-2-yl]-3-hydroxy-3-(1H-1,2,4-triazol-3-yl)-propenone
(1503) 3-Hydroxy-3-(1H-1,2,4-triazol-3-yl)-1-(4-(2-trifluoromethylphenoxy)furan-2-yl)-propenone
(1504) 1-(5-Benzenesulfonylpyrrol-3-yl)-3-hydroxy-3-(2H-tetrazol-5-yl)-propenone
(1505) 4-(4-(4-Aminobenzyl)pyrrol-3-yl)-2-hydroxy-4-oxo-2-butenoic acid
(1506) 1-(1H-1-(4-Aminobenzyl)pyrazol-3-yl)-3-hydroxy-3-(2H-tetrazol-5-yl)-propenone (1507) 1-(2-(4-Chlorobenzyl)furan-3-yl)-3-hydroxy-3-(1H-1,2,4-triazol-3-yl)-propenone
(1508) 3-Hydroxy-1-(4-(pyridin-2-ylmethyl)pyrrol-3-yl)-3-(2H-tetrazol-5-yl)-propenone
(1509) 4-(3-n-Butylfuran-2-yl)-2-hydroxy-4-oxo-2-butenoic acid
(1510) 3-Hydroxy-1-[(4-(2-phenylethyl)-2-(pyridin-4-ylmethyl))furan-3-yl]-3-(1H-1,2,4-triazol-3-yl)-propenone
(1511) 3-Hydroxy-1-(2H-2-phenylthiopyrazol-3-yl)-3-(2H-tetrazol-5-yl)-propenone
(1512) 1-(2H-5-Benzenesulfonylpyrazol-3-yl)-3-hydroxy-3-(2H-tetrazol-5-yl)-propenone
(1513) 2-Hydroxy-4-(4-(4-methoxybenzyl)pyrrol-3-yl)-4-oxo-2-butenoic acid
(1514) 1-(3-(4-Chlorobenzenesulfonyl)furan-2-yl)-3-hydroxy-3-(1H-1,2,4-triazol-3-yl)-propenone
(1515) 1-[(1-(4-Acetylbenzyl)-4-methoxymethyl)pyrrol-2-yl]-3-hydroxy-3-(2H-tetrazol-5-yl)-propenone
(1516) 2-Hydroxy-4-oxo-4-(5-(pyridin-2-ylmethyl)furan-3-yl)-2-butenoic acid
(1517) 3-Hydroxy-3-(1H-1,2,4-triazol-3-yl)-1-(3-(4-trifluoromethylphenoxy)furan-2-yl)-propenone
(1518) 1-(4-Benzenesulfonylthiophen-3-yl)-3-hydroxy-3-(1H-1,2,4-triazol-3-yl)-propenone
(1519) 1-[(1-(2-Fluorobenzyl)-5-phenoxymethyl)pyrrol-3-yl]-3-hydroxy-3-(2H-tetrazol-5-yl)-propenone
(1520) 4-(2H-2-(4-Chlorobenzenesulfonyl)pyrazol-3-yl)-2-hydroxy-4-oxo-2-butenoic acid
(1521) 1-[(4-Carboxy-1-(4-methylbenzyl))pyrrol-2-yl]-3-hydroxy-3-(1H-1,2,4-triazol-3-yl)-propenone
(1522) 3-Hydroxy-1-(2-(4-methoxybenzyl)thiazol-4-yl)-3-(1H-1,2,4-triazol-3-yl)-propenone
(1523) 4-(1H-1-(4-Fluorobenzyl)pyrazol-4-yl)-2-hydroxy-4-oxo-2-butenoic acid
(1524) 3-Hydroxy-1-[(1-(4-methoxybenzyl)-5-methoxymethyl)pyrrol-3-yl]-3-(2H-tetrazol-5-yl)-propenone
(1525) 3-Hydroxy-1-(2-(3-methoxybenzyl)furan-3-yl)-3-(1H-1,2,4-triazol-3-yl)-propenone
(1526) 1-(2-(4-Chlorophenylthio)furan-3-yl)-3-hydroxy-3-(1H-1,2,4-triazol-3-yl)-propenone
(1527) 4-(3-(4-Fluorobenzenesulfonyl)pyrrol-2-yl)-2-hydroxy-4-oxo-2-butenoic acid
(1528) 1-[(2-(4-Fluorobenzyl)-4-(2-phenylethyl))furan-3-yl]-3-hydroxy-3-(1H-1,2,4-triazol-3-yl)-propenone
(1529) 1-[(1-Benzenesulfonyl-5-phenoxymethyl)pyrrol-3-yl]-3-hydroxy-3-(2H-tetrazol-5-yl)-propenone
(1530) 1-(5-(4-Chlorobenzenesulfonyl)furan-2-yl)-3-hydroxy-3-(2H-tetrazol-5-yl)-propenone
(1531) 1-(1H-1-(3-Fluorobenzyl)pyrazol-3-yl)-3-hydroxy-3-(2H-tetrazol-5-yl)-propenone
(1532) 3-Hydroxy-1-(2H-5-phenylthiopyrazol-3-yl)-3-(1H-1,2,4-triazol-3-yl)-propenone
(1533) 4-(2H-4-(4-Acetylbenzyl)pyrazol-3-yl)-2-hydroxy-4-oxo-2-butenoic acid
(1534) 1-(5-(4-Aminobenzyl)thiophen-3-yl)-3-hydroxy-3-(2H-tetrazol-5-yl)-propenone
(1535) 3-Hydroxy-1-[(4-phenyl-5-(2-phenylethyl))furan-3-yl]-3-(1H-1,2,4-triazol-3-yl)-propenone
(1536) 3-Hydroxy-1-(3-(4-methoxybenzyl)furan-2-yl)-3-(1H-1,2,4-triazol-3-yl)-propenone
(1537) 1-(3-Benzylpyrrol-2-yl)-3-hydroxy-3-(2H-tetrazol-5-yl)-propenone
(1538) 1-[(5-Benzoyl-1-(4-fluorobenzyl))pyrrol-3-yl]-3-hydroxy-3-(1H-1,2,4-triazol-3-yl)-propenone
(1539) 1-[(5-Chloro-2-(pyridin-4-ylmethyl))furan-3-yl]-3-hydroxy-3-(1H-1,2,4-triazol-3-yl)-propenone
(1540) 3-Hydroxy-3-(1H-1,2,4-triazol-3-yl)-1-(2-(2-trifluoromethylphenylthio)furan-3-yl)-propenone
(1541) 3-Hydroxy-1-(2-(3-methoxyphenylthio)furan-3-yl)-3-(1H-1,2,4-triazol-3-yl)-propenone
(1542) 3-Hydroxy-3-(1H-1,2,4-triazol-3-yl)-1-(4-(4-trifluoromethylbenzyl)furan-3-yl)-propenone
(1543) 4-(2-Benzylpyrrol-3-yl)-2-hydroxy-4-oxo-2-butenoic acid
(1544) 2-Hydroxy-4-oxo-4-(4-phenylthiothiophen-2-yl)-2-butenoic acid
(1545) 3-Hydroxy-1-(2-(4-methylbenzyl)furan-3-yl)-3-(2H-tetrazol-5-yl)-propenone
(1546) 3-Hydroxy-1-(5-(pyridin-4-ylmethyl)pyrrol-3-yl)-3-(1H-1,2,4-triazol-3-yl)-propenone
(1547) 3-Hydroxy-1-(1H-1-(pyridin-4-ylmethyl)pyrazol-3-yl)-3-(1H-1,2,4-triazol-3-yl)-propenone
(1548) 1-(5-(2-chlorophenoxy)furan-3-yl)-3-hydroxy-3-(1H-1,2,4-triazol-3-yl)-propenone
(1549) 1-[(1-(3-Fluorobenzyl)-4-n-octyl)pyrrol-2-yl]-3-hydroxy-3-(1H-1,2,4-triazol-3-yl)-propenone
(1550) 3-Hydroxy-1-(2-(pyridin-2-ylmethyl)furan-3-yl)-3-(2H-tetrazol-5-yl)-propenone
(1551) 1-(4-(4-Fluorobenzyl)furan-3-yl)-3-hydroxy-3-(2H-tetrazol-5-yl)-propenone
(1552) 3-Hydroxy-1-(4-phenylthiothiophen-2-yl)-3-(1H-1,2,4-triazol-3-yl)-propenone
(1553) 1-(3-(4-Fluorobenzenesulfonyl)pyrrol-2-yl)-3-hydroxy-3-(2H-tetrazol-5-yl)-propenone
(1554) 1-(2-(4-Acetylbenzyl)thiophen-3-yl)-3-hydroxy-3-(1H-1,2,4-triazol-3-yl)-propenone
(1555) 4-(4-Benzenesulfonylthiophen-2-yl)-2-hydroxy-4-oxo-2-butenoic acid
(1556) 2-Hydroxy-4-oxo-4-(2-phenylthiothiophen-3-yl)-2-butenoic acid
(1557) 1-[(1-(2-Fluorobenzyl)-5-n-octyl)pyrrol-3-yl]-3-hydroxy-3-(2H-tetrazol-5-yl)-propenone
(1558) 1-[(4-Carboxy-1-(2-fluorobenzyl))pyrrol-2-yl]-3-hydroxy-3-(2H-tetrazol-5-yl)-propenone
(1559) 1-(4-(4-Fluorobenzenesulfonyl)pyrrol-2-yl)-3-hydroxy-3-(1H-1,2,4-triazol-3-yl)-propenone
(1560) 1-[(1-(4-Acetylbenzyl)-4-n-octyl)pyrrol-2-yl]-3-hydroxy-3-(1H-1,2,4-triazol-3-yl)-propenone
(1561) 1-[(1-Benzyl-4-ethyl)pyrrol-3-yl]-3-hydroxy-3-(1H-1,2,4-triazol-3-yl)-propenone
(1562) 1-[(2-(4-Fluorobenzyl)-5-methyl)furan-3-yl]-3-hydroxy-3-(1H-1,2,4-triazol-3-yl)-propenone
(1563) 1-[(5-Carboxy-1-(2-fluorobenzyl))pyrrol-2-yl]-3-hydroxy-3-(1H-1,2,4-triazol-3-yl)-propenone
(1564) 4-(2H-2-Benzenesulfonylpyrazol-3-yl)-2-hydroxy-4-oxo-2-butenoic acid
(1565) 3-Hydroxy-1-[(1-(4-methylbenzyl)-4-(2-phenylethyl))pyrrol-2-yl]-3-(2H-tetrazol-5-yl)-propenone
(1566) 3-Hydroxy-1-(4-(pyridin-4-ylmethyl)furan-2-yl)-3-(2H-tetrazol-5-yl)-propenone
(1567) 3-Hydroxy-1-(4-(pyridin-4-ylmethyl)furan-2-yl)-3-(1H-1,2,4-triazol-3-yl)-propenone
(1568) 1-(5-(4-Fluorobenzenesulfonyl)pyrrol-2-yl)-3-hydroxy-3-(1H-1,2,4-triazol-3-yl)-propenone
(1569) 1-[(1-Benzenesulfonyl-5-benzoyl)pyrrol-3-yl]-3-hydroxy-3-(1H-1,2,4-triazol-3-yl)-propenone
(1570) 1-(2-(2-Fluorobenzyl)thiazol-4-yl)-3-hydroxy-3-(2H-tetrazol-5-yl)-propenone
(1571) 1-(2-(4-Amino phenylthio)furan-3-yl)-3-hydroxy-3-(1H-1,2,4-triazol-3-yl)-propenone
(1572) 1-(1-(2-Fluorobenzyl)pyrrol-3-yl)-3-hydroxy-3-(1H-1,2,4-triazol-3-yl)-propenone
(1573) 1-[(5-Benzoyl-1-(2-fluorobenzyl))pyrrol-3-yl]-3-hydroxy-3-(2H-tetrazol-5-yl)-propenone (1574) 3-Hydroxy-1-(2-(4-methylbenzyl)thiophen-3-yl)-3-(2H-tetrazol-5-yl)-propenone
(1575) 3-Hydroxy-1-[(1-(4-methylbenzyl)-5-n-propyl)pyrrol-3-yl]-3-(1H-1,2,4-triazol-3-yl)-propenone
(1576) 1-[(4-n-Butyl-1-(4-chlorobenzenesulfonyl))pyrrol-2-yl]-3-hydroxy-3-(2H-tetrazol-5-yl)-propenone
(1577) 3-Hydroxy-1-[(4-phenoxymethyl-1-(pyridin-2-ylmethyl))pyrrol-2-yl]-3-(2H-tetrazol-5-yl)-propenone
(1578) 1-(4-(4-Fluorobenzyl)pyrrol-2-yl)-3-hydroxy-3-(1H-1,2,4-triazol-3-yl)-propenone
(1579) 4-(4-Benzylfuran-3-yl)-2-hydroxy-4-oxo-2-butenoic acid
(1580) 1-(4-Benzenesulfonylpyrrol-3-yl)-3-hydroxy-3-(1H-1,2,4-triazol-3-yl)-propenone
(1581) 1-(5-(4-Acetylbenzyl)pyrrol-2-yl)-3-hydroxy-3-(1H-1,2,4-triazol-3-yl)-propenone
(1582) 3-Hydroxy-1-(1-(4-methylbenzyl)pyrrol-2-yl)-3-(1H-1,2,4-triazol-3-yl)-propenone
(1583) 1-(4-(3-Fluorophenyl)furan-3-yl)-3-hydroxy-3-(1H-1,2,4-triazol-3-yl)-propenone
(1584) 1-(3-(4-Aminobenzyl)pyrrol-2-yl)-3-hydroxy-3-(1H-1,2,4-triazol-3-yl)-propenone
(1585) 3-Hydroxy-1-[(1-(4-methoxybenzyl)-4-(2-phenylethyl))pyrrol-2-yl]-3-(1H-1,2,4-triazol-3-yl)-propenone
(1586) 1-[(4-Ethoxycarbonyl-1-(4-fluorobenzenesulfonyl))pyrrol-2-yl]-3-hydroxy-3-(2H-tetrazol-5-yl)-propenone
(1587) 1-(3-(2-Chlorophenoxy)furan-2-yl)-3-hydroxy-3-(1H-1,2,4-triazol-3-yl)-propenone
(1588) 1-(4-(4-Acetylbenzyl)pyrrol-3-yl)-3-hydroxy-3-(2H-tetrazol-5-yl)-propenone
(1589) 1-(3-(4-Acetylphenylthio)furan-2-yl)-3-hydroxy-3-(1H-1,2,4-triazol-3-yl)-propenone
(1590) 1-[(4-Carboxy-1-phenylthio)pyrrol-2-yl]-3-hydroxy-3-(2H-tetrazol-5-yl)-propenone
(1591) 1-[(5-Benzenesulfonyl-2-(2-phenylethyl))furan-3-yl]-3-hydroxy-3-(1H-1,2,4-triazol-3-yl)-propenone
(1592) 1-[(4-Benzenesulfonyl-3-chloro)furan-2-yl]-3-hydroxy-3-(1H-1,2,4-triazol-3-yl)-propenone
(1593) 4-(1H-1-(4-Fluorobenzenesulfonyl)pyrazol-4-yl)-2-hydroxy-4-oxo-2-butenoic acid
(1594) 1-[(5-n-Butyl-1-(4-methylbenzyl))pyrrol-3-yl]-3-hydroxy-3-(2H-tetrazol-5-yl)-propenone
(1595) 1-(3-(2-Methoxybenzyl)furan-2-yl)-3-hydroxy-3-(1H-1,2,4-triazol-3-yl)-propenone
(1596) 1-(4-(4-Acetylbenzyl)thiazol-2-yl)-3-hydroxy-3-(2H-tetrazol-5-yl)-propenone
(1597) 3-Hydroxy-1-[(4-(2-phenylethyl)-1-(pyridin-4-ylmethyl))pyrrol-3-yl]-3-(2H-tetrazol-5-yl)-propenone
(1598) 1-[(3-(4-Fluorobenzyl)-4-methyl)furan-2-yl]-3-hydroxy-3-(1H-1,2,4-triazol-3-yl)-propenone
(1599) 4-(2H-2-(2-Fluorobenzyl)pyrazol-4-yl)-2-hydroxy-4-oxo-2-butenoic acid
(1600) 1-(2-Benzylfuran-3-yl)-3-hydroxy-3-(2H-tetrazol-5-yl)-propenone
(1601) 2-Hydroxy-4-oxo-4-(2-(pyridin-4-ylmethyl)pyrrol-3-yl)-2-butenoic acid
(1602) 3-Hydroxy-1-(5-(4-methoxybenzyl)thiophen-2-yl)-3-(1H-1,2,4-triazol-3-yl)-propenone
(1603) 1-(2-(2-Methoxybenzyl)furan-3-yl)-3-hydroxy-3-(1H-1,2,4-triazol-3-yl)-propenone
(1604) 3-Hydroxy-1-(2-(4-methylphenylthio)furan-3-yl)-3-(1H-1,2,4-triazol-3-yl)-propenone
(1605) 1-[(1-(4-Fluorobenzyl)-4-n-propyl)pyrrol-2-yl]-3-hydroxy-3-(1H-1,2,4-triazol-3-yl)-propenone
(1606) 1-[(4-Ethoxycarbonyl-1-(2-fluorobenzyl))pyrrol-2-yl]-3-hydroxy-3-(2H-tetrazol-5-yl)-propenone
(1607) 3-Hydroxy-1-(4-(4-methoxybenzyl)furan-2-yl)-3-(2H-tetrazol-5-yl)-propenone
(1608) 3-Hydroxy-1-[(4-methyl-5-phenyl)furan-3-yl]-3-(1H-1,2,4-triazol-3-yl)-propenone
(1609) 3-Hydroxy-1-(4-(pyridin-4-ylmethyl)pyrrol-3-yl)-3-(2H-tetrazol-5-yl)-propenone
(1610) 1-[(1-Benzenesulfonyl-4-carboxy)pyrrol-2-yl]-3-hydroxy-3-(1H-1,2,4-triazol-3-yl)-propenone
(1611) 3-Hydroxy-1-(2-(pyridin-2-ylmethyl)furan-3-yl)-3-(1H-1,2,4-triazol-3-yl)-propenone
(1612) 1-[(5-Chloro-3-phenyl)furan-2-yl]-3-hydroxy-3-(1H-1,2,4-triazol-3-yl)-propenone
(1613) 3-Hydroxy-1-(2-(2-methoxyphenylthio)furan-3-yl)-3-(1H-1,2,4-triazol-3-yl)-propenone
(1614) 1-[(1-Benzenesulfonyl-5-n-propyl)pyrrol-3-yl]-3-hydroxy-3-(1H-1,2,4-triazol-3-yl)-propenone
(1615) 2-Hydroxy-4-(2-(4-methylbenzyl)thiophen-3-yl)-4-oxo-2-butenoic acid
(1616) 1-(5-(4-Chlorobenzenesulfonyl)pyrrol-3-yl)-3-hydroxy-3-(1H-1,2,4-triazol-3-yl)-propenone
(1617) 1-(3-(4-Fluorobenzenesulfonyl)thiophen-2-yl)-3-hydroxy-3-(2H-tetrazol-5-yl)-propenone
(1618) 1-[(5-(4-Fluorobenzyl)-4-methyl)furan-2-yl]-3-hydroxy-3-(1H-1,2,4-triazol-3-yl)-propenone
(1619) 3-Hydroxy-1-[(1-(4-methylbenzyl)-4-phenoxymethyl)pyrrol-2-yl]-3-(2H-tetrazol-5-yl)-propenone
(1620) 3-Hydroxy-1-(4-(pyridin-4-ylmethyl)furan-3-yl)-3-(1H-1,2,4-triazol-3-yl)-propenone
(1621) 1-(2H-2-(4-Chlorobenzenesulfonyl)pyrazol-4-yl)-3-hydroxy-3-(2H-tetrazol-5-yl)-propenone
(1622) 4-(4-(4-Fluorobenzenesulfonyl)thiophen-3-yl)-2-hydroxy-4-oxo-2-butenoic acid
(1623) 2-Hydroxy-4-oxo-4-(1-(pyridin-2-ylmethyl)pyrrol-3-yl)-2-butenoic acid
(1624) 4-(4-(2-Fluorobenzyl)furan-3-yl)-2-hydroxy-4-oxo-2-butenoic acid
(1625) 3-Hydroxy-1-(4-(pyridin-2-ylmethyl)furan-2-yl)-3-(2H-tetrazol-5-yl)-propenone
(1626) 1-[(1-(4-Chlorobenzenesulfonyl)-4-ethyl)pyrrol-2-yl]-3-hydroxy-3-(2H-tetrazol-5-yl)-propenone
(1627) 1-(2-(4-Aminobenzyl)thiophen-3-yl)-3-hydroxy-3-(1H-1,2,4-triazol-3-yl)-propenone
(1628) 1-[(4-Chloro-5-phenyl)furan-2-yl]-3-hydroxy-3-(1H-1,2,4-triazol-3-yl)-propenone
(1629) 1-[(3-Fluoro-4-phenyl)furan-2-yl]-3-hydroxy-3-(1H-1,2,4-triazol-3-yl)-propenone
(1630) 3-Hydroxy-1-(2H-2-(4-methoxybenzyl)pyrazol-3-yl)-3-(1H-1,2,4-triazol-3-yl)-propenone
(1631) 1-(2H-2-(4-Fluorobenzyl)pyrazol-4-yl)-3-hydroxy-3-(1H-1,2,4-triazol-3-yl)-propenone
(1632) 2-Hydroxy-4-oxo-4-(4-(pyridin-2-ylmethyl)thiophen-3-yl)-2-butenoic acid
(1633) 3-Hydroxy-3-(1H-1,2,4-triazol-3-yl)-1-(5-(4-trifluoromethylbenzyl)furan-3-yl)-propenone
(1634) 1-(2-(3-Chlorobenzyl)furan-3-yl)-3-hydroxy-3-(1H-1,2,4-triazol-3-yl)-propenone
(1635) 1-[(1-(4-Fluorobenzyl)-4-(2-phenylethyl))pyrrol-2-yl]-3-hydroxy-3-(1H-1,2,4-triazol-3-yl)-propenone
(1636) 4-(3-Benzylpyrrol-2-yl)-2-hydroxy-4-oxo-2-butenoic acid
(1637) 1-[(4-Fluoro-5-(4-fluorobenzyl))furan-2-yl]-3-hydroxy-3-(1H-1,2,4-triazol-3-yl)-propenone
(1638) 1-[(1-Benzenesulfonyl-4-n-octyl)pyrrol-2-yl]-3-hydroxy-3-(2H-tetrazol-5-yl)-propenone
(1639) 1-(4-(3-Chlorophenylthio)furan-3-yl)-3-hydroxy-3-(1H-1,2,4-triazol-3-yl)-propenone (1640) 1-(2(4-Aminobenzyl)pyrrol-3-yl)-3-hydroxy-3-(2H-tetrazol-5-yl)-propenone
(1641) 1-[(1-(4-Aminobenzyl)-5-benzoyl)pyrrol-3-yl]-3-hydroxy-3-(2H-tetrazol-5-yl)-propenone
(1642) 3-Hydroxy-1-(2H-2-phenylthiopyrazol-4-yl)-3-(1H-1,2,4-triazol-3-yl)-propenone
(1643) 4-(2H-5-Benzenesulfonylpyrazol-3-yl)-2-hydroxy-4-oxo-2-butenoic acid
(1644) 4-(5-(4-Chlorobenzenesulfonyl)thiophen-2-yl)-2-hydroxy-4-oxo-2-butenoic acid
(1645) 2-Hydroxy-4-(2-(4-methylbenzyl)thiazol-4-yl)-4-oxo-2-butenoic acid
(1646) 1-(2H-2-(4-Aminobenzyl)pyrazol-4-yl)-3-hydroxy-3-(1H-1,2,4-triazol-3-yl)-propenone
(1647) 2-Hydroxy-4-(4-(4-methoxybenzyl)thiazol-2-yl)-4-oxo-2-butenoic acid
(1648) 4-(1H-1-(3-Fluorobenzyl)pyrazol-4-yl)-2-hydroxy-4-oxo-2-butenoic acid
(1649) 1-(4-(4-Aminophenoxy)furan-2-yl)-3-hydroxy-3-(1H-1,2,4-triazol-3-yl)-propenone
(1650) 4-(5-Benzenesulfonylfuran-3-yl)-2-hydroxy-4-oxo-2-butenoic acid
(1651) 3-Hydroxy-1-[(4-methoxymethyl-1-(4-methylbenzyl))pyrrol-2-yl]-3-(2H-tetrazol-5-yl)-propenone
(1652) 1-(2-(4-Acetylbenzyl)pyrrol-3-yl)-3-hydroxy-3-(1H-1,2,4-triazol-3-yl)-propenone
(1653) 3-Hydroxy-1-(2H-5-(pyridin-2-ylmethyl)pyrazol-3-yl)-3-(1H-1,2,4-triazol-3-yl)-propenone
(1654) 1-[(4-Chloro-2-(pyridin-4-ylmethyl))furan-3-yl]-3-hydroxy-3-(1H-1,2,4-triazol-3-yl)-propenone
(1655) 1-[(1-(4-Chlorobenzenesulfonyl)-4-(2-phenylethyl))pyrrol-3-yl]-3-hydroxy-3-(1H-1,2,4-triazol-3-yl)-propenone
(1656) 3-Hydroxy-1-[(1-phenylthio-5-n-propyl)pyrrol-3-yl]-3-(1H-1,2,4-triazol-3-yl)-propenone
(1657) 3-Hydroxy-1-(1H-1-(4-methoxybenzyl)pyrazol-3-yl)-3-(1H-1,2,4-triazol-3-yl)-propenone
(1658) 1-[(1-Benzenesulfonyl-5-methoxymethyl)pyrrol-3-yl]-3-hydroxy-3-(1H-1,2,4-triazol-3-yl)-propenone
(1659) 1-[(5-Ethoxycarbonyl-1-(2-fluorobenzyl))pyrrol-3-yl]-3-hydroxy-3-(2H-tetrazol-5-yl)-propenone
(1660) 1-[(4-Benzenesulfonyl-5-(2-phenylethyl))furan-2-yl]-3-hydroxy-3-(1H-1,2,4-triazol-3-yl)-propenone
(1661) 1-[(1-(4-Fluorobenzyl)-4-(2-phenylethyl))pyrrol-3-yl]-3-hydroxy-3-(1H-1,2,4-triazol-3-yl)-propenone
(1662) 3-Hydroxy-1-(5-pyridin-4-ylmethyl)pyrrol-2-yl)-3-(2H-tetrazol-5-yl)-propenone
(1663) 1-(2-(3-Fluorobenzyl)thiophen-3-yl)-3-hydroxy-3-(2H tetrazol-5-yl)-propenone
(1664) 3-Hydroxy-1-(5-(pyridin-4-ylmethyl)thiophen-3-yl)-3-(1H-1,2,4-triazol-3-yl)-propenone
(1665) 3-Hydroxy-1-[(1-(4-methoxybenzyl)-5-n-octyl)pyrrol-3-yl]-3-(2H-tetrazol-5-yl)-propenone
(1666) 1-[(5-(4-Fluorobenzyl)-2-(2-phenylethyl))furan-3-yl]-3-hydroxy-3-(1H-1,2,4-triazol-3-yl)-propenone
(1667) 1-[(1-Benzyl-4-n-butyl)pyrrol-2-yl]-3-hydroxy-3-(1H-1,2,4-triazol-3-yl)-propenone
(1668) 1-[(4-Ethyl-1-(2-fluorobenzyl))pyrrol-3-yl]-3-hydroxy-3-(1H-1,2,4-triazol-3-yl)-propenone
(1669) 1-(2-(3-Chlorophenylthio)furan-3-yl)-3-hydroxy-3-(1H-1,2,4-triazol-3-yl)-propenone
(1670) 3-Hydroxy-1-(1-phenylthiopyrrol-2-yl)-3-(1H-1,2,4-triazol-3-yl)-propenone
(1671) 3-Hydroxy-1-(2-(4-methylbenzyl)thiazol-4-yl)-3-(1H-1,2,4-triazol-3-yl)-propenone
(1672) 1-(5-(4-Acetylbenzyl)furan-3-yl)-3-hydroxy-3-(2H-tetrazol-5-yl)-propenone
(1673) 1-(5-Benzenesulfonylpyrrol-3-yl)-3-hydroxy-3-(1H-1,2,4-triazol-3-yl)-propenone
(1674) 1-(5-Benzylpyrrol-3-yl)-3-hydroxy-3-(1H-1,2,4-triazol-3-yl)-propenone
(1675) 3-Hydroxy-1-[(1-(4-methylbenzyl)-5-phenoxymethyl)pyrrol-3-yl]-3-(1H-1,2,4-triazol-3-yl)-propenone
(1676) 3-Hydroxy-1-[(4-methoxymethyl-1-(pyridin-4-ylmethyl))pyrrol-2-yl]-3-(2H-tetrazol-5-yl)-propenone
(1677) 4-(4-(4-Fluorobenzenesulfonyl)thiazol-2-yl)-2-hydroxy-4-oxo-2-butenoic acid
(1678) 1-(4-(2-Fluorobenzyl)pyrrol-2-yl)-3-hydroxy-3-(1H-1,2,4-triazol-3-yl)-propenone
(1679) 1-(1H-1-(4-Chlorobenzenesulfonyl)pyrazol-3-yl)-3-hydroxy-3-(2H-tetrazol-5-yl)-propenone
(1680) 1-(5-(4-Aminobenzyl)pyrrol-2-yl)-3-hydroxy-3-(1H-1,2,4-triazol-3-yl)-propenone
(1681) 1-[(5-Benzenesulfonyl-4-chloro)furan-2-yl]-3-hydroxy-3-(1H-1,2,4-triazol-3-yl)-propenone
(1682) 1-[(4-Carboxy-1-(pyridin-4-ylmethyl))pyrrol-2-yl]-3-hydroxy-3-(2H-tetrazol-5-yl)-propenone
(1683) 1-[(4-Benzenesulfonyl-2-fluoro)furan-3-yl]-3-hydroxy-3-(1H-1,2,4-triazol-3-yl)-propenone
(1684) 1-[(4-Carboxy-1-(4-methoxybenzyl))pyrrol-2-yl]-3-hydroxy-3-(1H-1,2,4-triazol-3-yl)-propenone
(1685) 2-Hydroxy-4-oxo-4-(3-(pyridin-2-ylmethyl)pyrrol-2-yl)-2-butenoic acid
(1686) 1-[(5-n-Butyl-1-(4-methoxybenzyl))pyrrol-3-yl]-3-hydroxy-3-(2H-tetrazol-5-yl)-propenone
(1687) 3-Hydroxy-3-(1H-1,2,4-triazol-3-yl)-1-(4-(2-trifluoromethylphenoxy)furan-3-yl)-propenone
(1688) 1-[(5-Fluoro-4-(4-fluorobenzyl))furan-3-yl]-3-hydroxy-3-(1H-1,2,4-triazol-3-yl)-propenone
(1689) 3-Hydroxy-1-[(3-(2-phenylethyl)-4-(pyridin-4-ylmethyl))furan-2-yl]-3-(1H-1,2,4-triazol-3-yl)-propenone
(1690) 2-Hydroxy-4-oxo-4-(4-phenylthiofuran-2-yl)-2-butenoic acid
(1691) 1-[(4-Ethyl-1-(4-methylbenzyl))pyrrol-3-yl]-3-hydroxy-3-(2H-tetrazol-5-yl)-propenone
(1692) 3-Hydroxy-1-(3-(4-methoxybenzyl)thiophen-2-yl)-3-(1H-1,2,4-triazol-3-yl)-propenone
(1693) 1-[(1-(4-Fluorobenzenesulfonyl)-4-(2-phenylethyl))pyrrol-3-yl]-3-hydroxy-3-(2H-tetrazol-5-yl)-propenone
(1694) 1-(3-Benzenesulfonylfuran-2-yl)-3-hydroxy-3-(2H-tetrazol-5-yl)-propenone
(1695) 1-[(1-(4-Acetylbenzyl)-5-phenoxymethyl)pyrrol-3-yl]-3-hydroxy-3-(1H-1,2,4-triazol-3-yl)-propenone
(1696) 1-[(1-(4-Aminobenzyl)-4-n-propyl)pyrrol-2-yl]-3-hydroxy-3-(1H-1,2,4-triazol-3-yl)-propenone
(1697) 3-Hydroxy-1-(5-(4-methylbenzyl)thiophen-2-yl)-3-(1H-1,2,4-triazol-3-yl)-propenone
(1698) 3-Hydroxy-1-(2-(pyridin-4-ylmethyl)thiophen-3-yl)-3-(1H-1,2,4-triazol-3-yl)-propenone
(1699) 3-Hydroxy-1-(5-(4-methoxybenzyl)furan-2-yl)-3-(2H-tetrazol-5-yl)-propenone
(1700) 4-(2-(4-Acetylbenzyl)thiazol-4-yl)-2-hydroxy-4-oxo-2-butenoic acid
(1701) 1-[(1-(4-Chlorobenzenesulfonyl)-5-n-octyl)pyrrol-3-yl]-3-hydroxy-3-(1H-1,2,4-triazol-3-yl)-propenone
(1702) 1-[(5-Benzenesulfonyl-4-fluoro)furan-3-yl]-3-hydroxy-3-(1H-1,2,4-triazol-3-yl)-propenone
(1703) 1-[(4-Ethoxycarbonyl-1-(4-methoxybenzyl))pyrrol-2-yl]-3-hydroxy-3-(1H-1,2,4-triazol-3-yl)-propenone
(1704) 4-(2-(4-Chlorobenzenesulfonyl)furan-3-yl)-2-hydroxy-4-oxo-2-butenoic acid
(1705) 1-(1-(3-fluorobenzyl)pyrrol-2-yl)-3-hydroxy-3-(2H-tetrazol-5-yl)-propenone (1706) 1-[(3-fluoro-4-(4-fluorobenzyl))furan-2-yl]-3-hydroxy-3-(1H-1,2,4-triazol-3-yl)-propenone
(1707) 3-Hydroxy-1-(4-(4-methoxybenzyl)thiophen-3-yl)-3-(1H-1,2,4-triazol-3-yl)-propenone
(1708) 1-(4-(3-Fluorobenzyl)furan-2-yl)-3-hydroxy-3-(2H-tetrazol-5-yl)-propenone
(1709) 1-[(5-n-Butyl-1-(4-chlorobenzenesulfonyl))pyrrol-3-yl]-3-hydroxy-3-(1H-1,2,4-triazol-3-yl)-propenone
(1710) 1-(2H-4-(2-Fluorobenzyl)pyrazol-3-yl)-3-hydroxy-3-(1H-1,2,4-triazol-3-yl)-propenone
(1711) 1-[(5-n-Butyl-1-(3-fluorobenzyl))pyrrol-3-yl]-3-hydroxy-3-(2H-tetrazol-5-yl)-propenone
(1712) 2-Hydroxy-4-(3-(4-methylbenzyl)thiophen-2-yl)-4-oxo-2-butenoic acid
(1713) 3-Hydroxy-1-(4-(3-methoxyphenylthio)furan-2-yl)-3-(1H-1,2,4-triazol-3-yl)-propenone
(1714) 4-(2H-5-(4-fluorobenzenesulfonyl)pyrazol-3-yl)-2-hydroxy-4-oxo-2-butenoic acid
(1715) 4-(5-Benzenesulfonylthiophen-2-yl)-2-hydroxy-4-oxo-2-butenoic acid
(1716) 1-(4-(2-Fluorobenzyl)thiazol-2-yl)-3-hydroxy-3-(1H-1,2,4-triazol-3-yl)-propenone
(1717) 3-Hydroxy-1-[(4-(2-phenylethyl)-1-(pyridin-4-ylmethyl))pyrrol-2-yl]-3-(1H-1,2,4-triazol-3-yl)-propenone
(1718) 3-Hydroxy-1-(3-(pyridin-4-ylmethyl)furan-2-yl)-3-(1H-1,2,4-triazol-3-yl)-propenone
(1719) 3-Hydroxy-1-(4-(pyridin-2-ylmethyl)thiazol-2-yl)-3-(2H-tetrazol-5-yl)-propenone
(1720) 3-Hydroxy-1-(2-(4-methoxybenzyl)furan-3-yl)-3-(2H-tetrazol-5-yl)-propenone
(1721) 4-(3-(4-Fluorobenzyl)thiophen-2-yl)-2-hydroxy-4-oxo-2-butenoic acid
(1722) 1-[(1-(4-Fluorobenzyl)-4-n-octyl)pyrrol-2-yl]-3-hydroxy-3-(1H-1,2,4-triazol-3-yl)-propenone
(1723) 1-(4-(2-Fluorobenzyl)pyrrol-2-yl)-3-hydroxy-3-(2H-tetrazol-5-yl)-propenone
(1724) 1-[(4-Ethyl-1-(4-methoxybenzyl))pyrrol-2-yl]-3-hydroxy-3-(1H-1,2,4-triazol-3-yl)-propenone
(1725) 2-Hydroxy-4-oxo-4-(3-(pyridin-4-ylmethyl)furan-2-yl)-2-butenoic acid
(1726) 3-Hydroxy-1-(2H-4-(pyridin-2-ylmethyl)pyrazol-3-yl)-3-(1H-1,2,4-triazol-3-yl)-propenone
(1727) 1-(2-(4-Fluorobenzenesulfonyl)furan-3-yl)-3-hydroxy-3-(2H-tetrazol-5-yl)-propenone
(1728) 1-(2H-4-(4-Aminobenzyl)pyrazol-3-yl)-3-hydroxy-3-(2H-tetrazol-5-yl)-propenone
(1729) 4-(2-Benzylthiazol-4-yl)-2-hydroxy-4-oxo-2-butenoic acid
(1730) 3-Hydroxy-1-[(1-(4-methoxybenzyl)-4-n-octyl)pyrrol-2-yl]-3-(2H-tetrazol-5-yl)-propenone
(1731) 4-(5-(4-Fluorobenzyl)pyrrol-3-yl)-2-hydroxy-4-oxo-2-butenoic acid
(1732) 1-(1-(2-Fluorobenzyl)pyrrol-3-yl)-3-hydroxy-3-(2H-tetrazol-5-yl)-propenone
(1733) 4-(1H-1-Benzylpyrazol-4-yl)-2-hydroxy-4-oxo-2-butenoic acid
(1734) 1-(5-(2-Fluorobenzyl)pyrrol-3-yl)-3-hydroxy-3-(2H-tetrazol-5-yl)-propenone
(1735) 3-Hydroxy-3-(1H-1,2,4-triazol-3-yl)-1-(5-(2-trifluoromethylphenylthio)furan-2-yl)-propenone
(1736) 3-Hydroxy-1-(3-(4-methylbenzyl)pyrrol-2-yl)-3-(1H-1,2,4-triazol-3-yl)-propenone
(1737) 1-[(1-(4-Aminobenzyl)-4-methoxymethyl)pyrrol-2-yl]-3-hydroxy-3-(1H-1,2,4-triazol-3-yl)-propenone
(1738) 1-(5-(3-Fluorobenzyl)furan-2-yl)-3-hydroxy-3-(2H-tetrazol-5-yl)-propenone
(1739) 1-(5-(4-Acetylbenzyl)thiophen-3-yl)-3-hydroxy-3-(2H-tetrazol-5-yl)-propenone
(1740) 3-Hydroxy-1-[(4-phenoxymethyl-1-phenylthio)pyrrol-2-yl]-3-(1H-1,2,4-triazol-3-yl)-propenone
(1741) 3-Hydroxy-1-[(5-phenyl-4-(2-phenylethyl))furan-3-yl]-3-(1H-1,2,4-triazol-3-yl)-propenone
(1742) 3-Hydroxy-1-(3-phenylfuran-2-yl)-3-(1H-1,2,4-triazol-3-yl)-propenone
(1743) 1-(4-(4-Fluorobenzenesulfonyl)thiophen-3-yl)-3-hydroxy-3-(2H-tetrazol-5-yl)-propenone
(1744) 3-Hydroxy-3-(1H-1,2,4-triazol-3-yl)-1-(3-(4-trifluoromethylbenzyl)furan-2-yl)-propenone
(1745) 3-Hydroxy-1-(4-(2-methoxyphenylthio)furan-2-yl)-3-(1H-1,2,4-triazol-3-yl)-propenone
(1746) 1-(3-Benzenesulfonylthiophen-2-yl)-3-hydroxy-3-(1H-1,2,4-triazol-3-yl)-propenone
(1747) 1-[(5-Chloro-2-phenyl)furan-3-yl]-3-hydroxy-3-(1H-1,2,4-triazol-3-yl)-propenone
(1748) 3-Hydroxy-1-[(3-phenyl-4-(2-phenylethyl))furan-2-yl]-3-(1H-1,2,4-triazol-3-yl)-propenone
(1749) 1-(1H-1-Benzenesulfonylpyrazol-3-yl)-3-hydroxy-3-(1H-1,2,4-triazol-3-yl)-propenone
(1750) 1-[(5-Benzenesulfonyl-4-(2-phenylethyl))furan-3-yl]-3-hydroxy-3-(1H-1,2,4-triazol-3-yl)-propenone
(1751) 1-[(1-(4-Fluorobenzenesulfonyl)-4-(2-phenylethyl))pyrrol-3-yl]-3-hydroxy-3-(1H-1,2,4-triazol-3-yl)-propenone
(1752) 4-(1-(4-Fluorobenzyl)pyrrol-3-yl)-2-hydroxy-4-oxo-2-butenoic acid
(1753) 3-Hydroxy-3-(1H-1,2,4-triazol-3-yl)-1-(4-(3-trifluoromethylphenylthio)furan-3-yl)-propenone
(1754) 1-(4-(3-Chlorobenzyl)furan-2-yl)-3-hydroxy-3-(1H-1,2,4-triazol-3-yl)-propenone
(1755) 2-Hydroxy-4-(2-(4-methoxybenzyl)furan-3-yl)-4-oxo-2-butenoic acid
(1756) 1-[(4-Chloro-3-pyridin-4-ylmethyl))furan-2-yl]-3-hydroxy-3-(1H-1,2,4-triazol-3-yl)-propenone
(1757) 2-Hydroxy-4-(5-(4-methoxybenzyl)furan-3-yl)-4-oxo-2-butenoic acid
(1758) 2-Hydroxy-4-(2H-4-(4-methylbenzyl)pyrazol-3-yl)-4-oxo-2-butenoic acid
(1759) 1-(1H-1-(3-Fluorobenzyl)pyrazol-4-yl)-3-hydroxy-3-(1H-1,2,4-triazol-3-yl)-propenone
(1760) 3-Hydroxy-1-(5-(4-methoxyphenoxy)furan-2-yl)-3-(1H-1,2,4-triazol-3-yl)-propenone
(1761) 1-(2-Benzenesulfonylpyrrol-3-yl)-3-hydroxy-3-(1H-1,2,4-triazol-3-yl)-propenone
(1762) 1-(4-(4-Chlorobenzenesulfonyl)thiazol-2-yl)-3-hydroxy-3-(1H-1,2,4-triazol-3-yl)-propenone
(1763) 1-[(1-(2-Fluorobenzyl)-5-phenoxymethyl)pyrrol-3-yl]-3-hydroxy-3-(1H-1,2,4-triazol-3-yl)-propenone
(1764) 1-(2-Benzylpyrrol-3-yl)-3-hydroxy-3-(1H-1,2,4-triazol-3-yl)-propenone
(1765) 1-(3-n-butylfuran-2-yl)-3-hydroxy-3-(1H-1,2,4-triazol-3-yl)-propenone
(1766) 2-Hydroxy-4-oxo-4-(5-(pyridin-4-ylmethyl)pyrrol-3-yl)-2-butenoic acid
(1767) 3-Hydroxy-3-(1H-1,2,4-triazol-3-yl)-1-(4-(3-trifluoromethylphenoxy)furan-3-yl)-propenone
(1768) 3-Hydroxy-1-(2-(4-methoxybenzyl)pyrrol-3-yl)-3-(2H-tetrazol-5-yl)-propenone
(1769) 1-[(4-Ethyl-1-(4-methylbenzyl))pyrrol-2-yl]-3-hydroxy-3-(2H-tetrazol-5-yl)-propenone
(1770) 3-Hydroxy-1-(1-(pyridin-2-ylmethyl)pyrrol-3-yl)-3-(1H-1,2,4-triazol-3-yl)-propenone
(1771) 1-[(1-(4-Aminobenzyl)-4-carboxy)pyrrol-2-yl]-3-hydroxy-3-(2H-tetrazol-5-yl)-propenone (1772) 1-[(5-Fluoro-4-(4-fluorobenzyl))furan-2-yl]-3-hydroxy-3-(1H-1,2,4-triazol-3-yl)-propenone
(1773) 1-(5-Benzenesulfonylpyrrol-2-yl)-3-hydroxy-3-(1H-1,2,4-triazol-3-yl)-propenone
(1774) 3-Hydroxy-1-[(5-methoxymethyl-1-(4-methylbenzyl))pyrrol-3-yl]-3-(2H-tetrazol-5-yl)-propenone
(1775) 2-Hydroxy-4-oxo-4-(2-phenylthiothiazol-4-yl)-2-butenoic acid
(1776) 3-Hydroxy-1-[(5-n-propyl-1-(pyridin-4-ylmethyl))pyrrol-3-yl]-3-(1H-1,2,4-triazol-3-yl)-propenone
(1777) 4-(2-Benzylfuran-3-yl)-2-hydroxy-4-oxo-2-butenoic acid
(1778) 4-(1H-1-(4-fluorobenzenesulfonyl)pyrazol-3-yl)-2-hydroxy-4oxo-2-butenoic acid
(1779) 3-Hydroxy-1-(2-(4-methylbenzyl)pyrrol-3-yl)-3-(1H-1,2,4-triazol-3-yl)-propenone
(1780) 1-(2-(2-Fluorobenzyl)furan-3-yl)-3-hydroxy-3-(1H-1,2,4-triazol-3-yl)-propenone
(1781) 4-(4-(4-Acetylbenzyl)pyrrol-3-yl)-2-hydroxy-4-oxo-2-butenoic acid
(1782) 1-[(1-(4-Acetylbenzyl)-5-carboxy)pyrrol-3-yl]-3-hydroxy-3-(2H-tetrazol-5-yl)-propenone
(1783) 3-Hydroxy-1-[(3-methyl-4-phenyl)furan-2-yl]-3-(1H-1,2,4-triazol-3-yl)-propenone
(1784) 3-Hydroxy-1-(4-(3-methoxyphenoxy)furan-2-yl)-3-(1H-1,2,4-triazol-3-yl)-propenone
(1785) 1-[(4-Ethyl-1-(3-fluorobenzyl))pyrrol-3-yl]-3-hydroxy-3-(2H-tetrazol-5-yl)-propenone
(1786) 3-Hydroxy-1-(1H-1-(4-methylbenzyl)pyrazol-3-yl)-3-(2H-tetrazol-5-yl)-propenone
(1787) 2-Hydroxy-4-(1H-1-(4-methoxybenzyl)pyrazol-3-yl)-4-oxo-2-butenoic acid
(1788) 3-Hydroxy-1-[(1-(4-methylbenzyl)-4-(2-phenylethyl))pyrrol-2-yl]-3-(1H-1,2,4-triazol-3-yl)-propenone
(1789) 1-(4-(4-Acetylbenzyl)pyrrol-2-yl)-3-hydroxy-3-(2H-tetrazol-5-yl)-propenone
(1790) 1-[(4-Benzoyl-1-(4-methoxybenzyl))pyrrol-2-yl]-3-hydroxy-3-(2H-tetrazol-5-yl)-propenone
(1791) 4-(5-(4-Fluorobenzyl)furan-3-yl)-2-hydroxy-4-oxo-2-butenoic acid
(1792) 1-[(4-n-Butyl-1-(4-chlorobenzenesulfonyl))pyrrol-2-yl]-3-hydroxy-3-(1H-1,2,4-triazol-3-yl)-propenone
(1793) 1-[(5-Benzoyl-1-(4-fluorobenzenesulfonyl))pyrrol-3-yl]-3-hydroxy-3-(1H-1,2,4-triazol-3-yl)-propenone
(1794) 1-[(5-Chloro-4-phenyl)furan-2-yl]-3-hydroxy-3-(1H-1,2,4-triazol-3-yl)-propenone
(1795) 2-Hydroxy-4-oxo-4-(2-phenylthiofuran-3-yl)-2-butenoic acid
(1796) 3-Hydroxy-1-[(3-phenyl-5-(2-phenylethyl))furan-2-yl]-3-(1H-1,2,4-triazol-3-yl)-propenone
(1797) 3-Hydroxy-1-(3-(2-methoxyphenoxy)furan-2-yl)-3-(1H-1,2,4-triazol-3-yl)-propenone
(1798) 2-Hydroxy-4-oxo-4-(1-(pyridin-2-ylmethyl)pyrrol-2-yl)-2-butenoic acid
(1799) 3-Hydroxy-1-(5-(pyridin-4-ylmethyl)furan-3-yl)-3-(2H-tetrazol-5-yl)-propenone
(1800) 1-[(1-(4-Fluorobenzenesulfonyl)-4-(2-phenylethyl))pyrrol-2-yl]-3-hydroxy-3-(2H-tetrazol-5-yl)-propenone
(1801) 4-(5-(4-Fluorobenzyl)thiophen-3-yl)-2-hydroxy-4-oxo-2-butenoic acid
(1802) 3-Hydroxy-1-(4-(4-methylbenzyl)furan-2-yl)-3-(2H-tetrazol-5-yl)-propenone
(1803) 3-Hydroxy-1-[(1-(4-methoxybenzyl)-4-(2-phenylethyl))pyrrol-3-yl]-3-(1H-1,2,4-triazol-3-yl)-propenone
(1804) 4-(2H-2-benzylpyrazol-3-yl)-2-hydroxy-4-oxo-2-butenoic acid
(1805) 1-[(1-Benzenesulfonyl-4-ethoxycarbonyl)pyrrol-2-yl]-3-hydroxy-3-(2H-tetrazol-5-yl)-propenone
(1806) 1-[(1-Benzenesulfonyl-4-benzoyl)pyrrol-2-yl]-3-hydroxy-3-(2H-tetrazol-5-yl)-propenone
(1807) 1-(3-(2-Chlorophenylthio)furan-2-yl)-3-hydroxy-3-(1H-1,2,4-triazol-3-yl)-propenone
(1808) 3-Hydroxy-1-(1H-1-(pyridin-4-ylmethyl)pyrazol-4-yl)-3-(1H-1,2,4-triazol-3-yl)-propenone
(1809) 1-[(5-Ethoxycarbonyl-1-(4-methylbenzyl))pyrrol-3-yl]-3-hydroxy-3-(1H-1,2,4-triazol-3-yl)-propenone
(1810) 2-Hydroxy-4-(2-(4-methylbenzyl)pyrrol-3-yl)-4-oxo-2-butenoic acid
(1811) 3-Hydroxy-1-[(1-phenylthio-4-n-propyl)pyrrol-2-yl]-3-(1H-1,2,4-triazol-3-yl)-propenone
(1812) 3-Hydroxy-1-[(2-phenyl-4-(2-phenylethyl))furan-3-yl]-3-(1H-1,2,4-triazol-3-yl)-propenone
(1813) 1-[(1-(4-Fluorobenzyl)-5-n-octyl)pyrrol-3-yl]-3-hydroxy-3-(2H-tetrazol-5-yl)-propenone
(1814) 4-(4-(4-Chlorobenzenesulfonyl)thiophen-2-yl)-2-hydroxy-4-oxo-2-butenoic acid
(1815) 4-(3-Benzenesulfonylthiophen-2-yl)-2-hydroxy-4-oxo-2-butenoic acid
(1816) 1-(4-Benzenesulfonylpyrrol-3-yl)-3-hydroxy-3-(2H-tetrazol-5-yl)-propenone
(1817) 2-Hydroxy-4-(2H-5-(4-methoxybenzyl)pyrazol-3-yl)-4-oxo-2-butenoic acid
(1818) 1-(4-(3-Chlorophenylthio)furan-2-yl)-3-hydroxy-3-(1H-1,2,4-triazol-3-yl)-propenone
(1819) 3-Hydroxy-1-(4-(pyridin-4-ylmethyl)thiophen-2-yl)-3-(1H-1,2,4-triazol-3-yl)-propenone
(1820) 1-[(1-(4-Aminobenzyl)-4-(2-phenylethyl))pyrrol-3-yl]-3-hydroxy-3-(2H-tetrazol-5-yl)-propenone
(1821) 3-Hydroxy-1-(4-(pyridin-2-ylmethyl)furan-3-yl)-3-(1H-1,2,4-triazol-3-yl)-propenone
(1822) 1-(5-(4-Aminobenzyl)thiophen-2-yl)-3-hydroxy-3-(1H-1,2,4-triazol-3-yl)-propenone
(1823) 1-(2-(4-Fluorobenzenesulfonyl)furan-3-yl)-3-hydroxy-3-(1H-1,2,4-triazol-3-yl)-propenone
(1824) 3-Hydroxy-1-(2-(4-methoxybenzyl)thiazol-4-yl)-3-(2H-tetrazol-5-yl)-propenone
(1825) 1-[(1-(4-Fluorobenzyl)-4-phenoxymethyl)pyrrol-2-yl]-3-hydroxy-3-(2H-tetrazol-5-yl)-propenone
(1826) 1-[(4-Benzoyl-1-(2-fluorobenzyl))pyrrol-2-yl]-3-hydroxy-3-(2H-tetrazol-5-yl)-propenone
(1827) 3-Hydroxy-1-(4-(pyridin-2-ylmethyl)pyrrol-2-yl)-3-(2H-tetrazol-5-yl)-propenone
(1828) 1-[(1-(4-Fluorobenzenesulfonyl)-4-methoxymethyl)pyrrol-2-yl]-3-hydroxy-3-(2H-tetrazol-5-yl)-propenone
(1829) 1-(1H-1-(4-fluorobenzenesulfonyl)pyrazol-3-yl)-3-hydroxy-3-(2H-tetrazol-5-yl)-propenone
(1830) 1-[(5-Benzenesulfonyl-3-chloro)furan-2-yl]-3-hydroxy-3-(1H-1,2,4-triazol-3-yl)-propenone
(1831) 1-(5-(2-Fluorobenzyl)thiophen-3-yl)-3-hydroxy-3-(1H-1,2,4-triazol-3-yl)-propenone
(1832) 3-Hydroxy-1-(4-(4-methoxybenzyl)furan-2-yl)-3-(1H-1,2,4-triazol-3-yl)-propenone
(1833) 1-[(4-Ethyl-1-(4-fluorobenzenesulfonyl))pyrrol-2-yl]-3-hydroxy-3-(1H-1,2,4-triazol-3-yl)-propenone
(1834) 3-Hydroxy-1-[(1-(4-methylbenzyl)-5-phenoxymethyl)pyrrol-3-yl]-3-(2H-tetrazol-5-yl)-propenone
(1835) 4-(2H-5-(4-Acetylbenzyl)pyrazol-3-yl)-2-hydroxy-4-oxo-2-butenoic acid
(1836) 1-[(1-(4-Acetylbenzyl)-5-n-octyl)pyrrol-3-yl]-3-hydroxy-3-(1H-1,2,4-triazol-3-yl)-propenone (1837) 1-(2H-4-(4-Fluorobenzyl)pyrazol-3-yl)-3-hydroxy-3-(2H-tetrazol-5-yl)-propenone
(1838) 2-Hydroxy-4-oxo-4-(5-(pyridin-2-ylmethyl)pyrrol-3-yl)-2-butenoic acid
(1839) 3-Hydroxy-1-(2H-5-(4-methoxybenzyl)pyrazol-3-yl)-3-(1H-1,2,4-triazol-3-yl)-propenone
(1840) 1-(1H-1-(4-Acetylbenzyl)pyrazol-4-yl)-3-hydroxy-3-(2H-tetrazol-5-yl)-propenone
(1841) 3-Hydroxy-1-(3-(3-methoxybenzyl)furan-2-yl)-3-(1H-1,2,4-triazol-3-yl)-propenone
(1842) 3-Hydroxy-1-(4-(3-methoxyphenylthio)furan-3-yl)-3-(1H-1,2,4-triazol-3-yl)-propenone
(1843) 3-Hydroxy-1-(1H-1-(4-methoxybenzyl)pyrazol-4-yl)-3-(1H-1,2,4-triazol-3-yl)-propenone
(1844) 1-[(5-Ethoxycarbonyl-1-(pyridin-4-ylmethyl))pyrrol-3-yl]-3-hydroxy-3-(2H-tetrazol-5-yl)-propenone
(1845) 3-Hydroxy-1-(5-(pyridin-2-ylmethyl)furan-2-yl)-3-(1H-1,2,4-triazol-3-yl)-propenone
(1846) 1-[(1-(4-Aminobenzyl)-4-(2-phenylethyl))pyrrol-2-yl]-3-hydroxy-3-(2H-tetrazol-5-yl)-propenone
(1847) 4-(1H-1-(4-Chlorobenzenesulfonyl)pyrazol-3-yl)-2-hydroxy-4-oxo-2-butenoic acid
(1848) 3-Hydroxy-1-[(5-methyl-3-phenyl)furan-2-yl]-3-(1H-1,2,4-triazol-3-yl)-propenone
(1849) 3-Hydroxy-1-(4-(4-methylbenzyl)thiazol-2-yl)-3-(1H-1,2,4-triazol-3-yl)-propenone
(1850) 1-(3-(4-Fluorobenzenesulfonyl)thiophen-2-yl)-3-hydroxy-3-(1H-1,2,4-triazol-3-yl)-propenone
(1851) 1-[(4-n-Butyl-1-(4-fluorobenzyl))pyrrol-2-yl]-3-hydroxy-3-(2H-tetrazol-5-yl)-propenone
(1852) 4-(5-(4-Chlorobenzenesulfonyl)furan-3-yl)-2-hydroxy-4-oxo-2-butenoic acid
(1853) 1-[(1-(4-Acetylbenzyl)-4-phenoxymethyl)pyrrol-2-yl]-3-hydroxy-3-(2H-tetrazol-5-yl)-propenone
(1854) 3-Hydroxy-1-[(1-(4-methoxybenzyl)-5-n-propyl)pyrrol-3-yl]-3-(1H-1,2,4-triazol-3-yl)-propenone
(1855) 1-(5-(2-Fluorobenzyl)pyrrol-2-yl)-3-hydroxy-3-(1H-1,2,4-triazol-3-yl)-propenone
(1856) 1-(5-(4-Acetylbenzyl)furan-2-yl)-3-hydroxy-3-(1H-1,2,4-triazol-3-yl)-propenone
(1857) 1-(2-Benzylfuran-3-yl)-3-hydroxy-3-(1H-1,2,4-triazol-3-yl)-propenone
(1858) 1-(4-Benzenesulfonylfuran-3-yl)-3-hydroxy-3-(2H-tetrazol-5-yl)-propenone
(1859) 1-(4-(2-Fluorobenzyl)furan-3-yl)-3-hydroxy-3-(1H-1,2,4-triazol-3-yl)-propenone
(1860) 4-(1-(3-fluorobenzyl)pyrrol-2-yl)-2-hydroxy-4-oxo-2-butenoic acid
(1861) 1-[(5-Benzoyl-1-(4-methoxybenzyl))pyrrol-3-yl]-3-hydroxy-3-(1H-1,2,4-triazol-3-yl)-propenone
(1862) 2-Hydroxy-4-(1-(4-methylbenzyl)pyrrol-3-yl)-4-oxo-2-butenoic acid
(1863) 1-(4-(4-Fluorophenyl)furan-3-yl)-3-hydroxy-3-(1H-1,2,4-triazol-3-yl)-propenone
(1864) 2-Hydroxy-4-oxo-4-(3-phenylthiothiophen-2-yl)-2-butenoic acid
(1865) 1-[(3-Benzenesulfonyl-4-chloro)furan-2-yl]-3-hydroxy-3-(1H-1,2,4-triazol-3-yl)-propenone
(1866) 1-(1H-1-Benzylpyrazol-4-yl)-3-hydroxy-3-(1H-1,2,4-triazol-3-yl)-propenone
(1867) 1-(5-(4-Acetylbenzyl)pyrrol-2-yl)-3-hydroxy-3-(2H-tetrazol-5-yl)-propenone
(1868) 4-(2-(3-Fluorobenzyl)pyrrol-3-yl)-2-hydroxy-4-oxo-2-butenoic acid
(1869) 3-Hydroxy-1-(4-(4-methoxybenzyl)pyrazol-3-yl)-3-(1H-1,2,4-triazol-3-yl)-propenone
(1870) 3-Hydroxy-1-[(4-phenoxymethyl-1-(pyridin-4-ylmethyl))pyrrol-2-yl]-3-(2H-tetrazol-5-yl)-propenone
(1871) 4-(4-(2-Fluorobenzyl)thiophen-2-yl)-2-hydroxy-4-oxo-2-butenoic acid
(1872) 4-(5-(3-Fluorobenzyl)furan-2-yl)-2-hydroxy-4-oxo-2-butenoic acid
(1873) 1-(2H-5-(4-aminobenzyl)pyrazol-3-yl)-3-hydroxy-3-(1H-1,2,4-triazol-3-yl)-propenone
(1874) 2-Hydroxy-4-(3-(4-methoxybenzyl)furan-2-yl)-4-oxo-2-butenoic acid
(1875) 3-Hydroxy-1-[(3-methyl-4-(pyridin-4-ylmethyl))furan-2-yl]-3-(1H-1,2,4-triazol-3-yl)-propenone
(1876) 2-Hydroxy-4-(1H-1-(4-methylbenzyl)pyrazol-4-yl)-4-oxo-2-butenoic acid
(1877) 3-Hydroxy-1-(5-phenylthiofuran-3-yl)-3-(1H-1,2,4-triazol-3-yl)-propenone
(1878) 1-[(1-(3-Fluorobenzyl)-4-methoxymethyl)pyrrol-2-yl]-3-hydroxy-3-(1H-1,2,4-triazol-3-yl)-propenone
(1879) 1-(2-(4-Fluorobenzenesulfonyl)thiophen-3-yl)-3-hydroxy-3-(2H-tetrazol-5-yl)-propenone
(1880) 1-[(1-(4-Acetylbenzyl)-5-n-propyl)pyrrol-3-yl]-3-hydroxy-3-(1H-1,2,4-triazol-3-yl)-propenone
(1881) 1-[(1-(4-Fluorobenzenesulfonyl)-5-methoxymethyl)pyrrol-3-yl]-3-hydroxy-3-(2H-tetrazol-5-yl)-propenone
(1882) 1-(4-(4-Fluorobenzenesulfonyl)pyrrol-2-yl)-3-hydroxy-3-(2H-tetrazol-5-yl)-propenone
(1883) 1-[(4-Fluoro-2-phenyl)furan-3-yl]-3-hydroxy-3-(1H-1,2,4-triazol-3-yl)-propenone
(1884) 1-[(1-(4-Aminobenzyl)-4-ethoxycarbonyl)pyrrol-2-yl]-3-hydroxy-3-(2H-tetrazol-5-yl)-propenone
(1885) 1-[(4-Benzoyl-1-(4-chlorobenzenesulfonyl))pyrrol-2-yl]-3-hydroxy-3-(1H-1,2,4-triazol-3-yl)-propenone
(1886) 1-(4-Benzenesulfonylthiophen-2-yl)-3-hydroxy-3-(2H-tetrazol-5-yl)-propenone
(1887) 1-[(4-Chloro-3-phenyl)furan-2-yl]-3-hydroxy-3-(1H-1,2,4-triazol-3-yl)-propenone
(1888) 3-Hydroxy-1-[(1-(4-methylbenzyl)-4-n-octyl)pyrrol-2-yl]-3-(2H-tetrazol-5-yl)-propenone
(1889) 1-[(1-(4-Fluorobenzenesulfonyl)-5-n-octyl)pyrrol-3-yl]-3-hydroxy-3-(2H-tetrazol-5-yl)-propenone
(1890) 4-(4-(4-Aminobenzyl)thiazol-2-yl)-2-hydroxy-4-oxo-2-butenoic acid
(1891) 1-[(4-n-Butyl-1-(pyridin-4-ylmethyl))pyrrol-2-yl]-3-hydroxy-3-(1H-1,2,4-triazol-3-yl)-propenone
(1892) 4-(2H-4-(4-aminobenzyl)pyrazol-3-yl)-2-hydroxy-4-oxo-2-butenoic acid
(1893) 3-Hydroxy-3-(1H-1,2,4-triazol-3-yl)-1-(3-(4-trifluoromethylphenylthio)furan-2-yl)-propenone
(1894) 1-[(5-Carboxy-1-(2-fluorobenzyl))pyrrol-2-yl]-3-hydroxy-3-(2H-tetrazol-5-yl)-propenone
(1895) 1-[(4-Ethyl-1-(2-fluorobenzyl))pyrrol-3-yl]-3-hydroxy-3-(2H-tetrazol-5-yl)-propenone
(1896) 1-(4-Benzylthiophen-2-yl)-3-hydroxy-3-(2H-tetrazol-5-yl)-propenone
(1897) 4-(5-Benzylthiophen-2-yl)-2-hydroxy-4-oxo-2-butenoic acid
(1898) 1-(4-(2-Chlorophenylthio)furan-3-yl)-3-hydroxy-3-(1H-1,2,4-triazol-3-yl)-propenone
(1899) 3-Hydroxy-1-[(4-n-propyl-1-(pyridin-2-ylmethyl))pyrrol-2-yl]-3-(2H-tetrazol-5-yl)-propenone
(1900) 4-(2H-2-(4-Fluorobenzyl)pyrazol-3-yl)-2-hydroxy-4-oxo-2-butenoic acid
(1901) 4-(5-(4-Fluorobenzenesulfonyl)thiophen-2-yl)-2-hydroxy-4-oxo-2-butenoic acid
(1902) 1-(2-(2-Fluorobenzyl)pyrrol-3-yl)-3-hydroxy-3-(1H-1,2,4-triazol-3-yl)-propenone
(1903) 1-[(3-(4-Fluorobenzyl)-5-(2-phenylethyl))furan-2-yl]-3-hydroxy-3-(1H-1,2,4-triazol-3-yl)-propenone
(1904) 3-Hydroxy-1-(5-phenoxyfuran-3-yl)-3-(1H-1,2,4-triazol-3-yl)-propenone (1905) 1-[(1-Benzyl-5-phenoxymethyl)pyrrol-3-yl]-3-hydroxy-3-(1H-1,2,4-triazol-3-yl)-propenone
(1906) 3-Hydroxy-1-(3-(pyridin-2-ylmethyl)thiophen-2-yl)-3-(1H-1,2,4-triazol-3-yl)-propenone
(1907) 1-[(1-Benzenesulfonyl-4-n-butyl)pyrrol-2-yl]-3-hydroxy-3-(2H-tetrazol-5-yl)-propenone
(1908) 1-[(1-(2-Fluorobenzyl)-4-methoxymethyl)pyrrol-2-yl]-3-hydroxy-3-(2H-tetrazol-5-yl)-propenone
(1909) 1-[(1-Benzenesulfonyl-5-ethoxycarbonyl)pyrrol-3-yl]-3-hydroxy-3-(2H-tetrazol-5-yl)-propenone
(1910) 3-Hydroxy-1-(3-(pyridin-4-ylmethyl)pyrrol-2-yl)-3-(2H-tetrazol-5-yl)-propenone
(1911) 1-(1-(4-Aminobenzyl)pyrrol-2-yl)-3-hydroxy-3-(2H-tetrazol-5-yl)-propenone
(1912) 3-Hydroxy-1-(5-(4-methylbenzyl)pyrrol-2-yl)-3-(1H-1,2,4-triazol-3-yl)-propenone
(1913) 1-[(4-Benzoyl-1-(pyridin-2-ylmethyl))pyrrol-2-yl]-3-hydroxy-3-(2H-tetrazol-5-yl)-propenone
(1914) 3-Hydroxy-1-(5-phenylthiothiophen-3-yl)-3-(1H-1,2,4-triazol-3-yl)-propenone
(1915) 1-[(1-Benzenesulfonyl-5-ethoxycarbonyl)pyrrol-3-yl]-3-hydroxy-3-(1H-1,2,4-triazol-3-yl)-propenone
(1916) 1-(3-(4-Acetylbenzyl)thiophen-2-yl)-3-hydroxy-3-(1H-1,2,4-triazol-3-yl)-propenone
(1917) 1-[(3-Chloro-5-phenyl)furan-2-yl]-3-hydroxy-3-(1H-1,2,4-triazol-3-yl)-propenone
(1918) 1-(3-(2-Fluorophenyl)furan-2-yl)-3-hydroxy-3-(1H-1,2,4-triazol-3-yl)-propenone
(1919) 3-Hydroxy-3-(1H-1,2,4-triazol-3-yl)-1-(4-(2-trifluoromethylphenylthio)furan-3-yl)-propenone
(1920) 3-Hydroxy-1-(5-(2-methoxyphenoxy)furan-3-yl)-3-(1H-1,2,4-triazol-3-yl)-propenone
(1921) 1-(5-(4-Chlorobenzenesulfonyl)thiophen3-yl)-3-hydroxy-3-(2H-tetrazol-5-yl)-propenone
(1922) 1-[(5-Benzenesulfonyl-3-methyl)furan-2-yl]-3-hydroxy-3-(1H-1,2,4-triazol-3-yl)-propenone
(1923) 1-(4-Benzylthiazol-2-yl)-3-hydroxy-3-(1H-1,2,4-triazol-3-yl)-propenone
(1924) 1-(1H-1-(4-fluorobenzyl)pyrazol-4-yl)-3-hydroxy-3-(2H-tetrazol-5-yl)-propenone
(1925) 4-(4-(4-Acetylbenzyl)furan-3-yl)-2-hydroxy-4-oxo-2-butenoic acid
(1926) 3-Hydroxy-1-(1H-1-phenylthiopyrazol-3-yl)-3-(2H-tetrazol-5-yl)-propenone
(1927) 1-(3-(4-Chlorobenzenesulfonyl)thiophen-2-yl)-3-hydroxy-3-(2H-tetrazol-5-yl)-propenone
(1928) 1-(1-(3-Fluorobenzyl)pyrrol-3-yl)-3-hydroxy-3-(1H-1,2,4-triazol-3-yl)-propenone
(1929) 1-[(1-(2-Fluorobenzyl)-5-n-octyl)pyrrol-3-yl]-3-hydroxy-3-(1H-1,2,4-triazol-3-yl)-propenone
(1930) 1-(4-Benzylpyrrol-3-yl)-3-hydroxy-3-(2H-tetrazol-5-yl)-propenone
(1931) 3-Hydroxy-1-[(2-methyl-4-(pyridin-4-ylmethyl))furan-3-yl]-3-(1H-1,2,4-triazol-3-yl)-propenone
(1932) 3-Hydroxy-1-[(1-(4-methoxybenzyl)-4-phenoxymethyl)pyrrol-2-yl]-3-(2H-tetrazol-5-yl)-propenone
(1933) 4-(5-(4-Acetylbenzyl)thiophen-2-yl)-2-hydroxy-4-oxo-2-butenoic acid
(1934) 1-[(5-Chloro-2-(4-fluorobenzyl))furan-3-yl]-3-hydroxy-3-(1H-1,2,4-triazol-3-yl)-propenone
(1935) 1-(5-(2-Fluorobenzyl)pyrrol-3-yl)-3-hydroxy-3-(1H-1,2,4-triazol-3-yl)-propenone
(1936) 2-Hydroxy-4-oxo-4-(3-phenylthiofuran-2-yl)-2-butenoic acid
(1937) 3-Hydroxy-1-(4-phenylthiothiophen-3-yl)-3-(2H-tetrazol-5-yl)-propenone
(1938) 4-(1-(3-Fluorobenzyl)pyrrol-3-yl)-2-hydroxy-4-oxo-2-butenoic acid
(1939) 1-(4-(4-Acetylbenzyl)thiophen-3-yl)-3-hydroxy-3-(1H-1,2,4-triazol-3-yl)-propenone
(1940) 1-(2H-5-benzylpyrazol-3-yl)-3-hydroxy-3-(2H-tetrazol-5-yl)-propenone
(1941) 1-(4-(4-Aminobenzyl)thiazol-2-yl)-3-hydroxy-3-(1H-1,2,4-triazol-3-yl)-propenone
(1942) 1-[(1-Benzenesulfonyl-4-methoxymethyl)pyrrol-2-yl]-3-hydroxy-3-(1H-1,2,4-triazol-3-yl)-propenone
(1943) 3-Hydroxy-1-(1-(4-methoxybenzyl)pyrrol-3-yl)-3-(2H-tetrazol-5-yl)-propenone
(1944) 1-(4-(4-Aminobenzyl)thiophen-3-yl)-3-hydroxy-3-(1H-1,2,4-triazol-3-yl)-propenone
(1945) 3-Hydroxy-1-(2H-2-phenylthiopyrazol-4-yl)-3-(2H-tetrazol-5-yl)-propenone
(1946) 1-[(1-(4-Fluorobenzenesulfonyl)-5-n-propyl)pyrrol-3-yl]-3-hydroxy-3-(1H-1,2,4-triazol-3-yl)-propenone
(1947) 1-(2-(4-Chlorobenzenesulfonyl)pyrrol-3-yl)-3-hydroxy-3-(1H-1,2,4-triazol-3-yl)-propenone
(1948) 2-Hydroxy-4-(2H-2-(4-methoxybenzyl)pyrazol-4-yl)-4-oxo-2-butenoic acid
(1949) 1-[(4-(4-Fluorobenzyl)-2-(2-phenylethyl))furan-3-yl]-3-hydroxy-3-(1H-1,2,4-triazol-3-yl)-propenone
(1950) 1-(4-(2-Fluorobenzyl)thiazol-2-yl)-3-hydroxy-3-(2H-tetrazol-5-yl)-propenone
(1951) 1-[(5-Ethoxycarbonyl-1-phenylthio)pyrrol-3-yl]-3-hydroxy-3-(1H-1,2,4-triazol-3-yl)-propenone
(1952) 4-(2-benzenesulfonylthiophen-3-yl)-2-hydroxy-4-oxo-2-butenoic acid
(1953) 2-Hydroxy-4-oxo-4-(4-phenylthiothiophen-3-yl)-2-butenoic acid
(1954) 4-(5-(4-Chlorobenzenesulfonyl)furan-2-yl)-2-hydroxy-4-oxo-2-butenoic acid
(1955) 1-[(1-(4-Aminobenzyl)-4-n-propyl)pyrrol-2-yl]-3-hydroxy-3-(2H-tetrazol-5-yl)-propenone
(1956) 3-Hydroxy-1-(4-(4-methoxybenzyl)thiophen-2-yl)-3-(1H-1,2,4-triazol-3-yl)-propenone
(1957) 2-Hydroxy-4-(4-(4-methoxybenzyl)thiophen-2-yl)-4-oxo-2-butenoic acid
(1958) 1-[(4-Benzenesulfonyl-5-(2-phenylethyl))furan-3-yl]-3-hydroxy-3-(1H-1,2,4-triazol-3-yl)-propenone
(1959) 1-[(1-(4-Aminobenzyl)-4-phenoxymethyl)pyrrol-2-yl]-3-hydroxy-3-(2H-tetrazol-5-yl)-propenone
(1960) 4-(4-Benzylfuran-2-yl)-2-hydroxy-4-oxo-2-butenoic acid
(1961) 1-(5-Benzylfuran-3-yl)-3-hydroxy-3-(2H-tetrazol-5-yl)-propenone
(1962) 1-(1H-1-(4-aminobenzyl)pyrazol-3-yl)-3-hydroxy-3-(1H-1,2,4-triazol-3-yl)-propenone
(1963) 3-Hydroxy-1-(4-(4-methoxybenzyl)pyrrol-3-yl)-3-(2H-tetrazol-5-yl)-propenone
(1964) 3-Hydroxy-1-(2-(pyridin-4-ylmethyl)thiazol-4-yl)-3-(1H-1,2,4-triazol-3-yl)-propenone
(1965) 3-Hydroxy-1-(2-(pyridin-4-ylmethyl)thiazol-4-yl)-3-(2H-tetrazol-5-yl)-propenone
(1966) 4-(2-(2-Fluorobenzyl)pyrrol-3-yl)-2-hydroxy-4-oxo-2-butenoic acid
(1967) 1-(5-Benzylthiophen-2-yl)-3-hydroxy-3-(1H-1,2,4-triazol-3-yl)-propenone
(1968) 1-[(5-Benzoyl-1-(pyridin-2-ylmethyl))pyrrol-3-yl]-3-hydroxy-3-(1H-1,2,4-triazol-3-yl)-propenone
(1969) 1-[(1-(4-Acetylbenzyl)-4-(2-phenylethyl))pyrrol-2-yl]-3-hydroxy-3-(2H-tetrazol-5-yl)-propenone
(1970) 1-(5-(4-Acetylphenoxy)furan-2-yl)-3-hydroxy-3-(1H-1,2,4-triazol-3-yl)-propenone
(1971) 3-Hydroxy-1-(5-(pyridin-2-ylmethyl)pyrrol-3-yl)-3-(1H-1,2,4-triazol-3-yl)-propenone (1972) 1-(2H-4-Benzylpyrazol-3-yl)-3-hydroxy-3-(2H-tetrazol-5-yl)-propenone
(1973) 1-[(4-Carboxy-1-(4-chlorobenzenesulfonyl))pyrrol-2-yl]-3-hydroxy-3-(1H-1,2,4-triazol-3-yl)-propenone
(1974) 1-[(5-(4-Fluorobenzyl)-2-methyl)furan-3-yl]-3-hydroxy-3-(1H-1,2,4-triazol-3-yl)-propenone
(1975) 1-[(2-Benzenesulfonyl-5-fluoro)furan-3-yl]-3-hydroxy-3-(1H-1,2,4-triazol-3-yl)-propenone
(1976) 1-[(4-Ethyl-1-(4-methylbenzyl))pyrrol-3-yl]-3-hydroxy-3-(1H-1,2,4-triazol-3-yl)-propenone
(1977) 3-Hydroxy-1-[(5-methoxymethyl-1-(pyridin-4-ylmethyl))pyrrol-3-yl]-3-(1H-1,2,4-triazol-3-yl)-propenone
(1978) 3-Hydroxy-1-[(4-methyl-2-phenyl)furan-3-yl]-3-(1H-1,2,4-triazol-3-yl)-propenone
(1979) 3-Hydroxy-1-(4-(4-methylbenzyl)furan-3-yl)-3-(1H-1,2,4-triazol-3-yl)-propenone
(1980) 1-(4-(4-Aminobenzyl)thiophen-2-yl)-3-hydroxy-3-(1H-1,2,4-triazol-3-yl)-propenone
(1981) 1-(4-(4-Chlorobenzenesulfonyl)furan-3-yl)-3-hydroxy-3-(2H-tetrazol-5-yl)-propenone
(1982) 4-(1-Benzylpyrrol-2-yl)-2-hydroxy-4-oxo-2-butenoic acid
(1983) 3-Hydroxy-1-(4-pyridin-4-ylmethyl)pyrrol-2-yl)-3-(2H-tetrazol-5-yl)-propenone
(1984) 2-Hydroxy-4-oxo-4-(2H-2-phenylthiopyrazol-4-yl)-2-butenoic acid
(1985) 1-[(2-Fluoro-4-phenyl)furan-3-yl]-3-hydroxy-3-(1H-1,2,4-triazol-3-yl)-propenone
(1986) 3-Hydroxy-1-(3-(pyridin-4-ylmethyl)pyrrol-2-yl)-3-(1H-1,2,4-triazol-3-yl)-propenone
(1987) 1-(2-(2-Fluorobenzyl)thiazol-4-yl)-3-hydroxy-3-(1H-1,2,4-triazol-3-yl)-propenone
(1988) 1-(5-(4-Fluorobenzyl)furan-3-yl)-3-hydroxy-3-(2H-tetrazol-5-yl)-propenone
(1989) 3-Hydroxy-1-(4-(pyridin-4-ylmethyl)thiophen-2-yl)-3-(2H-tetrazol-5-yl)-propenone
(1990) 4-(5-n-Butylfuran-3-yl)-2-hydroxy-4-oxo-2-butenoic acid
(1991) 1-[(1-(4-Chlorobenzenesulfonyl)-4-ethoxycarbonyl)pyrrol-2-yl]-3-hydroxy-3-(2H-tetrazol-5-yl)-propenone
(1992) 4-(2H-2-(4-Acetylbenzyl)pyrazol-3-yl)-2-hydroxy-4-oxo-2-butenoic acid
(1993) 1-(2-(3-Fluorobenzyl)pyrazol-3-yl)-3-hydroxy-3-(2H-tetrazol-5-yl)-propenone
(1994) 4-(1H-1-Benzenesulfonylpyrazol-3-yl)-2-hydroxy-4-oxo-2-butenoic acid
(1995) 1-[(4-n-Butyl-1-(2-fluorobenzyl))pyrrol-2-yl]-3-hydroxy-3-(1H-1,2,4-triazol-3-yl)-propenone
(1996) 3-Hydroxy-1-[(4-phenyl-2-(2-phenylethyl))furan-3-yl]-3-(1H-1,2,4-triazol-3-yl)-propenone
(1997) 1-[(5-Benzoyl-1-(4-methylbenzyl))pyrrol-3-yl]-3-hydroxy-3-(2H-tetrazol-5-yl)-propenone
(1998) 1-(2H-5-(4-Aminobenzyl)pyrazol-3-yl)-3-hydroxy-3-(2H-tetrazol-5-yl)-propenone
(1999) 4-(5-(4-Acetylbenzyl)furan-2-yl)-2-hydroxy-4-oxo-2-butenoic acid
(2000) 1-(3-(3-Chlorophenylthio)furan-2-yl)-3-hydroxy-3-(1H-1,2,4-triazol-3-yl)-propenone
(2001) 1-(2-(3-Fluorobenzyl)pyrrol-3-yl)-3-hydroxy-3-(1H-1,2,4-triazol-3-yl)-propenone
(2002) 3-Hydroxy-1-(3-(4-methoxybenzyl)pyrrol-2-yl)-3-(1H-1,2,4-triazol-3-yl)-propenone
(2003) 2-Hydroxy-4-(5-(4-methylbenzyl)furan-2-yl)-4-oxo-2-butenoic acid
(2004) 4-(2-Benzenesulfonylthiazol-4-yl)-2-hydroxy-4-oxo-2-butenoic acid
(2005) 4-(2-(4-Fluorobenzenesulfonyl)furan-3-yl)-2-hydroxy-4-oxo-2-butenoic acid
(2006) 1-[(1-Benzyl-4-(2-phenylethyl))pyrrol-3-yl]-3-hydroxy-3-(2H-tetrazol-5-yl)-propenone
(2007) 1-(4-(4-Fluorobenzyl)thiophen-3-yl)-3-hydroxy-3-(2H-tetrazol-5-yl)-propenone
(2008) 1-[(1-(4-Acetylbenzyl)-5-benzoyl)pyrrol-3-yl]-3-hydroxy-3-(1H-1,2,4-triazol-3-yl)-propenone
(2009) 1-(4-(4-Chlorobenzenesulfonyl)furan-3-yl)-3-hydroxy-3-(1H-1,2,4-triazol-3-yl)-propenone
(2010) 1-(2H-5-(4-Acetylbenzyl)pyrazol-3-yl)-3-hydroxy-3-(2H-tetrazol-5-yl)-propenone
(2011) 1-(5-(4-Fluorobenzyl)pyrrol-3-yl)-3-hydroxy-3-(1H-1,2,4-triazol-3-yl)-propenone
(2012) 3-Hydroxy-1-(2-(4-methoxybenzyl)pyrrol-3-yl)-3-(1H-1,2,4-triazol-3-yl)-propenone
(2013) 4-(2H-2-(3-Fluorobenzyl)pyrazol-4-yl)-2-hydroxy-4-oxo-2-butenoic acid
(2014) 3-Hydroxy-1-(4-(4-methoxyphenoxy)furan-2-yl)-3-(1H-1,2,4-triazol-3-yl)-propenone
(2015) 3-Hydroxy-3-(1H-1,2,4-triazol-3-yl)-1-(2-(2-trifluoromethylphenoxy)furan-3-yl)-propenone
(2016) 3-Hydroxy-1-(5-(2-methoxyphenoxy)furan-2-yl)-3-(1H-1,2,4-triazol-3-yl)-propenone
(2017) 4-(2H-5-(4-Aminobenzyl)pyrazol-3-yl)-2-hydroxy-4-oxo-2-butenoic acid
(2018) 1-(4-(4-Fluorobenzenesulfonyl)pyrrol-3-yl)-3-hydroxy-3-(1H-1,2,4-triazol-3-yl)-propenone
(2019) 1-[(5-Chloro-4-(pyridin-4-ylmethyl))furan-3-yl]-3-hydroxy-3-(1H-1,2,4-triazol-3-yl)-propenone
(2020) 3-Hydroxy-1-[(1-(4-methylbenzyl)-4-n-propyl)pyrrol-2-yl]-3-(2H-tetrazol-5-yl)-propenone
(2021) 1-[(1-(2-Fluorobenzyl)-4-(2-phenylethyl))pyrrol-2-yl]-3-hydroxy-3-(1H-1,2,4-triazol-3-yl)-propenone
(2022) 2-Hydroxy-4-oxo-4-(2H-4-phenylthiopyrazol-3-yl)-2-butenoic acid
(2023) 3-Hydroxy-1-(1-phenylthiopyrrol-3-yl)-3-(1H-1,2,4-triazol-3-yl)-propenone
(2024) 3-Hydroxy-1-(2-(4-methoxyphenoxy)furan-3-yl)-3-(1H-1,2,4-triazol-3-yl)-propenone
(2025) 1-(2-(4-Chlorophenoxy)furan-3-yl)-3-hydroxy-3-(1H-1,2,4-triazol-3-yl)-propenone
(2026) 3-Hydroxy-1-(4-(4-methoxybenzyl)thiazol-2-yl)-3-(1H-1,2,4-triazol-3-yl)-propenone
(2027) 1-(4-n-Butylfuran-2-yl)-3-hydroxy-3-(2H-tetrazol-5-yl)-propenone
(2028) 1-[(5-Ethoxycarbonyl-1-(2-fluorobenzyl))pyrrol-3-yl]-3-hydroxy-3-(1H-1,2,4-triazol-3-yl)-propenone
(2029) 3-Hydroxy-1-[(4-(2-phenylethyl)-1-(pyridin-2-ylmethyl))pyrrol-3-yl]-3-(2H-tetrazol-5-yl)-propenone
(2030) 1-(2-(2-Chlorophenoxy)furan-3-yl)-3-hydroxy-3-(1H-1,2,4-triazol-3-yl)-propenone
(2031) 1-[(4-Ethyl-1-(4-fluorobenzyl))pyrrol-3-yl]-3-hydroxy-3-(1H-1,2,4-triazol-3-yl)-propenone
(2032) 1-[(1-Benzyl-4-phenoxymethyl)pyrrol-2-yl]-3-hydroxy-3-(2H-tetrazol-5-yl)-propenone
(2033) 1-[(4-(4-Fluorobenzyl)-5-(2-phenylethyl))furan-2-yl]-3-hydroxy-3-(1H-1,2,4-triazol-3-yl)-propenone
(2034) 2-Hydroxy-4-oxo-4-(5-(pyridin-2-ylmethyl)thiophen-2-yl)-2-butenoic acid
(2035) 1-[(1-Benzenesulfonyl-4-phenoxymethyl)pyrrol-2-yl]-3-hydroxy-3-(2H-tetrazol-5-yl)-propenone
(2036) 3-Hydroxy-1-(2-(4-methoxybenzyl)furan-3-yl)-3-(1H-1,2,4-triazol-3-yl)-propenone
(2037) 1-(5-(3-Fluorobenzyl)thiophen-3-yl)-3-hydroxy-3-(1H-1,2,4-triazol-3-yl)-propenone
(2038) 1-[(1-(4-Acetylbenzyl)-4-ethyl)pyrrol-2-yl]-3-hydroxy-3-(1H-1,2,4-triazol-3-yl)-propenone (2039) 1-(1-(4-Aminobenzyl)pyrrol-3-yl)-3-hydroxy-3-(1H-1,2,4-triazol-3-yl)-propenone
(2040) 3-Hydroxy-1-(3-(pyridin-2-ylmethyl)furan-2-yl)-3-(1H-1,2,4-triazol-3-yl)-propenone
(2041) 3-Hydroxy-1-(3-(4-methoxybenzyl)thiophen-2-yl)-3-(2H-tetrazol-5-yl)-propenone
(2042) 1-(4-(4-Acetylbenzyl)furan-2-yl)-3-hydroxy-3-(2H-tetrazol-5-yl)-propenone
(2043) 3-Hydroxy-1-[(5-(2-phenylethyl)-3-(pyridin-4-ylmethyl))furan-2-yl]-3-(1H-1,2,4-triazol-3-yl)-propenone
(2044) 3-Hydroxy-1-(4-(4-methoxyphenoxy)furan-3-yl)-3-(1H-1,2,4-triazol-3-yl)-propenone
(2045) 3-Hydroxy-1-(5-(pyridin-2-ylmethyl)furan-3-yl)-3-(1H-1,2,4-triazol-3-yl)-propenone
(2046) 1-[(1-(4-Fluorobenzenesulfonyl)-4-n-propyl)pyrrol-2-yl]-3-hydroxy-3-(2H-tetrazol-5-yl)-propenone
(2047) 4-(4-(4-Fluorobenzenesulfonyl)furan-2-yl)-2-hydroxy-4-oxo-2-butenoic acid
(2048) 3-Hydroxy-1-(3-phenylthiothiophen-2-yl)-3-(1H-1,2,4-triazol-3-yl)-propenone
(2049) 1-[(1-Benzenesulfonyl-5-n-octyl)pyrrol-3-yl]-3-hydroxy-3-(1H-1,2,4-triazol-3-yl)-propenone
(2050) 1-(2H-5-(4-Fluorobenzyl)pyrazol-3-yl)-3-hydroxy-3-(1H-1,2,4-triazol-3-yl)-propenone
(2051) 1-[(1-(4-Acetylbenzyl)-4-benzoyl)pyrrol-2-yl]-3-hydroxy-3-(2H-tetrazol-5-yl)-propenone
(2052) 1-[(4-Ethyl-1-(4-fluorobenzenesulfonyl))pyrrol-3-yl]-3-hydroxy-3-(1H-1,2,4-triazol-3-yl)-propenone
(2053) 1-[(2-Chloro-5-phenyl)furan-3-yl]-3-hydroxy-3-(1H-1,2,4-triazol-3-yl)-propenone
(2054) 3-Hydroxy-1-(4-(2-methoxyphenylthio)furan-3-yl)-3-(1H-1,2,4-triazol-3-yl)-propenone
(2055) 3-Hydroxy-1-[(4-methoxymethyl-1-phenylthio)pyrrol-2-yl]-3-(2H-tetrazol-5-yl)-propenone
(2056) 1-[(5-Benzoyl-1-(pyridin-4-ylmethyl))pyrrol-3-yl]-3-hydroxy-3-(2H-tetrazol-5-yl)-propenone
(2057) 1-[(1-(4-Chlorobenzenesulfonyl)-4-ethyl)pyrrol-3-yl]-3-hydroxy-3-(2H-tetrazol-5-yl)-propenone
(2058) 2-Hydroxy-4-oxo-4-(5-(pyridin-2-ylmethyl)furan-2-yl)-2-butenoic acid
(2059) 2-Hydroxy-4-(5-(4-methylbenzyl)pyrrol-3-yl)-4-oxo-2-butenoic acid
(2060) 3-Hydroxy-3-(1H-1,2,4-triazol-3-yl)-1-(3-(3-trifluoromethylbenzyl)furan-2-yl)-propenone
(2061) 1-(4-Benzylfuran-2-yl)-3-hydroxy-3-(2H-tetrazol-5-yl)-propenone
(2062) 3-Hydroxy-1-(5-(4-methylbenzyl)furan-2-yl)-3-(2H-tetrazol-5-yl)-propenone
(2063) 4-(1H-1-(4-Aminobenzyl)pyrazol-4-yl)-2-hydroxy-4-oxo-2-butenoic acid
(2064) 1-(2-Benzenesulfonylthiazol-4-yl)-3-hydroxy-3-(2H-tetrazol-5-yl)-propenone
(2065) 4-(3-(4-Chlorobenzenesulfonyl)pyrrol-2-yl)-2-hydroxy-4-oxo-2-butenoic acid
(2066) 3-Hydroxy-1-(4-(4-methylbenzyl)pyrrol-3-yl)-3-(2H-tetrazol-5-yl)-propenone
(2067) 1-[(5-n-Butyl-1-(4-fluorobenzenesulfonyl))pyrrol-3-yl]-3-hydroxy-3-(1H-1,2,4-triazol-3-yl)-propenone
(2068) 1-[(5-n-Butyl-1-(4-fluorobenzyl))pyrrol-3-yl]-3-hydroxy-3-(2H-tetrazol-5-yl)-propenone
(2069) 1-[(5-n-Butyl-1-(4-methylbenzyl))pyrrol-3-yl]-3-hydroxy-3-(1H-1,2,4-triazol-3-yl)-propenone
(2070) 4-(3-(2-Fluorobenzyl)pyrrol-2-yl)-2-hydroxy-4-oxo-2-butenoic acid
(2071) 1-(4-(4-Aminobenzyl)pyrrol-3-yl)-3-hydroxy-3-(2H-tetrazol-5-yl)-propenone
(2072) 1-(5-(3-Chlorophenoxy)furan-3-yl)-3-hydroxy-3-(1H-1,2,4-triazol-3-yl)-propenone
(2073) 1-(2-Benzylthiophen-3-yl)-3-hydroxy-3-(1H-1,2,4-triazol-3-yl)-propenone
(2074) 1-[(4-Benzenesulfonyl-5-methyl)furan-2-yl]-3-hydroxy-3-(1H-1,2,4-triazol-3-yl)-propenone
(2075) 1-(3-(4-Chlorophenoxy)furan-2-yl)-3-hydroxy-3-(1H-1,2,4-triazol-3-yl)-propenone
(2076) 1-(3-Benzenesulfonylpyrrol-2-yl)-3-hydroxy-3-(2H-tetrazol-5-yl)-propenone
(2077) 1-(2-Benzenesulfonylpyrrol-2-yl)-3-hydroxy-3-(2H-tetrazol-5-yl)-propenone
(2078) 1-(5-Benzylthiophen-3-yl)-3-hydroxy-3-(1H-1,2,4-triazol-3-yl)-propenone
(2079) 1-[(2-(4-Fluorobenzyl)-4-methyl)furan-3-yl]-3-hydroxy-3-(1H-1,2,4-triazol-3-yl)-propenone
(2080) 1-(4-(4-Fluorophenyl)furan-2-yl)-3-hydroxy-3-(1H-1,2,4-triazol-3-yl)-propenone
(2081) 1-[(1-(4-Fluorobenzyl)-5-n-propyl)pyrrol-3-yl]-3-hydroxy-3-(2H-tetrazol-5-yl)-propenone
(2082) 4-(4-(4-Fluorobenzyl)pyrrol-3-yl)-2-hydroxy-4-oxo-2-butenoic acid
(2083) 4-(5-(3-Fluorobenzyl)pyrrol-2-yl)-2-hydroxy-4-oxo-2-butenoic acid
(2084) 3-Hydroxy-1-[(1-(4-methylbenzyl)-4-n-octyl)pyrrol-2-yl]-3-(1H-1,2,4-triazol-3-yl)-propenone
(2085) 3-Hydroxy-1-[(5-phenyl-3-(2-phenylethyl))furan-2-yl]-3-(1H-1,2,4-triazol-3-yl)-propenone
(2086) 1-(2-(4-Aminobenzyl)furan-3-yl)-3-hydroxy-3-(2H-tetrazol-5-yl)-propenone
(2087) 1-[(4-Benzoyl-1-benzyl)pyrrol-2-yl]-3-hydroxy-3-(1H-1,2,4-triazol-3-yl)-propenone
(2088) 1-(2H-2-(4-Acetylbenzyl)pyrazol-3-yl)-3-hydroxy-3-(2H-tetrazol-5-yl)-propenone
(2089) 1-[(5-Carboxy-1-(pyridin-4-ylmethyl))pyrrol-3-yl]-3-hydroxy-3-(2H-tetrazol-5-yl)-propenone
(2090) 4-(5-(4-Aminobenzyl)pyrrol-2-yl)-2-hydroxy-4-oxo-2-butenoic acid
(2091) 2-Hydroxy-4-oxo-4-(2H-2-phenylthiopyrazol-3-yl)-2-butenoic acid
(2092) 3-Hydroxy-1-(5-(4-methoxybenzyl)thiophen-2-yl)-3-(2H-tetrazol-5-yl)-propenone
(2093) 2-Hydroxy-4-(2H-2-(4-methoxybenzyl)pyrazol-3-yl)-4-oxo-2-butenoic acid
(2094) 1-[(1-(4-Acetylbenzyl)-5-n-propyl)pyrrol-3-yl]-3-hydroxy-3-(2H-tetrazol-5-yl)-propenone
(2095) 1-(5-(2-Fluorobenzyl)thiophen-3-yl)-3-hydroxy-3-(2H-tetrazol-5-yl)-propenone
(2096) 1-[(4-Ethyl-1-(4-methoxybenzyl))pyrrol-3-yl]-3-hydroxy-3-(1H-1,2,4-triazol-3-yl)-propenone
(2097) 1-[(2-Fluoro-5-phenyl)furan-3-yl]-3-hydroxy-3-(1H-1,2,4-triazol-3-yl)-propenone
(2098) 3-Hydroxy-1-(2H-4-(pyridin-4-ylmethyl)pyrazol-3-yl)-3-(2-tetrazol-5-yl)-propenone
(2099) 1-[(1-Benzyl-5-n-octyl)pyrrol-3-yl]-3-hydroxy-3-(1H-1,2,4-triazol-3-yl)-propenone
(2100) 1-(4-(4-Fluorobenzenesulfonyl)thiophen-3-yl)-3-hydroxy-3-(1H-1,2,4-triazol-3-yl)-propenone
(2101) 1-(3-(3-Fluorobenzyl)pyrrol-2-yl)-3-hydroxy-3-(1H-1,2,4-triazol-3-yl)-propenone
(2102) 3-Hydroxy-1-(3-(pyridin-4-ylmethyl)thiophen-2-yl)-3(2H-tetrazol-5-yl)-propenone
(2103) 1-(4-Benzylthiophen-2-yl)-3-hydroxy-3-(1H-1,2,4-triazol-3-yl)-propenone
(2104) 1-[(4-n-Butyl-1-(4-methylbenzyl))pyrrol-2-yl]-3-hydroxy-3-(1H-1,2,4-triazol-3-yl)-propenone
(2105) 1-(2H-2-(2-fluorobenzyl)pyrazol-4-yl)-3-hydroxy-3-(2H-tetrazol-5-yl)-propenone (2106) 4-(4-n-Butylfuran-2-yl)-2-hydroxy-4-oxo-2-butenoic acid
(2107) 1-(2H-2-(4-aminobenzyl)pyrazol-3-yl)-3-hydroxy-3-(2H-tetrazol-5-yl)-propenone
(2108) 3-Hydroxy-1-(1H-1-(4-methylbenzyl)pyrazol-3-yl)-3-(1H-1,2,4-triazol-3-yl)-propenone
(2109) 2-Hydroxy-4-(1H-1-(4-methoxybenzyl)pyrazol-4-yl)-4-oxo-2-butenoic acid
(2110) 3-Hydroxy-1-(2H-5-phenylthiopyrazol-3-yl)-3-(2H-tetrazol-5-yl)-propenone

EXPERIMENTAL EXAMPLE 1

The inhibitory effects of the compounds of the present invention for HIV-1 integrase have been determined by the assay described below.

(1) Preparation of DNA Solutions.

Substrate DNA and target DNA, which sequences were indicated below, were synthesized by Amersham Pharmacia Biotech and dissolved in KTE buffer (composition: 100 mM KCl, 1 mM EDTA, 10 mM Tris-HCl (pH 7.6)) at concentration of 2 pmol/μl and 5 pmol/μl, respectively. The DNA solutions were annealed with each complement by slowly cooling after heating.

(Substrate DNA)
5'-Biotin-ACC CTT TTA GTC AGT GTG GAA AAT CTC TAG CAG T-3'

3'-          GAA AAT CAG TCA CAC CTT TTA GAG ATC GTC A-5'

(Target DNA)
5'-    TGA CCA AGG GCT AAT TCA CT-Dig-3'

3'-Dig-ACT GGT TCC GGA TTA AGT GA -5'

(2) Calculations of the Percent Inhibitions (the $IC_{50}$ Values of Test Compounds)

Streptavidin, obtained from Vector Laboratories, was dissolved in 0.1 M carbonate buffer (composition: 90 mM $Na_2CO_3$, 10 mM $NaHCO_3$) at concentration of 40 μg/ml. After coating each well of microtiter plates (obtained from NUNC) with 50 μl of the above solution at 4° C. over night, each well was washed twice with PBS (composition: 13.7 mM NaCl, 0.27 mM KCl, 0.43 mM $Na_2HPO_4$, 0.14 mM $KH_2PO_4$) and blocked with 300 μl of 1% skim milk in PBS for 30 min. Additionally, each well was washed twice with PBS and added 50 μl of substrate DNA solution (2 pmol/μl). The microtiter plates were kept at room temperature for 30 min. Then, each well was washed twice with PBS and once with $H_2O$.

Subsequently, in the each well prepared above were added 45 μl of the reaction buffer prepared from 12 μl of the buffer (composition: 150 mM MOPS (pH 7.2), 75 mM $MnCl_2$, 50 mM 2-mercaptoethanol, 25% glycerol, 500 μg/ml bovine serum albumin-fraction V), 1 μl of target DNA (5 pmol/μl), and 32 μl of the distilled water. Additionally, 6 μl of either a test compound in DMSO or DMSO for positive control (PC) was mixed with the above reaction buffer, then 9 μl of an integrase solution (30 pmol) was added and mixed well. In the well of negative control (NC) was added 9 μl of the integrase dilution buffer (composition: 20 mM MOPS (pH7.2), 400 mM potassium glutamate, 1 mM EDTA, 0.1% NP-40, 20% glycerol, 1 mM DTT, 4M urea).

The microtiter plates were incubated at 30° C. for 1 hour. The reaction solution was removed and each well was washed twice with PBS. Subsequently, each well of the microtiter plates was filled with 100 μl of anti-digoxigenin antibody labeled with alkaline phosphatase (Sheep Fab fragment: obtained from Boehringer) and incubated at 30° C. for 1 hour. Then, each well was washed twice with 0.05% Tween 20 in PBS and once with PBS. Next, 150 μl of the Alkaline phosphatase reaction buffer (composition: 10 mM p-Nitrophenylphosphate (obtained from Vector Laboratories), 5 mM $MgCl_2$, 100 mM NaCl, 100 mM Tris-HCl (pH 9.5)) was added in each well. The microtiter plates were incubated at 30° C. for 2 hours and the reaction was terminated by the addition of 50 μl of 1 N NaOH solution. The optical density (OD) at 405 nm of each well was measured and the percent inhibition was determined by the following expression.

The percent inhibition (%)=100[1−{(C abs.−NC abs.)/(PC abs.−NC abs.)}]

C abs.; the OD of the well of the compounds
NC abs.: the OD of the negative control (NC)
PC abs.: the OD of the positive control (PC)

When the percent inhibition (%) is X % at the concentration of x μg/ml and the percent inhibition (%) is Y % at the concentration of y μg/ml, one of which is more than 50% and the other is less than 50%, $IC_{50}$ can be determined by the following expression.

$IC_{50}$(μg/ml)=x−{(X−50)(x−y)/(X−Y)}

The $IC_{50}$ values, the concentration of the compounds at percent inhibition 50%, are shown in the following Table 1. Compound No. in the Table 1 is the same as compound No. of the above example.

TABLE 1

| compound No. | $IC_{50}$ (μg/ml) |
| --- | --- |
| I-2 | 1.0 |
| I-14 | 0.63 |
| I-25 | 0.59 |
| I-31 | 0.54 |
| I-35 | 1.6 |
| I-42 | 0.53 |
| I-45 | 0.43 |
| I-46 | 0.42 |
| I-49 | 0.48 |
| I-52 | 0.32 |
| I-53 | 2.4 |
| I-54 | 0.24 |
| I-55 | 0.40 |
| I-60 | 0.69 |
| I-61 | 0.68 |
| I-68 | 0.33 |
| I-70 | 0.42 |
| I-74 | 0.43 |
| I-80 | 0.53 |
| I-83 | 1.5 |
| I-85 | 1.4 |
| I-86 | 0.50 |
| I-91 | 0.60 |
| I-94 | 1.6 |
| I-96 | 0.84 |

TABLE 1-continued

| compound No. | IC$_{50}$ (μg/ml) |
|---|---|
| I-97 | 0.61 |
| I-98 | 0.46 |
| I-99 | 0.66 |
| I-100 | 1.6 |
| I-101 | 0.53 |
| I-104 | 0.58 |
| I-106 | 0.44 |
| I-112 | 0.61 |
| I-127 | 0.35 |
| I-150 | 0.98 |
| I-151 | 0.40 |
| I-152 | 0.48 |

EXPERIMENTAL EXAMPLE 2

(1) Molt-4 cells (2×10$^6$ cells) were infected with HIV-1 NL432 (4×10$^6$ cpm), HIV-2 Rod (8×10$^6$ cpm), SIVmac MA239 (8×10$^6$ cpm) and SIVagm SA212 (8×10$^6$ cpm), and incubated for 1 hr at room temperature.

Preparation of the Viruses

①Preparation of HIV-1 NL432 : SW480 cells were cultured in DMEM medium supplemented with 10% fetal bovine serum using 25 cm$^2$ flask. HIV-1 infectious molecular DNA (40 μg), pNL432, transfected to the cells by calcium phosphate coprecipitation method, and the supernatant (2 ml) at 2–3 days post-transfection was infected to M8166 cells (1×10$^6$ cells). The cells were cultured in 10 ml RPMI medium supplemented with 10% fetal bovine serum in CO$_2$ incubator at 37° C. After apparent giant cells were observed, the cells were removed by centrifugation and then the supernatant was filtrated by 0.45 μm filter, measured RT activity, and stored at –80° C. as HIV-1 stock virus.

②Preparation of HIV-1 Rod: HIV-2 Rod was infected to M8166 cells (1×10$^6$ cells). The cells were cultured in 10 ml RPMI medium supplemented with 10% fetal bovine serum in CO$_2$ incubator at 37° C. After apparent giant cells were observed, the cells were removed by centrifugation and then the supernatant was filtrated by 0.45 μm filter, measured RT activity, and stored at –80° C. as HIV-2 stock virus.

③Preparation of SIVmac MA239: SW480 cells were cultured in DMEM medium supplemented with 10% fetal bovine serum using 25 cm$^2$ flask. SIVmac MA239 infectious molecular DNA (40 μg), pMA239, transfected to the cells by calcium phosphate coprecipitation method, and the supernatant (2 ml) at 2–3 days post-transfection was infected to CEMX174 cells (1×10$^6$ cells). The cells were cultured in 10 ml RPMI medium supplemented with 10% fetal bovine serum in CO$_2$ incubator at 37° C. After apparent giant cells were observed, the cells were removed by centrifugation and then the supernatant was filtrated by 0.45 μm filter, measured RT activity, and stored at –80° C. as SIVmac stock virus.

④Preparation of SIVagm SA212: SW480 cells were cultured in DMEM medium supplemented with 10% fetal bovine serum using 25 cm$^2$ flask. SIVagm SA212 infectious molecular DNA (40 μg), pSA212, transfected to the cells by calcium phosphate coprecipitation methods, and the supernatant (2 ml) at 2–3 days post-transfection was infected to M8166 cells (1×10$^6$ cells). The cells were cultured in 10 ml RPMI medium supplemented with 10% fetal bovine serum in CO$_2$ incubator at 37° C. Every 3 days, the cells were separated from the supernatant by centrifugation and continued culture with new medium. The each supernatant was filtrated by 0.45 μm filter, measured RT activity, and stored at –80° C. as SIVagm stock virus.

(2) The cells were washed twice to remove the viruses and suspended in 10 ml RPMI medium supplemented with 10% fetal bovine serum. The infected cells (100 μl) were plated in 96 well microtiter plates containing with the serial 5 fold dilution of compounds (100 μl) and cultured in CO$_2$ incubator at 37° C.

(3) The supernatant at 5 days postinfection was harvested and measured the amount of the virus by RT activity.

Preparation of the Solution for RT Assay:

A reaction mixture (90 μl) were contained 50 mM Tris-HCl, pH 8.3, 150 mM KCl, 10 mM MgCl$_2$, 0.1% Nonidet P-40, 10 mM DTT (dithiothreitol), 5 μg/ml poly(rA), 5 μg/ml (dT)$_{12-18}$ and 1 μCi [$^3$H] dTTP at final concentration after mixture of a sample (10 μl).

The Procedure of RT Assay:

1. 10 μl of sample was plated to 3 wells of 96 well microtiter plate (triplicate assay).

2. Reaction mixture (90 μl) chilled at 4° C. was added to each well, mixed and then incubate at 37° C. for 3 hrs.

3. After incubation, the plate was chilled on ice, and passed through a DEAE-Filtermat using cell harvester. The filter was washed with 4.5% Na$_2$HPO$_4$ (20 sec) and H$_2$O (10 sec).

4. The filter was dried at 95° C. for 15 min.

5. 10 ml of scintilator was added and sealed.

6. Radioactivity was measured by LKB Beta Plate scintillation spectroscopy.

7. RT activity (cpm/ml) was calculated from average of three wells.

(4) RT activity in the absence of drug was calculated as 100% viral replication and then 50% inhibitory concentration (EC$_{50}$) of the sample was determined from the RT activity of each well as shown in Table 2.

TABLE 2

Anti-HIV/SIV activity (EC$_{50}$: ng/ml)

| | HIV-1 NL432 | HIV-2 Rod | SIVmac | SIVagm |
|---|---|---|---|---|
| I-42 | 57 | 35 | 57 | 44 |
| AZT | 0.51 | 0.28 | 0.35 | 0.36 |
| d4T | 6.1 | 4.1 | 3.4 | 4.5 |
| 3TC | 8.4 | 22 | 9.1 | 22 |
| S-1153 | 0.77 | >4000 | >4000 | 1500 |
| nevirapine | 13 | >20000 | >20000 | >20000 |

As shown in table 2, the compound I-42 showed antiviral activity against HIV-1, HIV-2, SIVmac and SIVagm. Thus, the compound I-42 was effective drug for not only HIV-1 but also HIV-2 and SIV infection. As shown in table 2, AZT, d4T and 3TC, nucleotide analogue inhibitors which inhibited RT activity of various retroviruses were used as positive control, and S-1153 and nevirapine, HIV-1 specific non-nucleotide inhibitors, were used as negative control.

EXPERIMENTAL EXAMPLE 3

(1) The serial 5 fold diluted samples were plated in 24 well microliter plate. Feline T-cell lines (MYA-1 cells: 4×10$^5$ cells/well) and feline immunodeficiency virus (FIV TM-2 strain: 3000 cpm/well) were added to each well. The cells were cultured with 1.5 ml RPMI medium supplemented with 10% fetal bovine serum, 2 μg/ml polybrene, 100 unit/ml human recombinant IL-2 and 50 μM 2-mercaptoethanol in CO$_2$ incubator at 37° C.

1. Preparation of FIV TM-2: FIV TM-2 was infected to MYA-1 cells (1×10$^6$ cells). The cells were cultured in 10 ml RPMI medium supplemented with 10% fetal bovine serum, 2 µg/ml polybrene, 100 unit/ml human recombinant IL-2 and 50 µM 2-mercaptoethanol in $CO_2$ incubator at 37° C. Every 1–2 days, the cells were separated from the supernatant by centrifugation and continued culture with new medium. Each of the supernatant was filtrated by 0.45 µm filter, measured RT activity, and stored at as −80° C. as FIV stock virus.

(2) Every 1–2 days, the supernatants were measured the amount of the virus by RT activity (as same as experimental example 2).

(3) Using from the data at 10 days postinfection, RT activity in the absence of drug was calculated as 100% viral replication and then 50% inhibitory concentration ($EC_{50}$) of the sample was determined from the RT activity of each well as shown in Table 3.

TABLE 3

Anti-HIV/SIV activity ($EC_{50}$: ng/ml)

|  | $EC_{50}$ |
|---|---|
| I-42 | 300 |
| S-1153 | >5000 |
| AZT | 48 |

As shown in table 3, the compound I-42 showed antiviral activity against not only HIV-1 and SIV but also FIV. Thus, the compound I-42 is effective drug for FIV infection.

EXPERIMENTAL EXAMPLE 4

The inhibitory effects of the compounds of the present invention for MoMLV integrase have been determined by the assay described below. Because the substrate and target DNA were the same as those used in the experimental example 1, the description of those are omitted. In each well of the plates prepared in the same way of the experimental example 1 was added 50 µl of the reaction buffer (composition: 30 mM MOPS (pH 7.2), 15 mM $MnCl_2$, 10 mM 2-mercaptoethanol, 5% glycerol, 100 µg/ml bovine serum albumin-fraction V). Next, 9 µl of an integrase solution (30 pmol) was added and mixed well. In the well for negative control, 9 µl of the integrase dilution buffer (composition: 20 mM MOPS (pH7.2), 400 mM potassium glutamate, 1 mM EDTA, 0.1% NP-40, 20% glycerol, 1 mM DTT, 4M urea) was added. After the microtiter plate was incubated at 30° C. for 30 min., the reaction solution was removed and each well was washed three times with 200 µl of the reaction buffer without 15 mM $MnCl_2$. In each well was added 53 µl of the newly prepared reaction buffer. Subsequently, 1 µl of target DNA (5 pmol/µl) and 6 µl of either a test compound in DMSO or DMSO for positive control (PC) were added in each well and mixed well. After the microtiter plates were incubated at 30° C. for 30 min., the reaction solution was removed and each well was washed twice with PBS. Subsequently, each well of the microtiter plates was filled with 100 µl of anti-digoxigenin antibody labeled with alkaline phosphatase (Sheep Fab fragment: obtained from Boehringer) and incubated at 30° C. for 1 hour. Then, each well was washed twice with 0.05% Tween 20 in PBS and once with PBS. Next, 150 µl of the Alkaline phosphatase reaction buffer (composition: 10 mM p-Nitrophenylphosphate (obtained from Vector Laboratories), 5 mM $MgCl_2$, 100 mM NaCl, 100 mM Tris-HCl (pH 9.5)) was added in each well. The microtiter plates were incubated at 30° C. for 2 hours and the reaction was terminated by the addition of 50 µl of 1 N NaOH solution. The optical density (OD) at 405 nm of each well was measured and the percent inhibition was determined by the following expression.

The percent inhibition (%)=100[1−{(C abs.−NC abs.)/(PC abs.−NC abs.)}]

C abs.; the OD of the well of the compounds

NC abs.: the OD of the negative control (NC)

PC abs.: the OD of the positive control (PC)

When the percent inhibition (%) is X % at the concentration of x µg/ml and the percent inhibition (%) is Y % at the concentration of y µg/ml, one of which is more than 50% and the other is less than 50%, $IC_{50}$ can be determined by the following expression.

$IC_{50}$(µg/ml)=x−{(X−50)(x−y)/(X−Y)}

The $IC_{50}$ value, the concentration of the compounds at percent inhibition 50%, is shown in the following Table 4. Compound No. of the Table 4 is the same as compound No. of the example.

TABLE 4

|  | $IC_{50}$ mg/ml |
|---|---|
| I-42 | 10 |

As shown in Table 4, the compound (I-42) inhibits not only an integrase of HIV classified in lentivirus genus, but also that of MoMLV classified in oncoretrovirus genus. Therefore, the compound of the present invention can be used as follows when a retrovirus vector derived from MLV is used in the gene therapy field. 1) The present compound can be used to suppress the spread of the retrovirus vector's infection over non-target tissues. Specially, a previous administration of the compound of the present invention prevents an unnecessary infection in the case that cells and the like are infected by such a vector in vitro and then are put back in a body. 2) If a replicatable virus is produced by the recombination with a vector and an endogenous virus, the present compound can be used as an inhibitor of an integrase of such a virus.

FORMULATION EXAMPLE

It is to be noted that the following Formulation Examples 1 to 8 are mere illustration, but not intended to limit the scope of the invention. The term "active ingredient" means the compounds of the present invention, the prodrugs thereof, their pharmaceutical acceptable salts, or their hydrates.

FORMULATION EXAMPLE 1

Hard gelatin capsules are prepared using of the following ingredients:

|  | Dose (mg/capsule) |
|---|---|
| Active ingredient | 250 |
| Starch, dried | 200 |
| Magnesium stearate | 10 |
| Total | 460 mg |

FORMULATION EXAMPLE 2

A tablet is prepared using of the following ingredients:

|  | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

FORMULATION EXAMPLE 3

An aerosol solution is prepared containing the following components:

|  | Weight |
|---|---|
| Active ingredient | 0.25 |
| Ethanol | 25.75 |
| Propellant 22 (chlorodifluoromethane) | 74.00 |
| Total | 100.00 |

The active ingredient is mixed with ethanol and the admixture added to a portion of the propellant 22, cooled to −30° C. and transferred to a filling device. The required amount is then fed to a stainless steel container and diluted with the reminder of the propellant. The valve units are then fitted to the container.

FORMULATION EXAMPLE 4

Tablets, each containing 60 mg of active ingredient, are made as follows.

| Active ingredient | 60 mg |
|---|---|
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

FORMULATION EXAMPLE 5

Capsules, each containing 80 mg of active ingredient, are made as follows:

| Active ingredient | 80 mg |
|---|---|
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION EXAMPLE 6

Suppositories, each containing 225 mg of active ingredient, are made as follows:

| Active ingredient | 225 mg |
|---|---|
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION EXAMPLE 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION EXAMPLE 8

An intravenous formulation may be prepared as follows:

| Active ingredient | 100 mg |
|---|---|
| Isotonic saline | 1000 ml |

The solution of the above ingredients is generally administered intravenously to a subject at a rate of 1 ml per minute.

Industrial Applicability

The present compound, the tautomer, the prodrug, the pharmaceutically acceptable salt, or the hydrate thereof has an inhibitory activity against integrase and efficient for treatment of AIDS and the like as an antiviral agent, an anti-HIV agent, and the like.

Moreover, the present invention provides the present compound, the tautomer, the prodrug, the pharmaceutically acceptable salt, or the hydrate thereof, the pharmaceutical composition containing them, the antiviral agent, the anti-HIV agent, the integrase inhibitor and the anti-HIV medical mixture, which are useful as not only an anti-HIV agent, but also an AIDS-treating agent, for example, AIDS and AIDS-related clinical condition such as AIDS-related complex, progressive generalized lymphadenia (PGL), Kaposi sarcoma, pneumocystis carini pneumonia, sudden thrombocytopenic purpura, AIDS-related neurological condition such as AIDS dementia complex, AIDS brain fever, multiple sclerosis or tropical paraparesis, treatment of a positive condition of anti-HIV antibody and HIV, which includes treatment of an asymptomatic patient.

On the other hand, an amino acid sequence of an integrase of a retrovirus is highly conserved. Since the present compound seems to bind the vicinity of an active site of an integrase, the present compound is useful to treat an infectious disease caused by other retroviruses. Therefore the present compound can inhibit not only an integrase of a HIV-1, but also that of an retrovirus such as HIV-2 (Human immunodeficiency virus type 2), HTLV-1 (Human T cell leukemia virus type 1), FIV (Feline immunodeficiency virus), SIV (Simian immunodeficiency virus) and suppress a replication thereof.

Therefore, the present compound, the tautomer, the prodrug, the pharmaceutically acceptable salt or the hydrate thereof, and the pharmaceutical composition containing them are useful as an antiviral agent, an antiretroviral agent, an anti-HIV agent, an anti-HTLV-1 agent, an anti-SIV agent, an anti-FIV agent.

Moreover, the present compound, which inhibits an integrase of a virus (especially, Lentivirus), can be used for the gene therapy.

The process for producing the present compound and the intermediate thereof is useful for preparing an integrase inhibitor, an antiviral agent, an antiretroviral agent, an anti-HIV agent, an anti-HTLV-1 agent, an anti-SIV agent, an anti-FIV agent and the like. Whereas a peptide protease inhibitor is very expensive, difficult to prepare continually, therefore, difficult to apply to a treatment for HIV infectious disease in the developing country, the present process enables to produce the present compound economically, to provide the present compound continually, and to apply the present compound to a treatment for HIV infectious disease in the developing country.

What is claimed is:

1. A method for treating AIDS related to HIV-1, HIV-2, SIV, and FIV infections, which comprises administering to a patient in need thereof a compound of the formula (I):

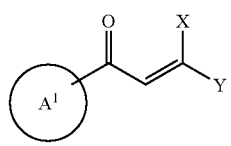

(I)

wherein

X is hydroxy, protected hydroxy or optionally substituted amino;

Y is —COOR$^A$, —CONR$^B$R$^C$, optionally substituted aryl or optionally substituted heteroaryl, wherein said R$^A$ is hydrogen or ester residue, said R$^B$ and R$^C$ each is independently hydrogen or amide residue, and said aryl is a monocyclic aromatic hydrocarbon group or a polycyclic aromatic hydrocarbon group;

A$^1$ is heteroaryl is selected from the group consisting of (1) a 5- to 8-membered heteroaromatic group containing 1 to 4 oxygen atom, sulfur atom and/or nitrogen atom in the ring and (2) a fused heteroaryl which is a heteroaromatic group wherein a 5- to 8-membered aromatic ring containing 1 to 4 oxygen atom, sulfur atom and/or nitrogen atom in the ring is fused with 1 to 4 5- to 8-membered aromatic carbon ring or other 5- to 8-membered heteroaromatic ring optionally substituted with -(Z$^4$-R$^2$)p and/or -Z$^1$-Z$^2$-Z$^3$-R$^1$, Z$^1$ and Z$^3$ each is independently a bond, lower alkylene or lower alkenylene;

Z$^2$ and Z$^4$ each is independently a bond, lower alkylene, lower alkenylene, —CH(OH)—, —S—, —SO—, —SO$_2$—, —SO$_2$NR$^{21}$, —NR$^{21}$SO$_2$—, —O—, —NR$^{21}$—, —NR$^{21}$CO—, —CONR$^{21}$—, —C(=O)—O—, —O—C(=O)— or —CO—;

R$^{21}$ is hydrogen, lower alkyl or lower alkenyl;

R$^1$ is optionally substituted aryl, optionally substituted heteroaryl, optionally substituted cycloalkyl, optionally substituted cycloalkenyl or optionally substituted heterocycle, wherein said aryl is a monocyclic aromatic hydrocarbon group or a polycyclic aromatic hydrocarbon group;

R$^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercapto, optionally substituted amino, nitro or halolgen, wherein said aryl is a monocyclic aromatic hydrocarbon group or a polycyclic aromatic hydrocarbon group; and p is 0 or 1;

or a tautomer, a prodrug, a pharmaceutically acceptable salt or a hydrate thereof, provided that a compound wherein Y and/or A$^1$ is optionally substituted indol-3-yl is excluded.

2. A compound of the formula (I):

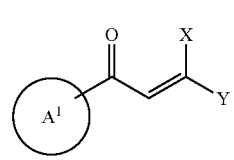

(I)

wherein

X is hydroxy, protected hydroxy or optionally substituted amino;

Y is —CONR$^B$R$^C$ optionally substituted aryl or optionally substituted heteroaryl, wherein said R$^B$ and R$^C$ each is independently hydrogen or amide residue, and said aryl is a monocyclic aromatic hydrocarbon group or a polycyclic aromatic hydrocarbon group;

A$^1$ is heteroaryl selected from the group consisting of (1) 5- to 8-membered heteroaromatic group containing 1 to 4 oxygen atom, sulfur atom and/or nitrogen atom in the ring and (2) a fused heteroaryl which is a heteroaromatic group wherein a 5- to 8-membered aromatic ring containing 1 to 4 oxygen atom, sulfur atom and/or nitrogen atom in the ring is fused with 1 to 4 5- to 8-membered aromatic carbon ring or other 5- to 8-membered heteroaromatic ring optionally substituted with -($Z^4$-$R^2$)p and/or -$Z^1$-$Z^2$-$Z^3$-$R^1$, $Z^1$ and $Z^3$ each is independently a bond, lower alkylene or lower alkenylene;

$Z^2$ and $Z^4$ each is independently a bond, lower alkylene, lower alkenylene, —CH(OH)—, —S—, —SO—, —$SO_2$—, —$SO_2NR^{21}$, —$NR^{21}SO_2$—, —O—, —$NR^{21}$—, —$NR^{21}$CO—, —$CONR^{21}$—, —C(=O)—O—, —O—C(=O)— or —CO—;

$R^{21}$ is hydrogen, lower alkyl or lower alkenyl;

$R^1$ is optionally substituted aryl, optionally substituted heteroaryl, optionally substituted cycloalkyl, optionally substituted cycloalkenyl or optionally substituted heterocycle, wherein said aryl is a monocyclic aromatic hydrocarbon group or a polycyclic aromatic hydrocarbon group;

$R^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercanto, optionally substituted amino, nitro or halogen, wherein said aryl is a monocyclic aromatic hydrocarbon group or a polycyclic aromatic hydrocarbon group; and p is 0 or 1;

or a tautomer, a prodrug, a pharmaceutically acceptable salt or a hydrate thereof, provided that compounds wherein (1) X is hydroxy, Y and $A^1$ are pyridyl; (2) X is hydroxy, Y and $A^1$ are 2-furyl; (3) X is hydroxy, one of Y and $A^1$ is 2-thienyl, the other is 5-ethoxycarbonylmethylsulfanyl-1H-1,2,4-triazol-3-yl, 5-p-tolylamino-1H-1,2,4-triazol-3-yl, 5-phenylamino-1H-1,2,4-triazol-3-yl, 5-hydrazino-1H-1,2,4-triazol-3-yl, 5-(3,6-dioxo-hexahydro-pyridazin-4-ylsulfanyl)-1H-1,2,4-triazol-3-yl, 5-[3-(3,4-dimethylphenyl)-6-oxo-1-phenyl-1,4,5,6-tetrahydro-pyridazin-4-ylsulfanyl]-1H-1,2,4-triazol-3-yl, 5-(1,2-dicarboxyethylsulfanyl)-1H-1,2,4-triazol-3-yl, 5-[1-carboxy-3-(3,4-dimethylphenyl)-3-oxo-propylsulfanyl]-1H-1,2,4-triazol-3yl or 5-(2-cyano-2-ethoxycarbonyl-1-phenyl-ethylsulfanyl)-1H-1,2,4-triazol-3-yl; (4) X is hydroxy, Y and $A^1$ are [3-(2-methoxycarbonylethyl)-4-methoxycarbonylmethyl-5-methyl]-1H-pyrrol-2-yl; (5) X is hydroxy, Y and $A^1$ are 3-methylpyrazol-1-yl; (6) X is hydroxy; Y and $A^1$ are 4-chloropyridin-3-yl; (7) X is hydroxy, one of Y and $A^1$ is 5-bromo-2-furyl, the other is 2-thienyl, 4-bromo-2-thienyl, 5-bromo-2-thienyl or 4,5-dibromo-2-thienyl; (8) X is hydroxy, one of Y and $A^1$ is 2-selenyl or 5-nitro-2-selenyl, the other is 2-furyl or 2 selenyl; (9) X is hydroxy, one of Y and $A^1$ is pyridin-2-yl, and the other is 6-[3-(pyridin-2-yl)-1,3-dioxopropyl]pyridin-2-yl; (10) X is hydroxy, Y and $A^1$ each is independently pyridin-2-yl or 6-methylpyridin-2-yl; (11) X is hydroxy, one of Y and $A^1$ is 2-thienyl, and the other is pyridyl; and (12) Y and/or $A^1$ is optionally substituted indol-3-yl are excluded.

3. A compound of the formula (II):

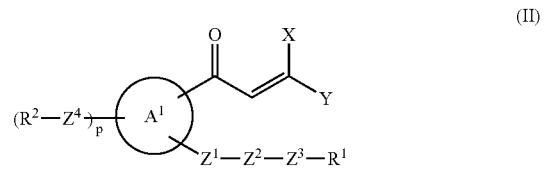

(II)

wherein

X is hydroxy, protected hydroxy or optionally substituted amino;

Y is —$COOR^A$, —$CONR^BR^C$, optionally substituted aryl or optionally substituted heteroaryl, wherein said $R^A$ is hydrogen or ester residue, and said $R^B$ and $R^C$ each is independently hydrogen or amide residue, and said aryl is a monocyclic aromatic hydrocarbon group or a polycyclic aromatic hydrocarbon group;

$A^1$ is heteroaryl selected from the group consisting of (1) 5- to 8-membered heteroaromatic group containing 1 to 4 oxygen atom, sulfur atom and/or nitrogen atom in the ring and (2) a fused heteroaryl which is a heteroaromatic group wherein a 5- to 8-membered aromatic ring2 containing 1 to 4 oxygen atom, sulfur atom and/or nitrogen atom in the ring is fused with 1 to 4 5- to 8-membered aromatic carbon ring or other 5- to 8-membered heteroaromatic ring substituted with -$Z^1$-$Z^2$-$Z^3$-$R^1$ and optionally substituted with -($Z^4$-$R^2$)p, $Z^1$ and $Z^3$ each is independently a bond, lower alkylene or lower alkenylene;

$Z^2$ and $Z^4$ each is independently a bond, lower alkylene, lower alkenylene, —CH(OH)—, —S—, —SO—, —$SO_2$—, —$SO_2NR^{21}$, —$NR^{21}SO_2$—, —O—, —$NR^{21}$—, —$NR^{21}$CO—, —$CONR^{21}$—, —C(=O)—O—, —O—C(=O)— or —CO—;

$R^{21}$ is hydrogen, lower alkyl or lower alkenyl;

$R^1$ is optionally substituted aryl, optionally substituted heteroaryl, optionally substituted cycloalkyl, optionally substituted cycloalkenyl or optionally substituted heterocycle, wherein said aryl is a monocyclic aromatic hydrocarbon group or a polycyclic aromatic hydrocarbon group;

$R^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercapto, optionally substituted amino, nitro or halogen, wherein said aryl is a monocyclic aromatic hydrocarbon group or a polycyclic aromatic hydrocarbon group;

and p is 0 or 1;

or a tautomer, a prodrug, a pharmaceutically acceptable salt or a hydrate thereof;

provided that compounds wherein (1) Y and/or $A^1$ is optionally substituted indol-3-yl; (2) X is hydroxy, Y is 2-thienyl, $A^1$ is 1H-1,2,4-triazol-3-yl, $Z^1$ and $Z^3$ each is a bond, $Z^2$ is —NH—, $R^1$ is phenyl or p-tolyl, and p is 0; (3) X is hydroxy, Y is 4-methoxyphenyl or 4-chlorophenyl, $A^1$ is thiazol-5-yl, $Z^1$, $Z^2$, $Z^3$ and $Z^4$ each is a bond, $R^1$ is phenyl, 4-methoxyphenyl or 4-chlorophenyl, $R^2$ is methyl and p is 1; (4) X is hydroxy, Y is phenyl, 4-methylphenyl, 4-bromophenyl or 4-chlorophenyl, $A^1$ is imidazol-2-yl, $Z^1$ and $Z^3$ each is a bond, $Z^2$ is methylene, $R^1$ is phenyl, $Z^4$ is a bond, $R^2$ is 4-dimethylaminophenyl or 4-methoxyphenyl, and p is 1; (5) X is hydroxy, Y is phenyl, 4-methylphenyl or 4-methoxyphenyl, $A^1$ is 1,2,3-triazol-4-yl, $Z^1$, $Z^2$ and $Z^3$ each is a bond, $R^1$ is phenyl, and p is 0; and (6) X is hydroxy, Y is —COOR$^A$ wherein R$^A$ is hydrogen or ethyl, $A^1$ is 3-indolidinyl, imidazo[1,2-a]pyridin-3-yl or imidazo[2,1-b]thiazol-5-yl, $Z^1$, $Z^2$ and $Z^3$ each is a bond and $R^1$ is optionally substituted phenyl are excluded.

4. The compound according to claim 2 or 3 wherein $A^1$ is optionally substituted furyl, optionally substituted thienyl, optionally substituted pyrrolyl, optionally substituted imidazolyl, optionally substituted pyrazolyl, optionally substituted benzofuryl, optionally substituted benzothienyl, optionally substituted benzimidazolyl, optionally substituted indolidinyl, optionally substituted quinolinyl, optionally substituted isoxazolyl, optionally substituted pyridyl, optionally substituted thiazolyl or optionally substituted oxazolyl, a tautomer, a prodrug, a pharmaceutically acceptable salt or a hydrate thereof.

5. The compound according to claim 4 wherein $A^1$ is optionally substituted furyl, optionally substituted thienyl, optionally substituted pyrrolyl, optionally substituted imidazolyl, optionally substituted pyrazolyl, optionally substituted isoxazolyl, optionally substituted pyridyl, optionally substituted thiazolyl or optionally substituted oxazolyl, a tautomer, a prodrug, a pharmaceutically acceptable salt or a hydrate thereof.

6. The compound according to claim 5 wherein $A^1$ is optionally substituted furyl, optionally substituted pyrrolyl or optionally substituted oxazolyl, a tautomer, a prodrug, a pharmaceutically acceptable salt or a hydrate thereof.

7. The compound according to claim 3 wherein
Y is —COOR$^A$, —CONR$^B$R$^C$, or said heteroaryl optionally substituted with a substituent selected from the group consisting of halogen, lower alkyl, lower haloalkyl, lower alkyloxy(lower)alkyl, carboxy, lower alkyloxycarbonyl, optionally substituted aryl lower alkyl and optionally substituted arylsulfonyl, wherein said R$^A$ is hydrogen or ester residue, and said R$^B$ and R$^C$ each is independently hydrogen or amide residue; or a tautomer, a prodrug, a pharmaceutically acceptable salt or a hydrate thereof.

8. The compound according to claim 7 wherein Y is —COOH; tetrazolyl optionally substituted with lower alkyl or lower alkyloxy(lower)alkyl; triazolyl optionally substituted with halogen, lower alkyl, lower haloalkyl or lower alkyloxy(lower)alkyl; pyridyl optionally substituted with lower alkyl, carboxy or lower alkyloxycarbonyl; pyrrolyl optionally substituted with lower alkyl or optionally substituted arylsulfonyl; isoquinolinyl optionally substituted with lower alkyl; pyradinyl optionally substituted with lower alkyl; pyrimidinyl optionally substituted with lower alkyl; oxadiazolyl optionally substituted with optionally substituted aryl or lower alkyl; isoxazolyl optionally substituted with lower alkyl; thiazolyl optionally substituted with lower alkyl; thienyl optionally substituted with lower alkyl; furyl optionally substituted with lower alkyl; thiadiazolyl optionally substituted with lower alkyl; oxazolyl optionally substituted with lower alkyl; or imidazolyl optionally substituted with lower alkyl, wherein said aryl is a monocyclic aromatic hydrocarbon group or a polycyclic aromatic hydrocarbon group; a tautomer, a prodrug, a pharmaceutically acceptable salt or a hydrate thereof.

9. The compound according to claim 8 wherein Y is tetrazolyl optionally substituted with lower alkyl or lower alkyloxy(lower)alkyl; triazolyl optionally substituted with halogen, lower alkyl, lower haloalkyl or lower alkyloxy(lower)alkyl; pyridyl optionally substituted with lower alkyl, carboxy or lower alkyloxycarbonyl; or pyrimidinyl optionally substituted with lower alkyl; a tautomer, a prodrug, a pharmaceutically acceptable salt or a hydrate thereof.

10. The compound according to claim 2 or 3 wherein X is hydroxy, a tautomer, a prodrug, a pharmaceutically acceptable salt or a hydrate thereof.

11. The compound according to claim 3 wherein $Z^1$ and $Z^3$ each is a bond, a tautomer, a prodrug, a pharmaceutically acceptable salt or a hydrate thereof.

12. The compound according to claim 3 wherein $Z^2$ is a bond, —CO—, —O—, —S—, —SO$_2$—, —CH$_2$— or —(CH$_2$)$_2$—, a tautomer, a prodrug, a pharmaceutically acceptable salt or a hydrate thereof.

13. The compound according to claim 3 wherein $R^1$ is optionally substituted phenyl, a tautomer, a prodrug, a pharmaceutically acceptable salt or a hydrate thereof.

14. The compound according to claim 13 wherein $R^1$ is p-fluorophenyl, a tautomer, a prodrug, a pharmaceutically acceptable salt or a hydrate thereof.

15. A compound of the formula (IV):

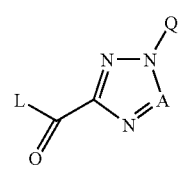

(IV)

wherein A is C—W wherein W is hydrogen, lower alkyl, lower haloalkyl or halogen, or A is N, Q is trityl and L is ethoxy.

16. The compound of formula (I) according to claim 2 wherein said monocyclic aromatic hydrocarbon is phenyl and said polycyclic aromatic hydrocarbon is naphthyl or phenanthryl.

17. The compound of formula (II) according to claim 3 wherein said monocyclic aromatic hydrocarbon is phenyl and said polycyclic aromatic hydrocarbon is naphthyl or phenanthryl.

18. A process for producing a compound of the formula (V):

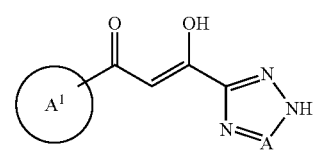

(V)

wherein $A^1$ is heteroaryl selected from the group consisting of (1) 5- to 8-membered heteroaromatic group containing 1 to 4 oxygen atom, sulfur atom and/or nitrogen atom in the ring and (2) a fused heteroaryl which is a heteroaromatic group wherein a 5- to 8-membered aromatic ring containing 1 to 4 oxygen atom, sulfur atom and/or nitrogen atom in the ring is fused with 1 to 4 5- to 8-membered aromatic carbon ring or other 5- to 8-membered heteroaromatic ring; optionally substituted with -($Z^4$-$R^2$)p and/or -$Z^1$-$Z^2$-$Z^3$-$R^1$, $Z^1$ and $Z^3$ each is independently a bond, lower alkylene or lower alkenylene;

$Z^2$ and $Z^4$ each is independently a bond, lower alkylene, lower alkenylene, —CH(OH)—, —S—, —SO—, —SO$_2$—, —SO$_2$NR$^{21}$, —NR$^{21}$SO$_2$—, —O—, —NR$^{21}$—, —NR$^{21}$CO—, —CONR$^{21}$—, —C(=O)—O—, —O—C(=O)— or —CO—;

$R^{21}$ is hydrogen, lower alkyl or lower alkenyl;

$R^1$ is optionally substituted aryl, optionally substituted heteroaryl, optionally substituted cycloalkyl, optionally substituted cycloalkenyl or optionally substituted heterocycle, wherein said aryl is a monocyclic aromatic hydrocarbon group or a polycyclic aromatic hydrocarbon group;

$R^2$ is optionally substituted lower alkyl, optionally substituted lower alkyloxy, optionally substituted lower alkyloxycarbonyl, optionally substituted aryl, optionally substituted aryloxy, optionally substituted aryloxycarbonyl, carboxy, optionally substituted cycloalkyl, hydroxy, mercapto, optionally substituted amino, nitro or halogen, wherein said aryl is a monocyclic aromatic hydrocarbon group or a polycyclic aromatic hydrocarbon group; and p is 0 or 1; and A is C—W wherein W is hydrogen, lower alkyl, lower haloalkyl or halogen, or N, provided that a compound wherein A$^1$ is optionally substituted indol-3-yl is excluded, which comprises reacting a compound of the formula (III):

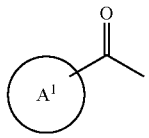

(III)

wherein A$^1$ is as defined above, with a compound of the formula (IV):

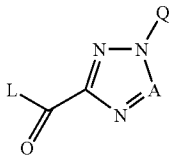

(IV)

wherein A is defined above, Q is a protective group and L is a leaving group, in the presence of a base, and deprotecting Q.

19. The process for producing the compound of formula (V) according to claim 18 wherein said monocyclic aromatic hydrocarbon is phenyl and said polycyclic aromatic hydrocarbon is naphthyl or phenanthryl.

20. The process according to claim 18 wherein a group of the formula:

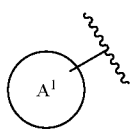

is a group of the formula:

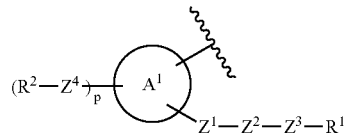

wherein

A$^1$ is heteroaryl selected from the group consisting of (1) 5- to 8-membered heteroaromatic group containing 1 to 4 oxygen atom, sulfur atom and/or nitrogen atom in the ring and (2) a fused heteroaryl which is a heteroaromatic group wherein a 5- to 8-membered aromatic ring containing 1 to 4 oxygen atom, sulfur atom and/or nitrogen atom in the ring is fused with 1 to 4 5- to 8-membered aromatic carbon ring or other 5- to 8-membered heteroaromatic ring optionally substituted with -(Z$^4$-R$^2$)p and/or -Z$^1$-Z$^2$-Z$^3$-R$^1$, $Z^1$ and $Z^3$ each is independently a bond, lower alkylene or lower alkenylene;

$Z^2$ and $Z^4$ each is independently a bond, lower alkylene, lower alkenylene, —CH(OH)—, —S—, —SO—, —SO$_2$—, —SO$_2$NR$^{21}$—, —NR$^{21}$SO$_2$—, —O—, —NR$^{21}$—, —NR$^{21}$CO—, —CONR$^{21}$—, —C(=O)—O—, —O—C(=O)— or CO—;

$R^{21}$ is hydrogen, lower alkyl or lower alkenyl;

$R^1$ is optionally substituted aryl, optionally substituted heteroaryl, optionally substituted cycloalkyl, optionally substituted cycloalkenyl or optionally substituted heterocycle, wherein said aryl is a monocyclic aromatic hydrocarbon around or a polycyclic aromatic hydrocarbon group; and $R^2$ is optionally substituted lower alkyl, optionally substituted loweralkyloxy, optionally substituted lower alkyloxycarbonyl, optionally substituted aryl, optionally substituted aryloxy, optionally substituted aryloxycarbonyl, carboxy, cycloalkyl, hydroxy, mercapto, optionally substituted amino, nitro or halogen, wherein said aryl is a monocyclic aromatic hydrocarbon group or a polycyclic aromatic hydrocarbon group; and p is 0 or 1;

provided that a group wherein A$^1$ is optionally substituted indol-3-yl is excluded.

21. The process according to claim 20 wherein A$^1$ is optionally substituted furyl, Z$^1$ and Z$^3$ each is a bond, Z$^2$ is a bond, —CO—, —O—, —S—, —SO$_2$—, —CH$_2$— or (CH$_2$)$_2$— and R$^1$ is optionally substituted phenyl.

22. A pharmaceutical composition which contains as an active ingredient the compound according to claim 2 or 3.

23. A method for treating AIDS related to HIV-1, HIV-2, SIV, and FIV infections, which comprises administering the compound according to claims 1, 2 or 3 together with one or two inhibitors selected from the group consisting of an adsorption inhibitor, a TAT inhibitor, a REV inhibitor, a reverse transcriptase inhibitor and a protease inhibitor.

24. The method for treating AIDS related to HIV-1, HIV-2, SIV, and FIV infections according to claim 1 wherein said monocyclic aromatic hydrocarbon is phenyl and said polycyclic aromatic hydrocarbon is naphthyl or phenanthryl.

* * * * *